US010053735B2

(12) United States Patent
Foekens et al.

(10) Patent No.: US 10,053,735 B2
(45) Date of Patent: Aug. 21, 2018

(54) MARKERS FOR THE PREDICTION OF OUTCOME OF ANTHRACYCLINE TREATMENT

(75) Inventors: John Foekens, Rotterdam (NL); John W. Martens, Rotterdam (NL); Serenella Eppenberger-Castori, Riehen (CH); Vincent Vuaroqueaux, Hesingue (FR); Frederique Spyratos, La Celle St-Cloud (FR); Nadia Harbeck, Otterfing (DE); Manfred Schmitt, Munich (DE); Heinz Hoefler, Munich (DE); Sabine Maier, Brussels (BE); Gunter Weiss, Berlin (DE); Ralf Lesche, Berlin (DE); Thomas Hildmann, Berlin (DE); Achim Plum, Berlin (DE)

(73) Assignee: THERAWIS DIAGNOSTICS GMBH, Munich (DE)

( * ) Notice: Subject to any disclaimer, the term of this patent is extended or adjusted under 35 U.S.C. 154(b) by 1551 days.

(21) Appl. No.: 12/067,633

(22) PCT Filed: Sep. 21, 2006

(86) PCT No.: PCT/EP2006/009193
§ 371 (c)(1),
(2), (4) Date: May 21, 2008

(87) PCT Pub. No.: WO2007/039128
PCT Pub. Date: Apr. 12, 2007

(65) Prior Publication Data
US 2009/0111707 A1 Apr. 30, 2009

(30) Foreign Application Priority Data

| Sep. 21, 2005 | (EP) | 05090266 |
| Jan. 30, 2006 | (EP) | 06090015 |
| Apr. 7, 2006 | (EP) | 06090050 |
| May 18, 2006 | (EP) | 06090081 |

(51) Int. Cl.
C07H 21/04 (2006.01)
C12Q 1/68 (2018.01)
C12Q 1/6886 (2018.01)

(52) U.S. Cl.
CPC ..... C12Q 1/6886 (2013.01); *C12Q 2600/106* (2013.01); *C12Q 2600/118* (2013.01); *C12Q 2600/154* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| 5,574,142 A | 11/1996 | Meyer, Jr. et al. |
| 5,585,481 A | 12/1996 | Arnold, Jr. et al. |
| 5,587,371 A | 12/1996 | Sessler et al. |
| 5,597,696 A | 1/1997 | Linn et al. |
| 5,786,146 A | 7/1998 | Herman et al. |
| 5,958,773 A | 9/1999 | Monia et al. |
| 6,265,171 B1 | 7/2001 | Herman |
| 6,331,393 B1 | 12/2001 | Laird et al. |
| 6,783,933 B1 * | 8/2004 | Issa ............... C07K 14/705 435/6.14 |
| 2003/0013091 A1 | 1/2003 | Dimitrov |
| 2006/0121467 A1 * | 6/2006 | Foekens ........... C12Q 1/6886 435/6.11 |
| 2009/0197250 A1 | 8/2009 | Cottrell et al. |

FOREIGN PATENT DOCUMENTS

| EP | 06090050.3 | 4/2004 |
| EP | 05090266.7 | 9/2005 |
| EP | 06090015.6 | 1/2006 |
| EP | 06090081.8 | 5/2006 |
| EP | 1945806 | 9/2006 |
| WO | WO 2004/035803 | 4/2004 |
| WO | WO 04/111603 | * 12/2004 |
| WO | WO 2004/111603 | 12/2004 |
| WO | WO 2007/039128 | 4/2007 |

OTHER PUBLICATIONS

Kanters et al. (Molecular and biological factors in the prognosis of non-small cell lung cancer, 1995, European Respiratory Journal, vol. 8, pp. 1389-1397).*
Gelmann et al. (Clinically relevant prognostic markers for prostate cancer: the search goes on, 2009, Annals of Internal Medicine, vol. 150, pp. 647-649 and W-117).*
Sarkar et al. (Utility of prognostic markers in management of breast cancer, The Internet Journal of Surgery, 2008, vol. 17, 18 pages).*
Asakawa et al. (Prediction of breast cancer sensitivity to neoadjuvant chemotherapy based on status of DNA damage repair proteins, Breast Cancer Research, 2010, vol. 12, pp. 1-11).*
Nimmrich et al. (DNA hypermethylation of PITX2 is a marker of poor prognosis in untreated lymph node-negative hormone receptor-positive breast cancer patients, 2008, Breast Cancer Research and Treatment, vol. 111, pp. 429-437).*
Widschwendter et al. (Methylation and expression of human telomerase reverse transcriptase in ovarian and cervical cancer, 2004, Gynecologic Oncology, vol. 93, pp. 407-416).*
Suyama et al. (The MAGE-A1 gene expression is not determined solely by methylation status of the promoter region in hematological malinancies, 2002, Leukemia Research, vol. 26, pp. 1113-1118).*
Wu (Analysing gene expression data from DNA microarrays to identify candidate genes, 2001, The Journal of Pathology, vol. 195, pp. 53-65).*
Lucentini (Gene association studies typically wrong, 2004, The Scientist, vol. 18, p. 20).*
Cameron et al. (Blood, vol. 94, No. 7, pp. 2445-2451, Oct. 1999).*
Pao et al. (Human Molecular Genetics, vol. 10, No. 9, pp. 903-910).*

(Continued)

*Primary Examiner* — Jeanine A Goldberg
(74) *Attorney, Agent, or Firm* — Lathrop Gage LLP; James H. Velema, Esq.

(57) ABSTRACT

The present invention relates to methods for predicting the outcome of anthracycline treatment of cell proliferative disorder patients. This is achieved by determining the expression level of at least one gene selected from the group consisting of PITX2; TFF1 and PLAU. The invention also relates to sequences, oligonucleotides and antibodies which can be used within the described methods.

12 Claims, 78 Drawing Sheets

(56) References Cited

OTHER PUBLICATIONS

Toyota et al. Cancer Research, vol. 59, pp. 4535-4541, Sep. 1999.*
Lopez-Otin et al., "Breast and Prostate Cancer: An Analysis of Common Epidemiological, Genetic, and Biochemical Features," Endocrine Reviews, 1998, pp. 365-396, vol. 19.
Asano et al., "Altered expression of topoisomerase IIα contributes to cross-resistant to etoposide K562/MX2 cell line by aberrant methylation," British Journal of Cancer, 2005, pp. 1486-1492, vol. 92.
Belyavsky et al., "PCR-based cDNA library construction: general cDNA libraries at the level of a few cells," Nucleic Acids Research, 1989, pp. 2919-2932, vol. 17, No. 8.
Burger et al., "RNA Expression of Breast Cancer Resistance Protein, Lung Resistance-related Protein, Multidrug Resistance-associated Proteins 1 and 2, and Multidrug Resistance Gene 1 in Breast Cancer: Correlation with Chemotherapeutic Response," Clinical Cancer Research, 2003, pp. 827-836, vol. 9.
Eads et al., "CpG Island Hypermethylation in Human Colorectal Tumors Is Not Associted with DNA Methyltransferase Overexpression," Cancer Research, May 15, 1999, pp. 2302-2306, vol. 59.
Galfre et al., "Preparation of monclonal antibodies: strategies and procedures," *Methods in Enzymology*, Colowick and Kaplan (editors-in-chief), Langone and Vunakis (editors), 1981, pp. 3-46, vol. 73, Immonochemical Techniques, Part B.
Gonzalgo et al., "Identification and Characterization of Differentially Methylated Regions of Genomic DNA by Methylation-sensitve Arbitrarily Primed PCR," Cancer Research, Feb. 15, 1997, pp. 594-599, vol. 57.
Gonzalgo et al., Rapid quantitation of methylation differences at specific sites using methylation-sensitive single nucleotide primer extension (Ms-SNuPE), Nucleic Acids Research, 1997, pp. 2529-2531, vol. 25, No. 12.
Gut et al, "DNA and Matrix Assisted Laser Desorption Ionization Mass Spectrometry," Molecular Biology: Current Innovations and Future Trends, 1995, pp. 147-157, Horizon Scientific Press, Wymondham, United Kingdom.
Gut et al., "A procedure for selection DNA alkylation and detection by mass spectrometry," Nucleic Acids Research, 1995, pp. 1367-1373, vol. 23, No. 8.
Harbeck et al., "Enhanced Benefit from Adjuvant Chemotherapy in Breast Cancer Patients Classified High-Risk according to Urokinase-type Plasminogen Activator (uPA) and Plasminogen Activator Inhibitor Rype 1 (n=3424)," Cancer Research, 2002, pp. 4617-4622, vol. 62.
Heid et al., "Real Time Quantitative PCR," Genome Research, 1996, pp. 986-994, vol. 6.
Herman et al., "Methylation-specific PCR: A novel PCR assay for methylation status of CpG islands," Sep. 1996, pp. 9821-9826, vol. 93.
Karas et al., "Laser Desorption Ionization of Proteins with Molecular Masses Exceeding 10 000 Daltons," Analytical Chemistry, Oct. 15, 1988, pp. 2299-2301, vol. 60, No. 20.
Koehler et al., "Continuous cultures of fused cells secreting antibody of predefined specificity," Nature, Aug. 7, 1975, pp. 495-497, vol. 256, No. 5517.
Krug et al., "First Strand cDNA Synthesis Primed with Oligo(dT)," Methods in Enzymology, 1987, pp. 316-325, vol. 152.
Martin et al., "Involvement of DNA Methylation in the Control of the Expression of an Estrogen-Induced Breast-Cancer-Associated Protein (pS2) in Human Breast Cancers," Journal of Cellular Biochemistry, 1997, pp. 95-106, vol. 65.
Model et al., "Statistical process control for large scale microarray experiments," Bioinformatics, 2002, pp. S155-S163, vol. 18, Supplement 1.
Momparler et al., "DNA Methylation and Cancer," Journal of Cellular Physiology, 2000, pp. 145-154, vol. 183.
Olek et al., "A modified and improved method for bisulphite based cytosine methylation analysis," Nucleic Acids Research, 1996, pp. 5064-5066, vol. 24, No. 24.
Ribieras et al., "The pS2/TFF1 trefoil factor, from basic research to clinical applications," Biochimica et Biophysica Acta, 1998, pp. F61-F77, vol. 1378.
Sanger et al., "DNA sequencing with chain-terminating inhibitors," The Proceedings of the National Academy of Sciences, 1977, pp. 5463-5468, vol. 74.
Stites et al., "Clinical laboratory methods for detection of antigens and antibodies," *Basic and Clinical Immunology*. 7th ed., 1991, pp. 217-262, Appleton & Lange, Norwalk, Conn.
Szyf et al., "DNA methylation and breast cancer," Biochemical Pharmacology, 2004, pp. 1187-1197, vol. 68.
Van Der Krol et al., "Modulation of Eukaryotic Gene Expression by Complementary RNA or DNA Sequences," BioTechniques, Nov.-Dec. 1988, pp. 958-976, vol. 6, No. 10.
Watson et al., "Isolation of Differentially Expressed Sequence Tags from Human Breast Cancer," Cancer Research, 1994, pp. 4598-4602, vol. 54.
Xiong et al., "COBRA: a sensitive and quantitative DNA methylation assay," Nucleic Acids Research, 1997, pp. 2532-2534, vol. 25, No. 12.
Yu et al., "Specific Inhibition of PCR by Non-Extendable Oligonucleotides Using a 5' to 3' Exonuclease-Deficient DNA Polymerase," BioTechniques, Oct. 1997, pp. 714-720, vol. 23.
Zon, "Oligonucleotide Analogues as Potential Chemotherapeutic Agents," Pharmaceutical Research, Sep. 1988, pp. 539-549, vol. 5, No. 9.
López-Otin and Diamandis, "Breast and Prostate Cancer: An Analysis of Common Epidemiological, Genetic, and Biochemical Features", Endocr. Rev. 19:365-396; 1998.

* cited by examiner

MARKERS FOR THE PREDICTION OF OUTCOME OF ANTHRACYCLINE TREATMENT

FIELD OF THE INVENTION

Aspects of the present invention relates generally to cancer and chemotherapy and more particularly to compositions and methods for predicting the outcome of anthracycline treatment, characterized in that the expression level of at least one of the genes and/or genomic sequences and/or regulatory or promoter regions thereof according to Table 1 herein, or the genetic or the epigenetic modifications of the genomic DNA associated with said genes and/or genomic sequences and/or regulatory or promoter regions thereof, are determined. Particular aspects also relate to nucleic acid sequences, oligonucleotides and antibodies having utility in the described methods.

CROSS REFERENCE TO RELATED APPLICATIONS

The present application is a national submission under 35 U.S.C. 371, and claims the benefit of priority to International Application PCT/EP2006/009193, filed 21 Sep. 2006, which claims the benefit of priority to European patent application numbers: EP05090266.7, filed 21 Sep. 2005; EP06090015.6, filed 30 Jan. 2006; EP06090050.3, filed 7 Apr. 2006; EP06090081.8, filed 18 May 2006, all of which are incorporated herein by reference in their entireties.

SEQUENCE LISTING

A Sequence Listing in paper (.pdf) form and electronic (.txt) comprising SEQ ID NOS:1-165 is included as part of this application and is incorporated by reference herein in its entirety.

BACKGROUND

Anthracyclines are a large group of compounds synthesized by different *Streptomyces* species. They possess antibiotic activity and have cytotoxic effects on eukaryotic cells. All anthracyclines have a tetrahydronaphthacenedione ring structure attached by a glycosidic linkage to a sugar molecule, structural diversity of anthracyclines is generated by modifications of the backbone including a large number of different side chains.

Anthracyclines have excellent antineoplastic activity in metastatic, neoadjuvant, and adjuvant settings and are used in the treatment of various haematopoietic and solid tumours. Commonly used anthracyclines include but are not limited to mitoxantrone, doxorubicin, aclarubicin, daunorubicin, epirubicin and idarubicin. Although their mechanism of chemotherapeutic action is unclear involves noncovalent DNA intercalation, formation of covalent DNA adducts, topoisomerase II (topo II) poisoning, and free radical effects on cellular membranes and DNA. However, the clinical utility of anthracyclines are limited due to acute and chronic toxicities, particularly cardiotoxicity, myelosuppression, nausea and vomiting, and alopecia.

Heart failure following anthracycline therapy is a major clinical problem in cancer treatment. The establishment of predictors of the anthracycline treatment outcome would allow the identification and exclusion of individuals who would not benefit from said treatment, and thus to increase the safety of anthracycline treatment. Furthermore by determining which patients would benefit from Anthracycline treatment, but wherein said predicted outcome is suboptimal patients can be recommended for further chemotherapeutic or other treatments. Conversely by determining which patients would be adequately treated by anthracycline treatment alone the over-treatment of patients can be prevented. Accordingly there is a longfelt need in the art for determining which patients will benefit from Anthracycline treatment.

Methylation of the gene Topo IIalpha gene was recently observed in the cell line K562/MX2, which displays resistance to the anthracyclines KRN 8602 (MX2), etoposide and doxorubicin (Asano et al. Br J. Cancer. 2005 Apr. 25; 92(8):1486-92.). Sensitivity to the drug was restored by treatment with the demethylating agent 5-Aza-2'-deoxycytidine, thereby implying that Topo IIalpha methylation is a mechanism of drug resistance. The person skilled in the art when considering WO 2004/035803 in light of Asano et al. would not have a reasonable expectation of success that a methylation marker indicative of response to treatment targeting a hormone pathway would be a predictor of response to a treatment with an unrelated mechanism of action.

The present invention provides a novel method for predicting the outcome of anthracycline treatment of a patient with a haematopoetic or solid tumour by determining the CpG methylation status of at least one gene selected from the group consisting of PITX2; TFF1 and PLAU and predicting therefrom the outcome of anthracycline treatment.

The technical differences between the state of the art and the present invention are that the present invention provides a means for the prediction of anthracycline treatment by means of analysis of the methylation of at least one gene selected from the group consisting of PITX2; TFF1 and PLAU. The technical effect of this is to provide a predictor of treatment outcome specific to haematopoeitic or solid tumour treatment, as opposed to other treatments that may be treated by means of anthracyclines.

Thus, the objective technical problem solved by the method of the present invention is to predict outcome of anthracycline treatment of haematopoietic and solid tumours.

Prior Art in Methylation Analysis 5-methylcytosine is the most frequent covalent base modification in the DNA of eukaryotic cells. Methylation of DNA can play an important role in the control of gene expression in mammalian cells. It plays a role, for example, in the regulation of the transcription, in genetic imprinting, and in tumorigenesis. DNA methyltransferases are involved in DNA methylation and catalyze the transfer of a methyl group from S-adenosylmethionine to cytosine residues to form 5-methylcytosine, a modified base that is found mostly at CpG sites in the genome. The presence of methylated CpG islands in the promoter region of genes can suppress their expression. This process may be due to the presence of 5-methylcytosine, which apparently interferes with the binding of transcription factors or other DNA-binding proteins to block transcription. In different types of tumors, aberrant or accidental methylation of CpG islands in the promoter region has been observed for many cancer-related genes, resulting in the silencing of their expression. Such genes include tumor suppressor genes, genes that suppress metastasis and angiogenesis, and genes that repair DNA (Momparler and Bovenzi (2000) J. Cell Physiol. 183:145-54). Therefore, the identification of 5-methylcytosine as a component of genetic information is of considerable interest._

However, 5-methylcytosine positions cannot be identified by sequencing since 5-methylcytosine has the same base pairing behaviour as cytosine. Moreover, the epigenetic information carried by 5-methylcytosine is completely lost during PCR amplification.

DESCRIPTION

Figure 1:
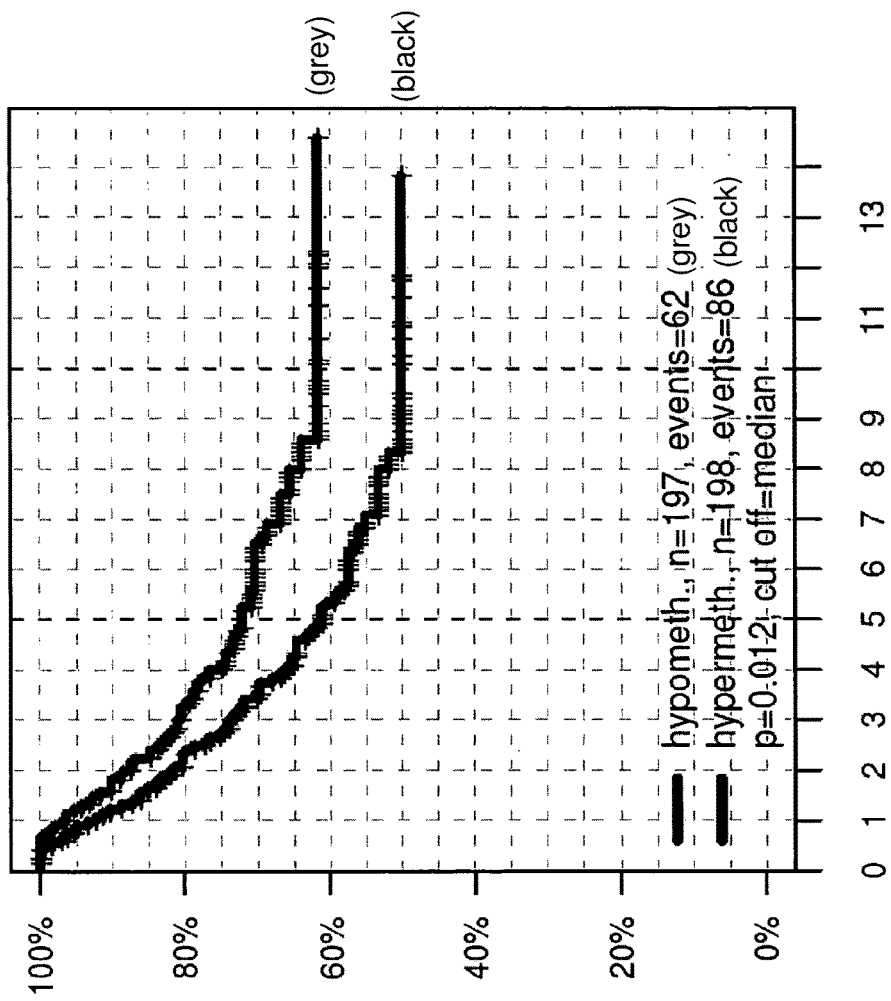
FIGS. 1 to 78 show the Kaplan-Meier estimated disease-free survival curves for single assays or combinations of assays according to Example 2 and Table 5. The black plot in FIGS. 1 to 78 shows the proportion of disease free patients in the sample set with above median or optimised cut off methylation levels, the grey plot in FIGS. 1 to 78 shows the proportion of disease free patients in the population with below median or optimised cut-off methylation levels. Also indicated on each plot are the number of events (i.e. metastasis) and number of individuals in each of the two sets. Proportion of metastasis free patients is shown on the Y-axis, time in years is shown on the X-axis.
Figure 2:
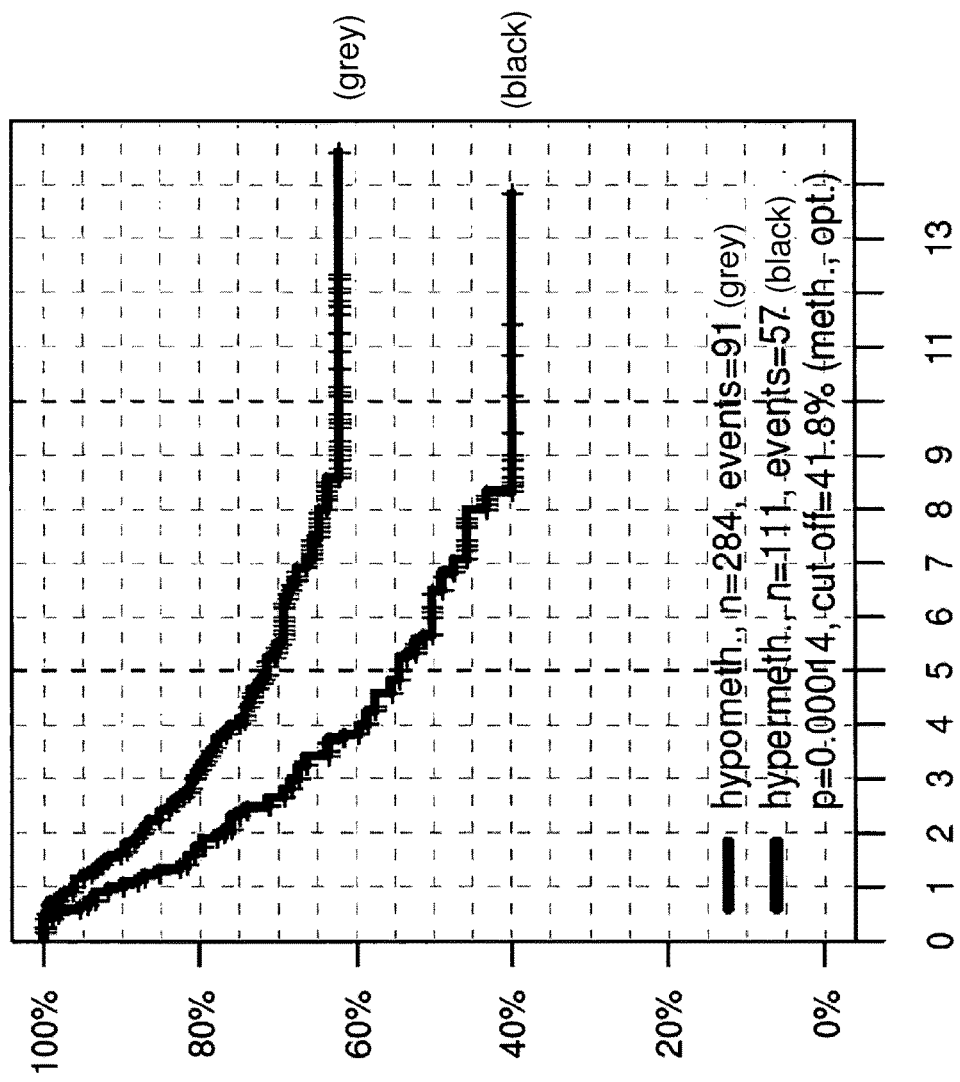
Figure 3:
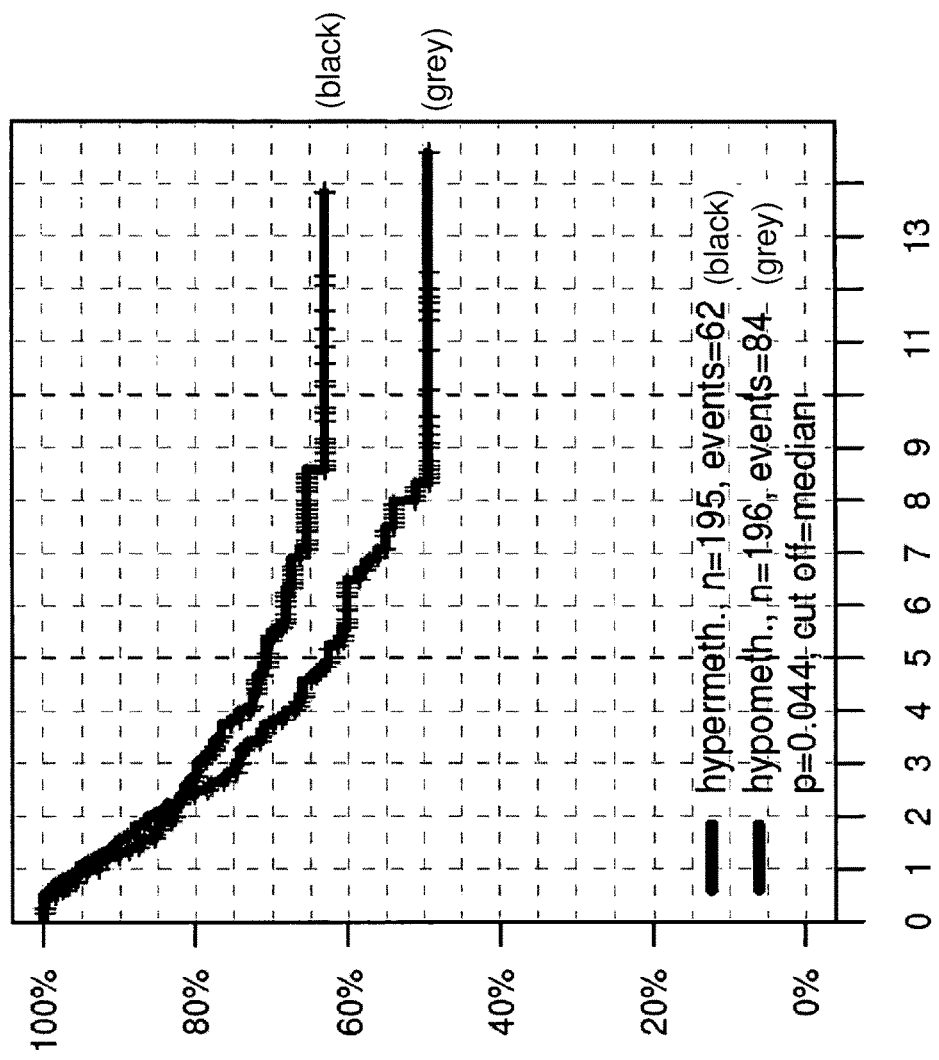
Figure 4:
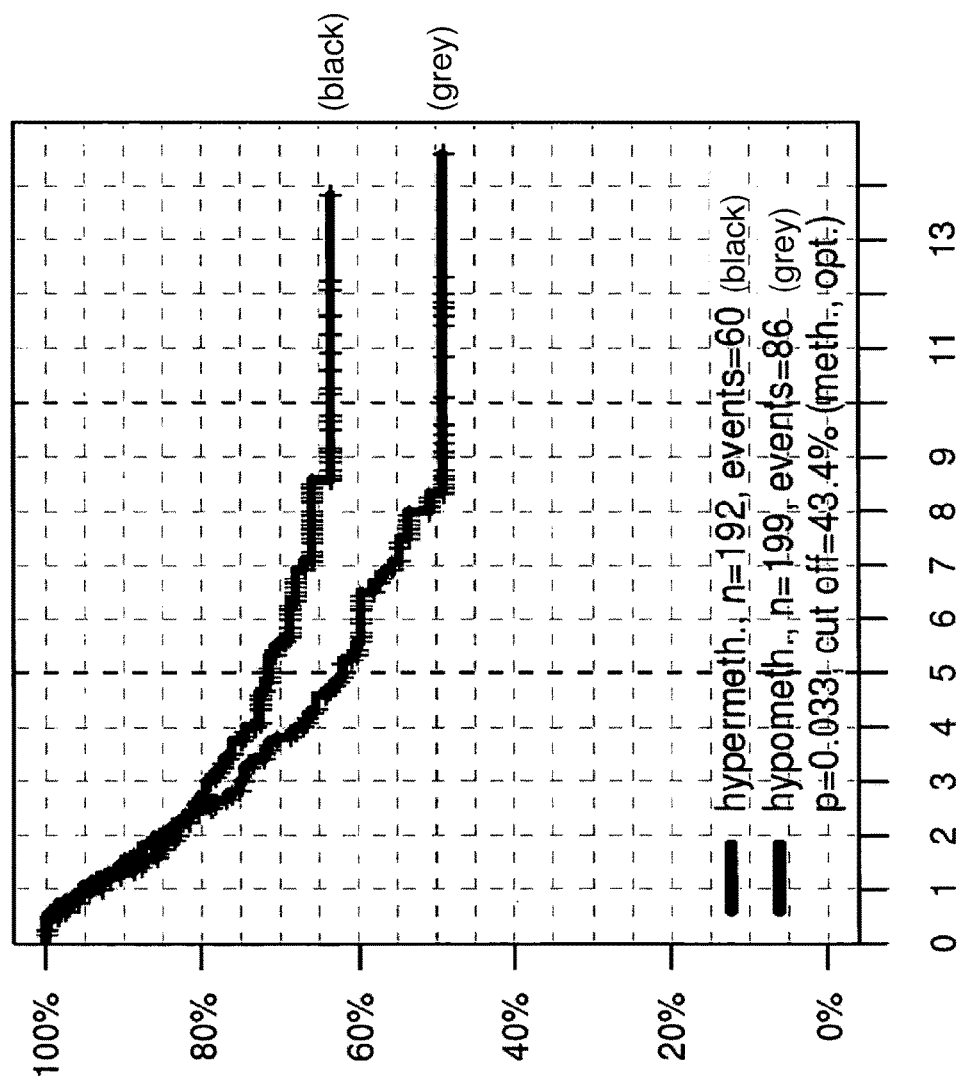
Figure 5:
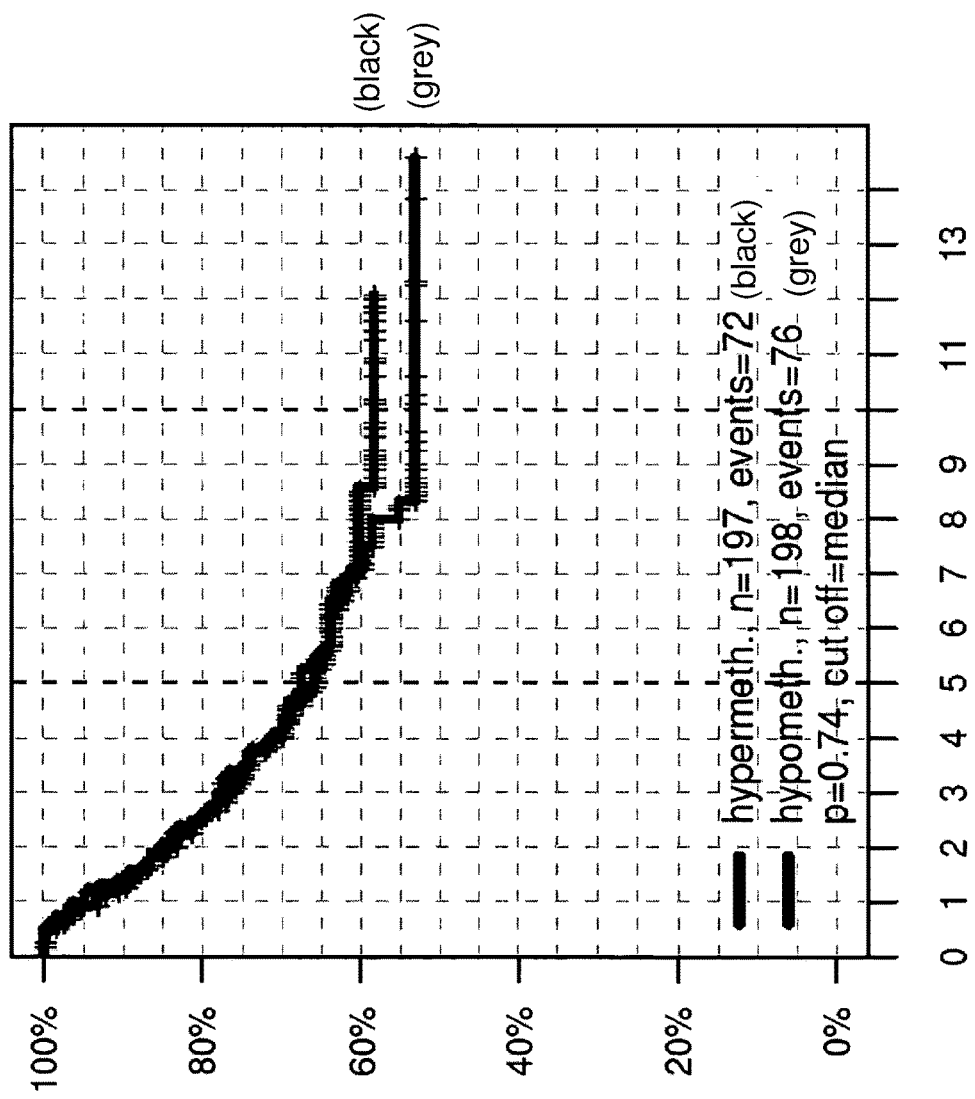
Figure 6:
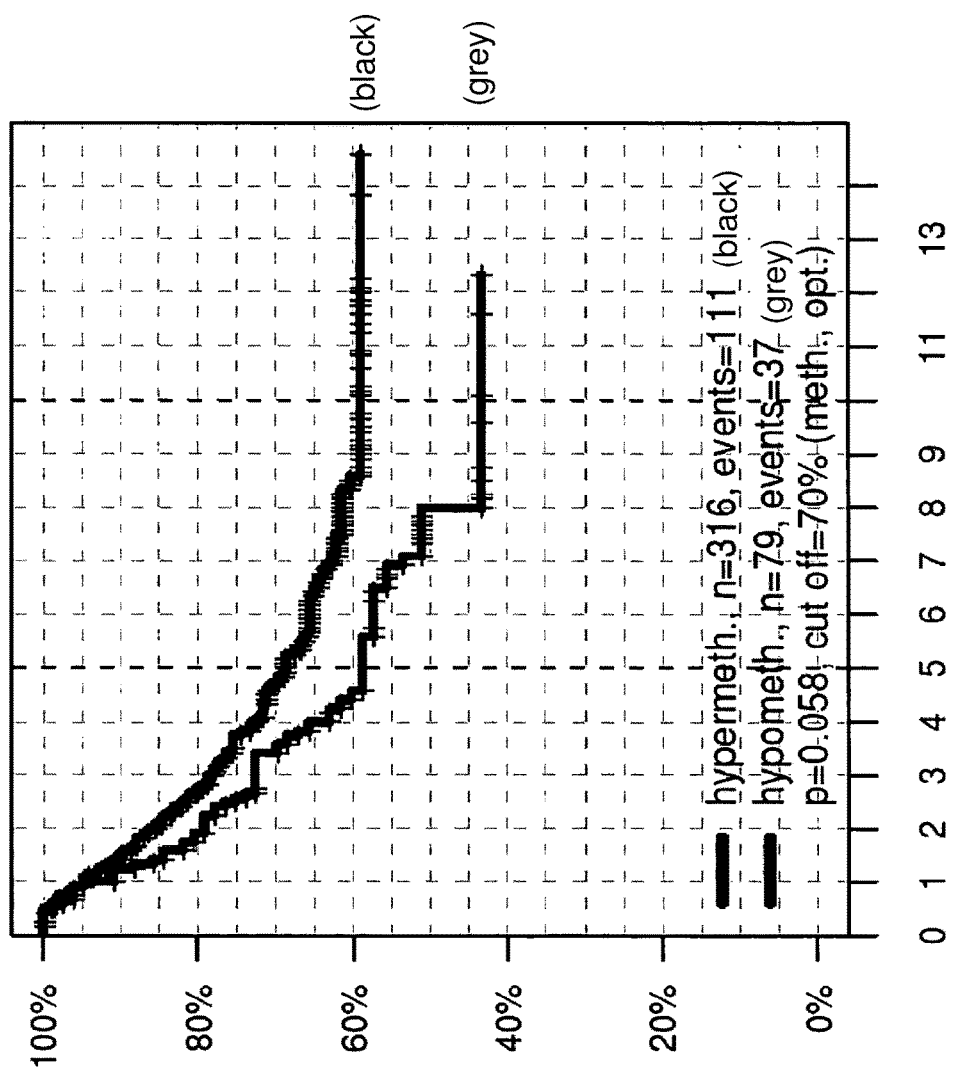
Figure 7:
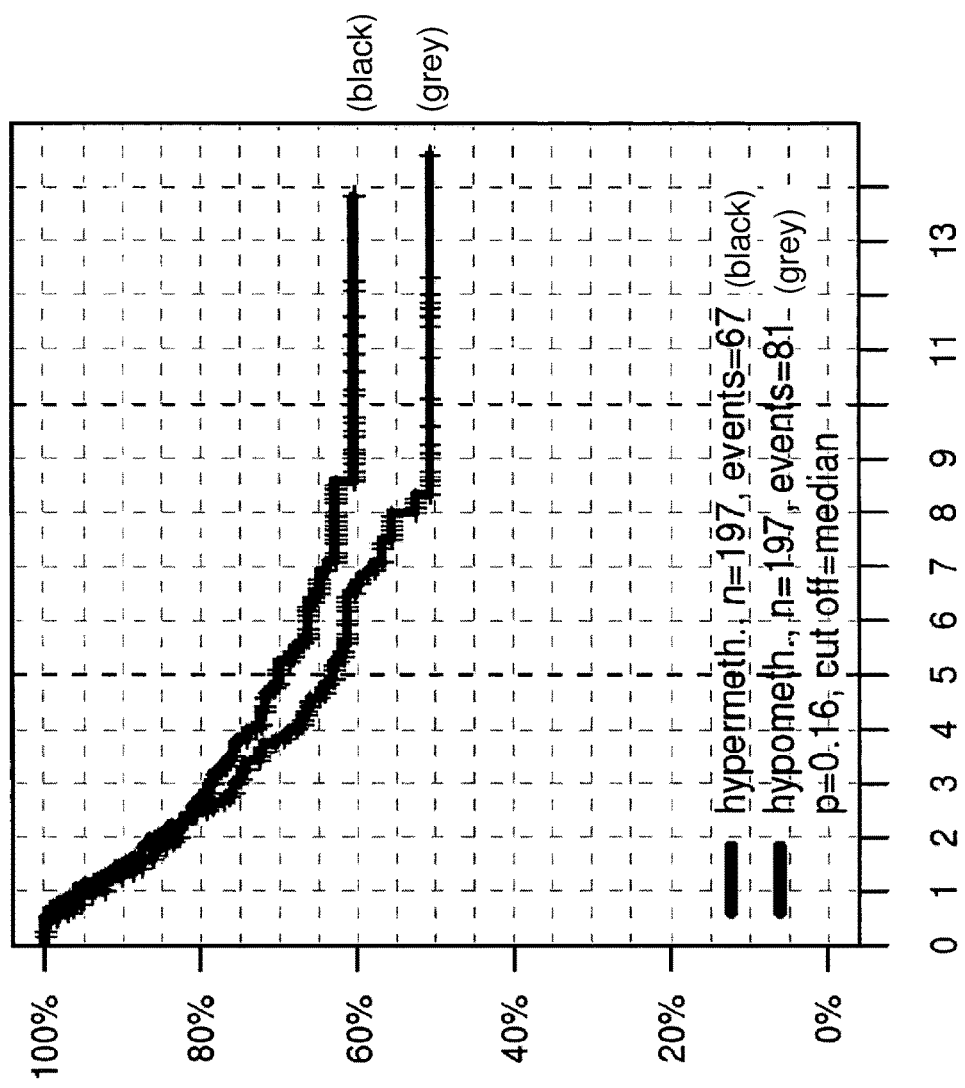
Figure 8:
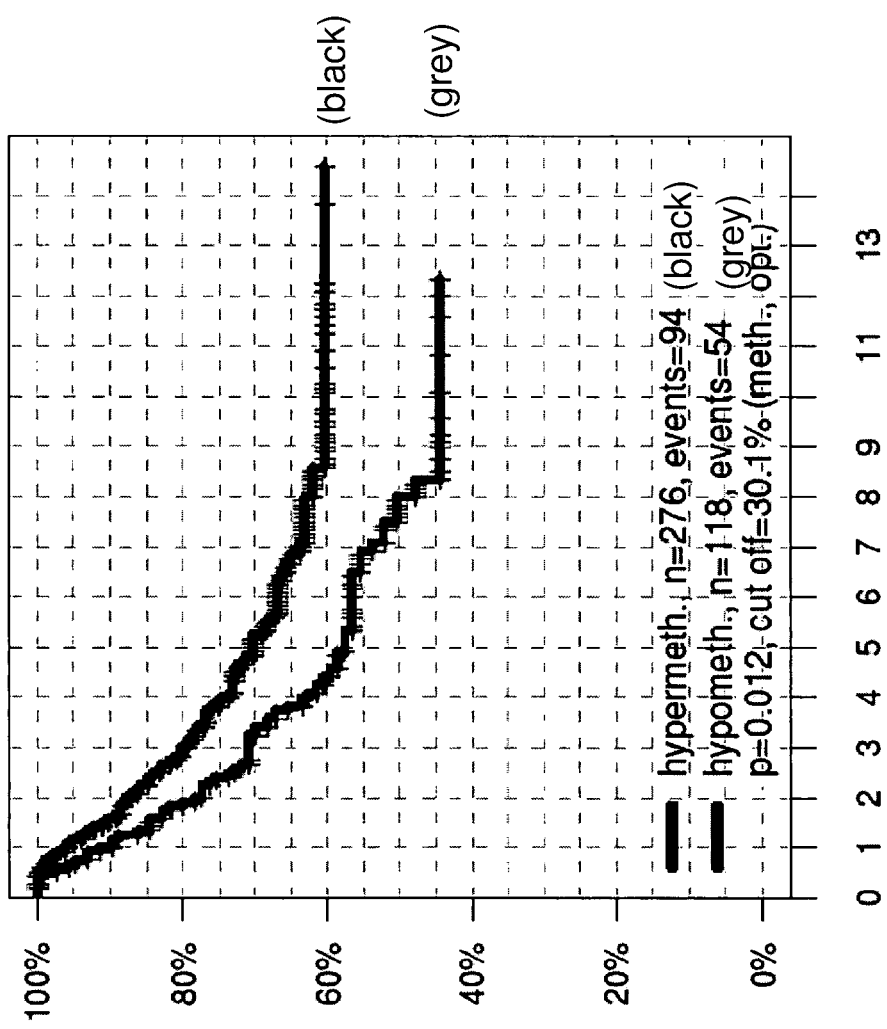
Figure 9:
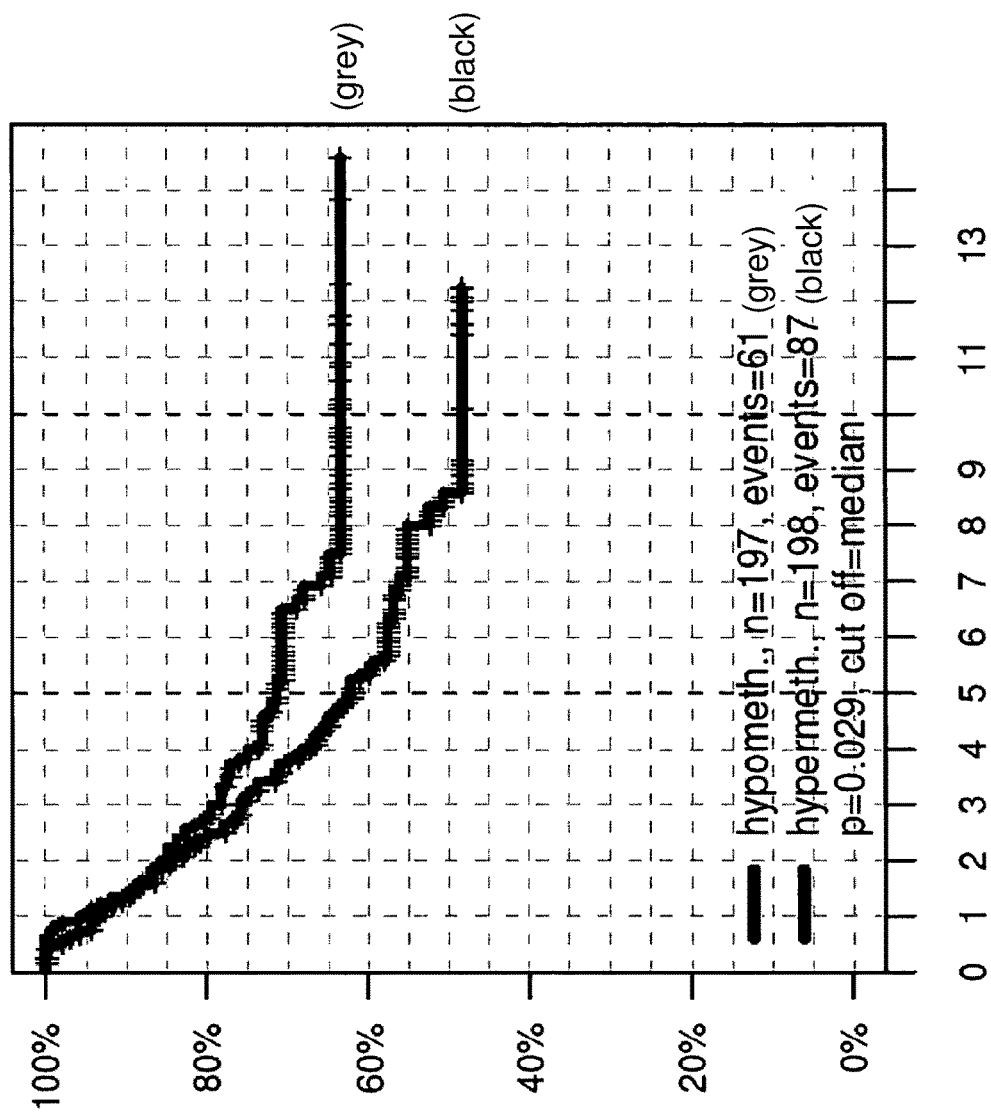
Figure 10:
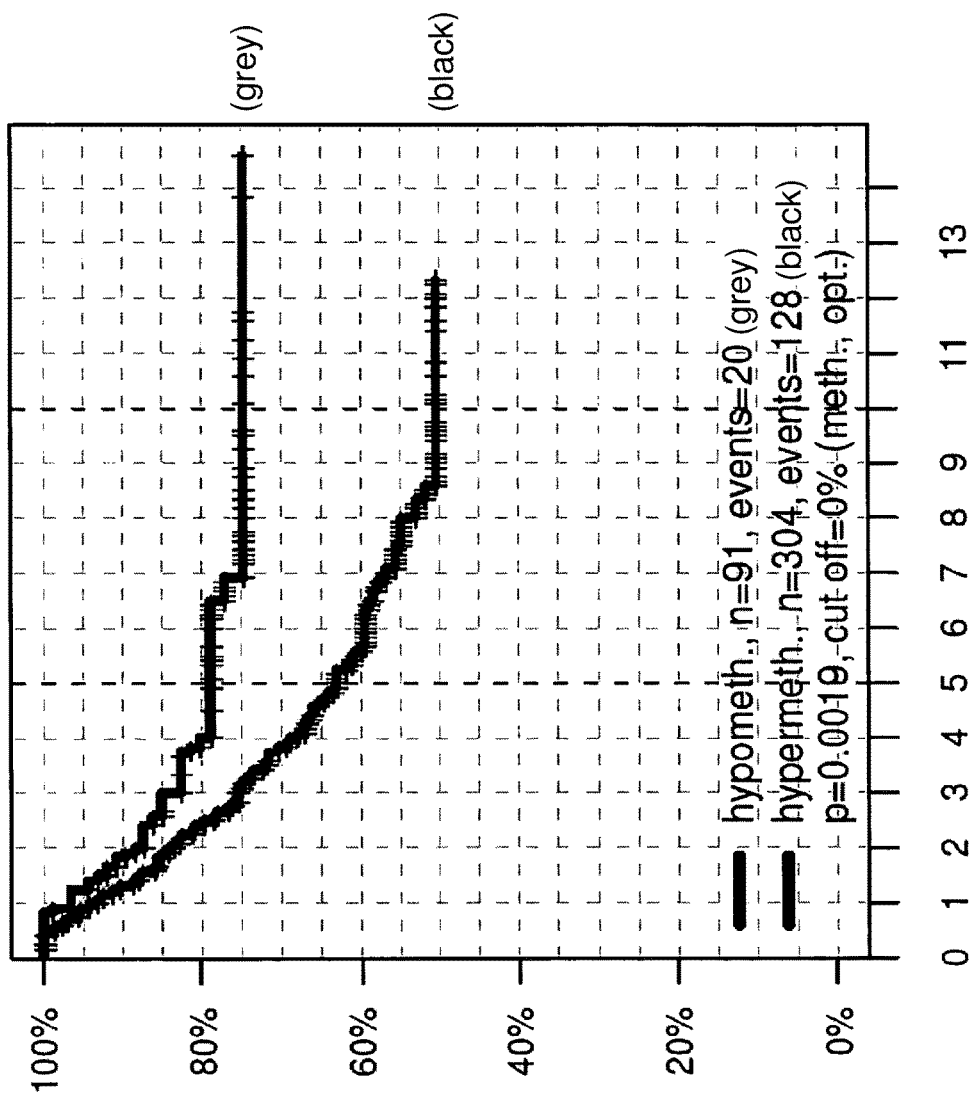
Figure 11:
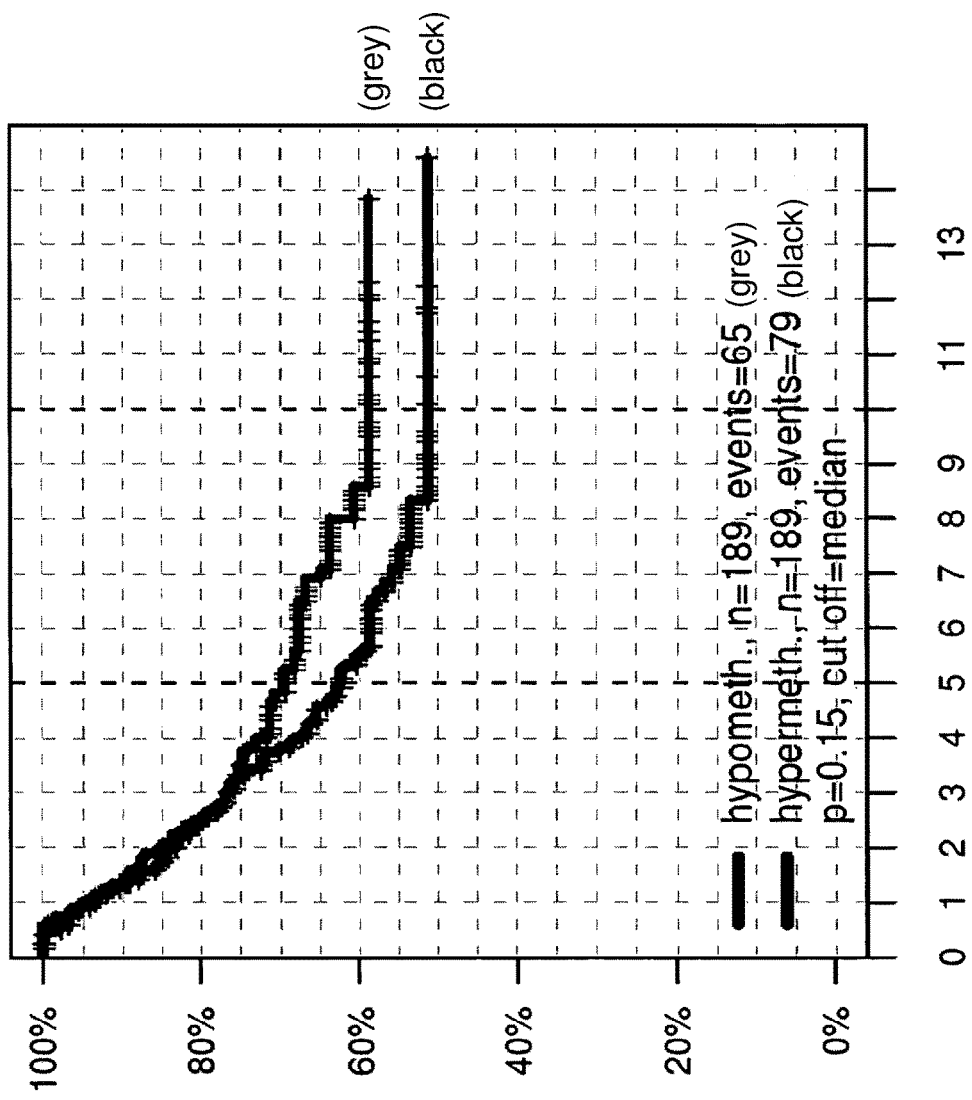
Figure 12:
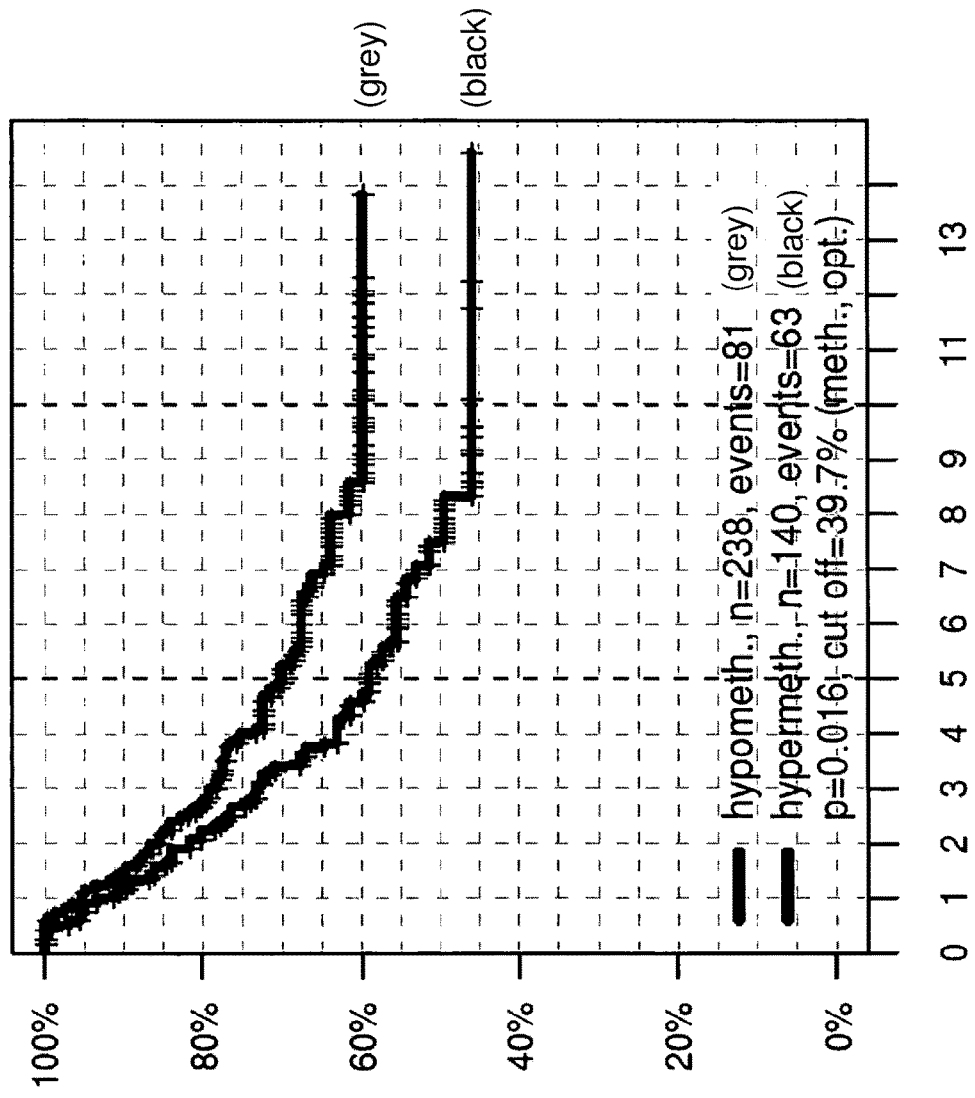
Figure 13:
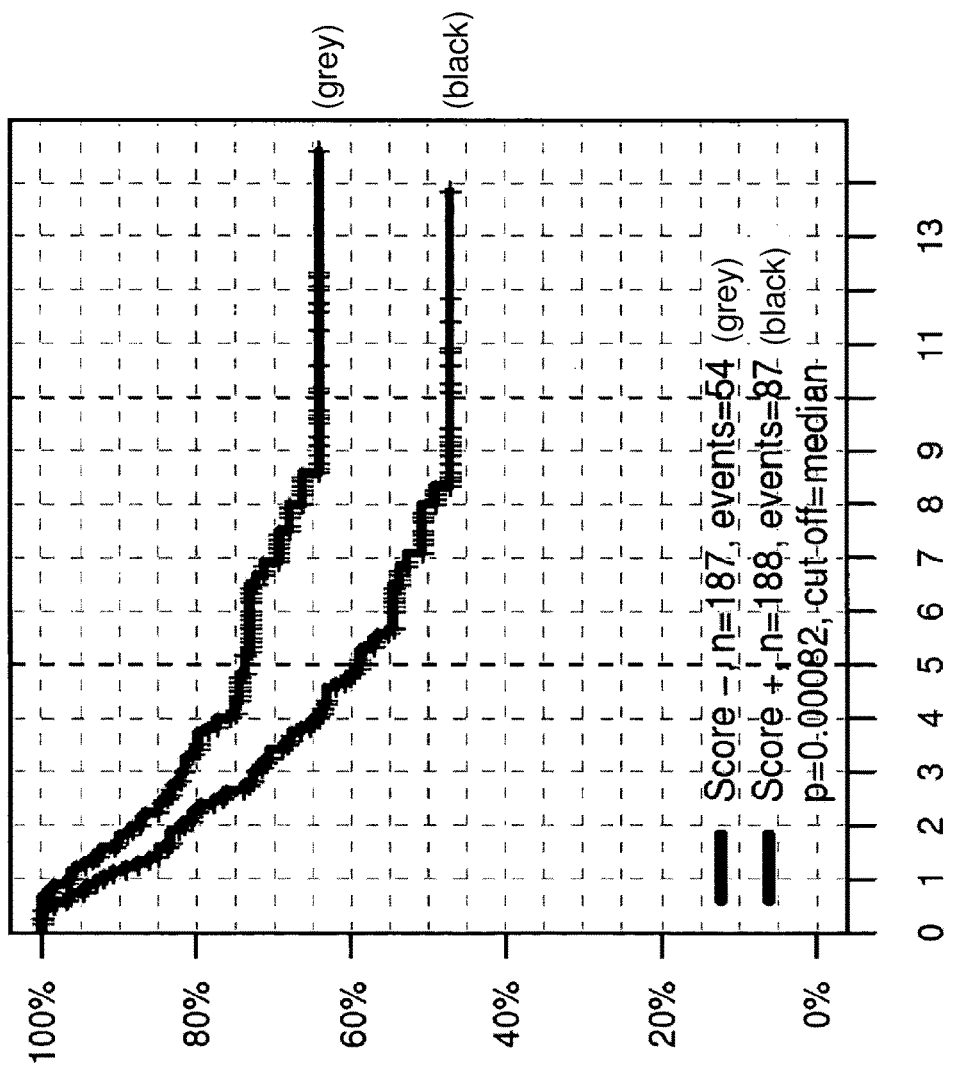
Figure 14:
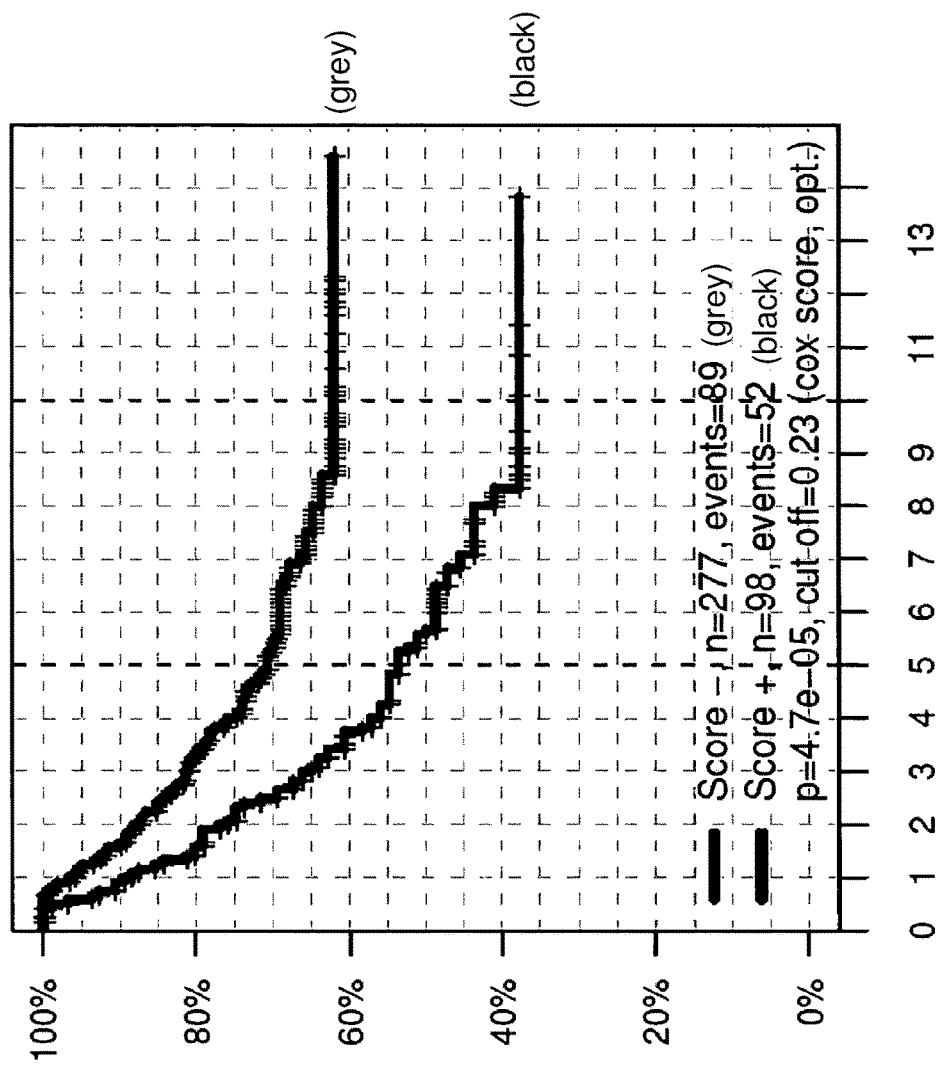
Figure 15:
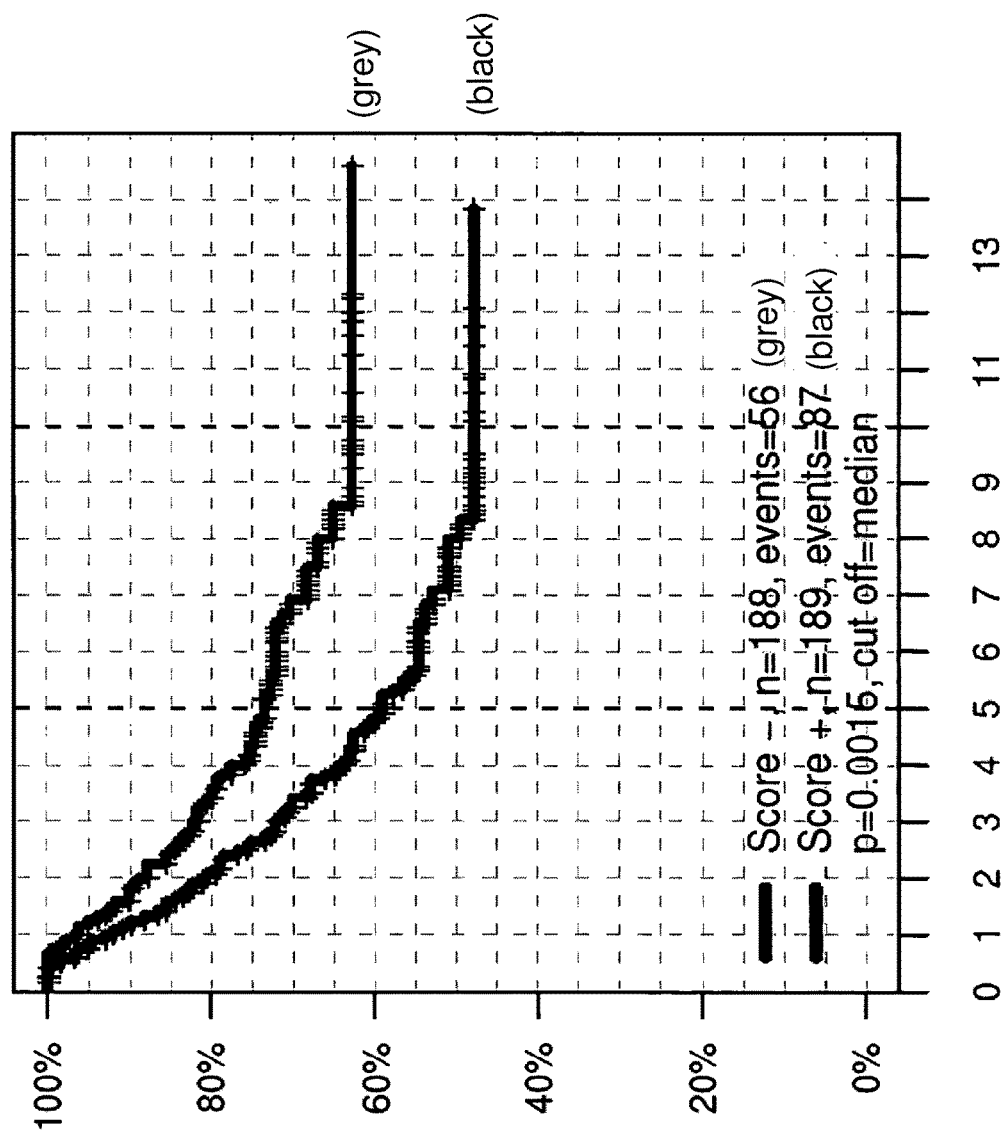
Figure 16:
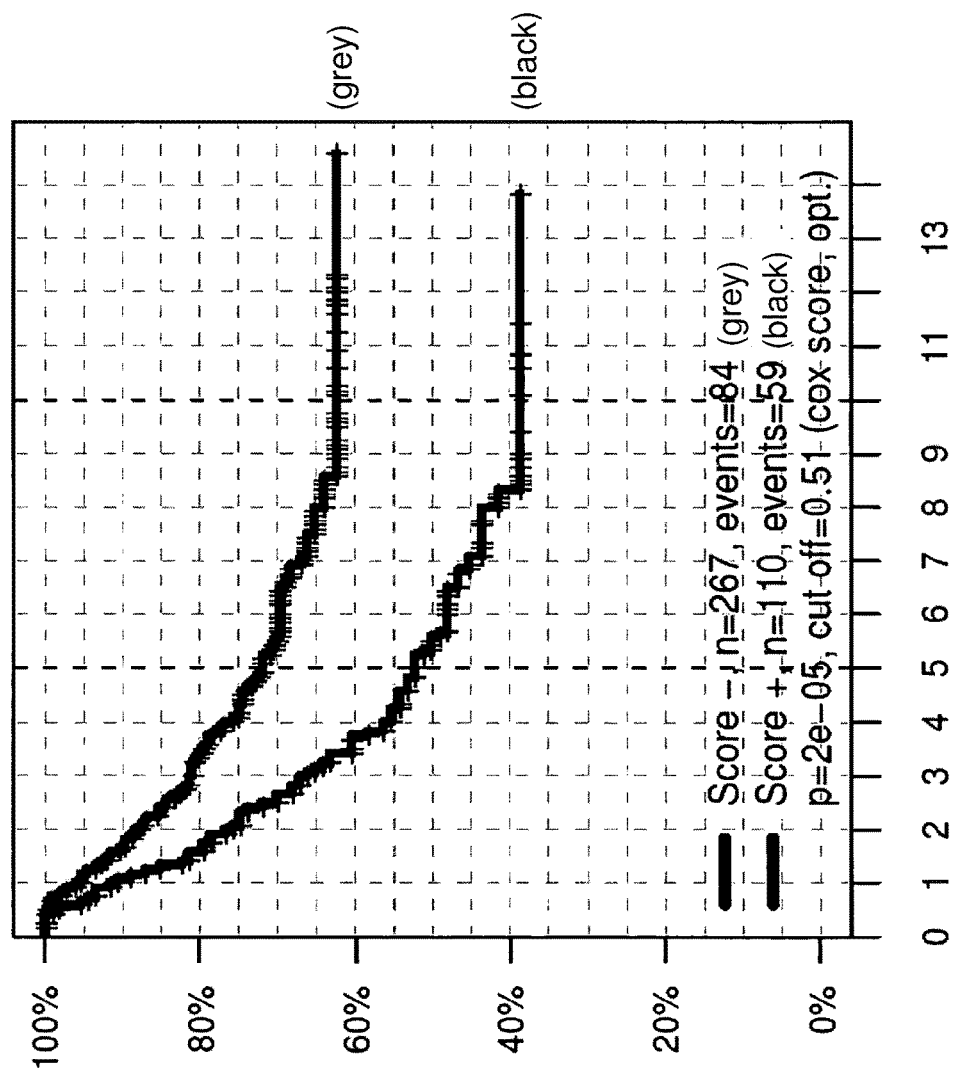
Figure 17:
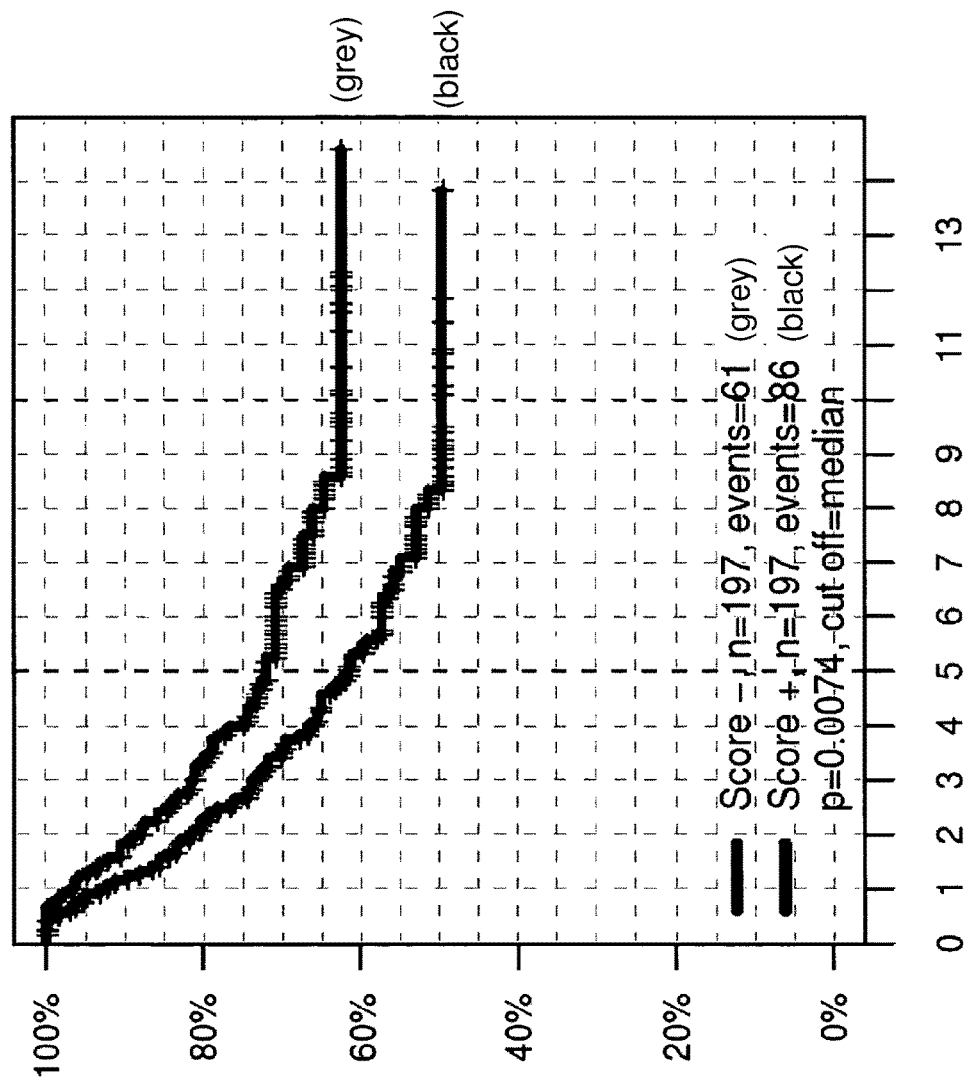
Figure 18:
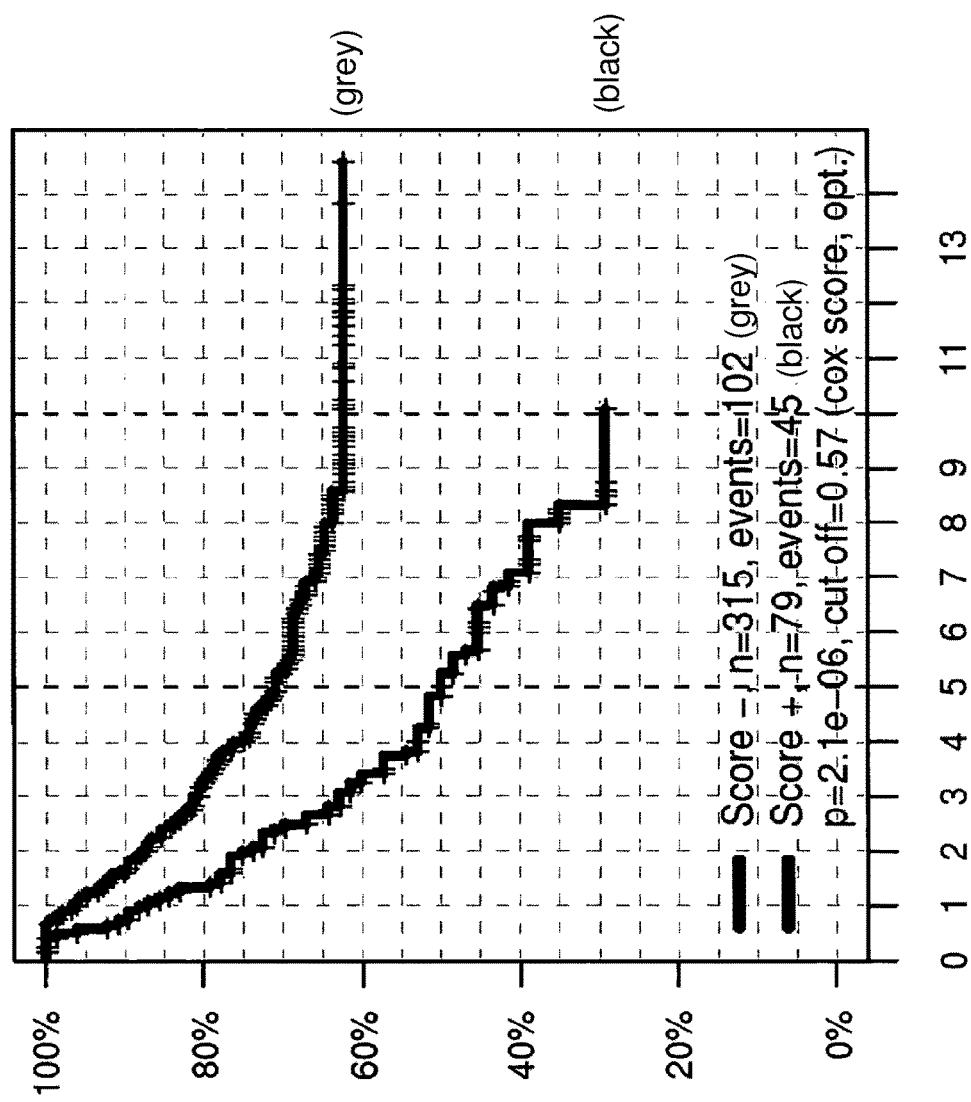
Figure 19:
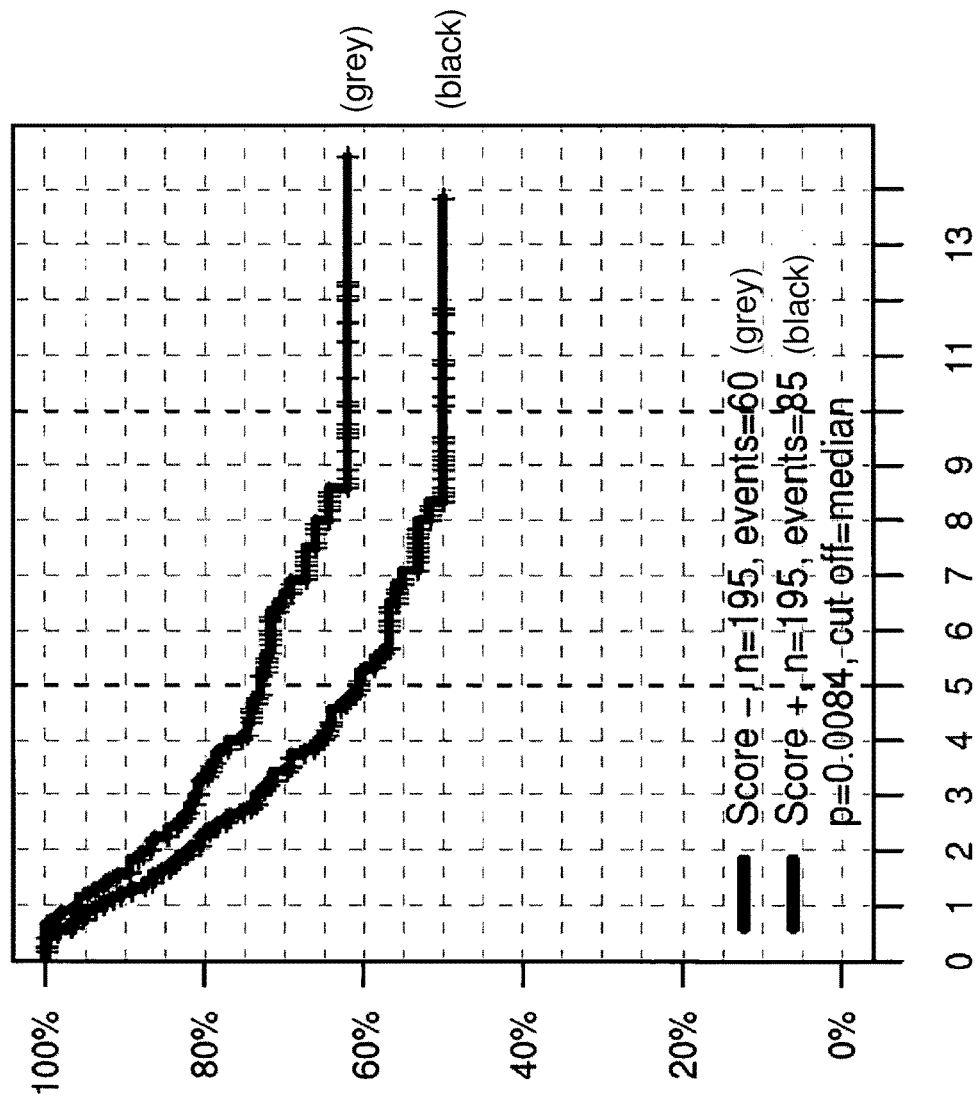
Figure 20:
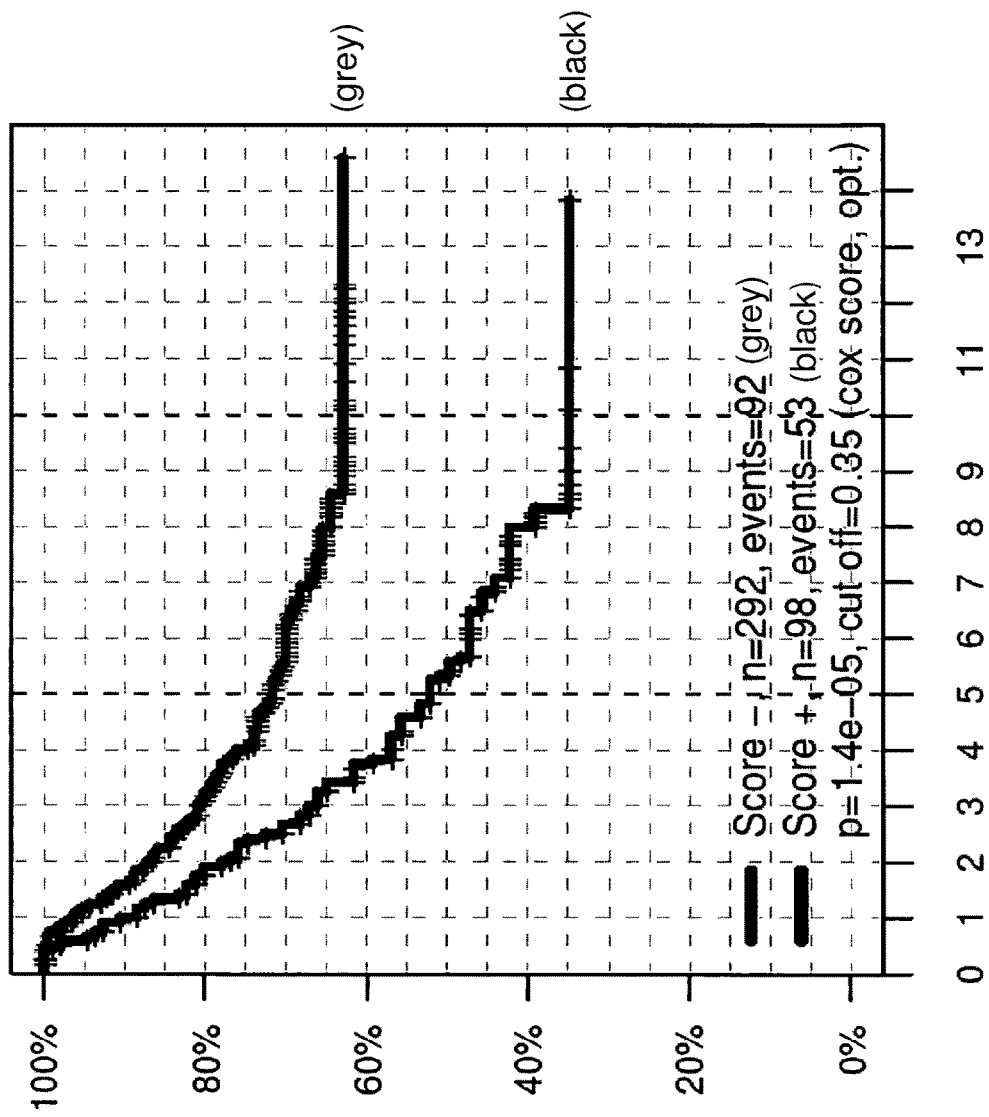
Figure 21:
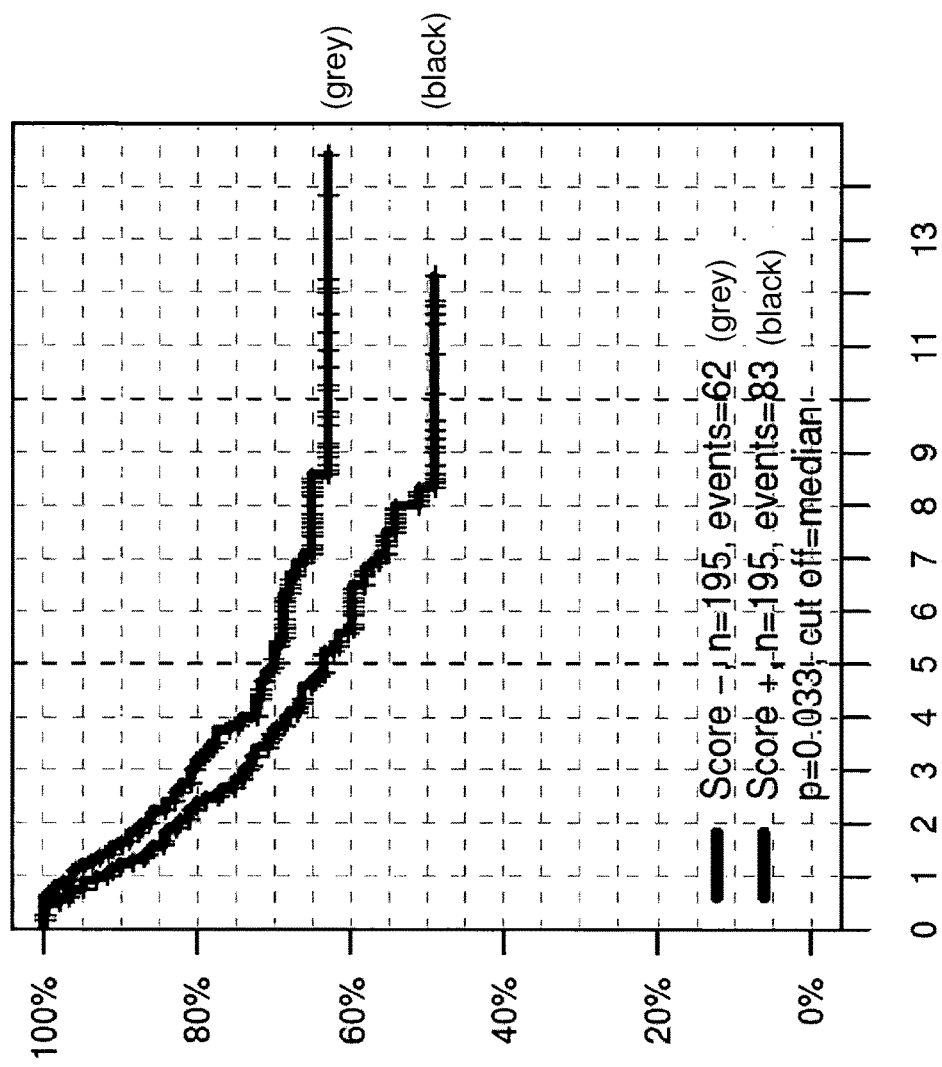
Figure 22:
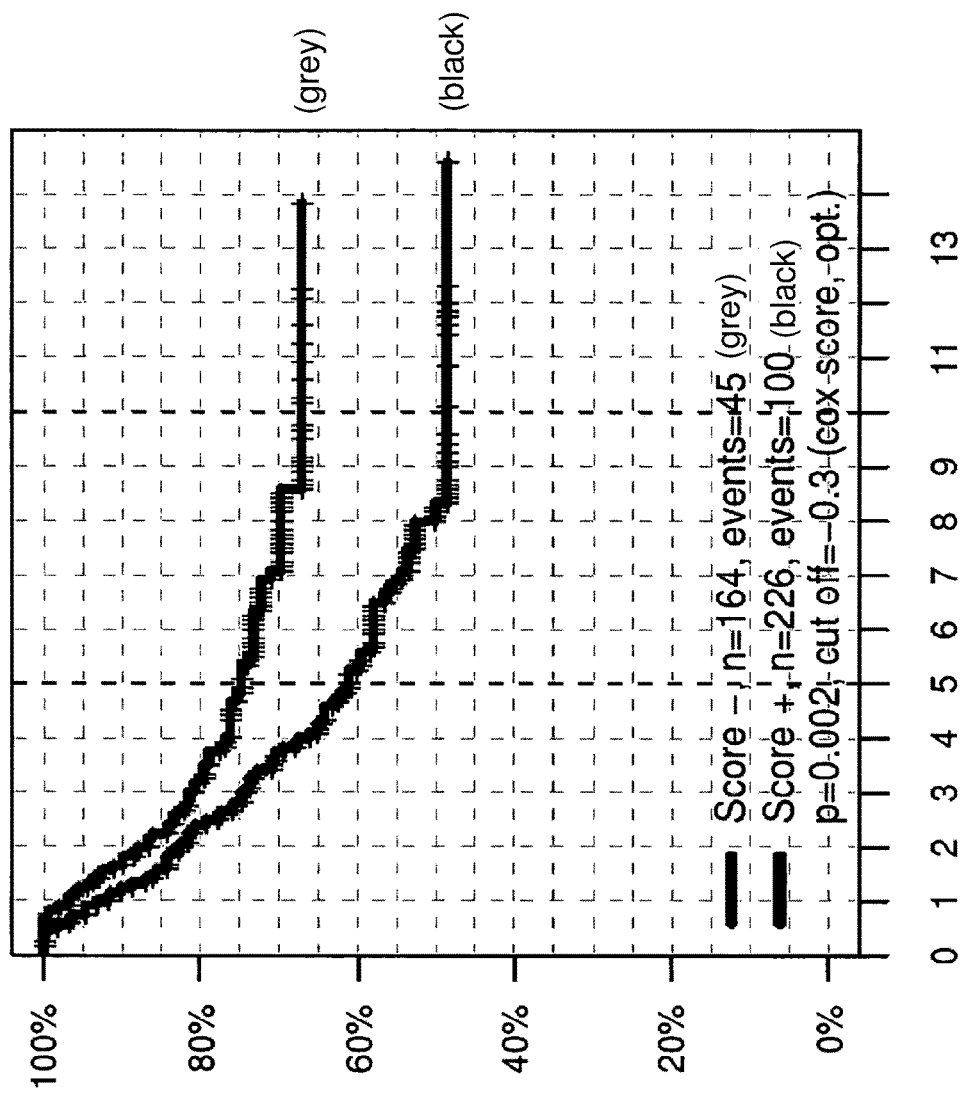
Figure 23:
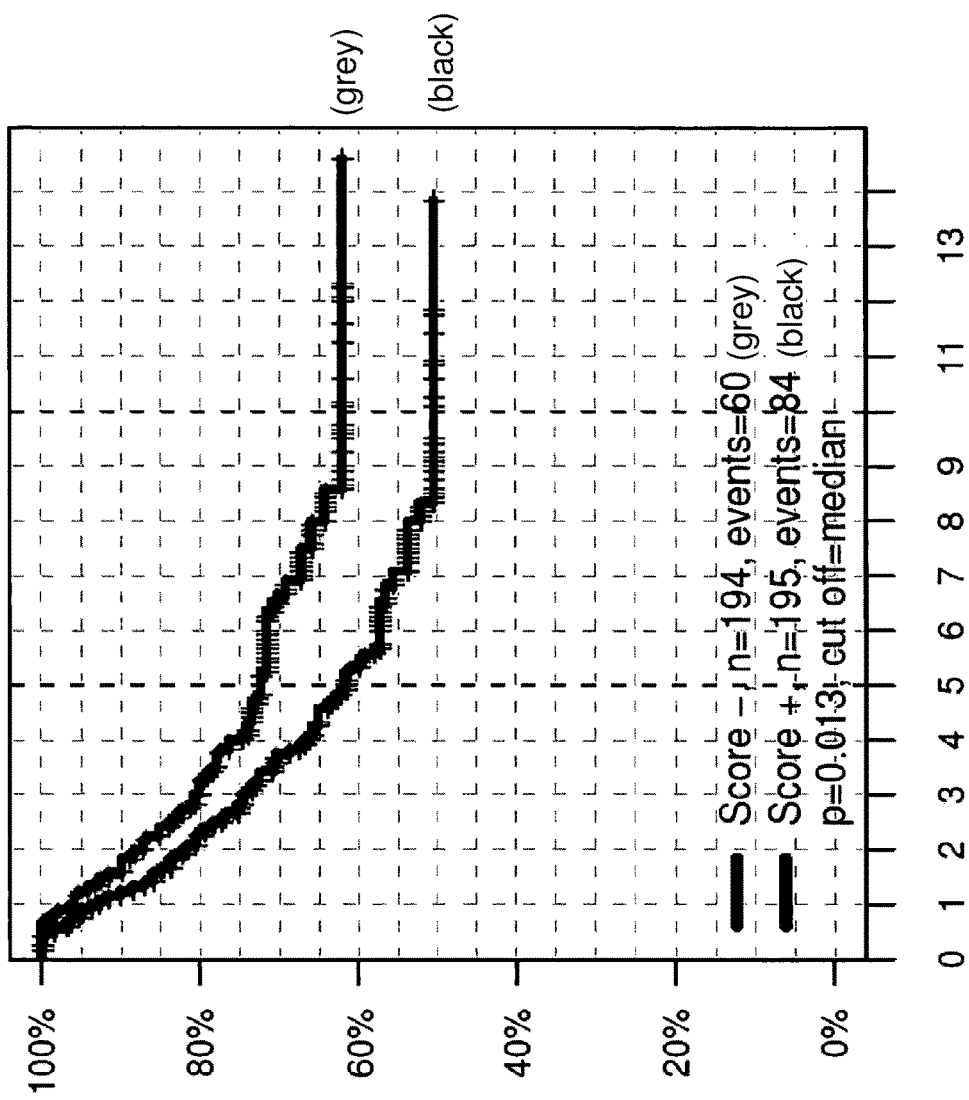
Figure 24:
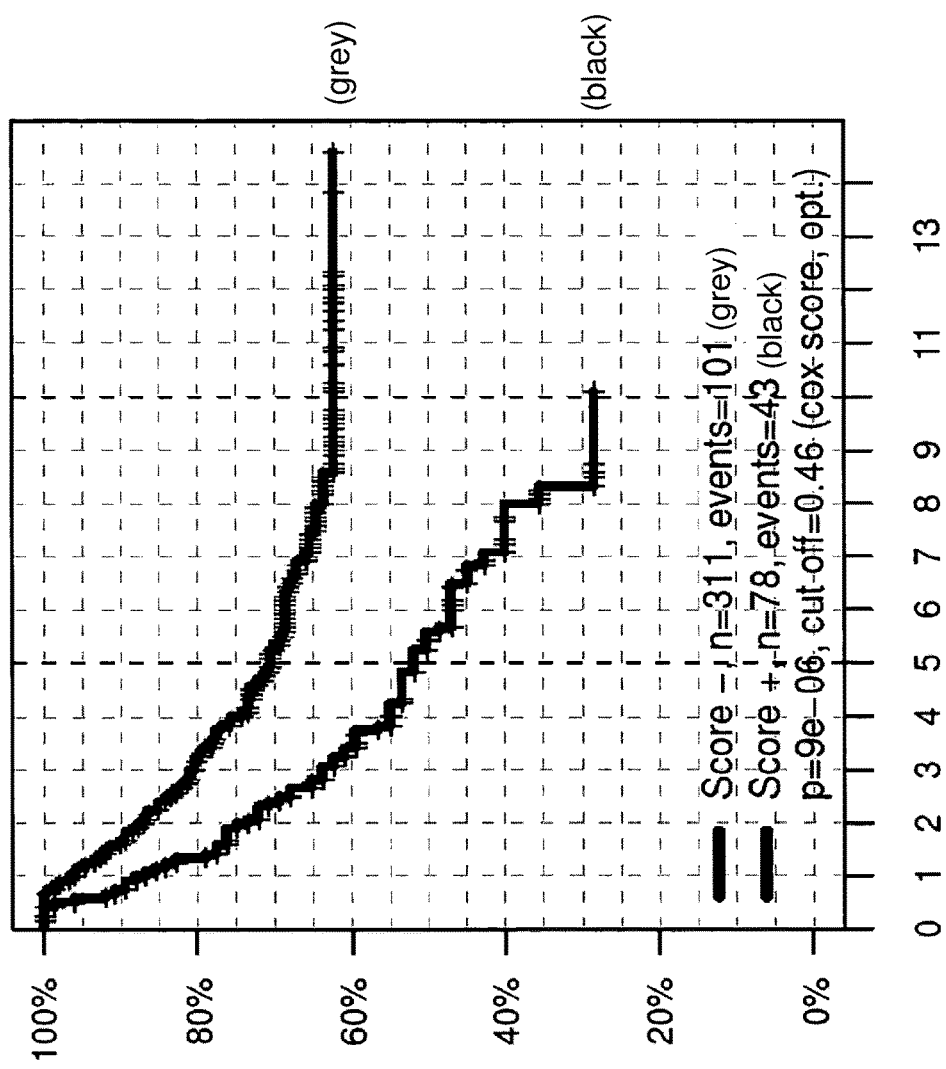
Figure 25:
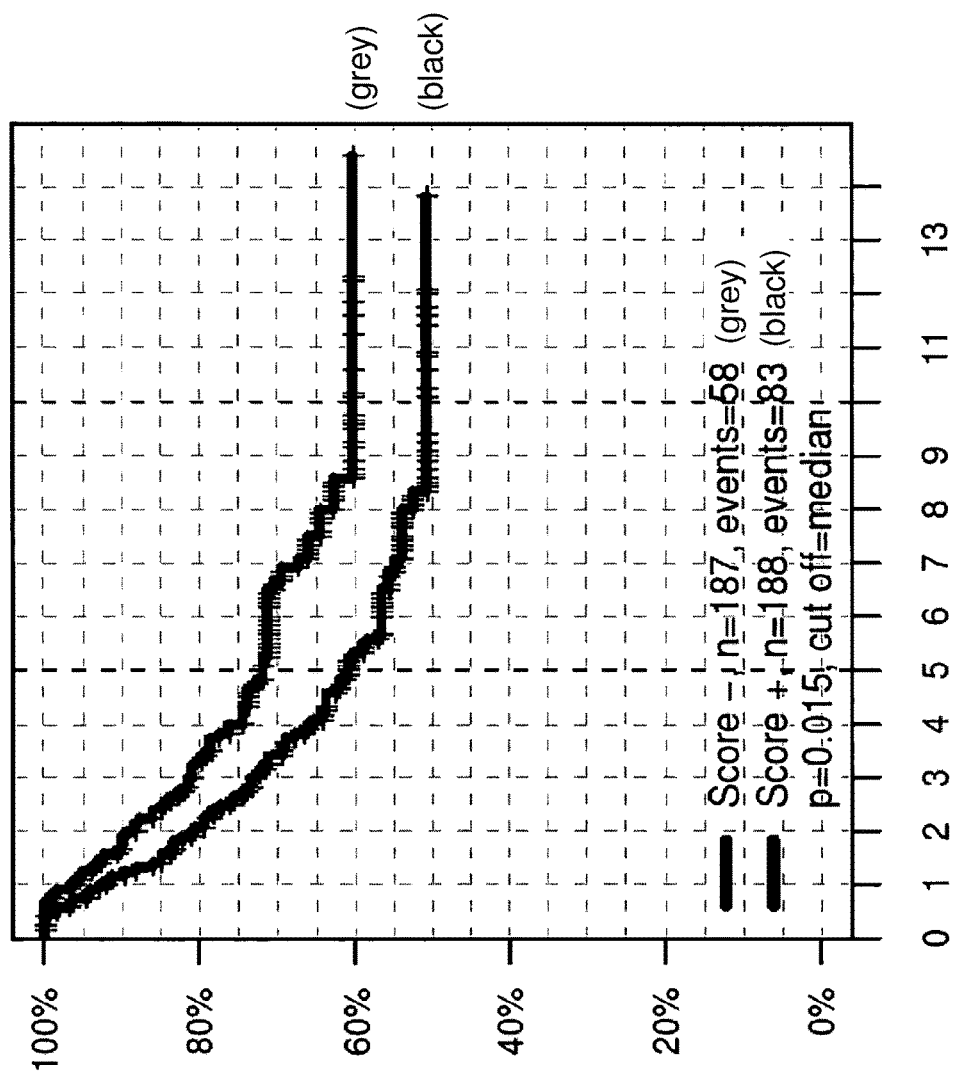
Figure 26:
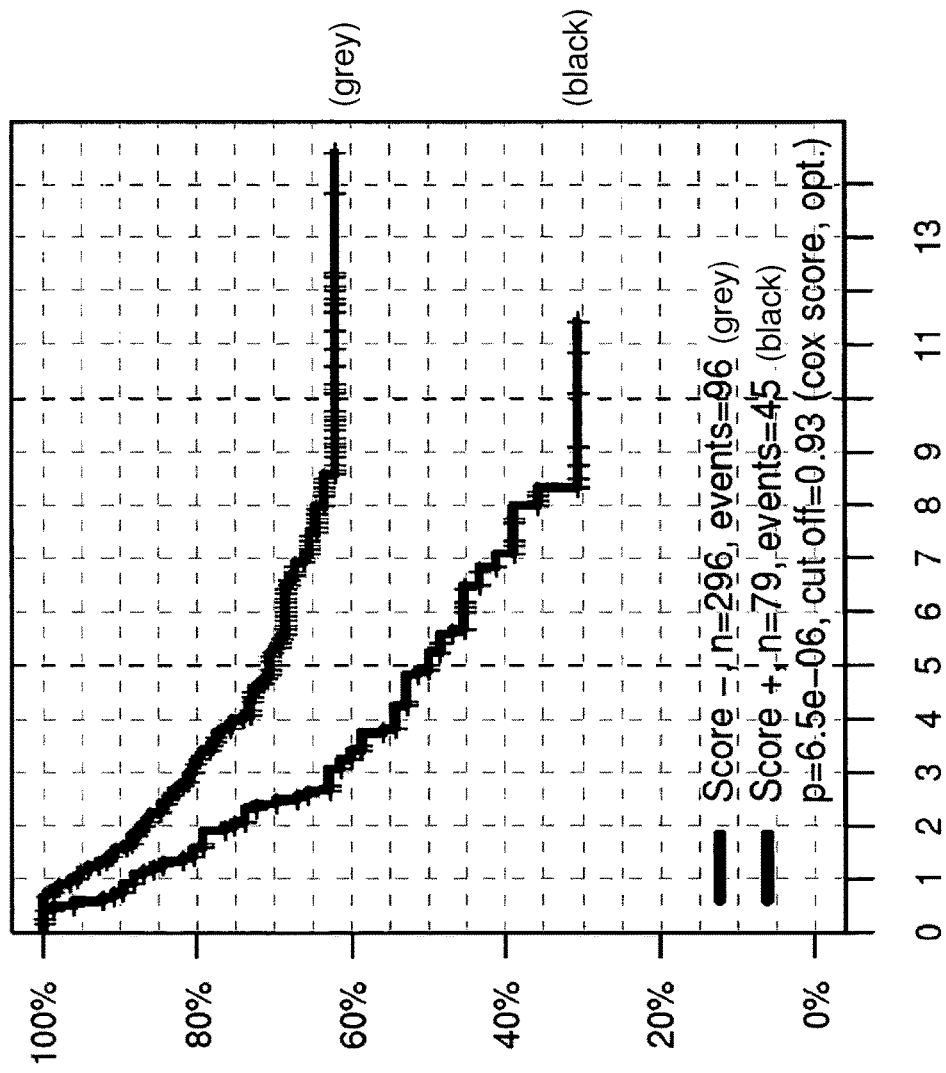
Figure 27:
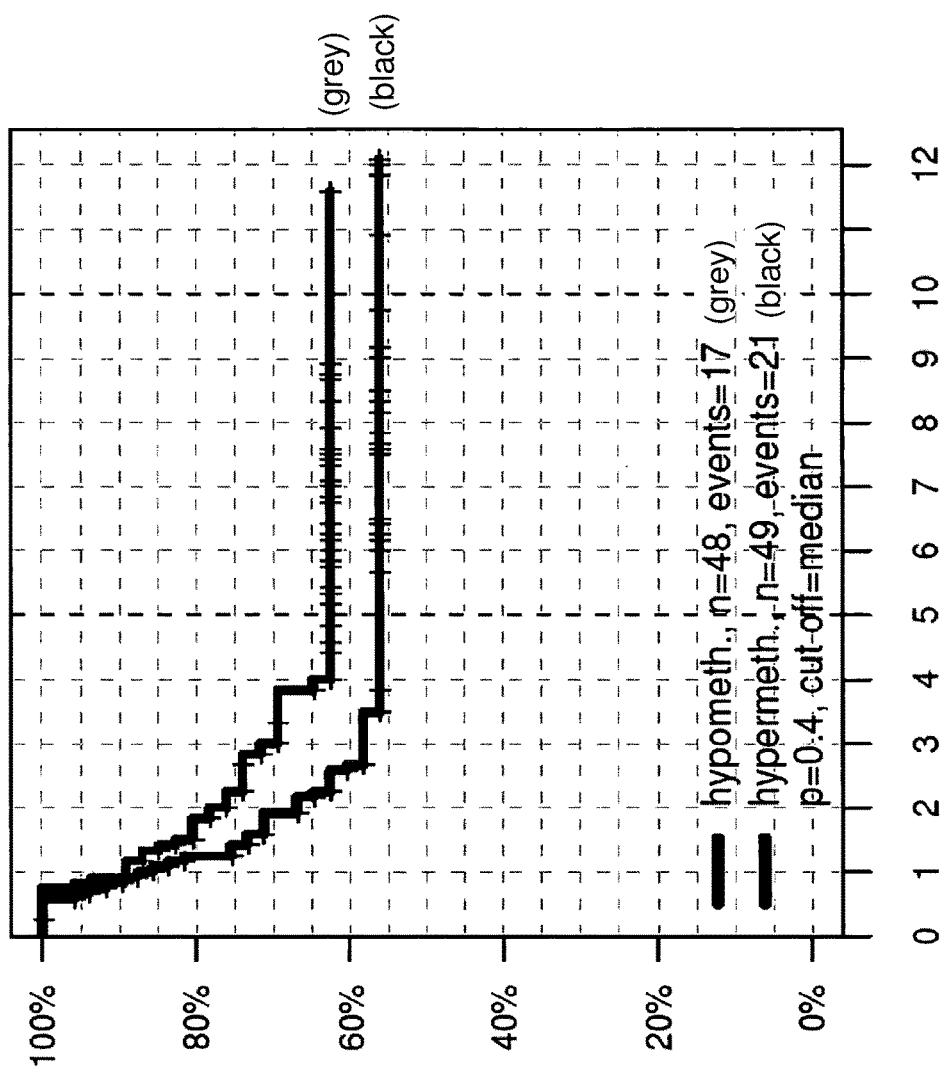
Figure 28:
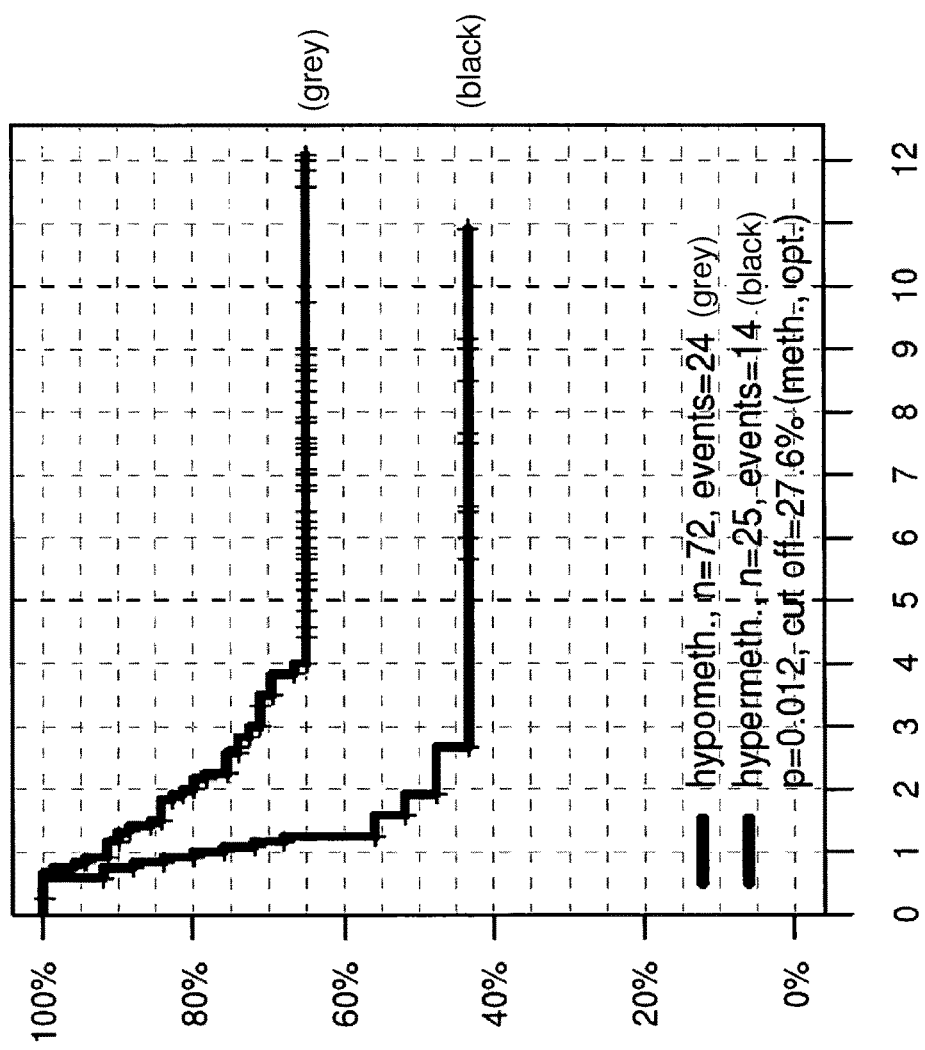
Figure 29:
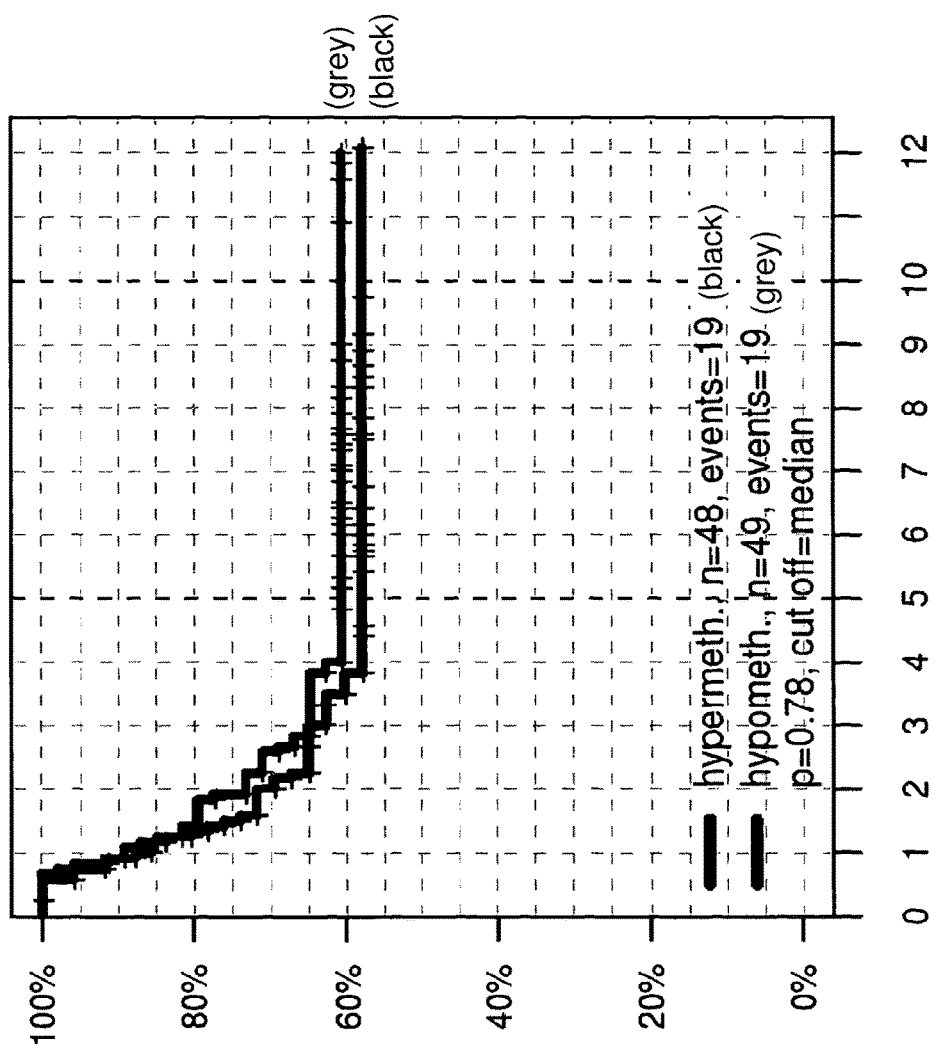
Figure 30:
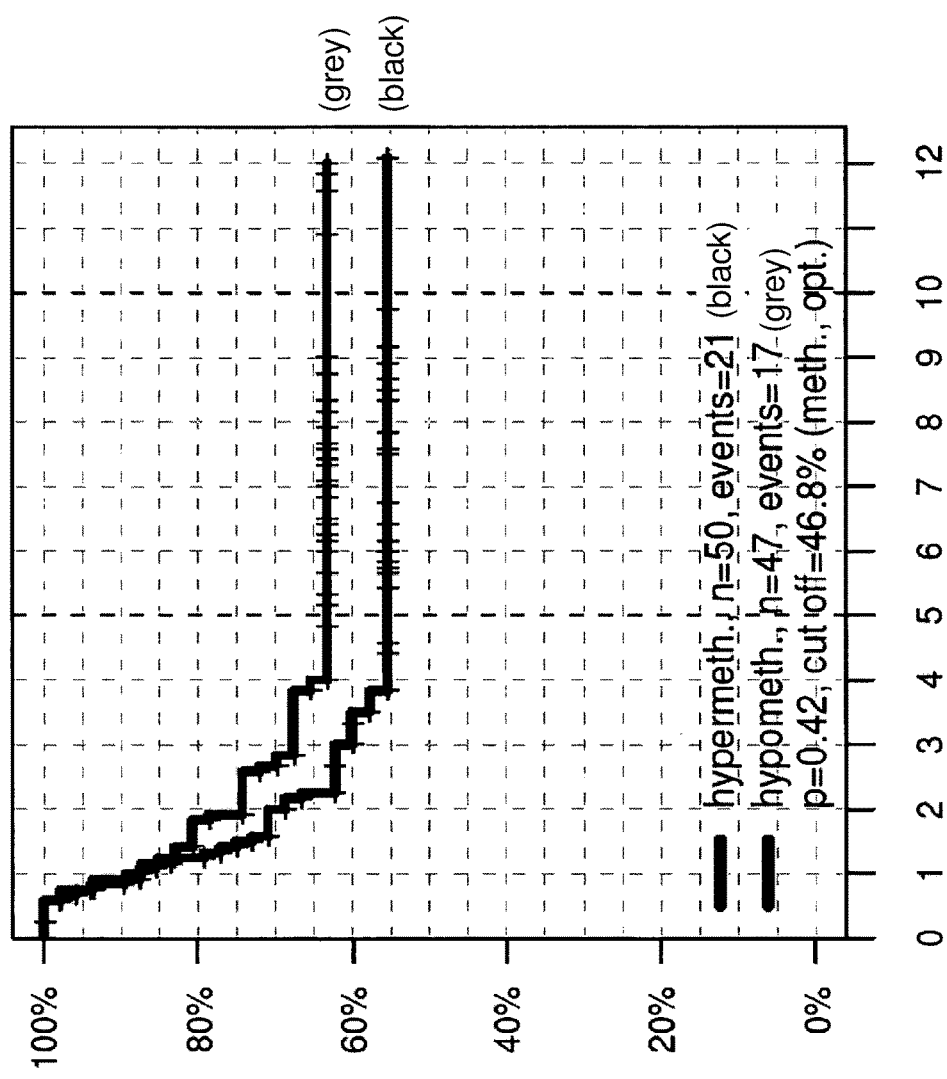
Figure 31:
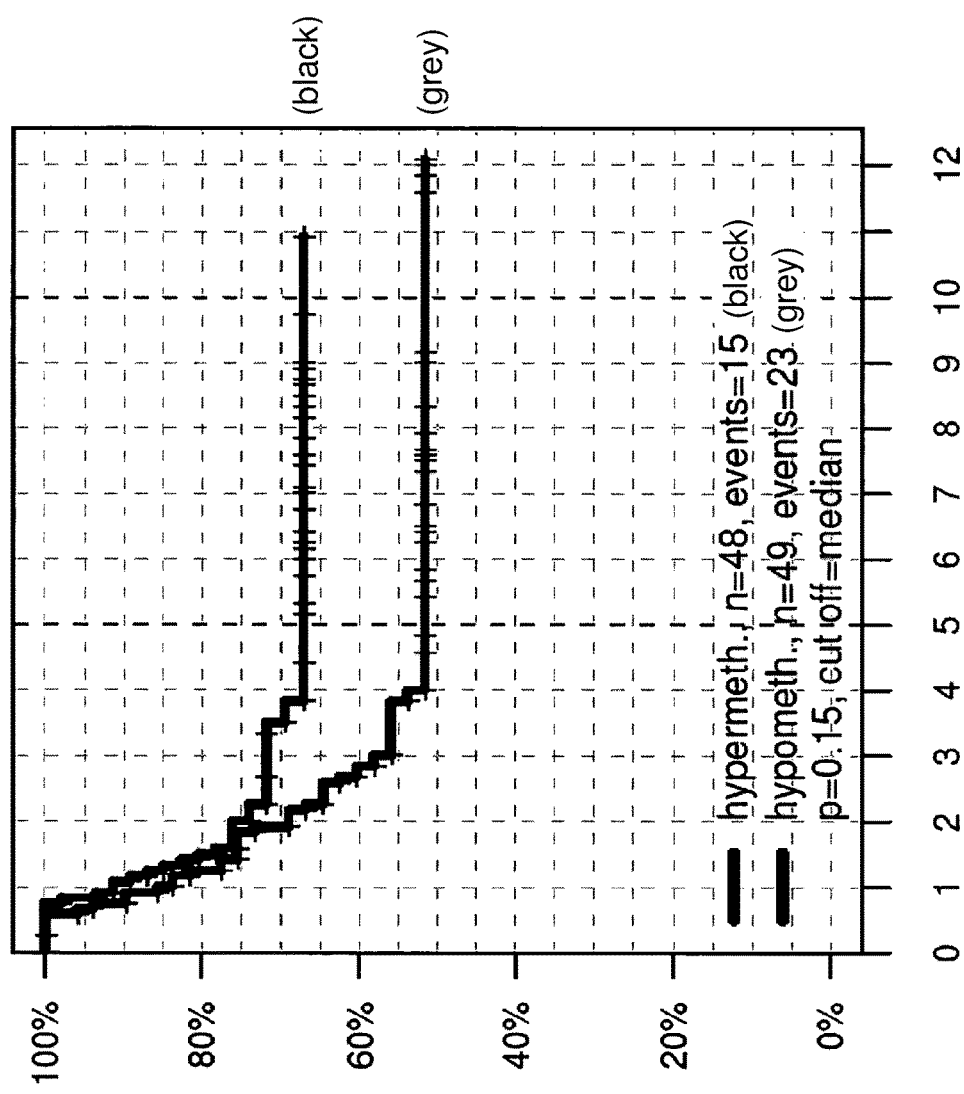
Figure 32:
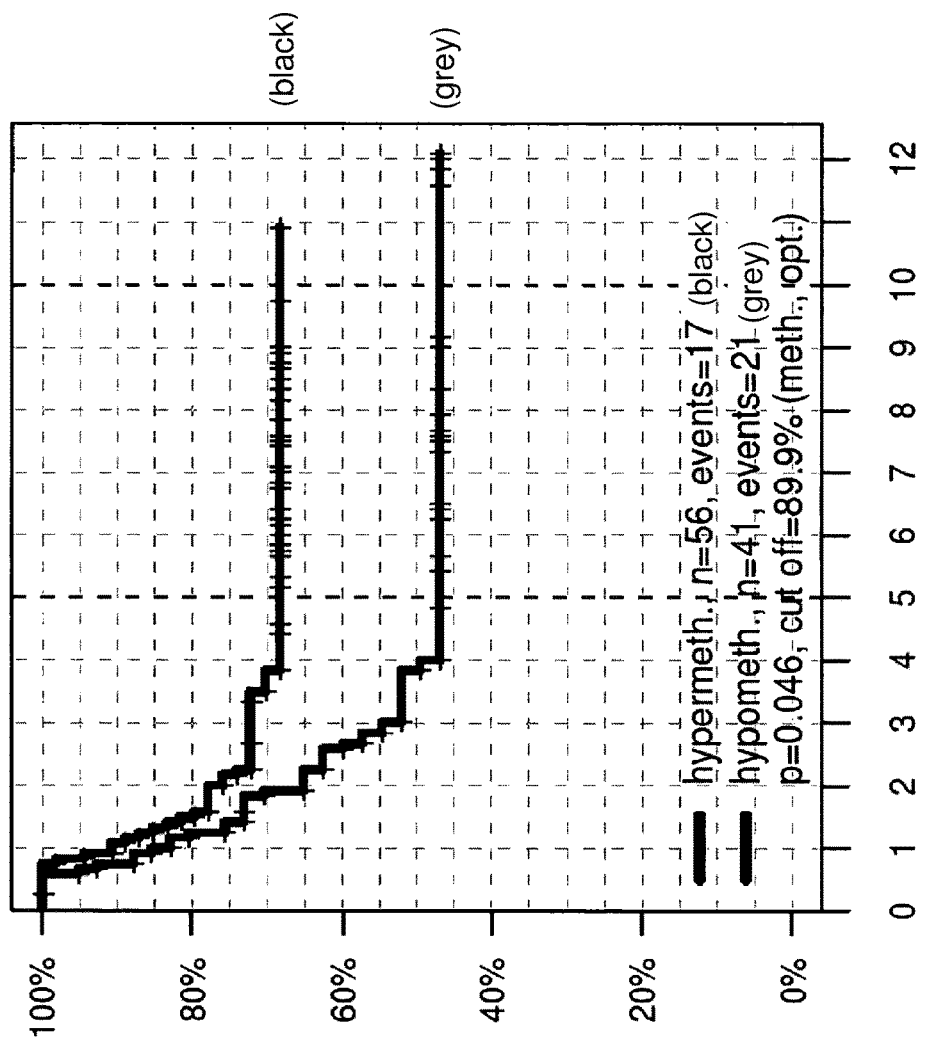
Figure 33:
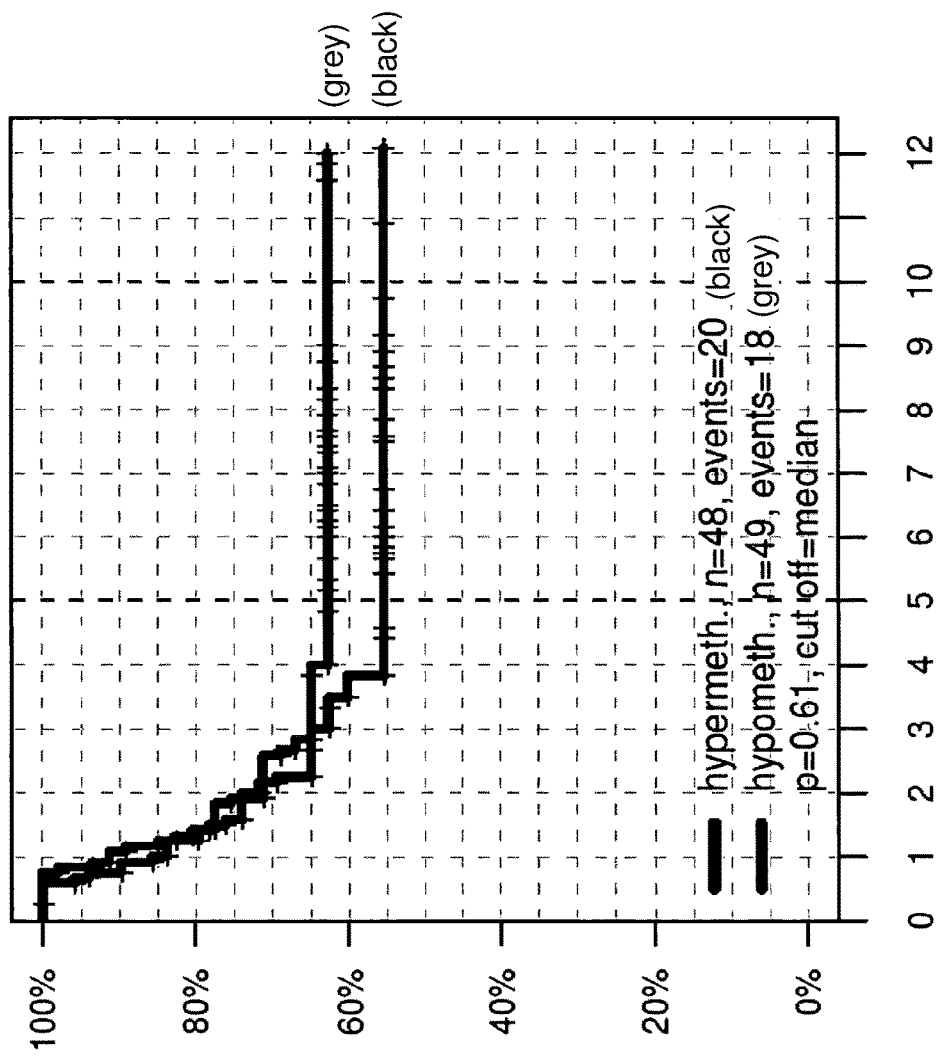
Figure 34:
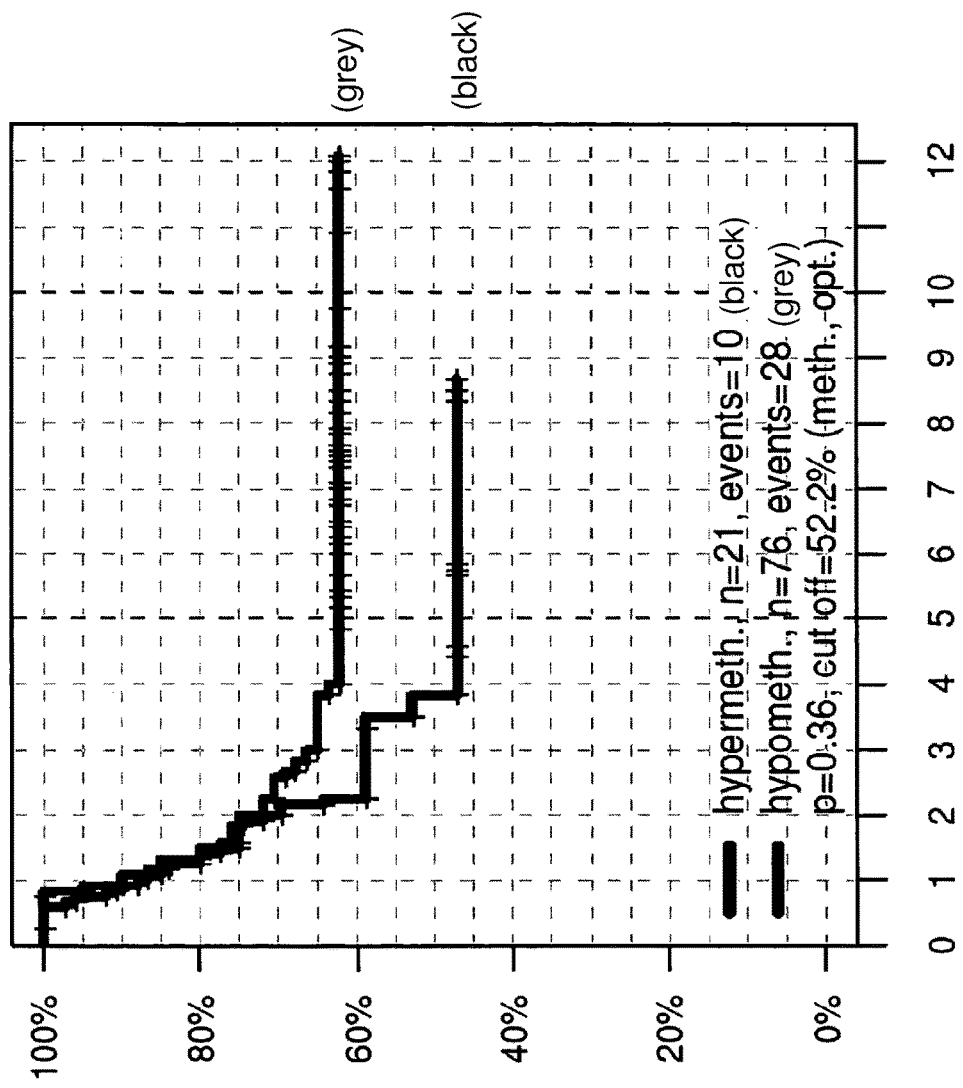
Figure 35:
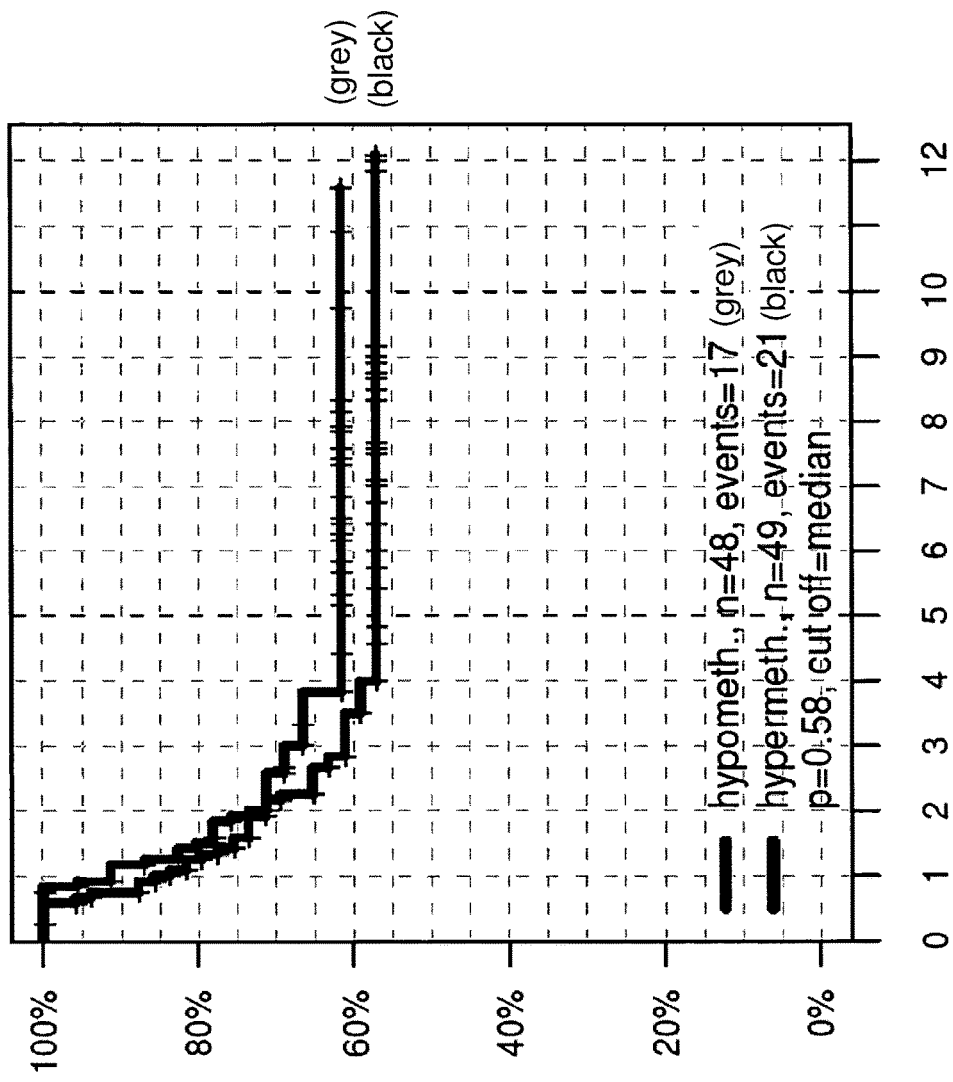
Figure 36:
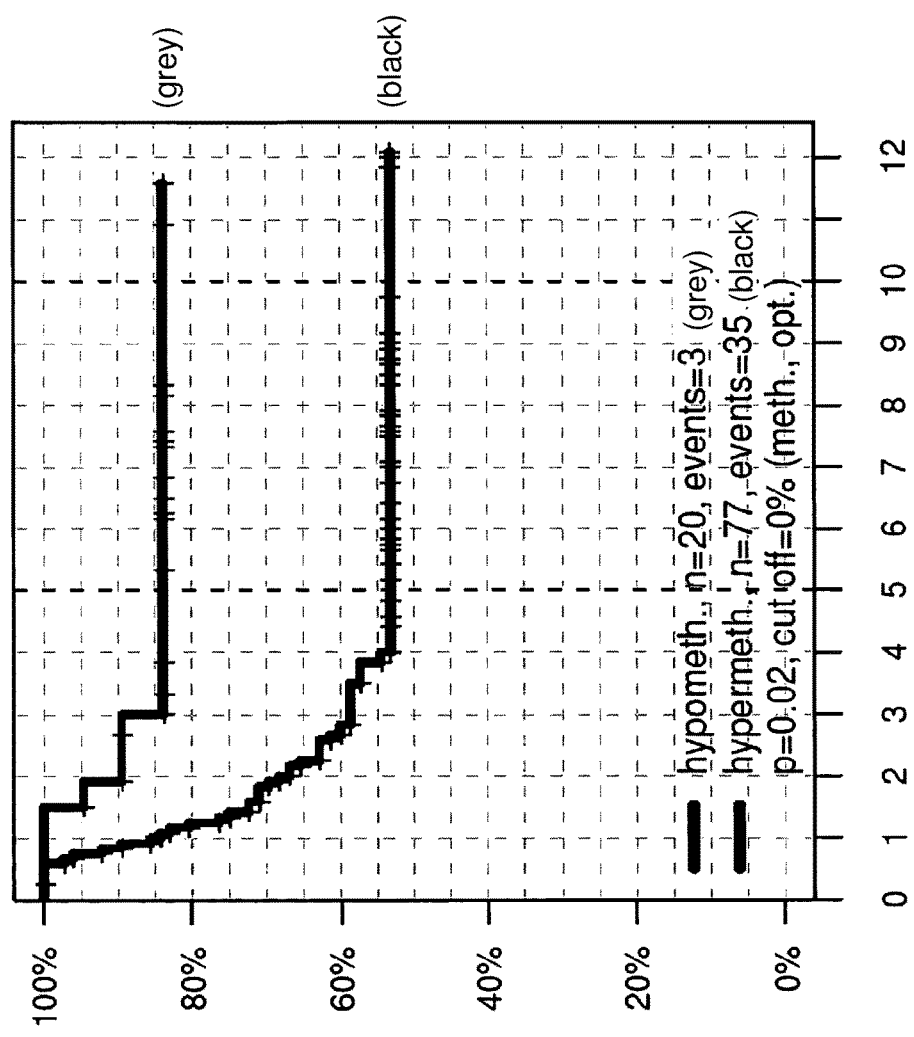
Figure 37:
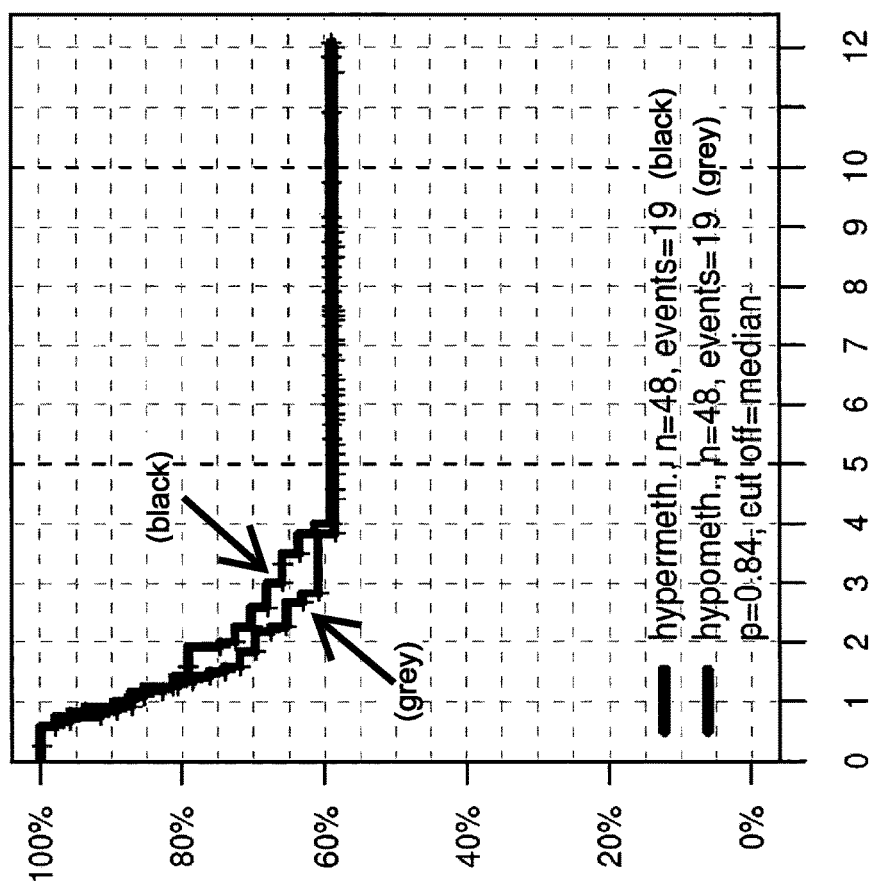
Figure 38:
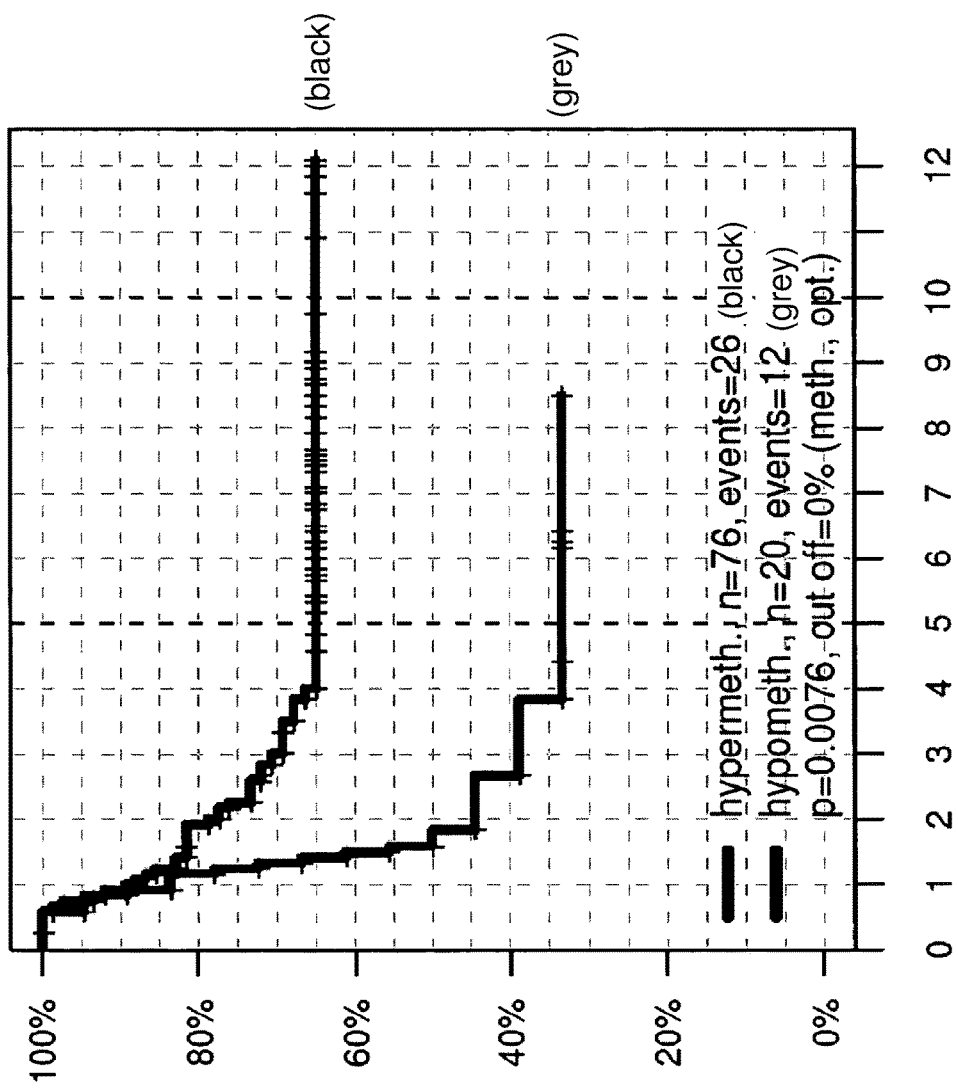
Figure 39:
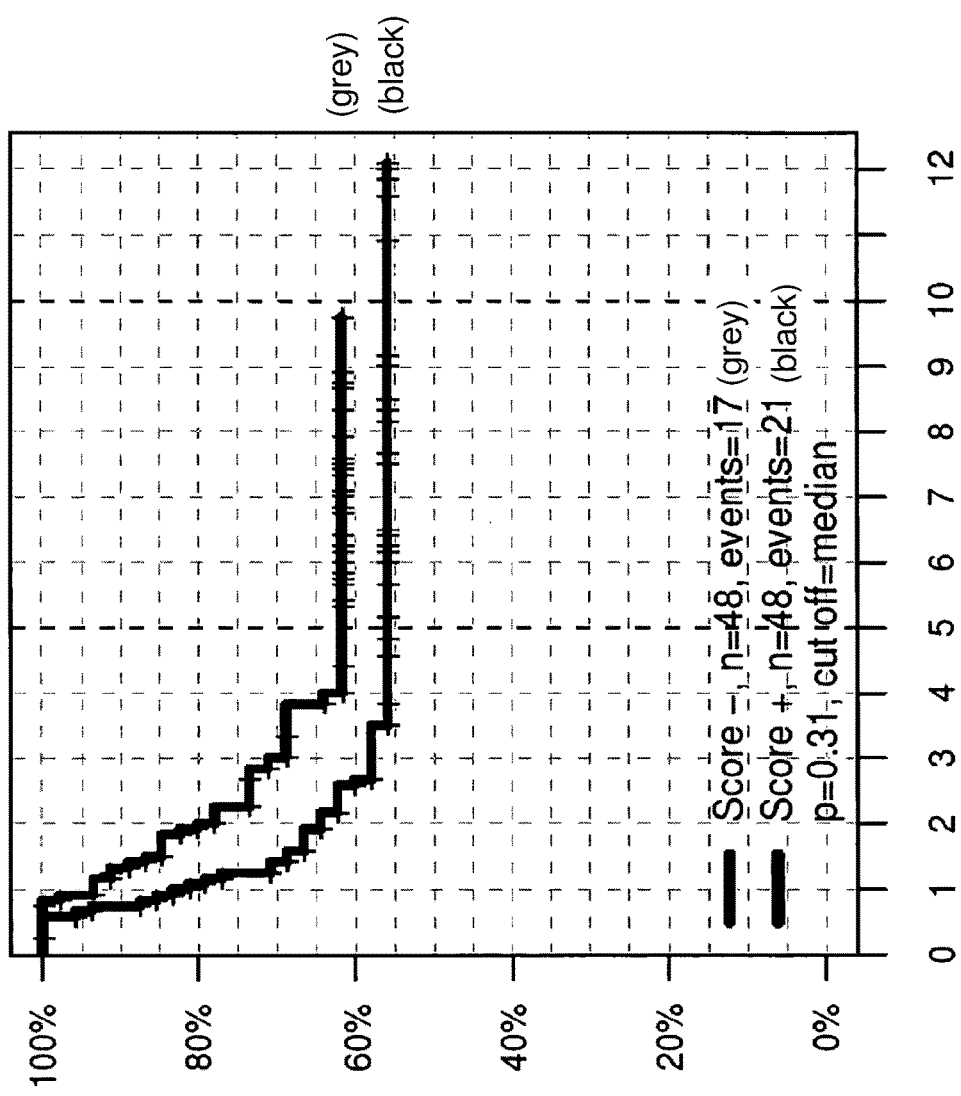
Figure 40:
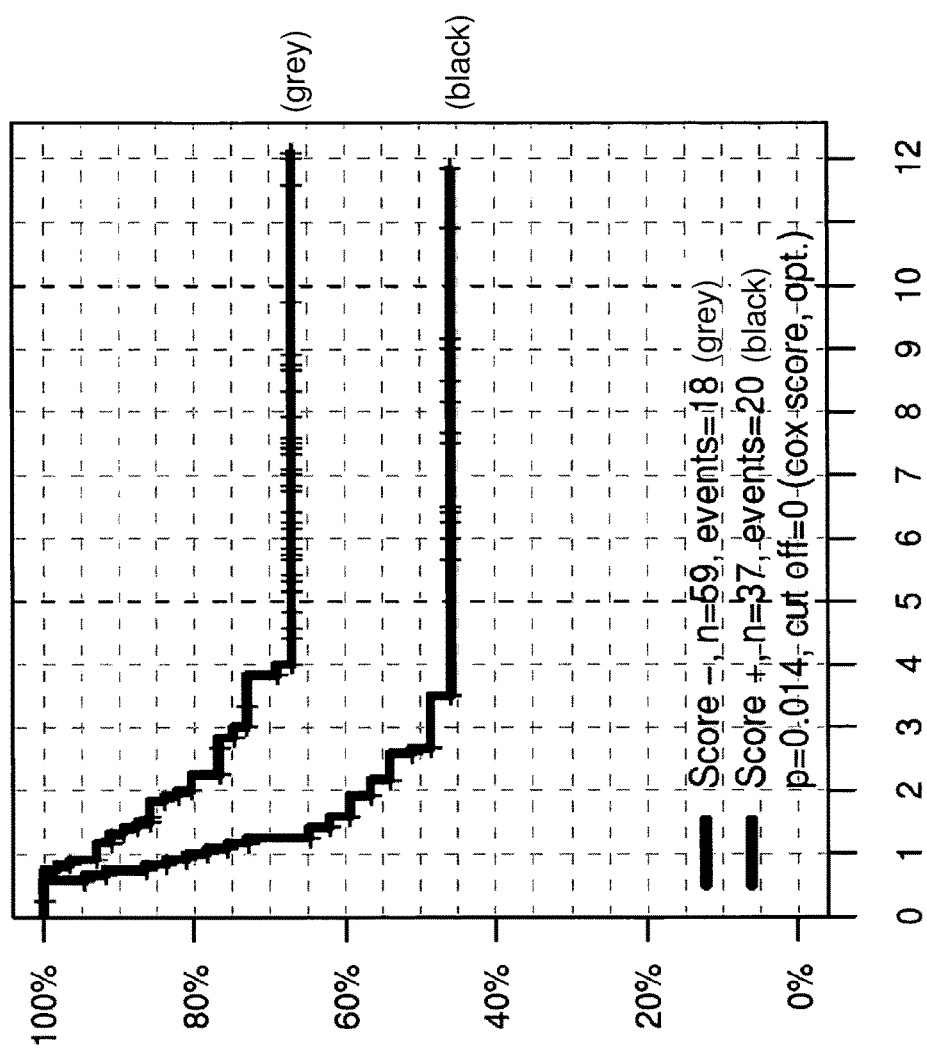
Figure 41:
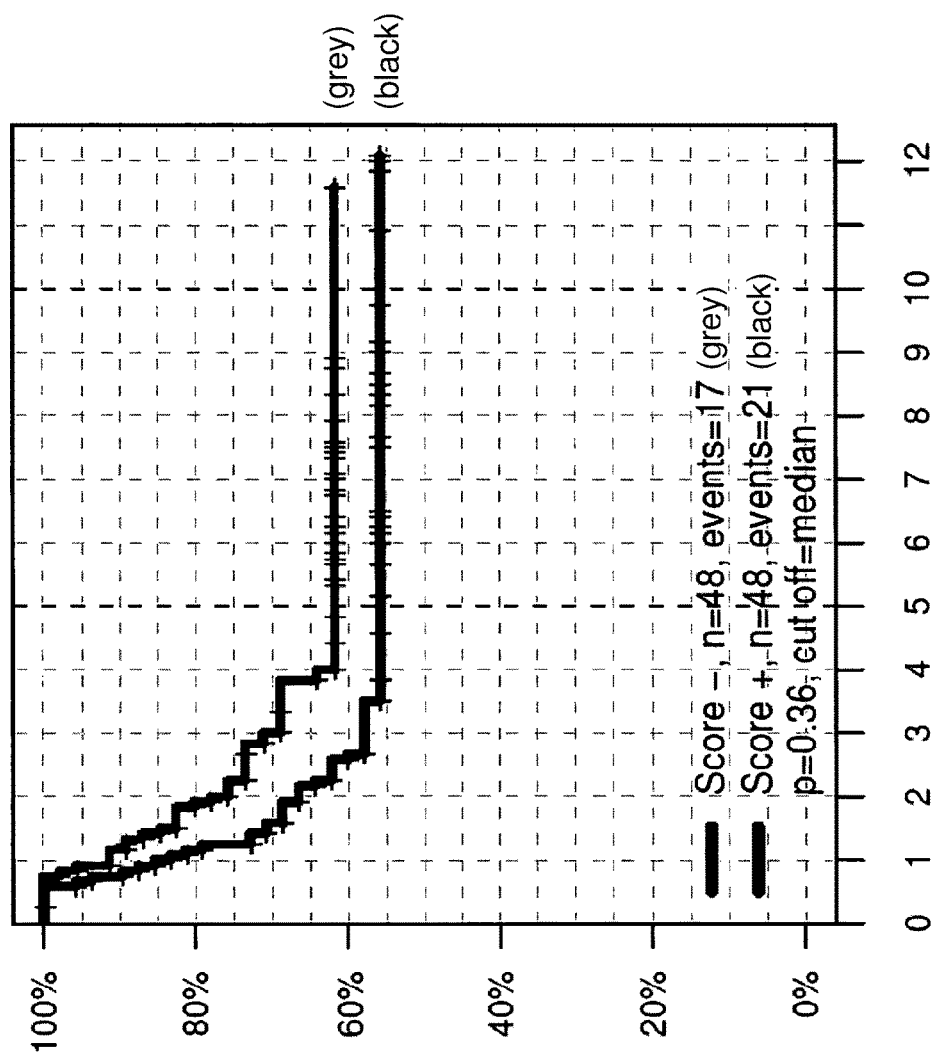
Figure 42:
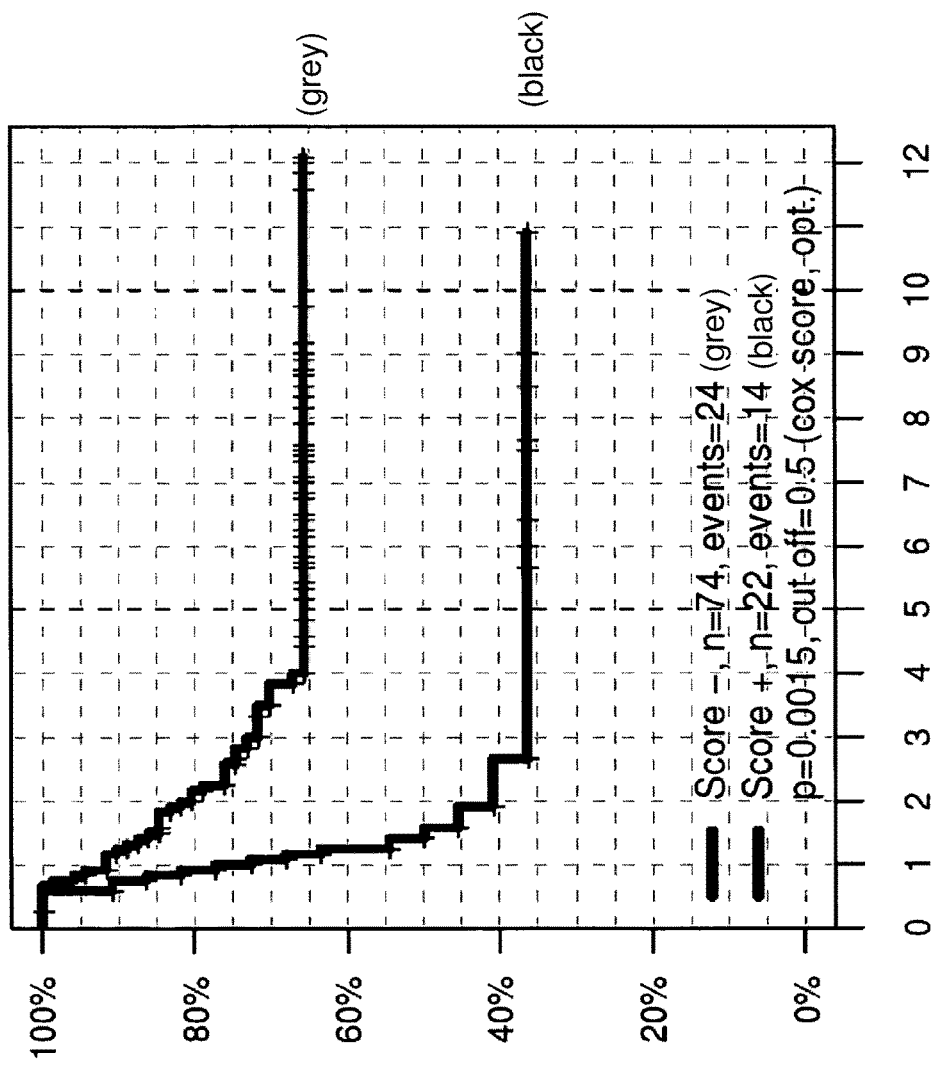
Figure 43:
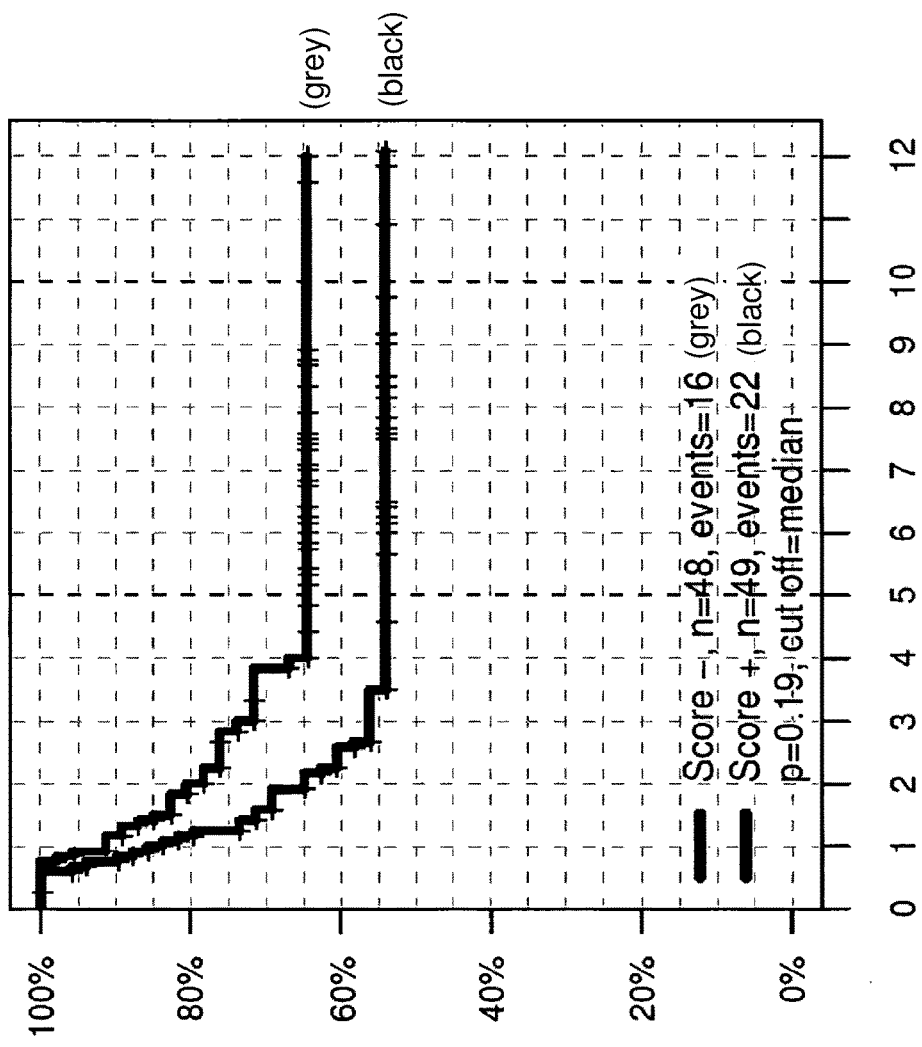
Figure 44:
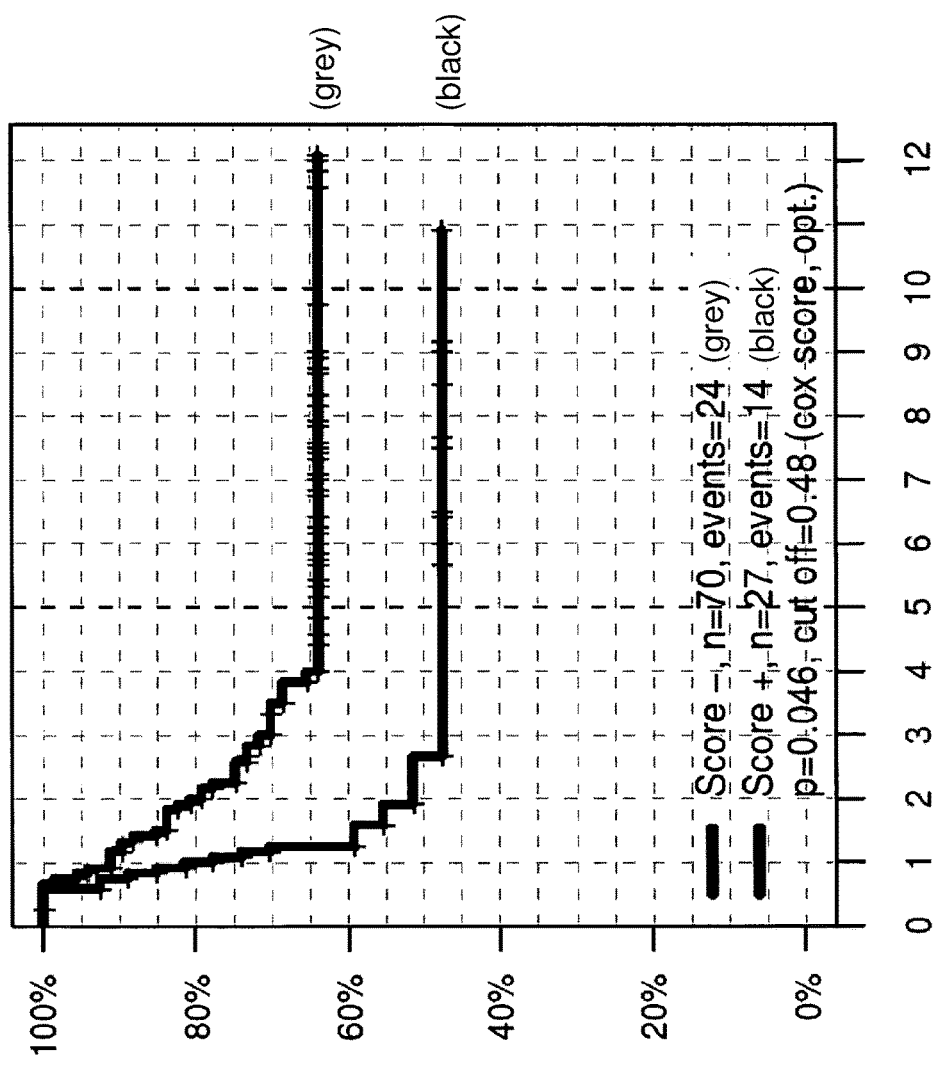
Figure 45:
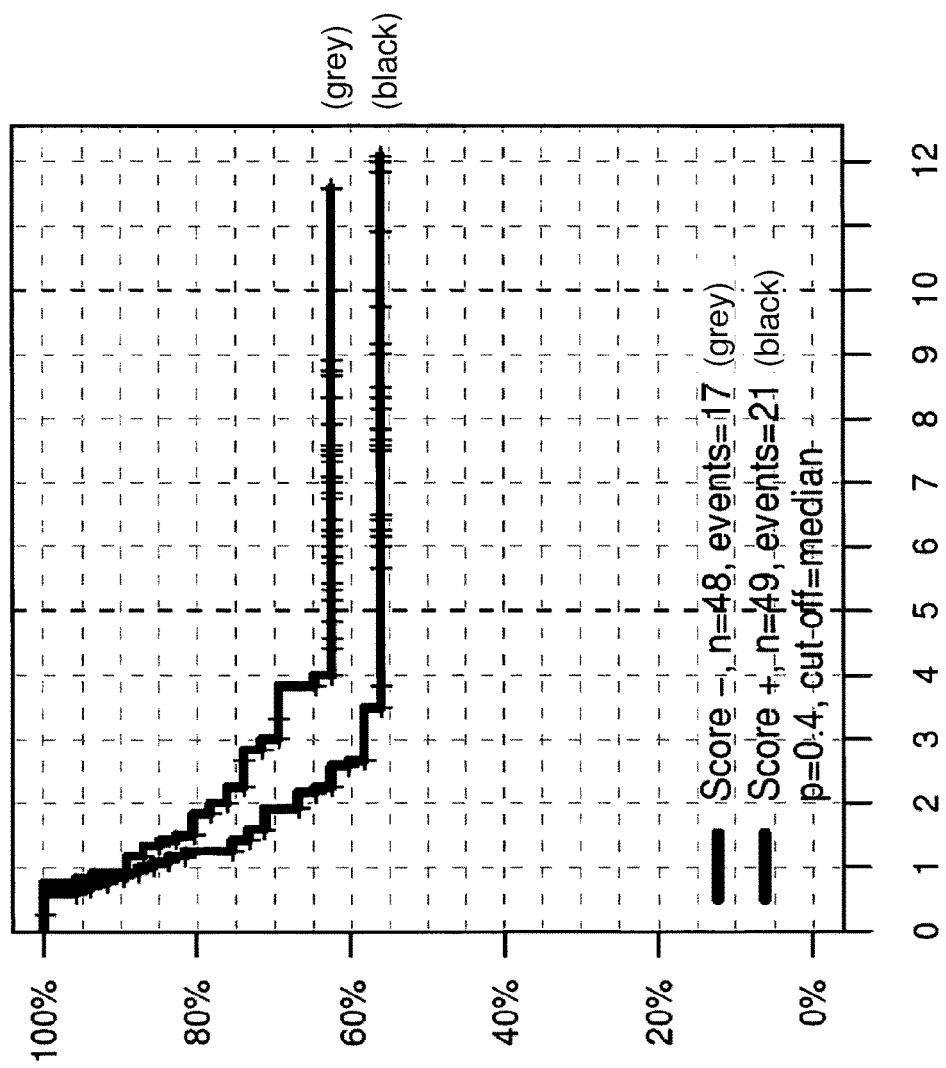
Figure 46:
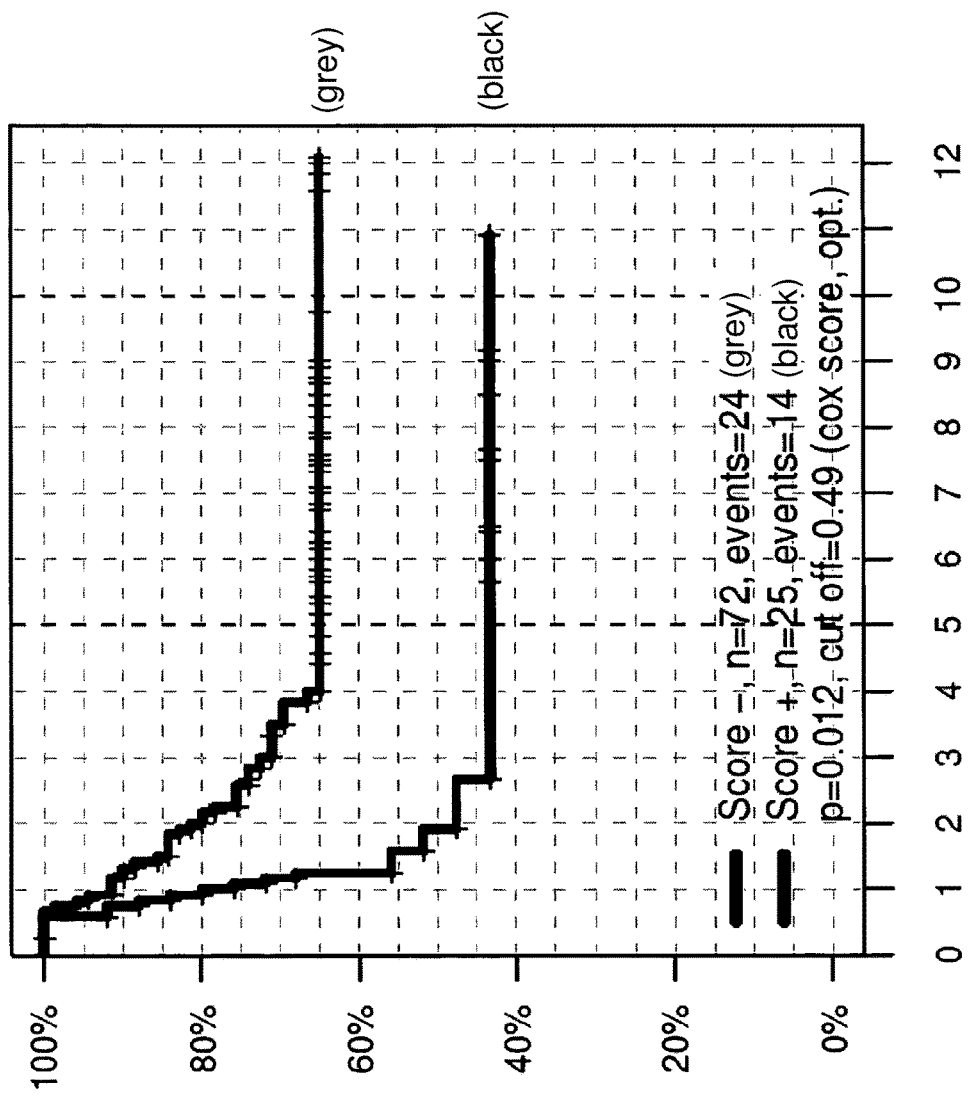
Figure 47:
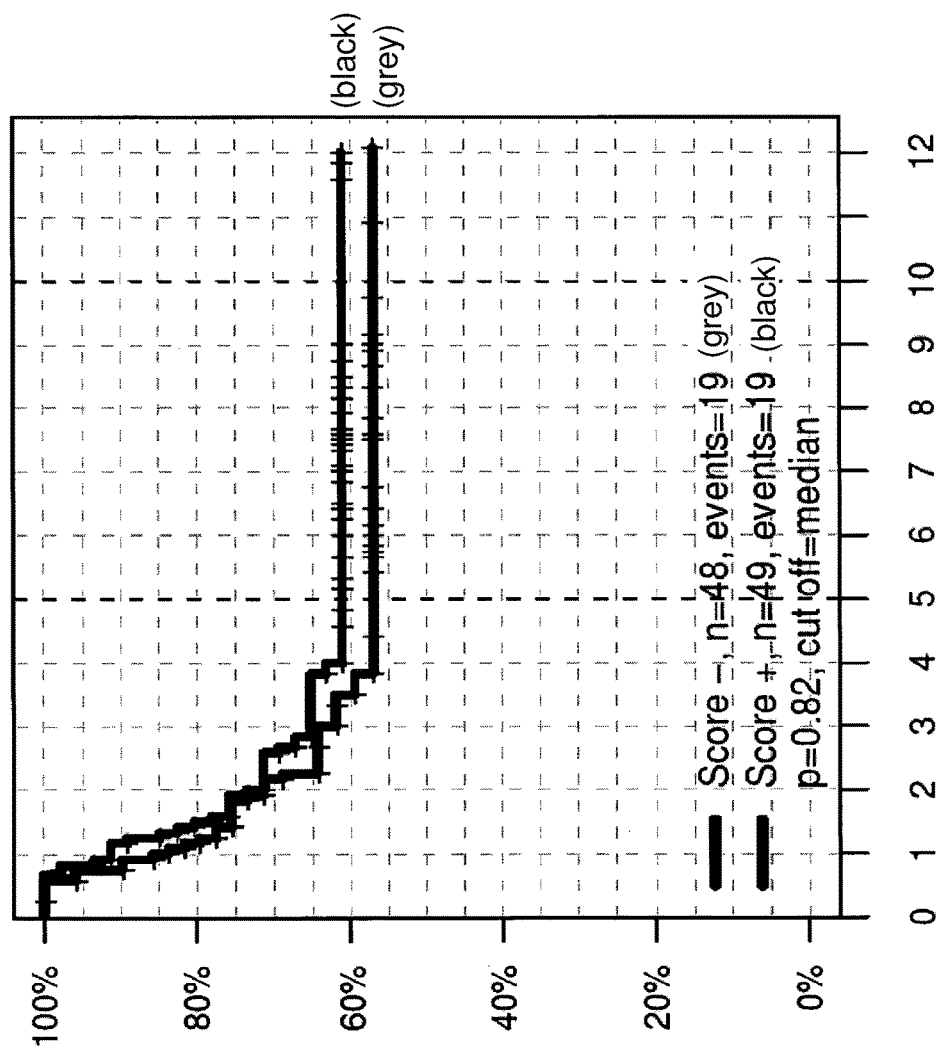
Figure 48:
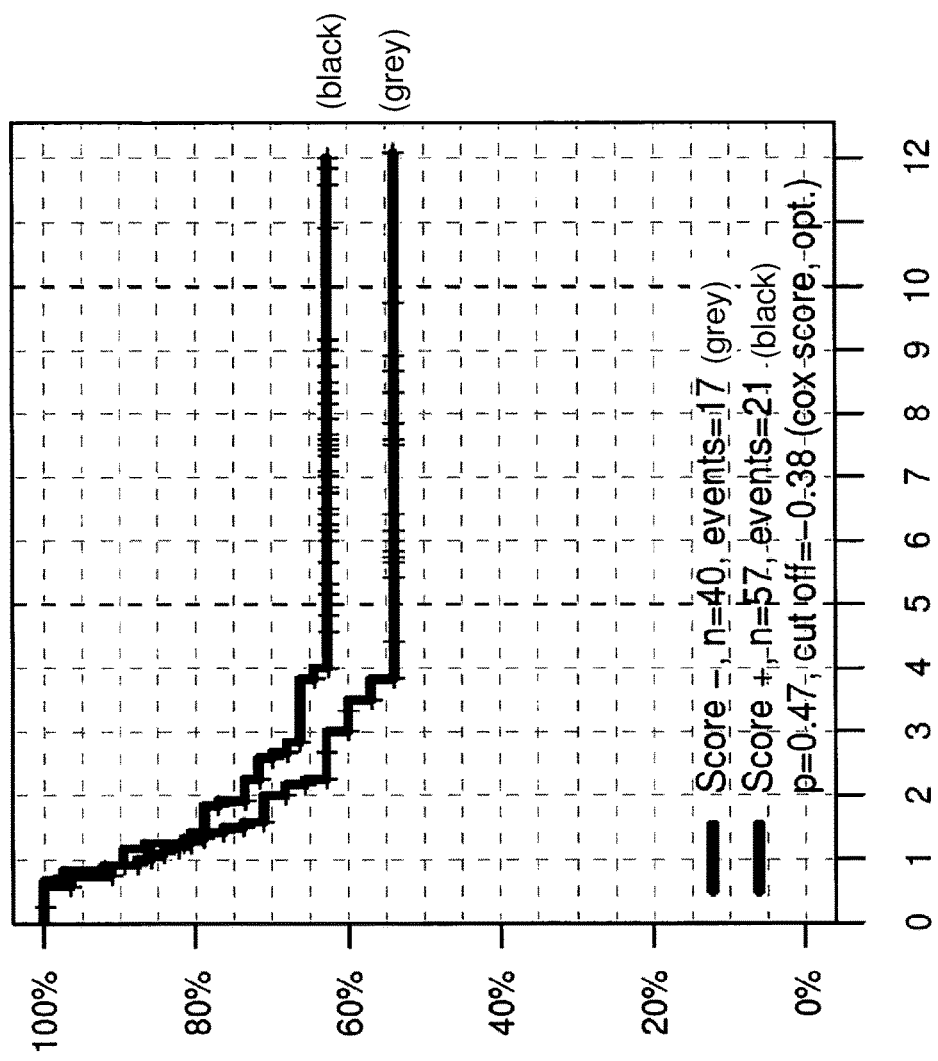
Figure 49:
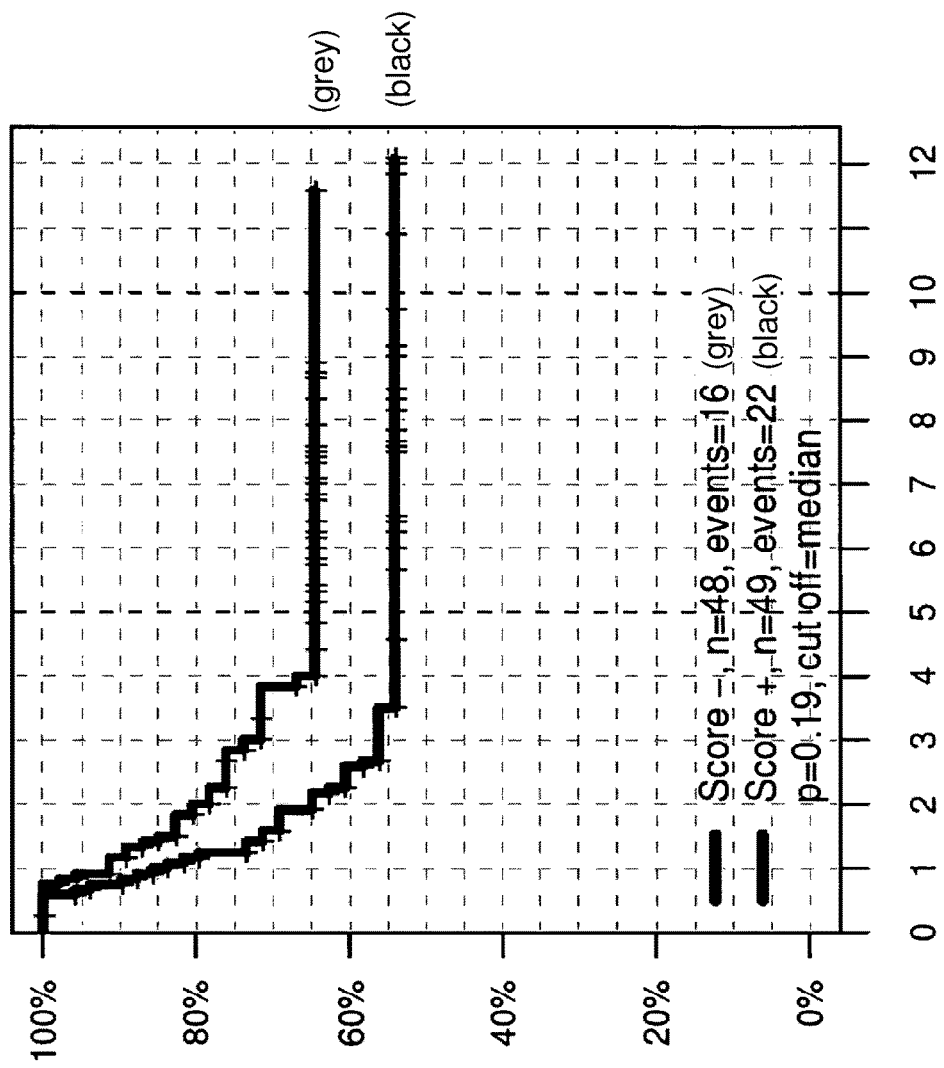
Figure 50:
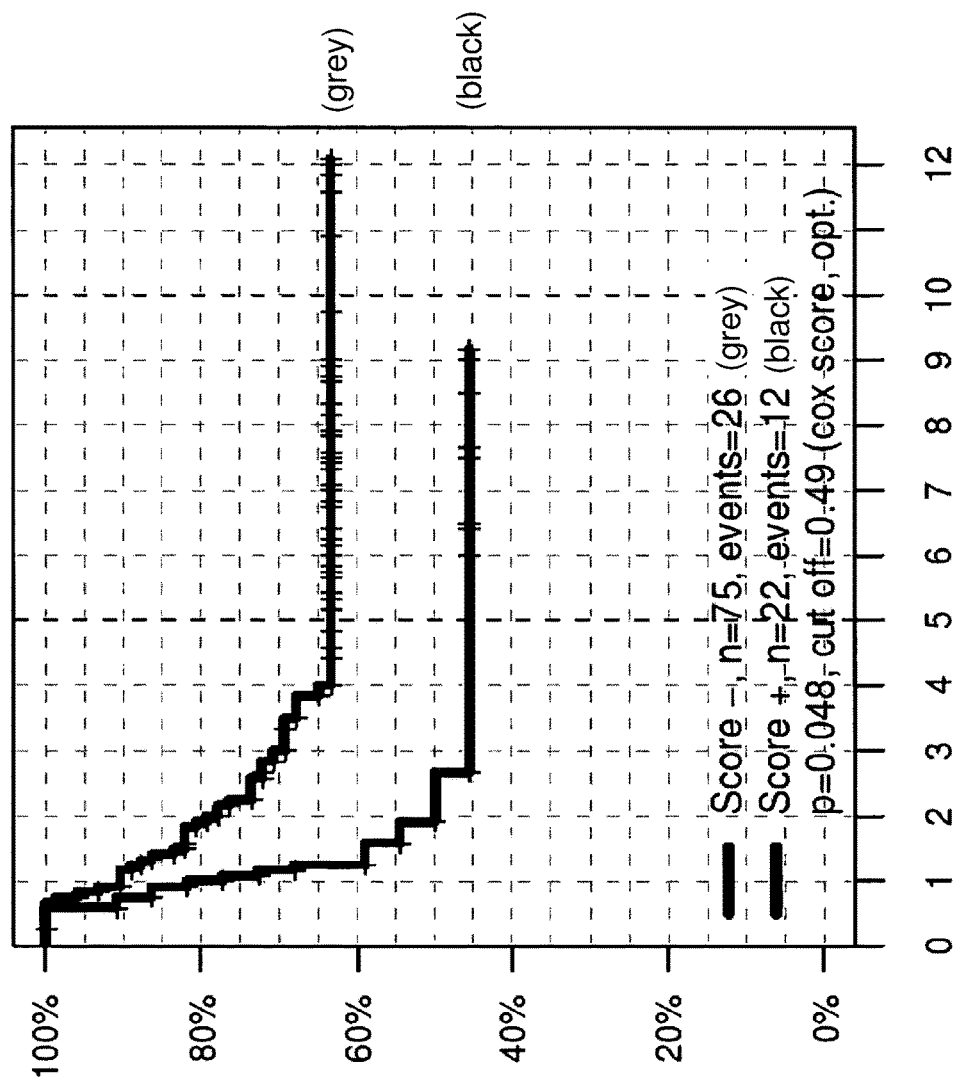
Figure 51:
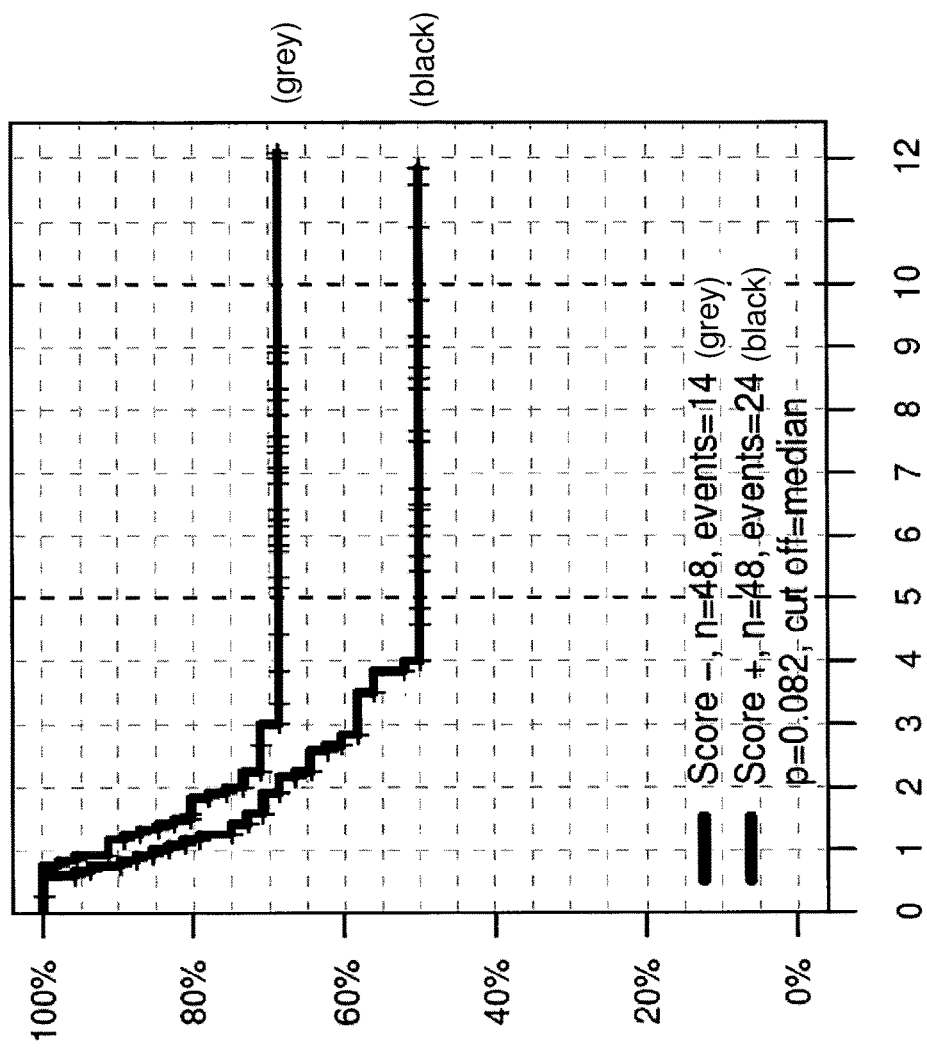
Figure 52:
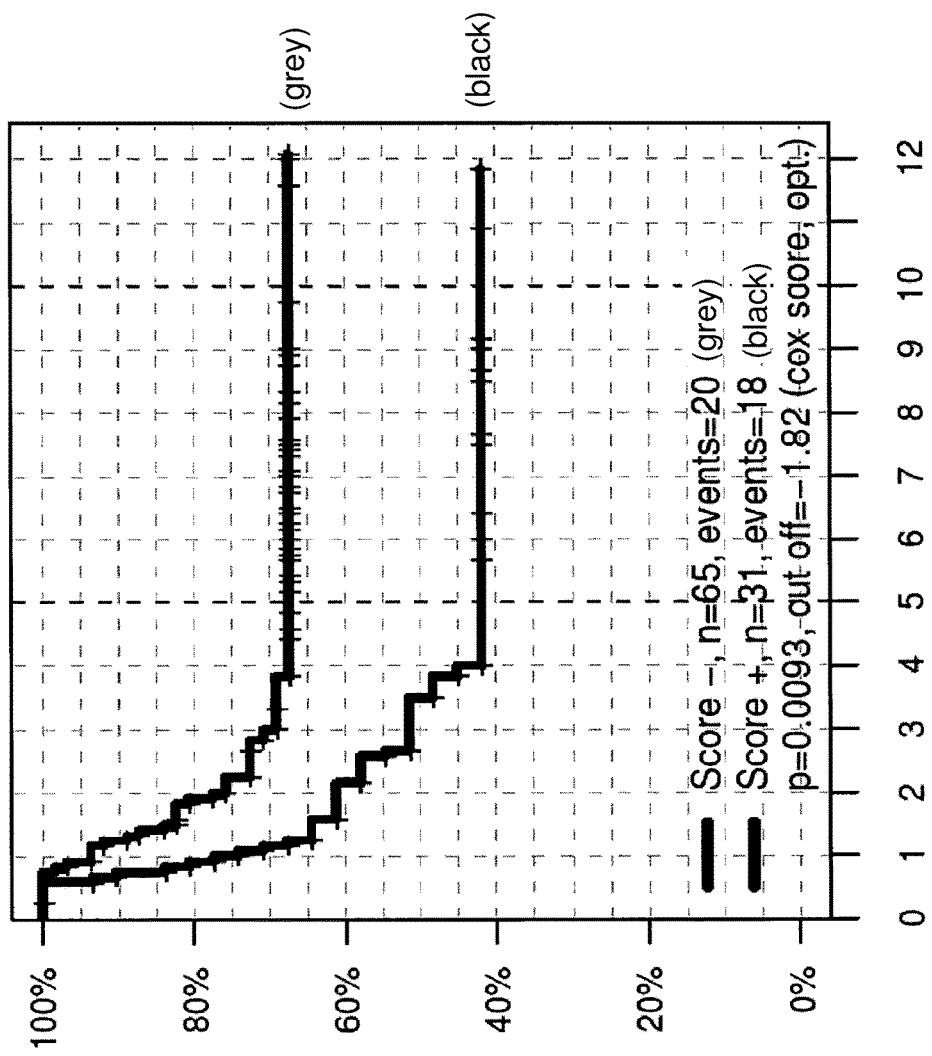
Figure 53:
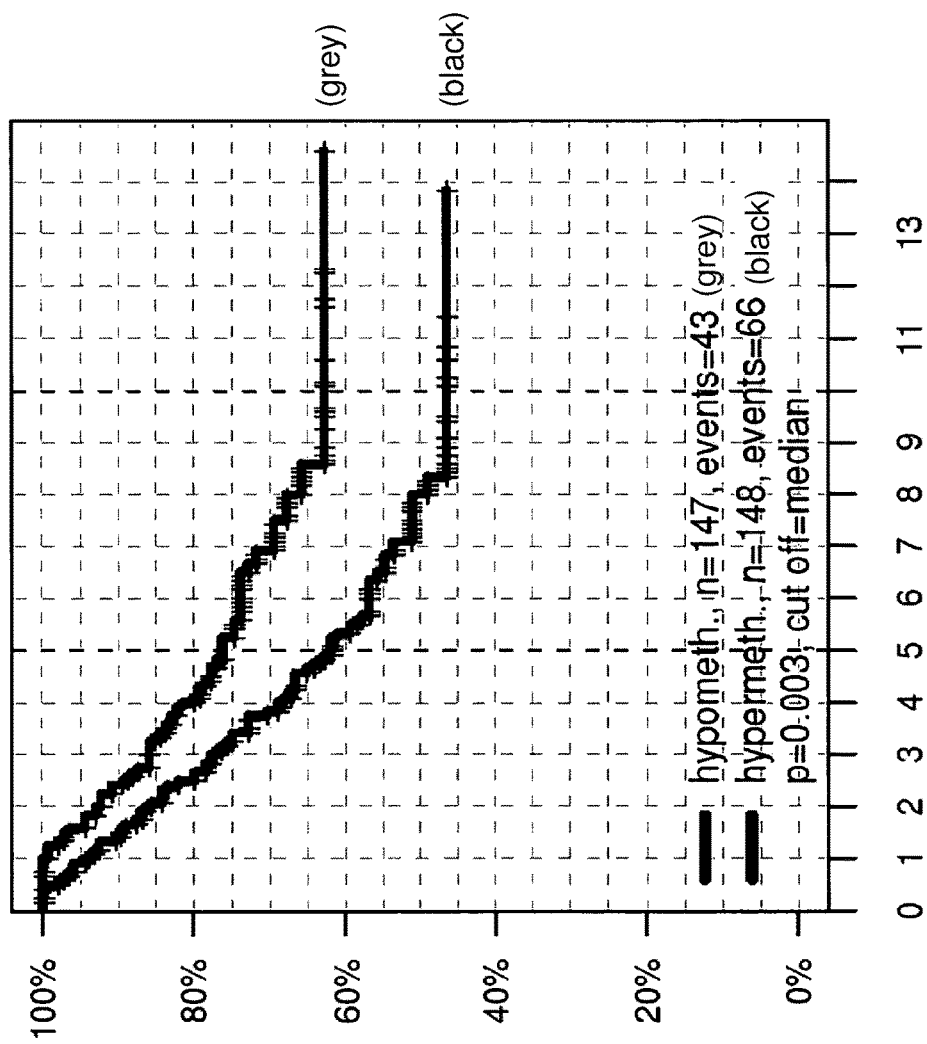
Figure 54:
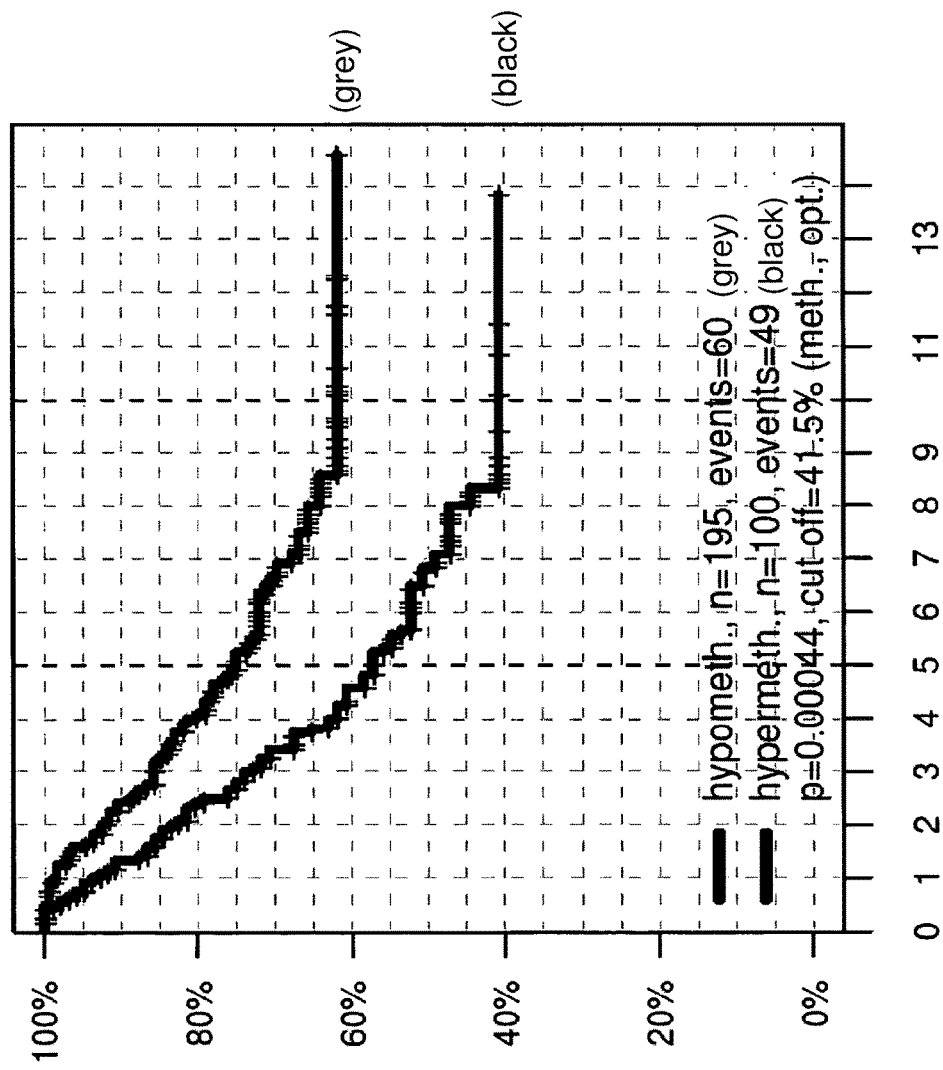
Figure 55:
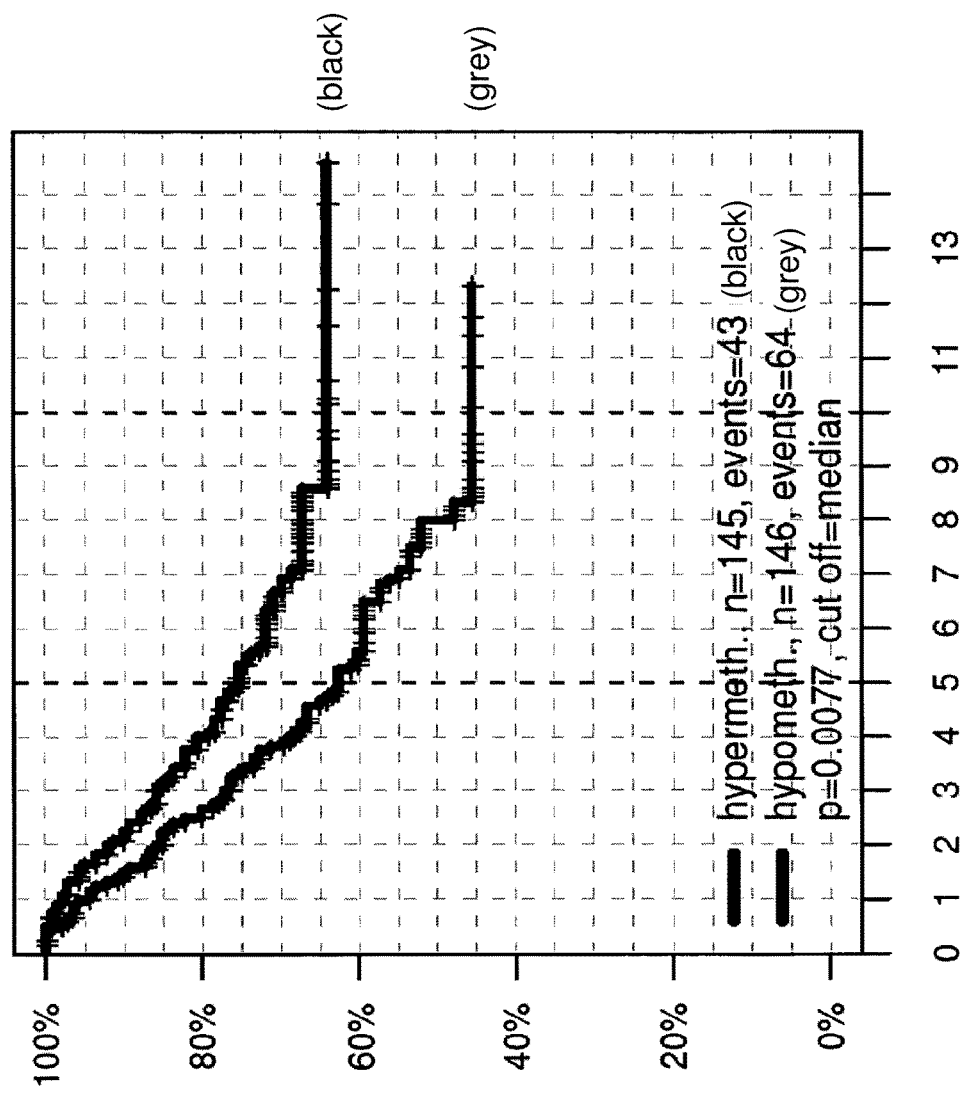
Figure 56:
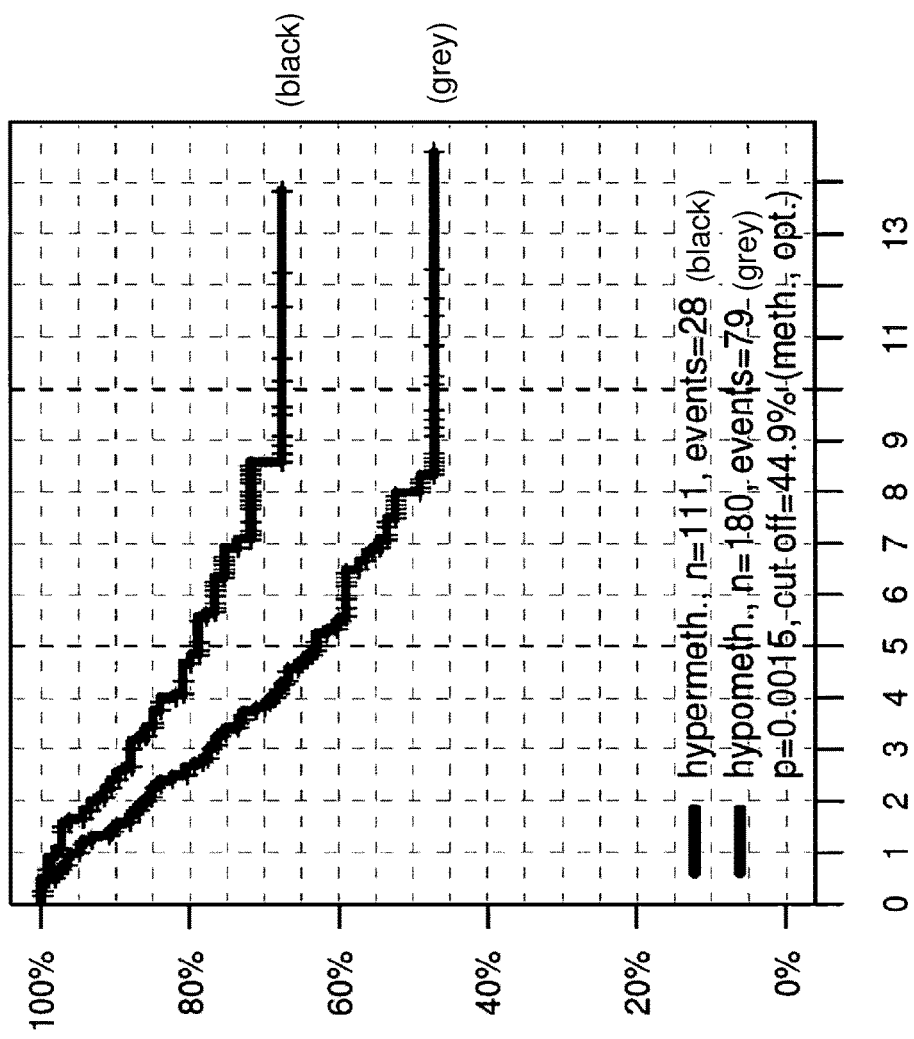
Figure 57:
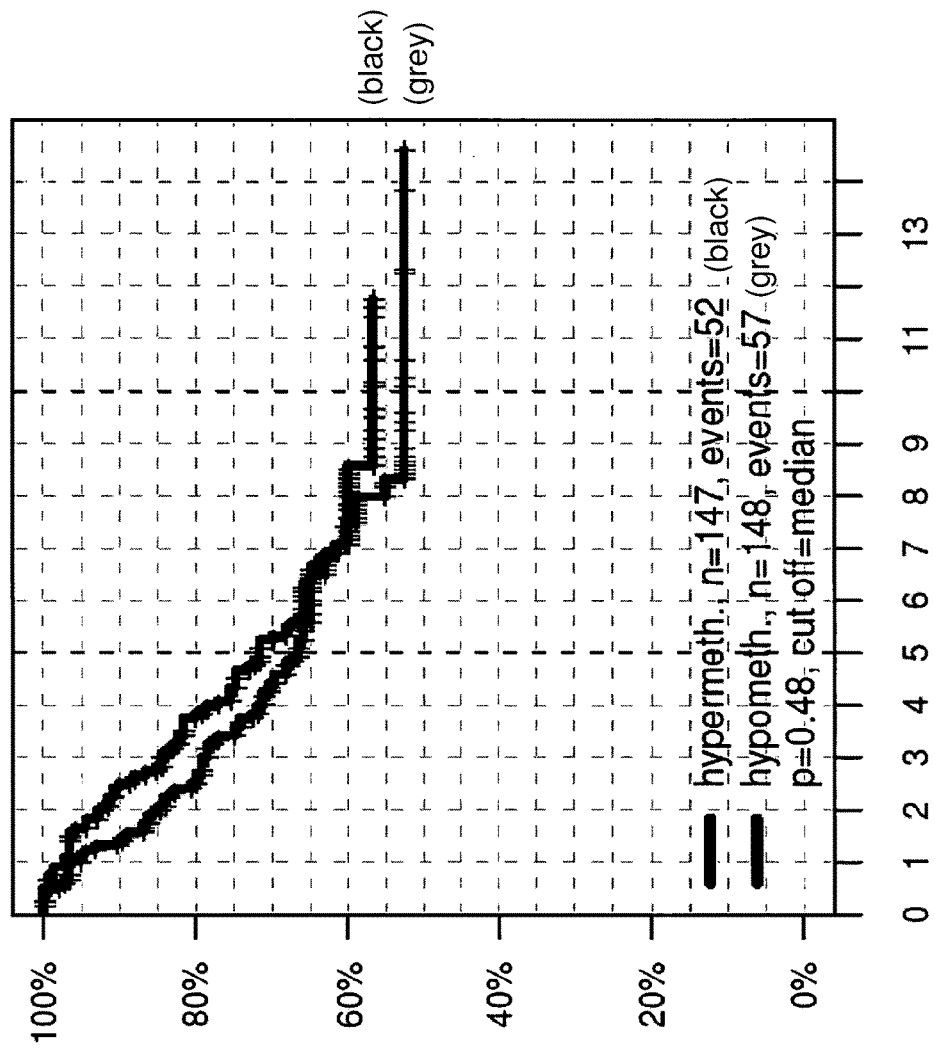
Figure 58:
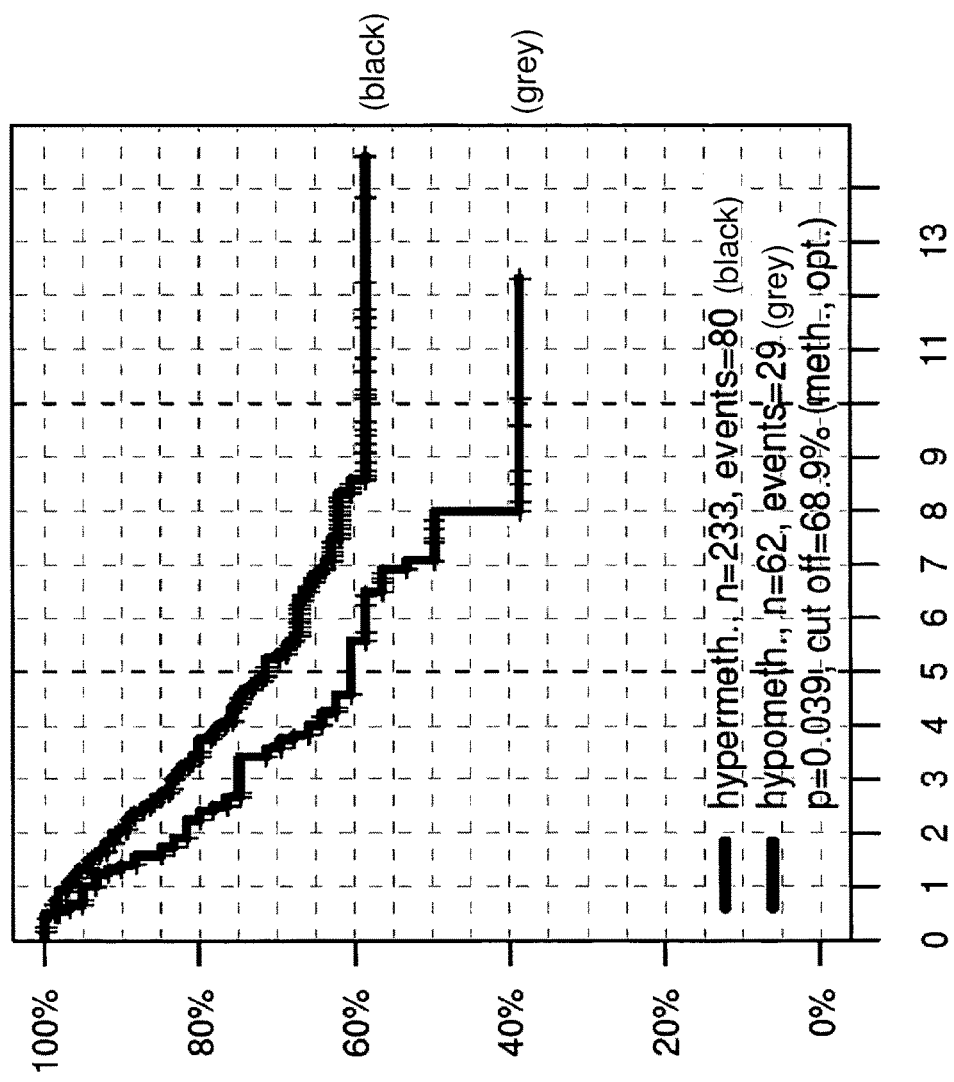
Figure 59:
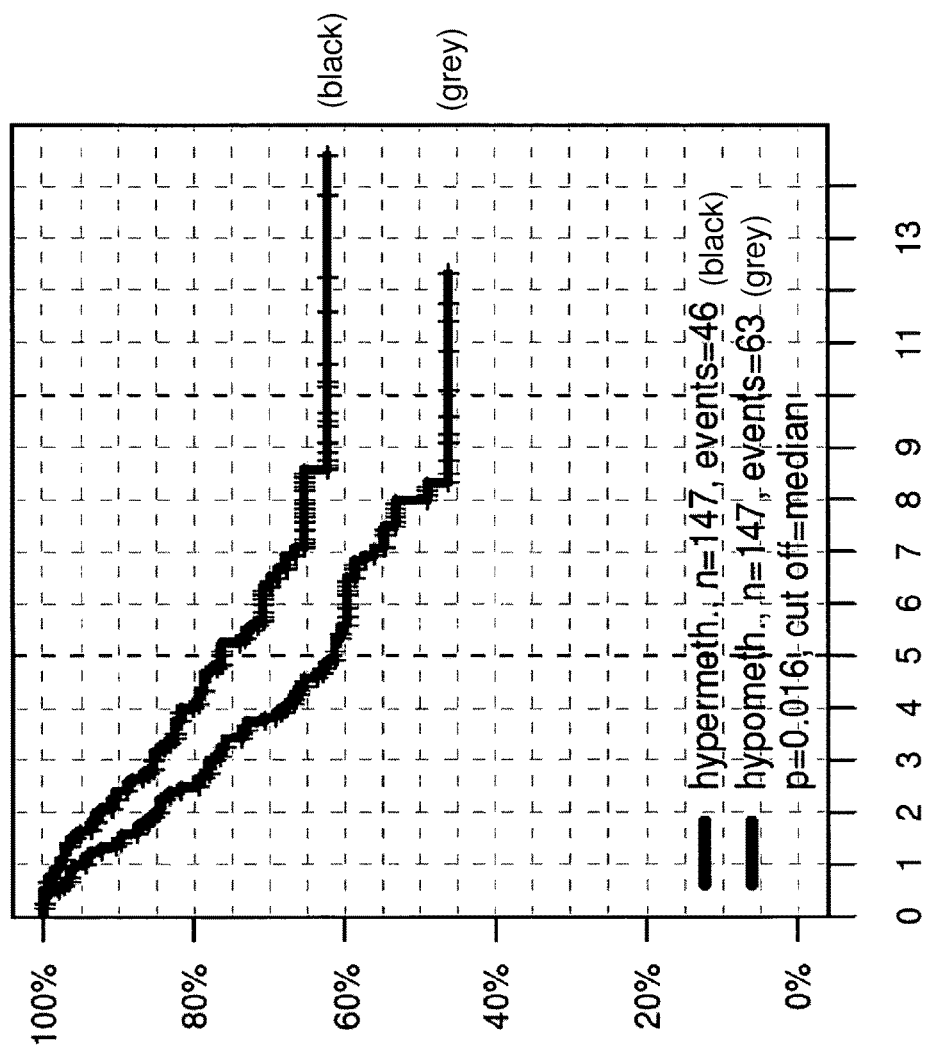
Figure 60:
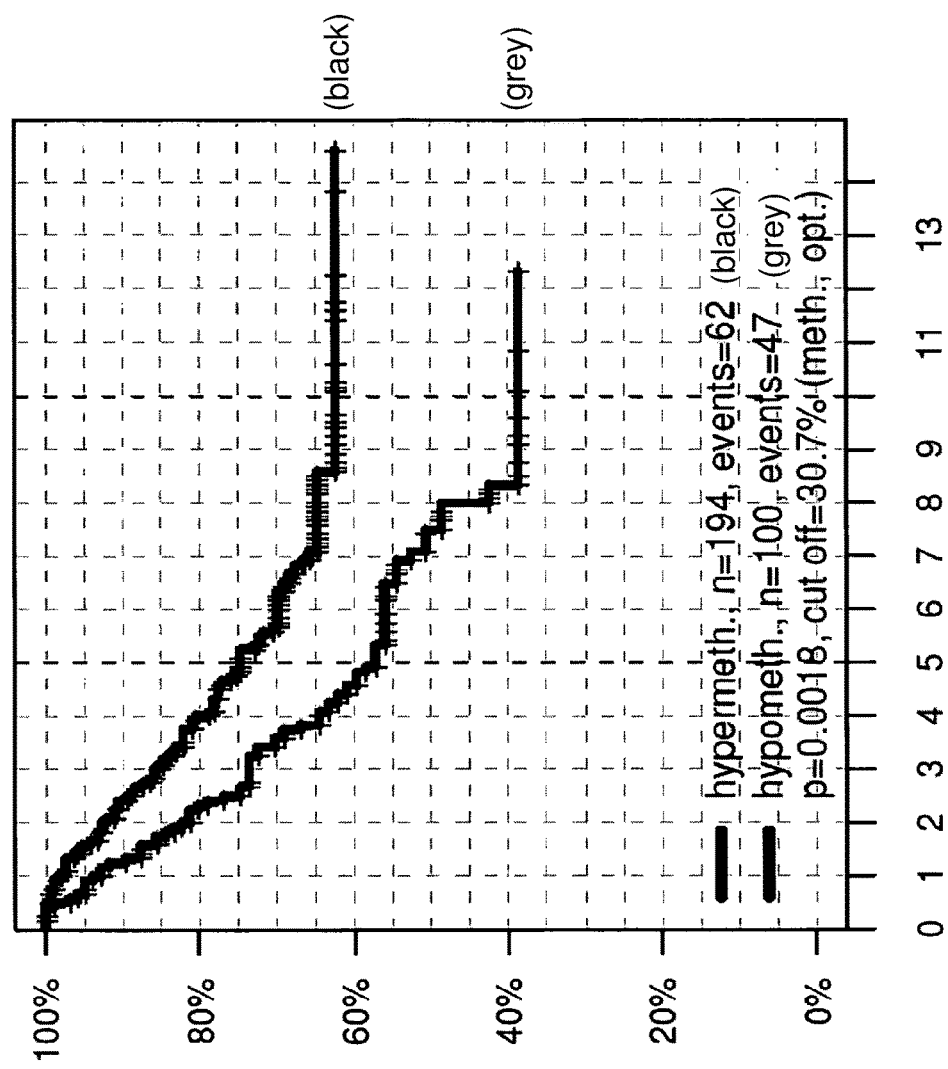
Figure 61:
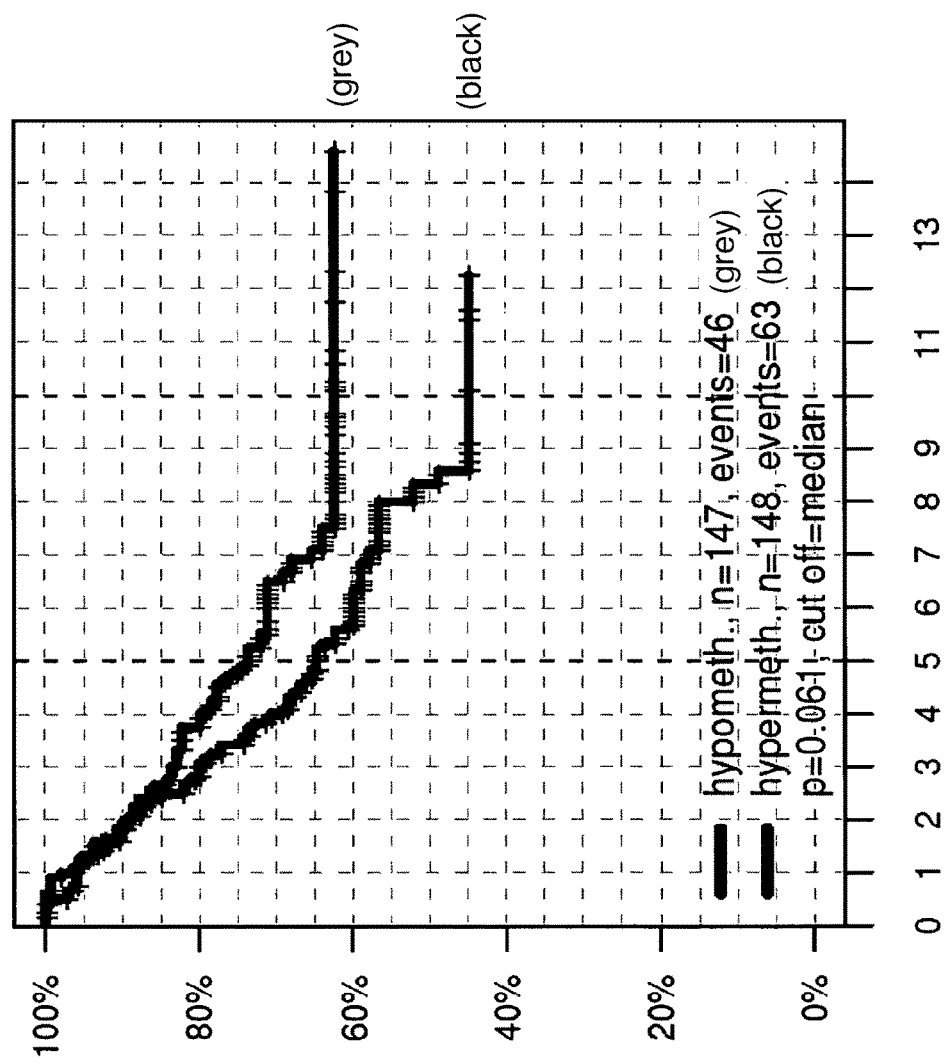
Figure 62:
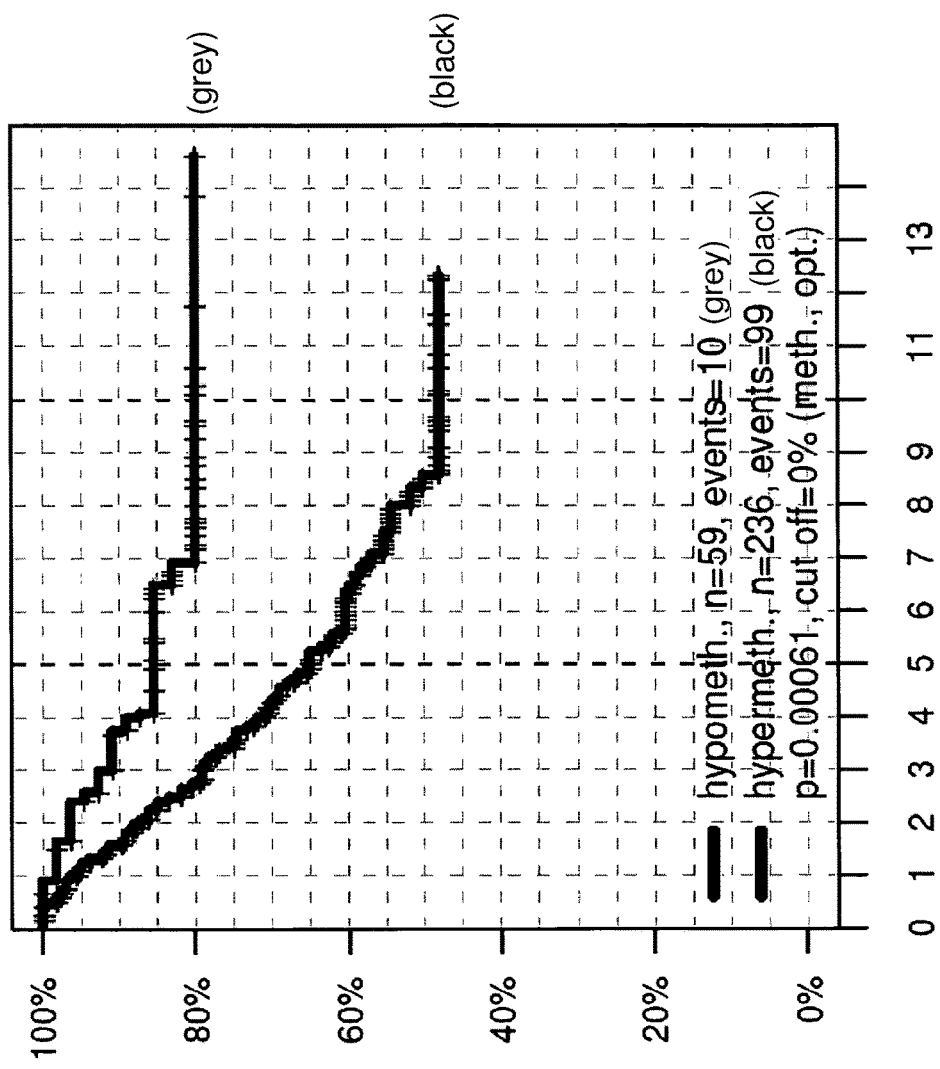
Figure 63:
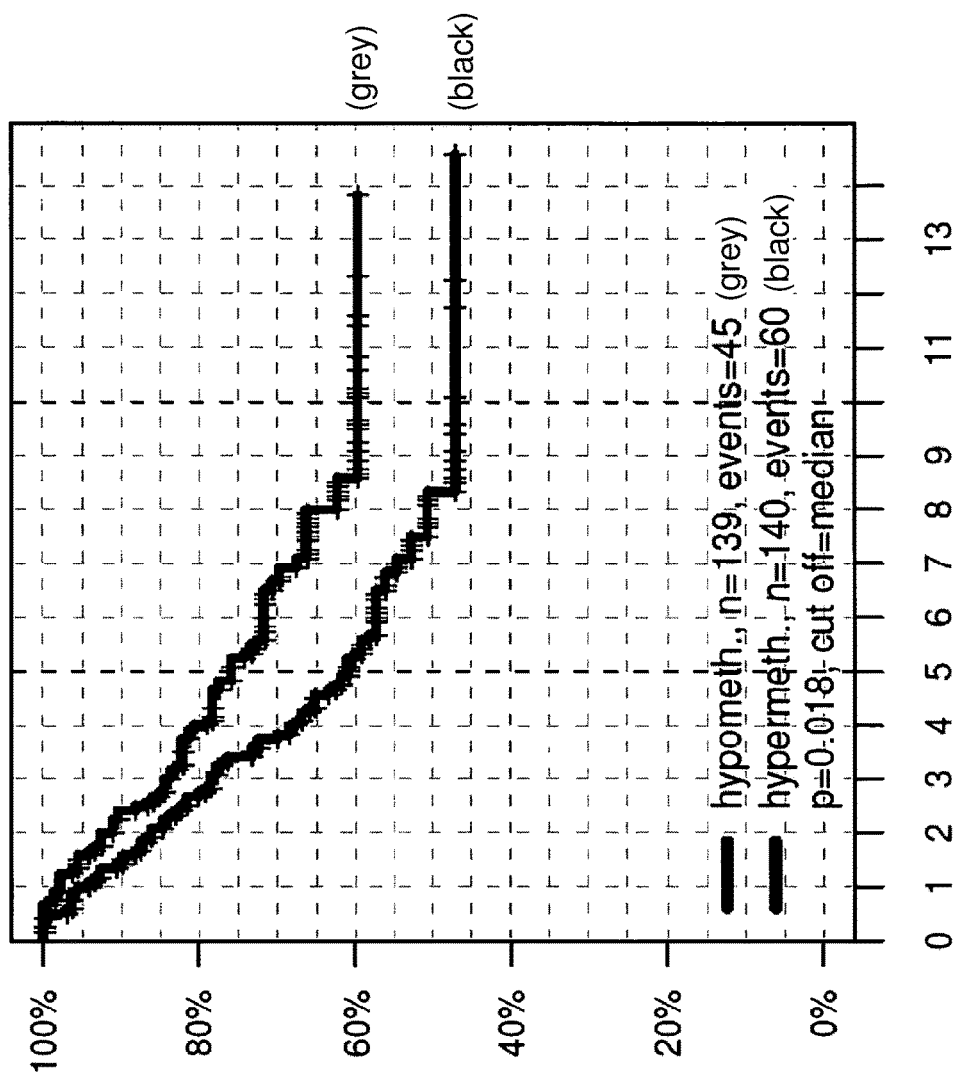
Figure 64:
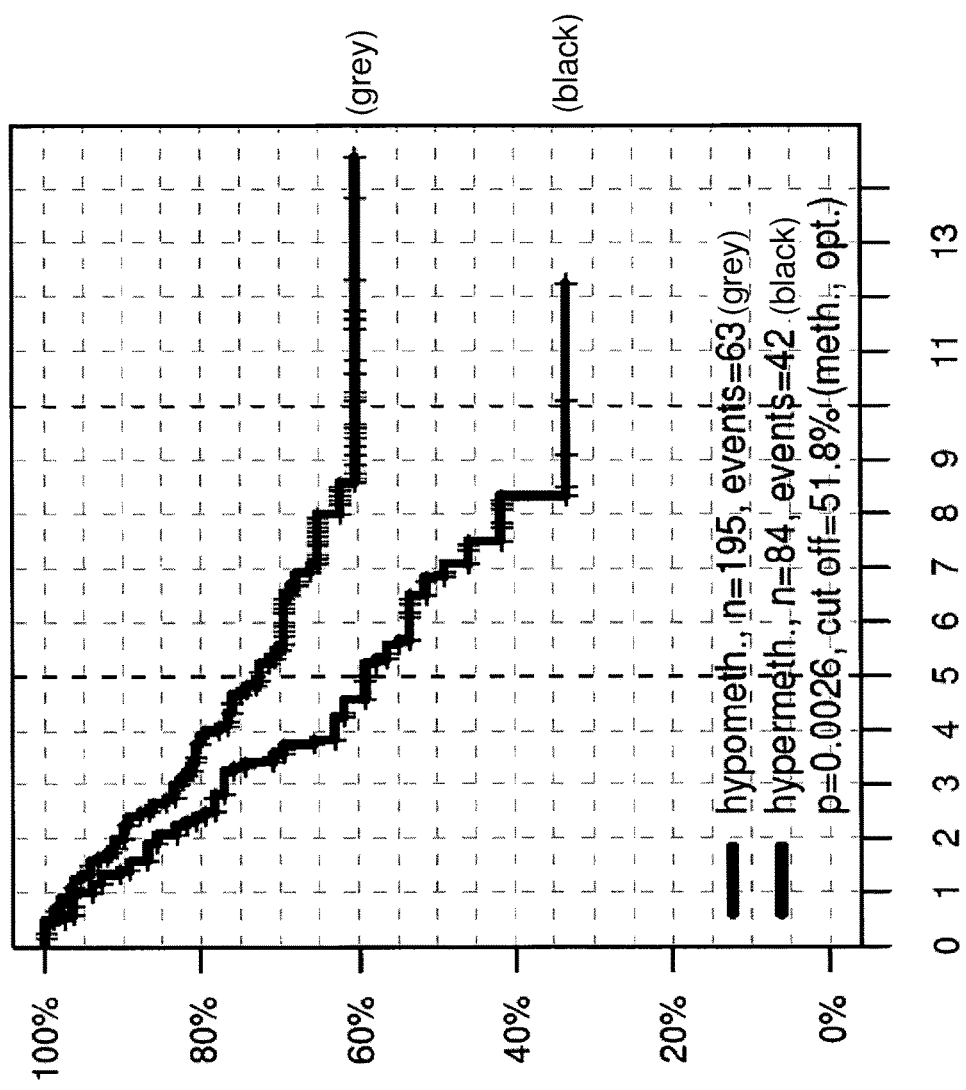
Figure 65:
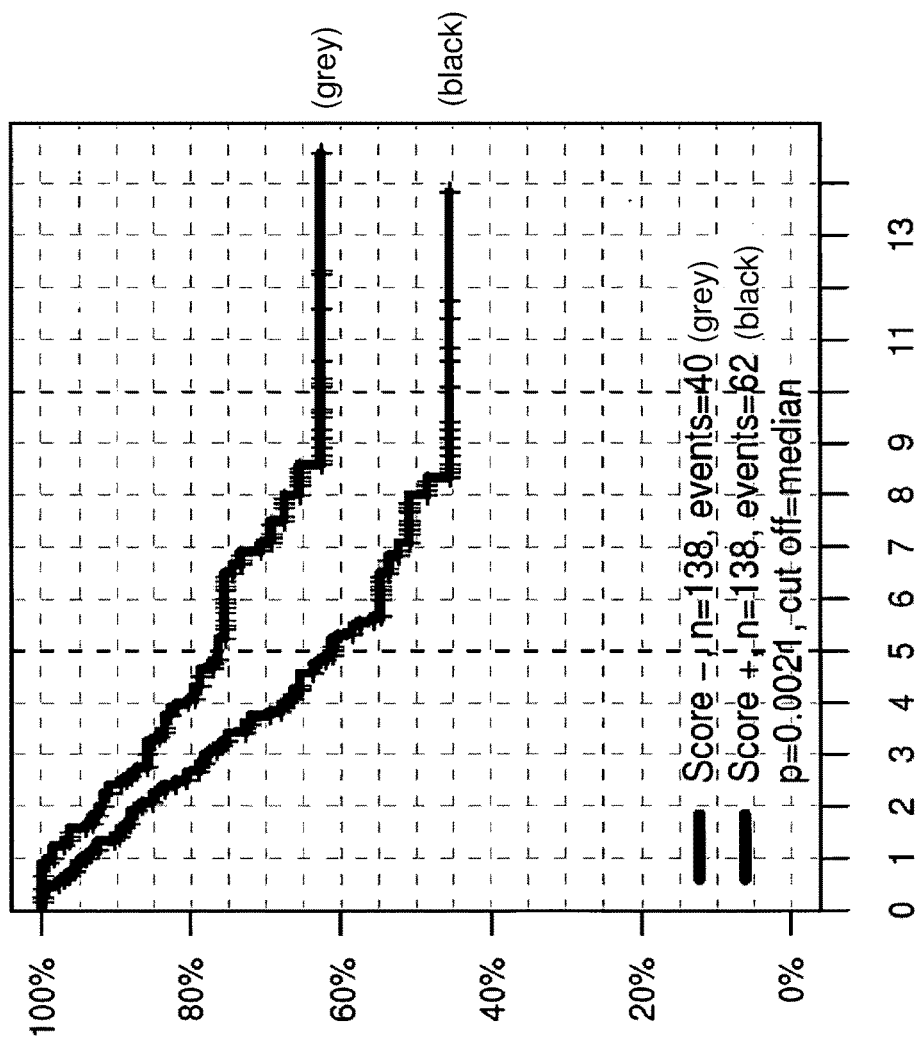
Figure 66:
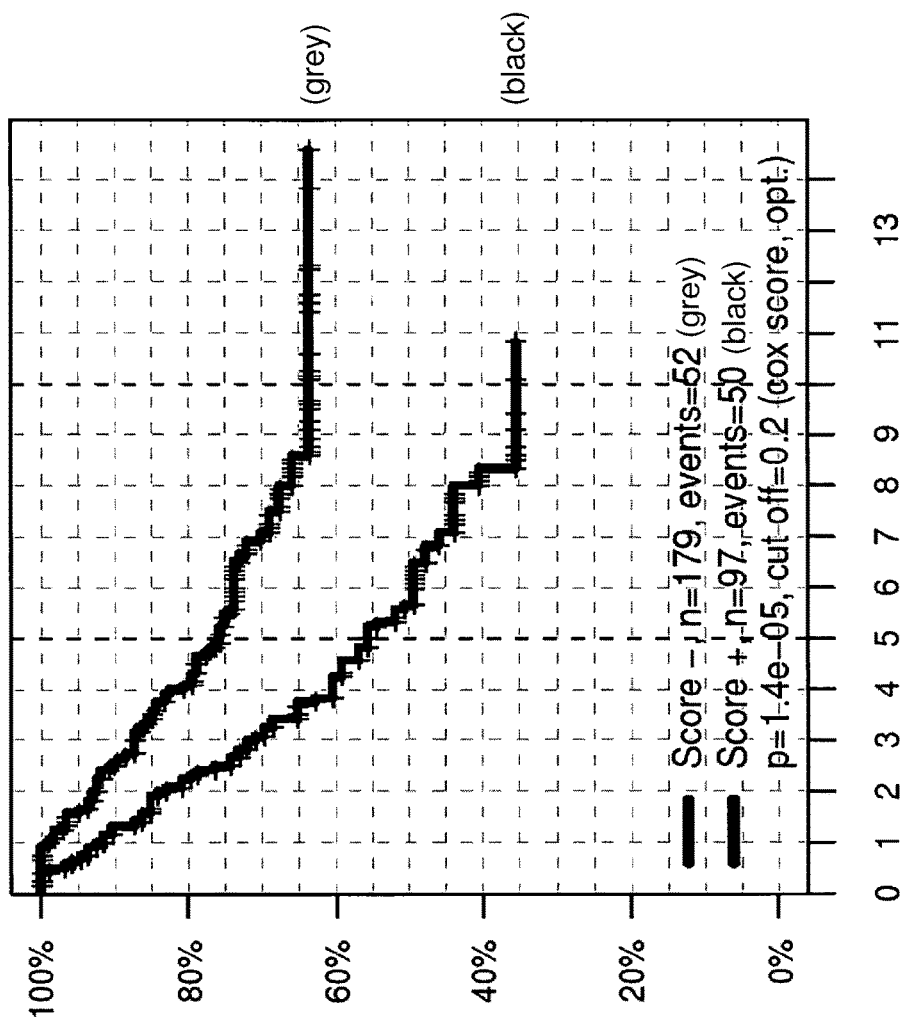
Figure 67:
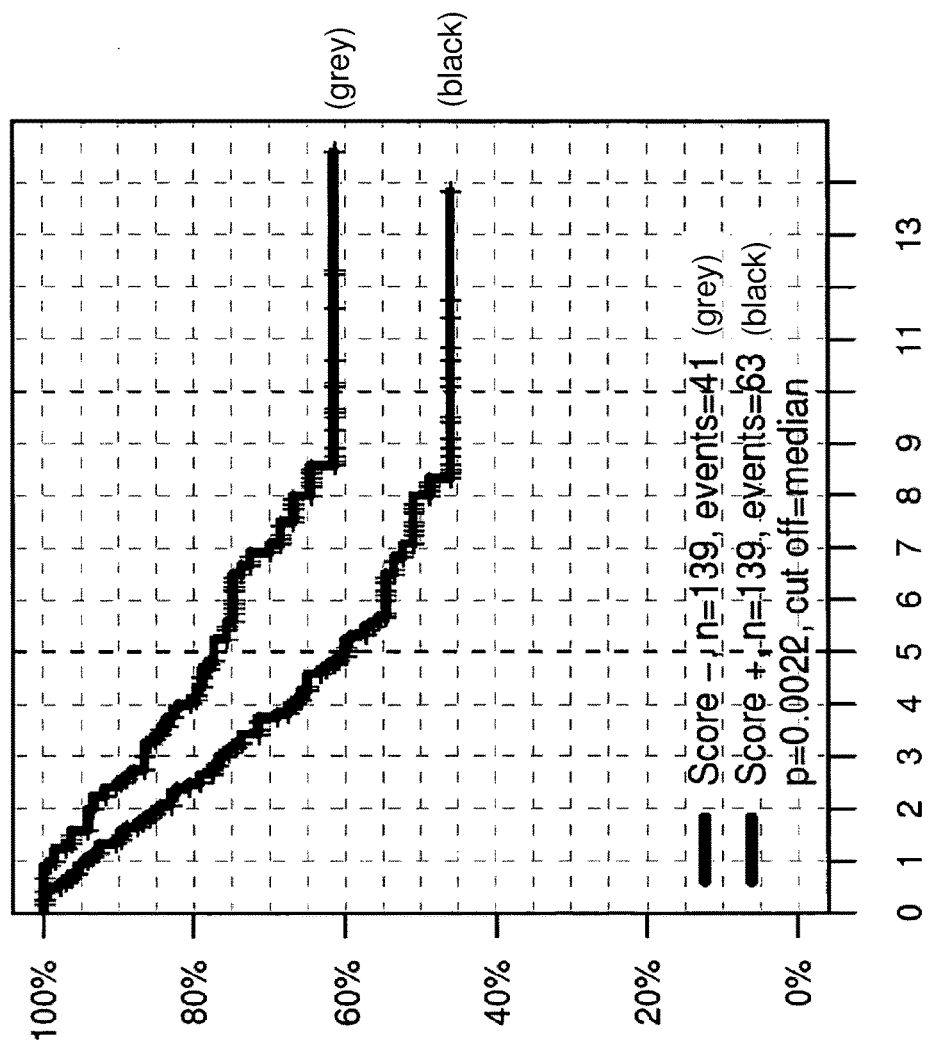
Figure 68:
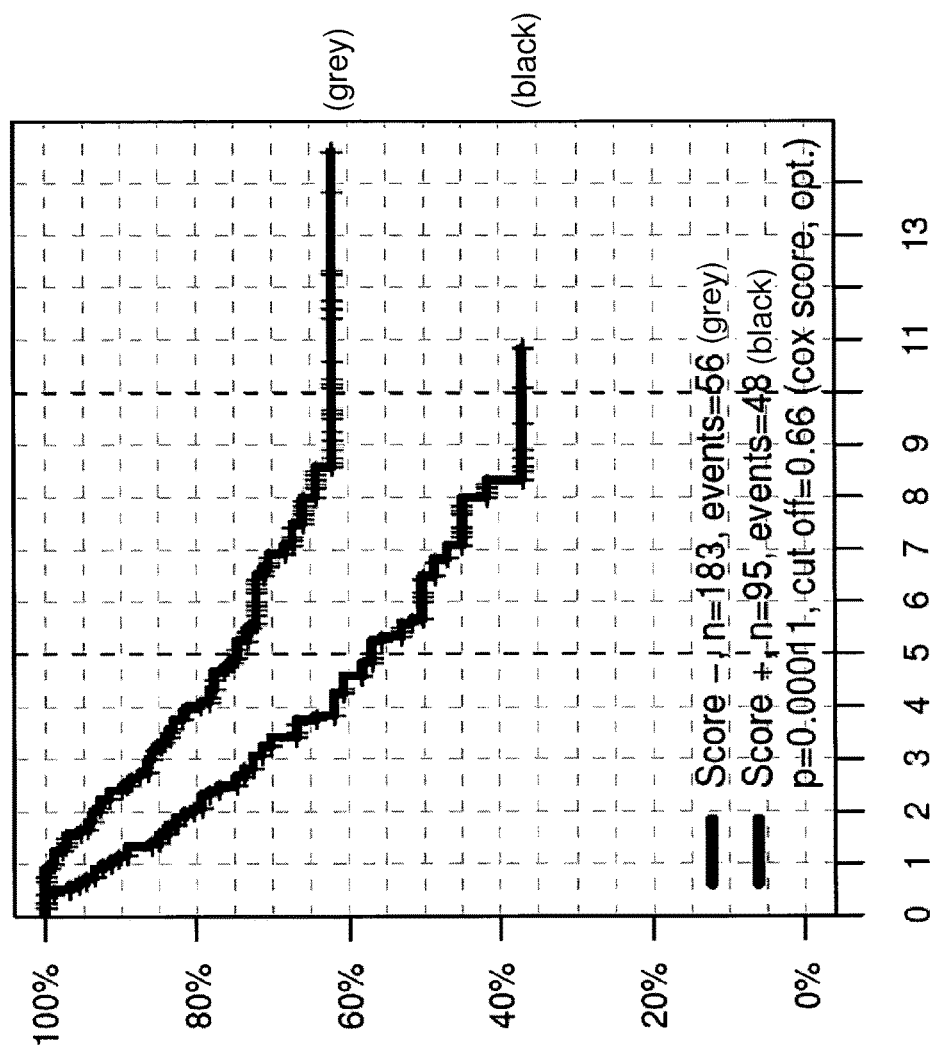
Figure 69:
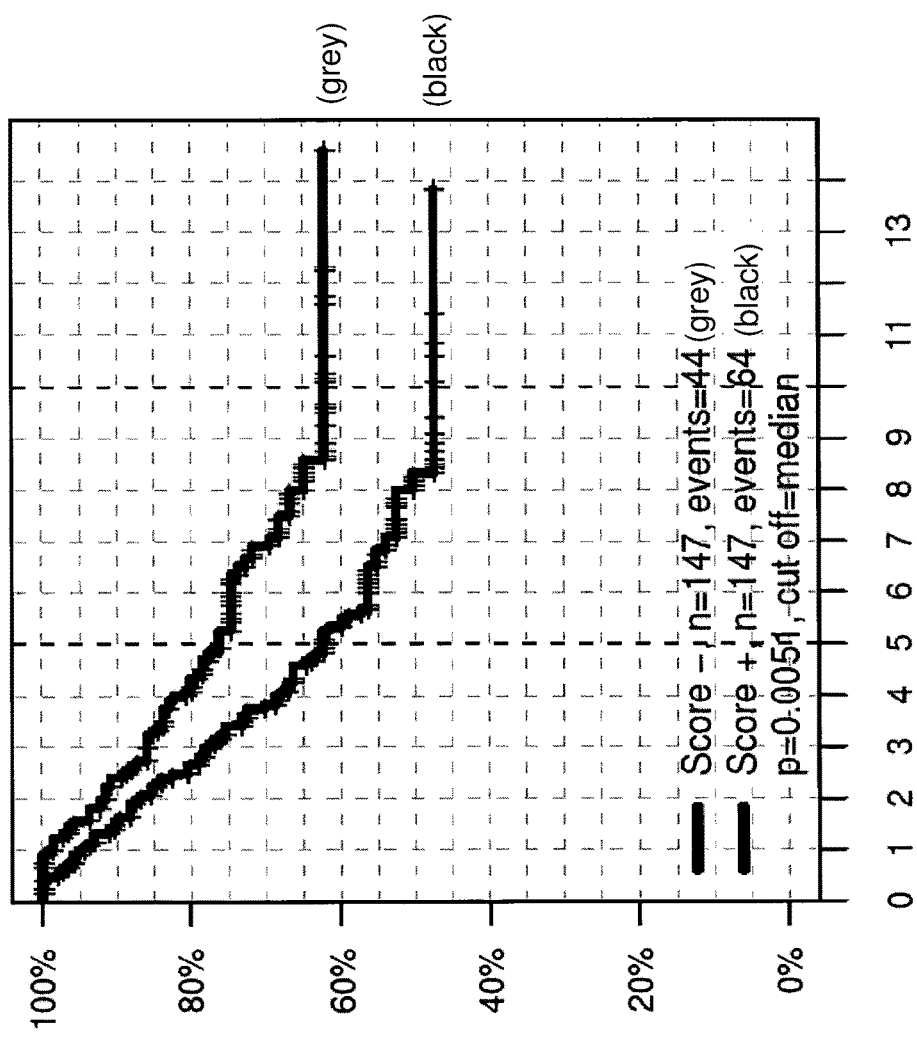
Figure 70:
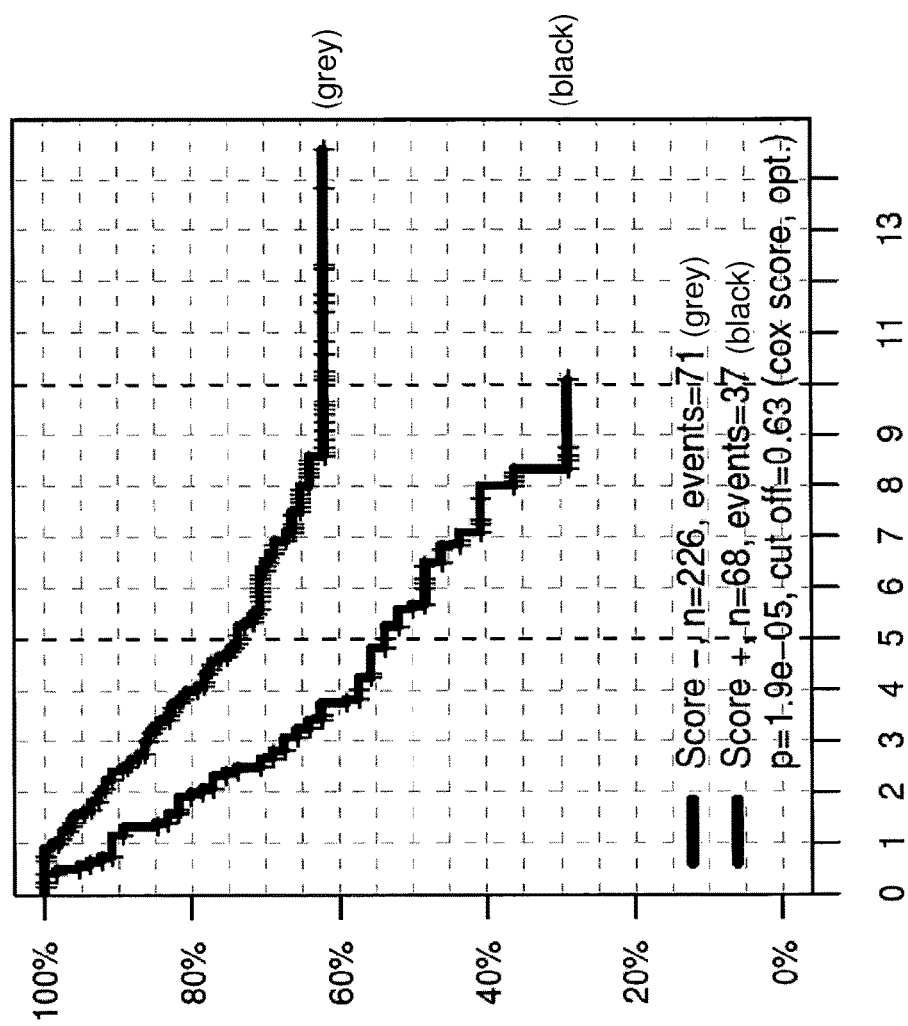
Figure 71:
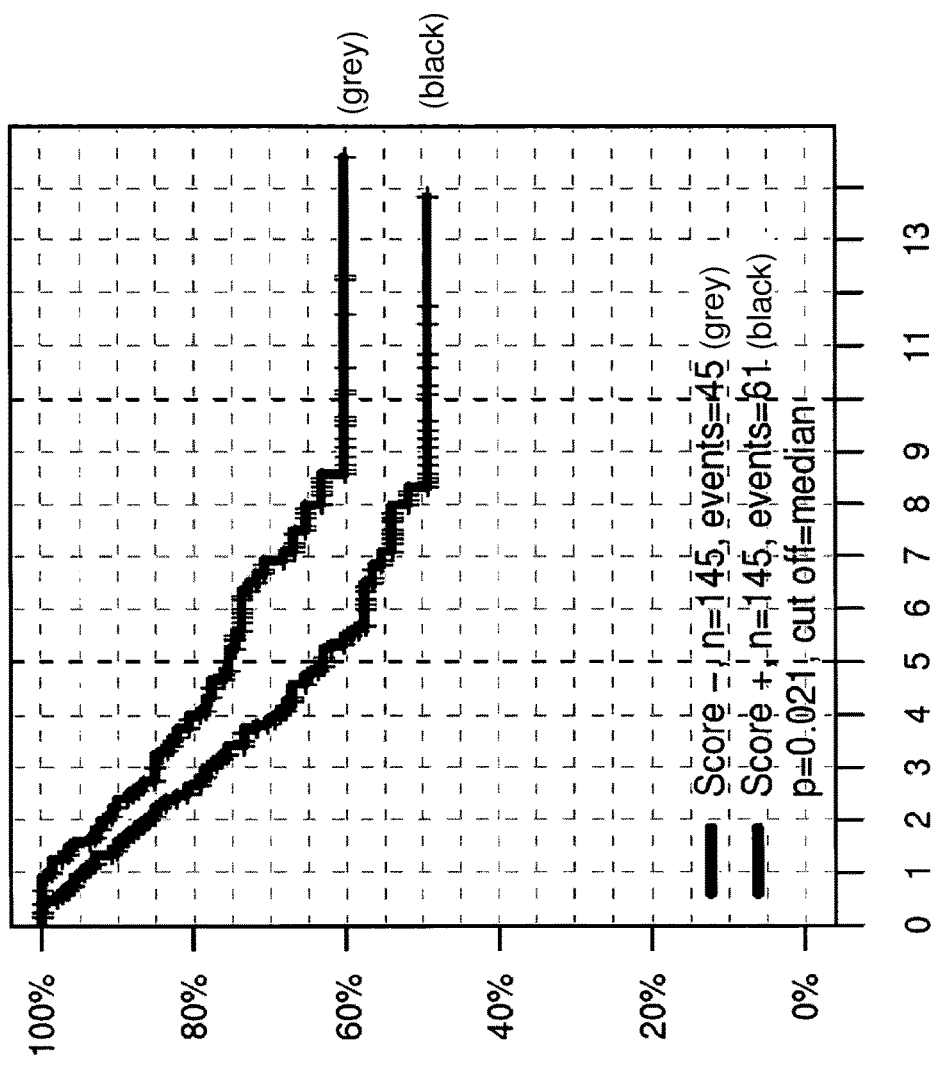
Figure 72:
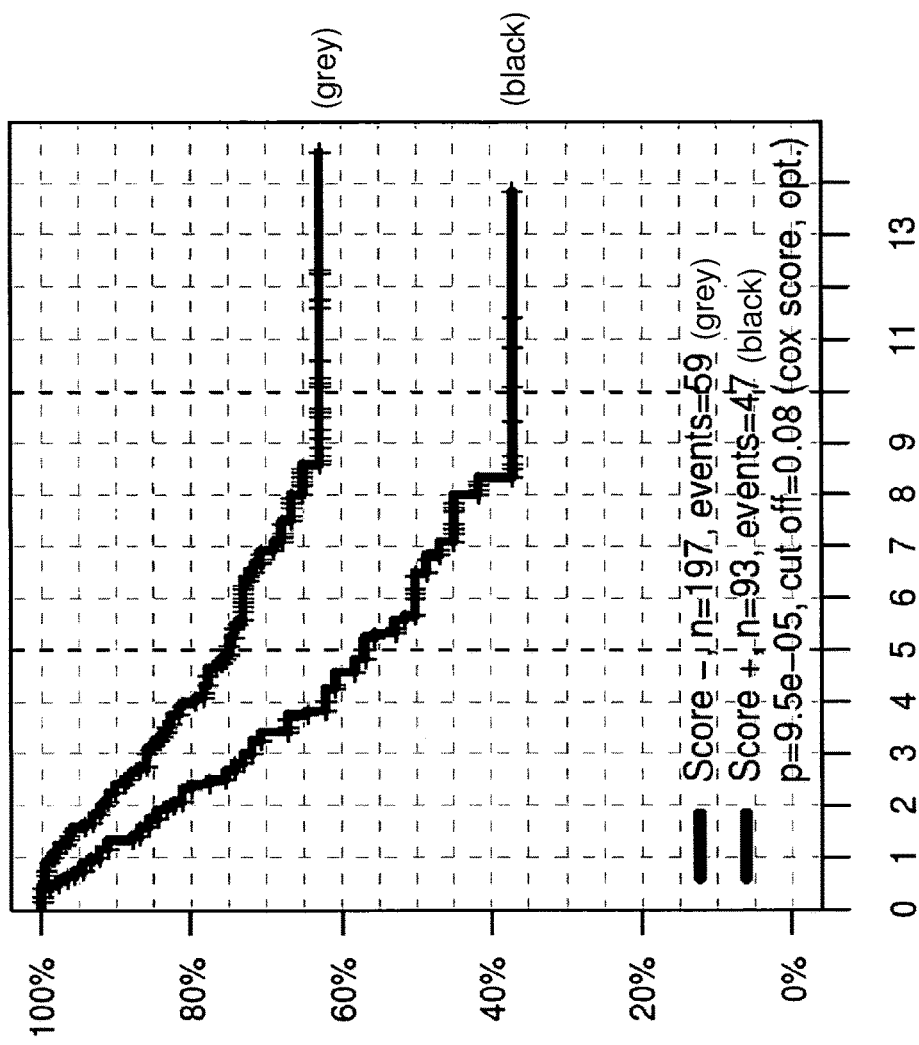
Figure 73:
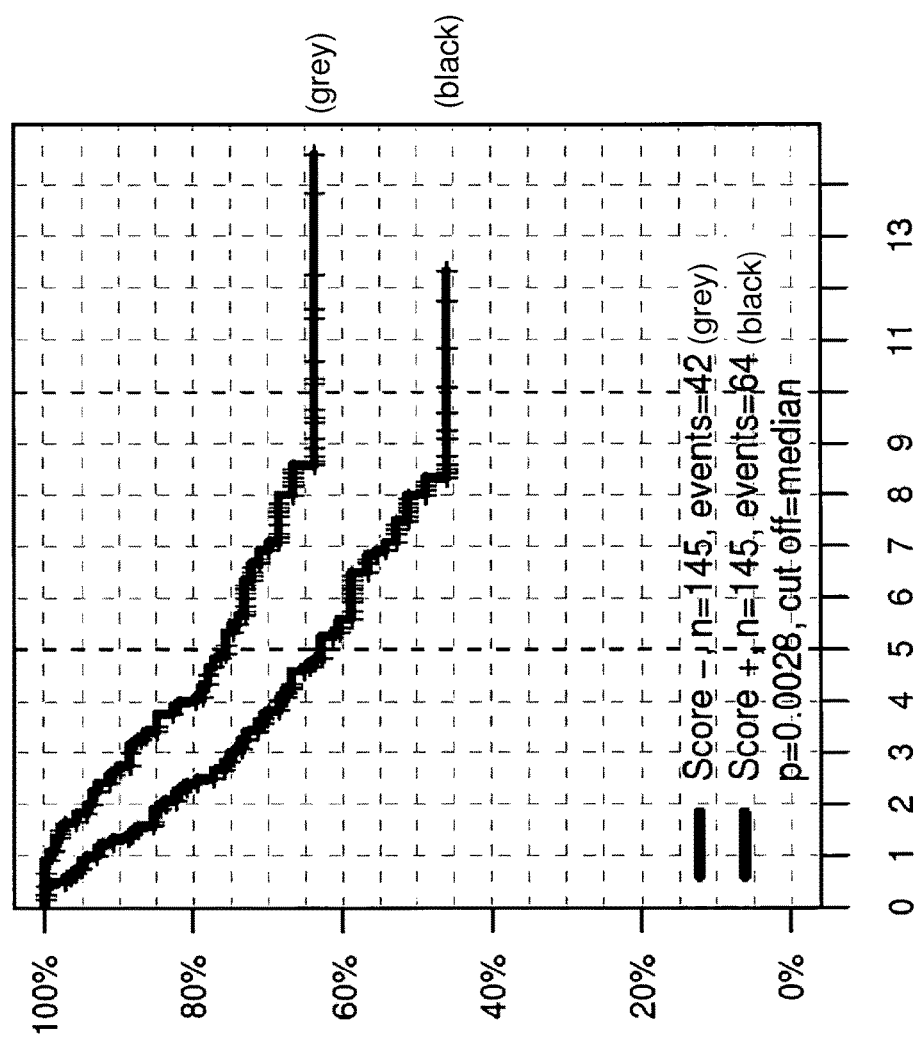
Figure 74:
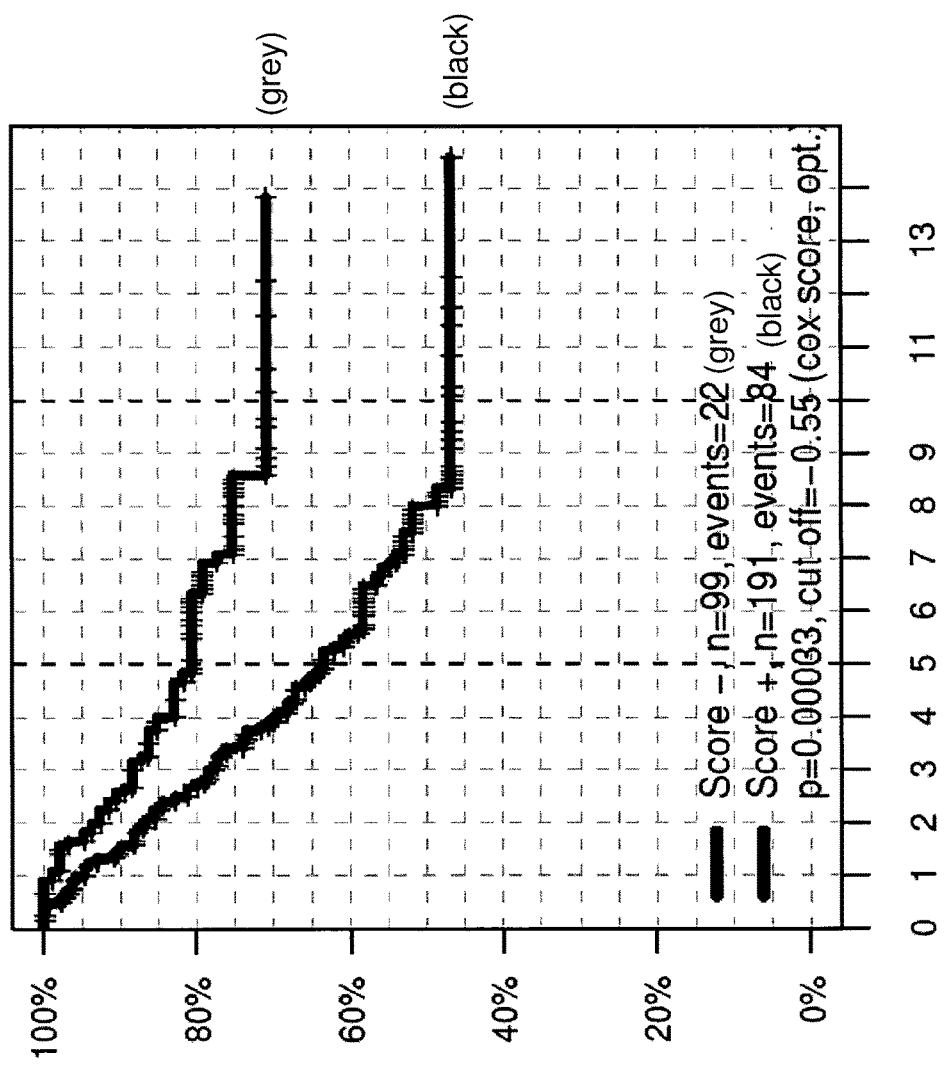
Figure 75:
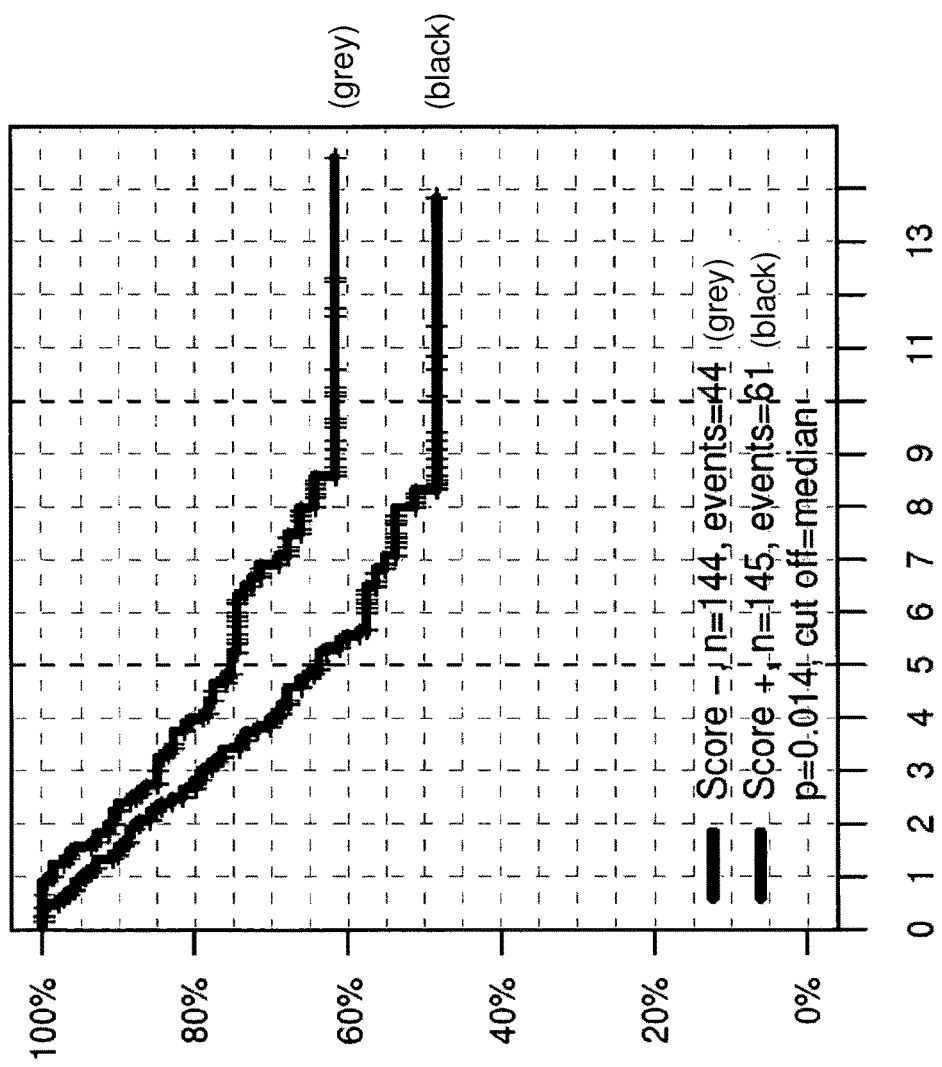
Figure 76:
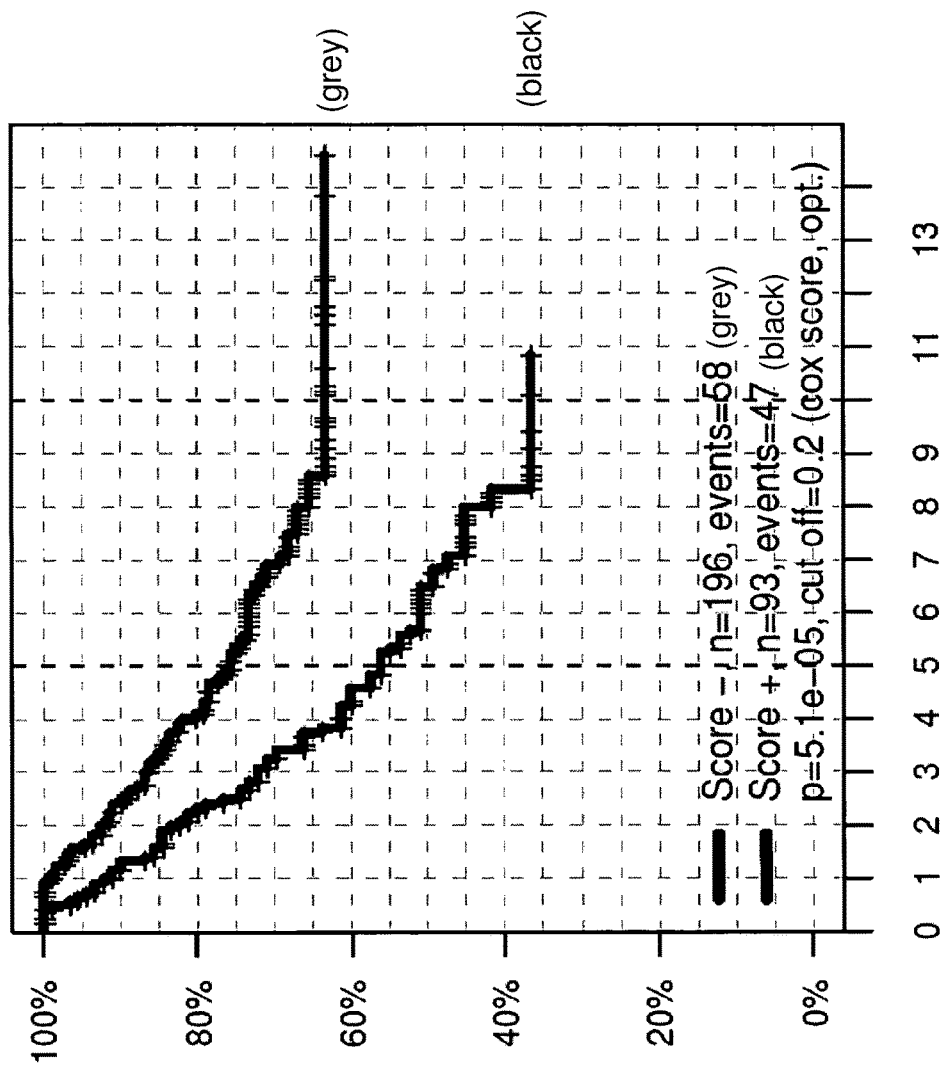
Figure 77:
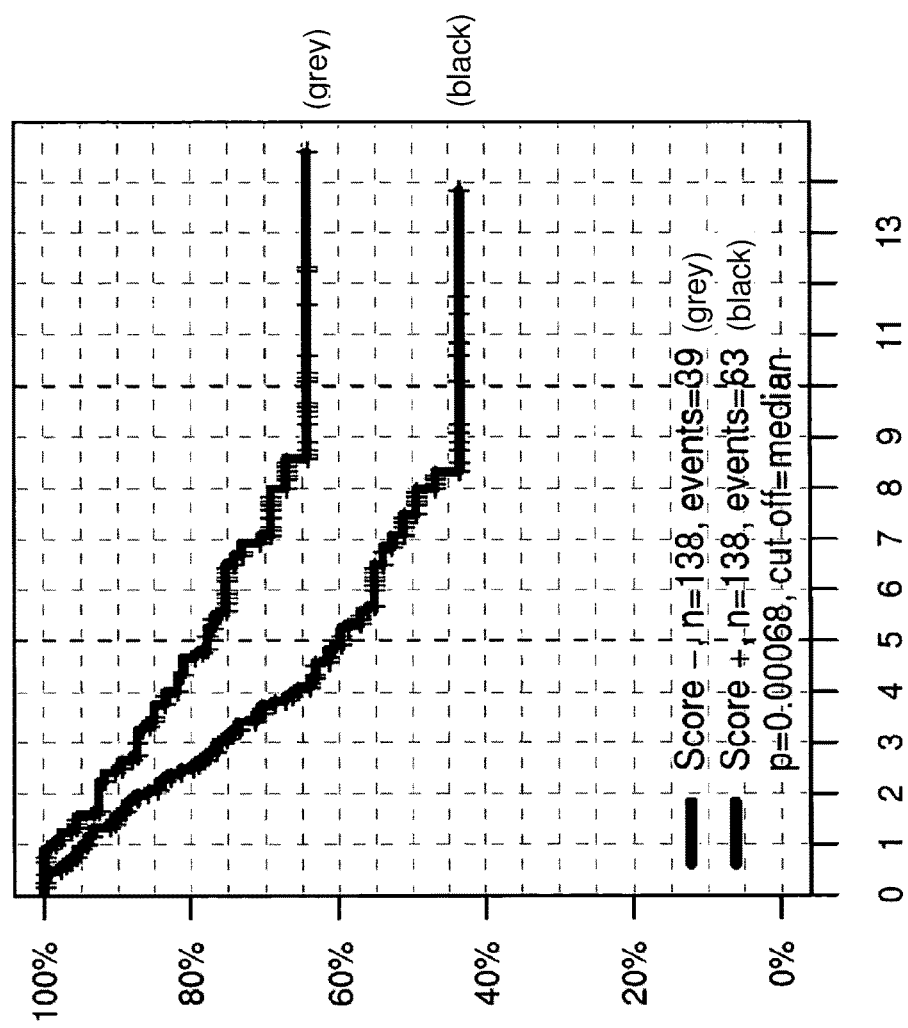

Characterization of a cancer in terms predicting treatment outcome enables the physician to make an informed decision as to a therapeutic regimen with appropriate risk and benefit trade offs to the patient.

In the context of the present invention the terms "estrogen receptor positive" and/or "progesterone receptor positive" when used to describe a cell proliferative disorder are taken to mean that the proliferating cells express said hormone receptor.

In the context of the present invention the term 'aggressiveness' is taken to mean one or more of high likelihood of relapse post surgery; below average or below median patient survival; below average or below median disease free survival; below average or below median relapse-free survival; above average tumor-related complications; fast progression of tumor or metastases. According to the aggressiveness of the disease an appropriate treatment or treatments may be selected from the group consisting of chemotherapy, radiotherapy, surgery, biological therapy, immunotherapy, antibody treatments, treatments involving molecularly targeted drugs, estrogen receptor modulator treatments, estrogen receptor down-regulator treatments, aromatase inhibitors treatments, ovarian ablation, treatments providing LHRH analogues or other centrally acting drugs influencing estrogen production. Wherein a cancer is characterized as 'aggressive' it is particularly preferred that a treatment such as, but not limited to, chemotherapy is provided in addition to or instead of an endocrine targeting therapy. Indicators of tumor aggressiveness standard in the art include but are not limited to, tumor stage, tumor grade, nodal status and survival.

Unless stated otherwise as used herein the term "survival" shall be taken to include all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis).

As used herein the term "prognostic marker" shall be taken to mean an indicator of the likelihood of progression of the disease, in particular aggressiveness and metastatic potential of a tumor.

As used herein the term 'predictive marker' shall be taken to mean an indicator of response to therapy, said response is preferably defined according to patient survival. It is preferably used to define patients with high, low and intermediate length of survival or recurrence after treatment, that is the result of the inherent heterogeneity of the disease process.

As defined herein the term predictive marker may in some situations fall within the remit of a herein described 'prognostic marker', for example, wherein a prognostic marker differentiates between patients with different survival outcomes pursuant to a treatment, said marker is also a predictive marker for said treatment. Therefore, unless otherwise stated the two terms shall not be taken to be mutually exclusive.

As used herein the term 'expression' shall be taken to mean the transcription and translation of a gene, as well as the genetic or the epigenetic modifications of the genomic DNA associated with the marker gene and/or regulatory or promoter regions thereof. Genetic modifications include SNPs, point mutations, deletions, insertions, repeat length, rearrangements and other polymorphisms. The analysis of either the expression levels of protein, or mRNA or the analysis of the patient's individual genetic or epigenetic modification of the marker gene are herein summarized as the analysis of expression of the gene.

The level of expression of a gene may be determined by the analysis of any factors associated with or indicative of the level of transcription and translation of a gene including but not limited to methylation analysis, loss of heterozygosity (hereinafter also referred to as LOH), RNA expression levels and protein expression levels.

Furthermore the activity of the transcribed gene may be affected by genetic variations such as but not limited to genetic modifications (including but not limited to SNPs, point mutations, deletions, insertions, repeat length, rearrangements and other polymorphisms).

The terms "endocrine therapy" or "endocrine treatment" are meant to comprise any therapy, treatment or treatments targeting the estrogen receptor pathway or estrogen synthesis pathway or estrogen conversion pathway, which is involved in estrogen metabolism, production or secretion. Said treatments include, but are not limited to estrogen receptor modulators, estrogen receptor down-regulators, aromatase inhibitors, ovarian ablation, LHRH analogues and other centrally acting drugs influencing estrogen production.

The term "monotherapy" shall be taken to mean the use of a single drug or other therapy.

In the context of the present invention the term "chemotherapy" is taken to mean the use of pharmaceutical or chemical substances to treat cancer. This definition excludes radiation therapy (treatment with high energy rays or particles), hormone therapy (treatment with hormones or hormone analogues) and surgical treatment.

In the context of the present invention the term "adjuvant treatment" is taken to mean a therapy of a cancer patient immediately following an initial non chemotherapeutical therapy, e.g. surgery. In general, the purpose of an adjuvant therapy is to decrease the risk of recurrence.

In the context of the present invention the term "determining a suitable treatment regimen for the subject" is taken to mean the determination of a treatment regimen (i.e. a single therapy or a combination of different therapies that are used for the prevention and/or treatment of the cancer in the patient) for a patient that is started, modified and/or ended based or essentially based or at least partially based on the results of the analysis according to the present invention. One example is starting an adjuvant endocrine therapy after surgery, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

In the context of this invention the terms "obtaining a biological sample" or "obtaining a sample from a subject", shall not be taken to include the active retrieval of a sample from an individual, e.g. the performance of a biopsy. Said terms shall be taken to mean the obtainment of a sample previously isolated from an individual. Said samples may be isolated by any means standard in the art, including but not limited to biopsy, surgical removal, body fluids isolated by means of aspiration. Furthermore said samples may be provided by third parties including but not limited to clinicians, couriers, commercial sample providers and sample collections.

In the context of the present invention, the term "CpG island" refers to a contiguous region of genomic DNA that satisfies the criteria of (1) having a frequency of CpG dinucleotides corresponding to an "Observed/Expected Ratio">0.6, and (2) having a "GC Content">0.5. CpG islands are typically, but not always, between about 0.2 to about 1 kb in length.

In the context of the present invention the term "regulatory region" of a gene is taken to mean nucleotide sequences which affect the expression of a gene. Said regulatory regions may be located within, proximal or distal to said gene. Said regulatory regions include but are not limited to constitutive promoters, tissue-specific promoters, developmental-specific promoters, inducible promoters and the like. Promoter regulatory elements may also include certain enhancer sequence elements that control transcriptional or translational efficiency of the gene.

In the context of the present invention, the term "methylation" refers to the presence or absence of 5-methylcytosine ("5-mCyt") at one or a plurality of CpG dinucleotides within a DNA sequence.

In the context of the present invention the term "methylation state" is taken to mean the degree of methylation present in a nucleic acid of interest, this may be expressed in absolute or relative terms i.e. as a percentage or other numerical value or by comparison to another tissue and therein described as hypermethylated, hypomethylated or as having significantly similar or identical methylation status.

In the context of the present invention, the term "hemimethylation" or "hemimethylation" refers to the methylation state of a CpG methylation site, where only a single cytosine in one of the two CpG dinucleotide sequences of the double stranded CpG methylation site is methylated (e.g., 5'-NNC-$^M$GNN-3' (top strand): 3'-NNGCNN-5' (bottom strand)).

In the context of the present invention, the term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

In the context of the present invention, the term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

In the context of the present invention, the term "microarray" refers broadly to both "DNA microarrays," and 'DNA chip(s),' as recognized in the art, encompasses all art-recognized solid supports, and encompasses all methods for affixing nucleic acid molecules thereto or synthesis of nucleic acids thereon.

"Genetic parameters" are mutations and polymorphisms of genes and sequences further required for their regulation. To be designated as genetic modifications or mutations are, in particular, insertions, deletions, point mutations, inversions and polymorphisms and, particularly preferred, SNPs (single nucleotide polymorphisms).

"Epigenetic modifications" or "epigenetic parameters" are modifications of DNA bases of genomic DNA and sequences further required for their regulation, in particular, cytosine methylations thereof. Further epigenetic parameters include, for example, the acetylation of histones which, however, cannot be directly analyzed using the described method but which, in turn, correlate with the DNA methylation.

In the context of the present invention, the term "bisulfite reagent" refers to a reagent comprising bisulfite, disulfite, hydrogen sulfite or combinations thereof, useful as disclosed herein to distinguish between methylated and unmethylated CpG dinucleotide sequences.

In the context of the present invention, the term "Methylation assay" refers to any assay for determining the methylation state of one or more CpG dinucleotide sequences within a sequence of DNA.

In the context of the present invention, the term "MS.AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al., *Cancer Research* 57:594-599, 1997.

In the context of the present invention, the term "MethyLight" refers to the art-recognized fluorescence-based real-time PCR technique described by Eads et al., *Cancer Res.* 59:2302-2306, 1999.

In the context of the present invention, the term "HeavyMethyl™" assay, in the embodiment thereof implemented herein, refers to a methylation assay comprising methylation specific blocking probes covering CpG positions between the amplification primers.

The term "Ms-SNuPE" (Methylation-sensitive Single Nucleotide Primer Extension) refers to the art-recognized assay described by Gonzalgo and Jones, *Nucleic Acids Res.* 25:2529-2531, 1997.

In the context of the present invention the term "MSP" (Methylation-specific PCR) refers to the art-recognized methylation assay described by Herman et al. *Proc. Natl. Acad. Sci. USA* 93:9821-9826, 1996, and by U.S. Pat. No. 5,786,146.

In the context of the present invention the term "COBRA" (Combined Bisulfite Restriction Analysis) refers to the art-recognized methylation assay described by Xiong and Laird, *Nucleic Acids Res.* 25:2532-2534, 1997.

In the context of the present invention the term "hybridization" is to be understood as a bond of an oligonucleotide to a complementary sequence along the lines of the Watson-Crick base pairings in the sample DNA, forming a duplex structure.

"Stringent hybridization conditions," as defined herein, involve hybridizing at 68° C. in 5×SSC/5×Denhardt's solution/1.0% SDS, and washing in 0.2×SSC/0.1% SDS at room temperature, or involve the art-recognized equivalent thereof (e.g., conditions in which a hybridization is carried out at 60° C. in 2.5×SSC buffer, followed by several washing steps at 37° C. in a low buffer concentration, and remains stable). Moderately stringent conditions, as defined herein, involve including washing in 3×SSC at 42° C., or the art-recognized equivalent thereof. The parameters of salt concentration and temperature can be varied to achieve the optimal level of identity between the probe and the target nucleic acid. Guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley and Sons, N.Y.) at Unit 2.10.

"Background DNA" as used herein refers to any nucleic acids which originate from sources other than the cancer cells to be analysed.

Using the methods and nucleic acids described herein, statistically significant models of patient relapse, disease free survival, metastasis free survival, overall survival and/or disease progression can be developed and utilized to assist patients and clinicians in determining suitable treatment options to be included in the therapeutic regimen.

In a further aspect of the invention said marker is used as a predictive marker of outcome of a anthracycline treatment, thereby enabling the physician to determine if said treatment is of benefit to a patient.

Using the methods and nucleic acids as described herein, patient survival can be evaluated before or during treatment for a cell proliferative disorder suitable for treatment with anthracyclines, in order to provide critical information to the patient and clinician as to the likely progression of the disease when treated by means of a therapy comprising at least one anthracycline. It will be appreciated, therefore, that the methods and nucleic acids exemplified herein can serve to improve a patient's quality of life and odds of treatment success by allowing both patient and clinician a more accurate assessment of the patient's treatment options.

The present invention makes available a method for the improved treatment of cell proliferative disorders, by enabling the improved prediction of a patient's survival, in particular by predicting the likelihood of relapse post-surgery both with or without anthracycline treatment.

The method according to the invention may be used for the analysis of a wide variety of cell proliferative disorders suitable for treatment with anthracyclines including, but not limited to, breast cancer, ovarian cancer, transitional cell bladder cancer, bronchogenic lung cancer, thyroid cancer, pancreatic cancer, prostate cancer, uterine cancer, testicular cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, Kaposi's sarcoma, Ewing's tumor, refractory multiple myeloma, squamous cell carcinomas of the head, neck, cervix, and vagina. Preferably the method according to the invention is used in the analysis of breast cancer patients.

The method according to the invention may be used to provide a prediction of patient survival and/or relapse following treatment by means of a therapy comprising at least one anthracycline.

It is particularly preferred that said prediction is defined in terms of patient survival and/or relapse. In this embodiment patients survival times and/or relapse are predicted according to their gene expression or genetic or epigenetic modifications thereof. In this aspect of the invention it is particularly preferred that said patients are tested prior to receiving any adjuvant anthracycline treatment.

It is herein described that aberrant expression of at least one gene selected from the group consisting PITX2; TFF1 and PLAU and/or regulatory or promoter regions thereof is correlated to outcome of treatment of cell proliferative disorder patients wherein said treatment comprises at least one anthracycline.

This marker thereby provides a novel means for the characterization of cell proliferative disorders. As described herein determination of the expression of at least one gene selected from the group consisting PITX2; TFF1 and PLAU and/or regulatory or promoter regions thereof enables the prediction of treatment response of a patient treated with a therapy comprising at least one anthracycline.

In a further embodiment of the invention the aberrant expression of at least two genes selected from the group consisting of PITX2; TFF1 and PLAU is determined.

In a further aspect the invention relates to new methods and sequences, which may be used as tools for the selection of suitable treatments of patients diagnosed with cell proliferative disease based on a prediction of likelihood of relapse, survival or outcome.

One aspect of the invention is the provision of methods for providing a prediction of outcome of a treatment comprising at least one anthracycline of a patient with a cell proliferative disorder. Preferably said prognosis and/or prediction is provided in terms of likelihood of relapse or the survival of said patient. It is further preferred that said survival is disease free survival or metastasis free survival. It is also preferred that said disease is breast cancer. These methods comprise the analysis of the expression levels of at least one gene selected form the group consisting of PITX2; TFF1 and PLAU and/or regulatory regions thereof.

In further embodiments the method comprises analysis of the expression of a 'gene panel' comprising at least two genes selected from the group consisting of PITX2; TFF1 and PLAU.

It is preferred that said patients are analyzed prior to receiving any treatment comprising at least one anthracycline.

The present invention discloses a method for the use of at least one gene selected from the group consisting PITX2; TFF1 and PLAU as a marker of the prediction of outcome of anthracycline treatment.

The sequences of said genes and preferred CpG rich regions thereof are disclosed in the sequence listing, it is preferred that any transcript thereof or polypeptide transcribed therefrom is analysed and that the predictive outcome of anthracycline treatment in a subject is determined therefrom.

Said method may be enabled by means of any analysis of the expression of a RNA transcribed therefrom or polypeptide or protein translated from said RNA, preferably by means of mRNA expression analysis or polypeptide expression analysis. Accordingly the present invention also provides prognostic assays and methods, both quantitative and qualitative for detecting the expression of at least one gene selected from the group consisting PITX2; TFF1 and PLAU in a subject with a cell proliferative disorder and determining therefrom upon the prediction of outcome of treatment comprising at least one anthracycline of said subject.

Aberrant expression of mRNA transcribed from the genes PITX2; TFF1 and PLAU are associated with prognosis and/or prediction of treatment outcome of carcinoma.

Over expression is associated with hypomethylation, under expression is associated with hypermethylation. The associated between the genes according to the invention and methylation status thereof is provided in Table 5.

To detect the presence of mRNA encoding a gene or genomic sequence, a sample is obtained from a patient. The sample may be any suitable sample comprising cellular matter of the tumour most preferably the primary tumour. Suitable sample types include cell lines, histological slides, paraffin embedded tissues, biopsies, tissue embedded in paraffin, bodily fluids (such as but not limited to nipple aspirate and blood) and all possible combinations thereof.

In a particularly preferred embodiment of the method said source is blood. The sample may be treated to extract the RNA contained therein. The resulting nucleic acid from the sample is then analysed. Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR.

Particularly preferred is the use of the reverse transcription/polymerisation chain reaction technique. The method of reverse transcription/PCR is well known in the art (for example, see Watson and Fleming, supra).

The reverse transcription/PCR method can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end primer. Typically, the primer contains an oligo(dT) sequence. The cDNA thus produced is then amplified by means of PCR. (Belyavsky et al, Nucl Acid Res 17:2919-2932, 1989; Krug and Berger, Methods in Enzymology, Academic Press, N.Y., Vol. 152, pp. 316-325, 1987 which are incorporated by reference). Further preferred is the "Real-time" variant of reverse transcription PCR, wherein the PCR product is detect by means of hybridisation probes (E.g TaqMan, Lightcycler, Molecular Beacons and Scorpion) or SYBR green. The detected signal from the probes or SYBR green is then quantitated either by reference to a standard curve or by comparing the Ct values to that of a calibration standard. Analysis of housekeeping genes is often used to normalize the results.

In Northern blot analysis total or poly(A)+ mRNA is run on a denaturing agarose gel and detected by hybridization to a labeled probe in the dried gel itself or on a membrane. The resulting signal is proportional to the amount of target RNA in the RNA population.

Comparing the signals from two or more cell populations or tissues reveals relative differences in gene expression levels. Absolute quantitation can be performed by comparing the signal to a standard curve generated using known amounts of an in vitro transcript corresponding to the target RNA. Analysis of housekeeping genes, genes whose expression levels are expected to remain relatively constant regardless of conditions, is often used to normalize the results, eliminating any apparent differences caused by unequal transfer of RNA to the membrane or unequal loading of RNA on the gel.

The first step in Northern analysis is isolating pure, intact RNA from the cells or tissue of interest. Because Northern blots distinguish RNAs by size, sample integrity influences the degree to which a signal is localized in a single band. Partially degraded RNA samples will result in the signal being smeared or distributed over several bands with an overall loss in sensitivity and possibly an erroneous interpretation of the data. In Northern blot analysis, DNA, RNA and oligonucleotide probes can be used and these probes are preferably labelled (e.g. radioactive labels, massa labels or fluorescent labels). The size of the target RNA, not the probe, will determine the size of the detected band, so methods such as random-primed labeling, which generates probes of variable lengths, are suitable for probe synthesis. The specific activity of the probe will determine the level of sensitivity, so it is preferred that probes with high specific activities (>$10^9$ cpm/µg), are used. Labeling methods that produce probes with lower specific activities can be used to detect more abundant RNAs.

In an RNase protection assay, the RNA target and an RNA probe of a defined length are hybridized in solution. Following hybridization, the RNA is digested with RNases specific for single-stranded nucleic acids to remove any unhybridized, single-stranded target RNA and probe. The RNases are inactivated, and the RNA is separated e.g. by denaturing polyacrylamide gel electrophoresis. The amount of intact RNA probe is proportional to the amount of target RNA in the RNA population. RPA can be used for relative and absolute quantitation of gene expression and also for mapping RNA structure, such as intron/exon boundaries and transcription start sites. The RNase protection assay is preferable to Northern blot analysis as it generally has a lower limit of detection.

The antisense RNA probes used in RPA are generated by in vitro transcription of a DNA template with a defined endpoint and are typically in the range of 50-600 nucleotides. The use of RNA probes that include additional sequences not homologous to the target RNA allows the protected fragment to be distinguished from the full-length probe. RNA probes are typically used instead of DNA probes due to the ease of generating single-stranded RNA probes and the reproducibility and reliability of RNA:RNA duplex digestion with RNases (Ausubel et al. 2003), particularly preferred are probes with high specific activities.

Particularly preferred is the use of microarrays. The microarray analysis process can be divided into two main parts. First is the immobilization of known gene sequences onto glass slides or other solid support followed by hybridization of the fluorescently labeled cDNA (comprising the sequences to be interrogated) to the known genes immobilized on the glass slide. After hybridization, arrays are scanned using a fluorescent microarray scanner. Analyzing the relative fluorescent intensity of different genes provides a measure of the differences in gene expression.

One method of creating DNA arrays is by immobilizing PCR products onto activated glass surfaces. Typically, probes are first generated by PCR or RT-PCR and cloned into a plasmid vector to create a library of 10,000 or more clones. This plasmid library may be stored in *E. coli*. To generate a new array, the *E. coli* are grown, plasmids are isolated and the cloned genes are amplified with primers common to the plasmid backbone. These amplified products are typically in the range of 100-1,000 bases. Automated means are then used to print the amplified clones on an array of 50-200 μm spots on a specially prepared glass slide or other suitable support.

DNA arrays can also be generated by immobilizing pre-synthesized oligonucleotides onto prepared glass slides. In this case, representative gene sequences are manufactured and prepared using standard oligonucleotide synthesis and purification methods. These synthesized gene sequences are complementary to the genes of interest (in this case PITX2; TFF1 and PLAU) and tend to be shorter sequences in the range of 25-70 nucleotides. Alternatively, immobilized oligos can be chemically synthesized in situ on the surface of the slide. In situ oligonucleotide synthesis involves the consecutive addition of the appropriate nucleotides to the spots on the microarray; spots not receiving a nucleotide are protected during each stage of the process using physical or virtual masks.

In expression profiling microarray experiments, the RNA templates used are representative of the transcription profile of the cells or tissues under study. RNA is first isolated from the cell populations or tissues to be compared. Each RNA sample is then used as a template to generate fluorescently labeled cDNA via a reverse transcription reaction. Fluorescent labeling of the cDNA can be accomplished by either direct labeling or indirect labeling methods. During direct labeling, fluorescently modified nucleotides (e.g., Cy®3- or Cy®5-dCTP) are incorporated directly into the cDNA during the reverse transcription. Alternatively, indirect labeling can be achieved by incorporating aminoallyl-modified nucleotides during cDNA synthesis and then conjugating an N-hydroxysuccinimide (NHS)-ester dye to the aminoallyl-modified cDNA after the reverse transcription reaction is complete. Alternatively, the probe may be unlabeled, but may be detectable by specific binding with a ligand which is labelled, either directly or indirectly. Suitable labels and methods for labelling ligands (and probes) are known in the art, and include, for example, radioactive labels which may be incorporated by known methods (e.g., nick translation or kinasing). Other suitable labels include but are not limited to biotin, fluorescent groups, chemiluminescent groups (e.g., dioxetanes, particularly triggered dioxetanes), enzymes, antibodies, and the like.

To perform differential gene expression analysis, cDNA generated from different RNA samples are labeled in different colors. For example, when comparing RNA from test and reference tissue samples, the cDNA generated from the test RNA can be labeled with Cy®3, while the cDNA generated from the reference RNA sample can be labeled with Cy®5. The resulting labeled cDNA is purified to remove unincorporated nucleotides, free dye and residual RNA. Following purification, the labeled cDNA samples are combined and then hybridized to the microarray. The stringency of hybridisation is determined by a number of factors during hybridisation and during the washing procedure, including temperature, ionic strength, length of time and concentration of formamide. These factors are outlined in, for example, Sambrook et al. (Molecular Cloning: A Laboratory Manual, 2nd ed., 1989). The microarray is scanned post-hybridization using a fluorescent microarray scanner. The fluorescent intensity of each spot indicates the level of expression for that gene; bright spots correspond to strongly expressed genes, while dim spots indicate weak expression. Multiple targets labeled in different dye colors can be analyzed simultaneously to determine which genes are differentially expressed.

Once the images are obtained, the raw data must be analyzed. First, the background fluorescence must be subtracted from the fluorescence of each spot. The data is then normalized to a control sequence, such as an exogenously added RNA, or a housekeeping gene to account for any nonspecific hybridization, array imperfections or variability in the array setup, cDNA labeling, hybridization or washing. Data normalization allows the results of multiple arrays to be compared.

The present invention further provides for methods for the detection of the presence of the polypeptide encoded by said gene sequences in a sample obtained from a patient.

Aberrant levels of polypeptide expression of the polypeptides encoded by PITX2; TFF1 and PLAU are associated with cell proliferative disorder Anthracycline treatment outcome.

Accordingly over or under expression of said polypeptides are associable with anthracycline treatment outcome according to Table 5.

Any method known in the art for detecting polypeptides can be used. Such methods include, but are not limited to immunodiffusion, immunoelectrophoresis, immunochemical methods, binder-ligand assays, immunohistochemical techniques, agglutination and complement assays. (e.g., see Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labelled polypeptide or derivative thereof.

Certain embodiments of the present invention comprise the use of antibodies specific to a polypeptide encoded by a gene selected from the group consisting PITX2; TFF1 and PLAU.

Such antibodies are useful for cancer prognostic and/or predictive applications. In certain embodiments production of monoclonal or polyclonal antibodies can be induced by the use of the coded polypeptide as an antigene. Such antibodies may in turn be used to detect expressed polypeptides as markers for cell proliferative disorder prognosis. The levels of such polypeptides present may be quantified by conventional methods. Antibody-polypeptide binding may be detected and quantified by a variety of means known in the art, such as labelling with fluorescent or radioactive ligands. The invention further comprises kits for performing the above-mentioned procedures, wherein such kits contain antibodies specific for the investigated polypeptides.

Numerous competitive and non-competitive polypeptide binding immunoassays are well known in the art. Antibodies employed in such assays may be unlabeled, for example as used in agglutination tests, or labelled for use a wide variety of assay methods. Labels that can be used include radionuclides, enzymes, fluorescers, chemiluminescers, enzyme substrates or cofactors, enzyme inhibitors, particles, dyes and the like. Preferred assays include but are not limited to radioimmunoassay (RIA), enzyme immunoassays, e.g., enzyme-linked immunosorbent assay (ELISA), fluorescent immunoassays and the like. Polyclonal or monoclonal antibodies or epitopes thereof can be made for use in immunoassays by any of a number of methods known in the art.

One approach for preparing antibodies to a polypeptide is the selection and preparation of an amino acid sequence of all or part of the polypeptide, chemically synthesising the amino acid sequence and injecting it into an appropriate animal, usually a rabbit or a mouse (Milstein and Kohler Nature 256:495-497, 1975; Gulfre and Milstein, Methods in Enzymology: Immunochemical Techniques 73:1-46, Langone and Banatis eds., Academic Press, 1981 which are incorporated by reference). Methods for preparation of the polypeptides or epitopes thereof include, but are not limited to chemical synthesis, recombinant DNA techniques or isolation from biological samples.

In the final step of the method the prognosis of the patient is determined, whereby overexpression is indicative of negative prognosis. The term overexpression shall be taken to mean expression at a detected level greater than a predetermined cut off which may be selected from the group consisting of the mean, median or an optimised threshold value.

Another aspect of the invention provides a kit for use in providing a prognosis of a subject with a cell proliferative disorder, comprising: a means for detecting polypeptides of at least one gen gene selected form the group consisting PITX2; TFF1 and PLAU.

The means for detecting the polypeptides comprise preferably antibodies, antibody derivatives, or antibody fragments. The polypeptides are most preferred detected by means of Western blotting utilizing a labelled antibody. In another embodiment of the invention the kit further comprising means for obtaining a biological sample of the patient. Preferred is a kit which further comprises a container suitable for containing the means for detecting the polypeptides and the biological sample of the patient, and most preferably further comprises instructions for use and interpretation of the kit results.

In a preferred embodiment the kit for use in determining treatment strategy for a patient with a cell proliferative disorder, comprises: (a) a means for detecting polypeptides of at least one gene selected from the group consisting PITX2; TFF1 and PLAU; (b) a container suitable for containing the said means and the biological sample of the patient comprising the polypeptides wherein the means can form complexes with the polypeptides; (c) a means to detect the complexes of (b); and optionally (d) instructions for use and interpretation of the kit results. The kit may also contain other components such as buffers or solutions suitable for blocking, washing or coating, packaged in a separate container.

In one embodiment of the method aberrant expression of at least one gene selected from the group consisting PITX2; TFF1 and PLAU may be detected by analysis of loss of heterozygosity of the gene.

In a first step genomic DNA is isolated from a biological sample of the patient's tumor. The isolated DNA is then analyzed for LOH by any means standard in the art including but not limited to amplification of the gene locus or associated microsatellite markers. Said amplification may be carried out by any means standard in the art including polymerase chain reaction (PCR), strand displacement amplification (SDA) and isothermal amplification.

The level of amplificate is then detected by any means known in the art including but not limited to gel electrophoresis and detection by probes (including Real Time PCR). Furthermore the amplificates may be labeled in order to aid said detection. Suitable detectable labels include but are not limited to fluorescence label, radioactive labels and mass labels the suitable use of which shall be described herein.

The detection of a decreased amount of an amplificate corresponding to one of the amplified alleles in a test sample as relative to that of a heterozygous control sample is indicative of LOH.

Another aspect of the invention relates to a kit for use in providing a prognosis of a subject with a cell proliferative disorder, said kit comprising: a means for measuring the level of transcription of at least one gene selected from the group consisting the genes PITX2; TFF1 and PLAU.

In a preferred embodiment the means for measuring the level of transcription comprise oligonucleotides or polynucleotides able to hybridise under stringent or moderately stringent conditions to the transcription products of at least one gene selected from the group consisting PITX2; TFF1 and PLAU.

In a most preferred embodiment the level of transcription is determined by techniques selected from the group of Northern blot analysis, reverse transcriptase PCR, real-time PCR, RNAse protection, and microarray. In another embodiment of the invention the kit further comprises means for obtaining a biological sample of the patient. Preferred is a kit which further comprises a container suitable for containing the means for measuring the level of transcription and the biological sample of the patient, and most preferably further comprises instructions for use and interpretation of the kit results.

In a preferred embodiment the kit for use in determining treatment strategy for a patient with a cell proliferative disorder comprises (a) a plurality of oligonucleotides or polynucleotides able to hybridise under stringent or moderately stringent conditions to the transcription products of at least one gene selected from the group consisting PITX2; TFF1 and PLAU; (b) a container suitable for containing the oligonucleotides or polynucleotides and a biological sample of the patient comprising the transcription products wherein the oligonucleotides or polynucleotide can hybridise under stringent or moderately stringent conditions to the transcription products, (c) means to detect the hybridisation of (b); and optionally, (d) instructions for use and interpretation of the kit results.

The kit may also contain other components such as hybridization buffer (where the oligonucleotides are to be used as a probe) packaged in a separate container. Alternatively, where the oligonucleotides are to be used to amplify a target region, the kit may contain, packaged in separate containers, a polymerase and a reaction buffer optimized for primer extension mediated by the polymerase, such as PCR.

Most preferably a kit according to the embodiments of the present invention is used for the determination of expression step of the methods according to other aspects of the invention.

In one aspect the invention provides significant improvements over the state of the art in that it provides the first cancer treatment response markers for a treatment comprising an anthracycline.

In the most preferred embodiment of the invention the analysis of expression is carried out by means of CpG methylation analysis of at least one of the genes selected from the group consisting PITX2; TFF1 and PLAU. It is further preferred that the methylation state of the CpG dinucleotides within the genomic sequence of said genes according to SEQ ID NO: 1 to SEQ ID NO: 8 and sequences complementary thereto are analyzed.

In one embodiment the methylation state of the CpG dinucleotides within the genomic sequence of said genes according to Table 1 (SEQ ID NO: 1 to SEQ ID NO: 3) and sequences complementary thereto are analyzed. Table 4 provides particularly preferred CpG rich sequences of the genes according to Table 1. Accordingly it is preferred that said CpG positions are within a CpG rich region of said genes as provided in Table 4 (SEQ ID NO: 4 to SEQ ID NO: 8).

The methylation pattern of the genes according to the present invention and their promoter and regulatory elements have heretofore not been analyzed with regard to prediction of outcome of anthracycline treatment. Due to the degeneracy of the genetic code, the genomic sequences as provided in the sequence listing should be interpreted so as to include all substantially similar and equivalent sequences of a gene which encodes a polypeptide with the biological activity of any of those encoded by the genes of Table 1.

Most preferably the following method is used to detect methylation within the genes PITX2; TFF1 and PLAU and/or regulatory or promoter regions thereof.

The method for the analysis of methylation comprises contacting a nucleic acid sample obtained from a subject with at least one reagent or a series of reagents, wherein said reagent or series of reagents, distinguishes between methylated and non-methylated CpG dinucleotides within the target nucleic acid.

Preferably, said method comprises the following steps: In the first step, a sample of the tissue to be analyzed is obtained. The source may be any suitable source, preferably, the source of the sample is selected from the group consisting of histological slides, biopsies, paraffin-embedded tissue, bodily fluids, plasma, serum, stool, urine, blood, nipple aspirate and combinations thereof. Preferably, the source is tumor tissue, biopsies, serum, urine, blood or nipple aspirate. The most preferred source, is the tumor sample, surgically removed from the patient or a biopsy sample of said patient.

The DNA is then isolated from the sample. Genomic DNA may be isolated by any means standard in the art, including the use of commercially available kits. Briefly, wherein the DNA of interest is encapsulated in/by a cellular membrane the biological sample must be disrupted and lysed by enzymatic, chemical or mechanical means. The DNA solution may then be cleared of proteins and other contaminants e.g. by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA.

The genomic DNA sample is then treated in such a manner that cytosine bases which are unmethylated at the 5'-position are converted to uracil, thymine, or another base which is dissimilar to cytosine in terms of hybridization behavior. This will be understood as "treatment" or "pretreatment" herein.

The above described pre-treatment of genomic DNA is preferably carried out with bisulfite (hydrogen sulfite, disulfite) and subsequent alkaline hydrolysis which results in a conversion of non-methylated cytosine nucleobases to uracil or to another base which is dissimilar to cytosine in terms of base pairing behavior. Enclosing the DNA to be analyzed in an agarose matrix, thereby preventing the diffusion and renaturation of the DNA (bisulfite only reacts with single-stranded DNA), and replacing all precipitation and purification steps with fast dialysis (Olek A, et al., A modified and improved method for bisulfite based cytosine methylation analysis, *Nucleic Acids Res.* 24:5064-6, 1996) is one preferred example how to perform said pre-treatment. It is further preferred that the bisulfite treatment is carried out in the presence of a radical scavenger or DNA denaturing agent.

The treated DNA is then analyzed in order to determine the methylation state of at least one of the genes selected from the group consisting PITX2; TFF1 and PLAU and/or regulatory regions thereof associated with outcome of a treatment comprising at least one anthracycline. It is further preferred that the sequences of said genes as described in the accompanying sequence listing (see Table 1, or more preferably Table 4) are analyzed.

In the third step of the method, fragments of the pretreated DNA are amplified. Wherein the source of the DNA is free DNA from serum, or DNA extracted from paraffin it is particularly preferred that the size of the amplificate fragment is between 100 and 200 base pairs in length, and wherein said DNA source is extracted from cellular sources (e.g. tissues, biopsies, cell lines) it is preferred that the amplificate is between 100 and 350 base pairs in length. It is particularly preferred that said amplificates comprise at least one 20 base pair sequence comprising at least three CpG dinucleotides. Said amplification is carried out using sets of primer oligonucleotides according to the present invention, and a preferably heat-stable polymerase. The amplification of several DNA segments can be carried out simultaneously in one and the same reaction vessel, in one embodiment of the method preferably six or more fragments are amplified simultaneously. Typically, the amplification is carried out using a polymerase chain reaction (PCR). The set of primer oligonucleotides includes at least two oligonucleotides whose sequences are each reverse complementary, identical, or hybridize under stringent or highly stringent conditions to an at least 18-base-pair long segment of a base sequence selected from the group consisting SEQ ID NO: 9 to SEQ ID NO: 40 and sequences complementary thereto. In a first embodiment the set of primer oligonucleotides includes at least two oligonucleotides whose sequences are each reverse complementary, identical, or hybridize under stringent or highly stringent conditions to an at least 18-base-pair long segment of a pretreated sequence as listed in Table 1 (SEQ ID NO: 9 to SEQ ID NO: 14 and SEQ ID NO: 25 to SEQ ID NO: 30) and sequences complementary thereto. In a further preferred embodiment the set of primer oligonucleotides includes at least two oligonucleotides whose sequences are each reverse complementary, identical, or hybridize under stringent or highly stringent conditions to an at least 18-base-pair long segment of a pretreated sequence as listed in Table 4 (SEQ ID NO: 15 to SEQ ID NO: 24 and SEQ ID NO: 31 to SEQ ID NO: 40) and sequences complementary thereto.

In an alternate embodiment of the method, the methylation status of pre-selected CpG positions within the nucleic acid sequences comprising SEQ ID NO: 1 to SEQ ID NO: 8 may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primers pairs contain at least one primer which hybridizes to a bisulfite treated CpG dinucleotide. Therefore, the sequence of said primers comprises at least one CpG, TpG or CpA dinucleotide. MSP primers specific for non-methylated DNA contain a "T" at the 3' position of the C position in the CpG. Preferably, therefore, the base sequence of said primers is required to comprise a sequence having a length of at least 18 nucleotides which hybridizes to a pretreated nucleic acid sequence according to SEQ ID NO: 9 to SEQ ID NO: 40 and sequences complementary thereto, wherein the base sequence of said oligomers comprises at least one CpG, tpG or Cpa dinucleotide. In a first embodiment said sequence has a length of at least 18 nucleotides which hybridizes to a pretreated nucleic acid sequence selected from Table 1 (SEQ ID NO: 9 to SEQ ID NO: 14 and SEQ ID NO: 25 to SEQ ID NO: 30) and sequences complementary thereto. However in a preferred embodiment said sequence has a length of at least 18 nucleotides which hybridizes to a pretreated nucleic acid sequence selected from Table 4 (SEQ ID NO: 15 to SEQ ID NO: 24 and SEQ ID NO: 31 to SEQ ID NO: 40), and sequences complementary thereto.

In this embodiment of the method according to the invention it is particularly preferred that the MSP primers comprise between 2 and 4 CpG, tpG or Cpa dinucleotides. It is further preferred that said dinucleotides are located within the 3' half of the primer e.g. wherein a primer is 18 bases in length the specified dinucleotides are located within the first 9 bases form the 3' end of the molecule. In addition to the CpG, tpG or Cpa dinucleotides it is further preferred that said primers should further comprise several bisulfite converted bases (i.e. cytosine converted to thymine, or on the hybridizing strand, guanine converted to adenosine). In a further preferred embodiment said primers are designed so as to comprise no more than 2 cytosine or guanine bases.

The fragments obtained by means of the amplification can carry a directly or indirectly detectable label. Preferred are labels in the form of fluorescence labels, radionuclides, or detachable molecule fragments having a typical mass which can be detected in a mass spectrometer. Where said labels are mass labels, it is preferred that the labeled amplificates have a single positive or negative net charge, allowing for better detectability in the mass spectrometer. The detection may be carried out and visualized by means of, e.g., matrix assisted laser desorption/ionization mass spectrometry (MALDI) or using electron spray mass spectrometry (ESI).

Matrix Assisted Laser Desorption/Ionization Mass Spectrometry (MALDI-TOF) is a very efficient development for the analysis of biomolecules (Karas and Hillenkamp, *Anal Chem.*, 60:2299-301, 1988). An analyte is embedded in a light-absorbing matrix. The matrix is evaporated by a short laser pulse thus transporting the analyte molecule into the vapor phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than bigger ones. MALDI-TOF spectrometry is well suited to the analysis of peptides and proteins. The analysis of nucleic acids is somewhat more difficult (Gut and Beck, *Current Innovations and Future Trends,* 1:147-57, 1995). The sensitivity with respect to nucleic acid analysis is approximately 100-times less than for peptides, and decreases disproportionally with increasing fragment size. Moreover, for nucleic acids having a multiply negatively charged backbone, the ionisation process via the matrix is considerably less efficient. In MALDI-TOF spectrometry, the selection of the matrix plays an eminently important role. For the desorption of peptides, several very efficient matrixes have been found which produce a very fine crystallisation. There are now several responsive matrixes for DNA, however, the difference in sensitivity between peptides and nucleic acids has not been reduced. This difference in sensitivity can be reduced, however, by chemically modifying the DNA in such a manner that it becomes more similar to a peptide. For example, phosphorothioate nucleic acids, in which the usual phosphates of the backbone are substituted with thiophosphates, can be converted into a charge-neutral DNA using simple alkylation chemistry (Gut and Beck, *Nucleic Acids Res.* 23: 1367-73, 1995). The coupling of a charge tag to this modified DNA results in an increase in MALDI-TOF sensitivity to the same level as that found for peptides. A further advantage of charge tagging is the increased stability of the analysis against impurities, which makes the detection of unmodified substrates considerably more difficult.

In a particularly preferred embodiment of the method the amplification of step three is carried out in the presence of at least one species of blocker oligonucleotides. The use of such blocker oligonucleotides has been described by Yu et al., *BioTechniques* 23:714-720, 1997. The use of blocking oligonucleotides enables the improved specificity of the amplification of a sub-population of nucleic acids. Blocking probes hybridized to a nucleic acid suppress, or hinder the polymerase mediated amplification of said nucleic acid. In one embodiment of the method blocking oligonucleotides are designed so as to hybridize to background DNA. In a further embodiment of the method said oligonucleotides are designed so as to hinder or suppress the amplification of unmethylated nucleic acids as opposed to methylated nucleic acids or vice versa.

Blocking probe oligonucleotides are hybridized to the bisulfite treated nucleic acid concurrently with the PCR primers. PCR amplification of the nucleic acid is terminated at the 5' position of the blocking probe, such that amplification of a nucleic acid is suppressed where the complementary sequence to the blocking probe is present. The probes may be designed to hybridize to the bisulfite treated nucleic acid in a methylation status specific manner. For example, for detection of methylated nucleic acids within a population of unmethylated nucleic acids, suppression of the amplification of nucleic acids which are unmethylated at the position in question would be carried out by the use of blocking probes comprising a 'TpG' at the position in question, as opposed to a 'CpG.' In one embodiment of the method the sequence of said blocking oligonucleotides should be identical or complementary to a sequence at least 18 base pairs in length selected from the group consisting of SEQ ID NO: 9 to SEQ ID NO: 40 preferably comprising one or more CpG, TpG or CpA dinucleotides. In a first embodiment of the method the sequence of said blocking oligonucleotides should be identical or complementary to a sequence at least 18 base pairs in length selected from a pretreated nucleic acid sequence selected from Table 1 (SEQ ID NO: 9 to SEQ ID NO: 14 and SEQ ID NO: 25 to SEQ ID NO: 30), and sequences complementary thereto preferably comprising one or more CpG, TpG or CpA dinucleotides. In a preferred embodiment of the method the sequence of said blocking oligonucleotides should be identical or complementary to a sequence at least 18 base pairs in length selected from a pretreated nucleic acid sequence selected from Table 4 (SEQ ID NO: 15 to SEQ ID NO: 24 and SEQ ID NO: 31 to SEQ ID NO: 40), and sequences complementary thereto preferably comprising one or more CpG, TpG or CpA dinucleotides.

For PCR methods using blocker oligonucleotides, efficient disruption of polymerase-mediated amplification requires that blocker oligonucleotides not be elongated by the polymerase. Preferably, this is achieved through the use of blockers that are 3'-deoxyoligonucleotides, or oligonucleotides derivatised at the 3' position with other than a "free" hydroxyl group. For example, 3'-O-acetyl oligonucleotides are representative of a preferred class of blocker molecule.

Additionally, polymerase-mediated decomposition of the blocker oligonucleotides should be precluded. Preferably, such preclusion comprises either use of a polymerase lacking 5'-3' exonuclease activity, or use of modified blocker oligonucleotides having, for example, thioate bridges at the 5'-termini thereof that render the blocker molecule nuclease-resistant. Particular applications may not require such 5' modifications of the blocker. For example, if the blockerand primer-binding sites overlap, thereby precluding binding of the primer (e.g., with excess blocker), degradation of the blocker oligonucleotide will be substantially precluded. This is because the polymerase will not extend the primer toward, and through (in the 5'-3' direction) the blocker—a process that normally results in degradation of the hybridized blocker oligonucleotide.

A particularly preferred blocker/PCR embodiment, for purposes of the present invention and as implemented herein, comprises the use of peptide nucleic acid (PNA) oligomers as blocking oligonucleotides. Such PNA blocker oligomers are ideally suited, because they are neither decomposed nor extended by the polymerase.

In one embodiment of the method, the binding site of the blocking oligonucleotide is identical to, or overlaps with that of the primer and thereby hinders the hybridization of the primer to its binding site. In a further preferred embodiment of the method, two or more such blocking oligonucleotides are used. In a particularly preferred embodiment, the hybridization of one of the blocking oligonucleotides hinders the hybridization of a forward primer, and the hybridization of another of the probe (blocker) oligonucleotides hinders the hybridization of a reverse primer that binds to the amplificate product of said forward primer.

In an alternative embodiment of the method, the blocking oligonucleotide hybridizes to a location between the reverse and forward primer positions of the treated background DNA, thereby hindering the elongation of the primer oligonucleotides.

It is particularly preferred that the blocking oligonucleotides are present in at least 5 times the concentration of the primers.

In the fourth step of the method, the amplificates obtained during the third step of the method are analyzed in order to ascertain the methylation status of the CpG dinucleotides prior to the treatment.

In embodiments where the amplificates are obtained by means of MSP amplification and/or blocking oligonucleotides, the presence or absence of an amplificate is in itself indicative of the methylation state of the CpG positions covered by the primers and or blocking oligonucleotide, according to the base sequences thereof. All possible known molecular biological methods may be used for this detection, including, but not limited to gel electrophoresis, sequencing, liquid chromatography, hybridizations, real time PCR analysis or combinations thereof. This step of the method further acts as a qualitative control of the preceding steps.

In the fourth step of the method amplificates obtained by means of both standard and methylation specific PCR are further analyzed in order to determine the CpG methylation status of the genomic DNA isolated in the first step of the method. This may be carried out by means of hybridization-based methods such as, but not limited to, array technology and probe based technologies as well as by means of techniques such as sequencing and template directed extension.

In one embodiment of the method, the amplificates synthesized in step three are subsequently hybridized to an array or a set of oligonucleotides and/or PNA probes. In this context, the hybridization takes place in the following manner: the set of probes used during the hybridization is preferably composed of at least 2 oligonucleotides or PNA-oligomers; in the process, the amplificates serve as probes which hybridize to oligonucleotides previously bonded to a solid phase; the non-hybridized fragments are subsequently removed; said oligonucleotides contain at least one base sequence having a length of at least 9 nucleotides which is reverse complementary or identical to a segment of the base sequences specified in the of SEQ ID NO: 9 to SEQ ID NO: 40 and the segment comprises at least one CpG, TpG or CpA dinucleotide. In a first embodiment said oligonucleotides contain at least one base sequence having a length of at least 9 nucleotides which is reverse complementary or identical to a segment of the pretreated sequences specified in Table 1 (SEQ ID NO: 9 to SEQ ID NO: 14 and SEQ ID NO: 25 to SEQ ID NO: 30) and the segment comprises at least one CpG, TpG or CpA dinucleotide.

In a preferred embodiment said oligonucleotides contain at least one base sequence having a length of at least 9 nucleotides which is reverse complementary or identical to a segment of the pretreated sequences specified in Table 4 (SEQ ID NO: 15 to SEQ ID NO: 24 and SEQ ID NO: 31 to SEQ ID NO: 40) and the segment comprises at least one CpG, TpG or CpA dinucleotide.

In further embodiments said oligonucleotides contain at least one base sequence having a length of at least 9 nucleotides which is reverse complementary or identical to a segment of the base sequences specified in the of SEQ ID NO: 9 to SEQ ID NO: 40; and the segment comprises at least one CpG, TpG or CpA dinucleotide.

In one embodiment said oligonucleotides contain at least one base sequence having a length of at least 9 nucleotides which is reverse complementary or identical to a segment of the pre-treated sequences specified in Table 1 (SEQ ID NO: 9 to SEQ ID NO: 14 and SEQ ID NO: 25 to SEQ ID NO: 30) and the segment comprises at least one CpG, TpG or CpA dinucleotide.

In a preferred embodiment said oligonucleotides contain at least one base sequence having a length of at least 9 nucleotides which is reverse complementary or identical to a segment of the pretreated sequences specified in Table 4 (SEQ ID NO: 15 to SEQ ID NO: 24 and SEQ ID NO: 31 to SEQ ID NO: 40) and the segment comprises at least one CpG, TpG or CpA dinucleotide.

In a preferred embodiment, said dinucleotide is present in the central third of the oligomer. For example, wherein the oligomer comprises one CpG dinucleotide, said dinucleotide is preferably the fifth to ninth nucleotide from the 5'-end of a 13-mer. In a further embodiment one oligonucleotide exists for the analysis of each CpG dinucleotide within the sequence according to of SEQ ID NO: 4 to SEQ ID NO: 8, and the equivalent positions within of SEQ ID NO: 15 to SEQ ID NO: 24 and SEQ ID NO: 31 to SEQ ID NO: 40. One oligonucleotide exists for the analysis of each CpG dinucleotide within the sequence according to SEQ ID NO: 1 to SEQ ID NO: 8, and the equivalent positions within SEQ ID NO: 9 to SEQ ID NO: 40. Said oligonucleotides may also be present in the form of peptide nucleic acids. The non-hybridized amplificates are then removed. The hybridized amplificates are detected. In this context, it is preferred that labels attached to the amplificates are identifiable at each position of the solid phase at which an oligonucleotide sequence is located.

In yet a further embodiment of the method, the genomic methylation status of the CpG positions may be ascertained by means of oligonucleotide probes that are hybridized to the bisulfite treated DNA concurrently with the PCR amplification primers (wherein said primers may either be methylation specific or standard).

A particularly preferred embodiment of this method is the use of fluorescence-based Real Time Quantitative PCR (Heid et al., *Genome Res.* 6:986-994, 1996; also see U.S. Pat. No. 6,331,393). There are two preferred embodiments of utilizing this method. One embodiment, known as the TaqMan™ assay employs a dual-labeled fluorescent oligonucleotide probe. The TaqMan™ PCR reaction employs the use of a non-extendible interrogating oligonucleotide, called a TaqMan™ probe, which is designed to hybridize to a CpG-rich sequence located between the forward and reverse amplification primers. The TaqMan™ probe further comprises a fluorescent "reporter moiety" and a "quencher moiety" covalently bound to linker moieties (e.g., phosphoramidites) attached to the nucleotides of the TaqMan™ oligonucleotide. Hybridized probes are displaced and broken down by the polymerase of the amplification reaction thereby leading to an increase in fluorescence. For analysis of methylation within nucleic acids subsequent to bisulfite treatment, it is required that the probe be methylation specific, as described in U.S. Pat. No. 6,331,393, (hereby incorporated by reference in its entirety) also known as the MethyLight assay. The second preferred embodiment of this MethyLight technology is the use of dual-probe technology (Lightcycler®), each probe carrying donor or recipient fluorescent moieties, hybridization of two probes in proximity to each other is indicated by an increase or fluorescent amplification primers. Both these techniques may be adapted in a manner suitable for use with bisulfite treated DNA, and moreover for methylation analysis within CpG dinucleotides.

Also any combination of these probes or combinations of these probes with other known probes may be used.

In a further preferred embodiment of the method, the fourth step of the method comprises the use of template-directed oligonucleotide extension, such as MS-SNuPE as described by Gonzalgo and Jones, *Nucleic Acids Res.* 25:2529-2531, 1997. In said embodiment it is preferred that the methylation specific single nucleotide extension primer (MS-SNuPE primer) is identical or complementary to a sequence at least nine but preferably no more than twenty five nucleotides in length of one or more of the sequences taken from the group of SEQ ID NO: 9 to SEQ ID NO: 40. In one embodiment said MS-SNuPE primer is identical or complementary to a sequence at least nine but preferably no more than twenty five nucleotides in length of one or more of the pretreated sequences selected from Table 1 (SEQ ID NO: 9 to SEQ ID NO: 14 and SEQ ID NO: 25 to SEQ ID NO: 30).

In a preferred embodiment said MS-SNuPE primer is identical or complementary to a sequence at least nine but preferably no more than twenty five nucleotides in length of one or more of the pretreated sequences selected from Table 4 (SEQ ID NO: 15 to SEQ ID NO: 24 and SEQ ID NO: 31 to SEQ ID NO: 40). It is preferred to use fluorescently labeled nucleotides, instead of radiolabeled nucleotides.

In yet a further embodiment of the method, the fourth step of the method comprises sequencing and subsequent sequence analysis of the amplificate generated in the third step of the method (Sanger F., et al., *Proc Natl Acad Sci USA* 74:5463-5467, 1977).

In the most preferred embodiment of the methylation analysis method the genomic nucleic acids are isolated and treated according to the first three steps of the method outlined above, namely:
a) obtaining, from a subject, a biological sample having subject genomic DNA;
b) extracting or otherwise isolating the genomic DNA;
c) treating the genomic DNA of b), or a fragment thereof, with one or more reagents to convert cytosine bases that are unmethylated in the 5-position thereof to uracil or to another base that is detectably dissimilar to cytosine in terms of hybridization properties; and wherein
d) amplifying subsequent to treatment in c) is carried out in a methylation specific manner, namely by use of methylation specific primers or blocking oligonucleotides, and further wherein
e) detecting of the amplificates is carried out by means of a real-time detection probe, as described above.

Preferably, where the subsequent amplification of d) is carried out by means of methylation specific primers, as described above, said methylation specific primers comprise a sequence having a length of at least 9 nucleotides which hybridizes to a treated nucleic acid sequence according to one of SEQ ID NO: 9 to SEQ ID NO: 40 and sequences complementary thereto, wherein the base sequence of said oligomers comprises at least one CpG dinucleotide. In one embodiment said methylation specific primers comprise a sequence having a length of at least 9 nucleotides which hybridizes to a pretreated nucleic acid sequence selected from Table 1 (SEQ ID NO: 9 to SEQ ID NO: 14 and SEQ ID NO: 25 to SEQ ID NO: 30) and sequences complementary thereto, wherein the base sequence of said oligomers comprises at least one CpG dinucleotide.

It is preferred that said methylation specific primers comprise a sequence having a length of at least 9 nucleotides which hybridizes to a pretreated nucleic acid sequence selected from Table 4 (SEQ ID NO: 15 to SEQ ID NO: 24 and SEQ ID NO: 31 to SEQ ID NO: 40) and sequences complementary thereto, wherein the base sequence of said oligomers comprises at least one CpG dinucleotide.

Additionally, further methylation specific primers may also be used for the analysis of a gene panel as described above wherein said primers comprise a sequence having a length of at least 9 nucleotides which hybridizes to a treated nucleic acid sequence according to one of SEQ ID NO: 9 to SEQ ID NO: 40 and sequences complementary thereto, wherein the base sequence of said oligomers comprises at least one CpG dinucleotide.

In an alternative most preferred embodiment of the method, the subsequent amplification of d) is carried out in the presence of blocking oligonucleotides, as described above. It is particularly preferred that said blocking oligonucleotides comprise a sequence having a length of at least 9 nucleotides which hybridizes to a treated nucleic acid sequence according to one of SEQ ID NO: 9 to SEQ ID NO: 40 and sequences complementary thereto, wherein the base sequence of said oligomers comprises at least one CpG, TpG or CpA dinucleotide.

It is preferred that said blocking oligonucleotides comprise a sequence having a length of at least 9 nucleotides which hybridizes to a pretreated nucleic acid sequence selected from Table 1 (SEQ ID NO: 9 to SEQ ID NO: 14 and SEQ ID NO: 25 to SEQ ID NO: 30) and sequences complementary thereto, wherein the base sequence of said oligomers comprises at least one CpG dinucleotide.

It is preferred that said blocking oligonucleotides comprise a sequence having a length of at least 9 nucleotides which hybridizes to a pretreated nucleic acid sequence selected from Table 4 (SEQ ID NO: 15 to SEQ ID NO: 24 and SEQ ID NO: 31 to SEQ ID NO: 40) and sequences complementary thereto, wherein the base sequence of said oligomers comprises at least one CpG dinucleotide.

Step e) of the method, namely the detection of the specific amplificates indicative of the methylation status of one or more CpG positions according to SEQ ID NO: 9 to SEQ ID NO: 14 and SEQ ID NO: 25 to SEQ ID NO: 30, is carried out by means of real-time detection methods as described above.

Additional embodiments of the invention provide a method for the analysis of the methylation status of at least one gene selected from the group consisting of PITX2; TFF1 and PLAU and/or regulatory regions thereof without the need for pre-treatment.

Methods are known in the art wherein a methylation sensitive restriction enzyme reagent, or a series of restriction enzyme reagents comprising methylation sensitive restriction enzyme reagents that distinguishes between methylated and non-methylated CpG dinucleotides within a target region are utilized in determining methylation, for example but not limited to DMH.

In the first step of such additional embodiments, the genomic DNA sample is isolated from tissue or cellular sources. Genomic DNA may be isolated by any means standard in the art, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA.

Once the nucleic acids have been extracted, the genomic double-stranded DNA is used in the analysis.

In a preferred embodiment, the DNA may be cleaved prior to treatment with methylation sensitive restriction enzymes. Such methods are known in the art and may include both physical and enzymatic means. Particularly preferred is the use of one or a plurality of restriction enzymes which are not methylation sensitive, and whose recognition sites are AT rich and do not comprise CG dinucleotides. The use of such enzymes enables the conservation of CpG islands and CpG rich regions in the fragmented DNA. The non-methylation-specific restriction enzymes are preferably selected from the group consisting of MseI, BfaI, Csp6I, Tru1I, Tvu1I, Tru9I, Tvu9I, MaeI and XspI. Particularly preferred is the use of two or three such enzymes. Particularly preferred is the use of a combination of MseI, BfaI and Csp6I.

The fragmented DNA may then be ligated to adaptor oligonucleotides in order to facilitate subsequent enzymatic amplification. The ligation of oligonucleotides to blunt and sticky ended DNA fragments is known in the art, and is carried out by means of dephosphorylation of the ends (e.g. using calf or shrimp alkaline phosphatase) and subsequent ligation using ligase enzymes (e.g. T4 DNA ligase) in the presence of dATPs. The adaptor oligonucleotides are typically at least 18 base pairs in length.

In the third step, the DNA (or fragments thereof) is then digested with one or more methylation sensitive restriction enzymes. The digestion is carried out such that hydrolysis of the DNA at the restriction site is informative of the methylation status of a specific CpG dinucleotide of at least one gene selected from the group consisting of PITX2; TFF1 and PLAU.

Preferably, the methylation-specific restriction enzyme is selected from the group consisting of Bsi EI, Hga I HinPI, Hpy99I, Ava I, Bce AI, Bsa HI, BisI, BstUI, BshI236I, AccII, BstFNI, McrBC, GlaI, MvnI, HpaII (HapII), HhaI, AciI, SmaI, HinP1I, HpyCH4IV, EagI and mixtures of two or more of the above enzymes. Preferred is a mixture containing the restriction enzymes BstUI, HpaII, HpyCH4IV and HinP1I.

In the fourth step, which is optional but a preferred embodiment, the restriction fragments are amplified. This is preferably carried out using a polymerase chain reaction, and said amplificates may carry suitable detectable labels as discussed above, namely fluorophore labels, radionuclides and mass labels. Particularly preferred is amplification by means of an amplification enzyme and at least two primers comprising, in each case a contiguous sequence at least 16 nucleotides in length that is complementary to, or hybridizes under moderately stringent or stringent conditions to a sequence selected from the group consisting SEQ ID NO: 1 TO SEQ ID NO: 9, or more preferably SEQ ID NO: 4 to SEQ ID NO: 8 and complements thereof. Preferably said contiguous sequence is at least 16, 20 or 25 nucleotides in length. In an alternative embodiment said primers may be complementary to any adaptors linked to the fragments.

In the fifth step the amplificates are detected. The detection may be by any means standard in the art, for example, but not limited to, gel electrophoresis analysis, hybridisation analysis, incorporation of detectable tags within the PCR products, DNA array analysis, MALDI or ESI analysis. Preferably said detection is carried out by hybridisation to at least one nucleic acid or peptide nucleic acid comprising in each case a contiguous sequence at least 16 nucleotides in length that is complementary to, or hybridizes under moderately stringent or stringent conditions to a sequence selected from the group consisting SEQ ID NO: 1 TO SEQ ID NO: 9 or more preferably SEQ ID NO: 4 to SEQ ID NO: 8, and complements thereof. Preferably said contiguous sequence is at least 16, 20 or 25 nucleotides in length.

In the final step of the method the prognosis of the patient after treatment with anthracyclines is determined.

Subsequent to the determination of the methylation state or level of the genomic nucleic acids the outcome of Anthracycline treatment is deduced based upon the methylation state or level of at least one CpG dinucleotide sequence of at least one gene selected from the group consisting of PITX2; TFF1 and PLAU. Wherein said methylation is determined by quantitative means the cut-off point for determining said the presence of methylation is preferably zero (i.e. wherein a sample displays any degree of methylation it is determined as having a methylated status at the analysed CpG position). Nonetheless, it is foreseen that the person skilled in the art may wish to adjust said cut-off value in order to provide an assay of a particularly preferred sensitivity or specificity. Accordingly said cut-off value may be increased (thus increasing the specificity), said cut off value may be within a range selected form the group consisting of 0%-5%, 5%-10%, 10%-15%, 15%-20%, 20%-30% and 30%-50%. Particularly preferred are the cut-offs 10%, 15%, 25%, and 30%.

The correlation of methylation (and the converse expression status) with prognosis after treatment with anthracyclines (i.e. treatment response) may be determined according to Table 5. Patients with predicted positive outcome after said treatment will accordingly have a decreased absolute reduction of risk of recurrence and death after treatment with primary or adjuvant treatment. Patients with predicted negative outcome after said treatment will accordingly have a relatively larger absolute reduction of risk of recurrence and death after said treatment. Accordingly patients with a negative outcome will be considered more suitable candidates for aggressive treatment such as chemotherapy or other adjuvant therapies than patients with a positive outcome. Patients with a positive outcome may accordingly be prevented from over prescription of e.g. chemotherapeutic treatment.

Preferably, the correlation of the expression level of the gene(s) with predicting outcome of treatment comprising at least one anthracycline is done substantially without human intervention.

It is particularly preferred that the classification of the sample is carried out by algorithmic means.

In one embodiment machine learning predictors are trained on the methylation patterns at the investigated CpG sites of the samples with known status. A selection of the CpG positions which are discriminative for the machine learning predictor are used in the panel. In a particularly preferred embodiment of the method, both methods are combined; that is, the machine learning classifier is trained only on the selected CpG positions that are significantly differentially methylated between the classes according to the statistical analysis.

The development of algorithmic methods for the classification of a sample based on the methylation status of the CpG positions within the panel are demonstrated in the examples.

The disclosed invention provides treated nucleic acids, derived from genomic SEQ ID NO: 1 to SEQ ID NO: 8, wherein the treatment is suitable to convert at least one unmethylated cytosine base of the genomic DNA sequence to uracil or another base that is detectably dissimilar to cytosine in terms of hybridization. The genomic sequences in question may comprise one, or more, consecutive or random methylated CpG positions. Said treatment preferably comprises use of a reagent selected from the group consisting of bisulfite, hydrogen sulfite, disulfite, and combinations thereof. In a preferred embodiment of the invention, the objective comprises analysis of a non-naturally occurring modified nucleic acid comprising a sequence of at least 16 contiguous nucleotide bases in length of a sequence selected from the group consisting of SEQ ID NO: 1 to SEQ ID NO: 8, wherein said sequence comprises at least one CpG, TpA or CpA dinucleotide and sequences complementary thereto. The sequences of SEQ ID NO: 9 to SEQ ID NO: 40 provide non-naturally occurring modified versions of the nucleic acid according to SEQ ID NO: 1 to SEQ ID NO: 8, wherein the modification of each genomic sequence results in the synthesis of a nucleic acid having a sequence that is unique and distinct from said genomic sequence as follows. For each sense strand genomic DNA, e.g., SEQ ID NO: 1, four converted versions are disclosed. A first version wherein "C" to "T," but "CpG" remains "CpG" (i.e., corresponds to case where, for the genomic sequence, all "C" residues of CpG dinucleotide sequences are methylated and are thus not converted); a second version discloses the complement of the disclosed genomic DNA sequence (i.e. antisense strand), wherein "C" to "T," but "CpG" remains "CpG" (i.e., corresponds to case where, for all "C" residues of CpG dinucleotide sequences are methylated and are thus not converted). The 'upmethylated' converted sequences of SEQ ID NO: 1 to SEQ ID NO: 8 correspond to SEQ ID NO: 9 to SEQ ID NO: 24. A third chemically converted version of each genomic sequences is provided, wherein "C" to "T" for all "C" residues, including those of "CpG" dinucleotide sequences (i.e., corresponds to case where, for the genomic sequences, all "C" residues of CpG dinucleotide sequences are unmethylated); a final chemically converted version of each sequence, discloses the complement of the disclosed genomic DNA sequence (i.e. antisense strand), wherein "C" to "T" for all "C" residues, including those of "CpG" dinucleotide sequences (i.e., corresponds to case where, for the complement (antisense strand) of each genomic sequence, all "C" residues of CpG dinucleotide sequences are unmethylated). The 'downmethylated' converted sequences of SEQ ID NO: 1 to SEQ ID NO: 8 correspond to SEQ ID NO: 25 to SEQ ID NO: 40.

The invention further discloses oligonucleotide or oligomer for detecting the cytosine methylation state within genomic or pre-treated DNA, according to SEQ ID NO: 1 to SEQ ID NO: 8 and SEQ ID NO: 9 to SEQ ID NO: 40. Said oligonucleotide or oligomer comprising a nucleic acid sequence having a length of at least nine (9) nucleotides which hybridizes, under moderately stringent or stringent conditions (as defined herein above), to a treated nucleic acid sequence according to SEQ ID NO: 9 to SEQ ID NO: 40 and/or sequences complementary thereto, or to a genomic sequence according to SEQ ID NO: 1 to SEQ ID NO: 8 and/or sequences complementary thereto.

Thus, the present invention includes nucleic acid molecules (e.g., oligonucleotides and peptide nucleic acid (PNA) molecules (PNA-oligomers)) that hybridize under moderately stringent and/or stringent hybridization conditions to all or a portion of the sequences SEQ ID NO: 9 to SEQ ID NO: 40, or to the complements thereof. The hybridizing portion of the hybridizing nucleic acids is typically at least 9, 15, 20, 25, 30 or 35 nucleotides in length. However, longer molecules have inventive utility, and are thus within the scope of the present invention.

Preferably, the hybridizing portion of the inventive hybridizing nucleic acids is at least 95%, or at least 98%, or 100% identical to the sequence, or to a portion thereof of SEQ ID NO: 9 to SEQ ID NO: 40, or to the complements thereof.

Hybridizing nucleic acids of the type described herein can be used, for example, as a primer (e.g., a PCR primer), or a diagnostic and/or prognostic probe or primer. Preferably, hybridization of the oligonucleotide probe to a nucleic acid sample is performed under stringent conditions and the probe is 100% identical to the target sequence. Nucleic acid duplex or hybrid stability is expressed as the melting temperature or Tm, which is the temperature at which a probe dissociates from a target DNA. This melting temperature is used to define the required stringency conditions.

For target sequences that are related and substantially identical to the corresponding sequence of SEQ ID NO: 1 to SEQ ID NO: 8 (such as allelic variants and SNPs), rather than identical, it is useful to first establish the lowest temperature at which only homologous hybridization occurs with a particular concentration of salt (e.g., SSC or SSPE). Then, assuming that 1% mismatching results in a 1° C. decrease in the Tm, the temperature of the final wash in the hybridisation reaction is reduced accordingly (for example, if sequences having >95% identity with the probe are sought, the final wash temperature is decreased by 5° C.). In practice, the change in Tm can be between 0.5° C. and 1.5° C. per 1% mismatch.

Examples of inventive oligonucleotides of length X (in nucleotides), as indicated by polynucleotide positions with reference to, e.g., SEQ ID NO:1, include those corresponding to sets (sense and antisense sets) of consecutively overlapping oligonucleotides of length X, where the oligonucleotides within each consecutively overlapping set (corresponding to a given X value) are defined as the finite set of Z oligonucleotides from nucleotide positions:

n to (n+(X−1));

where n=1, 2, 3, . . . (Y−(X−1));

where Y equals the length (nucleotides or base pairs) of SEQ ID NO: 1 (30001);

where X equals the common length (in nucleotides) of each oligonucleotide in the set (e.g., X=20 for a set of consecutively overlapping 20-mers); and where the number (Z) of consecutively overlapping oligomers of length X for a given SEQ ID NO of length Y is equal to Y−(X−1). For example Z=30001−19=29982 for either sense or antisense sets of SEQ ID NO: 1, where X=20.

Preferably, the set is limited to those oligomers that comprise at least one CpG, TpG or CpA dinucleotide.

Examples of inventive 20-mer oligonucleotides include the following set of oligomers (and the antisense set complementary thereto), indicated by polynucleotide positions with reference to SEQ ID NO: 1:1-20, 2-21, 3-22, 4-23, 5-24, . . . and 29982-30001.

Preferably, the set is limited to those oligomers that comprise at least one CpG, TpG or CpA dinucleotide.

Likewise, examples of inventive 25-mer oligonucleotides include the following set of oligomers (and the antisense set complementary thereto), indicated by polynucleotide positions with reference to SEQ ID NO: 1:1-25, 2-26, 3-27, 4-28, 5-29, . . . and 29977-30001.

Preferably, the set is limited to those oligomers that comprise at least one CpG, TpG or CpA dinucleotide.

The present invention encompasses, for each of SEQ ID NO: 1 to SEQ ID NO: 8 and SEQ ID NO: 9 to SEQ ID NO: 40 (sense and antisense), multiple consecutively overlapping sets of oligonucleotides or modified oligonucleotides of length X, where, e.g., X=9, 10, 17, 20, 22, 23, 25, 27, 30 or 35 nucleotides.

The oligonucleotides or oligomers according to the present invention constitute effective tools useful to ascertain genetic and epigenetic parameters of the genomic sequence corresponding to SEQ ID NO: 1 to SEQ ID NO: 8. Preferred sets of such oligonucleotides or modified oligonucleotides of length X are those consecutively overlapping sets of oligomers corresponding to SEQ ID NO: 9 to SEQ ID NO: 40 (and to the complements thereof). Preferably, said oligomers comprise at least one CpG, TpG or CpA dinucleotide.

Particularly preferred oligonucleotides or oligomers according to the present invention are those in which the cytosine of the CpG dinucleotide (or of the corresponding converted TpG or CpA dinucleotide) sequences is within the middle third of the oligonucleotide; that is, where the oligonucleotide is, for example, 13 bases in length, the CpG, TpG or CpA dinucleotide is positioned within the fifth to ninth nucleotide from the 5′-end.

The oligonucleotides of the invention can also be modified by chemically linking the oligonucleotide to one or more moieties or conjugates to enhance the activity, stability or detection of the oligonucleotide. Such moieties or conjugates include chromophores, fluorophores, lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,574,142, 5,585,481, 5,587,371, 5,597,696 and 5,958,773. The probes may also exist in the form of a PNA (peptide nucleic acid) which has particularly preferred pairing properties. Thus, the oligonucleotide may include other appended groups such as peptides, and may include hybridization-triggered cleavage agents (Krol et al., BioTechniques 6:958-976, 1988) or intercalating agents (Zon, Pharm. Res. 5:539-549, 1988). To this end, the oligonucleotide may be conjugated to another molecule, e.g., a chromophore, fluorophor, peptide, hybridization-triggered cross-linking agent, transport agent, hybridisation-triggered cleavage agent, etc.

The oligonucleotide may also comprise at least one art-recognized modified sugar and/or base moiety, or may comprise a modified backbone or non-natural internucleoside linkage.

The oligonucleotides or oligomers according to particular embodiments of the present invention are typically used in 'sets,' which contain at least one oligomer for analysis of each of the CpG dinucleotides of genomic sequences SEQ ID NO: 1 to SEQ ID NO: 8 and sequences complementary thereto, or to the corresponding CpG, TpG or CpA dinucleotide within a sequence of the treated nucleic acids according to SEQ ID NO: 9 to SEQ ID NO: 40 and sequences complementary thereto. However, it is anticipated that for economic or other factors it may be preferable to analyze a limited selection of the CpG dinucleotides within said sequences, and the content of the set of oligonucleotides is altered accordingly.

Therefore, in particular embodiments, the present invention provides a set of at least two (2) (oligonucleotides and/or PNA-oligomers) useful for detecting the cytosine methylation state of treated genomic DNA (SEQ ID NO: 9 to SEQ ID NO: 40), or in genomic DNA (SEQ ID NO: 1 to SEQ ID NO: 8 and sequences complementary thereto). These probes enable diagnosis, and/or classification of genetic and epigenetic parameters of cell proliferative disorders. The set of oligomers may also be used for detecting single nucleotide polymorphisms (SNPs) in treated genomic DNA (SEQ ID NO: 9 to SEQ ID NO: 40), or in genomic DNA (SEQ ID NO: 1 to SEQ ID NO: 8 and sequences complementary thereto).

In preferred embodiments, at least one, and more preferably all members of a set of oligonucleotides is bound to a solid phase.

In further embodiments, the present invention provides a set of at least two (2) oligonucleotides that are used as 'primer' oligonucleotides for amplifying DNA sequences of one of SEQ ID NO: 9 to SEQ ID NO: 40 and sequences complementary thereto, or segments thereof.

It is anticipated that the oligonucleotides may constitute all or part of an "array" or "DNA chip" (i.e., an arrangement of different oligonucleotides and/or PNA-oligomers bound to a solid phase). Such an array of different oligonucleotide- and/or PNA-oligomer sequences can be characterized, for example, in that it is arranged on the solid phase in the form of a rectangular or hexagonal lattice. The solid-phase surface may be composed of silicon, glass, polystyrene, aluminium, steel, iron, copper, nickel, silver, or gold. Nitrocellulose as well as plastics such as nylon, which can exist in the form of pellets or also as resin matrices, may also be used. An overview of the prior art in oligomer array manufacturing can be gathered from a special edition of Nature Genetics (Nature Genetics Supplement, Volume 21, January 1999, and from the literature cited therein). Fluorescently labeled probes are often used for the scanning of immobilized DNA arrays. The simple attachment of Cy3 and Cy5 dyes to the 5′-OH of the specific probe are particularly suitable for fluorescence labels. The detection of the fluorescence of the hybridized probes may be carried out, for example, via a confocal microscope. Cy3 and Cy5 dyes, besides many others, are commercially available.

It is also anticipated that the oligonucleotides, or particular sequences thereof, may constitute all or part of an "virtual array" wherein the oligonucleotides, or particular sequences thereof, are used, for example, as 'specifiers' as part of, or in combination with a diverse population of unique labeled probes to analyze a complex mixture of analytes. Such a method, for example is described in US 2003/0013091 (U.S. Ser. No. 09/898,743, published 16 Jan. 2003). In such methods, enough labels are generated so that each nucleic acid in the complex mixture (i.e., each analyte) can be uniquely bound by a unique label and thus detected (each label is directly counted, resulting in a digital read-out of each molecular species in the mixture).

The described invention further provides a composition of matter useful for providing a prediction of outcome of treatment comprising at least one anthracycline of cancer patients. Said composition comprising at least one nucleic acid 18 base pairs in length of a segment of the nucleic acid sequence disclosed in SEQ ID NO: 9 to SEQ ID NO: 40, and one or more substances taken from the group comprising: magnesium chloride, dNTP, taq polymerase, bovine serum albumen, an oligomer in particular an oligonucleotide or peptide nucleic acid (PNA)-oligomer, said oligomer comprising in each case at least one base sequence having a length of at least 9 nucleotides which is complementary to, or hybridizes under moderately stringent or stringent conditions to a pretreated genomic DNA according to one of the SEQ ID NO: 9 to SEQ ID NO: 40 and sequences complementary thereto. It is preferred that said composition of matter comprises a buffer solution appropriate for the stabilization of said nucleic acid in an aqueous solution and enabling polymerase based reactions within said solution. Suitable buffers are known in the art and commercially available.

Moreover, an additional aspect of the present invention is a kit comprising, for example: a bisulfite-containing reagent as well as at least one oligonucleotide whose sequences in each case correspond, are complementary, or hybridize under stringent or highly stringent conditions to a 18-base long segment of a sequence selected from SEQ ID NO: 9 to SEQ ID NO: 40. It is particularly preferred that said at least one oligonucleotide is complementary, or hybridizes under stringent or highly stringent conditions to an 18-base long segment of a pre-treated nucleic acid selected from Table 1 (SEQ ID NO: 9 to SEQ ID NO: 14 and SEQ ID NO: 25 to SEQ ID NO: 30) or more preferably from Table 4 (SEQ ID NO: 15 to SEQ ID NO: 24 and SEQ ID NO: 31 to SEQ ID NO: 40).

Said kit may further comprise at least one oligonucleotide whose sequences in each case correspond, are complementary, or hybridize under stringent or highly stringent conditions to a 18-base long segment of the sequences SEQ ID NO: 9 to SEQ ID NO: 40. Said kit may further comprise instructions for carrying out and evaluating the described method. In a further preferred embodiment, said kit may further comprise standard reagents for performing a CpG position-specific methylation analysis, wherein said analysis comprises one or more of the following techniques: MS-SNuPE, MSP, MethyLight®, HeavyMethyl®, COBRA, and nucleic acid sequencing. However, a kit along the lines of the present invention can also contain only part of the aforementioned components.

Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridization oligo; control hybridization oligo; kinase labeling kit for oligonucleotide probe; and radioactive nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Typical reagents (e.g., as might be found in a typical MethyLight®-based kit) for MethyLight® analysis may include, but are not limited to: PCR primers for specific gene (or methylation-altered DNA sequence or CpG island); TaqMan® probes; optimized PCR buffers and deoxynucleotides; and Taq polymerase.

Typical reagents (e.g., as might be found in a typical Ms-SNuPE-based kit) for Ms-SNuPE analysis may include, but are not limited to: PCR primers for specific gene (or methylation-altered DNA sequence or CpG island); optimized PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

Typical reagents (e.g., as might be found in a typical MSP-based kit) for MSP analysis may include, but are not limited to: methylated and unmethylated PCR primers for specific gene (or methylation-altered DNA sequence or CpG island), optimized PCR buffers and deoxynucleotides, and specific probes.

While the present invention has been described with specificity in accordance with certain of its preferred embodiments, the following examples and figures serve only to illustrate the invention and is not intended to limit the invention within the principles and scope of the broadest interpretations and equivalent configurations thereof.

TABLE 1

| | | | Genomic sequences and treated variants thereof according to the invention | | | |
|---|---|---|---|---|---|---|
| Gene | Accession No. | Genomic SEQ ID NO: | Pretreated methylated sequence (sense) SEQ ID NO: | Pretreated methylated strand (antisense) SEQ ID NO: | Pretreated unmethylated sequence (sense) SEQ ID NO: | Pretreated unmethylated sequence (antisense) SEQ ID NO: |
| PITX2 | NM_002658 | 1 | 9 | 10 | 25 | 26 |
| PLAU | NM_000325 | 2 | 11 | 12 | 27 | 28 |
| TFF1 | NM_003225 | 3 | 13 | 14 | 29 | 30 |

TABLE 2

Primers and amplificates according to Example 1

| Gene | Forward Primer SEQ ID NO: | Reverse Primer SEQ ID NO: | Amplificate Genomic SEQ ID NO: | Amplificate pretreated methylated sequence (sense) SEQ ID NO: | Amplificate pretreated methylated strand (antisense) SEQ ID NO: | Amplificate pretreated unmethylated sequence (sense) SEQ ID NO: | Amplificate pretreated unmethylated sequence (antisense) SEQ ID NO: |
|---|---|---|---|---|---|---|---|
| PITX2 | 41 | 42 | 53 | 59 | 60 | 71 | 72 |
| PITX2 | 43 | 44 | 54 | 61 | 62 | 73 | 74 |
| PLAU | 45 | 46 | 55 | 63 | 64 | 75 | 76 |
| PLAU | 47 | 48 | 56 | 65 | 66 | 77 | 78 |
| TFF1 | 49 | 50 | 57 | 67 | 68 | 79 | 80 |
| TFF1 | 51 | 52 | 58 | 69 | 70 | 81 | 82 |

TABLE 3

Detection oligonucleotides according to Example 1

| SEQ ID NO: | Gene | Oligo ID |
|---|---|---|
| 110 | PITX2 | 1214A167 |
| 111 | PITX2 | 1214B177 |
| 112 | PITX2 | 880A178 |
| 113 | PITX2 | 880B2210 |
| 114 | PITX2 | 930A163 |
| 115 | PITX2 | 930B203 |
| 116 | PITX2 | 984A164 |
| 117 | PITX2 | 984B214 |
| 118 | PITX2 | 1063A193 |
| 119 | PITX2 | 1063B226 |
| 120 | PITX2 | 50B183 |
| 121 | PITX2 | 50A164 |
| 122 | PITX2 | 180A194 |
| 123 | PITX2 | 180B234 |
| 124 | PITX2 | 216A182 |
| 125 | PITX2 | 216B184 |
| 126 | PITX2 | 341B174 |
| 127 | PITX2 | 341A166 |
| 128 | PITX2 | 24A182 |
| 129 | PITX2 | 24B182 |
| 130 | PLAU | 28A188 |
| 131 | PLAU | 28B2110 |
| 132 | PLAU | 134B242 |
| 133 | PLAU | 134A223 |
| 134 | PLAU | 188A177 |
| 135 | PLAU | 188B208 |
| 136 | PLAU | 404A177 |
| 137 | PLAU | 404B1810 |
| 138 | TFF1 | 361A183 |
| 139 | TFF1 | 361B193 |
| 140 | TFF1 | 386A178 |
| 141 | TFF1 | 386B198 |
| 142 | TFF1 | 390B222 |
| 143 | TFF1 | 390A203 |
| 144 | TFF1 | 386A172 |
| 145 | TFF1 | 386B194 |
| 146 | PLAU | 460A163 |
| 147 | PLAU | 460B186 |
| 148 | PLAU | 487B202 |
| 149 | PLAU | 487A173 |
| 150 | PLAU | 465B182 |
| 151 | PLAU | 465A163 |
| 152 | PLAU | 473A162 |
| 153 | PLAU | 473B174 |
| 154 | PLAU | 482A172 |
| 155 | PLAU | 482B183 |
| 156 | TFF1 | 102A166 |
| 157 | TFF1 | 102B187 |
| 158 | TFF1 | 150A194 |
| 159 | TFF1 | 150B215 |
| 160 | TFF1 | 140A174 |
| 161 | TFF1 | 140B218 |
| 162 | TFF1 | 144B212 |
| 163 | TFF1 | 144A163 |
| 164 | TFF1 | 140A182 |
| 165 | TFF1 | 140B212 |

TABLE 4

CpG rich regions of the genes according to Table 1

| Gene | Genomic SEQ ID NO: | Pretreated methylated sequence (sense) SEQ ID NO: | Pretreated methylated strand (antisense) SEQ ID NO: | Pretreated unmethylated sequence (sense) SEQ ID NO: | Pretreated unmethylated sequence (antisense) SEQ ID NO: |
|---|---|---|---|---|---|
| PITX2 | 4 | 15 | 16 | 31 | 32 |
| PITX2 | 5 | 17 | 18 | 33 | 34 |
| PLAU | 6 | 19 | 20 | 35 | 36 |
| TFF1 | 7 | 21 | 22 | 37 | 38 |
| TFF1 | 8 | 23 | 24 | 39 | 40 |

TABLE 5

Figures and results according to Example 2.

| Gene | Assay | Cut-off | Sample Set | Figure | Anthracycline treatment outcome when hypermethylated (or underexpressed) |
|---|---|---|---|---|---|
| PITX2 | 1 | Median | All | 1 | Negative |
| PITX2 | 1 | Optimized | All | 2 | Negative |

TABLE 5-continued

Figures and results according to Example 2.

| Gene | Assay | Cut-off | Sample Set | Figure | Anthracycline treatment outcome when hypermethylated (or underexpressed) |
|---|---|---|---|---|---|
| TFF1 | | Median | All | 3 | Positive |
| TFF1 | | Optimized | All | 4 | Positive |
| TFF1 | 1 | Median | All | 5 | Positive |
| TFF1 | 1 | Optimized | All | 6 | Positive |
| TFF1 | 2 | Median | All | 7 | Positive |
| TFF1 | 2 | Optimized | All | 8 | Positive |
| PLAU | 1 | Median | All | 9 | Negative |
| PLAU | 1 | Optimized | All | 10 | Negative |
| PITX2 | 1 + 7b | Median | All | 11 | Negative |
| PITX2 | 1 + 7b | Optimized | All | 12 | Negative |
| PITX2(1 + 7b) + PLAU + TFF1 | | Median | All | 13 | Negative |
| PITX2(1 + 7b) + PLAU + TFF1 | | Optimized | All | 14 | Negative |
| PITX2 | 7b | Median | All | 15 | Negative |
| PITX2 | 7b | Optimized | All | 16 | Negative |
| PITX21 + PLAU | | Median | All | 17 | Negative |
| PITX21 + PLAU | | Optimized | All | 18 | Negative |
| PITX2(1) + TFF1 | | Median | All | 19 | Negative |
| PITX2(1) + TFF1 | | Optimized | All | 20 | Negative |
| TFF1 + PLAU | | Median | All | 21 | Negative |
| TFF1 + PLAU | | Optimized | All | 22 | Negative |
| PITX2(1) + TFF1 + PLAU | | Median | All | 23 | Negative |
| PITX2(1) + TFF1 + PLAU | | Optimized | All | 24 | Negative |
| All | | Median | All | 25 | Negative |
| All | | Optimized | All | 26 | Negative |
| PITX2 | 1 | Median | ER− | 27 | Negative |
| PITX2 | 1 | Optimized | ER− | 28 | Negative |
| TFF1 | | Median | ER− | 29 | Negative |
| TFF1 | | Optimized | ER− | 30 | Negative |
| TFF1 | 1 | Median | ER− | 31 | Positive |
| TFF1 | 1 | Optimized | ER− | 32 | Positive |
| TFF1 | 2 | Median | ER− | 33 | Negative |
| TFF1 | 2 | Optimized | ER− | 34 | Negative |
| PLAU | 1 | Median | ER− | 35 | Negative |
| PLAU | 1 | Optimized | ER− | 36 | Negative |
| PITX2 | 1 + 7b | Median | ER− | 37 | Positive |
| PITX2 | 1 + 7b | Optimized | ER− | 38 | Positive |
| PITX2(1 + 7b) + PLAU + TFF1 | | Median | ER− | 39 | Negative |
| PITX2(1 + 7b) + PLAU + TFF1 | | Optimized | ER− | 40 | Negative |
| PITX2 | 7b | Median | ER− | 41 | Negative |
| PITX2 | 7b | Optimized | ER− | 42 | Negative |
| PITX21 + PLAU | | Median | ER− | 43 | Negative |
| PITX21 + PLAU | | Optimized | ER− | 44 | Negative |
| PITX2(1) + TFF1 | | Median | ER− | 45 | Negative |
| PITX2(1) + TFF1 | | Optimized | ER− | 46 | Negative |
| TFF1 + PLAU | | Median | ER− | 47 | Positive |
| TFF1 + PLAU | | Optimized | ER− | 48 | Positive |
| PITX2(1) + TFF1 + PLAU | | Median | ER− | 49 | Negative |
| PITX2(1) + TFF1 + PLAU | | Optimized | ER− | 50 | Negative |
| All | | Median | ER− | 51 | Negative |
| All | | Optimized | ER− | 52 | Negative |
| PITX2 | 1 | Median | ER+ | 53 | Negative |
| PITX2 | 1 | Optimized | ER+ | 54 | Negative |
| TFF1 | | Median | ER+ | 55 | Positive |
| TFF1 | | Optimized | ER+ | 56 | Positive |
| TFF1 | 1 | Median | ER+ | 57 | Positive |
| TFF1 | 1 | Optimized | ER+ | 58 | Positive |
| TFF1 | 2 | Median | ER+ | 59 | Positive |
| TFF1 | 2 | Optimized | ER+ | 60 | Positive |
| PLAU | 1 | Median | ER+ | 61 | Negative |
| PLAU | 1 | Optimized | ER+ | 62 | Negative |
| PITX2 | 1 + 7b | Median | ER+ | 63 | Negative |
| PITX2 | 1 + 7b | Optimized | ER+ | 64 | Negative |
| PITX2(1 + 7b) + PLAU + TFF1 | | Median | ER+ | 65 | Negative |
| PITX2(1 + 7b) + PLAU + TFF1 | | Optimized | ER+ | 66 | Negative |
| PITX2 | 7b | Median | ER+ | 67 | Negative |
| PITX2 | 7b | Optimized | ER+ | 68 | Negative |
| PITX21 + PLAU | | Median | ER+ | 69 | Negative |
| PITX21 + PLAU | | Optimized | ER+ | 70 | Negative |
| PITX2(1) + TFF1 | | Median | ER+ | 71 | Negative |
| PITX2(1) + TFF1 | | Optimized | ER+ | 72 | Negative |
| TFF1 + PLAU | | Median | ER+ | 73 | Negative |
| TFF1 + PLAU | | Optimized | ER+ | 74 | Negative |
| PITX2(1) + TFF1 + PLAU | | Median | ER+ | 75 | Negative |
| PITX2(1) + TFF1 + PLAU | | Optimized | ER+ | 76 | Negative |

TABLE 5-continued

Figures and results according to Example 2.

| Gene | Assay | Cut-off | Sample Set | Figure | Anthracycline treatment outcome when hypermethylated (or underexpressed) |
|---|---|---|---|---|---|
| All | | Median | ER+ | 77 | Negative |
| All | | Optimized | ER+ | 78 | Negative |

TABLE 6

Results of Example 1

| Sample set | Oligo | SepD | c index | 36AUC | 48AUC | 60AUC | 72AUC | p(LRT) |
|---|---|---|---|---|---|---|---|---|
| ER− | TFF1:102A166 | 0.08 | 0.507 | 0.5 | 0.53 | 0.53 | 0.53 | 0.97 |
| ER− | TFF1:140A174 | 0.09 | 0.514 | 0.49 | 0.52 | 0.52 | 0.52 | 0.82 |
| ER− | TFF1:140A182 | 0.09 | 0.496 | 0.5 | 0.53 | 0.53 | 0.53 | 0.79 |
| ER− | TFF1:144A163 | 0.23 | 0.541 | 0.58 | 0.54 | 0.54 | 0.54 | 0.49 |
| ER− | TFF1:150A194 | −0.01 | 0.497 | 0.51 | 0.54 | 0.54 | 0.54 | 0.9 |
| ER− | TFF1:361A183 | 0.23 | 0.535 | 0.54 | 0.56 | 0.56 | 0.56 | 0.31 |
| ER− | TFF1:386A172 | 0.43 | 0.585 | 0.59 | 0.61 | 0.61 | 0.61 | 0.47 |
| ER− | TFF1:386A178 | 0.1 | 0.506 | 0.49 | 0.52 | 0.52 | 0.52 | 0.73 |
| ER− | TFF1:390A203 | 0.52 | 0.608 | 0.62 | 0.63 | 0.63 | 0.63 | 0.34 |
| ER− | PLAU:134A223 | 0.8 | 0.626 | 0.67 | 0.68 | 0.68 | 0.68 | 0.01 |
| ER− | PLAU:188A177 | 0.04 | 0.51 | 0.49 | 0.52 | 0.52 | 0.52 | 0.97 |
| ER− | PLAU:28A188 | 0.11 | 0.52 | 0.54 | 0.54 | 0.54 | 0.54 | 0.78 |
| ER− | PLAU:404A177 | 0.16 | 0.507 | 0.52 | 0.53 | 0.53 | 0.53 | 0.51 |
| ER− | PLAU:460A163 | 0.22 | 0.543 | 0.55 | 0.55 | 0.55 | 0.55 | 0.67 |
| ER− | PLAU:465A163 | 0.26 | 0.527 | 0.53 | 0.55 | 0.55 | 0.55 | 0.24 |
| ER− | PLAU:473A162 | 0.72 | 0.648 | 0.67 | 0.67 | 0.67 | 0.67 | 0.012 |
| ER− | PLAU:482A172 | 0.49 | 0.594 | 0.6 | 0.59 | 0.59 | 0.59 | 0.17 |
| ER− | PLAU:487A173 | 0.2 | 0.542 | 0.56 | 0.55 | 0.55 | 0.55 | 0.35 |
| ER− | PITX2:1063A193 | 0.13 | 0.514 | 0.52 | 0.53 | 0.53 | 0.53 | 0.85 |
| ER− | PITX2:1214A167 | 0.4 | 0.549 | 0.56 | 0.59 | 0.59 | 0.59 | 0.14 |
| ER− | PITX2:180A194 | 0.21 | 0.558 | 0.57 | 0.57 | 0.57 | 0.57 | 0.8 |
| ER− | PITX2:216A182 | 0.34 | 0.578 | 0.6 | 0.6 | 0.6 | 0.6 | 0.15 |
| ER− | PITX2:24A182 | 0.32 | 0.572 | 0.56 | 0.58 | 0.58 | 0.58 | 0.071 |
| ER− | PITX2:341A166 | 0.07 | 0.523 | 0.52 | 0.49 | 0.49 | 0.49 | 0.97 |
| ER− | PITX2:50A164 | 0.26 | 0.545 | 0.56 | 0.54 | 0.54 | 0.54 | 0.42 |
| ER− | PITX2:880A178 | 0.34 | 0.54 | 0.58 | 0.58 | 0.58 | 0.58 | 0.22 |
| ER− | PITX2:930A163 | 0.36 | 0.56 | 0.57 | 0.57 | 0.57 | 0.57 | 0.2 |
| ER− | PITX2:984A164 | 0.16 | 0.548 | 0.54 | 0.55 | 0.55 | 0.55 | 0.28 |
| ER+ | TFF1:102A166 | 0.1 | 0.534 | 0.55 | 0.55 | 0.55 | 0.55 | 4.50E−01 |
| ER+ | TFF1:140A174 | 0.13 | 0.557 | 0.59 | 0.59 | 0.58 | 0.56 | 4.10E−01 |
| ER+ | TFF1:140A182 | 0.28 | 0.55 | 0.55 | 0.52 | 0.54 | 0.57 | 8.20E−02 |
| ER+ | TFF1:144A163 | 0.04 | 0.513 | 0.55 | 0.5 | 0.51 | 0.52 | 9.70E−01 |
| ER+ | TFF1:150A194 | 0.19 | 0.525 | 0.5 | 0.51 | 0.52 | 0.53 | 3.70E−01 |
| ER+ | TFF1:361A183 | 0.21 | 0.522 | 0.53 | 0.5 | 0.51 | 0.51 | 3.20E−01 |
| ER+ | TFF1:386A172 | 0.18 | 0.516 | 0.49 | 0.49 | 0.52 | 0.51 | 3.80E−01 |
| ER+ | TFF1:386A178 | 0.13 | 0.508 | 0.48 | 0.49 | 0.51 | 0.52 | 4.50E−01 |
| ER+ | TFF1:390A203 | 0.18 | 0.525 | 0.52 | 0.51 | 0.52 | 0.52 | 3.50E−01 |
| ER+ | PLAU:134A223 | 0.12 | 0.53 | 0.52 | 0.52 | 0.53 | 0.55 | 3.30E−01 |
| ER+ | PLAU:188A177 | 0.25 | 0.552 | 0.57 | 0.58 | 0.58 | 0.57 | 1.20E−01 |
| ER+ | PLAU:28A188 | 0.1 | 0.535 | 0.55 | 0.54 | 0.55 | 0.55 | 4.90E−01 |
| ER+ | PLAU:404A177 | 0.47 | 0.581 | 0.6 | 0.61 | 0.61 | 0.61 | 4.70E−03 |
| ER+ | PLAU:460A163 | 0.35 | 0.577 | 0.59 | 0.61 | 0.59 | 0.59 | 1.50E−02 |
| ER+ | PLAU:465A163 | 0.33 | 0.56 | 0.58 | 0.61 | 0.58 | 0.56 | 2.90E−02 |
| ER+ | PLAU:473A162 | 0.34 | 0.585 | 0.63 | 0.6 | 0.58 | 0.59 | 9.00E−03 |
| ER+ | PLAU:482A172 | 0.3 | 0.557 | 0.56 | 0.58 | 0.56 | 0.57 | 1.20E−02 |
| ER+ | PLAU:487A173 | 0.33 | 0.556 | 0.56 | 0.55 | 0.55 | 0.57 | 2.20E−02 |
| ER+ | PITX2:1063A193 | 0.09 | 0.538 | 0.57 | 0.57 | 0.54 | 0.52 | 6.70E−01 |
| ER+ | PITX2:1214A167 | 0.29 | 0.567 | 0.59 | 0.58 | 0.58 | 0.58 | 1.40E−01 |
| ER+ | PITX2:180A194 | 0.16 | 0.55 | 0.59 | 0.57 | 0.54 | 0.54 | 3.50E−01 |
| ER+ | PITX2:216A182 | 0.35 | 0.583 | 0.61 | 0.6 | 0.58 | 0.58 | 2.40E−02 |
| ER+ | PITX2:24A182 | 0.42 | 0.592 | 0.65 | 0.61 | 0.61 | 0.6 | 9.40E−04 |
| ER+ | PITX2:341A166 | 0.11 | 0.55 | 0.6 | 0.56 | 0.55 | 0.56 | 5.40E−01 |
| ER+ | PITX2:50A164 | 0.45 | 0.592 | 0.61 | 0.61 | 0.62 | 0.62 | 5.50E−03 |
| ER+ | PITX2:880A178 | 0.16 | 0.522 | 0.5 | 0.54 | 0.52 | 0.54 | 2.90E−01 |
| ER+ | PITX2:930A163 | 0.04 | 0.488 | 0.48 | 0.48 | 0.5 | 0.5 | 9.70E−01 |
| ER+ | PITX2:984A164 | 0.1 | 0.527 | 0.5 | 0.53 | 0.55 | 0.55 | 3.40E−01 |
| All | TFF1:102A166 | 0.11 | 0.533 | 0.54 | 0.55 | 0.55 | 0.55 | 0.45 |
| All | TFF1:140A174 | 0.08 | 0.534 | 0.53 | 0.55 | 0.55 | 0.54 | 0.57 |
| All | TFF1:140A182 | 0.17 | 0.535 | 0.54 | 0.5 | 0.53 | 0.54 | 0.19 |
| All | TFF1:144A163 | 0.1 | 0.524 | 0.56 | 0.52 | 0.52 | 0.53 | 0.67 |
| All | TFF1:150A194 | 0.11 | 0.508 | 0.49 | 0.48 | 0.5 | 0.51 | 0.6 |

TABLE 6-continued

Results of Example 1

| Sample set | Oligo | SepD | c index | 36AUC | 48AUC | 60AUC | 72AUC | p(LRT) |
|---|---|---|---|---|---|---|---|---|
| All | TFF1:361A183 | 0.17 | 0.514 | 0.5 | 0.51 | 0.52 | 0.52 | 0.28 |
| All | TFF1:386A172 | 0.19 | 0.52 | 0.5 | 0.51 | 0.53 | 0.53 | 0.36 |
| All | TFF1:386A178 | 0.06 | 0.492 | 0.45 | 0.47 | 0.5 | 0.51 | 0.61 |
| All | TFF1:390A203 | 0.23 | 0.539 | 0.53 | 0.53 | 0.54 | 0.54 | 0.28 |
| All | PLAU:134A223 | 0.1 | 0.513 | 0.52 | 0.52 | 0.52 | 0.5 | 0.56 |
| All | PLAU:188A177 | 0.18 | 0.54 | 0.55 | 0.56 | 0.56 | 0.56 | 0.18 |
| All | PLAU:28A188 | 0.03 | 0.515 | 0.52 | 0.52 | 0.52 | 0.52 | 0.74 |
| All | PLAU:404A177 | 0.36 | 0.558 | 0.57 | 0.58 | 0.58 | 0.59 | 0.0079 |
| All | PLAU:460A163 | 0.28 | 0.559 | 0.56 | 0.58 | 0.57 | 0.57 | 0.029 |
| All | PLAU:465A163 | 0.29 | 0.548 | 0.55 | 0.58 | 0.57 | 0.56 | 0.022 |
| All | PLAU:473A162 | 0.42 | 0.593 | 0.62 | 0.61 | 0.6 | 0.61 | 0.0008 |
| All | PLAU:482A172 | 0.32 | 0.554 | 0.55 | 0.56 | 0.56 | 0.57 | 0.0078 |
| All | PLAU:487A173 | 0.27 | 0.542 | 0.54 | 0.53 | 0.54 | 0.56 | 0.025 |
| All | PITX2:1063A193 | 0 | 0.513 | 0.52 | 0.53 | 0.51 | 0.5 | 0.99 |
| All | PITX2:1214A167 | 0.25 | 0.549 | 0.55 | 0.55 | 0.56 | 0.57 | 0.1 |
| All | PITX2:180A194 | 0.17 | 0.549 | 0.57 | 0.56 | 0.55 | 0.55 | 0.39 |
| All | PITX2:216A182 | 0.34 | 0.576 | 0.6 | 0.59 | 0.58 | 0.59 | 0.011 |
| All | PITX2:24A182 | 0.36 | 0.575 | 0.6 | 0.59 | 0.59 | 0.59 | 0.00056 |
| All | PITX2:341A166 | 0.07 | 0.532 | 0.56 | 0.55 | 0.54 | 0.55 | 0.64 |
| All | PITX2:50A164 | 0.34 | 0.565 | 0.56 | 0.57 | 0.58 | 0.59 | 0.016 |
| All | PITX2:880A178 | 0.02 | 0.511 | 0.54 | 0.51 | 0.51 | 0.49 | 0.91 |
| All | PITX2:930A163 | 0.08 | 0.535 | 0.55 | 0.55 | 0.53 | 0.52 | 0.42 |
| All | PITX2:984A164 | 0.05 | 0.513 | 0.48 | 0.51 | 0.53 | 0.53 | 0.37 |

Example 1: Microarray Analysis

Microarray Analysis

To evaluate marker candidates a significant number of patient samples were analyzed using the applicant's proprietary methylation sensitive Microarray technology.

Patient Samples

Samples were obtained from 384 lymphnode positive breast cancer patients who had received adjuvant treatment with an anthracycline based treatment regimen. Samples were received from four academic partners in the form of fresh frozen tissues.

DNA Extraction

DNA from samples was isolated using commercially available kits.

PCR Establishment and Multiplex PCR Optimization

To amplify all gene fragments, PCR assays were designed to match bisulfite treated DNA and to allow amplification independent of the methylation status of the respective fragment. A standardized primer design workflow optimized by the applicant for bisulfite treated DNA was employed. Individual PCR assays were considered established when successful amplification on bisulfite treated DNA was reproducible and no background amplification of genomic DNA was detectable, ensuring bisulfite DNA specific amplification. Primers are listed in Table 2.

To allow efficient amplification, individual PCR assays were combined into multiplex PCR (mPCR) assays usually combining up to 8 primer pairs into one mPCR assay. Several multiplex PCR sets were calculated based on the primer sequences of the individual PCR amplificates and tested on lymphocyte DNA. Based on ALF express analyses the best performing combination of multiplex PCR sets were chosen.

Bisulfite Treatment and Multiplex PCR

Total genomic DNA of all samples and controls was bisulfite treated converting unmethylated cytosines to uracil. Methylated cytosines are conserved. Bisulfite treatment was performed according to the applicant's optimized proprietary bisulfite treatment procedure. In order to avoid a potential process bias, the samples were randomized into processing batches.

Hybridization

All PCR products from each individual sample were then hybridized to glass slides carrying a pair of immobilized oligonucleotides for each CpG position under analysis. For hybridizations, the samples were grouped into processing batches in order to avoid a potential process-bias. The samples were processed randomized for bisulfite batches. Each detection oligonucleotide was designed to hybridize to the bisulphite converted sequence around one CpG site which was either originally unmethylated (TG) or methylated (CG). See Table 3 for further details of all hybridization oligonucleotides used (both informative and non-informative.) Hybridization conditions were selected to allow the detection of the single nucleotide differences between the TG and CG variants.

Fluorescent signals from each hybridized oligonucleotide were detected using genepix scanner and software. Ratios for the two signals (from the CG oligonucleotide and the TG oligonucleotide used to analyze each CpG position) were calculated based on comparison of intensity of the fluorescent signals.

The samples were processed in randomized batches. For each bisulfite treated DNA sample 2 hybridizations were performed. This means that for each sample a total number of 4 chips were processed.

1820 chips were processed in total. In addition to the 435 patients samples these further included 80 control chips; 40 hybridised to completely methylated control DNA and 40 hybridised to completely methylated control DNA. Of these a total of 153 were excluded due to poor quality. The remaining 1667 chips covered all 435 samples. Of these 435 samples only 384 had complete follow ups, the remaining were excluded.

Data Analysis

For the analysis of chip data, Epigenomics' proprietary software ('Episcape') was used. EpiScape contains a data warehouse that supports queries to sample, genome and laboratory management databases, respectively. It encompasses a variety of statistical tools for analyzing and visualizing methylation array data. In the following sections we summarize the most important data analysis techniques that were applied for analyzing the data.

From Raw Hybridization Intensities to Methylation Ratios

The log methylation ratio (log(CG/TG)) at each CpG position was determined according to a standardized preprocessing pipeline that includes the following steps:

For each spot the median background pixel intensity is subtracted from the median foreground pixel intensity. This gives a good estimate of background corrected hybridization intensities.

For both CG and TG detection oligonucleotides of each CpG position the background corrected median of the 4 redundant spot intensities is taken.

For each chip and each CG/TG oligo pair, the log(CG/TG) ratio is calculated.

For each sample the median of log(CG/TG) intensities over the redundant chip repetitions is taken.

This log ratio has the property that the hybridization noise has approximately constant variance over the full range of possible methylation rates (see e.g. Huber W, Von Heydebreck A, Sultmann H, Poustka A, Vingron M. 2002. Variance stabilization applied to Microarray data calibration and to the quantification of differential expression. Bioinformatics. 18 Suppl 1: S96-S104.)

Principle Component Analysis

Principle component analysis (PCA) projects measurement vectors (e.g. chip data, methylation profiles on several CpG sites etc.) onto a new coordinate system. The new coordinate axes are referred to as principal components. The first principal component spans the direction of largest variance of the data. Subsequent components are ordered by decreasing variance and are orthogonal to each other. Different CpG positions contribute with different weights to the extension of the data cloud along different components. PCA is an unsupervised technique, i.e. it does not take into account any group or label information of the data points (for further details see e.g. Ripley, B. D. 1996. Pattern Recognition and Neural Networks, Cambridge, UK, Cambridge University Press.).

PCA is typically used to project high dimensional data (in our case methylation-array data) onto lower dimensional subspaces in order to visualize or extract features with high variance from the data. In the present report we used 2 dimensional projections for statistical quality control of the data. We investigated the effect of different process parameters on the chip data in order to rule out that changing process parameters caused large alterations in the measurement values.

A robust version of PCA was used to detect single outlier chips and exclude them from further analysis (Model F, Koenig T, Piepenbrock C, Adorjan P. 2002. Statistical process control for large scale Microarray experiments. Bioinformatics. 18 Suppl 1:S155-163.).

$T^2$ Control Charts

To control the general stability of the chip production process we use methods from the field of multivariate statistical process control (MVSPC). Our major tool is the $T^2$ control chart, which is used to detect significant deviations of the chip process from normal working conditions (Model F, Koenig T, Piepenbrock C, Adorjan P. 2002. Statistical process control for large scale Microarray experiments. Bioinformatics. 18 Suppl 1:S155-163.).

Order the chip data with respect to a process parameter (e.g. hybridization data or spotting robot).

Define a historic data set, which describes the chip process under normal working conditions (e.g. the first 75 hybridized chips). In the chart, data from the historical data set are indicated by a special plot symbol.

Compute the distance of every new chip to the historic data set. If the distance of several consecutive chips exceeds a given control limit the process has to be regarded as out of control.

Use of $T^2$ charts to monitor the chip production process allows us to efficiently detect and eliminate most systematic error sources.

Statistical Methods

Cox Regression

The relation between metastases-free survival times (MFS) and covariates are analyzed using Cox Proportional Hazard models (Cox and Oates 1984; Harrel 2001).

The hazard, i.e. the instantaneous risk of a relapse, is modeled as $$h(t|x) = h_0(t) \cdot \exp(\beta x) \quad (3)$$

and $$h(t|x_1, \ldots, x_k) = h_0(t) \cdot \exp(\beta_1 x_1 + \ldots + \beta_k x_k) \quad (4)$$

for univariate and multiple regression analyses, respectively, where t is the time measured in months after surgery, $h_0(t)$ is the (unspecified) baseline hazard, $x_i$ are the covariates (e.g. measurements of the assays) and $\beta_i$ are the regression coefficients (parameters of the model). $\beta_i$ will be estimated by maximizing the partial likelihood of the Cox Proportional Hazard model.

Likelihood ratio tests are performed to test whether methylation is related to the hazard. The difference between $-2 \text{Log(Likelihood)}$ of full model and null-model is approximately $\chi^2$-distributed with k degrees of freedom under the null hypotheses $\beta_1 = \ldots = \beta_k = 0$.

Stepwise Regression Analysis

For multiple Cox regression models a stepwise procedure (Venables and Ripley 1999; Harrel 2001) is used in order to find sub-models including only relevant variables. Two effects are usually achieved by these procedures:

Variables (methylation rates) that are basically unrelated to the dependent variable (DFS/MFS) are excluded as they do not add relevant information to the model.

Out of a set of highly correlated variables, only the one with the best relation to the dependent variable is retained.

The applied algorithm aims at minimizing the Akaike information criterion (AIC), which is defined as AIC=−2□maximized log-likelihood+2□#parameters.

Kaplan-Meier Survival Curves and Log-Rank Tests

Survival curves are estimated from MFS data using Kaplan-Meier estimator for survival (Kaplan and Meier, 1958). Log-rank tests (Cox and Oates 1984) are used to test for differences of two survival curves, e.g. survival in hyper- vs. hypomethylated groups.

Analysis of Sensitivity and Specificity

The method of calculating sensitivity and specificity using the Bayes-formula is based on the Kaplan-Meier estimates (Heagerty et al. 2000) for the survival probabilities in the marker positive and marker negative groups for a given time $T_{Threshold}$.

The ROCs were calculated for different reference times $T_{Threshold}$ (36 months, 48 months, 60 months, 72 months) and time dependent AUCs were calculated.

Results are provided in Table 6, and show:
SepD: Separation Score D (Royston and Sauerbrei)
c index: Concordance index C (Harrel)
36AUC: time dependend area under the receiver operating curve, 36 months
48AUC: time dependend area under the receiver operating curve, 48 mths
60AUC: time dependend area under the receiver operating curve, 60 mths
72AUC: time dependend area under the receiver operating curve, 72 mths
p(LRT): p-value of likelihood ratio test for cox regression model Example 2: Real-Time Assay Analysis The preferred assay format for clinically useful CpG methylation detection is a Real-Time PCR based assay. Accordingly the markers were further analysed by means of a quantitative methylation assay (hereinafter also referred to as the "QM" assay).

The QM assay is based on non-methylation specific amplification of a target sequence and a methylation specific detection by competitive hybridization of two different probes specific for the CG or the TG status, respectively. For the present study, TaqMan probes were used that were labeled with two different fluorescence dyes (see below) and were further modified by a quencher molecule (see below).

Evaluation of the QM assay raw data is possible with two different methods:
1. Measuring absolute fluorescence intensities (FI) in the logarithmic phase of amplification
2. Difference in threshold cycles (Ct) of CG and TG specific probe.

Results of this study were generated by using the Ct method.

In the following series of quantitative methylation assays the amount of sample DNA amplified is quantified by reference to the gene GSTP1 to normalize for input DNA. For standardization, the primers and the probe for analysis of the GSTP1 gene lack CpG dinucleotides so that amplification is possible regardless of methylation levels. As there are no methylation variable positions, only one probe oligonucleotide is required.

Assays.

In total six assays were developed. TFF1 assay 1 (also referred to as TFF1(1) and TFF1-1) amplifies a target region of the promoter region of said gene on chromosome 21q22.3. TFF1 assay 2 (also referred to as TFF1(2) and TFF1-2) amplifies a target region of the exon 2 region of said gene, again on chromosome 21q22.3.

PLAU assay 1 (also referred to as PLAU(1) and PLAU-1) amplifies a target region of the promoter region of said gene on chromosome 10q42. PITX2 assay 7b (also referred to as PLAU(7b) and PLAU-7b) amplifies a target region of the promoter C region of said gene on chromosome 4q25-q27.

Primer and probe sequences were:

```
TFF1 (2)
Primer + Probe sequences              SEQ ID NO: Reporter
Quencher
Forward primer  GATGGTATTAGGATAGAAGTATTA    83
Reverse primer  CCCTCCCAATATACAAATAAAAACTA  84
CG-probe        CACCGTTCGTAAAATCC           85  FAM  BHQ
TG-probe        ACACCATTCATAAAATCCCCTAAT    86  HEX  BHQ PITX2 (7b)
Primer + Probe sequences              SEQ ID NO: Reporter
Quencher
Forward primer  GAtAGGTAGGTGATATTAGATttt    87
Reverse primer  CCTAAATACCTAAAACTAAACTAC    88
CG-probe        cgactcctattcgaccgcccg       89  FAM  BHQ
TG-probe        cccaactcctattcaaccacccaaaaa 90  HEX  BHQ PLAU (1)
Primer + Probe sequences              SEQ ID NO: Reporter
Quencher
Forward primer  gttttttttaaatttttgtgag      91
Reverse primer  cctcccctatcttacaa           92
CG-probe        ACCCGaACCCGCGTaCTTC         93  FAM  BHQ
TG-probe        ACCCAaACCCCACAtACTTCCACA    94  HEX  BHQ TFF1 (1)
Primer + Probe sequences              SEQ ID NO: Reporter
Quencher
Forward primer  ggtggttattgtttttttttgt      95
Reverse primer  taaacaaacaaaacctaccctataa   96
CG-probe        tccgaaactcgaacgacctct       97  FAM  BHQ
TG-probe        tccaaaactcaaacaacctctcatc   98  HEX  BHQ TFF1
Primer + Probe sequences              SEQ ID NO: Reporter
Quencher
Forward primer  CCCTCCCAaTaTaCAAATAAaaaCTa  99
Reverse primer  AGTTGGTGATGTTGATTAGAGTT     100
CG-probe        ACACCGTTCGTAAAA-            101 FAM  MGBNFQ
TG-probe        ACACCATTCATAAAAT            102 VIC  MGBNFQ
```

```
PITX2 (1)
Primer + Probe sequences              SEQ ID NO:   Reporter
Quencher
Forward primer   TTCTaaTCCTCCTTTCCACAaTaa   103
Reverse primer   GtAGGGGAGGGAAGtAGATGtt     104
CG-probe         AGtCGGAGtCGGGAGAGCGA       105   FAM   TAMRA
TG-probe         AGtTGGAGtTGGGAGAGTGAAAGGAGA 106  VIC   TAMRA
```

PCR Conditions

Detection was done at the end of each cycle for all assays.

|  | Temperature | Time |
|---|---|---|
| IFF1-1 | | |
| Initial Denaturation | 95° C. | 10 min |
| Denaturation | 95° C. | 15 sec |
| Annealing | 60° C. | 60 sec |
| Cycles | 50 | |
| Emulation | off | |
| TFF1-2 | | |
| Initial Denaturation | 95° C. | 10 min |
| Denaturation | 95° C. | 15 sec |
| Annealing | 58° C. | 60 sec |
| Cycles | 50 | |
| Emulation | off | |
| PLAU-1 | | |
| Initial Denaturation | 95° C. | 10 min |
| Denaturation | 95° C. | 15 sec |
| Annealing | 60° C. | 60 sec |
| Cycles | 50 | |
| Emulation | off | |
| PITX2-7b | | |
| Initial Denaturation | 95° C. | 10 min |
| Denaturation | 95° C. | 15 sec |
| Annealing | 62° C. | 60 sec |
| Cycles | 50 | |
| Emulation | off | |
| PITX2-1 | | |
| Initial Denaturation | 95° C. | 10 min |
| Denaturation | 95° C. | 15 sec |
| Annealing | 62° C. | 60 sec |
| Cycles | 50 | |
| Emulation | off | |
| TFF1 | | |
| Initial Denaturation | 95° C. | 10 min |
| Denaturation | 95° C. | 15 sec |
| Annealing | 60° C. | 60 sec |
| Cycles | 50 | |
| Emulation | off | |

Reaction solution was:

| Eurogentec reaction buffer | 1 x |
|---|---|
| Eurogentec MgCl2 | 3 mM |
| DNTPs (MBI) | 250 µM |
| Primer mix | 625 nM |
| CG Probe | 200 nM |
| TG Probe | 200 nM |
| HotGoldStar-Taq | 1 U |
| Water | |

Sample Sets

In total 395 anthracycline treated breast cancer samples were analysed. Of these 97 were confirmed as having estrogen receptor negative disease, and 276 were confirmed as having estrogen receptor positive disease.

Bisulfite Treatment

DNA was extracted using commercially available kits, DNA was then bisulfite treated based on the method disclosed by Olek et al. Nucleic Acids Res. 1996 Dec. 15; 24(24):5064-6, and optimised to the applicant's laboratory workflow.

Quantification Standards

The reactions are calibrated by reference to DNA standards of known methylation levels in order to quantify the levels of methylation within the sample. The DNA standards were composed of bisulfite treated phi29 amplified human genomic DNA (Promega) (i.e. unmethylated), and/or phi29 amplified genomic DNA treated with Sss1 Methylase enzyme (thereby methylating each CpG position in the sample), which is then treated with bisulfite solution. Seven different reference standards were used with 0%, (i.e. phi29 amplified genomic DNA only), 5%, 10%, 25%, 50%, 75% and 100% (i.e. phi29 Sss1 treated genomic only).

2000 ng batches of human genomic DNA (Promega) were treated with bisulfite. To generate methylated MDA DNA, 13 tubes of 4.5 µg MDA-DNA (700 ng/µl) was treated with Sss1.

Control Assay

The GSTP1-C3 assay design makes it suitable for quantitating DNAs from different sources.

The following oligonucleotides were used in the reaction to amplify the control amplificate:

```
Control Primer1:
                                   (SEQ ID NO: 107)
GGAGTGGAGGAAATTGAGAT Control Primer2:
                                   (SEQ ID NO: 108)
CCACACAACAAATACTCAAAAC Control Probe:
                                   (SEQ ID NO: 109)
FAM-TGGGTGTTTGTAATTTTTGTTTTGTGTTAGGTT-TAMRA Cycle program (40 cycles):
95° C., 10 min; 95° C., 15 sec; 58° C., 1 min
```

Raw Data Processing

All analyses were based on CT evaluation (evaluation using fluorescence intensities are available upon request). Assuming optimal real-time PCR conditions in the exponential amplification phase, the concentration of methylated DNA ($C_{meth}$) can be determined by $$C_{meth} = \frac{100}{1 + 2^{(CT_{CG} - CT_{TG})}} [\%],$$

where $CT_{CG}$ denotes the threshold cycle of the CG reporter (FAM channel) and $CT_{TG}$ denotes the threshold cycle of the TG reporter (VIC channel).

The thresholds for the cycles were determined by human experts after a visual inspection of the Amplification Plots [ABI PRISM 7900 HT Sequence Detection System User Guide]. The values for the cycles ($CT_{CG}$ and $CT_{TG}$) were calculated with these thresholds by the ABI 7900 software. Whenever the amplification curve did not exceed the threshold, the value of the cycle was set to the maximum cycle, i.e. 50.

Statistical Methods

Cox Regression

The relation between disease-free survival times (DFS) (or metastasis free survival, MFS) and covariates are modeled using Cox Proportional Hazard models (Cox and Oates, 1984; Harrel, 2001).

The hazard, i.e. the instantaneous risk of a relapse, is modeled as $$h(t|x) = h_0(t) \cdot \exp(\beta x) \quad (3)$$

and $$h(t|x_1, \ldots, x_k) = h_0(t) \cdot \exp(\beta_1 x_1 + \ldots + \beta_k x_k) \quad (4)$$

for univariate and multiple regression analyses, respectively, where t is the time measured in months after surgery, $h_0(t)$ is the baseline hazard, x is the vector of covariates (e.g. measurements of the assays) and β is the vector of regression coefficients (parameters of the model). β will be estimated by maximizing the partial likelihood of the Cox proportional hazard model Likelihood ratio tests are performed to test whether methylation is related to the hazard. The difference between −2 Log(Likelihood) of full model and null-model is approximately $\chi^2$-distributed with k degrees of freedom under the null hypotheses $\beta_i = \ldots = \beta_k = 0$.

The assumption of proportional hazards were checked by scaled Schoenfeld residuals (Thernau et al., 2000). For the calculation, analysis and diagnostic of the Cox Proportional Hazard Model the R functions coxph, coxph.zph of the "survival" package were used.

Stepwise Regression Analysis

For multivariate Cox regression models a stepwise procedure (Venables et al., 1999; Harrel, 2001) was used in order to find sub-models including only relevant variables. Two effects are usually achieved by these procedures:

Variables (methylation rates) that are basically unrelated to the dependent variable (DFS/MFS) are excluded as they do not add relevant information to the model.

Out of a set of highly correlated variables, only the one with the best relation to the dependent variable is retained.

Inclusion of both types of variables can lead to numerical instabilities and a loss of power. Moreover, the predictory performance can be low due to overfitting.

The applied algorithm aims at minimizing the Akaike information criterion (AIC) which is defined as AIC=−2□maximized log-likelihood+2□#parameters.

The AIC is related to the predictory performance of a model, smaller values promise better performance. Whereas the inclusion of additional variables always improves the model fit and thus increases the likelihood, the second term penalizes the estimation of additional parameters. The best model will present a compromise model with good fit and usually a small or moderate number of variables. Stepwise regression calculation with AIC was done with the R function "step".

Kaplan-Meier Survival Curves and Log-Rank Tests

Survival curves are estimated from DFS/MFS data using the Kaplan-Meier method (Kaplan and Meier, 1958). Log-rank tests were used to test for differences of two survival curves, e.g. survival in hyper- vs. hypomethylated groups. For a description of this test see (Cox and Oates, 1984). For the Kaplan Meier Analysis the functions "survfit" and "survdiff" of the "survival" package were used.

Independence of Markers from Other Covariates

To check whether our marker panel gives additional and independent information, other relevant clinical factors were included in the cox proportional hazard model and the p-values for the weights for every factor were calculated (Wald-Test) (Thernau et al., 2000). For the analysis of additional factors in the Cox Proportional Hazard model, the R function "coxph" was used.

Results

Evaluation of Single Markers

After filtering of measuring points not fulfilling quality criteria and performing a Cox analyses, Kaplan-Meier survival curves for each single marker were generated.

Two different cut-off points were used for analyses:

Median measured methylation

Optimized methylation cut-off

Panels

Based on the results of the single marker evaluations, it was decided to build models using the marker candidates PITX2, TFF1, and PLAU. All possible combinations of these markers were evaluated.

Figure 78:
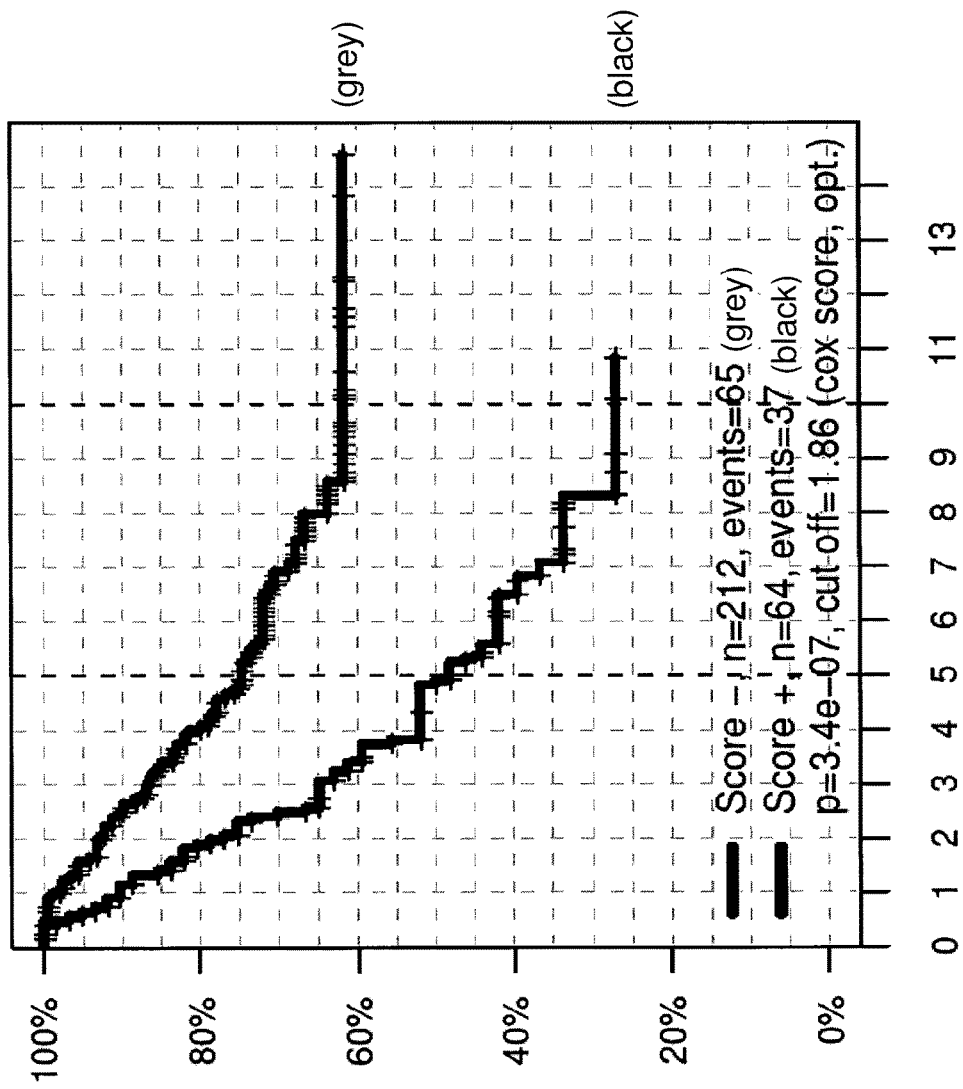

Results are provided in FIGS. 1 to 78 according to Table 5. For each assay and/or panel, a Kaplan-Maier plot is provided in all samples, ER+ only and ER− only. For each of said sample sets Kaplan-Maier plots are provided based on an optimised % methylation or cox score cut off, as well as the median cut-off.

---

The invention claimed is:

1. A method comprising:

obtaining a biological sample comprising tumor genomic DNA from a breast cancer surgery subject prior to any anthracycline treatment;

contacting the tumor genomic DNA isolated from the biological sample with at least one bisulfite reagent, or series of bisulfite reagents that distinguishes between methylated and non-methylated CpG dinucleotides, thereby producing treated genomic DNA;

detecting hypomethylation of at least one gene or genomic sequence selected from the group consisting of PITX2, PLAU and regulatory sequences thereof in the treated tumor genomic DNA; and treating the subject with an anthracycline after breast cancer surgery.

2. The method of claim 1, wherein the biological sample is at least one selected from the group consisting of cells, cell lines, histological slides, paraffin embedded tissues, biopsies, tissue embedded in paraffin, bodily fluids, nipple aspirate, and blood.

3. The method of claim 1, wherein the step of contacting the tumor genomic DNA isolated from the biological sample with at least one bisulfite reagent, or series of bisulfite reagents that distinguishes between methylated and non-methylated CpG dinucleotides is performed within at least one target region of the genomic DNA, wherein the target region comprises, or hybridizes under stringent conditions to a sequence of at least 16 contiguous nucleotides of at least one gene or genomic sequence selected from the group consisting of PITX2, PLAU and regulatory regions thereof, and wherein the 16 contiguous nucleotides comprise at least one CpG dinucleotide sequence.

4. The method of claim 1, wherein the at least one bisulfite reagent comprises a solution selected from the group consisting of bisulfite, hydrogen sulfite, disulfite, and combinations thereof.

5. The method of claim 1, wherein detecting hypomethylation is carried out using Real Time detection probes.

6. The method of claim 1, wherein detecting hypomethylation is carried out using an oligonucleotide hybridization analysis.

7. The method of claim 1, wherein detecting hypomethylation is carried out using Ms-SnuPE.

8. The method of claim 1, wherein detecting hypomethylation is carried out using sequencing.

9. The method of claim 1, wherein detecting hypomethylation is carried out using oligonucleotide array analysis.

10. The method of claim 1, wherein detecting hypomethylation is carried out by:
    contacting the treated genomic DNA, or the treated portion or fragment thereof, with an amplification enzyme and at least two primers comprising, in each case, a contiguous sequence at least 18 nucleotides in length that is complementary to, or hybridizes under moderately stringent or stringent conditions to a sequence selected from the group consisting of SEQ ID NOs: 9-10, 15-18, 25-28, and 31-34, sequences complementary thereto, and contiguous portions thereof, wherein the treated genomic DNA or a fragment thereof is either amplified to produce one or more amplificates, or is not amplified; and
    detecting hypomethylation based on the presence or absence of the amplificate, or on the quantity or on a property of the amplificate.

11. The method of claim 1, wherein detecting hypomethylation is carried out by:
    contacting the treated genomic DNA, or a treated portion or fragment thereof, with an amplification enzyme and at least two primers comprising, in each case, a contiguous sequence at least 18 nucleotides in length that is complementary to, or hybridizes under moderately stringent or stringent conditions to a sequence selected from the group consisting of SEQ ID NOs: 11-12, 19-20, 27-28, and 35-36, sequences complementary thereto, and contiguous portions thereof, wherein the treated genomic DNA or the treated portion or fragment thereof is either amplified to produce one or more amplificates, or is not amplified; and
    detecting hypomethylation based on the presence or absence of the amplificate, or on the quantity or on a property of the amplificate.

12. A method for treating a subject having a cell proliferative disorder of the breast, comprising:
    treating the subject with an anthracycline, wherein the subject is a breast cancer surgery subject, and wherein the subject has hypomethylated DNA in at least one gene or genomic sequence selected from the group consisting of PITX2, PLAU, and regulatory sequences thereof wherein the hypomethylation is detected prior to the treating with the anthracycline by
    obtaining a biological sample comprising tumor genomic DNA from the breast cancer surgery subject;
    contacting the tumor genomic DNA isolated from the biological sample with at least one bisulfite reagent, or series of bisulfite reagents that distinguishes between methylated and non-methylated CpG dinucleotides, thereby producing treated genomic DNA; and
    detecting hypomethylation of at least one gene or genomic sequence selected from the group consisting of PITX2, PLAU and regulatory sequences thereof in the treated genomic DNA.

* * * * *

SEQUENCE LISTING

```
<160> NUMBER OF SEQ ID NOS: 165

<210> SEQ ID NO 1
<211> LENGTH: 30001
<212> TYPE: DNA
<213> ORGANISM: Homo Sapiens

<400> SEQUENCE: 1
tggaagtggt cctgtcatga caaaaggtgt ggtatttgta caatttccag ataagaacaa      60
agtcatgacg ctaagacagt agcagcactg tttgttacac gtgatatttg aaaaatatga     120
caaccatctc aatctgctca agtagcactc atggtgaggg tgaaatttta tcaacattgg     180
```

```
ttaacttatg gtgttttaaa aaactagcaa ggagataaat tgatggatta aaagataaac      240
tactcacagg cagacaaaca gaaggacaga tagagttaca atcaaacatg tactttactc      300
aggcagaaag ataataacca gcccccaaga agtgatgtgt ctgctagaaa agccctgaac      360
atagaatttc ctgactttgt ttttaattta gttctttcag gcatcacgct gcataaccag      420
gtgtaactct ctaaaagtct ctatgacaga attttccatc tgttaaatta ggctaataat      480
attttcatct ttttttaggg taaagatgtg aaatatttgg agaactctgg aaaacatgcc      540
ccctactaat tagagctttt tgatgtgaca tcattttctt cagtacttgg agtttagtca      600
atagatatac agtgtagctg tgaaattatg aagcatgaga atgcattacc aagggaccgt      660
aggaggctct ttactgaaaa gtgtagctgg ctatatttct ggaagtaatt taaacatagg      720
ctgagggaga ggagtaccct ctagatcctt ccagacctt actttctatg aattctaatt      780
tctctttccc atttagaaaa aacaatgaga tccacagcgt agagatagaa aataaggctc      840
tgtgtgccct caaaccttac tttcaaaaat accacagcat tctggacgag atagtcttga      900
attcttgcaa cagcacaggt atgagagttt ttaccagaaa acaggagact ggattgattc      960
tttcattctc ctcctatgct tcctaaaact gaaaagccat atatacaaat tatatttatc     1020
tatccctcct ggaaaaggcc aaaatgaatc caattttgga tcattttcaa taatgggaca     1080
aacctgaatt gagaataacc tttagaatca gtcctgtctt tttgtgataa aatggacttg     1140
tagaaagcta cctggtgttc tccctagct aacattctac cacaaacaac gggtatgtaa     1200
tccagtattg ctccccacag gctatgtcct tggaatcact atctttgcac tccatttgtc     1260
tgctgacatc cttccaccca agatgtcttc ttcagcacaa gaagtcattt ctcttaaaat     1320
ttcaaatgac tttactacaa taatagagtt gctaactaga cctaggcaag taatgataat     1380
aaaaatctga tttctactta gagtgtagca tggtttaaca caacaaccag agtcctaaca     1440
ggttttctta gatttcactc ctactcaact tgcatgttct tgcaatatag atgttcttat     1500
tactcggtcc ttacttccat ctctctttgc ttctggaata aaactactta aacccaattc     1560 agagattta ttctccctg gaattactgg gaaacagttc tagtaaacca tattcctgag     1620
atcctatatt aggcttagtc caaactgacc atctaagcat taatttccct gtggctcagg     1680
aatatccctg agcttacctt tctcttccta aactgcccag gacaaatacc ggagtttggc     1740
ttttctgctt tctcatccaa tcatttctcg tttcctcctc tttagcattt aaaacatttc     1800 tgacttctc catccctcaa gaaatatatt tgctttcctg tctctgcatt attcttttgt     1860
ttatgaaata ttccataggt aagttctata tttccttccc ccagaggccc ctggtcttct     1920
ggttccagtt gccattggtt cagtgtacta gttaacattt tggactttgg agttacacaa     1980
acctagattc aaaattccac tatgccactt actgcctacg tgacctgaag caatatccta     2040
tccactgtgg cctccagcag ttataagctt gtgctctaac cagctgggtg accttgggcc     2100
agtgacacaa tcatggcaaa cctcactgtc ttcatttgta aaatgacagt acctaccttg     2160
tagtgttggc ataaggaata agtgtgattg tcaatacaaa agtgtttagt acaatagcta     2220
aattaactaa gcactctgta aatattagtt tttaccatta ttactaattc aaatgactag     2280
atgcattttg tgtataccag gtttcctgag ttcacttttgt tctcaacaaa tactattatt     2340
cctagcatgt ggcctatatc acacttcatt agccagagga catgtgaagc ttagagtgga     2400
aagctagggc agcaggaagc attgccacac tttacacagt caaagccatt taaacatgtc     2460
tgaatttgag ctctgctgag tccttacttg cccccatctc tcctgtgtgc tccagcttac     2520
```

```
taataaagca ggtttaatat aaatacacta aaagcctaaa cattgagatc atgataatga   2580
atatgagggc tatgactata aaatatcatt gaaccagaga cctgctacga aaccacatgg   2640
tgaagaccac aagggaggaa tctgcataca caccgagtgc cttgggatcc caaagtggga   2700
agagtcagtg ccccaattaa agagaaactc ggggtaggga atcaaccaca acatcagtca   2760
ccttactgaa cccaggcttg tttcagctga cgtagctgcc aatttccaat gtcccctccc   2820
tccctaattg ctctcaatct attcctccag aaactgaaag cccatcaaag aggatatctt   2880
cccagagagt tgttccagtt actacaagct cttgctagaa attccaagaa agtttacaag   2940
gtacctttat aaggtggcat tgagtaagtc agaagcattc caagtaccaa ttatcatgca   3000
aataagggct ttacttttag attttgttgt ttgtggtggt ggtgatgctg gtgttctctc   3060
tggaatccag cccaatctcc aaaaaagtaa aaggagtaca aatagtaata caaattatta   3120
ttacttacac caattaaaat agaagttttg aatgagcaag gagctagagg aggtaaaaac   3180
tgggaacttc gtatattaaa aggtttttat aatttgaaaa ctaagattat gctggccaaa   3240
taggctgttt taaaatcagc atagtaatca aatttgcttg taatgaatgt agacccaaac   3300
agtgatgtca gacctgataa ggacttgcaa accctaaaag agtgcaaaaa gaccatagaa   3360
gaacaatatt atattcctgc acttacagaa atggtcagct caagagatgt atccagttca   3420
gggtggctgt aagcttcatt ttctgaactt gctaccagaa gttaaaagaa attctgtata   3480
actgcttttg atggaaacac aaattggttg atgtaaatga aatacataaa gcagttggtg   3540
tcttattcat tcccacaatt ataaatgaaa ttaaatgatc aaaaattata gactttgggg   3600
atcttctttt cactgaggag cccatggaat tgtcttctc tagtaccaat aactgtgttg   3660
acctattttt tcctgtctaa ctctgtatat attaaaacta ggtggttacg aacaaaaccc   3720
agaaatacaa tttacattct aataaaatga ctttaaaatt attccacttt ttactgtggc   3780
tttacctgtt gtcccacaat gcaggtttct ctgggcctct gcttagaatg actctgtcaa   3840
tgtagatgac agccagagtt gaatggggaa tccagaaact ggggattcgg gctcttgatg   3900
caatctatat gccaatctac ttcattagtt cttcttttat ttacagtttg gtaaagaata   3960
tgggtggagc tgttctgggc tcacttgcac acatgtccaa actgctttga aaaaggaagg   4020
gcaagaaaga gtggtatcca agttggaatc aggcaggcat ttcagatcaa gagacgaact   4080
ggaaagggaa catctgttag ataccctggg tttgaaggca gtctgtgtaa gttttcatat   4140
ctctgagtgt gtgcacacag tggagagggt ggagcctgcc atcctcaaat ctgaaaagat   4200
tgagagattt cagagggccc agatgtgcca aaggtcagag ggatcaatat acaggcccta   4260
ccacggaaag gcggggaaaa ggttcgaata gaaaactgct gcagaaggga agccactgag   4320
aggtaaggga gtttctgaat aattaaaaag ttaagaataa gcaaaaggaa ggaggtcggg   4380
tgggggataa aaaaagcag ttgatgtggt aattaagaat ttggtgggag cctgggcagg   4440
tcacctcctt tctcagatca gagccccatc agaaattctt tcaagtgtcc ttctgcgtcg   4500
ccaaagatga caacagcaaa tcaataagtg cttgaaatga aagggatgt tgactagccc   4560 ccaggctaca gatttcccgc cgccagcctt ttctgaactc ctatagcgtg cctttgcacc   4620
gcctctctta agaagagcta ccttttattc ctattctcag gacgaaggta agtgctcagt   4680
tagcatatct attaaatgtc agctttggtt ccagctctcc gtttgcgcgg aaagctcact   4740
gccatagcgc gcccagcctg ccggaggggc agacagaaaa agcaagcttg gcctggcgac   4800
ttgcggggcc acgcacctcc agggctgccc cggagtcttc cagagtttaa cgctcctggg   4860
ttagaactgt aaggtcccgg tccgagcaaa gggcctgagc caccgtagcc gtgggagcgt   4920
```

```
tccttccact tgaatgcact cactcacaaa caagcacaaa atcttttaa cagcagagga   4980 gaaagacccc tgctccaaaa ttaaagctgg gaatcaccgg aaactccgtt ttgagtgcga   5040
gatattggtc tgttaccttt ctaatcttca tatccctcct gtaatatgtc ttgatttaac   5100
aatctttcca gcgcccagca ttgcccggac gttttaattg ggtaattcat tagtgagtca   5160
atacaggcat ttatatattc ttttagctca agtggttaag tactaatttc gaaatgatta   5220
taaaacaccg gaatcggcaa cgcatagtaa ttttaattta tatgcaaatc aattggttca   5280
tcttaaatgc cttttttaaa aaaacaatta ttgtattgta gcatcggagg catggatcaa   5340
acctctagaa tagacaattc ggaaacaaga cctggactag gaagacaatt tagaacagcc   5400
aacaaatcaa taatgtttga ggcagttaaa catcgctagc cattggtatt tacatactcg   5460
cttgttgtca gataaggagc tggggaaatt gcttgccagg gttgagatca taatccagag   5520
tgaagaaagt aaatggtagc acacagcccg tcacagcggg ctctgaaata atactgtacc   5580
tttcccaaat cctgactctt gggtgacagg gagttggcgg aggtcacccc acatttgtcc   5640
acggttttgc cccaatttga tcacgaaatt gttgttctcc ctgagctttc caatttgatt   5700
accattctaa cggttctgtc acttgtctca acatattggg gggaggagtg taattgagat   5760
tctcattaaa aattatctga acccacttag ccagcactgt ttcatctaag cttagtttta   5820
tgggctgtat ttaattccct gtgcccccca cacattaaaa tcagatcatc aaaatgtcgg   5880
taggaaaggg tgaaggaaat ggtccaatgc tccagtttac tggaagacta ttatctttag   5940
acatagttca aaattttgag gaaataaaaa ggatatacgc tttgggggga aaatgtttta   6000
atattctaga atgggggtat tactccccc attccagaga atccgcactg gagttgttta   6060
tgtaaaaatg taacatcctt gaaattcaca gatacgtaag gttagtgtct ccccttcccc   6120
aggctcccag tccaggcgat ctagccctaa aggagctagt acctttgatg ctacaatctt   6180
gtttacatct gcagggcaga gaattgcttg ctttgcttgg acgctccctc cacccccttc   6240
taatttgaag taatcggaat ctaaatacag tcgccaaggc ccgctcttcc tttactgctt   6300
tgacaaggga aaaacctgaa atccacgtct taaatcagct cggtggtttg tagcccccca   6360
gcaccctgct tctacgattg catgcctaat gtattccctg gtgattctgg gcattaatta   6420
gttgtttaat aggagtatga ctaaaaatgt aaagaagga ttaggagcgt gaaacgtatg   6480
tccagctcct tccacacact cgaggaggga atgagaatca ttctgtatct tctatttctc   6540
caggagccat ttgcatttcc caccagctgc tcacttcagc tgcactggcg ctgggcaagg   6600
cgaggaccca aaagctcagc gcagtgtctg cggcggccgg gactgggggtt aaccagcctc   6660 tggcgggcga gactccagac agaagggggg cgagaggaac gtgagcttcc cgagcccctt   6720
cctctcagcc ctggtttgca aacctctgaa acctgaaagg ggaggagtt gcacgcgcgt   6780 atctttgcgt cttttcagcg caactccctt ccctctccct gtgtctctcc gcggatctct   6840
gaatctttct gtctttggtt ttctcattct cttccaactt ttccatgaga ttgcctatcc   6900
tcgccaccag ctgaaggcaa ggccgttctg ctacgagcgc ctcttaatct ctacaaaatg   6960
aaaagaaaaa aagggaggat tattagccca ttactcagag gaatggggag gctgcaaaaa   7020
tcgtcgatgg gcagaggtga agatgtcttt ctcggactgc actttccggt gtcctgtaac   7080
tagagttcag ttgtgggact tgttgaagaa atttgatttt cttgcctcgg cgagatttca   7140
aaaaccagaa atgaaattc tcagagtcag agaggaata caattaaaca gcacgtgggc   7200
attttccccc tcatttctct ccccttaaat aacactgctt tgagttcca ctgggtaaag   7260
```

-continued

| | |
|---|---|
| agagaaagtt tgagttttca cggatgttac gtggaggtta gaaatggctt aaaatgtaga | 7320 |
| tctctaatca gttttcttcg tggctgaaga ggctaaccct ttccataaaa tgagtccatc | 7380 |
| tgtcgactgt tagctatttc aaagtgaagg gatttagcac tcaaaacaaa ttgagcaagt | 7440 |
| ttgtttgcct gttttactg ctaactcaaa tgaattcaaa acacggagta attcaagaaa | 7500 |
| acacataaca tgttccagac agcccccaaa agtagggaaa gcccagcacc tatatagtga | 7560 |
| ctagggttag ttttaagcgc caagcttttt taaacgtatc tattttatgc acattctccc | 7620 |
| gagtcactat atatttctaa aattgcgagt attggtatat tgatttagga agagcaatac | 7680 |
| aacttttaga gggaacttta ttctcaatta gggaccaaag agatgtcttt ttaatagcgg | 7740 |
| gcctgagttt tgctctcaag caggaattaa tattggtggg aaaatccgaa tccaggagca | 7800 |
| atggctgtgt tccggcactt tccaaaaaca tacattaaca ggatgccctt gagattgaaa | 7860 |
| aaacattgtc ccatatgcct ggcagaagcc ttcacacctg gtcctccagg cgaattatat | 7920 |
| ttatagtcct tccactcaga ggcaggacag agccaaaata ttctgctcac taccaaaata | 7980 |
| cacatctttg ctcaagtcaa gaaatcagaa atcaggggtt cagaagtaag gcacactttt | 8040 |
| cgagtgagaa tatgccctgt aatttcacat actctttgct ttgcaggagc aaatgtggac | 8100 |
| ttgagggaaa ctctctcccc caccccact tctatcccgt gcaatttaat accatcctcg | 8160 |
| ccaggaacct taacctcgtc attttaaaaa atgagatatc cgtgacccag ggtgaacttg | 8220 |
| ttgaatgtag gtacagcaga ggaaattcta gactctatga gcgtctgagc cttgtccagt | 8280 |
| gcaaacccct cgtgaacact gggtcagtgc gtggccgtgc ccacctgtgc gccgacactc | 8340 |
| tcagcatgcc tggtccaccc gccttgacct cgggcgcggt gtcccagcta agctgggccc | 8400 |
| agcgtcccgg ccttccccag ctgacaagcc tagctcgttc gctcccggct gtggccctcc | 8460 |
| caccctctcc cactagctca ctccattctt ctagatttct cttcactcat cctctcccat | 8520 |
| ccccaccgcg cccacctcca ctcccgccct ctaccggtct ctcactttcc tccctccgca | 8580 |
| gtccctctt gctgtgacct cttcctcaa ctctgcaggc ctgaaagaag gtcacacacg | 8640 |
| cacgctcaca cccacactcc acacgcctcg tcccaaacaa ccccatgaac attgtccttt | 8700 |
| gttccgtctc ttgggccact ttccctgtcg cttcctccca gcccgtcctg atttgctccc | 8760 |
| caaaagtacg tttctgtctc cccgctgccc tggcgctccc cctttgattt attagggctg | 8820 |
| ccgggttggc gcagattgct ttttcttctc ttccatccca tcctcccttc tggtcctcct | 8880 |
| ttccacagtg ggagtccgtg ctcctgctcc tcggttggct cctaagtgcc ccgccaggtc | 8940 |
| ccctctcctt tcgctctccc ggctccggct cccgactctt cggccgctg gcatctgctt | 9000 |
| ccctcccctg cctcgtttct cgtcgcccct gctcgctccc ccggcgctc gcccgggcgc | 9060 |
| tgtgctcgct cctggatcgc cagccgcgca gccgggctcg gccggccgcc cgcgcgccac | 9120 |
| tgtgcagtgg agtttggtgg aatctctgct gacgtcacgt cactcccac acggagtagg | 9180 |
| agcagaggga agagagaggg atgagaggga gggagaggag agagagtgcg agaccgagcg | 9240 |
| agaaagctgg agaggagcag aaagaaactg ccagtggcgg ctagatttcg gaggcccag | 9300 |
| tgcacccgtg gactccttcg gaacttggca ccctcaggag ccctgcagtc ctctcaggcc | 9360 |
| cggctttcgg gcgcttgccg tgcagccgga ggctcggctc gctggaaatc gccccgggaa | 9420 |
| gcagtgggac gcggagacag cagctctctc ccggtagccg gtaagtggag gccatctatc | 9480 |
| ccgcagggat gtgagataat gcgagtctgg aaatttgttc cacttcggag aatcttcacc | 9540 |
| gtaggtgatt tgtggctttt ggggctaagt ttcgcccaag gtaacgcagt cggcaaacag | 9600 |
| accttgcaaa gccctgttcc tttcgtcccc cgccacagac actaacaatc tacagggtgc | 9660 |

```
tgaagtcgag agggaagcca gaccgtggct ggcatttaaa acgaggtatc ttcccttaaa    9720
tctcggtgcc aacactgcag gaacaaatcc tcgggccaag gattagcatt ctcaagataa    9780
agggctgggt acaaagtttc agctactgga agattagccc ccttcccatt gttatccatt    9840
gggaaaaaaa agaaaagaaa aagattccat cttaactggc agttagtgac ctctcaggcc    9900
caagcgaatt acctgggagc caggcctgga tgccaagctc tcaccatttc tttggattgt    9960 aactcccttta aattgatcac cagtcaactc caatctggca cttcaggaga tacactttaa   10020
atggatgcag agaattattt tccagctgga gattaagaaa aaattttcg attctaaacc    10080 tccgaaatat gttcctcttt tccagtttaa ccactttact ttcttaagca atttagaaat   10140
caaactatca taaggtggtg tgattttttt ttactctttt gtgtgagtat tgtcttacta   10200
aactaaacgg aaaaaacttt taccattata aatgtaaata tcagaattca tacattctaa   10260
aatattttta tgaaaaatta atctgattta agaaatttc cttgcatttg ttttagtcta    10320
tcaatcaaaa ctaagatgc ttttatcaca caaaatatca ttttggcaga aatccatcta    10380
aaattcaaat accaataata tcaagaaaac aaagcacata agcaaaataa attgaagatt   10440
tttgttgatg taacatgagc atacaacatt tcaataacca aactttccct aaaaaattaa   10500
atagccactt catttgtgga atgttttact ttaactcagc aaaattacac ttaaattatt   10560
taggtgcttt gttccttaag ttaagcgtgt ttgtcttcaa atgttcctaa agcacttata   10620
ttaattggtt gtaaagaacg catacacatg gtaaaataca gaactgaact gagcagtatt   10680
ttaatttcct taaataatta cttactacaa attaatttac tggctaattt cacaatttag   10740
ttcatttaaa acacatgttc ctgtgctgtt tattttaaa ctttccatta aagattttgt    10800
tatggggtaa caaagtgtat gaaaaggggg gaaatgtgaa aggatctggg attattcgaa   10860
ctgtattttt cctgcacttt cagtcttgcg gtagtcatca gaaattattt tttagcaaat   10920 tgttttatt cttagggctt gcctgcctgc tttgccatgg ttcctcgtcc tccgttagcc    10980
gtgtagtgct ttttgtgtgc tcacaatata aaacccaagt tggccaaaac aagagtcctt   11040
ggcatataca ttccaactag aacatgaact ttggggggtga gaactacctc ccatcaggaa   11100
aagtctccca tctcaatttg tgagattagc cattgaagcc agttccgaag tctggcagcc   11160
aaatttctca cagaagactt gtcttgatag ggcaagttta aggatcagca ggcgggaatt   11220
ggaggtctct ttttaaaaaa ttatcttccc cagttattta gactcagttc ttctagtagg   11280
cctggtcatt aaatgaagca taaaaatgca agtctcaagg ctcattttga ctgcaaaata   11340
aatctccaag tcacaaggac atgtaggagt gagctaagga acacgccttg accttctttt   11400
cagtccttag agtggagctc tatgagttct tgaagatttg ttttgtattg ctttgtttgg   11460
tcttcagcac tgaagcacgg ggaagtgggg ggaagaatgt gtaataattg actgacttta   11520
caccaagcaa cgcaatcttt ttcttttgta tatttcattc tttaaaaaaa ataaataaat   11580
aaaaactatt tgcagttacc atctgcagtg ctccggctac cagctaataa tgcagccagt   11640
tcagacatat aaaaaaaaaa gattatcgaa atgatgatga catgcaaatt tcctccgaaa   11700
ttatcataag taaacatttg aagtctggac taataaaatc ccatctgtgt tacttcatat   11760
cgagttagta gaaagctgtg ataatgaatt ttgtaatatc tcacgaacag acatctcaat   11820
cagggactaa tcctgtgatt ttactgcaga atcactaaat ctggagccgc caaactgcta   11880
cttctgggcc cacgggccca caaggatcga atcggcagag tccccgcccg cgttctcgct   11940
agcgggtggg ggaaccgcct ggccgtcccc accctggatc cccacgccac agcgccgggc   12000
```

```
agccctcct gtaggcagcg accttggcca gaggctcccc agggcccagc tcccttcagg    12060
agaggccgag acgcagggaa acggtactca ggccagaggc aggcccgcag ctccctgccc    12120
cgcctctgtg cctccgccaa cccgacaacg cttgctccca ccccgatccc cgcacccgcg    12180
cgaagtgggc cctccggtcg tcggcgtacc ctggttagcg tggagagagg caggcgctga    12240
gatcgaaggg gcctagggag ccctggacct tcttttcttg tctttaaagc aaccgcggct    12300
cttctaccca cccggtggag cccctcgaga cccacctctc ccggcttgcc tgtggcagag    12360 aaggggagc gcgttaaatg cttggctcgc tgcgttgtgg ttgaaaacgt gaaaaagatt    12420
tggctcgccc gggagagaaa gggggagaac tgggtagcag ttataccaga gctatttctc    12480
cgtccttggc gggcagtaaa ccctccaaga acgtttgccc tgctctcctc agtctcgctc    12540
agtccaccca gtgtctctcc tctgcgatct taaatcatac tttagggtaa ttatttgtag    12600
taagtaaata aatggccggg ttagtatctc taggagaaag tgtggctaaa tatggaaaag    12660
tggctcctga tggatgagag gcccgaactc agctcgctcc tgaaacaccc taggccaaga    12720
gcccgttcgt ttcagaatta cagaaaaccg agggaaactg ctgtctagga caggggcacg    12780
ttggcgctga tgttctacaa atgtttaccg agctccaact aatggacaag cactgaaggg    12840
tggtctttgc atacagcttc ccaaagagaa aagtcctctc cacccaccca ctcccgctgc    12900
cattgcgttc agatgagttc ttaaccccgg caccgagatt cttgaaagta ggtccacagc    12960
ctccccagca cactgtggct ttatagtcct ctaacctctg ggcacttttg cggcaactct    13020
ggagggagat cccctcttga taaataaatg tcctgggccc gaggctaggc tggagatgct    13080
gctgcacagc cagaggctgt caggtcggaa aaacacgcct gaagcctagc acacagtagg    13140
cgcctaacag ctagtgtaac gtagtctcat ctgagccctg ctcactcgac ggccgccgct    13200
tcttacagcc ttccttctct tctgttttgc agataacggg gaatgagac caactgccgc    13260 aaactggtgt cggcgtgtgt gcaattaggt aagaaccccc ttctcctgcc cgggtcatcg    13320
gacgggaggc cgcgccacgt gagggcggca agagggcact ggccctgcgg cgaggccca    13380 gcgaggggcg cttccccgag gggccagcct gggcaggaag gaaatcagaa ccaaatcgcc    13440
agtggcctct ccctgtggcg gggcggtgga ctaggaagca gcggcgcgct gtgtaccgaa    13500
gccccccagc ctactcctcc cggctggaac cgccggcaac cggggaggcg cagaaagagt    13560
acgccatcct gccccgggtt gccagagggt ccggggacg gggatgccgt cagctctttc    13620
ctctaactgg gtctttgctc tttgtccctc tttctcctcc ggcctgcctc gcccctcccc    13680
ctcctcccgt cccggctcc tttcggccgc ggtccgggac gcctctctcc gcacgtgggg    13740
cgggcgcgcg cgtggcccag gcgtgcagcc ggcggccgtt gaatgtctct tctccaaaga    13800
ctccgaaatc aaaaaggtcg agttcacgga ctctcctgag agccgaaaag aggcagccag    13860
cagcaagttc ttcccgcggc agcatcctgg cgccaatggt aaggccggga gggaagcgca    13920
ggccgcgcgc tgggcacccg cctccgggac tctgggcctc gggcgaagcg caagaaggcg    13980
aggccgccag acctgacgcg cctgctgctt gaacttagac actccgcctc tgggtgggac    14040
gggaagcagc cgtcccaggg acgttaattc ctttccccaa attatactgc actcctgaga    14100
cccaacacct ctctctccct ctcgctcgct ccctgtggtc tgatcccctg cgcacgctcc    14160
agcaaacctc ggcgtctagg ctggcgtgga aaagtggtcc aacagcgacc tctgtcgctc    14220
gttatatccc gctgcgcgca gcaccaccag ggcccactca gtcactcagg ctctcagcca    14280
cgccccaccc agacttgtgg gtgcgcggtt catcgcggga ggcaagcaag ggaaacttga    14340
gttggcgaag gtttgctttg gctggttggg ggaggggcgg ggggccgaca acatccctga    14400
```

```
agagctggag ggcagccact gtgcttagca gcccagggta gaatggaggt ttgcccctgt   14460
cgacgcgaac ctgcctgaag tactggttgc caggccttgg gttttggcga tgtcgttgct   14520
tgattggctg gtttcactct ggaggaatcg agggacattg ccagaggagg tctacaggct   14580
tatgtaaaaa gttaaaaagt ctccaaccta cgccacaggc ctttcctgaa ttgaaacttg   14640
ttctatgggg cggaggggggg ggtgtaaggg atggaggagg gaagatgcct ttcttttcaa   14700
atacatggaa aaaacccct caaatttact gttcctctat tttcctggct ccgtagtaaa   14760
taagtgccta gccttaggag gctattgacc tttgataatg tgagcagata agccccccc   14820 ccccccacag ccctcggccc ctaacccct cttccggat aaagtgtaa gaatacaaat   14880 gtaatatggg atggagggggg gcgatttggg accccggtca aaaaacaaa ccgtattact   14940 aagaagaaaa caaggtctt gcattggagt ttccccgtga atctgagaga aaatgatcat   15000
ttgttgaaat gaagcgtcta aagcgatcca gtgcttcacg cccggacact gcactacacc   15060
gccagtcgcc ctgctgggcc agttaaacgc tcacttgtcc gggattaacc ccatggggtt   15120 aaatggggggc aatgcagaga taacgtcgcg tgatttctgt catttagatt gtgttaaatt   15180
cttcttctgt ttgataatcg gtagtaaaaa taaattatta gaccgtagta tgtttgggat   15240
atggttaaaa atcaagagca gcgatgactt ctggggagaa tgctttgcgc gggctcagcc   15300
ctggctccgg ccagactaga ggagctcccc aatctcgctt cgcgcgggc gggctcgcag   15360 tcgccaagcc gaggctgaca tttcttattg tgctgggagc cagagagacg caaaatgtct   15420
ccttccccca gtccctaccc caggtttcct agacatgggg aatgcattct gaggacaggt   15480
ggagaagcct acggtaggat ggggtcctcg taggtgagca ggaaacggct aagagcagag   15540
gagttctgct tgcgccagtc acaagccgcg caggcgcccc tggtcgttcg cttttgataa   15600
ctagcacata aagaactaga aataatgaat gattgctttc ttaaccatta ctttcaggcc   15660
cgcattgttt tagtgcacgt gaaaggctct tcccctacac tcaatatgtc ttttctact   15720 ttttgaccga aaagaaaaat tgctgcctaa acacgtttaa tgccattaat taagaaaagg   15780
catgtaatgg gaagaaatgc tgaaaatctt gattaattg gcttttaagg aactagtaga   15840
cgacaaaaaa aaatcacacg agtgggcaaa gctatagcac tgctgaagga tagagcacct   15900
atccttccct gattttaagt taacttatgg aatatccaaa gtcctggcca cagcctgctt   15960
gtaaaacaaa aggatttatt tcttgtgttt ttttaaagtt tttctttgct tttaaagaga   16020
aaaaaagttc acaatgacat atgacttctt caaaaggccg tgatagtcta ttacgctacc   16080
ctctccgcct ctgcccccaa cgccgcccaa aaataccatg tcctcgttaa agactaaacg   16140
ttctgtatag gcagagtcca cctctaagca gtccaggctc tgccttcctt ccctagtgag   16200
tcccattctc cttggtatcc attgggcgga tgcccagcct ggatagaacc ccgaaacggg   16260
ggtagcacga gagcgactgg agaccctaa aagccagagg tttgagagag ggtggacgca   16320
gctagcagaa gatggtgtag aagccagctg agaacgaccc cctagagcaa agagacctt   16380 ctttggcttt tcttgctttg ggggtcctga aaggaactca taaaatggtc ttcaccctca   16440
ggaggaggac ggactgaccc tcctctgtca ctggcttaaa aagtttcagg gcggcggctc   16500
tgggttccgt gctgaaatcg gactgcactg cagccccttt ggacctgacg cctggctttg   16560
cgtcccgaca aggggcgggt acttcccccg gcctccccca ggaacgcatt aattgttaaa   16620
tagctttggc ccagtggatg ggctgaaagt gttcgaccca agtcgctggt gtgcacagac   16680
ttcctccctc tgggaggtgg gctccatggc ccgttgtggc accccagcc gcgacacaca   16740
```

```
ccttcacacg cggcagcagc tcggtcccaa ccttcttcga aggacctggg ttaaccctgg    16800
cggccttggc ggccgcagac ccctctccgc cgccccgccc ccgcgcctct cattcaatca    16860
gcgaatgttt gcggagcata tactacgtgg actcctaatg taccccctga aagcaaataa    16920
tacagttttc ctcgccgtca tgaagggatt ttaatcctaa catggacacc agcgagatca    16980
gcccagaccg tctctagcaa aacgcaaaat ggtggtgcgt ggggtggtga ccaaggtcct    17040
gagccttgtc agaaagaagg ggatgtgtag agaaaggtgg agaactctag ctgtggctag    17100
cgcggaaggg acaggtgctt gccgaagggg gcatgaggct tgaggaaaaa gcaacgaaat    17160
aggggtaagg agagttttcc attttctttc ctccgcccga cctccgccat cccattctcc    17220
cctcccctcc cccacccccc gcgccaatca aatctgcagc tcacttgaaa ggtgccccgc    17280
cgcgttgtgg ttttccaccc ccaggggaaa ttgtaccagt tgtccgaaag tagtcagtcc    17340
ctgcggatcc ctgcccgcaa aagtggtctt cacaggtcgc gttcctcgct gctgactcgg    17400
tacacaaagt ttcttaaggc tggttcggct gttattcctc accgcccgct gctaatatat    17460
gcagcagttg ttagagcggc tcgggggaaa aggaaatgta taacgaaagc ttattcgtga    17520
gcaggaatat actaatggaa caatctgatg tcttcttaat cctatgtaaa aagctttgtc    17580
gtcttcctaa tattgactga atgggtaatt aatggctctt catctaggcg aatacccttgt   17640
aatccaagat aggcaaaaga caacaagccc aaggtagaag acaaaaggcc caactgcagc    17700
ggcgtttgcc cgcctcctac cccccagggt ctctgactag gaaagttttc tctcaggaga    17760
gaaaaggca ggagtgggag aatatatacc tatcatttcg gggctagact tcaccgcagc     17820
acctgaccac ccagctcagt tttctgttac tctgtctttc cacctccagt ccttctccct    17880
gcatttttt ttcttcttaa ctcctctagg atgacctcct accaccaccg ccattatggt     17940
cctaataacc tttccccccta aaccccacat ctttcacttc agcaaccaat gaggctgttt   18000
tctgatccag gaggagattc ttttcttta gaacccaatg cgtagagtct ttgagaacta     18060
aagtagttgg taggggagga agaaattaat agaaagggag agagcataca gaattgtgtg    18120
tgtatgttaa agagcgacca ggaatgacag agtcaacttc tttgtgagga tctgacggga    18180
agagtgtcca agactctacc agcatgtttt taacaggctg acattttaat ttaaaccttt    18240
agaagtaata tattacttgg gttactacaa tgaggtgggt tcctttttt ttgtcagctg     18300
acagcttta aaatattatt tcgctaggga aataaaagct tcatctcaga ttataggtgg     18360
gtatttttgg atttaggtga tttatggtca ccatgacaac taatgctgaa tgttagctac    18420
cagcatgtct gggagagaga aaacagaaag aagggagagc aaaagaaata gaaagggag     18480
atggacataa gctggagagg gaagaaaaga gaaaagagg aagacagatg agtgtttaat     18540
ccaactgttg tttaaaaaag tggcgggggg gtgggacttc atttagcccc ttgccacttc    18600
cttctttcct gacctggata tctatgctca atttcatatt ccaccttcc ttcccctttct    18660
ccaaacacat gtgctatacc attctcctta ttttacttag ttcggcaagt agttgctttc    18720
tggagactca gtgacaccta ggaaaactgt ggcagtaaca tgcaaatgtg aggaagcatt    18780
aacagcatgt tcgttgagtg attttagcaa atgccccctc ctctaatctc tttctcttct    18840
cttccccagg ccactgtgag gtggtaactc ccactgccat ctgaacactg ttccccccagg   18900
tagttacccc aaatctcaaa tggttgagca gctagagctg tgggttggaa aaatgggtac    18960
catttgcagg gacccagaga gggtggctgt tgctcaatat atctcagac ttccaattca     19020
gaaaataatc ttccccttt gacaagccag agcttttaa attccattta ggaaatgggg      19080
aaaaggacag ctacagtgaa gcttttaatt tctgggttat ttggttccat agctatgagg    19140
```

```
ggtggtgggt agtggactgt tttcagcttg gtttgtatgc agagaaaagc cagatattgg    19200
aggggtgggg gcacttctcg ggcaggatgc aaggtctcca tctgacctct gcgccttacc    19260
aggagctcac acactcacgc ccatcacgtg gctccaagct gagtccaggc gggcctcgtc    19320
cttgagctag cttgggcagg gcaggactcc cacccgtcta aggcctaaca gctcagggag    19380
atgtctaatt aagccatctt ctgggtgaac tctgaagaca gactctttcc aaaagtcaga    19440
gatcacttgg ttgagtccca ggccagattg atacggagag tttggcggca cagcccaacc    19500
gctcactgcc atggccagag ggactttgca caactaacac tgaagagtgt gaaattaaat    19560
aagactttaa gactggtaat cggtggcaaa taccagcaca aaacacggct gaccccatgt    19620
cacacatttc cctcctctag ggtctttctt tgaaagaata agcaagaaac cccaatcgag    19680 acaaccctg atgtctccca gactcaaaac ctcacgccgg cactgggctt tccttctttg    19740
ccccacgtga gccatgcagc acctctagtt tccctaccag gatcccacca atgttctccg    19800
tattggaaat ttctgtgtta gaggctgaac tcatagtaat ttctaaaacc aattaagaag    19860
aacttagcca gaggtcacag taatgctgga atcacaaaat gcataagatt tattttcttc    19920
tggccccttt ctcatccatg ctgcctatgc ctgtgcaccc acaagtctta tgtacattaa    19980
atctccaaaa tcaaccacca ccatgccaca gagttttcac tggacagtgt tccttagttc    20040
ccaccacata cctccttttc cccatgcaga cttatcatgt tggtgtcctg ccacacaggg    20100
ggcctgagaa gaatgtcacc caatcgccgc tgctgtgagt gtgtaaagtg attaggagat    20160
taggagaatg ttgaaactcc tgctggaaaa atgcaaagaa aatcctcact ttgagtcagt    20220
tgtttacaga gccagtgtgt gtgtgcgtgt gtgtgtctgt aatataaaat ggatgtgaat    20280
atatatatac aaatagatat ggttttgctt ttactttaat ctgaattatc tagataattg    20340
tctttattca ccacttgact tcaatgggtc cacacaaatt aggacacctt atcttttag     20400 gcatctaggc tgctgctgat ccccagtgct tccaacatct cgcacacgtt ggcactatga    20460
ggagcagtca cgtgcccttg ggttttttcaa ccactttgga ggctgattga ggtccttcat    20520
acatgtatat ttgtcgtgat gaaagttcca tcggtagagt ggagccacca gagctttat    20580 caaaattctg tgggtttatg agagatgggt ttagaaatct atatggctct gtggggcttc    20640
tcggctttct aaaataaggc attaacaccc aagcttccaa aaatatttgc agctctgggg    20700
tttgaatctt gaaaaacaag gagtgagggg ctgtgtatac taactacagt ggagattttt    20760
ttcattcttt aatgtgatgg agtcccttca tgaaatgaag ctttaagggg catggtattg    20820
tggggaccac agctattctg aggtttaaaa gaagaaactg gaatatgatt agtaaacaca    20880
ttcagcagaa aagagctgga ttcttattga cttagttata ggtcatcggc tggcagtgca    20940
atgggaggaa atatttactt tacacatata ctttatgatc ttgggggaat tagaggaaat    21000
tcaataagaa aacggctaga aacatttaaa acccttattt aaaagactta agcaaattag    21060
agtcttatca gattaaaaac cactacaaat gtaagagcat tgtcttcagt gaaacgctgt    21120
ggggtctgag aaggagattc tccgccaaat ctccgggata aaatgcgtca tttaagcacc    21180
agataatgag cagaatgtaa attaatttaa ccttctttac caacaggctg ctagtgtaat    21240
gtgtataatt tagtgataag attgcaggac ctaatatagc tggatgtatg agcctcagct    21300
aatgcagacc tgtcacatga ggatgtgttt tactctgagc aggtgtctgt atgtgtggaa    21360
tggggtaaag tggaataaaa ggttaaaagc agaaatgctg atttaaagct tactatgaag    21420
aaattcctcc cttgcagcta aattattctt aaagtgggat gatactggtg aagaaagact    21480
```

```
gaaaaacaat tctcatgtgc gtctttggac tgcaagttta aaatggggag gagttgcaga    21540
tagggtttgg gggtggtcag ggcaaaggag agacacataa gttgcaaata tatttgtagt    21600
ctgcttcatc cactttgttc cacatcgaat aagtttccca atcttgtgaa caaggacaag    21660
gagggagtgt tttaaagata cttcatgctg gcattgcaaa tcattgactg taatgtcaaa    21720
caaatacaca ttcagagatg ataacactaa ctccatagta aaacaatcgc ccatgcagaa    21780
acccagagga gattagtttg tcctctccag ctgacctatg ctgggggaca aaaggacttt    21840
caaaaattat tttgaatatg tttggatttc tttctttaat ttctttggaa attaaatttg    21900
cttggaaaca gtgctataaa gagttgatgt ctccaaaggt gattttttt gttttatata    21960 aataaggttt tgcttttgct agttgagcgc agttctaggc ttttcgccct tagctcacac    22020
acaccccttc tgcctgcttg gactttaatg gctcaagaca gccttgagct cactgggaaa    22080
agaaaatgac tgttaaaaat tatccttgaa attggttatt tggcaacatt cttaattgta    22140
tggaaattca ttaaggcata tttcatatat aattagctca aggttgttga ttctacaggc    22200
tttatggatt taaatctgat tgataataaa gtaaacaaga gagtcgaatt taaagcgtgg    22260
ctctctcggg ttaggacgag cttaatacag tgtacaagga atttgaaaga tctaggatat    22320
gtgtcttaat caacgttaag tagaatggat aagctttcag cattttgaaa acgctgggtt    22380
agggtttctc ttctattgtg tgttttctgt ctggggacta ataagcatca cagagaacgt    22440
gatctgaggc gactttttat tcttgtataa atccagagtg aaccaccaaa cagttgttcg    22500
tttaaagtca aggtaatttt cttttgacgg gtccatttgc ttctcgattt ctaatttatt    22560
agcctgcctt ttcagggctc tgtcttcttt gcaattaaag cttcttcaga ttagcgcagc    22620
attcacttga caggctgttt ggaaaattta agatcggaga ggtgatttgt tgctgttttt    22680
caaattttct agtttttaagt aacgtgtctc ctttttatat ggggtggggg attggaaatg    22740
gatgtagtga gacacaaaga gtgggtgtct tgttgatcct tgtacctttc tcttcttgac    22800
cattccactc tcttctccca agccttcgac tcctagcctc atctcttcac ctttgggttc    22860
gtactaaaag ccggatcgcc ttgggctggg caggagctga attcccggga gcttgcctgt    22920
gtagacccag tgcgcacggc gaggcagtag cccggccccg cactgctgat aggtgcaggc    22980
aggacagtcc ctccaccgcg gctcggggcg tcctgattgg tgcggagcca cgtcagtcgc    23040
acccggagaa gggtctggga ggaggcggag gcggagaggg ctgggggaggg ccgcggcgga    23100 gtgacgtctc ggcaccagga agcccgcctc tggttttaag atgttaggcc aacagggaag    23160
cgcggagccg cagatctggt ccgtcgctcg cctgggtgcc tggagctgag ctgcggcaag    23220
gcccggctcc tgttcgaccg cccgaggggt gtgcgtgtgc gcgttgcgga gggtgcgctc    23280
agagggccgc gtcgtggctg cagcggctgc tgccgccgca ggggatctaa tatcacctac    23340
ctgtccctgt cactcttgac acttctctgt cagggctgcc gcgtgggggg gggcgggca    23400 gagcgcggtc ggcgttagct ttccttattg gaggggttct tgggggaggg agggagagaa    23460 gaaggggggtc tttgcccact cttgtttcgc tttggagctt ggaagcctgc tccctaaaga    23520
cgctctgagt ggtgcccttc tgcccacatc ccatgtcttc gtttgcccgc tgactttccg    23580
tctccggact ttttcgcttg agccttccgg aggagacggg ggcagcttgg cttgagaact    23640 cggcggggt tgcgtcccct ggctctcccc gcagcgggga aactccgcgc ctagagcgcg    23700
acccggagcg ggcagcggcg gctacggggg ctcggcgggg cagtagccaa ggactagtag    23760
agcgtcgcgc tccctcgtcc atgaactgca tgaaaggccc gcttcacttg gagcaccgag    23820
cagcggggac caagctgtcg gccgtctcct catcttcctg tcaccatccc cagccgttag    23880
```

```
ccatggcttc ggttctggct cccggtcagc cccggtcgct ggactcctcc aagcacaggc    23940
tggaggtgca caccatctcc gacacctcca gcccggaggc cgcaggtaag gcgccgcgcc    24000
gccctgcaga cattcccgct cagctgctct gcgccacccg ctccctctcg ccccaaggaa    24060
gtcagcccct ccggggggag gcgtggtggg agtggtcgtt cgcctggctc cccgcagaac    24120
ttccgggagc cggaattttg actaccccgc atccctttag ttctccctcg accggcccgg    24180
ctcctggggc gctaagggcg cgagcaattc tgccgccctc tctattcgta ccctggcctc    24240
ccttctgttt cctgggtcac aaaaatccca gcatcttgat tcgaggacct tcagaggccg    24300
ccgacctctg tccctgtttt cctctcggct ttcagctccc gaggagctcc actcgttagg    24360
aaattgcctg aaaccactca gaaatgccct tcgcgaagag gcatttttt tttttttttg    24420 ggaaagggcc ggcgaacttc ggtgcccaac cgaatcccca catcttttcc tagccttccc    24480
aaaccgcatg gaaatctgag ctttctgcga gggggagggg ggtctgtaaa ccacgcgcgt    24540
gtgcgcgtcc caggagattt ggtgtgtctg cgcagaggtg tataaatata cttgaaagca    24600
caggctataa aagtgaatgt gccgctgcag tgagataaac atgtaaataa aacgtgcggc    24660
gctgggggag gggaggaaat ggggcgcgga cacccacact tgcgcctgca caccccacag    24720
gcgcagcgct cctcgcggcc cggagccgcc gcgcgcaccc tcctccggcg ccaggcagcc    24780
cagctcttcc acggcttctg ccgccggtcc agttggcgtc cgcgttgcag gtgggcatgc    24840
tgacgggaaa gtgtgtgtgt ttcgttttca gagaaagata aaagccagca ggggaagaat    24900
gaggacgtgg gcgccgagga cccgtctaag aagaagcggc aaaggcggca gcggactcac    24960
tttaccagcc agcagctcca ggagctggag gccactttcc agaggaaccg ctacccggac    25020
atgtccacac gcgaagaaat cgctgtgtgg accaaccttg cggaagcccg agtccgggta    25080
ggagccagca cggagtctgg gagggatggg gggaggatgt tgtggaggta caggccaagt    25140
agaccaggag agaatgtgga aggcagcgcc gcctgggagg gcgccggtgg ggcgcagctt    25200
tgcaaaggca gaaggcctcg cggcggcctg gttgcgagat tacagttccc tctccgaggc    25260
cgacaggact gccgccctgg ctcaggctcc cagagcggca ccggctcact gccccgccat    25320
cccgcgatct cacgagctgg gctgcatggg caatcccctg cacaggacat tgtgttcctg    25380
gcttgcagtt gccagagcag agctaataaa atccctacca ggccaagagc cgcgaacagg    25440
ctccaacctg tgagccttta acaaggaaaa cccgccagag acacgaagga gttggccctc    25500
cctgggaaac ctttgtcccg gccctggccc agcttttttcc ctcctgggct cgcgcttctt    25560
acaccttctt tacggttgtt tcggccattc aggtctctcc cacacaccct atttcctagt    25620
tttgtgatct ccgggagcaa agttttaata cacaactact agtcctctta gaaggagaaa    25680
gaaaaaaaga agaaagactt ttctgcttgg tttatttatc ttctctcagg agttgaactc    25740
tggaaattga aactcacacc ccctcttcta aattataatc atagttttgt aaaaagggct    25800
taccttaact ttgtagcaaa tctgtacttt atggattggc aaaaatgagc tcaaataaat    25860
aacccaatag caacgtcctg gtttatgctg gtcggtggaa gattccaaat tgttaggat    25920 tctggaagca gaaaacagaa tcaagcaaat caagcggcat ccagaggctt tgctgttaaa    25980
aaaaaaaaat taagtgctct gggtagaaaa aataaagccc ccggttagag cagagcaaac    26040
aaaaagaaga aaacaacgat aaaaagaata aagaccaaaa tgctctccca aatcagaggg    26100
aatgaagaca ctctctgggt ggcatttgtg caaggcatga ggctatgctg gtggataaaa    26160
ggccgggaag aagttgaaaa tggttttagt ttaactgtcc agagccagag ctgggtcctg    26220
```

-continued

```
ggcggcgtgg tttttgagcaa ggtcagtctt tcattagctc tcttgcacat caagggaacg    26280
ggcctctcac gtactcttct cgcctgagca aagtttagat ggcctagggt agaaatggca    26340
agtaattaaa gacagagtct atgggttttc tgggatcctt cgaaaacgcc ctcccacccc    26400
gcccgctatt ccgcagctcc accctagtgc tttgtagccg cggcgctggg ctctccttgc    26460
agctgcctct ccttccaggg cggctgcttg tcgagccaag tgggagtgag gcgtgctttt    26520
tatagcagtc gggtgcaaag aggaaggggg ataaaaagga aatcaagaat gaaaggaaaa    26580
agagaaaaag cggattacac ggctgggccc ggcggagatg tgtaatgtga aacatcactg    26640
gtgtcagctc ggatatctca ggccaggcct ctctccaata cacaaaagcc gccgtctggg    26700
gcgacaggga ggcccgatgt ggattgggat cggggttgcg gctgggccac cggacacggg    26760
tggaagccgg ccggcctggg tggccgcctg caaagccaaa cgacccggct gggcctggcg    26820
cgcggacagg cctgtggtgg cttagggta aagaagaggc agagcgaaag aagggggaat    26880
ctccaaaact acccctttccg ggttcccgga gtttaatatg ccaagctcct ggagttaacg    26940
agctgacgaa gaggtggtct tttgctcttt atttggttgt tttgctaggc gagaaagagt    27000
gttggcggcc tagtccctgt taagggagca cgtaccaggg ggtgggggac gacagtggag    27060
gtcagggaag gaagggagga attgcgtggg agaaagagc atcctctagt gcccttccag    27120
ccccttctcc tcatccgtgg gtctgtggct ttggaatgga agcaagtttg caaggtgccc    27180
cgggaagggt tggaaaagcc tgctgccccg cgtttgtttt acattaagtg ttttttggacc    27240 tggagaaacg cctggctgag tgatcaaacc gtccgcaggt ctccatgcgt tcggctgagg    27300
tttgtggcgt agctccgagt cccagctcgc aggccagagc agaccaggtc tcctgcgctt    27360
ggtggagacc cgggccagta actgaaagct ggccctggta tcttggtgtg cagggcggtg    27420
cagtgaagcg aggccagggt gtgtgagtgc gctagcgtgt gtgtcggggg aaggcggggg    27480
ttggcctccg atggaagttt tagtaatctg cactgtggca tctgtttgct cccttgcccc    27540
aaccgccccc aggtttggtt caagaatcgt cgggccaaat ggagaaagag ggagcgcaac    27600
cagcaggccg agctatgcaa gaatggcttc gggccgcagt tcaatgggct catgcagccc    27660
tacgacgaca tgtacccagg ctattcctac aacaactggg ccgccaaggg ccttacatcc    27720
gcctccctat ccaccaagag cttccccttc ttcaactcta tgaacgtcaa ccccctgtca    27780
tcacagagca tgttttcccc acccaactct atctcgtcca tgagcatgtc gtccagcatg    27840
gtgccctcag cagtgacagg cgtcccgggc tccagtctca acagcctgaa taacttgaac    27900
aacctgagta gcccgtcgct gaattccgcg gtgccgacgc ctgcctgtcc ttacgcgccg    27960
ccgactcctc cgtatgttta tagggacacg tgtaactcga gcctggccag cctgagactg    28020
aaagcaaagc agcactccag cttcggctac gccagcgtgc agaacccggc ctccaacctg    28080
agtgcttgcc agtatgcagt ggaccggccc gtgtgagccg cacccacagc gccgggatcc    28140
taggaccttg ccggatgggg caactccgcc cttgaaagac tgggaattat gctagaaggt    28200
cgtgggcact aaagaaaggg agagaaagag aagctatata gagaaaagga aaccactgaa    28260
tcaaagagag agctcctttg atttcaaagg gatgtcctca gtgtctgaca tctttcacta    28320
caagtatttc taacagttgc aaggacacat acacaaacaa atgtttgact ggatatgaca    28380
ttttaacatt actataagct tgttatttt taagtttagc attgttaaca tttaaatgac    28440
tgaaaggatg tatatatatc gaaatgtcaa attaatttta taaaagcagt tgttagtaat    28500 atcacaaacag tgttttttaaa ggttaggctt taaaataaag catgttatac agaagcgatt    28560 aggattttc gcttgcgagc aagggagtgt atatactaaa tgccacactg tatgtttcta    28620
```

| | | | | |
|---|---|---|---|---|
| acatattatt | attattataa | aaaatgtgtg | aatatcagtt | ttagaatagt ttctctggtg | 28680 |
| gatgcaatga | tgtttctgaa | actgctatgt | acaacctacc | ctgtgtataa catttcgtac | 28740 |
| aatattattg | ttttactttt | cagcaaatat | gaaacaaatg | tgttttattt catgggagta | 28800 |
| aaatatactg | catacaaatt | ggtctggatt | ctttctcccc | tcctctgtca ctaacttggc | 28860 |
| caggacatct | cagtcactgc | ttcctaaaca | aaccagttcc | ctctgcctgc ctagttaaac | 28920 |
| atacaaggca | gcagtcctta | tttaaatttg | gtagaaataa | atgatagcca ttcatcagaa | 28980 |
| actaaaaaga | aaaaaaaagg | cattcccggg | ggggaaaagg | gctacaaaat ctaattttgt | 29040 |
| ctctccaatt | tttctttggc | ttaaacctag | aggattccat | tatggctagc aaataatatg | 29100 |
| aaaagaaaa | aagaagaaag | aaatttagca | agtccatcag | cttaaaatga ctctcaagtt | 29160 |
| tactcctta | cggggaaacc | tacacctcta | gcaaattgtt | ctggagaaat atttgtgcat | 29220 |
| gtatacatgt | atagtttata | tgcatttctc | tcaggaggaa | tacatctata ataaatttac | 29280 |
| agggaaacat | ctccagttca | aaatatttag | gcttccacgt | ttatcttcag gcttaagtag | 29340 |
| agagatcctt | catgttatat | tgcattacta | tttccaaatc | ctttggagac attaaaagaa | 29400 |
| acaaagatga | tttctaataa | ctacagccct | tcagtttctc | aaagaactca ggggttgaga | 29460 |
| ggttagagtg | gagtttcctg | agtcttgtcg | agcaatatgt | agttgaggca aaggtcatgc | 29520 |
| tcccggtgtt | ttgttttaaa | taatattgac | ccattaattc | taaacctgct tgttcctgaa | 29580 |
| attatacagg | attatagttt | gcaaactgca | ggacaatgaa | gcaaatcaag atgaattaca | 29640 |
| gccctggccc | tccctgccat | cctctgacat | ctaaacaggg | aatgagttcg gtgtgagtgt | 29700 |
| ttaaatgaac | tttaagcacc | cgatccttct | ttatccgcga | ttttcagctt taaaaaaatg | 29760 |
| tgaaatttga | tttcataaca | aatagaaaca | aataccactt | agtcccagag aattcatcct | 29820 |
| catggcgcta | ggagggtcgt | tgtggaggtg | ggggagggga | tgtgctgaga tcttttgtta | 29880 |
| tgcttgtcaa | ccccccgcac | aaccaaagtg | ggcgagaaca | acaccacgc tggggaactt | 29940 |
| agagcaaaaa | gtaaccgccg | attttctgga | gccgacaata | tcattgtttt ttcgccttag | 30000 |
| t | | | | | 30001 |

<210> SEQ ID NO 2
<211> LENGTH: 9001
<212> TYPE: DNA
<213> ORGANISM: Homo Sapiens

<400> SEQUENCE: 2

| | | | | |
|---|---|---|---|---|
| aggaagggtg | gatgcagtca | tttacacatg | gtctgttttt | ctggaggaca atttatttg | 60 |
| ataaacaatt | gtttctatct | gaatagaata | aacaaggctc | tatgatgaag taaaacacta | 120 |
| aatacacatg | cattaaaaaa | tgcataatta | tcttttgga | atgggctata cagagatgtg | 180 |
| cttttaaaa | tgttaagagt | gtaaaaggac | aaacagtgaa | aaataaatct tcctcttatt | 240 |
| ttgtcctcca | gtctcccaat | tcctctactc | agaggtgaga | acagaacttc cacaccctcc | 300 |
| agaacctcca | cagttagaac | tgtctacatg | tttccattgt | ctttactttt attcttgcct | 360 |
| gcacaaataa | atgaattgct | cattatggaa | acttcccaaa | agacccgtta acacttcaat | 420 |
| aggaagcacc | aacagtttat | gccctaggac | tttgttccca | caatcctgta acatcatatc | 480 |
| acgacaccta | acccaatcct | tatcaagccc | tgtcaaaaac | ggactttaaa ccaagctgca | 540 |
| aattttcagt | aatctggcct | tgcctttccc | cctctgatag | caccatcaaa caacccccct | 600 |
| tactgccgaa | agcaataagc | ccggctttgt | tccatccact | ggttgtgttg gtgatatctg | 660 |

```
gggactgcca ctgaacagac gcacagaggg agcccctaca ggcagggggtt tttctgtctg    720
tgcttctggg agagtatgtc tcgtacattt gtcgcgttga tgaagacttc acagctccat    780
cagctgcggg caagggggtc tgaggcagtc ttaggcaagt tgggggcccag cggggagaag   840
ttgcagaaga actgattaga ggaccccagg aggcttcaga gctgggcgag gtagagagtc    900
tcctgtgcgc cttctctcct ctctgcaatt cggggactcc ttgcactggg gcaggccccc    960
ggccaggtgc atgggaggaa gcacggagaa tttacaagcc tctcgattcc tcagtccaga   1020
cgctgttggg tccctccgc tggagatcgc gcttccccca aatctttgtg agcgttgcgg    1080
aagcacgcgg ggtccgggtc gctgagcgct gcaagacagg ggaggagcc gggcgggaga    1140
gggaggggcg gcgccggggc gggccctgat atagagcagg cgccgcgggt cgcagcacag   1200
tgcggagacc gcagccccgg agccggggcc agggtccacc tgtccccgca gcgccggctc   1260
gcgccctcct gccgcagcca ccggtgagtg ccgcggtcct gagatcccg ggccggatgc    1320
gcggcggccc cagctcccga gcgtctgcct ccccgccct gggctgcccg gctccctgg    1380
gctccccggc ggctgcacgg agtcaaggcg ccccgtcccg ggcgtcccc gcgggtgccg    1440
atccaggctg cccggagtcc ggagcccaga gaggagagag acagctgggg agcctggtca   1500
ccgcgggcat ctcccctgcg ctgcagtcgc ccgcctggcc tgccttcccg ttcctccgcc   1560
tcttgccctg acttctcctt cctttgcaga gccgccgtct agcgcccga cctcgccacc    1620
atgagagccc tgctggcgcg cctgcttctc tgcgtcctgg tcgtgagcga ctccaaagtg   1680
agtgcgctct gcttgact gatgctgccc aaggacctct gatcagcacc aggggagagg    1740
aggggctgct cagggagctg gggtcctccg gattccatcc acagcagggc cagactctcc   1800
ccaggaaatg ggacagggtg gcagcggagg cttgagaacc acgggggttg gcactggctg   1860
gcaagggagg aagaggccgc cgggactgcc ccagcctgcg ggcatctggt agatgaagct   1920
tgcttgggtc aatccatttc tcctggctgg aaacccatgg tcttccattt gagaactaga   1980
tacgaacagg gtgaggcgag agggagaggg aagagtgggg tttgggattg gggccagttt   2040
accctcaccc tggagtccct ggagcatggg acctttgatg aagcctcctc ccgaatctct   2100
tccagggcag caatgaactt catcaagttc catgtgagta tccacccta caacagttgg    2160
ctgcacagac aagttgggaa ggcttcaggg gacatcccct ccctgccctc tgctgcaggg   2220
ctgcgccacc ccttaccact tccactcccc ctcgcttacc ccacctttgt tctctccagc   2280
gaactgtgac tgtctaaatg gaggaacatg tgtgtccaac aagtacttct ccaacattca   2340
ctggtgcaac tgcccaaaga aattcggagg gcagcactgt gaaataggta tgggatctc    2400
cactgcaact gggagagaaa tttggggaca gggagggatg ggtgggaggc aagagcaggc   2460
aggagttagg agctggaggt agggtgggtg acatcttcat ccctatgtga caagcataaa   2520
cacacacaca cgctcacgaa acagtggcca cacaaatgtg aggtggggtt ggaaggagac   2580
cctgtccagt cttctggcag gtctgaaacg acatctttaa aatgtccgtt ggcagccggg   2640
catggtggct cacgcttgta atcccagcat tttgagaggt caaggtgagt ggatcatttg   2700
aggtcaggag ttcaagacca gcctggacaa catggtgtaa ccctgcctct actaaaaatg   2760
caaaaatcag cctggcatgg tagtggatgc ctgtagtccc agctacttgg gaggctgagg   2820
caggagaatt gcttgaacct gggaggcaga gatctcagtg agctgagatc acaccactgc   2880
actccaactg ggcgacagag caagactcca tctcaaaaaa aaaaaataaa agttagttgg   2940
aatgttcttc tcttttctcat attctctcat cctcctgtcc ccttgtagat aagtcaaaaa   3000
cctgctatga ggggaatggt cacttttacc gaggaaaggc cagcactgac accatgggcc   3060
```

```
ggccctgcct gccctggaac tctgccactg tccttcagca aacgtaccat gcccacagat    3120
ctgatgctct tcagctgggc ctggggaaac ataattactg caggtgaggt gggggcaaca    3180
aggaccaaaa gccctcccta cagcttccca gaaaccttgt taccatcccc ttctcccaga    3240
gggctggcca tagcacaaga gaagtgcggc ctctggttga gtcttccctg aggggaggag    3300
gcagggaagg ccctctgggt tggaatgaca tcccctatct ttctgtgttg ccaggaaccc    3360
agacaaccgg aggcgaccct ggtgctatgt gcaggtgggc ctaaagctgc ttgtccaaga    3420
gtgcatggtg catgactgcg cagatggtga gcatcactga cctgctgatg acagtggggt    3480 ggaagggac aaacttacat gtcccttat tccatcacag gaggactgag gaggtggggg    3540
gtgcccgaga gggatgcttt ctcctacctg cctccctaag acatccctct gtttgtcctc    3600
caggaaaaaa gccctcctct cctccagaag aattaaaatt tcagtgtggc caaaagactc    3660 tgaggcccg ctttaagatt attggggag aattcaccac catcgagaac cagccctggt    3720
ttgcggccat ctacaggagg caccgggggg gctctgtcac ctacgtgtgt ggaggcagcc    3780
tcatcagccc ttgctgggtg atcagcgcca cacactgctt catgtacggc cctgggtttc    3840
tcctcttcga ctcttctgcc ccaccccaag cacatccctt tctccttccc agcaaagtgt    3900
tccgcctcat ttctccctca tctgcccctg tccatgcagc ccatggcctt ggggacaagt    3960
cgtgctttga ggcctctagg gagggaagga agaagtggca gatttcatgg gactaagctg    4020
tttgatgggt atcttctccc acagtgatta cccaaagaag gaggactaca tcgtctacct    4080
gggtcgctca aggcttaact ccaacacgca agggagatg aagtttgagg tggaaaacct    4140
catcctacac aaggactaca gcgctgacac gcttgctcac cacaacgaca ttggtgaggg    4200
ggaaccccgc gactactgtg gccataatgg cttggggaga gtgggaccca gggagagact    4260
ggagctgagg ttgaagctgc ccggtggggc aggggtgggg cgagggacct tgaagcctcg    4320
atatacatga caaagggagt ggcagggaag agttccatga agtctgaggg gcctggtgct    4380
cctctggaga gaccctgaat tccccaaca agtagcctct tgcgagtgga aacagccctg    4440
tgggtatatg gcttgggctg ggaaggcct gtttatatga attagaaaaa gacacacctt    4500
cctttgtggg atgcagcctc tgtctgtgct aggatataga acttggagaa tggagccttg    4560
ggatggattc cagcctaact acctcagctg ggagttttg cagaaacgac ctgtacagct    4620
gtatgcagtg gctctggcca tccaagcctt tttcaacacc tggaacaaag cccttggggc    4680
atggggcagg ggaggtttcc aggtgataag cgaccagcag acctccctgg atgactgacc    4740
tagggatagg catagctact tcctcggcac ttggagggga cagatgggga ccgcctaacc    4800
agtagtgatc tttctcctct gaccctctgt cctcccccag ccttgctgaa gatccgttcc    4860
aaggagggca ggtgtgcgca gccatcccgg actatacaga ccatctgcct gccctcgatg    4920
tataacgatc cccagtttgg cacaagctgt gagatcactg gctttggaaa agagaattct    4980
agtaagtgac aattgcgact gacttagaag gtcctgagga gtgttttgac ctgaaaatga    5040
gcccagcgtg atcaagggaa gactgcagag ttagaggtgg gagcactgag gcggtggcag    5100
atgggtccag ggatggatga agagtgttgt ttagggagcg atgggctgca aaggtaaata    5160
gatggtaggg gctataggtg gagtaaaggc tcagatttgc atggaagaga ataagggcct    5220
tccctggtag agatactttta tggttcccct ctctggcaga ctcccagtgg acagataaat    5280
cttgatgcaa acgcctccct gttttctcca cctagccgac tatctctatc cggagcagct    5340
gaaaatgact gttgtgaagc tgatttccca ccgggagtgt cagcagcccc actactacgg    5400
```

-continued

```
ctctgaagtc accaccaaaa tgctgtgtgc tgctgaccca cagtggaaaa cagattcctg      5460
ccaggtgagt gttccaagca tctctctcca cctcttccat atctccccag agctcctggg      5520
cttgttccag ccagcttaag ggtgtctctc tctagccaaa gccctaagta gccagaatca      5580
ggagctcagg tctttgaggg tttaaaccag tccttatgtg tttgccagac attaccaaaa      5640
aaatcccagc tctgcgctag tcacttcaga ctgggggcac gagatcctag aaagaggaaa      5700
cagtaaaaga caatgtaact cagtgcccag ggtgtgttgt gaactataaa tgatcaggtg      5760
ttcaggagag ggaggtgagt gccaacctga gggtcaggga ggggaggctt taaaggaaat      5820
gtgacttgat aggcatttga agaggcagag ggaagaaagg aaggtgtttc agttgaaaga      5880
tacaaaactg agaaggaggc tggcatattc cgggtgggga ggagaactag ggtctgggag      5940
tgtggatgga atagtggcag atgacagggc ttttaaagcc aagcagggga ttttaaactt      6000
gatgtggtag aaaatggggc tgcgtcaggc acagtggctc atgcctgtaa tcccagcact      6060
ttgggaggcc gaggtggatg gatcacttga ggccaggagt ttgagaccgg cctggccaac      6120
atggtgaaac cctgtgtcta ctaaaaatgc aaaaaaaaat tagccaggtg tggtggtgcc      6180
tgcctgtaat cccagctaat caggaggctg agacatggga atcgcttgag cacaggaggc      6240
aagtttgcag tgagctgaga tcacgtcatt gcacgccagc ctgggcgaca gagcgagatt      6300
ctgtcctccc cccgaaaaaa agaaagaaaa tgggaagtcg ctaaggactt tgactgggaa      6360
actcttccct ctctctggta tggttgggtg atgggatcag aaatcccctc ctcacttctc      6420
tagggctcat cttttgtatc tttggcgtca cagggagact cagggggacc cctcgtctgt      6480
tccctccaag gccgcatgac tttgactgga attgtgagct ggggccgtgg atgtgccctg      6540
aaggacaagc caggcgtcta cacgagagtc tcacacttct taccctggat ccgcagtcac      6600
accaaggaag agaatggcct ggccctctga gggtccccag ggaggaaacg ggcaccaccc      6660
gctttcttgc tggttgtcat ttttgcagta gagtcatctc catcagctgt aagaagagac      6720
tgggaagata ggctctgcac agatggattt gcctgtgcca cccaccaggg cgaacgacaa      6780
tagctttacc ctcaggcata ggcctgggtg ctggctgccc agacccctct ggccaggatg      6840
gaggggtggt cctgactcaa catgttactg accagcaact tgtcttttc tggactgaag       6900 cctgcaggag ttaaaaaggg cagggcatct cctgtgcatg ggtgaaggga gagccagctc      6960 cccccgacggt gggcatttgt gaggcccatg gttgagaaat gaataatttc ccaattagga     7020
agtgtaacag ctgaggtctc ttgagggagc ttagccaatg tgggagcagc ggtttgggga      7080
gcagagacac taacgacttc agggcagggc tctgatattc catgaatgta tcaggaaata     7140
tatatgtgtg tgtatgtttg cacacttgtg tgtgggctgt gagtgtaagt gtgagtaaga     7200
gctggtgtct gattgttaag tctaaatatt tccttaaact gtgtggactg tgatgccaca     7260
cagagtggtc tttctggaga ggttataggt cactcctggg gcctcttggg tcccccacgt     7320
gacagtgcct gggaatgtat tattctgcag catgacctgt gaccagcact gtctcagttt     7380
cactttcaca tagatgtccc tttcttggcc agttatccct tccttttagc ctagttcatc     7440
caatcctcac tgggtggggt gaggaccact cctgtacact gaatatttat atttcactat     7500
ttttatttat attttgtaa ttttaaataa aagtgatcaa taaatgtga tttttctgat       7560 gacaaatctc cctggtgctt gtatgggaag gagttggagt acataaaaag gagaaaataa     7620
caaaggtgga ctgcaccta gagtttctta tgggactgca tctctggact taatggagct      7680
ttgggaggta gaggttagga gagctgtagg gcagggccac cacagcactt aatgtataca     7740
aagtttcccc aaaccacaat cccatggctg tgtaagtagt gtacaggctt agtgtcagct     7800
```

```
cccaattgcc tccttaacct gatgcctttg tgcagtgcac atcttgtaca gctgtacatg    7860
gtggtcttct ttagggttaa ctccacaaca gtctcttcac tctgccccca acaatccttg    7920
agctgacctc aaccaagaag aacacctgtg gccaggtgta gtggctcatg cctgtaatcc    7980
taacattttg agaggctgag gtgggagaat cgcttgagcc caggagtttg agaccagcct    8040
gggaaactta gtgagaccct gtctctgcaa aaataaaaa aattagccag gtgtggtagc    8100
acatgtctgt agtcctagct acttgggagg ctgaggcagg aggatcctaa gccaaggagt    8160
tcaagtttac agtcagctga ttgtgccact gcactccagc ctaggtgaca gagcaagacc    8220
ctgtctcaaa aaaaaaaaa aaaaaaaag aagaagaaga cctgtaagtg aaaattgctg    8280
gccaggctca gtggctcacg cctgtaatcc agcactttgg gaagccgagg tgtgtggatc    8340
acctgaggtc aggagtttga gaccagcctg accaacatag tgaaacccca tctctactaa    8400
aaatacaaaa aaattagccg ggtgtggggg tgggtgcctg taatcccagc tactcgggag    8460
gctgaggcag gagaatcatt tgaacccggg aggcagaggt tgcagtgagc cgagatcgca    8520
ccactgcact ccagcctggg cgacagaggg aagacttcgc ctcaaataaa taaaaaaata    8580
aataaagaaa gaaaattgct tatccagaat gccagcttga ctctgtggca ttcaggaaac    8640
aaaaaacata atttcccatc atctgtgtgt gggactgatg ctggaatttt ctcagtgtgt    8700
taacagagct tgtgaccagc cattgctatg cctatgatta gggggcccag aatctcaaag    8760
ctggatgatg tcctaatggg ggtgactata tattttgaac aaaacatcaa gttctgaaaa    8820
gctggggtgt agaaggcagg ttgggagata attgggtatc aaaaattaga attgccaagc    8880
tgtgttaatg ggttggggca gtgtttctta atcgagtcat ctgaggacct tttaaaatat    8940
gcacacctac actccacctg tagagattgt gattcaggtc agggctggct ccaggtctcg    9000
t                                                                   9001

<210> SEQ ID NO 3
<211> LENGTH: 6501
<212> TYPE: DNA
<213> ORGANISM: Homo Sapiens

<400> SEQUENCE: 3
cctgtgtttt cttctgccca agtatgaaca tgtttctggg attaagagac caggcctgga     60
aacagaagaa tttgctgagc tgtaaaatct gtatggctta aacctcaccg aacactgccc    120
accttttctc caaatgattg tgcaatttac atcccatttc caagagcccc cattttgatc    180
cgagaaatta gagcagcgaa aaccaccgtc actatgagca ccaccctggg cctggtgccc    240
ccgtcctgtt ttcaataaac ttaagctgac cacagaggac accaggcctc ggcccctccc    300
tgggtcctgc ggtcaggccc ctcctggaga ccctggccca ggagtggaga ccccggtgca    360
ggagtggcag ccctggagga ggggctgggt cctgggatgg agcgaagagg aacatggccg    420
cccccattct ggcccaggct cccctcccag aggggctgca gaaatgtact gactaggtca    480
cccaagaaaa gatagtacct tgttaggct agcatgcatt ttcctcaggg cctaatttct    540
cactgaagaa gaaagagttt ctcctgttgt ccatttcttc atgcagctct tcaacagctg    600
tttctcgaat gccaatcaaa gccactgttc tagggtctgg ggccacctca aggcactagg    660
agatgaggac ttctgctccc atgcgccctc ccgtctgctg cagggaggag tgcaatgaat    720
aaataaccaa cataatgtgt cagtcacttg ttttatccac caggaggtaa taagagctat    780
gaaagagaaa gctccgagca ggggagggga gtgaggcatg gtacaggaga gcaggaggct    840
```

```
gtcctctaaa atacaggagt ccaggggacc aactgggaag gtgtgggagg gggagggagg    900
gagccccata gacacagggg agtgaaccac gttcactttg tcagtttttg atggcagctc    960
gtatatacta ttttttttctc cctcctgccc ccagcccctc ccagaaggag acttaatctg   1020
tcgctcaggc tggagtgcag tagggtgatc tcgactcact gcaacctccg cctcccaggt   1080
tcaagtgatt ctcctgactt aacctccaga gtagctagga ttacaggcac ccgccaccat   1140
gcctggctaa ttttttgtatt ttttttttt gtagagacgg ggtttcgcca tgttggccag   1200
gctagtctca aactcctgac tttaagtgat ccgcctgctt tggcctccca aagtgttggg   1260
attacaggcg tgagccactg cgccaggcct acaatttcat tattaaaaca attccactgt   1320
aaaagaatta gcttaggcct agacggaatg ggcttcatga gctccttccc ttcccctgc    1380
aaggtcacgg tggccacccc gtgagccact gttgtcacgg ccaagccttt ttccggccat   1440
ctctcactat gaatcacttc tgcagtgagt acagtattta ccctggcggg agggcctctc   1500
agatatgagt aggacctgga ttaaggtcag gttggaggag actcccatgg gaaagaggga   1560
cttttctgaat ctcagatccc tcagccaaga tgacctcacc acatgtcgtc tctgtctatc   1620
agcaaatcct tccatgtagc ttgaccatgt ctaggaaaca cctttgataa aaatcagtgg   1680
agattattgt ctcagaggat ccccgggcct ccttaggcaa atgttatcta acgctcttta   1740
agcaaacaga gcctgcccta taaaatccgg ggctcgggcg gcctctcatc cctgactcgg   1800
ggtcgccttt ggagcagaga ggaggcaatg gccaccatgg agaacaaggt gatctgcgcc   1860
ctggtcctgg tgtccatgct ggccctcggc accctggccg aggcccagac aggtaaggcg   1920
tgcttcttcc tgctctgtgg ggccacagcc agctctggca gcctccgcca ggagccactg   1980
ttttacatac atattttga gcacctgttt tgtgccaggt gctgttctag gcccttaaaa    2040
gtatatccaa tttacaggat cggcaaaagc aggtggagag taactcaggg tggcagggcc   2100
cccggagacc ttcgagaagt gcgacgagga gggggctgcc ttcagtcggg gctgttttcc   2160
tgtgttagga agactataca atcctcccaa gtgtcatgtt tcaaagagga agtgttggcg   2220
tggggtctca gaatagtgct tttgactgtt catgccaaca tctcccccag gggcagaccc   2280
tcccaaggcc catccagata ggcccaaatg ccggtcccag tgatggccac ctgggagacc   2340
ctctcccaca ggcccgaatg cccgtcccag tggtggccaa ctgggagacc ctctcctaca   2400
ggttcctggg ctccctggg atccatgctc tgggagtcaa agccacctct tcatgagtg    2460
cgtggctggc aacccatatt ccctggtgtt gtcaagtgga tcggttgccc tgggtccttc   2520
tagggagtgg aggaggaggc cattcttgct tccttgggaa gtgtttgcat ctcaactcct   2580
ttacctgcag aatggatcaa cggtctgccc tagggctgtc aggaaatgct gtgtggcagc   2640
atctgcgact tgcactttgc cagctgtggg gagctgaata acttatttgc cgttattagg   2700
tacagtttca aggtggggc aggagaaagg gctttctacg tttccaaagc aagggtttcc    2760
agagaggcct gaagagggag cgcccagtgg tgctgtccgt gccccactg ccctccagcc    2820
acctcttgat ctctgctgtg gggtaccggg cctgaggggg gggcttgggc agcgtagaag   2880
agcagccagc attgggctgc agtgggaaga cccccaagcc catggcaggg agcggggag    2940
ctttggaacc cgagagagga agtggcctcg gtgtacagaa cgaactgggt gggtccccgt   3000
gctggccacc cccaggccca tctgcctgcg cccttgcccc caccccagcc cccagctctg   3060
cccctgtgc tgtgggatca cagaggccgt ggcaaactcc cctcccacc ccacacaccc     3120
tctggctcaa ggctcagagc gtctttgcgg gtcactcagg tccatgatcc tgttacaact   3180
gaaatctaga aaattgtgat tacagtttag tgcattcgtg tgtggaaacc atttccattt   3240
```

```
atttccatca tgcgacaaag acaaagcggg tgggcaagac agagtctgcc ggaggcagag      3300
caccggggct ggaaatcttc ctccctgagg aggaaacccc cccgacccc aggatgatga       3360 tcctccctca ccacggggcc tctcttgacc cccacagtgt cccggggtg ggcgatgatc       3420 accttcacgt cgcgatggat ccagacccca ggagggcaag gttcccatgg aagctgctgg      3480
gcagcgggag ctgaacacgg atccttccca gcaagccagg aacactttct ccaaagacat      3540
ctcgaggcag tccctgatag caaagcagac aagagaacag cccctctcgg cctcccctgg     3600
ggcgccctca cctgagccag tgtggccaga ctgagttcct cccctcctat gccccaaggc     3660
agggacaggg accggagggt gctctgggct cctctttcac cccctgctgc aggctgtcaa     3720
ccaccagatc ctaataggtt gcttctgag accttgatt ccgcggagct cagagcctga       3780
agctctggtg ttagaacctc ttgcataaga tcctgcggca gccccagcc agccccatct       3840 gtccacgtgt cttcctcctc tagatccctt tcctcactgc cctgcttcaa gctgtttcac     3900
agcttgtacc ctctgtcggc tcctcctaga ccacccacc cggtcctctc accttacctg      3960
caatgggttt ccacctcctg aacacacctg ggtctctgga atggcctttg cccatgcggc     4020
tccatcttca cctggtgaac ctcctcctgc agggagcccc cctgctttgt tcaacctgct     4080
tgtcattggc ctctccgggg agtgccctac ccccgtggtt accctgggca ccctgggacg     4140
atggccttgc gttgtctcgc acatgttctt gcctttctcc tccatcagat ccttagactc     4200
tttttttttt tttttgaga tggagtcttg ctctgtcact caggctggag tgcaatggtg     4260
cgatcttggc tcactacaac ctctgcctcc tgggttcaag tgattctcct gcctcagcct    4320
cccaagtagc tgggattaca gacgtgtgcc acaatgcccg cctaatttt tgtatttta     4380 gtagagatgg ggcttcacca ttttggtcag gctggtcttg aactcctgac ctcaagtgat    4440
tcacctcctt cagcctccca agtgctggg attacaggca tgagcctggg cccagatatt     4500
tagactctta ttaatgactt ctctggtttt aatttctggg tctctctcac ctggcacagt    4560
gcctggcttt tgccatgcta gctcccactt ctcatgcaca caaatggtgc tcagtaaata    4620
tttatgtatt gagtaaaatt taataatcat ttgttgaaat taaaaagtga ataaataagt    4680
tacctagaaa gatgcaaagt ccacaaacct ggggcacctt gcattttccc tgagcgtaat    4740
gtttgcacat caggatgtga ggaccacgtc tccctctcat gtcctgaggg ttttatatcc    4800
gcctcactgg acagttgctg atgtcattgg agaaggaagc tggatgggtg tgtgcatgat    4860
aacatcaagg aattcagccc acaacttact ttgcttctta cctgtgcact ttcagagacg    4920
tgtacagtgg ccccccgtga aagacagaat tgtggttttc ctggtgtcac gccctcccag    4980
tgtgcaaata agggctgctg tttcgacgac accgttcgtg gggtcccctg gtgcttctat    5040
cctaatacca tcgacgtccc tccagaaggt atggcctttt tatacgatgg gttctgaaga   5100
tttagaatta gttagaaaag tcatttaaga ctacagaggc tctgatcagc atcaccagct    5160
atgcctttac acagagtcac ggccgccagt ggtggtgcaa tggggtagcc tgagtcaggc    5220
tgcattcagg tccaggaata gaaaggcagg gctaagggac ttgggaagaa acctgatttc    5280
cccccggctt ctcttcacat ctctaaccaa aagcctggga agagccactg ttggtaacgc    5340
tttctagctt gcctaggata gaggggggaag gcatgacgaa atctgaagac atttcatgta   5400
ttcttttttt ttttttttt ttgaaatgga gtctcgctcc gttgcccctg agctggagtg     5460
caatggtgcg atcttggctc actgcaatct ctgcctcctg agttcaacct cagcttccta    5520
gtagctgaga ttacaggtgt gtgccactac gcccagctaa attttttttg tatttttagt    5580
```

| | |
|---|---:|
| atagacgggg tttcaccatg ttggccagac cggtcttgaa ctcttgacct caggtgatct | 5640 |
| gcccgcctca gcctcccaga gagctgggat tacaggcgtg agccaccgtg cccggctgac | 5700 |
| agttcatgtt ttctaaagaa tgtgcctatg gatactttaa agtaaaaact ctgtaattgt | 5760 |
| ttaaatgtga aagaaaatgt ttatcctcac taaagcatct ctttctccct cccctcacc | 5820 |
| cctgtagagg agtgtgaatt ttagacactt ctgcagggat ctgcctgcat cctgacgcgg | 5880 |
| tgccgtcccc agcacggtga ttagtccag agctcggctg ccacctccac cggacacctc | 5940 |
| agacacgctt ctgcagctgt gcctcggctc acaacacaga ttgactgctc tgactttgac | 6000 |
| tactcaaaat tggcctaaaa attaaaagag atcgatatta atctgtgctg ttcattcttt | 6060 |
| taaagaatat gaatgatttt cctttctttg aaagtgaagc gcagcgtttc accctgggct | 6120 |
| ctcgcagagg ttctgcatct tctgggcttc ctgagctggg atacaagtgg gcagctgagt | 6180 |
| gcagaaagca gggatggtgg ggtgtacagt aggacagtgg ggtgtgcagt aggacagtgg | 6240 |
| ggtgtgcagt aggacggtgg ggtgtacagt aggacagtgg ggtgtgcagt aggacggtgg | 6300 |
| ggtgtgcagc gggacggtgg ggtgtgcagc aggacgcaag tccaagacgc actcttgtcc | 6360 |
| aggcatgaaa atggacaccg actcccctgg catttcttaa ctactcactg cggatgcccc | 6420 |
| agcgaccaag tgacacaagt tagctttccg tttatttgct ttcccaaata gaaattggcg | 6480 |
| taggagatga aacctgtagc a | 6501 |

<210> SEQ ID NO 4
<211> LENGTH: 12001
<212> TYPE: DNA
<213> ORGANISM: Homo Sapiens

<400> SEQUENCE: 4

| | |
|---|---:|
| catggactgc gtgatcacta aacttggcac ttcaggggc atatctttt tgagtaactc | 60 |
| tcataaacat gcctgcctgc aggacatcca gattttctgg tttggtagta aagcaacata | 120 |
| agaataatct tgaacctgat gttcatcctt gccttcttc taattccagg agccctctga | 180 |
| ggtctggact aactcactga ttaggaaata gtatttggaa aggctaaaca aaatactatt | 240 |
| tccagggaaa tagtatttgg aaaggctaaa caaaatatac tttcttagtt ttctcaaacc | 300 |
| tctcagaaga tatatttttt aaaaaataaa ctaagctagc aacatttaaa ctaaatcttt | 360 |
| gccttgctta caatacaaaa gatgataaaa aaattgttgg gaaggtgaga attaacttc | 420 |
| acctataatt agaagtaaag ttttcattta aaaatgtaat accacttaaa ttcaatttgg | 480 |
| gaaacaaaaa ggactcaaaa aacagtctgc taaagccaat ttgcaaacaa gtgcgctctc | 540 |
| tttttctta agttgtatct caggttcaga gcacatgtgc aggtttgtta tgtaggtaaa | 600 |
| cctgtcacag ggatttgttg tacagattat tttgtcaccc aggtactaag cctcgtaccc | 660 |
| aatagttatt ttttctgatc ctctcccctc tcccatccgc caccttccaa taggccccag | 720 |
| tgtctgttgt tcctctcttt gtatctatga gttctcctca tttagctccc acttataagt | 780 |
| gagaacatgc gttatttggt tttctggtcc tgatttagtt tgctaaggat aatggcctcc | 840 |
| agctccatcc atatttctgc aaaaggcatg atctcattct ttttttaact attccactct | 900 |
| ctctattact ctttcttctt cccccaatcc tgaaccctac catgtcagtt taaccactcc | 960 |
| ttttcttcc tttttctttg ctcatttgca catagttaaa agatgccatg aattttcctt | 1020 |
| tttaattcag catatgccca ttaaagatct aaaaatatta tttacatcat ccagaactca | 1080 |
| gcttaagaaa ttaccaaaaa ataaagctac cagaaagtaa ctgaatcatc ttgttgagcc | 1140 |
| acaatcctag acctcgactc tgcttttcc tcatttagg caggtcattc ctttccttt | 1200 |

```
cttaaattgt tttctctgta ttcaataaca cattcttgtg gattcagaaa gggtggagta   1260
tgaggaaaag gaatatgata tatgtaccct agaggaaaac aataaataaa tatttcagga   1320
tggaaaacat tattttattt tttattgagt tttctagagt ctatttgatt tgtgtaaatc   1380
agaaaccagt agaatgacat taatgaatta atgaaaagca gaatgagtta tcagttgtaa   1440
caaaaagaat aaagaatttc aagaacacag ctttaatcat gcatggctgc ggggagagaa   1500
aaataacaaa atgctctcag tgaatacatc tctgagagaa gaaggaaat acttaaggag    1560 aggataaaaa gagcaaatat caaaatagg agtaagaacc ctattgcttt ttttagttga    1620
caaataaaaa ttgtatatat ttactgtgga caacatgata ttttgaggat tacgatcact   1680
tttgattcat aaattacatt caagaaaaag aaattctcaa aaagtttggg aacatatgaa   1740
gttgaaagaa cattaatact cagataagga cagtacatga caaattattc ttgctccaac   1800
attttctctc aggaaattta aacatctttc agtgaagcac cagtttcttg aaatcaagca   1860
tgagaaaaaa aactaaattc acctgtggaa aaaagacac agctaaacaa aaaagcggtt    1920
gttataacct caagagtggc atgaacaaaa tgatcaacat tctcccaagt gacagcacaa   1980
atatcaaaag tcctaataag tggaagtggt cctgtcatga caaaggtgt ggtatttgta    2040 caatttccag ataagaacaa agtcatgacg ctaagacagt agcagcactg tttgttacac   2100
gtgatatttg aaaaatatga caaccatctc aatctgctca gtagcactc atggtgaggg    2160 tgaaatttta tcaacattgg ttaacttatg gtgttttaaa aaactagcaa ggagataaat   2220
tgatggatta aaagataaac tactcacagg cagacaaaca gaaggacaga tagagttaca   2280
atcaaacatg tactttactc aggcagaaag ataataacca gcccccaaga agtgatgtgt   2340
ctgctagaaa agccctgaac atagaatttc ctgactttgt ttttaattta gttcttcag    2400 gcatcacgct gcataaccag gtgtaactct ctaaaagtct ctatgacaga attttccatc   2460
tgttaaatta ggctaataat attttcatct ttttttaggg taaagatgtg aaatatttgg   2520
agaactctgg aaaacatgcc ccctactaat tagagctttt tgatgtgaca tcattttctt   2580
cagtacttgg agtttagtca atagatatac agtgtagctg tgaaattatg aagcatgaga   2640
atgcattacc aagggaccgt aggaggctct ttactgaaaa gtgtagctgg ctatatttct   2700
ggaagtaatt taaacatagg ctgagggaga ggagtaccct ctagatcctt tccagaccctt   2760 actttctatg aattctaatt tctctttccc atttagaaaa aacaatgaga tccacagcgt   2820
agagatagaa aataaggctc tgtgtgccct caaaccttac tttcaaaaat accacagcat   2880
tctggacgag atagtcttga attcttgcaa cagcacaggt atgagagttt ttaccagaaa   2940
acaggagact ggattgattc tttcattctc ctcctatgct tcctaaaact gaaaagccat   3000
atatacaaat tatatttatc tatccctcct ggaaaaggcc aaaatgaatc caattttgga   3060
tcattttcaa taatgggaca aacctgaatt gagaataacc tttagaatca gtcctgtctt   3120
tttgtgataa aatggacttg tagaaagcta cctggtgttc tccccctagct aacattctac   3180 cacaaacaac gggtatgtaa tccagtattg ctccccacag gctatgtcct tggaatcact   3240
atctttgcac tccatttgtc tgctgacatc cttccaccca agatgtcttc ttcagcacaa   3300
gaagtcattt ctcttaaaat ttcaaatgac tttactacaa taatagagtt gctaactaga   3360
cctaggcaag taatgataat aaaaatctga tttctactta gagtgtagca tggtttaaca   3420
caacaaccag agtcctaaca ggttttttcta gatttcactc ctactcaact tgcatgttct   3480
tgcaatatag atgttcttat tactcggtcc ttacttccat ctctctttgc ttctggaata   3540
```

```
aaactactta aacccaattc agagatttta ttctcccttg gaattactgg gaaacagttc    3600
tagtaaacca tattcctgag atcctatatt aggcttagtc caaactgacc atctaagcat    3660
taattttcct gtggctcagg aatatccctg agcttacctt tctcttccta aactgcccag    3720
gacaaatacc ggagtttggc ttttctgctt tctcatccaa tcatttctcg tttcctcctc    3780
tttagcattt aaaacatttc tgactttctc catccctcaa gaaatatatt tgctttcctg    3840
tctctgcatt attcttttgt ttatgaaata ttccataggt aagttctata tttccttccc    3900
ccagaggccc ctggtcttct ggttccagtt gccattggtt cagtgtacta gttaacattt    3960
tggactttgg agttacacaa acctagattc aaattcccac tatgccactt actgcctacg    4020
tgacctgaag caatatccta tccactgtgg cctccagcag ttataagctt gtgctctaac    4080
cagctgggtg accttgggcc agtgacacaa tcatggcaaa cctcactgtc ttcatttgta    4140
aaatgacagt acctaccttg tagtgttggc ataaggaata agtgtgattg tcaatacaaa    4200
agtgtttagt acaatagcta aattaactaa gcactctgta aatattagtt tttaccatta    4260
ttactaattc aaatgactag atgcattttg tgtataccag gtttcctgag ttcactttgt    4320
tctcaacaaa tactattatt cctagcatgt ggcctatatc acacttcatt agccagagga    4380
catgtgaagc ttagagtgga aagctagggc agcaggaagc attgccacac tttacacagt    4440
caaagccatt taaacatgtc tgaatttgag ctctgctgag tccttacttg cccccatctc    4500
tcctgtgtgc tccagcttac taataaagca ggtttaatat aaatacacta aaagcctaaa    4560
cattgagatc atgataatga atatgagggc tatgactata aaatatcatt gaaccagaga    4620
cctgctacga aaccacatgg tgaagaccac aaggaggaa tctgcataca caccgagtgc    4680
cttgggatcc caaagtggga agagtcagtg ccccaattaa agagaaactc ggggtaggga    4740
atcaaccaca acatcagtca ccttactgaa cccaggcttg tttcagctga cgtagctgcc    4800
aatttccaat gtcccctccc tccctaattg ctctcaatct attcctccag aaactgaaag    4860
cccatcaaag aggatatctt cccagagagt tgttccagtt actacaagct cttgctagaa    4920
attccaagaa agtttacaag gtacctttat aaggtggcat tgagtaagtc agaagcattc    4980
caagtaccaa ttatcatgca aataagggct ttacttttag attttgttgt ttgtggtggt    5040
ggtgatgctg gtgttctctc tggaatccag cccaatctcc aaaaaagtaa aaggagtaca    5100
aatagtaata caaattatta ttacttacac caattaaaat agaagttttg aatgagcaag    5160
gagctagagg aggtaaaaac tgggaacttc gtatattaaa aggtttttat aatttgaaaa    5220
ctaagattat gctggccaaa taggctgttt taaaatcagc atagtaatca aatttgcttg    5280
taatgaatgt agacccaaac agtgatgtca gacctgataa ggacttgcaa accctaaaag    5340
agtgcaaaaa gaccatagaa gaacaatatt atattcctgc acttacagaa atggtcagct    5400
caagagatgt atccagttca gggtggctgt aagcttcatt ttctgaactt gctaccagaa    5460
gttaaaagaa attctgtata actgcttttg atggaaacac aaattggttg atgtaaatga    5520
aatacataaa gcagttggtg tcttattcat tcccacaatt ataaatgaaa ttaaatgatc    5580
aaaaattata gactttgggg atcttctttt cactgaggag cccatggaat tgtcttctc     5640 tagtaccaat aactgtgttg acctattttt tcctgtctaa ctctgtatat attaaaacta    5700
ggtggttacg aacaaaaccc agaaatacaa tttacattct aataaaatga ctttaaaatt    5760
attccacttt ttactgtggc tttacctgtt gtcccacaat gcaggtttct ctgggcctct    5820
gcttagaatg actctgtcaa tgtagatgac agccagagtt gaatgggaa tccagaaact     5880 ggggattcgg gctcttgatg caatctatat gccaatctac ttcattagtt cttctttat     5940
```

```
ttacagtttg gtaaagaata tgggtggagc tgttctgggc tcacttgcac acatgtccaa      6000
actgctttga aaaaggaagg gcaagaaaga gtggtatcca agttggaatc aggcaggcat      6060
ttcagatcaa gagacgaact ggaaagggaa catctgttag ataccctggg tttgaaggca      6120
gtctgtgtaa gttttcatat ctctgagtgt gtgcacacag tggagagggt ggagcctgcc      6180
atcctcaaat ctgaaaagat tgagagattt cagagggccc agatgtgcca aaggtcagag      6240
ggatcaatat acaggcccta ccacggaaag gcggggaaaa ggttcgaata gaaaactgct      6300
gcagaaggga agccactgag aggtaaggga gtttctgaat aattaaaaag ttaagaataa      6360
gcaaaaggaa ggaggtcggg tgggggataa aaaaaagcag ttgatgtggt aattaagaat      6420
ttggtgggag cctgggcagg tcacctcctt tctcagatca gagccccatc agaaattctt      6480
tcaagtgtcc ttctgcgtcg ccaaagatga caacagcaaa tcaataagtg cttgaaatga      6540
aaggggatgt tgactagccc ccaggctaca gatttcccgc cgccagcctt ttctgaactc      6600
ctatagcgtg cctttgcacc gcctctctta agaagagcta cctttattc ctattctcag      6660 gacgaaggta agtgctcagt tagcatatct attaaatgtc agctttggtt ccagctctcc      6720
gtttgcgcgg aaagctcact gccatagcgc gcccagcctg ccggaggggc agacagaaaa      6780
agcaagcttg gcctggcgac ttgcggggcc acgcacctcc agggctggcc cggagtcttc      6840
cagagtttaa cgctcctggg ttagaactgt aaggtcccgg tccgagcaaa gggcctgagc      6900
caccgtagcc gtgggagcgt tccttccact tgaatgcact cactcacaaa caagcacaaa      6960 atcttttttaa cagcagagga gaaagacccc tgctccaaaa ttaaagctgg gaatcaccgg      7020
aaactccgtt ttgagtgcga gatattggtc tgttaccttt ctaatcttca tatccctcct      7080
gtaatatgtc ttgatttaac aatctttcca gcgcccagca ttgcccggac gttttaattg      7140
ggtaattcat tagtgagtca atacaggcat ttatatattc ttttagctca agtggttaag      7200
tactaatttc gaaatgatta taaaacaccg gaatcggcaa cgcatagtaa ttttaattta      7260
tatgcaaatc aattggttca tcttaaatgc ctttttttaaa aaaacaatta ttgtattgta      7320
gcatcggagg catggatcaa acctctagaa tagacaattc ggaaacaaga cctggactag      7380
gaagacaatt tagaacagcc aacaaatcaa taatgtttga ggcagttaaa catcgctagc      7440
cattggtatt tacatactcg cttgttgtca gataaggagc tggggaaatt gcttgccagg      7500
gttgagatca taatccagag tgaagaaagt aaatggtagc acacagcccg tcacagcggg      7560
ctctgaaata atactgtacc tttcccaaat cctgactctt gggtgacagg gagttggcgg      7620
aggtcacccc acatttgtcc acggttttgc cccaatttga tcacgaaatt gttgttctcc      7680
ctgagctttc caatttgatt accattctaa cggttctgtc acttgtctca acatattggg      7740
gggaggagtg taattgagat tctcattaaa aattatctga acccacttag ccagcactgt      7800
ttcatctaag cttagttttta tgggctgtat ttaattccct gtgcccccca cacattaaaa      7860
tcagatcatc aaaatgtcgg taggaaaggg tgaaggaaat ggtccaatgc tccagtttac      7920
tggaagacta ttatctttag acatagttca aaattttgag gaaataaaaa ggatatacgc      7980 tttggggggga aaatgtttta atattctaga atgggggtat tactcccccc attccagaga      8040
atccgcactg gagttgttta tgtaaaaatg taacatcctt gaaattcaca gatacgtaag      8100
gttagtgtct cccctccccc aggctcccag tccaggcgat ctagccctaa aggagctagt      8160
acctttgatg ctacaatctt gtttacatct gcagggcaga gaattgcttg ctttgcttgg      8220
acgctccctc cacccccttc taatttgaag taatcggaat ctaaatacag tcgccaaggc      8280
```

```
ccgctcttcc tttactgctt tgacaaggga aaaacctgaa atccacgtct taaatcagct    8340
cggtggtttg tagccccca gcaccctgct tctacgattg catgcctaat gtattccctg     8400
gtgattctgg gcattaatta gttgtttaat aggagtatga ctaaaaatgt aaagaagga     8460
ttaggagcgt gaaacgtatg tccagctcct tccacacact cgaggaggga atgagaatca    8520
ttctgtatct tctatttctc caggagccat ttgcatttcc caccagctgc tcacttcagc    8580
tgcactggcg ctgggcaagg cgaggaccca aaagctcagc gcagtgtctg cggcggccgg    8640
gactggggtt aaccagcctc tggcgggcga ctccagac agaagggggg cgagaggaac      8700
gtgagcttcc cgagcccctt cctctcagcc ctggtttgca aacctctgaa acctgaaagg    8760
ggagggagtt gcacgcgcgt atctttgcgt cttttcagcg caactccctt ccctctccct    8820
gtgtctctcc gcggatctct gaatctttct gtctttggtt ttctcattct cttccaactt    8880
ttccatgaga ttgcctatcc tcgccaccag ctgaaggcaa ggccgttctg ctacgagcgc    8940
ctcttaatct ctacaaaatg aaagaaaaa aagggaggat tattagccca ttactcagag     9000
gaatggggag gctgcaaaaa tcgtcgatgg cagaggtga agatgtcttt ctcggactgc     9060
actttccggt gtcctgtaac tagagttcag ttgtgggact tgttgaagaa atttgatttt    9120
cttgcctcgg cgagatttca aaaccagaaa atagaaattc tcagagtcag agaggaaata    9180
caattaaaca gcacgtgggc attttccccc tcatttctct cccttaaat aacactgctt     9240
tgagtttcca ctgggtaaag agagaaagtt tgagttttca cggatgttac gtggaggtta    9300
gaaatggctt aaaatgtaga tctctaatca gttttcttcg tggctgaaga ggctaaccct    9360
ttccataaaa tgagtccatc tgtcgactgt tagctatttc aaagtgaagg gatttagcac    9420
tcaaaacaaa ttgagcaagt ttgtttgcct gttttactg ctaactcaaa tgaattcaaa     9480
acacggagta attcaagaaa acacataaca tgttccagac agcccccaaa agtagggaaa    9540
gcccagcacc tatatagtga ctagggttag ttttaagcgc caagcttttt taaacgtatc    9600
tattttatgc acattctccc gagtcactat atatttctaa aattgcgagt attggtatat    9660
tgatttagga agagcaatac aacttttaga gggaacttta ttctcaatta gggaccaaag    9720
agatgtcttt ttaatagcgg gcctgagttt tgctctcaag caggaattaa tattggtggg    9780
aaaatccgaa tccaggagca atggctgtgt tccggcactt tccaaaaaca tacattaaca    9840
ggatgccctt gagattgaaa aaacattgtc ccatatgcct ggcagaagcc ttcacacctg    9900
gtcctccagg cgaattatat ttatagtcct tccactcaga ggcaggacag agccaaaata    9960
ttctgctcac taccaaaata cacatctttg ctcaagtcaa gaaatcagaa atcagggtt   10020
cagaagtaag gcacactttt cgagtgagaa tatgccctgt aatttcacat actctttgct   10080
ttgcaggagc aaatgtggac ttgagggaaa ctctctcccc cacccccact tctatcccgt   10140
gcaatttaat accatcctcg ccaggaacct taacctcgtc attttaaaaa atgagatatc   10200
cgtgacccag ggtgaacttg ttgaatgtag gtacagcaga ggaaattcta gactctatga   10260
gcgtctgagc cttgtccagt gcaaaccctt cgtgaacact gggtcagtgc gtggccgtgc   10320
ccacctgtgc gccgacactc tcagcatgcc tggtccaccc gccttgacct cgggcgcggt   10380
gtcccagcta agctgggccc agcgtccgg ccttccccag ctgacaagcc tagctcgttc    10440
gctcccggct gtggccctcc caccctctcc cactagctca ctccattctt ctagatttct   10500
cttcactcat cctctcccat ccccaccgcg cccacctcca ctcccgccct taccggtct    10560
ctcactttcc tccctccgca gtccctcttt gctgtgacct cttcctcaa ctctgcaggc    10620
ctgaaagaag gtcacacacg cacgctcaca cccacactcc acacgcctcg tcccaaacaa   10680
```

```
cccatgaac attgtccttt gttccgtctc ttgggccact ttccctgtcg cttcctccca    10740
gcccgtcctg atttgctccc caaaagtacg tttctgtctc cccgctgccc tggcgctccc    10800
cctttgattt attagggctg ccggggttggc gcagattgct ttttcttctc ttccatccca    10860
tcctcccttc tggtcctcct ttccacagtg ggagtccgtg ctcctgctcc tcggttggct    10920
cctaagtgcc ccgccaggtc ccctctcctt tcgctctccc ggctccggct cccgactctt    10980
cggcccgctg gcatctgctt ccctcccctg cctcgtttct cgtcgcccct gctcgctccc    11040
cccggcgctc gcccgggcgc tgtgctcgct cctggatcgc cagccgcgca gccgggctcg    11100
gccggccgcc cgcgcgccac tgtgcagtgg agtttggtgg aatctctgct gacgtcacgt    11160
cactccccac acggagtagg agcagaggga agagagaggg atgagaggga gggagaggag    11220
agagagtgcg agaccgagcg agaaagctgg agaggagcag aaagaaactg ccagtggcgg    11280
ctagatttcg gaggccccag tgcacccgtg gactccttcg gaacttggca ccctcaggag    11340
ccctgcagtc ctctcaggcc cggctttcgg gcgcttgccg tgcagccgga ggctcggctc    11400
gctggaaatc gccccgggaa gcagtgggac gcggagacag cagctctctc ccggtagccg    11460
gtaagtggag gccatctatc ccgcagggat gtgagataat gcgagtctgg aaatttgttc    11520
cacttcggag aatcttcacc gtaggtgatt tgtggctttt ggggctaagt ttcgcccaag    11580
gtaacgcagt cggcaaacag accttgcaaa gccctgttcc tttcgtcccc cgccacagac    11640
actaacaatc tacagggtgc tgaagtcgag agggaagcca gaccgtggct ggcatttaaa    11700
acgaggtatc ttcccttaaa tctcggtgcc aacactgcag gaacaaatcc tcgggccaag    11760
gattagcatt ctcaagataa agggctgggt acaaagtttc agctactgga agattagccc    11820
ccttcccatt gttatccatt gggaaaaaaa agaaaagaaa aagattccat cttaactggc    11880
agttagtgac ctctcaggcc caagcgaatt acctgggagc caggcctgga tgccaagctc    11940
tcaccatttc tttggattgt aactccttta aattgatcac cagtcaactc caatctggca    12000
c                                                                   12001
```

<210> SEQ ID NO 5
<211> LENGTH: 4001
<212> TYPE: DNA
<213> ORGANISM: Homo Sapiens

<400> SEQUENCE: 5

```
ttttcgccct tagctcacac acacccttc tgcctgcttg gactttaatg gctcaagaca      60
gccttgagct cactgggaaa agaaaatgac tgttaaaaat tatccttgaa attggttatt     120
tggcaacatt cttaattgta tggaaattca ttaaggcata tttcatatat aattagctca     180
aggttgttga ttctacaggc tttatggatt taaatctgat tgataataaa gtaaacaaga     240
gagtcgaatt taaagcgtgg ctctctcggg ttaggacgag cttaatacag tgtacaagga     300
atttgaaaga tctaggatat gtgtcttaat caacgttaag tagaatggat aagctttcag     360
cattttgaaa acgctgggtt agggtttctc ttctattgtg tgttttctgt ctggggacta     420
ataagcatca cagagaacgt gatctgaggc gacttttttat tcttgtataa atccagagtg     480
aaccaccaaa cagttgttcg tttaaagtca aggtaatttt cttttgacgg gtccatttgc     540
ttctcgattt ctaatttatt agcctgcctt ttcagggctc tgtcttcttt gcaattaaag     600
cttcttcaga ttagcgcagc attcacttga caggctgttg ggaaaattta agatcggaga     660
ggtgatttgt tgctgttttt caaatttttct agttttaagt aacgtgtctc ctttttatat     720
```

```
ggggtggggg attggaaatg gatgtagtga gacacaaaga gtgggtgtct tgttgatcct    780
tgtacctttc tcttcttgac cattccactc tcttctccca agccttcgac tcctagcctc    840
atctcttcac ctttgggttc gtactaaaag ccggatcgcc ttgggctggg caggagctga    900
attcccggga gcttgcctgt gtagacccag tgcgcacggc gaggcagtag cccgccccg     960
cactgctgat aggtgcaggc aggacagtcc ctccaccgcg gctcggggcg tcctgattgg   1020
tgcggagcca cgtcagtcgc acccggagaa gggtctggga ggaggcggag gcggagaggg   1080
ctggggaggg ccgcggcgga gtgacgtctc ggcaccagga agcccgcctc tggttttaag   1140
atgttaggcc aacagggaag cgcggagccg cagatctggt ccgtcgctcg cctgggtgcc   1200
tggagctgag ctgcggcaag gcccggctcc tgttcgaccg cccgaggggt gtgcgtgtgc   1260
gcgttgcgga gggtgcgctc agagggccgc gtcgtggctg cagcggctgc tgccgccgca   1320
ggggatctaa tatcacctac ctgtccctgt cactcttgac acttctctgt cagggctgcc   1380
gcgtgggggg gggcgggca gagcgcggtc ggcgttagct ttccttattg gagggggttct   1440
tgggggaggg agggagagaa gaaggggggtc tttgcccact cttgtttcgc tttggagctt   1500
ggaagcctgc tccctaaaga cgctctgagt ggtgcccttc tgcccacatc ccatgtcttc   1560
gtttgcccgc tgacttttccg tctccggact ttttcgcttg agccttccgg aggagacggg   1620
ggcagcttgg cttgagaact cggcgggggt tgcgtcccct ggctctcccc gcagcgggga   1680
aactccgcgc ctagagcgcg acccgagcg ggcagcggcg gctacggggg ctcggcgggg    1740
cagtagccaa ggactagtag agcgtcgcgc tccctcgtcc atgaactgca tgaaaggccc   1800
gcttcacttg gagcaccgag cagcggggac caagctgtcg gccgtctcct catcttcctg   1860
tcaccatccc cagccgttag ccatggcttc ggttctggct cccggtcagc ccggtcgct    1920
ggactcctcc aagcacaggc tggaggtgca caccatctcc gacacctcca gcccggaggc   1980
cgcaggtaag gcgccgcgcc gccctgcaga cattcccgct cagctgctct gcgccacccg   2040
ctccctctcg ccccaaggaa gtcagcccct ccgggggag gcgtggtggg agtggtcgtt    2100
cgcctggctc cccgcagaac ttccgggagc cggaattttg actaccccgc atcccttag    2160
ttctccctcg accggcccgg ctcctgggc gctaagggcg cgagcaattc tgccgccctc    2220
tctattcgta ccctggcctc ccttctgttt cctgggtcac aaaaatccca gcatcttgat   2280
tcgaggacct tcagaggccg ccgacctctg tccctgtttt cctctcggct ttcagctccc   2340
gaggagctcc actcgttagg aaattgcctg aaaccactca gaaatgccct tcgcgaagag   2400
gcatttttt ttttttttg ggaaagggcc ggcgaacttc ggtgcccaac cgaatcccca    2460
catcttttcc tagccttccc aaaccgcatg gaaatctgag ctttctgcga gggggagggg   2520
ggtctgtaaa ccacgcgcgt gtgcgcgtcc caggagattt ggtgtgtctg cgcagaggtg   2580
tataaatata cttgaaagca caggctataa aagtgaatgt gccgctgcag tgagataaac   2640
atgtaaataa aacgtgcggc gctgggggag gggaggaaat ggggcgcgga cacccacact   2700
tgcgcctgca caccccacag gcgcagcgct cctcgcggcc cggagccgcc gcgcgcaccc   2760
tcctccggcg ccaggcagcc cagctcttcc acggcttctg ccgccggtcc agttggcgtc   2820
cgcgttgcag gtgggcatgc tgacgggaaa gtgtgtgtgt ttcgttttca gagaaagata   2880
aaagccagca ggggaagaat gaggacgtgg gcgccgagga cccgtctaag aagaagcggc   2940
aaaggcggca gcggactcac tttaccagcc agcagctcca ggagctggag gccacttttcc  3000
agaggaaccg ctacccggac atgtccacac gcgaagaaat cgctgtgtgg accaacctta   3060
cggaagcccg agtccgggta ggagccagca cggagtctgg gagggatggg gggaggatgt   3120
```

| | |
|---|---:|
| tgtggaggta caggccaagt agaccaggag agaatgtgga aggcagcgcc gcctgggagg | 3180 |
| gcgccggtgg ggcgcagctt tgcaaaggca gaaggcctcg cggcggcctg gttgcgagat | 3240 |
| tacagttccc tctccgaggc cgacaggact gccgccctgg ctcaggctcc cagagcggca | 3300 |
| ccggctcact gccccgccat cccgcgatct cacgagctgg gctgcatggg caatcccctg | 3360 |
| cacaggacat tgtgttcctg gcttgcagtt gccagagcag agctaataaa atccctacca | 3420 |
| ggccaagagc cgcgaacagg ctccaacctg tgagccttta caaggaaaaa cccgccagag | 3480 |
| acacggaaga gttggccctc cctgggaaac ctttgtcccg gccctggccc agcttttttcc | 3540 |
| ctcctgggct cgcgcttctt acaccttctt tacggttgtt tcggccattc aggtctctcc | 3600 |
| cacacaccct atttcctagt tttgtgatct ccgggagcaa agttttaata cacaactact | 3660 |
| agtcctctta gaaggagaaa gaaaaaaaga agaaagactt ttctgcttgg tttatttatc | 3720 |
| ttctctcagg agttgaactc tggaaattga aactcacacc ccctcttcta aattataatc | 3780 |
| atagttttgt aaaagggct taccttaact ttgtagcaaa tctgtacttt atggattggc | 3840 |
| aaaaatgagc tcaaataaat aacccaatag caacgtcctg gtttatgctg gtcggtggaa | 3900 |
| gattccaaat ttgttaggat tctggaagca gaaaacagaa tcaagcaaat caagcggcat | 3960 |
| ccagaggctt tgctgttaaa aaaaaaaaat taagtgctct g | 4001 |

<210> SEQ ID NO 6
<211> LENGTH: 2501
<212> TYPE: DNA
<213> ORGANISM: Homo Sapiens

<400> SEQUENCE: 6

| | |
|---|---:|
| aggaagggtg gatgcagtca tttacacatg gtctgttttt ctggaggaca atttttatttg | 60 |
| ataaacaatt gtttctatct gaatagaata aacaaggctc tatgatgaag taaaacacta | 120 |
| aatacacatg cattaaaaaa tgcataatta tcttttttgga atgggctata cagagatgtg | 180 |
| cttttttaaaa tgttaagagt gtaaaaggac aaacagtgaa aaataaatct tcctcttatt | 240 |
| ttgtcctcca gtctcccaat tcctctactc agaggtgaga acagaacttc cacaccctcc | 300 |
| agaacctcca cagttagaac tgtctacatg tttccattgt ctttactttt attcttgcct | 360 |
| gcacaaataa atgaattgct cattatggaa acttcccaaa agacccgtta acacttcaat | 420 |
| aggaagcacc aacagtttat gccctaggac tttgttccca caatcctgta acatcatatc | 480 |
| acgacaccta acccaatcct tatcaagccc tgtcaaaaac ggactttaaa ccaagctgca | 540 |
| aattttcagt aatctggcct tgccttttccc cctctgatag caccatcaaa caaaccccct | 600 |
| tactgccgaa agcaataagc ccggctttgt tccatccact ggttgtgttg gtgatatctg | 660 |
| gggactgcca ctgaacagac gcacagaggg agcccctaca ggcagggtt tttctgtctg | 720 |
| tgcttctggg agagtatgtc tcgtacattt gtcgcgttga tgaagacttc acagctccat | 780 |
| cagctgcgga caaggggtc tgaggcagtc ttaggcaagt tggggcccag cggggagaag | 840 |
| ttgcagaaga actgattaga ggaccccagg aggcttcaga gctgggcgag gtagagagtc | 900 |
| tcctgtgcgc cttctctcct ctctgcaatt cggggactcc ttgcactggg gcaggccccc | 960 |
| ggccaggtgc atgggaggaa gcacggagaa tttacaagcc tctcgattcc tcagtccaga | 1020 |
| cgctgttggg tcccctccgc tggagatcgc gcttccccca aatctttgtg agcgttgcgg | 1080 |
| aagcacgcgg ggtccgggtc gctgagcgct gcaagacagg ggaggagcc gggcgggaga | 1140 |
| gggaggggcg gcgccggggc gggccctgat atagagcagg cgccgcgggt cgcagcacag | 1200 |

| | |
|---|---|
| tgcggagacc gcagccccgg agcccgggcc agggtccacc tgtccccgca gcgccggctc | 1260 |
| gcgccctcct gccgcagcca ccggtgagtg ccgcggtcct gagatccccg ggccggatgc | 1320 |
| gcggcggccc cagctcccga gcgtctgcct ccccgccct gggctgcccg gctccctgg | 1380 |
| gctccccggc ggctgcacgg agtcaaggcg ccccgtcccg ggcgtccccc gcgggtgccg | 1440 |
| atccaggctg cccggagtcc ggagcccaga gaggagagag acagctgggg agcctggtca | 1500 |
| ccgcgggcat ctcccctgcg ctgcagtcgc ccgcctggcc tgccttcccg ttcctccgcc | 1560 |
| tcttgccctg acttctcctt cctttgcaga gccgccgtct agcgccccga cctcgccacc | 1620 |
| atgagagccc tgctggcgcg cctgcttctc tgcgtcctgg tcgtgagcga ctccaaagtg | 1680 |
| agtgcgctct tgctttgact gatgctgccc aaggacctct gatcagcacc aggggagagg | 1740 |
| aggggctgct cagggagctg gggtcctccg gattccatcc acagcagggc cagactctcc | 1800 |
| ccaggaaatg ggacagggtg gcagcggagg cttgagaacc acggggttg gcactggctg | 1860 |
| gcaagggagg aagaggccgc cgggactgcc ccagcctgcg ggcatctggt agatgaagct | 1920 |
| tgcttgggtc aatccatttc tcctggctgg aaacccatgg tcttccattt gagaactaga | 1980 |
| tacgaacagg gtgaggcgag agggagaggg aagagtgggt tttgggattg gggccagttt | 2040 |
| accctcaccc tggagtccct ggagcatggg acctttgatg aagcctcctc ccgaatctct | 2100 |
| tccagggcag caatgaactt catcaagttc catgtgagta ccacccccta caacagttgg | 2160 |
| ctgcacagac aagttgggaa ggcttcaggg gacatcccct ccctgccctc tgctgcaggg | 2220 |
| ctgcgccacc ccttaccact tccactcccc ctcgcttacc ccacctttgt tctctccagc | 2280 |
| gaactgtgac tgtctaaatg gaggaacatg tgtgtccaac aagtacttct ccaacattca | 2340 |
| ctggtgcaac tgcccaaaga aattcggagg gcagcactgt gaaataggta tggggatctc | 2400 |
| cactgcaact gggagagaaa tttggggaca gggagggatg ggtgggaggc aagagcaggc | 2460 |
| aggagttagg agctggaggt agggtgggtg acatcttcat c | 2501 |

<210> SEQ ID NO 7
<211> LENGTH: 901
<212> TYPE: DNA
<213> ORGANISM: Homo Sapiens

<400> SEQUENCE: 7

| | |
|---|---|
| caaatggtgc tcagtaaata tttatgtatt gagtaaaatt taataatcat ttgttgaaat | 60 |
| taaaaagtga ataaataagt tacctagaaa gatgcaaagt ccacaaacct ggggcacctt | 120 |
| gcattttccc tgagcgtaat gtttgcacat caggatgtga ggaccacgtc tccctctcat | 180 |
| gtcctgaggg ttttatatcc gcctcactgg acagttgctg atgtcattgg agaaggaagc | 240 |
| tggatgggtg tgtgcatgat aacatcaagg aattcagccc acaacttact ttgcttctta | 300 |
| cctgtgcact ttcagagacg tgtacagtgg cccccgtga agacagaat tgtggttttc | 360 |
| ctggtgtcac gccctcccag tgtgcaaata agggctgctg tttcgacgac accgttcgtg | 420 |
| gggtcccctg gtgcttctat cctaatacca tcgacgtccc tccagaaggt atggcctttt | 480 |
| tatacgatgg gttctgaaga tttagaatta gttagaaaag tcatttaaga ctacagaggc | 540 |
| tctgatcagc atcaccagct atgcctttac acagagtcac ggccgccagt ggtggtgcaa | 600 |
| tggggtagcc tgagtcaggc tgcattcagg tccaggaata gaaaggcagg gctaagggac | 660 |
| ttgggaagaa acctgatttc cccccggctt ctcttcacat ctctaaccaa agcctgggga | 720 |
| agagccactg ttggtaacgc tttctagctt gcctaggata gaggggaag gcatgacgaa | 780 |
| atctgaagac atttcatgta ttcttttttt tttttttttt ttgaaatgga gtctcgctcc | 840 |

```
gttgccsctg agctggagtg caatggtgcg atcttggctc actgcaatct ctgcctcctg         900
a                                                                          901

<210> SEQ ID NO 8
<211> LENGTH: 1301
<212> TYPE: DNA
<213> ORGANISM: Homo Sapiens

<400> SEQUENCE: 8
gctagtctca aactcctgac tttaagtgat ccgcctgctt tggcctccca agtgttggg          60 attacaggcg tgagccactg cgccaggcct acaatttcat tattaaaaca attccactgt         120
aaaagaatta gcttaggcct agacggaatg ggcttcatga gctccttccc ttccccctgc         180
aaggtcacgg tggccacccc gtgagccact gttgtcacgg ccaagccttt ttccggccat         240
ctctcactat gaatcacttc tgcagtgagt acagtattta ccctggcggg agggcctctc         300
agatatgagt aggacctgga ttaaggtcag gttggaggag actcccatgg gaaagaggga         360
cttcctgaat ctcagatccc tcagccaaga tgacctcacc acatgtcgtc tctgtctatc         420
agcaaatcct tccatgtagc ttgaccatgt ctaggaaaca cctttgataa aaatcagtgg         480
agattattgt ctcagaggat ccccgggcct ccttaggcaa atgttatcta acgctcttta         540
agcaaacaga gcctgcccta taaaatccgg ggctcgggcg gcctctcatc cctgactcgg         600
ggtcgccttt ggagcagaga ggaggcaatg gccaccatgg agaacaaggt gatctgcgcc         660
ctggtcctgg tgtccatgct ggccctcggc accctggccg aggcccagac aggtaaggcg         720
tgcttcttcc tgctctgtgg ggccacagcc agctctggca gcctccgcca ggagccactg         780
ttttacatac atattttga gcacctgttt tgtgccaggt gctgttctag gcccttaaaa          840
gtatatccaa tttacaggat cggcaaaagc aggtggagag taactcaggg tggcagggcc         900
cccggagacc ttcgagaagt gcgacgagga ggggctgcc ttcagtcggg gctgttttcc          960
tgtgttagga agactataca atcctcccaa gtgtcatgtt tcaaagagga agtgttggcg        1020
tggggtctca gaatagtgct tttgactgtt catgccaaca tctcccccag gggcagaccc        1080
tcccaaggcc catccagata ggcccaaatg ccggtcccag tgatggccac ctgggagacc        1140
ctctcccaca ggcccgaatg cccgtcccag tggtggccaa ctgggagacc ctctcctaca        1200
ggttcctggg ctcccctggg atccatgctc tgggagtcaa agccacctct ctcatgagtg        1260
cgtggctggc aacccatatt ccctggtgtt gtcaagtgga t                           1301

<210> SEQ ID NO 9
<211> LENGTH: 30001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 9
tggaagtggt tttgttatga taaaaggtgt ggtatttgta taattttag ataagaataa          60 agttatgacg ttaagatagt agtagtattg tttgttatac gtgatatttg aaaaatatga         120
taattatttt aatttgttta gtagtatttt atggtgaggg tgaaatttta ttaatattgg         180
ttaatttatg gtgttttaaa aaattagtaa ggagataaat tgatggatta aagataaat          240 tatttatagg tagataaata gaaggataga tagagttata attaaatatg tattttattt         300
aggtagaaag ataataatta gttttttaaga agtgatgtgt ttgttagaaa agttttgaat         360
```

```
atagaattttt ttgattttgt ttttaattta gttttttag gtattacgtt gtataattag      420
gtgtaatttt ttaaaagttt ttatgataga attttttatt tgttaaatta ggttaataat      480 attttattt ttttttaggg taaagatgtg aaatatttgg agaattttgg aaaatatgtt       540
ttttattaat tagagttttt tgatgtgata ttatttttt tagtatttgg agtttagtta       600
atagatatat agtgtagttg tgaaattatg aagtatgaga atgtattatt aagggatcgt      660
aggaggtttt ttattgaaaa gtgtagttgg ttatattttt ggaagtaatt taaatatagg      720
ttgagggaga ggagtatttt ttagatttt tttagatttt attttttatg aattttaatt      780 ttttttttt atttagaaaa aataatgaga tttatagcgt agagatagaa ataaggttt        840 tgtgtgtttt taaattttat ttttaaaaat attatagtat tttggacgag atagttttga      900 attttttgtaa tagtataggt atgagagttt ttattagaaa ataggagatt ggattgatt     960 tttatttt tttttatgtt ttttaaaatt gaaaagttat atatataaat tatatttatt      1020 tatttttt ggaaaaggtt aaatgaatt taattttgga ttattttaa taatgggata         1080 aatttgaatt gagaataatt tttagaatta gtttgttt tttgtgataa aatggatttg       1140
tagaaagtta tttggtgttt ttttttagtt aatattttat tataaataac gggtatgtaa     1200
tttagtattg tttttatag gttatgtttt tggaattatt attttgtat tttatttgtt       1260 tgttgatatt tttttattta agatgttttt tttagtataa gaagttattt ttttaaaat     1320 tttaaatgat tttattataa taatagagtt gttaattaga tttaggtaag taatgataat    1380
aaaaatttga tttttattta gagtgtagta tggtttaata taataattag agttttaata   1440 ggtttttta gattttattt ttatttaatt tgtatgtttt tgtaatatag atgttttat      1500 tattcggttt ttatttttat ttttttgt tttggaata aaattattta aatttaattt       1560
agagatttta tttttttg gaattattgg gaaatagttt tagtaaatta tattttgag       1620 attttatatt aggtttagtt taaattgatt atttaagtat taattttttt gtggtttagg    1680 aatattttg agtttatttt ttttttta aattgtttag gataaatatc ggagtttggt      1740 tttttgttt ttatttaa ttattttcg ttttttttt tttagtattt aaaatatttt         1800 tgattttt tatttttaa gaaatatatt tgttttttg ttttgtatt attttttgt          1860 ttatgaaata ttttataggt aagttttata tttttttt ttagaggttt tggttttt        1920 ggttttagtt gttattggtt tagtgtatta gttaatattt tggattttgg agttatataa    1980
atttagattt aaatttat tatgttattt attgtttacg tgatttgaag taatattta       2040 tttattgtgg ttttagtag ttataagttt gtgttaat tagttgggtg attttgggtt      2100
agtgatataa ttatggtaaa ttttattgtt tttatttgta aaatgatagt atttatttg     2160 tagtgttggt ataaggaata agtgtgattg ttaatataaa agtgtttagt ataatagtta    2220
aattaattaa gtattttgta aatattagtt tttattatta ttattaattt aaatgattag    2280
atgtattttg tgtatattag gttttttgag tttattttgt tttaataaaa tattattatt    2340
tttagtatgt ggtttatatt atattttatt agtagagga tatgtgaagt ttagagtgga    2400
aagttagggt agtaggaagt attgttatat tttatatagt taaagttatt taaatatgtt    2460
tgaatttgag ttttgttgag tttttatttg ttttattt ttttgtgtgt ttagtttat       2520 taataaagta ggtttaatat aaatatatta aaagtttaaa tattgagatt atgataatga    2580
atatgagggt tatgattata aaatattatt gaattagaga tttgttacga aattatatgg    2640
tgaagattat aagggaggaa tttgtatata tatcgagtgt tttgggattt taaagtggga    2700
agagttagtg tttaattaa agagaaattc ggggtaggga attaattata atattagtta    2760
```

```
ttttattgaa tttaggtttg ttttagttga cgtagttgtt aatttttaat gtttttttt     2820
tttttaattg tttttaattt atttttttag aaattgaaag tttattaaag aggatatttt     2880
tttagagagt tgttttagtt attataagtt tttgttagaa attttaagaa agtttataag     2940
gtatttttat aaggtggtat tgagtaagtt agaagtattt taagtattaa ttattatgta     3000
aataagggtt ttatttttag attttgttgt ttgtggtggt ggtgatgttg gtgtttttt      3060
tggaatttag tttaattttt aaaaagtaa aaggagtata aatagtaata taaattatta     3120
ttatttatat taattaaaat agaagttttg aatgagtaag gagttagagg aggtaaaaat     3180
tgggaatttc gtatattaaa aagttttat aatttgaaaa ttaagattat gttggttaaa     3240
taggttgttt taaaattagt atagtaatta aatttgtttg taatgaatgt agatttaaat     3300
agtgatgtta gatttgataa ggatttgtaa atttaaaag agtgtaaaaa gattatagaa     3360
gaataatatt atattttgt atttatagaa atggttagtt taagagatgt atttagttta     3420
gggtggttgt aagttttatt ttttgaattt gttattagaa gttaaagaa attttgtata     3480
attgttttg atggaaatat aaattggttg atgtaaatga aatatataaa gtagttggtg     3540
ttttatttat ttttataatt ataaatgaaa ttaaatgatt aaaaattata gattttgggg     3600
atttttttt tattgaggag tttatggaat ttgttttttt tagtattaat aattgtgttg     3660
atttatttt ttttgtttaa ttttgtatat attaaaatta ggtggttacg aataaaattt      3720
agaaatataa tttatatttt aataaaatga ttttaaaatt atttatttt ttattgtggt     3780
tttatttgtt gttttataat gtaggttttt tgggtttttt gtttagaatg attttgttaa     3840
tgtagatgat agttagagtt gaatggggaa tttagaaatt ggggattcgg ttttttgatg     3900
taatttatat gttaatttat tttattagtt tttttttat ttatagtttg gtaaagaata     3960
tgggtggagt tgttttgggt ttatttgtat atatgtttaa attgttttga aaaaggaagg     4020
gtaagaaaga gtggtattta agttggaatt aggtaggtat tttagattaa gagacgaatt     4080
ggaaagggaa tatttgttag atattttggg tttgaaggta gtttgtgtaa gttttatat     4140
ttttgagtgt gtgtatatag tggagagggt ggagtttgtt attttttaaat ttgaaaagat     4200
tgagagattt tagagggttt agatgtgtta aaggttagag ggattaatat ataggtttta     4260
ttacggaaag gcgggggaaaa ggttcgaata gaaaattgtt gtagaaggga agttattgag     4320
aggtaaggga gttttttgaat aattaaaaag ttaagaataa gtaaaggaa ggaggtcggg     4380
tggggataa aaaaaagtag ttgatgtggt aattaagaat ttggtgggag tttgggtagg     4440
ttattttttt tttagatta gagttttatt agaaattttt ttaagtgttt ttttgcgtcg     4500
ttaaagatga taatagtaaa ttaataagtg tttgaaatga aagggggatgt tgattagttt     4560
ttaggttata gattttttcgt cgttagtttt ttttgaattt ttatagcgtg ttttttgtatc     4620
gttttttta agaagagtta tttttttattt ttatttttag gacgaaggta agtgtttagt     4680
tagtatattt attaaatgtt agttttggtt ttagttttttc gtttgcgcgg aaagtttatt     4740
gttatagcgc gtttagtttg tcggagggggt agatagaaaa agtaagtttg gtttggcgat     4800
ttgcgggggtt acgtattttt agggttggtt cggagttttt tagagtttaa cgttttttggg     4860
ttagaattgt aaggtttcgg ttcgagtaaa gggtttgagt tatcgtagtc gtgggagcgt     4920
ttttttttatt tgaatgtatt tatttataaa taagtataaa attttttttaa tagtagagga     4980
gaaagatttt tgttttaaaa ttaaagttgg gaattatcgg aaatttcgtt ttgagtgcga     5040
gatattggtt tgttattttt ttaatttta tattttttt gtaatatgtt ttgatttaat     5100
```

-continued

| | | | | | |
|---|---|---|---|---|---|
| aatttttta | gcgtttagta | ttgttcggac | gttttaattg | ggtaatttat | tagtgagtta | 5160 |
| atataggtat | ttatatattt | ttttagttta | agtggttaag | tattaatttc | gaaatgatta | 5220 |
| taaaatatcg | gaatcggtaa | cgtatagtaa | tttttaattta | tatgtaaatt | aattggttta | 5280 |
| ttttaaatgt | tttttttaaa | aaaataatta | ttgtattgta | gtatcggagg | tatggattaa | 5340 |
| atttttagaa | tagataattc | ggaaataaga | tttggattag | gaagataatt | tagaatagtt | 5400 |
| aataaattaa | taatgtttga | ggtagttaaa | tatcgttagt | tattggtatt | tatatattcg | 5460 |
| tttgttgtta | gataaggagt | tggggaaatt | gtttgttagg | gttgagatta | taatttagag | 5520 |
| tgaagaaagt | aaatggtagt | atatagttcg | ttatagcggg | ttttgaaata | atattgtatt | 5580 |
| tttttaaat | tttgattttt | gggtgatagg | gagttggcgg | aggttatttt | atatttgttt | 5640 |
| acggttttgt | tttaatttga | ttacgaaatt | gttgtttttt | ttgagttttt | taatttgatt | 5700 |
| attattttaa | cggttttgtt | atttgtttta | atatattggg | gggaggagtg | taattgagat | 5760 |
| ttttattaaa | aatttattga | atttatttag | ttagtattgt | tttatttaag | tttagttta | 5820 |
| tgggttgtat | ttaatttttt | gtgttttta | tatattaaaa | ttagattatt | aaaatgtcgg | 5880 |
| taggaaaggg | tgaaggaaat | ggtttaatgt | tttagtttat | tggaagatta | ttattttag | 5940 |
| atatagttta | aaatttgag | gaaataaaaa | ggatatacgt | tttgggggga | aaatgtttta | 6000 |
| atatttaga | atggggtat | tatttttttt | atttttagaga | attcgtattg | gagttgttta | 6060 |
| tgtaaaaatg | taatatttt | gaatttata | gatacgtaag | gttagtgttt | ttttttttt | 6120 |
| aggttttag | tttaggcgat | ttagttttaa | aggagttagt | attttgatg | ttataattt | 6180 |
| gtttatattt | gtagggtaga | gaattgtttg | tttttgttgg | acgttttttt | ttttttttt | 6240 |
| taatttgaag | taatcggaat | ttaaatatag | tcgttaaggt | tcgttttttt | tttattgttt | 6300 |
| tgataaggga | aaaatttgaa | atttacgttt | taaattagtt | cggtggttg | tagttttta | 6360 |
| gtattttgtt | tttacgattg | tatgtttaat | gtatttttg | gtgatttttgg | gtattaatta | 6420 |
| gttgtttaat | aggagtatga | ttaaaaatgt | aaagaagga | ttaggagcgt | gaaacgtatg | 6480 |
| tttagtttt | tttatatatt | cgaggaggga | atgagaatta | ttttgtattt | ttatttttt | 6540 |
| taggagttat | ttgtatttt | tattagttgt | ttatttagt | tgtattggcg | ttgggtaagg | 6600 |
| cgaggattta | aaagtttagc | gtagtgtttg | cggcggtcgg | gattggggtt | aattagttt | 6660 |
| tggcgggcga | gatttagat | agaagggggg | cgagaggaac | gtgagttttt | cgagttttt | 6720 |
| tttttagtt | ttggtttgta | aatttttgaa | atttgaaagg | ggagggagtt | gtacgcgcgt | 6780 |
| attttgcgt | tttttagcg | taattttttt | tttttttt | gtgttttttc | gcggattttt | 6840 |
| gaatttttt | gttttggtt | tttttattt | tttttaattt | tttatgaga | ttgttattt | 6900 |
| tcgttattag | ttgaaggtaa | ggtcgttttg | ttacgagcgt | tttttaattt | ttataaaatg | 6960 |
| aaagaaaaa | aagggaggat | tattagttta | ttatttagag | gaatggggag | gttgtaaaaa | 7020 |
| tcgtcgatgg | gtagaggtga | agatgttttt | ttcggattgt | atttttcggt | gttttgtaat | 7080 |
| tagagtttag | ttgtgggatt | tgttgaagaa | atttgattt | tttgtttcgg | cgagatttta | 7140 |
| aaaattagaa | atagaaattt | ttagagttag | agaggaaata | taattaaata | gtacgtgggt | 7200 |
| atttttttt | ttattttttt | tttttaaat | aatattgttt | tgagttttta | ttgggtaaag | 7260 |
| agagaaagtt | tgagttttta | cggatgttac | gtggaggtta | gaaatggttt | aaaatgtaga | 7320 |
| ttttaatta | gttttttcg | tggttgaaga | ggtaatttt | ttttataaaa | tgagtttatt | 7380 |
| tgtcgattgt | tagttatttt | aaagtgaagg | gatttagtat | ttaaaataaa | ttgagtaagt | 7440 |
| ttgtttgttt | gttttattg | ttaatttaaa | tgaatttaaa | atacggagta | atttaagaaa | 7500 |

-continued

```
atatataata tgttttagat agtttttaaa agtagggaaa gtttagtatt tatatagtga   7560
ttagggttag ttttaagcgt taagttttt  taaacgtatt tattttatgt atattttttc   7620
gagttattat atattttaa  aattgcgagt attggtatat tgatttagga agagtaatat   7680
aatttttaga gggaatttta ttttaatta  gggattaaag agatgttttt ttaatagcgg   7740
gtttgagttt tgttttaag  taggaattaa tattggtggg aaaattcgaa tttaggagta   7800
atggttgtgt ttcggtattt tttaaaaata tatattaata ggatgttttt gagattgaaa   7860
aaatattgtt ttatatgttt ggtagaagtt tttatatttg gtttttagg  cgaattatat   7920 ttatagtttt tttatttaga ggtaggatag agttaaaata ttttgtttat tattaaaata   7980 tatattttg  tttaagttaa gaaattagaa aattagggtt tagaagtaag gtatatttt    8040 cgagtgagaa tatgttttgt aatttttatat attttttgtt ttgtaggagt aaatgtggat   8100
ttgagggaaa tttttttttt tattttttatt tttatttcgt gtaatttaat attattttcg   8160
ttaggaattt taatttcgtt atttttaaaaa atgagatatt cgtgatttag ggtgaatttg   8220
ttgaatgtag gtatagtaga ggaaatttta gattttatga gcgtttgagt tttgtttagt   8280 gtaaatttt  cgtgaatatt gggttagtgc gtggtcgtgt ttatttgtgc gtcgatattt   8340
ttagtatgtt tggtttattc gttttgattt cgggcgcggt gttttagtta agttgggttt   8400
agcgtttcgg ttttttttag ttgataagtt tagttcgttc gttttcggtt gtggttttt    8460 tatttttttt tattagttta ttttattttt ttagattttt tttatttttat ttttttttat   8520 ttttatcgcg tttattttta ttttcgtttt ttatcggttt tttatttttt tttttcgta    8580 gttttttttt gttgtgattt ttttttttaa ttttgtaggt ttgaaagaag gttatatacg   8640
tacgtttata tttatattt  atacgtttcg ttttaaataa ttttatgaat attgttttt    8700 gtttcgtttt ttgggttatt tttttgtcg  tttttttta  gttcgttttg atttgttttt   8760
taaaagtacg tttttgtttt ttcgttgttt tggcgttttt ttttgatttt attagggttg   8820
tcgggttggc gtagattgtt tttttttttt ttttattta  tttttttttt tggtttttt    8880 ttttatagtg ggagttcgtg tttttgtttt tcggttggtt tttaagtgtt tcgttaggtt   8940
tttttttttt tcgttttttc ggtttcggtt ttcgattttt cggttcgttg gtatttgttt   9000 ttttttttg  tttcgttttt cgtcgttttt gttcgttttt ttcggcgttc gttcgggcgt   9060
tgtgttcgtt tttggatcgt tagtcgcgta gtcgggttcg gtcggtcgtt cgcgcgttat   9120
tgtgtagtgg agtttggtgg aattttttgtt gacgttacgt tatttttat  acggagtagg   9180 agtagaggga agagagaggg atgagaggga gggagaggag agagagtgcg agatcgagcg   9240
agaaagttgg agaggagtag aaagaaattg ttagtggcgg ttagatttcg gaggttttag   9300
tgtattcgtg gattttttcg gaatttggta ttttaggag  ttttgtagtt ttttaggtt    9360 cggttttcgg gcgtttgtcg tgtagtcgga ggttcggttc gttggaaatc gtttcgggaa   9420
gtagtgggac gcggagatag tagttttttt tcggtagtcg gtaagtggag gttatttatt   9480
tcgtagggat gtgagataat gcgagtttgg aaatttgttt tatttcggag aattttatc    9540 gtaggtgatt tgtggttttt ggggttaagt ttcgtttaag gtaacgtagt cggtaaatag   9600
attttgtaaa gttttgtttt tttcgttttt cgttatagat attaataatt tatagggtgt   9660
tgaagtcgag agggaagtta gatcgtggtt ggtatttaaa acgaggtatt ttttttaaa    9720 tttcggtgtt aatattgtag gaataaattt tcgggttaag gattagtatt tttaagataa   9780
agggttgggt ataaagtttt agttattgga agattagttt tttttttatt gttatttatt   9840
```

```
gggaaaaaaa agaaaagaaa aagattttat tttaattggt agttagtgat ttttttaggtt      9900
taagcgaatt atttgggagt taggtttgga tgttaagttt ttattatttt tttggattgt      9960
aattttttta aattgattat tagttaattt taatttggta ttttaggaga tatattttaa     10020
atggatgtag agaattattt tttagttgga gattaagaaa aaaattttcg attttaaatt     10080
ttcgaaatat gttttttttt tttagtttaa ttattttatt tttttaagta atttagaaat     10140
taaattatta taaggtggtg tgattttttt ttattttttt gtgtgagtat tgttttatta     10200
aattaaacgg aaaaaatttt tattattata aatgtaaata ttagaattta tatattttaa     10260
aatattttta tgaaaaatta atttgattta aagaaatttt tttgtatttg ttttagttta     10320
ttaattaaaa ttaaagatgt ttttattata taaaatatta ttttggtaga aatttattta     10380
aaatttaaat attaataata ttaagaaaat aaagtatata agtaaaataa attgaagatt     10440
tttgttgatg taatatgagt atataatatt ttaataatta aattttttt aaaaaattaa     10500
atagttattt tatttgtgga atgttttatt ttaatttagt aaaattatat ttaaattatt     10560
taggtgtttt gttttttaag ttaagcgtgt ttgttttaa atgttttaa agtatttata     10620
ttaattggtt gtaaagaacg tatatatatg gtaaaatata gaattgaatt gagtagtatt     10680
ttaattttt taaataatta tttattataa attaatttat tggttaattt tataatttag     10740
tttatttaaa atatatgttt ttgtgttgtt tatttttaaa tttttttatta aagattttgt     10800
tatggggtaa taaagtgtat gaaaagggg gaaatgtgaa aggatttggg attattcgaa     10860
ttgtattttt tttgtatttt tagttttgcg gtagttatta gaaattattt tttagtaaat     10920
tgttttattt tttaggtttt gtttgtttgt tttgttatgg ttttttcgttt ttcgttagtc     10980
gtgtagtgtt ttttgtgtgt ttataatata aaatttaagt tggttaaaat aagagttttt     11040
ggtatatata ttttaattag aatatgaatt tggggggtga gaattatttt ttattaggaa     11100
aagtttttta ttttaatttg tgagattagt tattgaagtt agttcgaag tttggtagtt     11160
aaattttta tagaagattt gttttgatag ggtaagtta aggattagta ggcgggaatt     11220
ggaggttttt ttttaaaaaa ttatttttt tagttatta gatttagttt ttttagtagg     11280
tttggttatt aaatgaagta taaaaatgta agttttaagg tttatttga ttgtaaaata     11340
aatttttaag ttataaggat atgtaggagt gagttaagga atacgttttg attttttttt     11400
tagttttag agtggagttt tatgagtttt tgaagatttg ttttgtattg ttttgtttgg     11460
tttttagtat tgaagtacgg ggaagtgggg ggaagaatgt gtaataattg attgattta     11520
tattaagtaa cgtaattttt ttttttgta tattttattt tttaaaaaa ataaataaat     11580
aaaaattatt tgtagttatt atttgtagtg tttcggttat tagttaataa tgtagttagt     11640
ttagatatat aaaaaaaaaa gattatcgaa atgatgatga tatgtaaatt tttttcgaaa     11700
ttattataag taaatatttg aagtttggat taataaaatt ttatttgtgt tatttatat     11760
cgagttagta gaaagttgtg ataatgaatt ttgtaatatt ttacgaatag atattttaat     11820
tagggattaa ttttgtgatt ttattgtaga attattaaat ttggagtcgt taaattgtta     11880
tttttgggtt tacgggttta taaggatcga atcggtagag ttttcgttcg cgttttcgtt     11940
agcgggtggg ggaatcgttt ggtcgttttt attttggatt tttacgttat agcgtcgggt     12000
agtttttttt gtaggtagcg attttggtta gaggtttttt agggtttagt tttttttagg     12060
agaggtcgag acgtagggaa acggtattta ggttagaggt aggttcgtag tttttttgttt     12120
cgttttttgt ttttcgttaa ttcgataacg tttgttttta tttcgatttt cgtattcgcg     12180
cgaagtgggt ttttcggtcg tcggcgtatt ttggttagcg tggagagagg taggcgttga     12240
```

```
gatcgaaggg gtttagggag ttttggattt ttttttttg tttttaaagt aatcgcggtt    12300
tttttattta ttcggtggag tttttcgaga tttatttttt tcggtttgtt tgtggtagag    12360 aaggggagc gcgttaaatg tttggttcgt tgcgttgtgg ttgaaaacgt gaaaaagatt    12420
tggttcgttc gggagagaaa gggggagaat tgggtagtag ttatattaga gttatttttt    12480 cgttttggc gggtagtaaa ttttttaaga acgtttgttt tgtttttttt agtttcgttt    12540
agtttattta gtgttttttt tttgcgattt taaattatat tttagggtaa ttatttgtag    12600
taagtaaata aatggtcggg ttagtatttt taggagaaag tgtggttaaa tatggaaaag    12660 tggttttga tggatgagag gttcgaattt agttcgtttt tgaaatattt taggttaaga    12720
gttcgttcgt tttagaatta tagaaaatcg agggaaattg ttgtttagga taggggtacg    12780
ttggcgttga tgtttataa atgtttatcg agttttaatt aatggataag tattgaaggg    12840 tggttttgt atatagtttt ttaaagagaa aagttttttt tatttatta ttttcgttgt    12900 tattgcgttt agatgagttt ttaatttcgg tatcgagatt tttgaaagta ggtttatagt    12960
ttttttagta tattgtggtt ttatagtttt ttaatttttg ggtattttg cggtaatttt    13020 ggagggagat ttttttttga taaataaatg tttgggttc gaggttaggt tggagatgtt    13080
gttgtatagt tagaggttgt taggtcggaa aaatacgttt gaagtttagt atatagtagg    13140
cgtttaatag ttagtgtaac gtagttttat ttgagtttg tttattcgac ggtcgtcgtt    13200
ttttatagtt ttttttttt tttgttttgt agataacggg gaatggagat taattgtcgt    13260
aaattggtgt cggcgtgtgt gtaattaggt aagaatttt tttttttgtt cgggttatcg    13320
gacgggaggt cgcgttacgt gagggcggta agagggtatt ggttttgcgg cgaggtttta    13380 gcgagggcg ttttttcgag gggttagttt gggtaggaag gaaattagaa ttaaatcgtt    13440
agtggttttt ttttgtggcg gggcggtgga ttaggaagta gcggcgcgtt gtgtatcgaa    13500
gttttttagt ttatttttt cggttggaat cgtcggtaat cggggaggcg tagaaagagt    13560
acgttatttt gtttcgggtt gttagagggt tcggggacg gggatgtcgt tagttttttt    13620
ttttaattgg gttttttgttt tttgttttt tttttttttc ggtttgtttc gtttttttt    13680 ttttttttcgt tttcggtttt tttcggtcgc ggttcgggac gttttttttc gtacgtgggg    13740
cgggcgcgcg cgtggtttag gcgtgtagtc ggcggtcgtt gaatgttttt tttttaaaga    13800
tttcgaaatt aaaaaggtcg agtttacgga ttttttgag agtcgaaaag aggtagttag    13860
tagtaagttt ttttcgcggt agtatttgg cgttaatggt aaggtcggga gggaagcgta    13920
ggtcgcgcgt tgggtattcg ttttcgggat tttgggtttc gggcgaagcg taagaaggcg    13980
aggtcgttag atttgacgcg tttgttgttt gaatttagat atttcgtttt tgggtgggac    14040
gggaagtagt cgtttaggg acgttaattt tttttttaa attatattgt attttgaga    14100 tttaatattt tttttttttt ttcgttcgtt ttttgtggtt tgatttttg cgtacgtttt    14160 agtaaatttc ggcgtttagg ttggcgtgga aaagtggtg aatagcgatt tttgtcgttc    14220
gttatatttc gttgcgcgta gtattattag ggtttattta gttatttagg ttttagtta    14280 cgttttattt agatttgtgg gtgcgcggtt tatcgcggga ggtaagtaag ggaaatttga    14340
gttggcgaag gtttgttttg gttggttggg ggagggcgg ggggtcgata atattttga    14400 agagttggag ggtagttatt gtgtttagta gttagggta gaatggaggt ttgttttgt    14460 cgacgcgaat ttgtttgaag tattggttgt taggttttgg gttttggcga tgtcgttgtt    14520
tgattggttg gttttatttt ggaggaatcg agggatattg ttagaggagg tttataggtt    14580
```

```
tatgtaaaaa gttaaaaagt ttttaattta cgttataggt tttttttgaa ttgaaatttg    14640
ttttatgggg cggagggggg ggtgtaaggg atggaggagg gaagatgttt ttttttttaa    14700
atatatggaa aaaattttt taaatttatt gtttttttat ttttttggtt tcgtagtaaa     14760
taagtgttta gttttaggag gttattgatt tttgataatg tgagtagata aagttttttt    14820 tttttttatag ttttcggttt ttaatttttt ttttcggat taaagtgtaa gaatataaat    14880
gtaatatggg atgaggggg gcgatttggg atttcggtta aaaaaataaa tcgtattatt     14940
aagaagaaaa taaaggtttt gtattggagt ttttcgtga atttgagaga aaatgattat    15000
ttgttgaaat gaagcgttta aagcgattta gtgttttacg ttcggatatt gtattatatc    15060
gttagtcgtt ttgttgggtt agttaaacgt ttatttgttc gggattaatt ttatggggtt    15120 aaatggggt aatgtagaga taacgtcgcg tgattttgt tatttagatt gtgttaaatt     15180 tttttttgt ttgataatcg gtagtaaaaa taaattatta gatcgtagta tgtttgggat    15240
atggttaaaa attaagagta gcgatgattt tggggagaa tgttttgcgc gggtttagtt     15300
ttggtttcgg ttagattaga ggagtttttt aatttcgttt cgcgcggggc gggttcgtag    15360
tcgttaagtc gaggttgata ttttttattg tgttgggagt tagagagacg taaaatgttt    15420
ttttttttta gttttattt taggtttttt agatatgggg aatgtatttt gaggataggt    15480
ggagaagttt acggtaggat ggggttttcg taggtgagta ggaaacggtt aagagtagag    15540
gagttttgtt tgcgttagtt ataagtcgcg taggcgtttt tggtcgttcg ttttttgataa    15600 ttagtatata aagaattaga aataatgaat gattgttttt ttaattatta tttttaggtt    15660
cgtattgttt tagtgtacgt gaaaggtttt ttttttatat ttaatatgtt ttttttttatt    15720 ttttgatcga aagaaaaat tgttgtttaa atacgtttaa tgttattaat taagaaaagg    15780
tatgtaatgg gaagaaatgt tgaaaatttt gatttaattg gttttaagg aattagtaga    15840 cgataaaaaa aaattatacg agtgggtaaa gttatagtat tgttgaagga tagagtattt    15900 atttttttt gattttaagt taatttatgg aatatttaaa gttttggtta tagtttgttt    15960
gtaaaataaa aggattttatt ttttgtgttt tttaaagtt tttttttgtt tttaaagaga    16020 aaaaagttt ataatgatat atgattttttt taaaaggtcg tgatagttta ttacgttatt    16080
ttttcgtttt ttgttttttaa cgtcgtttaa aaatatattg ttttcgttaa agattaaacg    16140
ttttgtatag gtagagttta tttttaagta gtttaggttt tgtttttttt ttttagtgag    16200 tttattttt tttggtatt attgggcgga tgtttagttt ggatagaatt tcgaaacggg    16260
ggtagtacga gagcgattgg agattttaa aagttagagg tttgagagag ggtggacgta    16320
gttagtagaa gatggtgtag aagttagttg agaacgattt tttagagtaa agagattttt    16380
ttttggtttt ttttgttttg ggggttttga aaggaattta taaaatggtt tttattttta    16440
ggaggaggac ggattgattt ttttttgtta ttggtttaaa aagttttagg gcggcggttt    16500
tgggtttcgt gttgaaatcg gattgtattg tagtttttt ggattgacg tttggtttg     16560 cgtttcgata aggggcgggt attttttcg gttttttta ggaacgtatt aattgttaaa     16620
tagttttggt ttagtggatg ggttgaaagt gttcgattta agtcgttggt gtgtatagat    16680
tttttttttt tgggaggtgg gttttatggt tcgttgtggt atttttagtc gcgatatata    16740 ttttttatacg cggtagtagt tcggttttaa tttttttcga aggatttggg ttaattttgg    16800
cggttttggc ggtcgtagat ttttttttcgt cgtttcgttt tcgcgttttt tatttaatta    16860
gcgaatgttt gcggagtata tattacgtgg atttttaatg tattttttga aagtaaataa    16920
tatagttttt ttcgtcgtta tgaagggatt ttaatttttaa tatggatatt agcgagatta    16980
```

```
gtttagatcg tttttagtaa aacgtaaaat ggtggtgcgt ggggtggtga ttaaggtttt    17040
gagttttgtt agaagaagg ggatgtgtag agaaaggtgg agaattttag ttgtggttag    17100
cgcggaaggg ataggtgttt gtcgaagggg gtatgaggtt tgaggaaaaa gtaacgaaat    17160
aggggtaagg agagtttttt attttttttt tttcgttcga ttttcgttat tttattttt    17220 ttttttttt tttatttttc gcgttaatta aatttgtagt ttatttgaaa ggtgtttcgt    17280
cgcgttgtgg ttttttattt ttaggggaaa ttgtattagt tgttcgaaag tagttagttt    17340
ttgcggattt ttgttcgtaa aagtggtttt tataggtcgc ttttttcgtt gttgattcgg    17400
tatataaagt ttttaaggt tggttcggtt gttatttttt atcgttcgtt gttaatatat    17460
gtagtagttg ttagagcggt tcgggggaaa aggaaatgta taacgaaagt ttattcgtga    17520
gtaggaatat attaatggaa taatttgatg ttttttttaat tttatgtaaa aagttttgtc    17580 gttttttttaa tattgattga atgggtaatt aatggttttt tatttaggcg aatattttgt    17640
aatttaagat aggtaaaaga taataagttt aaggtagaag ataaaaggtt taattgtagc    17700
ggcgtttgtt cgttttttat tttttagggt ttttgattag gaaagttttt ttttagagga    17760
gaaaaaggta ggagtgggag aatatatatt tattattttcg gggttagatt ttatcgtagt    17820
atttgattat ttagtttagt tttttgttat tttgttttt tattttagt tttttttttt    17880 gtattttttt tttttttaa tttttttagg atgattttt attattatcg ttattatggt    17940
tttaataatt ttttttttta aatttatat tttttatttt agtaattaat gaggttgttt    18000
tttgatttag gaggagattt ttttttttta gaatttaatg cgtagagttt ttgagaatta    18060
aagtagttgg taggggagga agaaattaat agaaagggag agagtatata gaattgtgtg    18120
tgtatgttaa agagcgatta ggaatgtagg agttaatttt tttgtgagga tttgacggga    18180
agagtgttta agatttttat agtatgtttt taataggttg atattttaat ttaaattttt    18240
agaagtaata tattatttgg gttattataa tgaggtgggt tttttttttt ttgttagttg    18300
atagttttta aaatattatt tcgttaggga aataaaagtt ttattttaga ttataggtgg    18360 gtattttttgg atttaggtga tttatggtta ttatgataat taatgttgaa tgttagttat    18420
tagtatgttt gggagagaga aaatagaaag aagggagagt aaaagaaata gaaagggag    18480 atggatataa gttggagagg gaagaaaaga gaaaagagg aagatagatg agtgtttaat    18540
ttaattgttg tttaaaaaag tggcgggggg gtgggatttt atttagtttt ttgttatttt    18600 ttttttttt gatttggata tttatgttta attttatatt ttattttttt ttttttttt    18660 ttaaatatat gtgttatatt atttttttta tttttatttag ttcggtaagt agttgttttt    18720
tggagattta gtgatattta ggaaaattgt ggtagtaata tgtaaatgtg aggaagtatt    18780
aatagtatgt tcgttgagtg attttagtaa atgttttttt ttttaatttt ttttttttt    18840 tttttttagg ttattgtgag gtggtaattt ttattgttat ttgaatattg ttttttagg    18900 tagttatttt aaattttaaa tggttgagta gttagagttg tgggtggaa aaatgggtat    18960 tatttgtagg gatttagaga gggtggttgt tgtttaatat atttatagat ttttaattta    19020 gaaataatt tttttttttt gataagttag agttttttaa atttatttta ggaaatgggg    19080
aaaaggatag ttatagtgaa gtttttaatt tttgggttat ttggttttat agttatgagg    19140
ggtggtgggt agtggattgt ttttagtttg gtttgtatgt agagaaaagt tagatattgg    19200 aggggggtggg gtattttcg ggtaggatgt aaggttttta tttgattttt gcgttttatt    19260
aggagtttat atatttacgt ttattacgtg gttttaagtt gagtttaggc gggtttcgtt    19320
```

```
tttgagttag tttgggtagg gtaggatttt tattcgtttta aggtttaata gtttagggag    19380
atgtttaatt aagttatttt ttgggtgaat tttgaagata gattttttt aaaagttaga     19440 gattatttgg ttgagtttta ggttagattg atacggagag tttggcggta tagtttaatc    19500
gtttattgtt atggttagag ggattttgta taattaatat tgaagagtgt gaaattaaat    19560 aagatttaa gattggtaat cggtggtaaa tattagtata aaatacggtt gattttatgt     19620
tatatatttt tttttttttag ggtttttttt tgaaagaata agtaagaaat tttaatcgag   19680 ataattttg atgtttttta gatttaaaat tttacgtcgg tattgggttt tttttttttg     19740
ttttacgtga gttatgtagt attttttagtt ttttttattag gattttatta atgttttcg   19800 tattggaaat ttttgtgtta gaggttgaat ttatagtaat ttttaaaatt aattaagaag    19860
aatttagtta gaggttatag taatgttgga attataaaat gtaagagatt tatttttttt    19920 tggtttttt tttatttatg ttgtttatgt ttgtgtattt ataagtttta tgtatattaa    19980
atttttaaaa ttaattatta ttatgttata gagtttttat tggatagtgt ttttttagtt     20040
ttattatata ttttttttt tttatgtaga tttattatgt tggtgtttg ttatataggg    20100 ggtttgagaa gaatgttatt taatcgtcgt tgttgtgagt gtgtaaagtg attaggagat    20160
taggagaatg ttgaaatttt tgttggaaaa atgtaaagaa aatttttatt ttgagttagt    20220
tgtttataga gttagtgtgt gtgtgcgtgt gtgtgtttgt aatataaaat ggatgtgaat    20280
atatatatat aaatagatat ggttttgttt ttattttaat ttgaattatt tagataattg    20340
tttttattta ttatttgatt ttaatgggtt tatataaatt aggatatttt attttttag    20400 gtatttaggt tgttgttgat ttttagtgtt tttaatatttt cgtatacgtt ggtattatga   20460
ggagtagtta cgtgttttg ggttttttaa ttattttgga ggttgattga gttttttat    20520 atatgtatat ttgtcgtgat gaaagtttta tcggtagagt ggagttatta gagttttat    20580 taaaatttg tgggtttatg agagatgggt ttagaaattt atatggtttt gtgggttttt    20640
tcggtttttt aaaataaggt attaatatt aagtttttaa aaatatttgt agttttgggg    20700
tttgaatttt gaaaaataag gagtgagggg ttgtgtatat taattatagt ggagattttt    20760 tttattttt aatgtgatgg agttttttta tgaaatgaag tttaagggg tatggtattg    20820 tggggattat agttatttg aggtttaaaa gaagaaattg gaatatgatt agtaaatata    20880
tttagtagaa aagagttgga tttttattga tttagttata ggttatcggt tggtagtgta    20940
atgggaggaa atatttattt tatatatata ttttatgatt ttgggggaat tagaggaaat    21000
ttaataagaa aacggttaga aatatttaaa attttattt aaaagattta agtaaattag    21060 agtttatta gattaaaaat tattataaat gtaagagtat tgtttttagt gaaacgttgt     21120
ggggtttgag aaggagattt ttcgttaaat tttcgggata aaatgcgtta tttaagtatt    21180
agataatgag tagaatgtaa attaattttaa ttttttttat taataggttg ttagtgtaat    21240
gtgtataatt tagtgataag attgtaggat ttaatatagt tggatgtatg agttttagtt    21300
aatgtagatt tgttatatga ggatgtgttt tattttgagt aggtgtttgt atgtgtggaa    21360
tggggtaaag tggaataaaa ggttaaaagt agaaatgttg atttaaagtt tattatgaag    21420
aaattttttt tttgtagtta aattattttt aaagtgggat gatattggtg aagaaagatt    21480
gaaaaataat ttttatgtgc gttttggat tgtaagttta aaatggggag gagttgtaga    21540
tagggtttgg gggtggttag ggtaaaggag agatatataa gttgtaaata tatttgtagt    21600
ttgttttatt tattttgttt tatatcgaat aagttttta attttgtgaa taaggataag    21660
gagggagtgt tttaaagata ttttatgttg gtattgtaaa ttattgattg taatgttaaa    21720
```

```
taaatatata tttagagatg ataatattaa ttttatagta aaataatcgt ttatgtagaa   21780
atttagagga gattagtttg ttttttttag ttgatttatg ttgggggata aaaggatttt   21840
taaaaattat tttgaatatg tttggatttt ttttttttaat tttttttggaa attaaatttg  21900 tttggaaata gtgttataaa gagttgatgt ttttaaaggt gattttttttt gttttatata   21960 aataaggttt tgttttttgtt agttgagcgt agtttaggt ttttcgtttt tagtttatat   22020 atatttttt tgtttgtttg gattttaatg gttaagata gttttgagtt tattgggaaa   22080
agaaaatgat tgttaaaaat tattttttgaa attggttatt tggtaatatt tttaattgta   22140
tggaaattta ttaaggtata ttttatatat aattagttta aggttgttga ttttataggt   22200
tttatggatt taaatttgat tgataataaa gtaaataaga gagtcgaatt taaagcgtgg   22260
ttttttcggg ttaggacgag tttaatatag tgtataagga atttgaaaga tttaggatat   22320
gtgttttaat taacgttaag tagaatggat aagttttttag tattttgaaa acgttgggtt   22380 agggttttttt ttttattgtg tgtttttttgt ttggggatta ataagtatta tagagaacgt   22440
gatttgaggc gatttttttat ttttgtataa atttagagtg aattattaaa tagttgttcg   22500
tttaaagtta aggtaatttt tttttgacgg gtttatttgt ttttcgatttt ttaatttatt   22560 agtttgtttt tttagggttt tgttttttttt gtaattaaag ttttttttaga ttagcgtagt   22620 atttatttga taggttgttt ggaaaattta agatcggaga ggtgatttgt tgttgttttt   22680
taaatttttt agttttaagt aacgtgtttt tttttatat ggggtggggg attggaaatg   22740
gatgtagtga gatataaaga gtgggtgttt tgttgatttt tgtatttttt ttttttttgat   22800 tatttttattt ttttttttta agttttcgat ttttagtttt attttttttat ttttgggttc   22860 gtattaaaag tcggatcgtt ttgggttggg taggagttga attttcggga gtttgtttgt   22920
gtagatttag tgcgtacggc gaggtagtag ttcggtttcg tattgttgat aggtgtaggt   22980
aggatagttt ttttatcgcg gttcggggcg ttttgattgg tgcggagtta cgttagtcgt   23040
attcggagaa gggtttggga ggaggcggag gcggagaggg ttgggagggg tcgcggcgga   23100
gtgacgtttc ggtattagga agttcgtttt tggttttaag atgttaggtt aatagggaag   23160
cgcggagtcg tagatttggt tcgtcgttcg tttgggtgtt tggagttgag ttgcggtaag   23220
gttcggtttt tgttcgatcg ttcgagggggt gtgcgtgtgc gcgttgcgga gggtgcgttt   23280
agagggtcgc gtcgtggttg tagcggttgt tgtcgtcgta ggggatttaa tattatttat   23340 ttgttttttgt tattttttgat attttttttgt tagggttgtc gcgtgggggg gggcgggta   23400 gagcgcggtc ggcgttagtt tttttttattg gagggggtttt tggggggaggg agggagagaa   23460 gaaggggggtt tttgtttatt tttgtttcgt tttggagttt ggaagtttgt ttttttaaaga   23520 cgttttgagt ggtgtttttt tgtttatatt ttatgttttc gtttgttcgt tgattttttcg   23580 ttttcggatt ttttcgtttg agttttttcgg aggagacggg ggtagtttgg tttgagaatt   23640 cggcggggt tgcgtttttt ggttttttttc gtagcgggga aatttcgcgt ttagagcgcg   23700
attcggagcg ggtagcggcg gttacggggg ttcggcgggg tagtagttaa ggattagtag   23760
agcgtcgcgt ttttttcgttt atgaattgta tgaaaggttc gttttatttg gagtatcgag   23820
tagcggggat taagttgtcg gtcgtttttt tattttttttg ttattatttt tagtcgttag   23880
ttatggtttc ggttttggtt ttcggttagt ttcggtcgtt ggatttttttt aagtataggt   23940 tggaggtgta tattattttc gatatttttta gttcggaggt cgtaggtaag gcgtcgcgtc   24000
gttttgtaga tattttcgtt tagttgtttt gcgttattcg ttttttttttcg ttttaaggaa   24060
```

```
gttagttttt tcggggggag gcgtggtggg agtggtcgtt cgtttggttt ttcgtagaat   24120
tttcgggagt cggaattttg attatttcgt attttttag ttttttttcg atcggttcgg   24180
tttttgggc gttaagggcg cgagtaattt tgtcgttttt tttattcgta ttttggtttt   24240
tttttgttt tttgggttat aaaaatttta gtattttgat tcgaggattt ttagaggtcg   24300
tcgatttttg tttttgtttt tttttcggtt tttagtttc gaggagtttt attcgttagg   24360
aaattgtttg aaattattta gaaatgtttt tcgcgaagag gtatttttt ttttttttg    24420
ggaaagggtc ggcgaatttc ggtgtttaat cgaattttta tattttttt tagttttttt   24480
aaatcgtatg gaaatttgag tttttttgcga ggggagggg ggtttgtaaa ttacgcgcgt   24540
gtgcgcgttt taggagattt ggtgtgtttg cgtagaggtg tataaatata tttgaaagta   24600
taggttataa aagtgaatgt gtcgttgtag tgagataaat atgtaaataa aacgtgcggc   24660
gttgggggag gggaggaaat ggggcgcgga tatttatatt tgcgtttgta tattttatag   24720
gcgtagcgtt tttcgcggtt cggagtcgtc gcgcgtattt ttttcggcg ttaggtagtt   24780
tagttttttt acggttttg tcgtcggttt agttggcgtt cgcgttgtag gtgggtatgt   24840
tgacgggaaa gtgtgtgtgt ttcgttttta gagaaagata aaagttagta ggggaagaat   24900
gaggacgtgg gcgtcgagga ttcgtttaag aagaagcggt aaaggcggta gcggatttat   24960
tttattagtt agtagtttta ggagttggag gttattttt agaggaatcg ttattcggat   25020
atgtttatac gcgaagaaat cgttgtgtgg attaattta cggaagttcg agttcgggta   25080
ggagttagta cggagtttgg gagggatggg gggaggatgt tgtggaggta taggttaagt   25140
agattaggag agaatgtgga aggtagcgtc gtttgggagg gcgtcggtgg ggcgtagttt   25200
tgtaaaggta gaaggtttcg cggcggtttg gttgcgagat tatagttttt tttcgaggt    25260
cgataggatt gtcgttttgg tttaggtttt tagagcggta tcggtttatt gtttcgttat   25320
ttcgcgattt tacgagttgg gttgtatggg taattttttg tataggatat tgtgtttttg   25380
gtttgtagtt gttagagtag agttaataaa attttattta ggttaagagt cgcgaatagg   25440
ttttaatttg tgagttttta ataaggaaaa ttcgttagag atacggaaga gttggttttt   25500
tttgggaaat ttttgtttcg gttttggttt agttttttt tttttgggtt cgcgttttt    25560
atatttttt tacggttgtt tcggttattt aggttttttt tatataatttt atttttttag   25620
tttgtgattt tcgggagtaa agttttaata tataattatt agttttttta gaaggagaaa   25680
gaaaaaaga agaaagattt ttttgtttgg tttatttatt tttttttagg agttgaattt    25740
tggaaattga aatttatatt tttttttta aattataatt atagttttgt aaaaagggtt    25800
tattttaatt ttgtagtaaa tttgtatttt atggattggt aaaaatgagt ttaaataaat   25860
aatttaatag taacgttttg gtttatgttg gtcggtggaa gattttaaat ttgttaggat   25920
tttggaagta gaaaatagaa ttaagtaaat taagcggtat ttagaggttt tgttgttaaa   25980
aaaaaaaat taagtgtttt gggtagaaaa aataaagttt tcggttagag tagagtaaat   26040
aaaagaaga aataacgat aaaaagaata aagattaaaa tgttttttta aattagaggg    26100
aatgaagata ttttttgggt ggtatttgtg taaggtatga ggttatgttg gtggataaaa   26160
ggtcgggaag aagttgaaaa tggttttagt ttaattgttt agagttagag ttgggttttg   26220
ggcggcgtgg tttgagtaa ggttagtttt ttattagttt ttttgtatat aagggaacg    26280
ggtttttac gtatttttt cgtttgagta aagtttagat ggtttagggt agaaatggta    26340
agtaattaaa gatagagttt atgggttttt tgggattttt cgaaaacgtt ttttattc    26400
gttcgttatt tcgtagtttt attttagtgt tttgtagtcg cggcgttggg tttttttgt    26460
```

```
agttgttttt tttttttaggg cggttgtttg tcgagttaag tgggagtgag gcgtgttttt    26520
tatagtagtc gggtgtaaag aggaaggggg ataaaaagga aattaagaat gaaaggaaaa    26580
agagaaaaag cggattatac ggttgggttc ggcggagatg tgtaatgtga aatattattg    26640
gtgttagttc ggatattta ggttaggttt tttttaata tataaaagtc gtcgtttggg    26700
gcgataggga ggttcgatgt ggattgggat cggggttgcg gttgggttat cggatacggg    26760
tggaagtcgg tcggtttggg tggtcgtttg taaagttaaa cgattcggtt gggtttggcg    26820
cgcggatagg tttgtggtgg gtttagggta aagaagaggt agagcgaaag aaggggggaat   26880
ttttaaaatt attttttcg ggttttcgga gtttaatatg ttaagttttt ggagttaacg    26940
agttgacgaa gaggtggttt tttgtttttt atttggttgt tttgttaggc gagaaagagt    27000
gttggcggtt tagttttgt taagggagta cgtattaggg ggtgggggac gatagtggag    27060
gttagggaag gaagggagga attgcgtggg agaaagagcg atttttagt gtttttttag    27120
ttttttttt ttattcgtgg gtttgtggtt ttggaatgga agtaagtttg taaggtgttt    27180
cgggaagggt tggaaaagtt tgttgtttcg cgtttgtttt atattaagtg ttttttggatt   27240
tggagaaacg tttggttgag tgattaaatc gttcgtaggt tttatgcgt tcggttgagg    27300
tttgtggcgt agtttcgagt tttagttcgt aggttagagt agattaggtt ttttgcgttt   27360
ggtggagatt cggttagta attgaaagtt ggttttggta ttttggtgtg tagggcggtg    27420
tagtgaagcg aggttagggt gtgtgagtgc gttagcgtgt gtgtcggggg aaggcggggg   27480
ttggttttcg atggaagttt tagtaatttg tattgtggta tttgtttgtt tttttgtttt    27540
aatcgttttt aggtttggtt taagaatcgt cgggttaaat ggagaaagag ggagcgtaat    27600
tagtaggtcg agttatgtaa gaatggtttc gggtcgtagt ttaatgggtt tatgtagttt    27660
tacgacgata tgtatttagg ttatttttat aataattggg tcgttaaggg ttttatattc    27720
gttttttat ttattaagag ttttttttt tttaattta tgaacgttaa ttttttgtta    27780
ttatagagta tgtttttttt atttaattt atttcgttta tgagtatgtc gtttagtatg   27840
gtgttttag tagtgatagg cgtttcgggt tttagttta atagtttgaa taatttgaat    27900
aatttgagta gttcgtcgtt gaattcgcg gtgtcgacgt ttgtttgttt ttacgcgtcg    27960
tcgattttt cgtatgttta tagggatacg tgtaattcga gtttggttag tttgagattg    28020
aaagtaaagt agtattttag tttcggttac gttagcgtgt agaattcggt ttttaatttg   28080
agtgtttgtt agtatgtagt ggatcggttc gtgtgagtcg tatttatagc gtcgggattt    28140
taggattttg tcggatgggg taattcgtt tttgaaagat tggaattat gttagaaggt    28200
cgtgggtatt aaagaagggg agagaaagag aagttatata gagaaaagga aattattgaa   28260
ttaaagagag agttttttg attttaagg gatgttttta gtgtttgata ttttttatta   28320
taagtattt taatagttgt aaggatatat ataaaataa atgtttgatt ggatatgata    28380
ttttaatatt attataagtt tgttatttt taagtttagt attgttaata tttaaatgat   28440
tgaaaggatg tatatatatc gaaatgttaa attaattta taaaagtagt tgttagtaat    28500
attataatag tgttttaa ggttaggttt taaaataaag tatgttatat agaagcgatt   28560
aggattttc gtttgcgagt aagggagtgt atatattaaa tgttatattg tatgttttta    28620
atatattatt attattataa aaaatgtgtg aatattagtt ttagaatagt tttttggtg   28680
gatgtaatga tgttttgaa attgttatgt ataatttatt ttgtgtataa tatttcgtat    28740
aatattattg ttttatttt tagtaaatat gaaataaatg tgtttatttt tatgggagta    28800
```

```
aaatatattg tatataaatt ggtttggatt tttttttttt tttttttgtta ttaatttggt    28860 taggatattt tagttattgt tttttaaata aattagtttt ttttgtttgt ttagttaaat    28920
atataaggta gtagttttta tttaaatttg gtagaaataa atgatagtta tttattagaa    28980
attaaaaaga aaaaaaaagg tattttcggg ggggaaaagg gttataaaat ttaattttgt    29040
ttttttaatt ttttttttggt ttaaatttag aggatttat tatggttagt aaataatatg    29100
aaaaagaaaa aagaagaaag aaatttagta agtttattag tttaaaatga ttttaagtt    29160 tattttttta cggggaaatt tatatttta gtaaattgtt ttggagaaat atttgtgtat    29220
gtatatatgt atagtttata tgtatttttt ttaggaggaa tatatttata ataaatttat    29280
agggaaatat ttttagtta aaatatttag gttttacgt ttattttag gtttaagtag    29340 agagattttt tatgttatat tgtattatta tttttaaatt ttttggagat attaaaagaa    29400
ataaagatga tttttaataa ttatagttttt ttagtttttt aaagaattta ggggttgaga    29460
ggttagagtg gagttttttg agtttttgtcg agtaatatgt agttgaggta aaggttatgt    29520
tttcggtgtt ttgtttttaaa taatattgat ttattaattt taaatttgtt tgttttttgaa    29580 attatatagg attatagttt gtaaattgta ggataatgaa gtaaattaag atgaattata    29640
gttttggttt ttttttgttat tttttgatat ttaaatgggg aatgagttcg gtgtgagtgt    29700
ttaaatgaat tttaagtatt cgattttttt ttattcgcga ttttagttt taaaaaaatg    29760 tgaaatttga ttttataata aatagaaata aatattattt agtttagag aatttatttt    29820 tatggcgtta ggagggtcgt tgtggaggtg gggggaggga tgtgttgaga tttttttgtta    29880 tgtttgttaa ttttcgtat aattaaagtg ggcgagaata aatattacgt tgggaattt    29940 agagtaaaaa gtaatcgtcg attttttgga gtcgataata ttattgtttt ttcgttttag    30000
t                                                                   30001
```

<210> SEQ ID NO 10
<211> LENGTH: 30001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 10

```
attaaggcga aaaataatg atattgtcgg ttttagaaaa tcggcggtta ttttttgttt        60 taagttttt agcgtggtgt ttgttttcgt ttattttggt tgtgcggggg gttgataagt       120
ataataaaag attttagtat atttttttt ttattttat aacgattttt ttagcgttat       180
gaggatgaat tttttgggat taagtggtat ttgttttat ttgttatgaa attaaatttt       240 atatttttt aaagttgaaa atcgcggata aagaaggatc gggtgtttaa agtttattta       300
aatatttata tcgaatttat tttttgttta gatgttagag gatggtaggg agggttaggg       360
ttgtaattta ttttgatttg ttttattgtt ttgtagtttg taaattataa ttttgtataa       420
ttttaggaat aagtaggttt agaattaatg ggttaatatt atttaaaata aaatatcggg       480
agtatgattt ttgttttaat tatatattgt tcgataagat ttaggaaatt ttattttaat       540
tttttaattt ttgagttttt tgagaaattg aaggggttgta gttattagaa attattttg       600 tttttttaa tgttttaaa ggatttggaa atagtaatgt aatataatat gaaggatttt       660
tttatttaag tttgaagata aacgtggaag tttaaatatt ttgaattgga gatgttttt       720 tgtaaattta ttatagatgt atttttttg agagaaatgt atataaatta tatatgtata       780
tatgtataaa tatttttta gaataatttg ttagaggtgt aggttttttc gtaaaggagt       840
```

```
aaatttgaga gttattttaa gttgatggat ttgttaaatt tttttttttt tttttttttt    900
ttatattatt tgttagttat aatggaattt tttaggttta agttaaagaa aaattggaga    960
gataaaatta gattttgtag ttttttttt tttcgggaat gttttttttt ttttttttag   1020
tttttgatga atggttatta tttattttta ttaaatttaa ataaggattg ttgttttgta   1080
tgtttaatta ggtaggtaga gggaattggt ttgtttagga agtagtgatt gagatgtttt   1140
ggttaagtta gtgatagagg aggggagaaa gaatttagat taatttgtat gtagtatatt   1200 ttattttat gaaataaaat atatttgttt tatatttgtt gaaaagtaaa ataataatat    1260
tgtacgaaat gttatatata gggtaggttg tatatagtag ttttagaaat attattgtat   1320
ttattagaga aattattta aaattgatat ttatatattt tttataataa taataatatg    1380
ttagaaatat atagtgtggt atttagtata tatattttt tgttcgtaag cgaaaaattt    1440
taatcgtttt tgtataatat gttttatttt aaagtttaat ttttaaaaat attgttgtga   1500
tattattaat aattgttttt ataaaattaa tttgatattt cgatatatat atattttttt   1560
agttatttaa atgttaataa tgttaaattt aaaaaataat aagtttatag taatgttaaa   1620
atgttatatt tagttaaata tttgtttgtg tatgtgtttt tgtaattgtt agaaatattt   1680
gtagtgaaag atgttagata ttgaggatat tttttgaaa ttaaaggagt ttttttttg     1740 atttagtggt tttttttt ttatatagtt tttttttt ttttttttt tagtgtttac        1800 gattttttag tataatttt agtttttaa gggcggagtt gttttattcg gtaaggtttt    1860
aggatttcgg cgttgtgggt gcggtttata cgggtcggtt tattgtatat tggtaagtat   1920
ttaggttgga ggtcgggttt tgtacgttgg cgtagtcgaa gttggagtgt tgttttgttt   1980
ttagttttag gttggttagg ttcgagttat acgtgttttt ataaatatac ggaggagtcg   2040
gcggcgcgta aggataggta ggcgtcggta tcgcggaatt tagcgacggg ttatttaggt   2100
tgtttaagtt atttaggttg ttgagattgg agttcgggac gtttgttatt gttgagggta   2160
ttatgttgga cgatatgttt atggacgaga tagagttggg tggggaaaat atgttttgtg   2220 atgataggg gttgacgttt atagagttga agaaggggaa gttttggtg gatagggagg    2280 cggatgtaag gttttggcg gtttagttgt tgtaggaata gtttgggtat atgtcgtcgt    2340
agggttgtat gagtttattg aattgcggtt cgaagttatt tttgtatagt tcggtttgtt   2400
ggttgcgttt ttttttttt tatttggttc gacgattttt gaattaaatt tggggcggt    2460 tggggtaagg gagtaaatag atgttatagt gtagattatt aaaatttta tcggaggtta    2520 attttcgttt ttttcgata tatacgttag cgtatttata tattttggtt tcgttttatt   2580
gtatcgtttt gtatattaag atattagggt tagttttag ttattggttc gggttttat    2640 taagcgtagg agatttggtt tgttttgtt tgcgagttgg gattcggagt tacgttataa   2700
attttagtcg aacgtatgga gatttgcgga cggtttgatt attagttag gcgttttttt    2760 aggtttaaaa atatttaatg taaaataaac gcggggtagt aggttttttt aatttttttc   2820
ggggtatttt gtaaatttgt tttattttta aagttataga tttacggatg aggagaaggg   2880
gttggaaggg tattagagga tcgttttttt ttttacgtaa tttttttttt tttttttga    2940 tttttattgt cgttttttat tttttggtac gtgtttttt aatagggatt aggtcgttaa    3000 tatttttt cgtttagtaa aataattaaa taaagagtaa aagattattt tttcgttagt     3060
tcgttaattt taggagtttg gtatattaaa tttcggaat tcggaaaggg tagttttgga    3120 gattttttt ttttcgttt tgtttttttt ttattttaag tttattatag gtttgttcgc    3180
```

```
gcgttaggtt tagtcgggtc gttttggtttt gtaggcggtt atttaggtcg gtcggttttt      3240
attcgtgttc ggtggtttag tcgtaatttc gattttaatt tatatcgggt ttttttgtcg      3300
ttttagacgg cggttttttgt gtattggaga gaggtttggt ttgagatatt cgagttgata     3360
ttagtgatgt tttatattat atattttcgt cgggtttagt cgtgtaattc gttttttttt      3420
tttttttttt tattttttgat ttttttttta tttttttttt ttttttgtatt cgattgttat    3480 aaaaagtacg ttttatttttt atttggttcg ataagtagtc gttttggaag gagaggtagt    3540
tgtaaggaga gtttagcgtc gcggttataa agtattaggg tggagttgcg gaatagcggg     3600
cggggtggga gggcgttttc gaaggatttt agaaaattta tagattttgt ttttaattat     3660
ttgttatttt tattttaggt tatttaaatt ttgtttaggc gagaagagta cgtgagaggt      3720
tcgttttttt gatgtgtaag agagttaatg aaagattgat tttgtttaaa attacgtcgt     3780
ttaggattta gttttggttt tggatagtta aattaaaatt attttttaatt ttttttcggt    3840 tttttattta ttagtatagt tttatgtttt gtataaatgt tatttagaga gtgttttttat   3900 tttttttgat ttgggagagt atttttggttt ttattttttt tatcgttgtt tttttttttt   3960 tgtttgttttt gttttaatcg ggggtttttat tttttttatt tagagtatttt aattttttttt 4020 ttttaatagt aaagttttttg gatgtcgttt gatttgtttg attttgttttt ttgttttttag  4080 aattttaata aatttggaat ttttttatcga ttagtataaa ttaggacgtt gttattgggt    4140
tatttatttg agtttatttt tgttaattta taaagtatag atttgttata aagttaaggt     4200 aagtttttttt tataaaatta tgattataat ttagaagagg gggtgtgagt tttaattttt   4260
agagtttaat ttttgagaga agataaataa attaagtaga aaagttttttt tttttttttt   4320 tttttttttt ttaagaggat tagtagttgt gtattaaaat tttgttttcg gagattataa    4380
aattaggaaa taggtgtgt gggagagatt tgaatggtcg aaataatcgt aaagaaggtg      4440
taagaagcgc gagtttagga gggaaaaagt tgggttaggg tcgggataaa ggttttttag     4500
ggagggttaa ttttttcgtg tttttggcgg gtttttttttg ttaaaggttt ataggttgga   4560
gtttgttcgc ggttttttggt ttggtaggga ttttattagt tttgttttgg taattgtaag   4620
ttaggaatat aatgttttgt gtaggggatt gtttatgtag tttagttcgt gagatcgcgg    4680
gatggcgggg tagtgagtcg gtgtcgtttt gggagtttga gttagggcgg tagttttgtc    4740 ggttttcggag agggaattgt aatttcgtaa ttaggtcgtc gcgaggtttt ttgttttttgt  4800 aaagttgcgt tttatcggcg tttttttagg cggcgttgtt ttttatattt tttttttggtt  4860 tatttggttt gtatttttat aatatttttt ttttatttttt tttagatttc gtgttggttt  4920
ttattcggat tcgggttttc gtaaggttgg tttatatagc gatttttttcg cgtgtggata   4980 tgttcgggta gcggttttttt tggaaagtgg tttttagttt ttggagttgt tggttggtaa   5040
agtgagttcg ttgtcgtttt tgtcgttttt ttttagacgg gttttcggcg tttacgtttt    5100
tatttttttt ttgttggttt ttatttttttt ttgaaaacga aatatatata ttttttcgtt  5160
agtatgttta tttgtaacgc ggacgttaat tggatcggcg gtagaagtcg tggaagagtt    5220
gggttgtttg gcgtcggagg agggtgcgcg cggcggtttc gggtcgcgag gagcgttgcg    5280 tttgtgggggt gtgtaggcgt aagtgtgggt gttcgcgttt tatttttttt tttttttag    5340 cgtcgtacgt tttatttata tgtttatttt attgtagcgg tatatttatt tttatagttt   5400 gtgttttttaa gtatatttat atattttttgc gtagatatat taaatttttt gggacgcgta   5460
tacgcgcgtg gttatagat ttttttttttt ttcgtagaaa gtttagattt ttatgcggtt    5520
tgggaaggtt aggaaaagat gtggggattc ggttgggtat cgaagttcgt cggtttttttt  5580
```

```
ttaaaaaaaa aaaaaaaatg ttttttcgcg aagggtattt ttgagtggtt ttaggtaatt    5640
ttttaacgag tggagttttt cgggagttga aagtcgagag gaaataggg atagaggtcg    5700 gcggttttg aaggttttcg aattaagatg ttgggatttt tgtgatttag gaaatagaag    5760
ggaggttagg gtacgaatag agagggcggt agaattgttc gcgttttag cgttttagga    5820 gtcgggtcgg tcgagggaga attaaggga tgcggggtag ttaaaattc ggttttcgga    5880 agttttgcgg ggagttaggc gaacgattat ttttattacg tttttttcg gaggggttga    5940 tttttttggg gcgagaggga gcgggtggcg tagagtagtt gagcgggaat gtttgtaggg    6000
cggcgcggcg tttatttgc ggtttcggg ttggaggtgt cggagatggt gtgtattttt    6060
agtttgtgtt tggaggagtt tagcgatcgg ggttgatcgg gagttagaat cgaagttatg    6120
gttaacggtt ggggatggtg ataggaagat gaggagacgg tcgatagttt ggttttcgtt    6180
gttcggtgtt ttaagtgaag cgggttttt atgtagttta tggacgaggg agcgcgacgt    6240
tttattagtt tttggttatt gtttcgtcga gttttcgtag tcgtcgttgt tcgtttcggg    6300
tcgcgtttta ggcgcggagt ttttcgttg cggggagagt taggggacgt aattttcgtc    6360
gagtttttaa gttaagttgt tttcgttttt ttcggaaggt ttaagcgaaa aagttcggag    6420
acggaaagtt agcgggtaaa cgaagatatg ggatgtgggt agaagggtat tatttagagc    6480
gtttttaggg agtaggtttt taagttttaa agcgaaataa gagtgggtaa agatttttt    6540 tttttttttt ttttttttt aagaattttt ttaataagga aagttaacgt cgatcgcgtt    6600
ttgttcgttt tttttttacg cggtagtttt gatagagaag tgttaagagt gatagggata    6660
ggtaggtgat attagatttt ttgcggcggt agtagtcgtt gtagttacga cgcggttttt    6720
tgagcgtatt tttcgtaacg cgtatacgta tattttcgg gcggtcgaat aggagtcggg    6780
ttttgtcgta gtttagtttt aggtatttag gcgagcgacg gattagattt gcggtttcgc    6840
gtttttttgt tggtttaata ttttaaaatt agaggcgggt ttttggtgt cgagacgtta    6900 tttcgtcgcg gtttttttta gttttttcg ttttcgtttt ttttagatt tttttcggg    6960 tgcgattgac gtggtttcgt attaattagg acgtttcgag tcgcggtgga gggattgttt    7020
tgtttgtatt tattagtagt gcggggtcgg gttattgttt cgtcgtgcgt attgggttta    7080
tataggtaag ttttcgggaa tttagttttt gtttagttta aggcgattcg gttttagta    7140 cgaatttaaa ggtgaagaga tgaggttagg agtcgaaggt ttgggagaag agagtggaat    7200
ggttaagaag agaaaggtat aaggattaat aagatattta ttttttgtgt tttattatat    7260 ttattttaa tttttatt tatataaaa ggagatacg tatttaaaat tagaaaattt    7320
gaaaaatagt aataaattat ttttcgatt taaattttt taaatagttt gttaagtgaa    7380
tgttgcgtta atttgaagaa gttttaattg taaagaagat agagttttga aaaggtaggt    7440
taataaatta gaaatcgaga agtaaatgga ttcgttaaaa gaaaattatt ttgattttaa    7500
acgaataatt gtttggtggt ttattttgga tttatataag aataaaaagt cgttttagat    7560
tacgtttttt gtgatgttta ttagttttta gatagaaaat atataataga agagaaattt    7620
taatttagcg ttttaaaat gttgaaagtt tattatttt atttaacgtt gattaagata    7680
tatattttag attttttaaa tttttgtat attgtattaa gttcgttta attcgagaga    7740 gttacgtttt aaattcgatt ttttgttta tttattatt aattagattt aaatttataa    7800
agtttgtaga attaataatt ttgagttaat tatatatgaa atatgtttta atgaattttt    7860
atataattaa gaatgttgtt aaataattaa ttttaaggat aattttaat agttattttt    7920
```

```
tttttttagt gagtttaagg ttgttttgag ttattaaagt ttaagtaggt agaagggGtg    7980
tgtgtgagtt aagggcgaaa agtttagaat tgcgtttaat tagtaaaagt aaaatttat    8040
ttatataaaa taaaaaaaat tattttggga gatattaatt ttttatagta ttgtttttaa    8100
gtaaatttaa tttttaaaga aattaaagaa agaaatttaa atatatttaa aataattttt    8160
gaaagttttt ttgtttttta gtataggtta gttggagagg ataaattaat tttttttggg    8220
tttttgtatg ggcgattgtt ttattatgga gttagtgtta ttattttga atgtgtattt    8280
gtttgatatt atagttaatg atttgtaatg ttagtatgaa gtattttaa aatattttt     8340
ttttgttttt gtttataaga ttgggaaatt tattcgatgt ggaataaagt ggatgaagta    8400
gattataaat atatttgtaa tttatgtgtt tttttttgt tttgattatt tttaaatttt     8460
atttgtaatt tttttttatt ttaaatttgt agtttaaaga cgtatatgag aattgttttt    8520
tagtttttt ttattagtat tattttattt taagaataat ttagttgtaa gggaggaatt     8580
tttttatagt aagttttaaa ttagtatttt tgttttttaat tttttattt attttattt    8640
atttttatata tatagatatt tgtttagagt aaaatatatt tttatgtgat aggtttgtat   8700
tagttgaggt ttatatattt agttatatta ggttttgtaa ttttattatt aaattatata    8760
tattatatta gtagtttgtt ggtaaagaag gttaaattaa tttatatttt gtttattatt    8820
tggtgtttaa atgacgtatt ttatttcgga gatttggcgg agaatttttt tttagattt     8880
tatagcgttt tattgaagat aatgttttta tatttgtagt ggttttttaat ttgataagat   8940
tttaatttgt ttaagttttt taaataaggg tttttaaatgt ttttagtcgt ttttttattg   9000
aattttttt aatttttta agattataaa gtatatgtgt aaagtaaata ttttttttta     9060
ttgtattgtt agtcgatgat ttataattaa gttaataaga atttagtttt ttttttgttga  9120
atgtgtttat taattatatt ttagtttttt tttttaaatt ttagaatagt tgtggttttt    9180
ataatattat gttttttaaa gttttatttt atgaagggat tttattatat taaagaatga    9240
aaaaaatttt tattgtagtt agtatatata gtttttttatt ttttgttttt taagatttaa   9300
attttagagt tgtaaatatt tttggaagtt tgggtgttaa tgttttattt tagaaagtcg    9360
agaagtttta tagagttata tagatttta aatttatttt ttataaattt atagaattttt   9420
gataaaagtt ttggtggttt tattttatcg atggaatttt tattacgata aatatatatg   9480
tatgaaggat tttaattagt ttttaaagtg gttgaaaaat ttaagggtac gtgattgttt   9540
tttatagtgt taacgtgtgc gagatgttgg aagtattggg gattagtagt agtttagatg   9600
tttaaaaaga taaggtgttt taatttgtgt ggatttattg aagttaagtg gtgaataaag   9660
ataattattt agataattta gattaaagta aaagtaaaat tatatttatt tgtatatata   9720
tatttatatt tattttatat tatagatata tatacgtata tatatattgg ttttgtaaat   9780
aattgattta aagtgaggat ttttttgta ttttttagt aggagttta atattttttt      9840
aatttttaa ttattttata tatttatagt agcggcgatt gggtgatatt ttttttaggt    9900
tttttgtgtg gtaggatatt aatatgataa gtttgtatgg ggaaaaggag gtatgtggtg   9960
ggaattaaga aatattgttt agtgaaaatt ttgtggtatg gtggtggttg attttggaga   10020
tttaatgtat ataagatttg tgggtgtata ggtataggta gtatgggatga gaaagggGtt  10080
agaagaaaat aaattttatg tattttgtga ttttagtatt attgtgattt ttggttaagt   10140
tttttttaat tggttttaga aattattatg agtttagttt ttaatataga aattttttaat  10200
acggagaata ttggtgggat tttggtaggg aaattagagg tgttgtatgg tttacgtggg   10260
gtaaagaagg aaagtttagt gtcggcgtga ggttttgagt ttgggagata ttaggggttg   10320
```

```
tttcgattgg ggttttttgt ttatttttt aaagaaagat tttagaggag ggaaatgtgt   10380
gatatggggt tagtcgtgtt ttgtgttggt atttgttatc gattattagt tttaaagttt   10440
tatttaattt tatattttt agtgttagtt gtgtaaagtt ttttggtta tggtagtgag    10500 cggttgggtt gtgtcgttaa attttcgta ttaatttggt ttgggattta attaagtgat   10560
ttttgatttt tggaaagagt ttgtttttag agtttattta gaagatggtt taattagata   10620
tttttttgag ttgttaggtt ttagacgggt gggagttttg ttttgtttaa gttagtttaa   10680
ggacgaggtt cgtttggatt tagtttggag ttacgtgatg ggcgtgagtg tgtgagtttt   10740
tggtaaggcg tagaggttag atggagattt tgtattttgt tcgagaagtg ttttattttt   10800
tttaatattt ggttttttt tgtatataaa ttaagttgaa aatagtttat tatttattat   10860
tttttatagt tatggaatta aataatttag aaattaaaag ttttattgta gttgtttttt   10920
tttttatttt ttaaatggaa tttaaaaagt tttggtttgt taaaagggga agattatttt   10980
ttgaattgga agtttgtaga tatattgagt aatagttatt tttttgggt ttttgtaaat   11040 ggtatttatt ttttaattt atagtttag ttgtttaatt atttgagatt tggggtaatt   11100
atttggggga atagtgttta gatggtagtg ggagttatta ttttatagtg gtttgggaa    11160 gagaagagaa agagattaga ggagggggta tttgttaaaa ttatttaacg aatatgttgt   11220
taatgttttt ttatatttgt atgttattgt tatagttttt ttaggtgtta ttgagttttt   11280
agaaagtaat tatttgtcga attaagtaaa ataaggagaa tggtatagta tatgtgtttg   11340
gagaagggga aggaagggtg gaatatgaaa ttgagtatag atatttaggt taggaaagaa   11400
ggaagtggta aggggttaaa tgaagtttta ttttttcgtt atttttttaa ataatagttg   11460
gattaaatat ttatttgttt tttttttttt tttttttttt tttttttag tttatgttta   11520 tttttttttt ttattttttt tgtttttttt ttttttgtt tttttttt tagatatgtt   11580 ggtagttaat atttagtatt agttgttatg gtgattataa attatttaaa tttaaaaata   11640
tttatttata atttgagatg aagttttat tttttagcg aaataatatt ttaaaagttg   11700
ttagttgata aaaaaaaagg aatttatttt attgtagtaa tttaagtaat atattatttt   11760
taaaggttta aattaaaatg ttagtttgtt aaaaatatgt tggtagagtt ttggatattt   11820
ttttcgttag attttataa agaagttgat tttgttattt ttggtcgttt tttaatatat   11880
atatataatt ttgtatgttt tttttttttt tattaattttt ttttttttt attaattatt   11940 ttagttttta aagattttac gtattgggtt ttaaaagaaa agaattttt tttggattag   12000 aaaatagttt tattggttgt tgaagtgaaa gatgtgggt ttaggggaa aggttattag    12060 gattataatg gcggtggtgg taggaggtta ttttagagga gttaagaaga aaaaaaaatg   12120
tagggagaag gattggaggt ggaaagatag agtaatagaa aattgagttg ggtggttagg   12180
tgttgcggtg aagtttagtt tcgaaatgat aggtatatat ttttttattt ttgttttttt   12240
tttttttgag agaaaatttt tttagttaga gattttgggg ggtaggaggc gggtaaacgt   12300
cgttgtagtt gggttttttg tttttattt tgggtttgtt gttttttgtt tattttggat   12360
tatagggtat tcgtttagat gaagagttat taattattta tttagttaat attaggaaga   12420
cgataaagtt ttttatatag gattaagaag atattagatt gttttattag tatattttg   12480 tttacgaata agttttcgtt atatatttt ttttttttcg agtcgttta ataattgttg    12540 tatatattag tagcgggcgg tgaggaataa tagtcgaatt agttttaaga aattttgtgt   12600
atcgagttag tagcgaggaa cgcgatttgt gaagattatt tttgcgggta gggattcgta   12660
```

```
gggattgatt attttcggat aattggtata attttttttg ggggtgaaaa attataacgc    12720
ggcggggtat tttttaagtg agttgtagat ttgattggcg cgggggggtgg gggaggggag    12780 gggagaatgg gatggcggag gtcgggcgga ggaaagaaaa tggaaaattt ttttttatttt   12840 tatttcgttg tttttttttt aagttttatg tttttttcgg taagtatttg ttttttttcgc   12900 gttagttata gttagagttt tttattttt tttatatatt ttttttttt tgataaggtt     12960 taggattttg gttattattt tacgtattat tattttgcgt tttgttagag acggtttggg    13020
ttgatttcgt tggtgtttat gttaggatta aaattttttt atgacggcga ggaaaattgt    13080
attatttgtt tttagggggt atattaggag tttacgtagt atatgtttcg taaatattcg    13140
ttgattgaat gagaggcgcg ggggcgggc ggcggagagg ggtttgcggt cgttaaggtc     13200
gttagggtta atttaggttt ttcgaagaag gttgggatcg agttgttgtc gcgtgtgaag    13260
gtgtgtgtcg cggttggggg tgttataacg ggttatggag tttatttttt agagggagga    13320
agtttgtgta tattagcgat ttgggtcgaa tattttttagt ttatttattg ggttaaagtt   13380
atttaataat taatgcgttt ttgggggagg tcggggggaag tattcgtttt ttgtcgggac   13440
gtaaagttag gcgttaggtt taaagggtt gtagtgtagt tcgattttag tacggaattt     13500
agagtcgtcg ttttgaaatt ttttaagtta gtgatagagg agggttagtt cgttttttttt   13560 ttgagggtga agattatttt atgagttttt tttaggattt ttaaagtaag aaaagttaaa    13620
gaaaggtttt tttgttttag ggggtcgttt ttagttggtt tttatattat tttttgttag    13680
ttgcgtttat ttttttttaa atttttggtt tttagggggtt tttagtcgtt ttcgtgttat    13740 tttcgttttcg gggtttatt taggttgggt attcgtttaa tggatattaa ggagaatggg    13800
atttattagg gaaggaaggt agagtttgga ttgtttagag gtggattttg tttatataga    13860
acgtttagtt tttaacgagg atatggtatt tttgggcggc gttggggggta gaggcggaga    13920 gggtagcgta atagattatt acggttttt gaagaagtta tatgttattg tgaatttttt    13980
ttttttttaa aagtaaagaa aaattttaaa aaaatataag aaataaattt ttttgtttta    14040
taagtaggtt gtggttagga ttttggatat tttataagtt aatttaaaat tagggaagga    14100
taggtgtttt atttttttagt agtgttatag ttttgtttat tcgtgtgatt ttttttttgtc   14160 gtttattagt tttttaaaag ttaattaaat taagatttt agtatttttt tttattatat     14220
gttttttttt aattaatggt attaaacgtg tttaggtagt aattttttt ttcggttaaa    14280 aagtagaaaa agatatattg agtgtagggg aagagttttt tacgtgtatt aaaataatgc    14340
gggtttgaaa gtaatggtta agaaagtaat tatttattat ttttagttttt ttatgtgtta    14400 gttattaaaa gcgaacgatt aggggcgttt gcgcggtttg tgattggcgt aagtagaatt    14460 tttttgttttt tagtcgttttt ttgtttattt acgaggattt tatttatcg taggtttttt    14520 tatttgtttt tagaatgtat ttttttatgtt taggaaattt ggggtaggga ttgggggaag   14580
gagatatttt gcgtttttt ggttttagt ataataagaa atgttagttt cggtttggcg     14640
attgcgagtt cgtttcgcgc gaagcgagat tgggggagttt tttagtttg gtcggagtta    14700 gggttgagtt cgcgtaaagt atttttttta gaagttatcg ttgttttga ttttttaatta    14760 tattttaaat atattacggt ttaataattt atttttatta tcgattatta aatagaagaa    14820
gaatttaata taatttaaat gatagaaatt acgcgacgtt atttttgtat tgtttttatt     14880 taatttatg gggttaattt cggataagtg agcgtttaat tggtttagta gggcgattgg     14940
cggtgtagtg tagtgttcgg gcgtgaagta ttggatcgtt ttagacgttt tattttaata    15000
aatgattatt tttttttaga tttacgggga aattttaatg taagattttt gtttttttttt   15060
```

```
tagtaatacg gtttgttttt ttgatcgggg ttttaaatcg ttttttttta ttttatatta    15120
tatttgtatt tttatatttt aattcggaaa gaggggggtta ggggtcgagg gttgtggggg    15180 gggggggggtt ttatttgttt atattattaa aggttaatag ttttttaagg ttaggtattt    15240
atttattacg gagttaggaa aatagaggaa tagtaaattt gagggggtttt tttttatgta    15300 tttgaaaaga aaggtatttt tttttttttta tttttttatat tttttttttttc gttttataga    15360 ataagttttta atttaggaaa ggtttgtggc gtaggttgga gattttttaa ttttttatat    15420
aagtttgtag attttttttg gtaatgtttt tcgattttttt tagagtgaaa ttagttaatt    15480
aagtaacgat atcgttaaaa tttaaggttt ggtaattagt attttaggta ggttcgcgtc    15540 gatagggta aatttttatt ttattttggg ttgttaagta tagtggttgt tttttagttt    15600
tttagggatg ttgtcggttt ttcgttttttt ttttaattag ttaaagtaaa ttttcgttaa    15660 tttaagttttt ttttgtttgt ttttcgcgat gaatcgcgta tttataagtt tgggtggggc    15720
gtggttgaga gtttgagtga ttgagtgggg tttggtggtg ttgcgcgtag cgggatataa    15780
cgagcgatag aggtcgttgt tggattatttt ttttacgtta gtttagacgt cgaggtttgt    15840
tggagcgtgc gtaggggatt agattatagg gagcgagcga gagggagaga gaggtgttgg    15900
gttttaggag tgtagtataa tttggggaaa ggaattaacg ttttgggac ggttgttttt    15960 cgttttattt agaggcggag tgtttaagtt taagtagtag gcgcgttagg tttggcggtt    16020
tcgttttttt gcgtttcgtt cgaggtttag agtttcggag gcgggtgttt agcgcgcggt    16080
ttgcgttttt ttttcggttt tattattggc gttaggatgt tgtcgcggga agaatttgtt    16140
gttggttgtt tttttttcggt ttttaggaga gttcgtgaat tcgattttttt tgatttcgga    16200 gtttttggag aagagatatt taacggtcgt cggttgtacg tttgggttac gcgcgcgttc    16260
gttttacgtg cggagagagg cgtttcggat cgcggtcgaa aggagtcggg gacgggagga    16320 ggggggaggggg cgaggtaggt cggaggagaa agagggataa agagtaaaga tttagttaga    16380
ggaaagagtt gacggtatttt tcgttttttcg gattttttgg taattcgggg taggatggcg    16440
tatttttttt gcgttttttc ggttgtcggc ggttttagtc gggaggagta ggttgggggg    16500
tttcggtata tagcgcgtcg ttgttttttta gtttatcgtt tcgttatagg gagaggttat    16560
tggcgatttg gttttgattt tttttttgtt taggttggtt tttcggggaa gcgttttttcg    16620 ttgggggtttc gtcgtagggt tagtgttttt ttgtcgtttt tacgtggcgc ggttttttcgt    16680 tcgatgattc gggtaggaga agggggtttt tatttaattg tatatacgtc gatattagtt    16740
tgcggtagtt ggttttttatt tttcgttatt tgtaaaatag aagagaagga aggttgtaag    16800
aagcggcggt cgtcgagtga gtagggttta gatgagatta cgttatatta gttgttaggc    16860
gtttattgtg tgttaggttt taggcgtgtt ttttcgatttt gatagttttt ggttgtgtag    16920 tagtatttttt agtttagttt cgggtttagg atatttattt attaagaggg gattttttttt    16980 tagagttgtc gtaaaagtgt ttagaggtta gaggattata aagttatagt gtgttgggga    17040
ggttgtggat ttatttttaa gaatttcggt gtcggggtta agaatttatt tgaacgtaat    17100
ggtagcggga gtgggtgggt ggagaggatt tttttttttg ggaagttgta tgtaaagatt    17160
attttttagt gtttgtttat tagttggagt tcggtaaata tttgtagaat attagcgtta    17220
acgtgttttt gttttagata gtagtttttt tcggttttttt gtaatttttga aacgaacggg    17280 ttttttggttt agggtgtttt aggagcgagt tgagttcggg ttttttatttt attaggagtt    17340 attttttttat atttagttat attttttttt agagatatta attcggttat ttattttattt    17400
```

```
attataaata attattttaa agtatgattt aagatcgtag aggagagata ttgggtggat    17460
tgagcgagat tgaggagagt agggtaaacg tttttggagg gtttattgtt cgttaaggac    17520
ggagaaatag ttttggtata attgttattt agttttttt tttttttttt cgggcgagtt     17580
aaatttttt tacgttttta attataacgt agcgagttaa gtatttaacg cgttttttt      17640
ttttgttat aggtaagtcg ggagaggtgg gtttcgaggg gttttatcgg gtgggtagaa     17700
gagtcgcggt tgttttaaag ataagaaaag aaggttttagg gtttttttagg tttttcgat   17760
tttagcgttt gttttttttt acgttaatta gggtacgtcg acgatcggag ggtttatttc    17820
gcgcgggtgc ggggatcggg gtgggagtaa gcgttgtcgg gttggcggag gtatagaggc    17880
ggggtaggga gttgcgggtt tgttttggt ttgagtatcg ttttttttgcg tttcggtttt    17940
ttttgaaggg agttgggttt tggggagttt ttggttaagg tcgttgttta taggaggggt    18000
tgttcggcgt tgtggcgtgg ggatttaggg tggggacggt taggcggttt ttttattcgt    18060
tagcgagaac gcgggcgggg attttgtcga ttcgattttt gtgggttcgt gggtttagaa    18120
gtagtagttt ggcggtttta gatttagtga ttttgtagta aaattatagg attagttttt    18180
gattgagatg tttgttcgtg agatattata aaatttatta ttatagttttt ttattaattc   18240
gatatgaagt aatatagatg ggattttatt agtttagatt ttaaatgttt atttatgata    18300
atttcggagg aaatttgtat gttattatta tttcgataat tttttttttt tatatgtttg    18360
aattggttgt attattagtt ggtagtcgga gtattgtaga tggtaattgt aaatagtttt    18420
tatttattta tttttttaa agaatgaaat atataaaga aaagattgc gttgtttggt       18480
gtaaagttag ttaattatta tatttttt tttttatttt ttcgtgtttt agtgttgaag      18540
attaaataaa gtaatataaa ataaattttt aagaatttat agagttttat tttaaggatt    18600
gaaaagaagg ttaaggcgtg tttttagtt tattttata tgtttttgtg atttggagat      18660
ttatttgta gttaaaatga gtttgagat ttgtattttt atgtttatt taatgattag       18720
gtttattaga agaattgagt ttaaataatt ggggaagata attttttaaa aagagatttt    18780
taattttcgt ttgttgattt ttaaatttgt tttattaaga taagtttttt gtgagaaatt    18840
tggttgttag atttcggaat tggttttaat ggttaattt ataaattgag atgggagatt     18900
tttttgatg ggaggtagtt tttattttta aagtttatgt tttagttgga atgtatatgt     18960
taaggattt tgtttggtt aatttgggtt ttatattgtg agtatataaa agtattata       19020
cggttaacgg aggacgagga attatggtaa agtaggtagg taagttttaa gaaataaaat    19080
aatttgttaa aaaataattt ttgatgatta tcgtaagatt gaaagtgtag gaaaaatata    19140
gttcgaataa ttttagattt ttttatattt tttttttttt tatatatttt gttattttat   19200
aataaaattt ttaatggaaa gtttaaaaat aaatagtata ggaatatgtg ttttaaatga   19260
attaaattgt gaaattagtt agtaaattaa tttgtagtaa gtaattattt aaggaaatta   19320
aaatattgtt tagtttagtt ttgtatttta ttatgtgtat gcgttttttta taattaatta  19380
atataagtgt tttaggaata tttgaagata aatacgttta atttaaggaa taaagtatttt  19440
aaataattta agtgtaattt tgttgagtta agtaaaata ttttataaat gaagtggtta    19500
tttaattttt tagggaaagt ttggttattg aaatgttgta tgtttatgtt atattaataa   19560
aaatttttaa tttattttgt ttatgtgttt tgtttttttg atattattgg tatttgaatt   19620
ttagatggat ttttgttaaa atgatatttt gtgtgataaa agtattttta gttttgattg   19680
atagattaaa ataatgtaa ggaaattttt ttaaattaga ttaattttttt ataaaaatat   19740
tttagaatgt atgaattttg atatttatat ttataatggt aaaagttttt ttcgtttagt   19800
```

```
ttagtaagat aatatttata taaaagagta aaaaaaaatt atattatttt atgatagttt    19860
gatttttaaa ttgtttaaga aagtaaagtg gttaaattgg aaaagaggaa tatatttcgg    19920
aggtttagaa tcgaaaattt ttttttaat  ttttagttgg aaaataattt tttgtattta    19980
tttaaagtgt attttttgaa gtgttagatt ggagttgatt ggtgattaat ttaaaggagt    20040
tataatttaa agaaatggtg agagtttggt atttaggttt ggttttagg  taattcgttt    20100
gggtttgaga ggttattaat tgttagttaa gatggaattt tttttttttt ttttttttt     20160
taatggataa taatgggaag ggggttaatt ttttagtagt tgaaattttg tatttagttt    20220
tttattttga gaatgttaat ttttggttcg aggatttgtt tttgtagtgt tggtatcgag    20280
atttaaggga agatatttcg ttttaaatgt tagttacggt ttggtttttt tttcgatttt    20340
agtattttgt agattgttag tgtttgtggc ggggacgaa  aggaataggg ttttgtaagg    20400
tttgtttgtc gattgcgtta ttttgggcga aatttagttt taaaagttat aaattattta    20460
cggtgaagat ttttcgaagt ggaataaatt tttagattcg tattatttta tatttttgcg    20520
ggatagatgg ttttattta  tcggttatcg ggagagagtt gttgttttcg cgttttattg    20580
tttttcgggg cgattttag  cgagtcgagt tttcggttgt acggtaagcg ttcgaaagtc    20640
gggtttgaga ggattgtagg gttttgagg  gtgttaagtt tcgaaggagt ttacgggtgt    20700
attgggggttt tcgaaattta gtcgttattg gtagttttt  tttgttttt  tttagttttt   20760
tcgttcggtt tcgtatttt  tttttttttt ttttttttta ttttttttt  ttttttttgt    20820
ttttatttcg tgtggggagt gacgtgacgt tagtagagat tttattaaat tttattgtat    20880
agtggcgcgc gggcggtcgg tcgagttcgg ttgcgcggtt ggcgatttag gagcgagtat    20940
agcgttcggg cgagcgtcgg ggggagcgag taggggcgac gagaaacgag gtaggggagg    21000
gaagtagatg ttagcgggtc gaagagtcgg gagtcggagt cgggagagcg aaaggagagg    21060
ggatttggcg gggtatttag gagttaatcg aggagtagga gtacggattt ttattgtgga    21120
aaggaggatt agaagggagg atgggatgga agagaagaaa aagtaatttg cgttaattcg    21180
gtagttttaa taaattaaag ggggagcgtt agggtagcgg ggagatagaa acgtatttt     21240
ggggagtaaa ttaggacggg ttgggaggaa gcgatagga  aagtggttta agagacggaa    21300
taaaggataa tgtttatggg gttgtttggg acgaggcgtg tggagtgtgg gtgtgagcgt    21360
gcgtgtgtga ttttttttta ggtttgtaga gttgaggaaa gaggttatag taaagaggga    21420
ttgcggaggg aggaaagtga gagatcggta gagggcggga gtggaggtgg gcgcggtggg    21480
gatgggagag gatgagtgaa gagaaattta gaagaatgga gtgagttagt gggagagggt    21540
gggagggtta tagtcgggag cgaacgagtt aggtttgtta gttggggaag gtcgggacgt    21600
tgggtttagt ttagttggga tatcgcgttc gaggttaagg cgggtggatt aggtatgttg    21660
agagtgtcgg cgtataggtg ggtacggtta cgtattgatt tagtgtttac gaagggtttg    21720
tattggataa ggtttagacg tttatagagt ttagaatttt ttttgttgta tttatattta    21780
ataagtttat tttgggttac ggatatttta tttttttaaaa tgacgaggtt aaggtttttg    21840
gcgaggatgg tattaaattg tacgggatag aagtgggggt gggggagaga gttttttta    21900
agtttatatt tgttttttgta aagtaaagag tatgtgaaat tatagggtat attttttattc   21960
gaaaagtgtg ttttattttt gaattttgat tttttgattt tttgatttga gtaaagatgt    22020
gtatttggt  agtgagtaga atattttggt tttgttttgt tttgagtgg  aaggattata    22080
aatataattc gtttggagga ttaggtgtga aggttttgt  taggtatatg ggataatgtt    22140
```

```
tttttaattt taagggtatt tgttaatgt atgttttgg aaagtgtcgg aatatagtta      22200
ttgttttgg attcggattt ttttattaat attaattttt gtttgagagt aaaatttagg     22260
ttcgttatta aaagatatt ttttggttt taattgaga ataaagtttt ttttaaaagt      22320
tgtattgttt ttttaaatt aatatattaa tattcgtaat tttagaaata tatagtgatt    22380
cgggagaatg tgtataaaat agatacgttt aaaaagttt ggcgtttaaa attaattta     22440
gttattatat aggtgttggg tttttttat ttttggggt tgtttggaat atgttatgtg     22500
tttttttgaa ttatttcgtg ttttgaattt atttgagtta gtagtaaaaa taggtaaata   22560
aatttgttta atttgttttg agtgttaaat tttttatt tgaaatagtt aatagtcgat     22620
agatggattt atttatgga aagggttagt tttttagtt acgaagaaaa ttgattagag     22680
atttatattt taagttattt ttaattttta cgtaatattc gtgaaattt aaattttttt    22740
tttttattta gtggaaattt aaagtagtgt tatttaaggg gagagaaatg aggggaaaa    22800
tgtttacgtg ttgttaatt gtattttttt tttgattttg agaattttta ttttggttt    22860
ttgaaatttc gtcgaggtaa gaaaattaaa ttttttaat aagttttata attgaattt    22920
agttatagga tatcggaaag tgtagttcga gaaagatatt tttattttg tttatcgacg   22980
attttttgtag ttttttattt tttttgagta atggggtaat aattttttt ttttttttt   23040
ttattttgta gagattaaga ggcgttcgta gtagaacggt tttgtttta gttggtggcg   23100
aggataggta attttatgga aaagttggaa gagaatgaga aaattaaaga tagaaagatt  23160
tagagattcg cggagagata tagggagagg gaagggagtt gcgttgaaaa gacgtaaaga  23220
tacgcgcgtg taattttttt ttttttagg tttagaggt ttgtaaatta gggttgagag   23280
gaagggggttc gggaagttta cgttttttc gttttttttt tgtttggagt ttcgttcgtt  23340
agaggttggt taatttagt ttcggtcgtc gtagatattg cgttgagttt tgggtttc    23400
gttttgttta gcgttagtgt agttgaagtg agtagttggt gggaaatgta aatggttttt  23460
ggagaaatag aagatataga atgatttta ttttttttc gagtgtgtgg aaggagttgg   23520
atatacgttt tacgttttta atttttttt tatattttta gttatatttt tattaaataa   23580
ttaattaatg tttagaatta ttagggaata tattaggtat gtaatcgtag aagtagggtg  23640
ttgggggtt ataaattatc gagttgattt aagacgtgga ttttaggttt tttttttgtt   23700
aaagtagtaa aggaagagcg ggttttggcg attgtattta gatttcgatt attttaaatt  23760
agaaggggt ggagggagcg tttaagtaaa gtaagtaatt tttttgttttg tagatgtaaa  23820
taagattgta gtattaaagg tattagtttt tttagggtta gatcgttggg attgggagtt  23880
tggggaaggg gagatattaa ttttacgtat ttgtgaattt taaggatgtt atatttttat  23940
ataaataatt ttagtgcgga tttttggaa tgggggagt aatattttta ttttagaata   24000
ttaaaatatt ttttttaaa agcgtatatt tttttattt ttttaaaatt ttgaattatg   24060
tttaaagata atagttttt agtaaattgg agtattggat tatttttttt ttttttttt   24120
atcgatattt tgatgatttg attttaatgt gtgggggta tagggaatta aatatagttt  24180
ataaaattaa gtttagatga aatagtgttg gttaagtggg tttagataat ttttaatgag  24240
aattttaatt atattttttt ttttaatatg ttgagataag tgatagaatc gttagaatgg  24300
taattaaatt ggaaagttta gggagaataa taatttcgtg attaaattgg ggtaaaatcg  24360
tggataaatg tggggtgatt ttcgttaatt ttttgttatt taagagttag gatttgggaa  24420
aggtatagta ttatttaga gttcgttgtg acgggttgtg tgttattatt tattttttt   24480
attttggatt atgatttaa ttttggtaag taattttttt agttttttat ttgataataa   24540
```

```
gcgagtatgt aaatattaat ggttagcgat gtttaattgt tttaaatatt attgatttgt   24600
tggttgtttt aaattgtttt tttagtttag gtttgtttt  cgaattgttt attttagagg   24660
tttgatttat gttttcgatg ttataatata ataattgttt ttttaaaaaa ggtatttaag   24720
atgaattaat tgatttgtat ataaattaaa attattatgc gttgtcgatt tcggtgtttt   24780
ataattattt cgaaattagt atttaattat ttgagttaaa agaatatata aatgtttgta   24840
ttgatttatt aatgaattat ttaattaaaa cgttcgggta atgttgggcg ttggaaagat   24900
tgttaaatta agatatatta taggagggat atgaagatta gaaaggtaat agattaatat   24960
ttcgtattta aaacggagtt ttcggtgatt tttagtttta attttggagt aggggttttt   25020
tttttttgtt gttaaaaaga ttttgtgttt gtttgtgagt gagtgtattt aagtggaagg   25080
aacgttttta cggttacggt ggtttaggtt ttttgttcgg atcgggattt tatagttta   25140 atttaggagc gttaaatttt ggaagatttc gggttagttt tggaggtgcg tggtttcgta   25200
agtcgttagg ttaagtttgt tttttttgtt tgttttttcg gtaggttggg cgcgttatgg   25260
tagtgagttt ttcgcgtaaa cggagagttg gaattaaagt tgatatttaa tagatatgtt   25320
aattgagtat ttattttcgt tttgagaata ggaataaaag gtagtttttt ttaagagagg   25380
cggtgtaaag gtacgttata ggagtttaga aaaggttggc ggcgggaaat ttgtagtttg   25440
ggggttagtt aatatttttt tttattttaa gtatttattg atttgttgtt gttatttttg   25500
gcgacgtaga aggatatttg aaagaatttt tgatggggtt ttgatttgag aaaggaggtg   25560
atttgtttag gttttttatta aattttttaat tattatatta attgttttttt tttatttttt 25620 attcgattttt tttttttttg tttatttttta attttttaat tatttagaaa ttttttttatt 25680 ttttagtggt tttttttttg tagtagttt  ttattcgaat ttttttttcg ttttttcgtg   25740
gtaggggttg tatattgatt ttttttgattt ttggtatatt tgggttttt  gaaatttttt   25800 aattttttta gatttgagga tgtaggtttt tattttttt  attgtgtgta tatatttaga   25860
gatatgaaaa tttatataga ttgttttttaa atttagggta tttaatagat gtttttttt   25920 tagttcgttt tttgatttga aatgtttgtt tgattttaat ttggatatta ttttttttttg 25980 tttttttttt tttaaagtag tttggatatg tgtgtaagtg agtttagaat agttttattt   26040 atattttta  ttaaattgta aataaaagaa gaattaatga agtagattgg tatatagatt   26100
gtattaagag ttcgaatttt tagttttttgg atttttttatt taattttggt tgttatttat   26160
attgatagag ttattttaag tagaggttta gagaaatttg tattgtggga taataggtaa   26220
agttatagta aaaagtggaa taattttaaa gttattttat tagaatgtaa attgtatttt   26280
tgggttttgt tcgtaattat ttagttttaa tatatataga gttagatagg aaaaaatagg   26340
ttaatatagt tattggtatt agagaagata aattttatgg gttttttagt gaaaagaaga   26400
tttttaaagt ttataatttt tgattattta atttttattta taattgtggg aatgaataag   26460
atattaattg ttttatgtat tttatttata ttaattaatt tgtgttttta ttaaaagtag   26520
ttatatagaa tttttttttaa tttttggtag taagtttaga aaatgaagtt tatagttatt   26580
ttgaattgga tatattttt  gagttgatta ttttgtaag  tgtaggaata taatattgtt   26640
tttttatggt tttttttgtat tttttttaggg tttgtaagtt tttattaggt ttgatattat   26700
tgtttgggtt tatatttatt ataagtaaat ttgattatta tgttgatttt aaaatagttt   26760
atttggttag tataattta  gttttttaaat tataaaaatt tttttaatata cgaagttttt   26820 agttttattt ttttttagtt tttgtttat  ttaaaatttt tattttaatt ggtgtaagta   26880
```

```
ataataattt gtattattat ttgtatttttt tttatttttt tggagattgg gttggatttt   26940
agagagaata ttagtattat tattattata aataataaaa tttaaaagta aagtttttat   27000
ttgtatgata attggtattt ggaatgtttt tgatttattt aatgttattt tataaaggta   27060
ttttgtaaat ttttttggaa tttttagtaa gagtttgtag taattggaat aattttttgg   27120
gaagatattt tttttgatgg gttttagtt tttggaggaa tagattgaga gtaattaggg   27180
agggagggga tattggaaat tggtagttac gttagttgaa ataagtttgg gtttagtaag   27240
gtgattgatg ttgtggttga tttttattt cgagtttttt tttaattggg gtattgattt   27300
tttttatttt gggattttaa ggtattcggt gtgtatgtag attttttttt tgtggttttt   27360
attatgtggt ttcgtagtag gttttggtt taatgatatt ttatagttat agtttttata   27420
tttattatta tgattttaat gtttaggtt ttagtgtatt tatattaaat ttgttttatt   27480
agtaagttgg agtatatagg agagatgggg gtaagtaagg atttagtaga gtttaaattt   27540
agatatgttt aaatggtttt gattgtgtaa agtgtggtaa tgtttttgt tgttttagtt   27600 ttttatttta agttttatat gtttttggt taatgaagtg tgatataggt tatatgttag   27660
gaataatagt atttgttgag aataaagtga atttaggaaa tttggtatat ataaaatgta   27720
tttagttatt tgaattagta ataatggtaa aaattaatat ttatagagtg tttagttaat   27780
ttagttattg tattaaatat ttttgtattg ataattatat ttatttttta tgttaatatt   27840
ataaggtagg tattgttatt ttataaatga agatagtgag gtttgttatg attgtgttat   27900
tggtttaagg ttatttagtt ggttagagta taagtttata attgttggag gttatagtgg   27960
ataggatatt gttttaggtt acgtaggtag taagtgggtat agtgggaatt tgaatttagg   28020
tttgtgtaat tttaaagttt aaaatgttaa ttagtatatt gaattaatgg taattggaat   28080
tagaagatta ggggtttttg ggggaaggaa atatagaatt tatttatgga atattttata   28140
aataaaagaa taatgtagag ataggaaagt aaatatattt tttgagggat ggagaaagtt   28200
agaaatgttt taaatgttaa agaggaggaa acgagaaatg attggatgag aaagtagaaa   28260
agttaaattt cggtatttgt tttgggtagt ttaggaagag aaaggtaagt ttagggatat   28320
ttttgagtta taggaaaatt aatgtttaga tggttagttt ggattaagtt taatatagga   28380
ttttaggaat atggtttatt agaattgttt tttagtaatt ttaagggaga ataaaatttt   28440
tgaattgggt ttaagtagtt ttattttaga agtaaagaga gatggaagta aggatcgagt   28500
aataagaata tttatattgt aagaatatgt aagttgagta ggagtgaaat ttagaaaaat   28560
ttgttaggat tttggttgtt gtgttaaatt atgttatatt ttaagtagaa attagatttt   28620
tattattatt atttgtttag gtttagttag taattttatt attgtagtaa agttatttga   28680
aattttaaga gaaatgattt tttgtgttga agaagatatt ttgggtggaa ggatgttagt   28740
agataaatgg agtgtaaaga tagtgatttt aaggatatag tttgtgggga gtaatattgg   28800
attatatatt cgttgtttgt ggtagaatgt tagttagggg agaatattag gtagtttttt   28860
ataagtttat tttattataa aaagatagga ttgattttaa aggttatttt taatttaggt   28920
ttgttttatt attgaaaatg atttaaaatt ggatttattt tggttttttt taggagggat   28980 agataaaatat aatttgtata tatggttttt tagtttttagg aagtatagga ggagaatgaa   29040
agaattaatt tagtttttg tttttggta aaaattttta tatttgtgtt gttgtaagaa   29100
tttaagatta tttcgtttag aatgttgtgg tattttgaa agtaaggttt gagggtatat   29160
agagttttat ttttattttt tacgttgtgg atttattgt ttttttaaa tgggaaagag   29220 aaattagaat ttatagaaag taaggtttgg aaaggattta gagggtattt ttttttttta   29280
```

```
gtttatgttt aaattatttt tagaaatata gttagttata ttttttagta aagagttttt    29340
tacggttttt tggtaatgta ttttttatgtt ttataattttt atagttatat tgtatattta   29400
ttgattaaat tttaagtatt gaagaaaatg atgttatatt aaaaagtttt aattagtagg    29460
gggtatgttt tttagagttt tttaaatatt ttatattttt attttaaaaa aagatgaaaa    29520
tattattagt ttaatttaat agatggaaaa ttttgttata gagatttttta gagagttata   29580 tttggttatg tagcgtgatg tttgaaagaa ttaaattaaa aataaagtta ggaaattta    29640 tgtttagggt ttttttagta gatatattat tttttggggg ttggttatta tttttttgtt    29700
tgagtaaagt atatgtttga ttgtaatttt atttgttttt ttgtttgttt gtttgtgagt    29760
agtttatttt ttaatttatt aatttatttt tttgttagtt ttttaaaata ttataagtta    29820
attaatgttg ataaaatttt atttttatta tgagtgttat ttgagtagat tgagatggtt    29880
gttatatttt ttaaatatta cgtgtaataa atagtgttgt tattgtttta gcgttatgat    29940
tttgttttta tttggaaatt gtataaatat tatattttt gttatgatag gattattttt    30000
a                                                                   30001

<210> SEQ ID NO 11
<211> LENGTH: 9001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 11
aggaagggtg gatgtagtta tttatatatg gtttgttttt ttggaggata attttatttg      60
ataaataatt gttttatttt gaatagaata aataaggttt tatgatgaag taaaatatta    120
aatatatatg tattaaaaaa tgtataatta ttttttttgga atgggttata tagagatgtg    180
ttttttaaaa tgttaagagt gtaaaaggat aaatagtgaa aaataaattt ttttttttatt    240 ttgttttttta gtttttttaat tttttttattt agaggtgaga atagaatttt tatattttt    300 agaatttttta tagttagaat tgtttatatg tttttattgt tttatttttt attttttgttt   360 gtataaataa atgaattgtt tattatggaa attttttaaa agattcgtta atattttaat    420
aggaagtatt aatagtttat gttttaggat tttgtttttta taattttgta atattatatt    480 acgatatttta atttaatttt tattaagttt tgttaaaaac ggattttaaa ttaagttgta    540 aattttttagt aatttggttt tgttttttttt tttttgatag tattattaaa taaattttt     600 tattgtcgaa agtaataagt tcggttttgt tttatttatt ggttgtgttg gtgatattg      660 gggattgtta ttgaatagac gtatagaggg agttttttata ggtagggggt ttttttgtttg   720 tgttttttggg agagtatgtt tcgtatatt gtcgcgttga tgaagatttt atagttttat    780
tagttgcggg taaggggggtt tgaggtagtt ttaggtaagt tggggtttag cggggagaag    840
ttgtagaaga attgattaga ggattttagg aggttttaga gttgggcgag gtagagagtt    900
ttttgtgcgt tttttttttt ttttgtaatt cggggatttt ttgtattggg gtaggttttc    960
ggttaggtgt atgggaggaa gtacggagaa tttataagtt tttcgatttt ttagtttaga   1020
cgttgttggg ttttttttcgt tggagatcgc gttttttttta aattttttgtg agcgttgcgg  1080 aagtacgcgg ggttcgggtc gttgagcgtt gtaagatagg ggagggagtc gggcgggaga    1140
gggaggggcg gcgtcgggc gggttttgat atagagtagg cgtcgcgggt cgtagtatag    1200
tgcggagatc gtagtttcgg agttcgggtt agggtttatt tgttttcgta gcgtcggttc    1260
```

```
gcgttttttt gtcgtagtta tcggtgagtg tcgcggtttt gagattttcg ggtcggatgc    1320
gcggcggttt tagttttcga gcgtttgttt ttttcgtttt gggttgttcg gttttttgg     1380 gttttcggc ggttgtacgg agttaaggcg tttcgtttcg ggcgttttc gcgggtgtcg      1440 atttaggttg ttcggagttc ggagtttaga gaggagagag atagtggggg agtttggtta    1500
tcgcgggtat ttttttgcg ttgtagtcgt tcgtttggtt tgttttttcg tttttcgtt      1560 ttttgttttg attttttttt tttttgtaga gtcgtcgttt agcgtttcga tttcgttatt    1620
atgagagttt tgttggcgcg tttgttttttt tgcgttttgg tcgtgagcga ttttaaagtg   1680
agtgcgtttt tgttttgatt gatgttgttt aaggattttt gattagtatt agggagagg     1740 aggggttgtt tagggagttg gggtttttcg gattttatttt atagtagggt tagatttttt   1800
ttaggaaatg ggataggatg gtagcggagg tttgagaatt acggggttg gtattggttg     1860 gtaagggagg aagaggtcgt cgggattgtt ttagtttgcg ggtatttggt agatgaagtt    1920
tgtttgggtt aattttatttt ttttggttgg aaatttatgg tttttttattt gagaattaga  1980 tacgaatagg gtgaggcgag agggagaggg aagagtgggt tttgggattg gggttagttt    2040 atttttatttt tggagtttttt ggagtatggg attttttgatg aagtttttttt tcgaattttt 2100 tttagggtag taatgaattt tattaagttt tatgtgagta tttattttta taatagttgg    2160
ttgtatagat aagttgggaa ggttttaggg gatatttttt ttttgttttt tgttgtaggg    2220
ttgcgttatt ttttattatt tttatttttt ttcgtttatt ttatttttgt ttttttagc     2280 gaattgtgat tgtttaaatg gaggaatatg tgtgttaat aagtatttttt ttaatatttta   2340 ttggtgtaat tgtttaaaga aattcggagg gtagtattgt gaaataggta tggggattt     2400 tattgtaatt gggagagaaa tttggggata gggagggatg ggtgggaggt aagagtaggt    2460 aggagtagg agttggaggt agggtgggtg atattttttat ttttatgtga taagtataaa    2520
tatatatata cgtttacgaa atagtggtta tataaatgtg aggtggggtt ggaaggagat    2580
tttgtttagt tttttggtag gtttgaaacg atattttttaa aatgttcgtt ggtagtcggg   2640
tatggtggtt tacgtttgta atttagtat tttgagaggt taaggtgagt ggattatttg     2700
aggttaggag tttaagatta gtttggataa tatggtgtaa ttttgttttt attaaaaatg    2760
taaaaattag tttggtatgg tagtggatgt ttgtagtttt agttatttgg gaggttgagg    2820
taggagaatt gtttgaattt gggaggtaga gattttagtg agttgagatt atattattgt    2880
attttaattg ggcgatagag taagatttta ttttaaaaaa aaaaaataaa agttagttgg    2940 aatgttttttt tttttttttat attttttttat tttttttgttt tttttgtagat aagttaaaaa 3000 tttgttatga ggggaatggt tattttttatc gaggaaaggt tagtattgat attatgggtc   3060
ggttttgttt gttttggaat tttgttattg tttttttagta aacgtattat gtttatagat   3120
ttgatgtttt ttagttgggt ttggggaaat ataattattg taggtgaggt gggggtaata    3180
aggattaaaa gtttttttta tagttttta gaaattttgt tattatttttt ttttttttaga  3240 gggttggtta tagtataaga gaagtgcggt ttttggttga gtttttttttg aggggaggag   3300 gtagggaagg ttttttgggt tggaatgata ttttttattt ttttgtgttg ttaggaattt    3360
agataatcgg aggcgatttt ggtgttatgt gtaggtgggt ttaaagttgt ttgtttaaga    3420
gtgtatggtg tatgattgcg tagatggtga gtattattga tttgttgatg atagtggggt    3480 ggaagggggat aaatttatat gttttttttat tttattatag gaggattgag gaggtggggg  3540
gtgttcgaga gggatgtttt tttttatttg ttttttttaag atatttttttt gtttgttttt  3600 taggaaaaaa gttttttttttt tttttagaag aattaaaatt ttagtgtggt taaaagattt  3660
```

```
tgaggtttcg tttaagatt attggggag aatttattat tatcgagaat tagttttggt    3720
ttgcggttat ttataggagg tatcggggg gttttgttat ttacgtgtgt ggaggtagtt    3780
ttattagttt ttgttgggtg attagcgtta tatattgttt tatgtacggt tttgggtttt   3840
tttttttcga tttttttgtt ttattttaag tatatttttt ttttttttt agtaaagtgt    3900
ttcgttttat ttttttttta tttgttttg tttatgtagt ttatggtttt ggggataagt    3960
cgtgttttga ggttttagg gagggaagga agaagtggta gatttatgg gattaagttg    4020
tttgatgggt attttttttt atagtgatta tttaaagaag gaggattata tcgtttattt   4080
gggtcgttta aggtttaatt ttaatacgta aggggagatg aagtttgagg tggaaaattt   4140
tatttatat aaggattata gcgttgatac gtttgtttat tataacgata ttggtgaggg    4200
ggaatttcgc gattattgtg gttataatgg tttgggagaa gtgggattta gggagagatt   4260
ggagttgagg ttgaagttgt tcggtggggt aggggtgggg cgagggattt tgaagtttcg   4320
atatatatga taaagggagt ggtagggaag agttttatga agtttgaggg gtttggtgtt   4380
tttttggaga gattttgaat tttttttaata agtagttttt tgcgagtgga aatagttttg   4440
tgggtatatg gtttggttg ggaaggtttt gtttatatga attagaaaaa gatatatttt   4500
ttttgtggg atgtagtttt tgtttgtgtt aggatataga atttggagaa tggagttttg    4560
ggatggattt tagtttaatt attttagttg ggagttttg tagaaacgat tgtatagtt    4620
gtatgtagtg gttttggtta tttaagtttt tttaatatt tggaataaag ttttttgggt    4680
atggggtagg ggaggttttt aggtgataag cgattagtag attttttttgg atgattgatt   4740
tagggatagg tatagttatt ttttcggtat ttggagggga tagatgggga tcgtttaatt   4800
agtagtgatt tttttttttt gattttttgt tttttttttag ttttgttgaa gattcgttttt  4860
aaggagggta ggtgtgcgta gttatttcgg attatataga ttatttgttt gtttttcgatg   4920
tataacgatt tttagtttgg tataagttgt gagattattg gttttggaaa agagaattttt   4980
agtaagtgat aattgcgatt gatttagaag gttttgagga gtgttttgat ttgaaaatga    5040
gtttagcgtg attaagggaa gattgtagag ttagaggtgg gagtattgag gcggtggtag   5100
atgggtttag ggatggatga agagtgttgt ttagggagcg atgggttgta aaggtaaata    5160
gatggtaggg gttataggtg gagtaaaggt ttagatttgt atggaagaga ataagggttt    5220
tttttggtag agatattta tggtttttt tttttggtaga tttttagtgg atagataaat    5280
tttgatgtaa acgttttttt gttttttttta tttagtcgat tattttttatt cggagtagtt   5340
gaaaatgatt gttgtgaagt tgatttttta tcgggagtgt tagtagtttt attattacgg    5400
ttttgaagtt attattaaaa tgttgtgtgt tgttgattta tagtggaaaa tagatttttg    5460
ttaggtgagt gttttaagta tttttttta tttttttat atttttttag agtttttggg    5520
tttgttttag ttagtttaag ggtgtttttt tttagttaaa gttttaagta gttagaatta    5580
ggagtttagg ttttgaggg tttaaattag tttttatgtg tttgttagat attattaaaa    5640
aaatttagt tttgcgttag ttattttaga ttgggggtac gagattttag aaagaggaaa    5700
tagtaaaaga taatgtaatt tagtgtttag ggtgtgttgt gaattataaa tgattaggtg   5760
tttaggagag ggaggtgagt gttaatttga gggtagggga gggaggtttt taaaggaaat   5820
gtgatttgat aggtatttga agaggtagag ggaagaaagg aaggtgtttt agttgaaaga    5880
tataaaattg agaaggaggt tggtatattt cggtgggga ggagaattag ggtttgggag    5940
tgtggatgga atagtggtag atgataggggt tttaaagtt aagtagggga ttttaaattt    6000
```

```
gatgtggtag aaaatggggt tgcgttaggt atagtggttt atgtttgtaa ttttagtatt    6060
ttgggaggtc gaggtggatg gattatttga ggttaggagt ttgagatcgg tttggttaat    6120
atggtgaaat tttgtgttta ttaaaaatgt aaaaaaaaat tagttaggtg tggtggtgtt    6180
tgtttgtaat tttagttaat taggaggttg agatatggga atcgtttgag tataggaggt    6240
aagtttgtag tgagttgaga ttacgttatt gtacgttagt ttgggcgata gagcgagatt    6300
ttgttttttt ttcgaaaaaa agaaagaaaa tgggaagtcg ttaaggattt tgattgggaa    6360
attttttttt tttttttggta tggttgggtg atgggattag aaattttttt tttatttttt    6420
tagggtttat ttttgtatt tttggcgtta taggagatt taggggatt tttcgtttgt       6480
ttttttaag gtcgtatgat tttgattgga attgtgagtt ggggtcgtgg atgtgttttg     6540
aaggataagt taggcgttta tacgagagtt ttatatttt tattttggat tcgtagttat     6600
attaaggaag agaatggttt ggttttttga gggtttttag ggaggaaacg ggtattattc    6660
gtttttttgt tggttgttat ttttgtagta gagttatttt tattagttgt aagaagagat    6720
tgggaagata ggttttgtat agatggattt gtttgtgtta tttattaggg cgaacgataa    6780
tagtttattt tttaggtata ggtttgggtg ttggttgttt agattttttt ggttaggatg    6840
gaggggtggt tttgatttaa tatgttattg attagtaatt tgtttttttt tggattgaag    6900
tttgtaggag ttaaaaaggg tagggtattt tttgtgtatg ggtgaaggga gagttagttt    6960
tttcgacggt gggtatttgt gaggtttatg gttgagaaat gaataatttt ttaattagga    7020
agtgtaatag ttgaggtttt ttgagggagt ttagttaatg tgggagtagc ggtttgggga    7080
gtagagatat taacgatttt agggtagggt tttgatattt tatgaatgta ttaggaaata    7140
tatatgtgtg tgtatgtttg tatatttgtg tgtgggttgt gagtgtaagt gtgagtaaga    7200
gttggtgttt gattgttaag tttaaatatt ttttaaatt gtgtggattg tgatgttata    7260
tagagtggtt tttttggaga ggttataggt tattttgggg gttttttggg ttttttacgt    7320
gatagtgttt gggaatgtat tattttgtag tatgatttgt gattagtatt gttttagttt    7380
tattttata tagatgtttt ttttttggtt agttattttt tttttttagt ttagtttatt     7440
taattttat tgggtggggt gaggattatt tttgtatatt gaatatttat attttattat     7500
ttttatttat atttttgtaa ttttaaataa aagtgattaa taaaatgtga ttttttttgat   7560
gataaatttt tttggtgttt gtatgggaag gagttggagt atataaaaag gagaaaataa    7620
taaaggtgga ttgtattta gagtttttta tgggattgta ttttggatt taatggagtt     7680
ttgggaggta gaggttagga gagttgtagg gtagggttat tatagtattt aatgtatata    7740
aagtttttt aaattataat tttatggttg tgtaagtagt gtataggttt agtgttagtt     7800
tttaattgtt tttttaattt gatgtttttg tgtagtgtat attttgtata gttgtatatg    7860
gtggtttttt ttagggttaa ttttataata gtttttttat tttgttttta ataattttg    7920
agttgatttt aattaagaag aatatttgtg gttaggtgta gtggtttatg tttgtaatt    7980
taatatttg agaggttgag gtgggagaat cgtttgagtt taggagtttg agattagttt    8040
gggaaattta gtgagatttt gttttgtaa aaataaaaa aattagttag gtgtggtagt    8100
atatgtttgt agtttagtt atttgggagg ttgaggtagg aggattttaa gttaaggagt     8160
ttaagtttat agttagttga ttgtgttatt gtattttagt ttaggtgata gagtaagatt    8220
ttgttttaaa aaaaaaaaa aaaaaaaag aagaagaaga tttgtaagtg aaaattgttg     8280
gttaggttta gtggttacg tttgtaattt agtattttgg gaagtcgagg tgtgtggatt     8340
atttgaggtt aggagtttga gattagtttg attaatatag tgaaatttta tttttattaa    8400
```

```
aaatataaaa aaattagtcg ggtgtggggg tgggtgtttg taattttagt tattcgggag    8460
gttgaggtag gagaattatt tgaattcggg aggtagaggt tgtagtgagt cgagatcgta    8520
ttattgtatt ttagtttggg cgatagaggg aagatttcgt tttaaataaa taaaaaaata    8580
aataaagaaa gaaaattgtt tatttagaat gttagtttga ttttgtggta tttaggaaat    8640
aaaaaatata atttttttatt atttgtgtgt gggattgatg ttggaattttt tttagtgtgt    8700 taatagagtt tgtgattagt tattgttatg tttatgatta gggggtttag aattttaaag    8760
ttggatgatg ttttaatggg ggtgattata tattttgaat aaaatattaa gttttgaaaa    8820
gttggggtgt agaaggtagg ttgggagata attgggtatt aaaaattaga attgttaagt    8880
tgtgttaatg ggttggggta gtgtttttta atcgagttat ttgaggattt tttaaaatat    8940
gtatatttat attttatttg tagagattgt gatttaggtt agggttggtt ttaggtttcg    9000
t                                                                     9001

<210> SEQ ID NO 12
<211> LENGTH: 9001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 12
acgagatttg gagttagttt tgatttgaat tataattttt ataggtggag tgtaggtgtg      60
tatattttaa aaggttttta gatgattcga ttaagaaata ttgttttaat ttattaatat     120
agtttggtaa ttttaattttt tgatatttaa ttatttttta atttgttttt tatattttag    180 tttttttagaa tttgatgttt tgtttaaaat atatagttat ttttattagg atattattta    240
gttttgagat tttgggtttt ttaattatag gtatagtaat ggttggttat aagttttgtt    300
aatatattga gaaaatttta gtattagttt tatatataga tgatgggaaa ttatgttttt    360
tgttttttga atgttataga gttaagttgg tattttggat aagtaatttt tttttttat    420 ttatttttt atttatttga ggcgaagttt tttttttgtc gtttaggttg gagtgtagtg     480
gtgcgatttc ggtttattgt aattttttgtt tttcgggttt aaatgatttt tttgtttag    540 tttttcgagt agttgggatt ataggtattt attttttatat tcggttaatt tttttgtatt    600
tttagtagag atgggttttt attatgttgg ttaggttggt tttaaattttt tgattttagg    660 tgatttatat atttcggttt tttaaagtgt tggattatag gcgtgagtta ttgagtttgg    720
ttagtaattt ttatttatag gttttttttt ttttttttt ttttttttttt ttttgagata    780 gggttttgtt ttgttatttta ggttggagtg tagtggtata attagttgat tgtaaatttg    840
aattttttgg tttaggattt ttttgttttta gtttttaag tagttaggat tatagatatg    900
tgttattata tttggttaat ttttttattt tttgtagaga tagggttttta ttaagttttt    960 taggttggtt ttaaattttt gggtttaagc gatttttta ttttagtttt ttaaaatgtt    1020
aggattatag gtatgagtta ttatatttgg ttataggtgt tttttttggt tgaggttagt    1080
ttaaggattg ttgggggtag agtgaagaga ttgttgtgga gttaattttta aagaagatta    1140 ttatgtatag ttgtataaga tgtgtattgt ataaaggtat taggttaagg aggtaattgg    1200
gagttgatat taagtttgta tattattttat atagttatgg gattgtggtt tggggaaatt    1260
ttgtatatat taagtgttgt ggtggttttg tttatagtt tttttaattt ttatttttta    1320
aagttttatt aagtttagag atgtagtttt ataagaaatt ttagggtgta gtttattttt    1380
```

```
gttatttttt ttttttttatg tattttaatt ttttttttata taagtattag ggagatttgt    1440
tattagaaaa attatatttt attgattatt tttatttaaa attataaaaa tataaataaa    1500
aatagtgaaa tataaatatt tagtgtatag gagtggtttt tattttattt agtgaggatt    1560
ggatgaatta ggttaaaagg aagggataat tggttaagaa agggatattt atgtgaaagt    1620
gaaattgaga tagtgttggt tataggttat gttgtagaat aatatatttt taggtattgt    1680
tacgtggggg atttaagagg ttttaggagt gatttataat ttttttagaa agattatttt    1740
gtgtggtatt atagtttata tagtttaagg aaatatttag atttaataat tagatattag    1800
tttttattta tatttatatt tatagtttat atataagtgt gtaaatatat atatatatat    1860 atatttttg atatatttat ggaatattag agttttgttt tgaagtcgtt agtgttttg    1920 ttttttaaat cgttgttttt atattggtta agttttttta agagatttta gttgttatat    1980
tttttaattg ggaaattatt tatttttaa ttatgggttt tataaatgtt tatcgtcggg    2040
ggagttggtt tttttttat ttatgtatag gagatgtttt gttttttta attttgtag    2100 gttttagttt agaaaaagat aagttgttgg ttagtaaatat gttgagttag gattattttt    2160
ttattttggt tagagggggtt tgggtagtta gtatttaggt ttatgtttga gggtaaagtt    2220
attgtcgttc gttttggtgg gtggtatagg taaatttatt tgtgtagagt ttattttttt    2280
agtttttttt tatagttgat ggagatgatt ttattgtaaa aatgataatt agtaagaaag    2340
cgggtggtgt tcgtttttttt tttggggatt tttagagggt taggttattt tttttttttgg    2400 tgtgattgcg gatttagggt aagaagtgtg agattttcgt gtagacgttt ggtttgtttt    2460
ttagggtata tttacggttt tagtttataa ttttagttaa agttatgcgg ttttggaggg    2520
aatagacgag gggtttttt gagtttttt gtgacgttaa agatataaaa gatgagtttt    2580
agagaagtga ggaggggatt tttgattta ttatttaatt atattagaga gagggaagag    2640 tttttttagtt aaagtttta gcgattttt attttttt ttttttcgg ggggaggata    2700 gaatttcgtt ttgtcgttta ggttggcgtg taatgacgtg atttttagttt attgtaaatt    2760 tgttttttgt gtttaagcga tttttatgtt ttagtttttt gattagttgg gattataggt    2820
aggtattatt atatttggtt aattttttt tgtattttta gtagatatag gttttatta    2880 tgttggttag gtcggtttta aattttggt tttaagtgat ttatttattt cggtttttta    2940
aagtgttggg attataggta tgagttattg tgtttgacgt agtttatttt tttattatat    3000
taagtttaaa atttttgtt tggttttaaa agttttgtta tttgttatta tttatttat    3060 atttttagat tttagttttt tttttttattc ggaatatgtt agttttttt ttagttttgt    3120 attttttaat tgaaatattt ttttttttt tttttgtttt tttaaatgtt tattaagtta    3180 tattttttt aaagttttt ttttttgatt tttaggttgg tatttatttt tttttttga    3240 atatttgatt atttatagtt tataatatat tttgggtatt gagttatatt gttttttatt    3300 gtttttttt tttaggattt cgtgttttta gtttgaagtg attagcgtag agttgggatt    3360 ttttggtaa tgtttggtaa atatataagg attggtttaa atttttaaag atttgagttt    3420
ttgattttgg ttatttaggg ttttggttag agagagatat ttttaagttg gttggaataa    3480
gtttaggagt tttggggaga tatggaagag gtggagagag atgtttggaa tatttatttg    3540
gtaggaattt gtttttttatt gtgggttagt agtatatagt attttggtgg tgattttaga    3600
gtcgtagtag tggggttgtt gatattttcg gtgggaaatt agtttataa tagttatttt    3660 tagttgtttc ggatagagat agtcggttag gtggagaaaa tagggaggcg tttgtattaa    3720
gatttatttg tttattggga gtttgttaga gaggggaatt ataaagtatt tttattaggg    3780
```

```
aaggttttta ttttttttta tgtaaatttg agttttttatt ttatttatag tttttattat    3840
ttatttattt ttgtagttta tcgtttttta aataatattt tttatttatt tttggattta    3900
tttgttatcg ttttagtgtt ttattttta attttgtagt ttttttttga ttacgttggg    3960
tttattttta ggttaaaata ttttttagga tttttttaagt tagtcgtaat tgttatttat    4020 tagaatttt ttttttaaag ttagtgattt tatagtttgt gttaaattgg ggatcgttat    4080
atatcgaggg taggtagatg gtttgtatag ttcgggatgg ttgcgtatat ttgttttttt    4140
tggaacggat ttttagtaag gttggggag gatagagggt tagaggagaa agattattat    4200
tggttaggcg gttttatt gtttttta agtgtcgagg aagtagttat gtttattttt    4260
aggttagtta tttagggagg tttgttggtc gtttattatt tggaaatttt ttttgtttta    4320
tgttttaagg gttttgtttt aggtgttgaa aaaggtttgg atggtagag ttattgtata    4380 tagttgtata ggtcgttttt gtaaaaattt ttagttgagg tagttaggtt ggaatttatt    4440
ttaaggtttt attttttaag ttttatattt tagtatagat agaggttgta ttttataaag    4500
gaaggtgtgt tttttttaa tttatataaa tagggttttt ttagtttaag ttatatattt    4560
atagggttgt ttttattcgt aagaggttat ttgttggga aatttagggt ttttttagag    4620
gagtattagg tttttagat tttatggaat tttttttgt tattttttt gttatgtata    4680 tcgaggtttt aaggttttc gttttatttt tgttttatcg ggtagtttta atttagttt    4740 tagttttttt ttgggttta ttttttaa gttattatg ttatagtagt cgcggggtttt    4800 tttttatta atgtcgttgt ggtgagtaag cgtgttagcg ttgtagtttt tgtgtaggat    4860
gaggtttttt atttaaatt ttattttttt ttgcgtgttg gagttaagtt ttgagcgatt    4920
taggtagacg atgtagtttt ttttttttgg gtaattattg tgggagaaga tatttattaa    4980
atagtttagt tttatgaaat ttgttatttt ttttttttt ttttagaggt tttaaagtac    5040
gatttgtttt taaggttatg ggttgtatgg ataggggtag atgaggga aatgaggcgg    5100 aatattttgt tgggaaggag aaagggatgt gtttggggtg gggtagaaga gtcgaagagg    5160
agaaatttag ggtcgtatat gaagtagtgt gtggcgttga ttatttagta agggttgatg    5220
aggttgtttt tatatacgta ggtgatagag ttttttcggt gtttttgta gatggtcgta    5280 aattagggtt ggttttcgat ggtggtgaat tttttttaa taattttaaa gcggggtttt    5340 agagttttt ggttatattg aaattttaat tttttggag gagaggaggg tttttttttt    5400
ggaggataaa tagagggatg ttttaggag gtaggtagga gaaagtatt tttcgggta    5460 ttttttattt ttttagtttt ttgtgatgg aataagggga tatgtaagtt tgttttttt    5520 tattttattg ttattagtag gttagtgatg tttattatt gcgtagttat gtattatgta    5580
tttttggata agtagtttta ggtttatttg tatatagtat tagggtcgtt ttcggttgtt    5640
tgggtttttg gtaatataga aagatagggg atgttatttt aatttagagg gttttttttg    5700 ttttttttt ttaggggaaga tttaattaga ggtcgtattt tttttgtgtt atggttagtt    5760
ttttgggaga agggatggt aataaggttt ttgggaagtt gtagggaggg ttttttggttt    5820 ttgttgtttt tatttattt gtagtaatta tgttttttta ggtttagttg aagagtatta    5880
gatttgtggg tatggtacgt ttgttgaagg atagtggtag agttttaggg taggtagggt    5940
cggtttatgg tgttagtgtt ggtttttttt cggtaaaagt gattattttt tttatagtag    6000 gttttttgatt tatttataag gggataggag gatgagagaa tatgagaaag agaagaatat    6060
tttaattaat ttttattttt ttttttgag atggagtttt gttttgtcgt ttagttggag    6120
```

```
tgtagtggtg tgattttagt ttattgagat ttttgttttt taggtttaag taatttttt    6180 gttttagttt tttaagtagt tgggattata ggtatttatt attatgttag gttgattttt    6240 gtattttag tagaggtagg gttatattat gttgttagg ttggttttga attttgatt      6300 ttaaatgatt tatttatttt gattttttaa aatgttggga ttataagcgt gagttattat    6360
gttcggttgt taacggatat tttaaagatg tcgttttaga tttgttagaa gattggatag    6420
ggtttttttt taatttatt ttatatttgt gtggttattg tttcgtgagc gtgtgtgtgt    6480
gtttatgttt gttatatagg gatgaagatg ttatttattt tatttttagt ttttaattt    6540 tgtttgtttt tgttttttat ttatttttt tgtttttaa attttttttt tagttgtagt    6600
ggagattttt atatttattt tatagtgttg tttttcgaat ttttttgggt agttgtatta    6660
gtgaatgttg gagaagtatt tgttggatat atatgttttt ttatttagat agttatagtt    6720
cgttggagag aataaaggtg gggtaagcga gggggagtgg aagtggtaag gggtggcgta    6780
gttttgtagt agagggtagg gaggggatgt ttttttgaagt ttttttaatt tgtttgtgta    6840
gttaattgtt gtagggtgg atatttatat ggaatttgat gaagtttatt gttgttttgg    6900
aagagattcg ggaggaggtt ttattaaagg ttttatgttt tagggatttt agggtgaggg    6960
taaattggtt ttaattttaa aattttatttt ttttttttt tttcgttta ttttgttcgt    7020 atttagtttt taaatggaag attatgggtt tttagttagg agaaatggat tgatttaagt    7080 aagtttatt tattagatgt tcgtaggttg gggtagtttc ggcggttttt tttttttttg    7140
ttagttagtg ttaattttcg tggttttaa gttttcgttg ttatttgtt ttattttttg    7200 gggagagttt ggttttgttg tggatggaat tcggaggatt ttagttttt gagtagtttt    7260 ttttttttt tggtgttgat tagaggtttt tgggtagtat tagttaaagt aagagcgtat    7320
ttattttgga gtcgtttacg attaggacgt agagaagtag gcgcgttagt agggtttta    7380 tggtggcgag gtcggggcgt tagacggcgg ttttgtaaag gaaggagaag ttagggtaag    7440
aggcggagga acgggaaggt aggttaggcg ggcgattgta gcgtagggga gatgttcgcg    7500
gtgattaggt ttttagttg tttttttttt ttttgggttt cggatttcgg gtagtttgga    7560
tcggtattcg cggggacgt tcgggacggg gcgttttgat ttcgtgtagt cgtcggggag    7620
tttagggagt tcgggtagtt tagggcgggg gaggtagacg ttcgggagtt ggggtcgtcg    7680
cgtattcggt tcgggatttt taggatcgcg gtatttatcg gtggttgcgg taggagggcg    7740
cgagtcggcg ttgcggggat aggtggattt tggttcgggt ttcggggttg cggttttcgt    7800
attgtgttgc gattcgcggc gttttgtttta tattagggtt cgtttcggcg tcgtttttt    7860 ttttttcgtt cggtttttt ttttgtttg tagcgtttag cgattcggat ttcgcgtgtt    7920
ttcgtaacgt ttataaagat ttgggggaag cgcgatttt agcggagggg atttaatagc    7980
gtttggattg aggaatcgag aggtttgtaa attttcgtg tttttttta tgtatttggt    8040 cgggggtttg tttagtgta aggagttttc gaattgtaga gaggagagaa ggcgtatagg    8100
agatttttta tttcgtttag ttttgaagtt ttttggggtt ttttaattag ttttttgta    8160 attttttttc gttgggtttt aatttgttta agattgtttt agatttttt gttcgtagtt    8220 gatggagttg tgaagttttt attaacgcga taaatgtacg agatatattt ttttagaagt    8280
atagatagaa aaattttgt ttgtagggt tttttttgtg cgtttgttta gtggtagttt    8340
ttagatatta ttaatataat tagtggatgg aataaagtcg ggtttattgt tttcggtagt    8400 aaggggttt gtttgatggt gttattgag ggggaaaggt aaggttagat tattgaaaat    8460
ttgtagtttg gtttaaagtt cgttttttgat agggtttgat aaggattggg ttaggtgtcg    8520
```

```
tgatatgatg ttataggatt gtgggaataa agttttaggg tataaattgt tggtgttttt    8580
tattgaagtg ttaacgggtt ttttgggaag tttttataat gagtaattta tttatttgtg    8640
taggtaagaa taaaagtaaa gataatggaa atatgtagat agttttaatt gtggaggttt    8700
tggagggtgt ggaagttttg tttttatttt tgagtagagg aattgggaga ttggaggata    8760
aaataagagg aagatttatt tttattgtt tgttttttta tatttttaat atttttaaaaa    8820 gtatattttt gtatagttta ttttaaaaag ataattatgt attttttaat gtatgtgtat    8880
ttagtgtttt attttattat agagttttgt ttattttatt tagatagaaa taattgttta    8940
ttaaataaaa ttgttttta gaaaaataga ttatgtgtaa atgattgtat ttatttttt    9000 t                                                                   9001

<210> SEQ ID NO 13
<211> LENGTH: 6501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 13
tttgtgtttt tttttgttta agtatgaata tgtttttggg attaagagat taggtttgga      60
aatagaagaa tttgttgagt tgtaaaattt gtatggttta aattttatcg aatattgttt     120
attttttttt taaatgattg tgtaatttat attttatttt taagagtttt tattttgatt     180
cgagaaatta gagtagcgaa aattatcgtt attatgagta ttattttggg tttggtgttt     240
tcgttttgtt tttaataaat ttaagttgat tatagaggat attaggtttc ggttttttt     300 tgggttttgc ggttaggttt tttttggaga ttttggttta ggagtggaga tttcggtgta     360
ggagtggtag ttttggagga ggggttgggt tttgggatgg agcgaagagg aatatggtcg     420
tttttatttt ggtttaggtt tttttttag aggggttgta gaaatgtatt gattaggtta     480
tttaagaaaa gatagtattt ttgttaggtt agtatgtatt tttttaggg tttaattttt     540 tattgaagaa gaaaagattt tttttgttgt ttatttttt atgtagtttt ttaatagttg     600
tttttcgaat gttaattaaa gttattgttt tagggtttgg ggttatttta aggtattagg     660
agatgaggat ttttgttttt atgcgttttt tcgtttgttg tagggaggag tgtaatgaat     720
aaataattaa tataatgtgt tagttatttg ttttatttat taggaggtaa taagagttat     780
gaaagagaaa gtttcgagta ggggagggga gtgaggtatg gtataggaga gtaggaggtt     840
gttttttaaa atataggagt ttaggggatt aattgggaag gtgtgggagg gggagggagg     900
gagttttata gatataggg agtgaattac gtttattttg ttagttttg atggtagttc     960 gtatatatta tttttttttt ttttttgttt ttagtttttt ttagaaggag atttaatttg    1020
tcgtttaggt tggagtgtag tagggtgatt tcgatttatt gtaattttcg ttttttaggt    1080
ttaagtgatt tttttgattt aattttagaa gtagttagga ttataggtat tcgttattat    1140
gtttggttaa ttttgtatt tttttttttt gtagagacgg ggtttcgtta tgttggttag    1200
gttagtttta aatttttgat tttaagtgat tcgtttgttt tggttttta aagtgttggg    1260 attataggcg tgagttattg cgttaggttt ataatttat tattaaaata attttattgt    1320
aaaagaatta gtttaggttt agacggaatg ggttttatga gttttttttt tttttttgt    1380 aaggttacgg tggttatttc gtgagttatt gttgttacgg ttaagttttt tttcggttat    1440
tttttattat gaattatttt tgtagtgagt atagtattta ttttggcggg agggtttttt    1500
```

```
agatatgagt aggatttgga ttaaggttag gttggaggag atttttatgg gaaagaggga    1560
ttttttgaat tttagatttt ttagttaaga tgattttatt atatgtcgtt tttgtttatt    1620
agtaaatttt tttatgtagt ttgattatgt ttaggaaata tttttgataa aaattagtgg    1680
agattattgt tttagaggat tttcgggttt ttttaggtaa atgttattta acgttttta     1740 agtaaataga gtttgtttta taaaattcgg ggttcgggcg gttttttatt tttgattcgg    1800
ggtcgttttt ggagtagaga ggaggtaatg gttattatgg agaataaggt gatttgcgtt    1860
ttggttttgg tgtttatgtt ggttttcggt attttggtcg aggtttagat aggtaaggcg    1920 tgttttttt tgttttgtgg ggttatagtt agttttggta gttttcgtta ggagttattg    1980
ttttatatat atatttttga gtatttgttt tgtgttaggt gttgtttag gttttaaaa     2040 gtatatttaa tttataggat cggtaaaagt aggtggagag taattaggg tggtaggtt     2100 ttcggagatt ttcgagaagt gcgacgagga gggggttgtt tttagtcggg gttgtttttt    2160
tgtgttagga agattatata attttttta gtgttatgtt ttaaagagga agtgttggcg     2220
tggggtttta gaatagtgtt tttgattgtt tatgttaata ttttttttag gggtagattt    2280
ttttaaggtt tatttagata ggtttaaatg tcggttttag tgatggttat ttgggagatt    2340 ttttttata ggttcgaatg ttcgttttag tggtggtaa ttgggagatt ttttttata      2400 ggttttggg tttttttggg atttatgttt tgggagttaa agttatttt tttatgagtg     2460 cgtggttggt aatttatatt ttttggtgtt gttaagtgga tcggttgttt tgggttttt    2520 tagggagtgg aggaggaggt tatttttgtt tttttgggaa gtgtttgtat tttaattttt    2580
ttatttgtag aatggattaa cggtttgttt tagggttgtt aggaaatgtt gtgtggtagt    2640
atttgcgatt tgtatttgt tagtgtggg gagttgaata atttatttgt cgttattagg     2700
tatagtttta aggtgggggt aggagaaagg gttttttacg ttttaaagt aagggttttt    2760 agagaggttt gaagagggag cgtttagtgg tgttgttcgt gtttttattg tttttagtt    2820 attttttgat ttttgttgtg gggtatcggg tttgagggggt gggtttggggt agcgtagaag   2880 agtagttagt attgggttgt agtgggaaga ttttaagtt tatggtaggg agcgggggag     2940
ttttggaatt cgagagagga agtggtttcg gtgtatagaa cgaattgggt gggttttcgt    3000
gttggttatt tttaggttta tttgtttgcg ttttttgttt tattttagtt tttagttttg    3060 tttttttgtgt tgtgggatta tagaggtcgt ggtaaatttt tttttttatt ttatatattt   3120
tttggtttaa ggtttagagc gttttttgcgg gttatttagg tttatgattt tgttataatt    3180
gaaatttaga aaattgtgat tatagtttag tgtattcgtg tgtggaaatt ttttttattt    3240
attttattta tgcgataaag ataaagcggg tgggtaagat agagtttgtc ggaggtagag    3300 tatcgggggtt ggaaatttt tttttgagg aggaaatttt ttcgattttt aggatgatga    3360
ttttttttta ttacggggtt ttttttgatt tttatagtgt ttcgggggtg ggcgatgatt    3420
atttttacgt cgcgatggat ttagatttta ggagggtaag gttttatgg aagttgttgg     3480 gtagcgggag ttgaatacgg attttttta gtaagttagg aatatttttt ttaaagatat    3540
ttcgaggtag ttttgatag taaagtagat aagagaatag ttttttcgg ttttttttgg     3600 ggcgtttta tttgagttag tgtggttaga ttgagttttt ttttttttat gttttaaggt     3660
agggataggg atcggagggt gttttgggtt ttttttttat ttttgttgt aggttgttaa     3720 ttattagatt ttaataggtt gttttttgag atttttgatt tcgcggagtt tagagtttga    3780
agttttggtg ttagaatttt ttgtataaga ttttgcggta gttttagtt agttttattt     3840 gtttacgtgt ttttttttt tagatttttt tttttattgt tttgttttaa gttgttttat     3900
```

```
agtttgtatt ttttgtcggt tttttttaga ttattttatt cggttttttt attttatttg    3960
taatgggttt ttattttttg aatatatttg ggttttttgga atggttttg tttatgcggt    4020
tttatttta tttggtgaat ttttttttgt agggagtttt tttgttttgt ttaatttgtt     4080
tgttattggt ttttcggggg agtgtttat tttcgtggtt attttgggta ttttgggacg    4140
atggttttgc gttgtttcgt atatgttttt gttttttttt tttattagat tttagatttt    4200
tttttttttt tttttgaga tggagttttg ttttgttatt taggttggag tgtaatggtg     4260
cgatttggt ttattataat ttttgttttt tgggtttaag tgattttttt gttttagttt     4320
tttaagtagt tgggattata gacgtgtgtt ataatgttcg tttaattttt tgtatttta    4380
gtagagatgg ggttttatta ttttggttag gttggttttg aatttttgat tttaagtgat    4440
ttatttttt tagttttta aagtgttggg attataggta tgagtttggg tttagatatt    4500
tagatttta ttaatgattt ttttggtttt aattttgggg ttttttttat ttggtatagt    4560
gtttggtttt tgttatgtta gttttttattt tttatgtata taaatggtgt ttagtaaata    4620
tttatgtatt gagtaaaatt taataattat ttgttgaaat taaaaagtga ataaataagt    4680
tatttagaaa gatgtaaagt ttataaattt ggggtatttt gtattttttt tgagcgtaat    4740
gtttgtatat taggatgtga ggattacgtt ttttttttat gttttgaggg ttttatattc    4800
gttttattgg atagttgttg atgttattgg agaaggaagt tggatgggtg tgtgtatgat    4860
aatattaagg aatttagttt ataatttatt ttgttttta tttgtgtatt tttagagacg    4920
tgtatagtgg tttttcgtga aagatagaat tgtggttttt ttggtgttac gttttttttag  4980
tgtgtaaata agggttgttg tttcgacgat atcgttcgtg gggtttttg tgttttat    5040
tttaatatta tcgacgtttt tttagaaggt atggttttt tatacgatgg gttttgaaga    5100
tttagaatta gttagaaaag ttatttaaga ttatagaggt tttgattagt attattagtt    5160
atgttttat atagagttac ggtcgttagt ggtggtgtaa tggggtagtt tgagttaggt    5220
tgtatttagg tttaggaata gaaaggtagg gttaagggat ttgggaagaa atttgattt    5280
ttttcggttt tttttttatat ttttaattaa aagtttggga agagttattg ttggtaacgt   5340
tttttagttt gtttaggata gagggggaag gtatgacgaa atttgaagat attttatgta    5400
tttttttttt tttttttttt ttgaaatgga gtttcgtttc gttgttttg agttggagtg    5460
taatggtgcg attttggttt attgtaattt ttgtttttg agtttaattt tagttttta    5520
gtagttgaga ttataggtgt gtgttattac gtttagttaa attttttttg tattttagt    5580
atagacgggg ttttattatg ttggttagat cggttttgaa tttttgattt taggtgattt    5640
gttcgtttta gttttttaga gagttgggat tataggcgtg agttatcgtg ttcggttgat    5700
agtttatgtt ttttaaagaa tgtgtttatg gatattttaa agtaaaaatt ttgtaattgt    5760
ttaaatgtga aagaaaatgt ttatttttat taaagtatt ttttttttt ttttttatt      5820
tttgtagagt agtgtgaatt ttagatattt ttgtagggat ttgtttgtat tttgacgcgg    5880
tgtcgttttt agtacggtga ttagttttag agttcggttg ttattttttat cggatattt   5940
agatacgttt ttgtagttgt gtttcggttt ataatataga ttgattgttt tgattttgat    6000
tatttaaaat tggtttaaaa attaaaagag atcgatatta atttgtgttg tttattttttt    6060
taaagaatat gaatgattt ttttttttg aaagtgaagc gtagcgtttt attttgggtt      6120
ttcgtagagg ttttgtattt tttggttttt ttgagttggg atataagtgg gtagttgagt    6180
gtagaaagta gggatggtgg ggtgtatagt aggatagtgg ggtgtgtagt aggatagtgg    6240
```

```
ggtgtgtagt aggacggtgg ggtgtatagt aggatagtgg ggtgtgtagt aggacggtgg      6300
ggtgtgtagc gggacggtgg ggtgtgtagt aggacgtaag tttaagacgt atttttgttt      6360
aggtatgaaa atggatatcg attttttttgg tattttttaa ttatttattg cggatgtttt     6420
agcgattaag tgatataagt tagttttcg tttatttgtt tttttaaata gaaattggcg       6480
taggagatga aatttgtagt a                                                6501

<210> SEQ ID NO 14
<211> LENGTH: 6501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 14
tgttataggt tttatttttt acgttaattt ttatttggga aagtaaataa acggaaagtt        60
aatttgtgtt atttggtcgt tggggtattc gtagtgagta gttaagaaat gttaggggag       120
tcggtgttta tttttatgtt tggataagag tgcgttttgg atttgcgttt tgttgtatat       180
tttatcgttt cgttgtatat tttatcgttt tattgtatat tttattgttt tattgtatat       240
tttatcgttt tattgtatat tttattgttt tattgtatat tttattgttt tattgtatat       300
tttattattt ttgttttttg tatttagttg tttatttgta ttttagttta ggaagtttag       360
aagatgtaga attttgcga gagtttaggg tgaaacgttg cgttttattt ttaaagaaag        420
gaaaattatt tatattttt aaagaatga atagtataga ttaatatcga tttttttttaa       480 tttttaggtt aattttgagt agttaaagtt agagtagtta atttgtgttg tgagtcgagg       540
tatagttgta gaagcgtgtt tgaggtgttc ggtggaggtg gtagtcgagt tttgggatta       600
attatcgtgt tggggacggt atcgcgttag gatgtaggta gatttttgta gaagtgttta       660
aaatttatat ttttttatag gggtgagggg gagggagaaa gagatgtttt agtgaggata       720 aatattttt tttatattta aataattata gagtttttat tttaaagtat ttataggtat       780 atttttaga aaatatgaat tgttagtcgg gtacggtggt ttacgtttgt aattttagtt       840
ttttgggagg ttgaggcggg tagattattt gaggttaaga gtttaagatc ggtttggtta       900
atatggtgaa atttcgttta tattaaaaat ataaaaaaa tttagttggg cgtagtggta       960
tatatttgta atttttagtta ttaggaagtt gaggttgaat ttaggaggta gagattgtag      1020
tgagttaaga tcgtattatt gtattttagt ttaggggtaa cggagcgaga ttttatttta      1080 aaaaaaaaa aaaaaaaga atatatgaaa tgttttttaga tttcgttatg tttttttttt       1140 ttatttttagg taagttagaa agcgttatta atagtggttt tttttaggtt tttggttaga     1200
gatgtgaaga gaagtcgggg ggaaattagg ttttttttta agttttttag ttttgtttttt     1260 ttatttttgg atttgaatgt agtttgattt aggttatttt attgtattat tattggcggt      1320
cgtgattttg tgtaaaggta tagttggtga tgttgattag agttttttgta gttttaaatg     1380 attttttttaa ttaatttttaa attttttagaa tttatcgtat aaaaaggtta tatttttttgg  1440 agggacgtcg atggtattag gatagaagta ttagggggatt ttacgaacgg tgtcgtcgaa     1500
atagtagttt ttatttgtat attgggaggg cgtgatatta ggaaaattat aatttttgttt     1560 tttacggggg gttattgtat acgttttttga aagtgtatag gtaagaagta aagtaagttg     1620
tgggttgaat ttttgatgt tattatgtat atatttattt agtttttttt ttaatgata       1680 ttagtaattg tttagtgagg cggatataaa attttttagga tatgagaggg agacgtggtt    1740
tttatatttt gatgtgtaaa tattacgttt agggaaaatg taaggtgttt taggtttgtg     1800
```

```
gattttgtat ttttttaggt aatttattta tttattttt aattttaata aatgattatt    1860
aaattttatt taatatataa atatttattg agtattattt gtgtgtatga gaagtgggag    1920
ttagtatggt aaaagttagg tattgtgtta ggtgagagag atttagaaat taaaattaga   1980
gaagttatta ataagagttt aaatatttgg gtttaggttt atgtttgtaa ttttagtatt    2040
ttgggaggtt gaaggaggtg aattatttga ggttaggagt ttaagattag tttgattaaa    2100
atggtgaagt tttattttta ttaaaaatat aaaaaattag gcgggtattg tggtatacgt    2160
ttgtaatttt agttatttgg gaggttgagg taggagaatt atttgaattt aggaggtaga    2220
ggttgtagtg agttaagatc gtattattgt atttagttt gagtgataga gtaagattt    2280 attttaaaaa aaaaaaaaaa agagtttaag gatttgatgg aggagaaagg taagaatatg    2340
tgcgagataa cgtaaggtta tcgttttagg gtgtttaggg taattacggg ggtagggtat    2400
ttttcggaga ggttaatgat aagtaggttg aataaagtag ggggttttt tgtaggagga    2460 ggtttattag gtgaagatgg agtcgtatgg gtaaaggtta ttttagagat ttaggtgtgt    2520
ttaggaggtg gaaatttatt gtaggtaagg tgagaggatc gggtggggtg gtttaggagg    2580
agtcgataga gggtataagt tgtgaaatag tttgaagtag ggtagtgagg aaagggattt    2640
agaggaggaa gatacgtgga tagatggggt tggttggggg ttgtcgtagg attttatgta    2700
agaggtttta atattagagt tttaggtttt gagtttcgcg gaattaaagg ttttagaaag    2760
taatttatta ggatttggtg gttgatagtt tgtagtaggg ggtgaaagag gagtttagag    2820 tattttcgg ttttttgttt tgttttgggg tataggaggg gaggaattta gtttggttat    2880
attggtttag gtgagggcgt tttaggggag gtcgagaggg gttgtttttt tgtttgtttt    2940
gttattaggg attgtttcga gatgttttg gagaaagtgt ttttggtttg ttgggaagga    3000
ttcgtgttta gttttcgttg tttagtagtt tttatgggaa ttttgttttt ttggggtttg    3060
gatttatcgc gacgtgaagg tgattatcgt ttatttcgg gatattgtgg gggttaagag    3120
aggtttcgtg gtgagggagg attattattt tggggtcgg ggggttttt ttttaggga    3180 ggaagatttt tagtttcggt gttttgtttt cggtagattt tgttttgttt attcgttttg    3240
tttttgtcgt atgatggaaa taaatggaaa tggttttat atacgaatgt attaaattgt    3300
aattataatt tttagattt tagttgtaat aggattatgg atttgagtga ttcgtaaaga    3360
cgttttgagt tttgagttag aggtgtgtg ggtggggag gggagtttgt tacgttttt    3420 gtgattttat agtataggggg gtagagttgg gggttgggt ggggtaagg gcgtaggtag    3480 atgggtttgg gggtggttag tacggggatt tatttagttc gttttgtata tcgaggttat    3540 ttttttttc gggttttaaa gttttttcgt tttttgttat gggtttgggg gttttttat    3600 tgtagtttaa tgttggttgt ttttttacgt tgtttaagtt tatttttag gttcggtatt    3660 ttatagtaga gattaagagg tggttggagg gtagtgggggg tacggatagt attattgggc    3720
gttttttttt taggtttttt tggaaatttt tgttttggaa acgtagaaag ttttttttt    3780 tgttttatt ttgaaattgt atttaataac ggtaaataag ttatttagtt ttttatagtt    3840
ggtaaagtgt aagtcgtaga tgttgttata tagtatttt tgatagtttt agggtagatc    3900 gttgattat tttgtaggta aaggagttga gatgtaaata tttttaagg aagtaagaat    3960 ggttttttt tttattttt agaaggattt agggtaatcg atttatttga taatattagg    4020
gaatatgggt tgttagttac gtattttatga gagaggtggt tttgattttt agagtatgga    4080
ttttagggga gtttaggaat ttgtaggaga gggttttta gttggttatt attgggacgg    4140
```

```
gtattcgggt ttgtgggaga gggtttttta ggtggttatt attgggatcg gtatttgggt    4200
ttatttggat gggttttggg agggtttgtt tttgggggag atgttggtat gaatagttaa    4260
aagtattatt ttgagatttt acgttaatat tttttttttg aaatatgata tttgggagga    4320
ttgtatagtt tttttaatat aggaaaatag tttcgattga aggtagtttt tttttcgtcg    4380
tatttttcga aggttttcgg gggttttgtt attttgagtt attttttatt tgttttgtc     4440 gattttgtaa attggatata tttttaaggg tttagaatag tatttggtat aaaataggtg    4500
tttaaaaata tgtatgtaaa atagtggttt ttggcggagg ttgttagagt tggttgtggt    4560
tttatagagt aggaagaagt acgttttatt tgtttgggtt tcggttaggg tgtcgagggt    4620
tagtatggat attaggatta gggcgtagat tattttgttt tttatggtgg ttattgtttt    4680 tttttgttt taaaggcgat ttcgagttag ggatgagagg tcgttcgagt ttcggatttt     4740
atagggtagg ttttgtttgt ttaaagagcg ttagataata tttgtttaag gaggttcggg    4800
gattttttga gataataatt tttattgatt tttattaaag gtgttttta gatatggtta     4860 agttatatgg aaggatttgt tgatagatag agacgatatg tggtgaggtt attttggttg    4920
agggatttga gatttagaaa gttttttttt tttatgggag ttttttttaa tttgatttta    4980
atttaggttt tatttatatt tgagaggttt tttcgttagg gtaaatattg tatttattgt    5040
agaagtgatt tatagtgaga gatggtcgga aaaggtttg gtcgtgataa tagtggttta     5100
cggggtggtt atcgtgattt tgtagggga agggaaggag tttatgaagt ttatttcgtt     5160
taggtttaag ttaattttt tatagtggaa ttgttttaat aatgaaattg taggtttggc     5220
gtagtggttt acgtttgtaa ttttaatatt ttgggaggtt aaagtaggcg gattatttaa    5280
agttaggagt ttgagattag tttggttaat atggcgaaat ttcgttttta taaaaaaaaa    5340
aaatataaaa attagttagg tatggtggcg ggtgtttgta atttttagtta ttttggaggt    5400 taagttagga gaattatttg aatttgggag gcggaggttg tagtgagtcg agattatttt    5460
attgtatttt agtttgagcg atagattaag ttttttttg ggaggggttg ggggtaggag     5520
ggagaaaaaa atagtatata cgagttgtta ttaaaaattg ataaagtgaa cgtggtttat    5580
ttttttgtgt ttatggggtt tttttttttt ttttttata tttttttagt tggtttttg      5640 gattttgta ttttagagga tagtttttg tttttttgta ttatgttta ttttttttt       5700 ttgttcggag ttttttttt tatagttttt attatttttt ggtggataaa ataagtgatt    5760
gatatattat gttggttatt tatttattgt attttttttt gtagtagacg ggagggcgta    5820
tgggagtaga agtttttatt ttttagtgtt ttgaggtggt tttagatttt agaatagtgg    5880
ttttgattgg tattcgagaa atagttgttg aagagttgta tgaagaaatg gataatagga    5940 gaaattttt ttttttagt gagaaattag ttttgagga aaatgtatgt tagtttaata      6000
aaggtattat ttttttttgg gtgatttagt tagtatattt ttgtagtttt tttgggaggg    6060
gagtttgggt tagaatgggg gcggttatgt ttttttcgt tttattttag gatttagttt     6120
tttttttagg gttgttattt ttgtatcggg gttttttattt ttgggttagg gttttttagga    6180 ggggtttgat cgtaggattt agggaggggt cgaggtttgg tgttttttgt ggttagttta    6240
agtttattga aaataggacg gggggtattag gtttagggtg gtgtttatag tgacggtggt    6300
tttcgttgtt ttaattttc ggattaaaat gggggttttt ggaaatggga tgtaaattgt     6360
ataattattc ggagaaaagg tgggtagtgt tcggtgaggt ttaagttata tagatttat     6420 agtttagtaa atttttttgt ttttaggttt ggttttttaa tttagaaaat atgtttatat    6480
ttgggtagaa gaaaatatag g                                              6501
```

<210> SEQ ID NO 15
<211> LENGTH: 12001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 15

```
tatggattgc gtgattatta aatttggtat tttaggggggt atatttttttt tgagtaattt      60
ttataaatat gtttgtttgt aggatattta gattttttgg tttggtagta aagtaatata     120
agaataattt tgaatttgat gtttattttt gtttttttttt taattttagg agttttttga     180
ggtttggatt aatttattga ttaggaaata gtatttggaa aggttaaata aaatattatt     240
tttagggaaa tagtatttgg aaaggttaaa taaaatatat tttttttagtt tttttaaatt     300
ttttagaaga tatatttttt aaaaaataaa ttaagttagt aatatttaaa ttaaattttt     360
gttttgttta taatataaaa gatgataaaa aaattgttgg gaaggtgaga aattaatttt     420
atttataatt agaagtaaag ttttttattta aaaatgtaat attatttaaa tttaatttgg     480
gaaataaaaa ggatttaaaa aatagtttgt taaagttaat ttgtaaataa gtgcgttttt     540
tttttttttta agttgtattt taggtttaga gtatatgtgt aggtttgtta tgtaggtaaa     600
tttgttatag ggatttgttg tatagattat tttgttatttt aggtattaag tttcgtattt     660
aatagttatt tttttttgatt tttttttttttt ttttattcgt tattttttaa taggttttag     720
tgtttgttgt ttttttttttt gtatttatga gttttttttta tttagttttt atttataagt     780
gagaatatgc gttatttggt ttttggtttt tgatttagtt tgttaaggat aatggttttt     840
agttttattt atattttttgt aaaaggtatg atttttatttt tttttttaatt attttatttt     900
ttttattatt ttttttttttt tttttaattt tgaatttttat tatgttagtt taattatttt     960
ttttttttttt tttttttttttg tttatttgta tatagttaaa agatgttatg aattttttttt    1020
tttaatttag tatatgttta ttaaagattt aaaaatatta tttatattat ttagaattta    1080
gtttaagaaa ttattaaaaa ataaagttat tagaaagtaa ttgaattatt ttgttgagtt    1140
ataattttag atttcgattt tgtttttttttt ttattttttagg taggttattt ttttttttttt    1200
tttaaattgt ttttttttgta tttaataata tattttttgtg gatttagaaa gggtggagta    1260
tgaggaaaag gaatatgata tatgtatttt agaggaaaat aataaataaa tattttttagga    1320
tggaaaatat tattttttatt tttattgagt tttttagagt ttatttgatt tgtgtaaatt    1380
agaaattagt agaatgatat taatgaatta atgaaaagta gaatgagtta ttagttgtaa    1440
taaaaagaat aaagaatttt aagaatatag ttttaattat gtatggttgc ggggagagaa    1500
aaataataaa atgttttttag tgaatatatt tttgagagaa gaaaggaaat atttaaggag    1560
aggataaaaa gagtaaatat taaaaatagg agtaagaatt ttattgtttt tttttagttga    1620
taaataaaaa ttgtatatat ttattgtgga taatatgata ttttgaggat tacgattatt    1680
tttgatttat aaattatatt taagaaaaag aaattttttaa aaagtttggg aatatatgaa    1740
gttgaaagaa tattaatatt tagataagga tagtatatga taaattatttt ttgttttaat    1800
atttttttttt aggaaaattta aatatttttt agtgaagtat tagttttttg aaattaagta    1860
tgagaaaaaa aattaaattt atttgtggaa aaaaagatat agttaaataa aaaagcggtt    1920
gttataattt taagagtggt atgaataaaa tgattaatat ttttttaagt gatagtataa    1980
atattaaaag ttttaataag tggaagtggt tttgttatga taaaaggtgt ggtatttgta    2040
```

```
taatttttag ataagaataa agttatgacg ttaagatagt agtagtattg tttgttatac    2100
gtgatatttg aaaaatatga taattatttt aatttgttta agtagtattt atggtgaggg    2160
tgaaatttta ttaatattgg ttaatttatg gtgttttaaa aaattagtaa ggagataaat    2220
tgatggatta aaagataaat tatttatagg tagataaata gaaggataga tagagttata    2280
attaaatatg tattttattt aggtagaaag ataataatta gttttttaaga agtgatgtgt    2340 ttgttagaaa agttttgaat atagaatttt ttgattttgt ttttaattta gttttttttag    2400 gtattacgtt gtataattag gtgtaatttt ttaaaagttt ttatgataga attttttatt    2460
tgttaaatta ggttaataat attttttattt tttttttaggg taaagatgtg aaatatttgg    2520
agaattttgg aaaatatgtt ttttattaat tagagttttt tgatgtgata ttattttttt    2580
tagtatttgg agtttagtta atagatatat agtgtagttg tgaaattatg aagtatgaga    2640
atgtattatt aagggatcgt aggaggtttt ttattgaaaa gtgtagttgg ttatattttt    2700
ggaagtaatt taaatatagg ttgagggaga ggagtatttt ttagattttt tttagatttt    2760 atttttatg aattttaatt tttttttttt atttagaaaa aataatgaga tttatagcgt    2820
agagatagaa aataaggttt tgtgtgtttt taaattttat tttttaaaaat attatagtat    2880 tttggacgag atagttttga attttttgtaa tagtataggt atgagagttt ttattagaaa    2940
ataggagatt ggattgattt ttttatttttt tttttatgtt ttttaaaatt gaaaagttat    3000
atatataaat tatatttatt tattttttt ggaaaaggtt aaaatgaatt taattttgga    3060
ttatttttaa taatgggata aatttgaatt gagaataatt tttagaatta gttttgtttt    3120
tttgtgataa aatggatttg tagaaagtta tttggtgttt ttttttagtt aatatttat    3180 tataaataac gggtatgtaa tttagtattg ttttttatag gttatgtttt tggaattatt    3240 attttttgtat tttatttgtt tgttgatatt tttttatta agatgttttt tttagtataa    3300 gaagttatt tttttaaaat tttaaatgat tttattataa taatagagtt gttaattaga    3360
tttaggtaag taatgataat aaaaatttga ttttttattta gagtgtagta tggtttaata    3420
taataattag agttttaata ggtttttta gatttttttt ttatttaattt tgtatgtttt    3480 tgtaatatag atgttttttat tattcggttt ttatttttat ttttttttgt ttttggaata    3540
aaattattta aatttaattt agagatttta tttttttttg gaattattgg gaaatagttt    3600
tagtaaatta tatttttgag attttatatt aggtttagtt taaattgatt atttaagtat    3660
taattttttt gtggtttagg aatatttttg agtttatttt tttttttta aattgtttag    3720 gataaatatc ggagtttggt tttttgtttt ttttattttaa ttattttcg tttttttttt    3780 tttagtatt aaaatatttt tgattttttt tatttttaa gaaatatatt tgttttttg    3840 tttttgtatt atttttttgt ttatgaaata tttataggt aagttttata tttttttttt    3900
ttagaggttt ttggtttttt ggtttagtt gttattggtt tagtgtatta gttaatattt    3960
tggattttgg agttatataa atttagattt aaattttat tatgttattt attgtttacg    4020
tgatttgaag taatattta tttattgtgg ttttagtag ttataagttt gtgttttaat    4080
tagttgggtg attttgggtt agtgatataa ttatggtaaa ttttattgtt tttatttgta    4140
aaatgatagt atttatttg tagtgttggt ataaggaata agtgtgattg ttaatataaa    4200
agtgtttagt ataatagtta aattaattaa gtattttgta aatattagtt ttattatta    4260 ttattaattt aaatgattag atgtattttg tgtatattag gttttttgag tttattttgt    4320
ttttaataaa tattattatt tttagtatgt ggttatatatt atattttatt agttagagga    4380
tatgtgaagt ttagagtgga aagttagggt agtaggaagt attgttatat tttatatagt    4440
```

```
taaagttatt taaatatgtt tgaatttgag ttttgttgag tttttatttg tttttatttt    4500
ttttgtgtgt tttagtttat taataaagta ggtttaatat aaatatatta aaagtttaaa    4560
tattgagatt atgataatga atatgagggt tatgattata aaatattatt gaattagaga    4620
tttgttacga aattatatgg tgaagattat aagggaggaa tttgtatata tatcgagtgt    4680
tttgggattt taaagtggga agagttagtg ttttaattaa agagaaattc ggggtaggga    4740
attaattata atattagtta ttttattgaa tttaggtttg ttttagttga cgtagttgtt    4800 aattttttaat gtttttttttt tttttaattg ttttttaattt atttttttag aaattgaaag    4860
tttattaaag aggatatttt tttagagagt tgttttagtt attataagtt tttgttagaa    4920
attttaagaa agtttataag gtattttttat aaggtggtat tgagtaagtt agaagtattt    4980
taagtattaa ttattatgta aataagggtt ttatttttag attttgttgt ttgtggtggt    5040
ggtgatgttg gtgttttttt tggaatttag tttaattttt aaaaaagtaa aaggagtata    5100
aatagtaata taaattatta ttatttttat taattaaaat agaagttttg aatgagtaag    5160
gagttagagg aggtaaaaat tgggaatttc gtatattaaa aggttttttat aatttgaaaa    5220 ttaagattat gttggttaaa taggttgttt taaaattagt atagtaatta aatttgtttg    5280
taatgaatgt agatttaaat agtgatgtta gatttgataa ggatttgtaa attttaaaag    5340
agtgtaaaaa gattatagaa gaataatatt atattttttgt atttatagaa atggttagtt    5400
taagagatgt atttagttta gggtggttgt aagttttatt ttttgaattt gttattagaa    5460
gttaaaagaa attttgtata attgtttttg atggaaatat aaattggttg atgtaaatga    5520
aatatataaa gtagttggtg ttttatttat ttttataatt ataaatgaaa ttaaatgatt    5580
aaaaattata gatttggggg atttttttttt tattgaggag tttatggaat tgttttttt    5640 tagtattaat aattgtgttg atttattttt ttttgtttaa ttttgtatat attaaaatta    5700
ggtggttacg aataaaattt agaaatataa tttatatttt aataaaatga ttttaaaatt    5760 atttttatttt ttattgtggt tttatttgtt gttttataat gtaggttttt ttgggttttt    5820
gtttagaatg atttttgttaa tgtagatgat agttagagtt gaatgggaa tttagaaatt    5880 ggggattcgg gttttttgatg taatttatat gttaatttat tttattagtt ttttttttat    5940
ttatagtttg gtaaagaata tgggtggagt tgttttgggt ttatttgtat atatgtttaa    6000
attgttttga aaaggaagg gtaagaaaga gtggtattta agttgaatt aggtaggtat    6060 tttagattaa gagacgaatt ggaaagggaa tatttgttag atattttggg tttgaaggta    6120
gtttgtgtaa gtttttatat ttttgagtgt gtgtatatag tggagagggt ggagtttgtt    6180
atttttaaat ttgaaaagat tgagagattt tagagggttt agatgtgtta aaggttagag    6240
ggattaatat ataggtttta ttacggaaag gcggggaaaa ggttcgaata gaaaattgtt    6300
gtagaaggga agttattgag aggtaaggga gttttttgaat aattaaaaag ttaagaataa    6360
gtaaaaggaa ggaggtcggg tgggggataa aaaaaagtag ttgatgtggt aattaagaat    6420
ttggtgggag tttgggtagg ttattttttt tttttagatta gagtttttatt agaaatttttt    6480 ttaagtgttt ttttgcgtcg ttaaagatga taatagtaaa ttaataagtg tttgaaatga    6540
aaggggatgt tgattagttt ttaggttata gattttttcgt cgttagtttt ttttgaattt    6600
ttatagcgtg tttttgtatc gtttttttta agaagagtta tttttttattt ttatttttag    6660 gacgaaggta agtgtttagt tagtatattt attaaatgtt agtttggtt ttagtttttc    6720 gtttgcgcgg aaagtttatt gttatagcgc gtttagtttg tcggaggggt agatagaaaa    6780
```

```
agtaagtttg gtttggcgat tgcggggtt acgtattttt agggttggtt cggagttttt    6840
tagagtttaa cgttttgggg ttagaattgt aaggtttcgg ttcgagtaaa gggtttgagt    6900
tatcgtagtc gtgggagcgt tttttttatt tgaatgtatt tatttataaa taagtataaa    6960
attttttaa tagtagagga gaaagatttt tgttttaaaa ttaaagttgg gaattatcgg    7020
aaatttcgtt ttgagtgcga gatattggtt tgttattttt ttaatttta tatttttttt    7080
gtaatatgtt ttgatttaat aattttttta gcgtttagta ttgttcggac gttttaattg    7140
ggtaatttat tagtgagtta ataggtat ttatatattt ttttagttta agtggttaag    7200
tattaatttc gaaatgatta taaaatatcg gaatcggtaa cgtatagtaa ttttaattta    7260
tatgtaaatt aattggttta ttttaaatgt ttttttaaa aaaataatta ttgtattgta    7320
gtatcggagg tatggattaa attttagaa tagataattc ggaaataaga tttggattag    7380
gaagataatt tagaatagtt aataaattaa taatgtttga ggtagttaaa tatcgttagt    7440
tattggtatt tatatattcg tttgttgtta gataaggagt tggggaaatt gtttgttagg    7500
gttgagatta taatttagag tgaagaaagt aaatggtagt atatagttcg ttatagcggg    7560
ttttgaaata atattgtatt tttttaaat tttgattttt gggtgatagg gagttggcgg    7620
aggttatttt atatttgttt acggttttgt tttaatttga ttacgaaatt gttgtttttt    7680
ttgagttttt taatttgatt attatttta cggttttgtt atttgtttta atatattggg    7740
gggaggagtg taattgagat ttttattaaa aattatttga atttatttag ttagtattgt    7800
tttatttaag tttagtttta tgggttgtat ttaatttttt gtgttttta tatattaaaa    7860
ttagattatt aaaatgtcgg taggaaaggg tgaaggaaat ggtttaatgt tttagtttat    7920
tggaagatta ttatttttag atatagttta aaatttgag gaaataaaaa ggatatacgt    7980
tttgggggga aaatgtttta atattttaga atggggtat tatttttttt attttagaga    8040
attcgtattg gagttgttta tgtaaaaatg taatattttt gaaatttata gatacgtaag    8100
gttagtgttt tttttttttt aggttttag tttaggcgat ttagttttaa aggagttagt    8160
attttgatg ttataatttt gtttatattt gtagggtaga gaattgtttg ttttgtttgg    8220
acgtttttt tattttttt taatttgaag taatcggaat ttaaatatag tcgttaaggt    8280
tcgtttttt tttattgttt tgataaggga aaaatttgaa atttacgttt taaattagtt    8340
cggtggtttg tagtttttta gtattttgtt tttacgattg tatgtttaat gtattttttg    8400
gtgattttgg gtattaatta gttgtttaat aggagtatga ttaaaaatgt aaaagaagga    8460
ttaggagcgt gaaacgtatg tttagttttt tttatatatt cgaggaggga atgagaatta    8520
tttgtatt tttatttttt taggagttat ttgtattttt tattagttgt ttatttagt    8580
tgtattggcg ttgggtaagg cgaggattta aaagttagc gtagtgtttg cggcggtcgg    8640
gattgggtt aattagtttt tggcgggcga gattttgat agaagggggg cgagaggaac    8700
gtgagttttt cgagttttt ttttttagtt ttggttgta aatttttgaa atttgaaagg    8760
ggagggagtt gtacgcgcgt attttgcgt ttttttagcg taattttttt ttttttttt    8820
gtgtttttc gcggattttt gaattttttt gttttggtt ttttattttt tttttaattt    8880
ttttatgaga ttgtttattt tcgttattag ttgaaggtaa ggtcgttttg ttacgagcgt    8940
ttttttaattt ttataaaatg aaaagaaaaa aagggaggat tattagttta ttatttagag    9000
gaatggggag gttgtaaaaa tcgtcgatgg gtagaggtga agatgttttt tcggattgt    9060
attttcggt gttttgtaat tagagtttag ttgtgggatt tgttgaagaa atttgatttt    9120
tttgtttcgg cgagattta aaaattagaa atagaaattt ttagagttag agaggaaata    9180
```

```
taattaaata gtacgtgggt attttttttt ttattttttt tttttttaaat aatattgttt   9240
tgagttttta ttgggtaaag agagaaagtt tgagttttta cggatgttac gtggaggtta   9300
gaaatggttt aaaatgtaga tttttaatta gttttttcg tggttgaaga ggttaatttt    9360
ttttataaaa tgagtttatt tgtcgattgt tagttatttt aaagtgaagg gatttagtat   9420
ttaaaataaa ttgagtaagt ttgtttgttt gttttattg ttaatttaaa tgaatttaaa    9480
atacggagta atttaagaaa atatataata tgttttagat agtttttaaa agtagggaaa   9540
gtttagtatt tatatagtga ttagggttag tttaagcgt taagttttt taaacgtatt     9600
tattttatgt atattttttc gagttattat atatttttaa aattgcgagt attggtatat   9660
tgatttagga agagtaatat aattttaga gggaatttta tttttaatta gggattaaag    9720
agatgttttt ttaatagcgg gtttgagttt tgttttaag taggaattaa tattggtggg    9780
aaaattcgaa tttaggagta atggttgtgt ttcggtattt tttaaaaata tatattaata   9840
ggatgttttt gagattgaaa aaatattgtt ttatatgttt ggtagaagtt tttatatttg   9900
gtttttagg cgaattatat ttatagtttt tttatttaga ggtaggatag agttaaaata    9960
ttttgtttat tattaaaata tatattttg tttaagttaa gaaattagaa aattagggtt    10020
tagaagtaag gtatatttt cgagtgagaa tatgttttgt aattttatat attttttgtt    10080
ttgtaggagt aaatgtggat ttgagggaaa tttttttttt tatttttatt tttatttcgt   10140
gtaatttaat attattttcg ttaggaattt taatttcgtt attttaaaaa atgagatatt   10200
cgtgatttag ggtgaatttg ttgaatgtag gtatagtaga ggaaatttta gattttatga   10260
gcgtttgagt tttgtttagt gtaaattttt cgtgaatatt gggttagtgc gtggtcgtgt   10320
ttatttgtgc gtcgatattt ttagtatgtt tggtttattc gttttgattt cgggcgcggt   10380
gttttagtta agttgggttt agcgtttcgg ttttttttag ttgataagtt tagttcgttc   10440
gttttcggtt gtggttttt tattttttt tattagttta ttttattttt ttagatttt     10500
ttttatttat ttttttttat ttttatcgcg tttattttta ttttcgtttt ttatcggttt   10560
tttattttt tttttcgta gttttttttt gttgtgattt ttttttttaa ttttgtaggt    10620
ttgaaagaag gttatatacg tacgtttata tttatatttt atacgtttcg ttttaaataa   10680
ttttatgaat attgttttt gttcgtttt ttgggttatt tttttttgtcg ttttttttta   10740
gttcgttttg atttgttttt taaaagtacg ttttttgtttt ttcgttgttt tggcgttttt   10800
tttttgattt attagggttg tcgggttggc gtagattgtt ttttttttt ttttatttta    10860
ttttttttt tggtttttt ttttatagtg ggagttcgtg ttttgtttt tcggttggtt     10920
tttaagtgtt tcgttaggtt tttttttt tcgttttttc ggtttcggtt ttcgattttt     10980
cggttcgttg gtatttgttt tttttttg tttcgttttt cgtcgttttt gttcgttttt     11040
ttcggcgttc gttcgggcgt tgtgttcgtt tttggatcgt tagtcgcgta gtcgggttcg   11100
gtcggtcgtt cgcgcgttat tgtgtagtgg agtttggtgg aattttttgtt gacgttacgt   11160
tatttttat acggagtagg agtagaggga agagagaggg atgagaggga gggagaggag    11220
agagagtgcg agatcgagcg agaaagttgg agaggagtag aaagaaattg ttagtggcgg   11280
ttagatttcg gaggttttag tgtattcgtg gatttttcg gaatttggta tttttaggag   11340
ttttgtagtt ttttaggtt cggttttcgg gcgtttgtcg tgtagtcgga ggttcggttc   11400
gttggaaatc gtttcgggaa gtagtgggac gcggagatag tagtttttt tcggtagtcg   11460
gtaagtggag gttatttatt tcgtagggat gtgagataat gcgagtttgg aaatttgttt   11520
```

```
tatttcggag aattttatc gtaggtgatt tgtggttttt ggggttaagt ttcgtttaag    11580
gtaacgtagt cggtaaatag attttgtaaa gttttgtttt tttcgttttt cgttatagat    11640
attaataatt tatagggtgt tgaagtcgag agggaagtta gatcgtggtt ggtatttaaa    11700
acgaggtatt ttttttaaa tttcggtgtt aatattgtag gaataaattt tcgggttaag     11760
gattagtatt tttaagataa agggttgggt ataaagtttt agttattgga agattagttt    11820
tttttttatt gttatttatt gggaaaaaaa agaaaagaaa aagattttat tttaattggt    11880
agttagtgat ttttaggtt taagcgaatt atttgggagt taggtttgga tgttaagttt    11940
ttattatttt tttggattgt aattttttta aattgattat tagttaattt taatttggta    12000
t                                                                     12001

<210> SEQ ID NO 16
<211> LENGTH: 12001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 16
gtgttagatt ggagttgatt ggtgattaat ttaaaggagt tataatttaa agaaatggtg      60
agagtttggt atttaggttt ggttttagg taattcgttt gggtttgaga ggttattaat     120
tgttagttaa gatggaattt ttttttttt ttttttttt taatggataa taatgggaag      180
ggggttaatt tttagtagt tgaaattttg tatttagttt tttatttga gaatgttaat     240 ttttggttcg aggatttgtt tttgtagtgt tggtatcgag atttaaggga agatatttcg    300
ttttaaatgt tagttacggt ttggtttttt tttcgatttt agtatttgt agattgttag     360 tgtttgtggc ggggacgaa aggaataggg ttttgtaagg tttgtttgtc gattgcgtta    420
ttttgggcga aatttagttt taaaagttat aaattattta cggtgaagat ttttcgaagt    480
ggaataaatt tttagattcg tattatttta tatttttgcg ggatagatgg ttttatttta    540
tcggttatcg ggagagagtt gttgttttcg cgttttattg ttttttcgggg cgattttag   600 cgagtcgagt tttcggttgt acggtaagcg ttcgaaagtc gggtttgaga ggattgtagg    660 gttttgagg gtgttaagtt tcgaaggagt ttacgggtgt attggggttt tcgaaattta    720
gtcgttattg gtagttttttt tttgttttt tttagttttt tcgttcggtt tcgtattttt    780
tttttttttt tttttttta tttttttttt tttttttgt ttttatttcg tgtggggagt    840
gacgtgacgt tagtagagat tttattaaat tttattgtat agtggcgcgc gggcggtcgg     900
tcgagttcgg ttgcgcggtt ggcgatttag gagcgagtat agcgttcggg cgagcgtcgg    960
ggggagcgag taggggcgac gagaaacgag gtaggggagg gaagtagatg ttagcgggtc     1020
gaagagtcgg gagtcggagt cgggagagcg aaaggagagg ggatttggcg gggtatttag    1080
gagttaatcg aggagtagga gtacggattt ttattgtgga aaggaggatt agaagggagg    1140
atgggatgga agagaagaaa aagtaatttg cgttaattcg gtagttttaa taaattaaag    1200
ggggagcgtt agggtagcgg ggagatagaa acgtattttt ggggagtaaa ttaggacggg     1260 ttggaggaa gcgatagga aagtggttta agagacggaa taaggataa tgtttatggg      1320 gttgtttggg acgaggcgtg tggagtgtgg gtgtgagcgt gcgtgtgtga tttttttta    1380 ggtttgtaga gttgaggaaa gaggttatag taaagaggga ttgcggaggg aggaaagtga    1440
gagatcggta gagggcggga gtggaggtgg gcgcggtggg gatgggagag gatgagtgaa    1500
gagaaattta gaagaatgga gtgagttagt gggagagggt gggagggtta tagtcgggag    1560
```

```
cgaacgagtt aggtttgtta gttggggaag gtcgggacgt tgggtttagt ttagttggga    1620
tatcgcgttc gaggttaagg cgggtggatt aggtatgttg agagtgtcgg cgtataggtg    1680
ggtacggtta cgtattgatt tagtgtttac gaagggtttg tattggataa ggtttagacg    1740
tttatagagt ttagaatttt ttttgttgta tttatattta ataagtttat tttgggttac    1800
ggatatttta tttttaaaa tgacgaggtt aaggttttg gcgaggatgg tattaaattg    1860
tacgggatag aagtgggggt ggggagaga gttttttta agtttatatt tgttttgta    1920 aagtaaagag tatgtgaaat tatagggtat attttattc gaaagtgtg ttttatttt    1980 gaattttgat tttttgattt tttgatttga gtaaagatgt gtattttggt agtgagtaga    2040
atattttggt tttgttttgt tttgagtgg aaggattata aatataattc gtttggagga    2100
ttaggtgtga aggttttgt taggtatatg ggataatgtt ttttaatttt taagggtatt    2160
ttgttaatgt atgttttgg aaagtgtcgg aatatagtta ttgttttgg attcggattt    2220 ttttattaat attaattttt gtttgagagt aaaatttagg ttcgttatta aaagatatt    2280 ttttggttt ttaattgaga ataagtttt ttttaaagt tgtattgttt tttaaatt    2340 aatatattaa tattcgtaat tttagaaata tatagtgatt cgggagaatg tgtataaaat    2400
agatacgttt aaaaagttt ggcgtttaaa attaatttta gttatattat aggtgttggg    2460 ttttttat ttttgggggt tgtttggaat atgttatgtg ttttttgaa ttattcgtg    2520 ttttgaattt atttgagtta gtagtaaaaa taggtaaata aatttgttta atttgtttg    2580 agtgttaaat ttttttattt tgaaatagtt aatagtcgat agatggattt atttatgga    2640 aagggttagt ttttttagtt acgaagaaaa ttgattagag atttatattt taagttatt    2700 ttaatttta cgtaatatc gtgaaaattt aaattttttt tttttattta gtggaaattt    2760
aaagtagtgt tatttaaggg gagagaaatg aggggggaaaa tgtttacgtg ttgtttaatt    2820 gtatttttt tttgattttg agaatttta tttttggttt ttgaaatttc gtcgaggtaa    2880
gaaaattaaa tttttttaat aagttttata attgaatttt agttataggga tatcggaaag    2940 tgtagttcga gaaagatatt tttatttttg tttatcgacg atttttgtag tttttttatt    3000
tttttgagta atgggttaat aatttttttt ttttttttt ttattttgta gagattaaga    3060
ggcgttcgta gtagaacggt tttgttttta gttggtggcg aggataggta attttatgga    3120
aaagttggaa gagaatgaga aaattaaaga tagaaagatt tagagattcg cggagagata    3180
tagggagagg gaaagggagtt gcgttgaaaa gacgtaaaga tacgcgcgtg taatttttt    3240 ttttttagg ttttagaggt ttgtaaatta gggttgagag gaaggggttc ggggaagttta    3300 cgttttttc gttttttttt tgtttggagt ttcgttcgtt agaggttggt taatttagt    3360 ttcggtcgtc gtagatattg cgttgagttt ttgggttttc gttttgttta gcgttagtgt    3420
agttgaagtg agtagttggt gggaaatgta aatggttttt ggagaaatag aagatataga    3480 atgatttta tttttttttc gagtgtgtgg aaggagttgg atatacgttt tacgttttta    3540 atttttttt tatattttta gttatatttt tattaaataa ttaattaatg tttagaatta    3600
ttagggaata tattaggtat gtaatcgtag aagtagggtg ttgggggggtt ataaattatc    3660 gagttgattt aagacgtgga ttttaggttt tttttttgtt aaagtagtaa aggaagagcg    3720
ggttttggcg attgtattta gatttcgatt attttaaatt agaagggggt ggagggagcg    3780
tttaagtaaa gtaagtaatt ttttgttttg tagatgtaaa taagattgta gtattaaagg    3840
tattagtttt tttagggtta gatcgtttgg attgggagtt tggggaaggg gagatattaa    3900
```

```
ttttacgtat ttgtgaattt taaggatgtt atattttat ataataatt ttagtgcgga    3960 ttttttggaa tgggggagt aatattttta tttagaata ttaaatatt ttttttttaa    4020 agcgtatatt ttttttattt ttttaaaatt ttgaattatg tttaaagata atagttttt    4080 agtaaattgg agtattggat tatttttttt attttttttt atcgatattt tgatgatttg    4140
attttaatgt gtgggggta tagggaatta aatatagttt ataaaattaa gtttagatga    4200
aatagtgttg gttaagtggg tttagataat ttttaatgag aattttaatt atattttttt    4260
ttttaatatg ttgagataag tgatagaatc gttagaatgg taattaaatt ggaaagttta    4320
gggagaataa taatttcgtg attaaattgg ggtaaaatcg tggataaatg tggggtgatt    4380
ttcgttaatt ttttgttatt taagagttag gatttgggaa aggtatagta ttattttaga    4440 gttcgtgtg acgggttgtg tgttattatt tattttttt attttggatt atgattttaa    4500
ttttggtaag taattttttt agttttttat ttgataataa gcgagtatgt aaatattaat    4560
ggttagcgat gtttaattgt tttaaatatt attgatttgt tggttgtttt aaattgtttt    4620
tttagtttag gttttgtttt cgaattgttt atttagagg tttgatttat gttttcgatg    4680
ttataatata ataattgttt ttttaaaaaa ggtatttaag atgaattaat tgatttgtat    4740
ataaattaaa attattatgc gttgtcgatt tcggtgtttt ataattattt cgaaattagt    4800
atttaattat ttgagttaaa agaatatata atgttgta ttgatttatt aatgaattat    4860
ttaattaaaa cgttcgggta atgttgggcg ttggaaagat tgttaaatta agatatatta    4920
taggagggat atgaagatta gaaaggtaat agattaatat ttcgtattta aaacggagtt    4980
ttcggtgatt tttagtttta attttggagt aggggttttt tttttttgtt gttaaaaaga    5040
ttttgtgttt gtttgtgagt gagtgtattt aagtggaagg aacgttttta cggttacggt    5100
ggtttaggtt ttttgttcgg atcgggattt tatagttttta atttaggagc gttaaatttt    5160
ggaagatttc gggttagttt tggaggtgcg tggtttcgta agtcgttagg ttaagtttgt    5220 ttttttgtt tgtttttcg gtaggttggg cgcgttatgg tagtgagttt ttcgcgtaaa    5280
cggagagttg gaattaaagt tgatatttaa tagatatgtt aattgagtat ttattttcgt    5340
tttgagaata ggaataaaag gtagtttttt ttaagagagg cggtgtaaag gtacgttata    5400
ggagtttaga aaaggttggc ggcgggaaat ttgtagtttg ggggttagtt aatattttt    5460 tttattttaa gtatttattg atttgttgtt gttattttg gcgacgtaga aggatatttg    5520
aaagaatttt tgatggggtt ttgatttgag aaaggaggtg atttgtttag gttttatta    5580 aattttaat tattatatta attgttttt tttattttt attcgatttt tttttttttg    5640 tttatttta atttttaat tatttagaaa ttttttatt ttttagtggt ttttttttg    5700 tagtagtttt ttattcgaat ttttttttcg ttttttcgtg gtagggtttg tatattgatt    5760
tttttgattt ttggtatatt tgggttttt gaaattttt aattttttta gatttgagga    5820
tggtaggttt tattttttt attgtgtgta tatatttaga gatatgaaaa tttatataga    5880
ttgtttttaa atttagggta tttaatagat gttttttttt tagttcgttt tttgatttga    5940
aatgtttgtt tgatttttaat ttggatatta ttttttttg ttttttttt tttaaagtag    6000 tttggatatg tgtgtaagtg agtttagaat agttttattt atattttta ttaaattgta    6060 aataaaagaa gaattaatga agtagattgg tatatagatt gtattaagag ttcgaatttt    6120 tagttttttgg atttttatt taattttggt tgttatttat attgatagag ttattttaag    6180
tagaggttta gagaaatttg tattgtggga taataggtaa agttatagta aaaagtggaa    6240
taattttaaa gttatttat tagaatgtaa attgtatttt tgggttttgt tcgtaattat    6300
```

```
ttagttttaa tatatataga gttagatagg aaaaaatagg ttaatatagt tattggtatt    6360
agagaagata aattttatgg ttttttttagt gaaaagaaga ttttttaaagt ttataatttt   6420 tgattattta attttatttta taattgtggg aatgaataag atattaattg ttttatgtat   6480
tttatttata ttaattaatt tgtgttttta ttaaaagtag ttatatagaa ttttttttaa   6540
tttttggtag taagtttaga aaatgaagtt tatagttatt ttgaattgga tatattttt    6600 gagttgatta tttttgtaag tgtaggaata taatattgtt tttttatggt tttttgtat    6660 tttttaggg tttgtaagtt tttattaggt ttgatattat tgtttgggtt tatatttatt    6720
ataagtaaat ttgattatta tgttgatttt aaaatagttt atttggttag tataatttta   6780 gttttaaat tataaaaatt ttttaatata cgaagttttt agtttttatt ttttttagtt    6840
ttttgtttat ttaaaatttt tattttaatt ggtgtaagta ataataattt gtattattat    6900 ttgtatttt ttttatttttt tggagattgg gttggatttt agagagaata ttagtattat    6960
tattattata aataataaaa tttaaaagta aagttttat ttgtatgata attggtattt     7020
ggaatgtttt tgatttattt aatgttattt tataaaggta ttttgtaaat tttttttggaa  7080 tttttagtaa gagtttgtag taattggaat aattttttgg gaagatattt ttttttgatgg   7140 gtttttagtt tttggaggaa tagattgaga gtaattaggg agggagggga tattggaaat   7200
tggtagttac gttagttgaa ataagtttgg gttagtaag gtgattgatg ttgtggttga    7260 tttttttattt cgagttttttt tttaatttggg gtattgattt ttttttatttt gggatttttaa 7320 ggtattcggt gtgtatgtag attttttttttt tgtggtttttt attatgtggt ttcgtagtag   7380
gtttttggtt taatgatatt ttatagttat agtttttata tttattatta tgattttaat    7440
gtttaggttt ttagtgtatt tatattaaat ttgttttatt agtaagttgg agtatataggg    7500 agagatgggg gtaagtaagg atttagtaga gtttaaattt agatatgttt aaatggtttt   7560
gattgtgtaa agtgtggtaa tgtttttttgt tgtttttagtt ttttattttta agttttatat   7620 gttttttggt taatgaagtg tgatataggt tatatgttag gaataatagt atttgttgag   7680
aataaagtga atttaggaaa tttggtatat ataaaatgta tttagttatt tgaattagta    7740
ataatggtaa aaattaatat ttatagagtg tttagttaat ttagttattg tattaaatat    7800 tttgtattg ataattatat ttatttttta tgttaatatt ataaggtagg tattgttatt    7860
ttataaatga agatagtgag gtttgttatg attgtgttat tggtttaagg ttatttagtt    7920
ggttagagta taagtttata attgttggag gttatagtgg ataggatatt gttttaggtt    7980
acgtaggtag taagtggtat agtgggaatt tgaatttagg tttgtgtaat tttaaagttt    8040
aaaatgttaa ttagtatatt gaattaatgg taattggaat tagaagatta ggggtttttg    8100
ggggaaggaa atatagaatt tatttatgga atatttata aataaaagaa taatgtagag    8160
ataggaaagt aaatatattt tttgagggat ggagaaagtt agaaatgttt taaatgttaa    8220
agaggaggaa acgagaaatg attggatgag aaagtagaaa agttaaattt cggtatttgt    8280
tttgggtagt ttaggaagag aaaggtaagt ttagggatat ttttgagtta taggaaaatt    8340
aatgtttaga tggttagttt ggattaagtt taatataggga ttttaggaat atggtttatt    8400
agaattgttt tttagtaatt ttaagggaga ataaaatttt tgaattgggt ttaagtagtt    8460
ttattttaga agtaaagaga gatggaagta aggatcgagt aataagaata tttatattgt    8520
aagaatatgt aagttgagta ggagtgaaat ttagaaaaat ttgttaggat tttggttgtt    8580
gtgttaaatt atgttatatt ttaagtagaa attagatttt tattattatt atttgtttag    8640
```

```
gtttagttag taatttttatt attgtagtaa agttatttga aattttaaga gaaatgattt    8700
tttgtgttga agaagatatt tgggtggaa ggatgttagt agataaatgg agtgtaaaga     8760
tagtgatttt aaggatatag tttgtgggga gtaatattgg attatatatt cgttgtttgt    8820
ggtagaatgt tagttagggg agaatattag gtagtttttt ataagtttat tttattataa    8880
aaagatagga ttgattttaa aggttatttt taatttaggt ttgttttatt attgaaaatg    8940
atttaaaatt ggatttattt tggttttttt taggagggat agataaatat aatttgtata    9000
tatggttttt tagttttagg aagtatagga ggagaatgaa agaattaatt tagttttttg    9060
tttttttggta aaaatttta tatttgtgtt gttgtaagaa tttaagatta tttcgtttag    9120
aatgttgtgg tatttttgaa agtaaggttt gagggtatat agagttttat tttttatttt    9180
tacgttgtgg attttattgt ttttttaaa tgggaaagag aaattagaat ttatagaaag    9240
taaggtttgg aaaggattta gagggtattt ttttttttta gtttatgttt aaattattt     9300
tagaaatata gttagttata tttttttagta aagagttttt tacggttttt tggtaatgta    9360
ttttatgtt ttataatttt atagttatat tgtatattta ttgattaaat tttaagtatt    9420
gaagaaaatg atgttatatt aaaaagtttt aattagtagg gggtatgttt tttagagttt   9480
tttaaatatt ttatatttt attttaaaaa aagatgaaaa tattattagt ttaatttaat    9540
agatggaaaa ttttgttata gagatttta gagagttata tttggttatg tagcgtgatg    9600
tttgaaagaa ttaaattaaa aataaagtta ggaaatttta tgtttagggt tttttagta    9660
gatatattat tttttgggg ttggttatta ttttttttgtt tgagtaaagt atatgtttga   9720
ttgtaatttt atttgttttt ttgttgtttt gtttgtgagt agtttatttt ttaatttatt    9780
aatttatttt tttgttagtt ttttaaaata ttataagtta attaatgttg ataaaatttt    9840
attttttatta tgagtgttat ttgagtagat tgagatggtt gttatatttt ttaaatatta   9900
cgtgtaataa atagtgttgt tattgttta gcgttatgat tttgttttta tttggaaatt     9960
gtataaatat tatatttttt gttatgatag gattattttt atttattagg attttttgata  10020
tttgtgttgt tatttgggag aatgttgatt attttgttta tgttattttt gaggttataa   10080
taatcgtttt tttgttagt tgtgtttttt tttttatagg tgaatttagt tttttttttt    10140
atgtttgatt ttaagaaatt ggtgtttat tgaaagatgt ttaaattttt tgagagaaaa    10200
tgttggagta agaataattt gttatgtatt gtttttattt gagtattaat gtttttttaa    10260
ttttatatgt ttttaaattt tttgagaatt tttttttttt gaatgtaatt tatgaattaa    10320
aagtgatcgt aattttttaaa atattatgtt gtttatagta aatatatata atttttattt   10380
gttaattaaa aaaagtaata gggttttat ttttattttt gatatttgtt tttttattt     10440
tttttttaag tatttttttt tttttttag agatgtattt attgagagta ttttgttatt    10500
ttttttttt cgtagttatg tatgattaaa gttgtgtttt tgaaattttt tattttttt     10560
gttataattg ataatttatt ttgtttttta ttaatttatt aatgttattt tattggtttt    10620
tgatttatat aaattaaata gattttagaa aattaataa aaataaaaat aatgttttt     10680
attttgaaat atttatttat tgttttttt tagggtatat atattatatt tttttttttt    10740
atatttatt tttttgaat ttataagaat gtgttattga atatagagaa aataatttaa     10800
gaaaggaaaa ggaatgattt gtttaaaatg aggaaaaagt agagtcgagg tttaggattg    10860
tggtttaata agatgattta gttatttttt ggtagtttta tttttggta attttttaag   10920
ttgagttttg gatgatgtaa ataatatttt tagattttta atgggtatat gttgaattaa    10980
aaagaaaaat ttatggtatt ttttaattat gtgtaaatga gtaaagaaaa aggaaagaaa   11040
```

```
aggagtggtt aaattgatat ggtagggttt aggattgggg gaagaagaaa gagtaataga    11100
gagagtggaa tagttaaaaa aagaatgaga ttatgttttt tgtagaaata tggatggagt    11160
tggaggttat tattttttagt aaattaaatt aggattagaa aattaaataa cgtatgtttt    11220
tatttataag tgggagttaa atgaggagaa tttatagata taaagagagg aataatagat    11280
attggggttt attggaaggt ggcggatggg agaggggaga ggattagaaa aaataattat    11340
tgggtacgag gtttagtatt tgggtgataa aataaatttgt ataataaatt tttgtgatag    11400
gtttatttat ataataaatt tgtatatgtg ttttgaattt gagatataat ttaaagaaaa    11460
agagagcgta tttgtttgta aattggtttt agtagattgt tttttgagtt ttttttgttt    11520
tttaaattga atttaagtgg tattatattt ttaaatgaaa attttatttt taattatagg    11580
tgaagttaat ttttttatttt tttaataatt tttttattat tttttgtatt gtaagtaagg    11640
taaagattta gtttaaatgt tgttagttta gtttattttt taaaaaatat attttttgag    11700
aggtttgaga aaattaagaa agtatatttt gtttagtttt tttaaatatt attttttttgg    11760 aaatagtatt ttgtttagtt tttttaaata ttattttttta attagtgagt tagtttagat    11820
tttagagggt ttttggaatt agaaagaagg taaggatgaa tattaggttt aagattattt    11880
ttatgttgtt ttattattaa attagaaaat ttggatgttt tgtaggtagg tatgtttatg    11940 agagttatttt aaaaaagata tgttttttga agtgttaagt ttagtgatta cgtagtttat    12000
g                                                                   12001

<210> SEQ ID NO 17
<211> LENGTH: 4001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 17
ttttcgtttt tagtttatat atattttttt tgtttgtttg gattttaatg gtttaagata      60
gttttgagtt tattgggaaa agaaaatgat tgttaaaaat tattttttgaa attggttatt     120 tggtaatatt tttaattgta tggaaattta ttaaggtata ttttatatat aattagttta     180
aggttgttga ttttataggt tttatggatt taaatttgat tgataataaa gtaaataaga     240
gagtcgaatt taaagcgtgg tttttttcggg ttaggacgag tttaatatag tgtataagga     300
atttgaaaga tttaggatat gtgttttaat taacgttaag tagaatggat aagttttttag     360 tattttgaaa acgttgggtt agggtttttt ttttattgtg tgtttttttgt ttggggatta     420 ataagtatta tagagaacgt gatttgaggc gatttttttat ttttgtataa atttagagtg     480
aattattaaa tagttgttcg tttaaagtta aggtaatttt tttttgacgg gtttatttgt     540
ttttcgattt taatttatt agttgtttt tttagggttt tgttttttttt gtaattaaag     600 ttttttttaga ttagcgtagt atttatttga taggttgttt ggaaaattta agatcggaga     660
ggtgatttgt tgttgttttt taaattttttt agttttaagt aacgtgttttt tttttttatat     720 ggggtggggg attggaaatg gatgtagtga gatataaaga gtgggtgttt tgttgatttt     780 tgtattttttt tttttttgat tatttatttt tttttttttta agttttcgat ttttagttttt     840 attttttttat ttttgggttc gtattaaaag tcggatcgtt ttgggttggg taggagttga     900
attttcggga gtttgtttgt gtagatttag tgcgtacggc gaggtagtag ttcggtttcg     960
tattgttgat aggtgtaggt aggatagttt ttttatcgcg gttcggggcg ttttgattgg    1020
```

```
tgcggagtta cgttagtcgt attcggagaa gggtttggga ggaggcggag gcggagaggg    1080
ttggggaggg tcgcggcgga gtgacgtttc ggtattagga agttcgtttt tggttttaag    1140
atgttaggtt aatagggaag cgcggagtcg tagatttggt tcgtcgttcg tttgggtgtt    1200
tggagttgag ttgcggtaag gttcggtttt tgttcgatcg ttcgagggg tgtgcgtgtgc    1260
gcgttgcgga gggtgcgttt agagggtcgc gtcgtggttg tagcggttgt tgtcgtcgta    1320
ggggatttaa tattatttat ttgttttttgt tattttttgat attttttttgt tagggttgtc    1380
gcgtgggggg gggcgggta gagcgcggtc ggcgttagtt ttttttattg gagggggtttt    1440
tgggggaggg agggagagaa gaaggggggtt tttgtttatt tttgtttcgt tttggagttt    1500
ggaagtttgt ttttaaaga cgttttgagt ggtgtttttt tgtttatatt ttatgttttc    1560
gtttgttcgt tgatttttcg ttttcggatt ttttcgtttg agttttttcgg aggagacggg    1620
ggtagtttgg tttgagaatt cggcggggggt tgcgtttttt ggttttttc gtagcgggga    1680
aatttcgcgt ttagagcgcg attcggagcg ggtagcggcg gttacggggg ttcggcgggg    1740
tagtagttaa ggattagtag agcgtcgcgt ttttttcgttt atgaattgta tgaaaggttc    1800
gttttatttg gagtatcgag tagcggggat taagttgtcg gtcgttttttt tatttttttttg    1860
ttattatttt tagtcgttag ttatggttttc ggttttggtt ttcggttagt ttcggtcgtt    1920
ggatttttt aagtataggt tggaggtgta tattatttttc gatattttta gttcggaggt    1980
cgtaggtaag gcgtcgcgtc gttttgtaga tattttcgtt tagttgtttt gcgttattcg    2040
tttttttttcg ttttaaggaa gttagttttt tcggggggag gcgtggtggg agtggtcgtt    2100
cgtttggttt ttcgtagaat tttcgggagt cggaattttg attatttcgt attttttttag    2160
ttttttttcg atcggttcgg ttttttgggc gttaagggcg cgagtaattt tgtcgttttt    2220
tttattcgta ttttggtttt tttttgtttt tttgggttat aaaaattttta gtattttgat    2280
tcgaggattt ttagaggtcg tcgatttttg ttttttgtttt tttttcggtt tttagttttttc    2340
gaggagtttt attcgttagg aaattgtttg aaattattta gaaatgtttt tcgcgaagag    2400
gtatttttttt tttttttttttg ggaaagggtc ggcgaatttc ggtgtttaat cgaattttta    2460
tatttttttt tagttttttttt aaatcgtatg gaaatttgag ttttttgcga ggggggaggggg    2520
ggtttgtaaa ttacgcgcgt gtgcgcgttt taggagattt ggtgtgtttg cgtagaggtg    2580
tataaatata tttgaaagta taggttataa aagtgaatgt gtcgttgtag tgagataaat    2640
atgtaaataa aacgtgcggc gttggggggag gggaggaaat ggggcgcgga tatttatatt    2700
tgcgtttgta tatttttatag gcgtagcgtt tttcgcggtt cggagtcgtc gcgcgtattt    2760
tttttcggcg ttaggtagtt tagttttttttt acggttttttg tcgtcggttt agttggcgtt    2820
cgcgttgtag gtgggtatgt tgacgggaaa gtgtgtgtgt ttcgttttta gagaaagata    2880
aaagttagta ggggaagaat gaggacgtgg gcgtcgagga ttcgtttaag aagaagcggt    2940
aaaggcggta gcggatttat tttattagtt agtagttttta ggagttggag ttattttttt    3000
agaggaatcg ttattcggat atgtttatac gcgaagaaat cgttgtgtgg attaattttta    3060
cggaagttcg agttcgggta ggagttagta cggagtttgg gagggatggg gggaggatgt    3120
tgtggaggta taggttaagt agattaggag agaatgtgga aggtagcgtc gtttgggagg    3180
gcgtcggtgg ggcgtagttt tgtaaaggta gaaggtttcg cggcggtttg gttgcgagat    3240
tatagttttt ttttcgaggt cgataggatt gtcgttttgg tttaggtttt tagagcggta    3300
tcggtttatt gtttcgttat ttcgcgattt tacgagttgg gttgtatggg taattttttg    3360
tataggatat tgtgttttttg gtttgtagtt gttagagtag agttaataaa attttttatta    3420
```

```
ggttaagagt cgcgaatagg ttttaatttg tgagttttta ataaggaaaa ttcgttagag   3480
atacggaaga gttggttttt tttgggaaat ttttgtttcg gttttggttt agttttttt    3540 tttttgggtt cgcgttttt atattttttt tacggttgtt tcggttattt aggttttttt    3600
tatatatttt atttttttagt tttgtgattt tcgggagtaa agttttaata tataattatt   3660
agttttttta gaaggagaaa gaaaaaaga agaaagattt ttttgtttgg tttatttatt    3720
tttttttagg agttgaattt tggaaattga aatttatatt tttttttta aattataatt    3780 atagttttgt aaaaagggtt tattttaatt ttgtagtaaa tttgtatttt atggattggt   3840
aaaaatgagt ttaaataaat aatttaatag taacgttttg gttatgttg gtcggtggaa    3900 gattttaaat ttgttaggat tttggaagta gaaaatagaa ttaagtaaat taagcggtat   3960
ttagaggttt tgttgttaaa aaaaaaaaat taagtgtttt g                       4001

<210> SEQ ID NO 18
<211> LENGTH: 4001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 18 tagagtatt aatttttttt ttttaatagt aaagttttg gatgtcgttt gatttgtttg     60
attttgtttt ttgttttag aattttaata aatttggaat tttttatcga ttagtataaa    120
ttaggacgtt gttattgggt tatttatttg agtttatttt tgttaattta taaagtatag   180
atttgttata aagttaaggt aagttttttt tataaaatta tgattataat ttagaagagg   240
gggtgtgagt tttaattttt agagtttaat ttttgagaga agataaataa attaagtaga   300 aaagttttttt tttttttttt tttttttttt ttaagaggat tagtagttgt gtattaaaat   360
tttgttttcg gagattataa aattaggaaa tagggtgtgt gggagagatt tgaatggtcg   420
aaataatcgt aaagaaggtg taagaagcgc gagtttaggg gggaaaagt tgggttaggg    480 tcgggataaa ggttttttag ggagggttaa ttttttcgtg tttttggcgg ttttttttg    540 ttaaaggttt ataggttgga gtttgttcgc ggttttggt ttggtaggga ttttattagt    600
tttgttttgg taattgtaag ttaggaatat aatgttttgt gtaggggatt gtttatgtag   660
tttagttcgt gagatcgcgg gatggcgggg tagtgagtcg gtgtcgtttt gggagtttga   720
gttagggcgg tagttttgtc ggtttcggag agggaattgt aatttcgtaa ttaggtcgtc   780
gcgaggtttt ttgttttttgt aaagttgcgt tttatcgcg ttttttttagg cggcgttgtt   840 ttttatattt tttttggtt tatttggttt gtatttttat aatatttttt ttttattttt    900
tttagatttc gtgttggttt ttattcggat tcggttttc gtaaggttgg tttatatagc    960 gatttttcg cgtgtggata tgttcgggta gcggttttt tggaaagtgg tttttagttt     1020
ttggagttgt tggttggtaa agtgagttcg ttgtcgtttt tgtcgttttt tttagacgg    1080 gttttcggcg tttacgtttt tattttttt ttgttggttt ttattttttt ttgaaaacga   1140
aatatatata ttttttcgtt agtatgttta tttgtaacgc ggacgttaat tggatcggcg   1200
gtagaagtcg tggaagagtt gggttgtttg gcgtcggagg agggtgcgcg cggcggtttc   1260
gggtcgcgag gagcgttgcg tttgtggggt gtgtaggcgt aagtgtgggt gttcgcgttt   1320 tattttttttt tttttttag cgtcgtacgt tttatttata tgtttatttt attgtagcgg   1380
tatatttatt tttatagttt gtgttttttaa gtatatttat atattttgc gtagatatat   1440
```

-continued

```
taaatttttt gggacgcgta tacgcgcgtg gtttatagat ttttttttt ttcgtagaaa     1500 gtttagattt ttatgcggtt tgggaaggtt aggaaaagat gtggggattc ggttgggtat     1560
cgaagttcgt cggttttttt ttaaaaaaaa aaaaaaatg tttttcgcg aagggtattt      1620 ttgagtggtt ttaggtaatt ttttaacgag tggagttttt cgggagttga aagtcgagag     1680
gaaaataggg atagaggtcg gcggtttttg aaggttttcg aattaagatg ttgggatttt     1740
tgtgatttag gaaatagaag ggaggttagg gtacgaatag agagggcggt agaattgttc     1800 gcgttttttag cgttttagga gtcgggtcgg tcgagggaga attaaaggga tgcggggtag     1860
ttaaaatttc ggttttcgga agttttgcgg ggagttaggc gaacgattat ttttattacg     1920
ttttttttcg gaggggttga ttttttgggg gcgagaggga gcgggtggcg tagagtagtt     1980
gagcgggaat gtttgtaggg cggcgcggcg tttatttgc ggttttcggg ttggaggtgt     2040
cggagatggt gtgtatttt agtttgtgtt tggaggagtt tagcgatcgg ggttgatcgg     2100
gagttagaat cgaagttatg gttaacggtt ggggatggtg ataggaagat gaggagacgg     2160
tcgatagttt ggttttcgtt gttcggtgtt ttaagtgaag cgggttttttt atgtagttta     2220 tggacgaggg agcgcgacgt tttattagtt tttggttatt gtttcgtcga gttttcgtag     2280
tcgtcgttgt tcgtttcggg tcgcgttta ggcgcggagt ttttcgttg cggggagagt      2340 taggggacgt aattttcgtc gagttttaa gttaagttgt tttcgttttt ttcggaaggt     2400
ttaagcgaaa aagttcggag acggaaagtt agcgggtaaa cgaagatatg ggatgtgggt     2460
agaagggtat tatttagagc gttttaaggg agtaggtttt taagttttaa agcgaaataa     2520
gagtgggtaa agatttttt ttttttttt ttttttttt aagaatttt ttaataagga        2580 aagttaacgt cgatcgcgtt ttgttcgttt ttttttacg cggtagtttt gatagagaag     2640
tgttaagagt gatagggata ggtaggtgat attgatttt ttgcggcggt agtagtcgtt     2700
gtagttacga cgcggttttt tgagcgtatt tttcgtaacg cgtatacgta tatttttcgg     2760
gcggtcgaat aggagtcggg ttttgtcgta gtttagtttt aggtatttag gcagcgacg     2820 gattagattt gcggtttcgc gttttttttgt tggtttaata ttttaaaatt agaggcgggt    2880
tttttggtgt cgagacgtta tttcgtcgcg gttttttta gtttttttcg ttttcgtttt     2940
tttttagatt tttttttcggg tgcgattgac gtggtttcgt attaattagg acgtttcgag    3000
tcgcggtgga gggattgttt tgtttgtatt tattagtagt gcggggtcgg gttattgttt    3060
cgtcgtgcgt attgggttta taggtaag ttttcgggaa tttagttttt gtttagttta      3120
aggcgattcg gttttagta cgaatttaaa ggtgaagaga tgaggttagg agtcgaaggt     3180
ttgggagaag agagtggaat ggttaagaag agaaaggtat aaggattaat aagatattta     3240 tttttttgtgt tttattatat ttatttttaa tttttattt tatataaaaa ggagatacgt    3300
tatttaaaat tagaaaattt gaaaaatagt aataaattat ttttcgatt ttaaattttt     3360 taaatagttt gttaagtgaa tgttgcgtta atttgaagaa gttttaattg taaagaagat     3420
agagttttga aaaggtaggt taataaatta gaaatcgaga agtaaatgga ttcgttaaaa     3480
gaaaattatt ttgatttaa acgaataatt gtttggtggt ttattttgga tttatataag     3540
aataaaaagt cgtttagat tacgttttt gtgatgttta ttagttttta gatagaaaat      3600
atataataga agagaaattt taatttagcg ttttaaaaat gttgaaagtt tatttatttt     3660
atttaacgtt gattaagata tatattttag atttttttaaa tttttgtat attgtattaa    3720 gttcgtttta attcgagaga gttacgtttt aaattcgatt ttttgttta ttttattatt     3780 aattagattt aaatttataa agtttgtaga attaataatt ttgagttaat tatatatgaa     3840
```

```
atatgtttta atgaattttt atataattaa gaatgttgtt aaataattaa ttttaaggat    3900 aattttaat agttatttt tttttttagt gagtttaagg ttgttttgag ttattaaagt     3960
ttaagtaggt agaaggggtg tgtgtgagtt aagggcgaaa a                       4001
```

<210> SEQ ID NO 19
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 19

```
aggaagggtg gatgtagtta tttatatatg gtttgttttt ttggaggata attttatttg     60
ataaataatt gttttatttt gaatagaata aataaggttt tatgatgaag taaaatatta   120
aatatatatg tattaaaaaa tgtataatta tttttttgga atgggttata tagagatgtg   180
tttttttaaa tgttaagagt gtaaaaggat aaatagtgaa aaataaattt ttttttttatt  240 ttgtttttta gttttttaat ttttttattt agaggtgaga atagaatttt tatattttt    300 agaatttttta tagttagaat tgtttatatg ttttttattgt tttattttt attttgtttt 360 gtataaataa atgaattgtt tattatggaa attttttaaa agattcgtta atattttaat   420
aggaagtatt aatagtttat gttttaggat tttgttttta taattttgta atattatatt   480 acgatatttta atttaatttt tattaagttt tgttaaaaac ggattttaaa ttaagttgta  540 aattttagt aatttggttt tgttttttt ttttgatag tattattaaa taaatttttt     600
tattgtcgaa agtaataagt tcggttttgt tttatttatt ggttgtgttg gtgatatttg   660
gggattgtta ttgaatagac gtatagaggg agttttttata ggtaggggtt ttttgtttg  720 tgtttttggg agagtatgtt tcgtatattt gtcgcgttga tgaagatttt atagttttat  780
tagttgcggg taaggggtt tgaggtagtt ttaggtaagt tggggtttag cggggagaag   840
ttgtagaaga attgattaga ggattttagg aggttttaga gttgggcgag gtagagagtt   900
ttttgtgcgt tttttttttt ttttgtaatt cggggattt ttgtattggg gtaggttttc    960
ggttaggtgt atgggaggaa gtacggagaa tttataagtt tttcgattt ttagttaga  1020 cgttgttggg ttttttcgt tggagatcgc gtttttttta aatttttgtg agcgttgcgg   1080
aagtacgcgg ggtcgggtc gttgagcgt gtaagatagg ggaggagtc gggcgggaga   1140 gggaggggcg gcgtcggggc gggttttgat atagagtagg cgtcgcgggt cgtagtatag  1200
tgcggagatc gtagtttcgg agttcggtt agggtttatt tgttttcgta gcgtcggttc   1260
gcgttttttt gtcgtagtta tcggtgagtg tcgcggtttt gagattttcg ggtcggatgc  1320
gcggcggttt tagttttcga gcgttgttt ttttcgtttt ggggttgttcg ggttttttgg  1380 gtttttcggc ggttgtacgg agttaaggcg tttcgtttcg ggcgttttc gcgggtgtcg   1440 atttaggttg ttcggagttc ggagtttaga gaggagagag atagtggggg agtttggtta  1500
tcgcgggtat ttttttgcg ttgtagtcgt tcgtttggtt tgtttttcg ttttcgtt      1560 ttttgtttg atttttttt ttttgtaga gtcgtcgttt agcgtttcga tttcgttatt    1620
atgagagttt tgttggcgcg tttgttttt tgcgttttgg tcgtgagcga ttttaaagtg  1680
agtgcgtttt tgttttgatt gatgttgttt aaggattttt gattagtatt aggggagagg  1740
aggggttgtt tagggagttg gggttttttcg gattttattt atagtagggt tagattttt   1800 ttaggaaatg ggataggtg gtagcggagg tttgagaatt acggggttg gtattggttg  1860
```

```
gtaagggagg aagaggtcgt cgggattgtt ttagtttgcg ggtatttggt agatgaagtt    1920
tgtttgggtt aatttatttt ttttggttgg aaatttatgg ttttttattt gagaattaga    1980
tacgaatagg gtgaggcgag agggagaggg aagagtgggt tttgggattg ggttagtttt    2040 attttttattt tggagttttt ggagtatggg attttttgatg aagttttttt tcgaattttt    2100
tttagggtag taatgaattt tattaagttt tatgtgagta tttattttta taatagttgg    2160
ttgtatagat aagttgggaa ggttttaggg gatatttttt ttttgttttt tgttgtaggg    2220
ttgcgttatt ttttattatt tttattttttt ttcgtttatt ttattttttgt tttttttagc    2280 gaattgtgat tgtttaaatg gaggaatatg tgtgttaat aagtattttt ttaatatttta    2340 ttggtgtaat tgtttaaaga aattcggagg gtagtattgt gaaataggta tggggatttt    2400
tattgtaatt gggagagaaa tttggggata gggagggatg ggtgggaggt aagagtaggt    2460
aggagttagg agttggaggt agggtgggtg atattttttat t                      2501

<210> SEQ ID NO 20
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 20
gatgaagatg ttatttattt tattttttagt ttttaatttt tgtttgttttt tgttttttat      60 ttatttttttt ttgtttttaa attttttttt tagttgtagt ggagattttt ataattttattt   120 tatagtgttg ttttttcgaat tttttgggt agttgtatta gtgaatgttg gagaagtatt    180
tgttggatat atatgttttt ttatttagat agttatagtt cgttggagag aataaaggtg    240
gggtaagcga gggggagtgg aagtggtaag gggtggcgta gttttgtagt agagggtagg    300
gaggggatgt ttttttgaagt tttttttaatt tgtttgtgta gttaattgtt gtaggggtgg    360 ataatttttatat ggaatttgat gaagtttatt gttgttttgg aagagattcg ggaggaggtt    420
ttattaaagg ttttatgttt tagggatttt agggtgaggg taaattggtt ttaatttttaa   480 aatttatttttt ttttttttttt tttcgttttta ttttgttcgt atttagttttt taaatggaag    540 attatgggtt tttagttagg agaaatggat tgatttaagt aagttttatt tattagatgt       600
tcgtaggttg gggtagtttc ggcggttttt tttttttttg ttagttagtg ttaatttttcg     660 tggttttttaa gttttcgttg ttattttttgtt ttattttttg gggagagttt ggttttgttg    720
tggatggaat tcggaggatt ttagttttttt gagtagttttt tttttttttt tggtgttgat    780
tagaggtttt tgggtagtat tagttaaagt aagagcgtat ttattttgga gtcgtttacg     840
attaggacgt agagaagtag gcgcgttagt agggttttta tggtggcgag gtcggggcgt    900
tagacggcgg ttttgtaaag gaaggagaag ttagggtaag aggcggagga acgggaaggt    960
aggttaggcg ggcgattgta gcgtagggga gatgttcgcg gtgattaggt ttttttagttg   1020 ttttttttttt tttttgggttt cggatttcgg gtagtttgga tcggtattcg cggggggacgt   1080 tcgggacggg gcgttttgat ttcgtgtagt cgtcggggag tttagggagt tcgggtagtt    1140
tagggcgggg gaggtagacg ttcgggagtt ggggtcgtcg cgtattcggt tcgggggattt   1200 taggatcgcg gtatttatcg gtggttgcgg taggagggcg cgagtcggcg ttgcggggat    1260 aggtggatttt tggttcgggt ttcggggttg cggttttcgt attgtgttgc gattcgcggc    1320 gtttgttttta tattagggtt cgtttcgcg tcgtttttttt tttttttcgtt cggttttttt    1380 ttttgttttg tagcgtttag cgattcggat ttcgcgtgtt ttcgtaacgt ttataaagat    1440
```

```
ttggggaag cgcgattttt agcggagggg atttaatagc gtttggattg aggaatcgag    1500
aggtttgtaa attttcgtg tttttttta tgtatttggt cggggttttg ttttagtgta    1560
aggagttttc gaattgtaga gaggagagaa ggcgtatagg agatttttta tttcgtttag   1620
ttttgaagtt ttttgggtt tttaattag tttttttgta atttttttc gttgggtttt     1680 aatttgttta agattgtttt agatttttt gttcgtagtt gatggagttg tgaagttttt   1740
attaacgcga taaatgtacg agatatattt ttttagaagt atagatagaa aaatttttgt   1800
ttgtaggggt tttttttgtg cgtttgttta gtggtagttt ttagatatta ttaatataat   1860
tagtggatgg aataaagtcg ggtttattgt tttcggtagt aaggggttt gtttgatggt   1920 gttattagag ggggaaaggt aaggttagat tattgaaaat ttgtagtttg gtttaaagtt   1980 cgttttgat agggtttgat aaggattggg ttaggtgtcg tgatatgatg ttataggatt    2040
gtgggaataa agtttaggg tataaattgt tggtgttttt tattgaagtg ttaacgggtt   2100
ttttgggaag tttttataat gagtaattta tttatttgtg taggtaagaa taaaagtaaa   2160
gataatggaa atatgtagat agtttaatt gtggaggttt tggagggtgt ggaagttttg   2220
tttttatttt tgagtagagg aattgggaga ttggaggata aaataagagg aagatttatt   2280 tttattgtt tgttttttta tattttaat attttaaaaa gtatatttt gtatagttta     2340 ttttaaaaag ataattatgt attttttaat gtatgtgtat ttagtgtttt atttattat   2400 agagttttgt ttattttatt tagatagaaa taattgttta ttaaataaaa ttgtttttta   2460
gaaaaataga ttatgtgtaa atgattgtat ttatttttt t                        2501
```

<210> SEQ ID NO 21
<211> LENGTH: 901
<212> TYPE: DNA
<213> ORGANISM: Artificial Sequence
<220> FEATURE:
<223> OTHER INFORMATION: chemically treated genomic DNA (Homo sapiens)

<400> SEQUENCE: 21

```
taaatggtgt ttagtaaata tttatgtatt gagtaaaatt taataattat ttgttgaaat    60
taaaaagtga ataaataagt tatttagaaa gatgtaaagt ttataaattt ggggtatttt   120
gtattttttt tgagcgtaat gtttgtatat taggatgtga ggattacgtt ttttttttat   180
gttttgaggg ttttatattc gttttattgg atagttgttg atgttattgg agaaggaagt   240
tggatgggtg tgtgtatgat aatattaagg aatttagttt ataatttatt ttgttttta   300 tttgtgtatt tttagagacg tgtatagtgg ttttcgtga aagatagaat tgtggttttt   360
ttggtgttac gtttttttag tgtgtaaata agggttgttg tttcgacgat atcgttcgtg   420
gggttttttg tgtttttat tttaatatta tcgacgtttt tttagaaggt atggtttttt    480
tatacgatgg gttttgaaga tttagaatta gttagaaaag ttatttaaga ttatagaggt   540
tttgattagt attattagtt atgttttat atagagttac ggtcgttagt ggtggtgtaa   600
tggggtagtt tgagttaggt tgtatttagg tttaggaata gaaaggtagg gttaagggat   660
ttgggaagaa atttgatttt ttttcggttt tttttatat ttttaattaa agtttgggga   720
agagttattg ttggtaacgt ttttagttt gtttaggata gaggggaag gtatgacgaa    780 atttgaagat attttatgta tttttttttt tttttttttt ttgaaatgga gtttcgtttc   840 gttgttttg agtggagtg taatggtgcg attttggttt attgtaattt ttgtttttg    900 a                                                                   901
```

<210> SEQ ID NO 22
<211> LENGTH: 901
<212> TYPE: DNA
<213> ORGANISM: Artificial Sequence
<220> FEATURE:
<223> OTHER INFORMATION: chemically treated genomic DNA (Homo sapiens)

<400> SEQUENCE: 22

```
ttaggaggta gagattgtag tgagttaaga tcgtattatt gtattttagt ttaggggtaa      60
cggagcgaga ttttatttta aaaaaaaaaa aaaaaaaga atatatgaaa tgttttttaga    120 tttcgttatg tttttttttt ttattttagg taagttagaa agcgttatta atagtggttt    180
tttttaggtt tttggttaga gatgtgaaga gaagtcgggg ggaaattagg tttttttttta   240 agttttttag ttttgttttt ttattttttgg atttgaatgt agtttgattt aggttatttt    300
attgtattat tattggcggt cgtgattttg tgtaaaggta tagttggtga tgttgattag    360 agttttttgta gttttaaatg atttttttaa ttaattttaa attttttagaa tttatcgtat    420 aaaaaggtta tattttttgg agggacgtcg atggtattag atagaagta ttaggggatt     480 ttacgaacgg tgtcgtcgaa atagtagttt ttatttgtat attgggaggg cgtgatatta    540
ggaaaattat aattttgttt tttacgggg gttattgtat acgttttttga aagtgtatag     600 gtaagaagta aagtaagttg tgggttgaat ttttttgatgt tattatgtat atatttattt    660 agttttttt tttaatgata ttagtaattg tttagtgagg cggatataaa attttttagga     720 tatgagaggg agacgtggtt ttatatttt gatgtgtaaa tattacgttt agggaaaatg      780
taaggtgttt taggtttgtg gattttgtat tttttaggt aatttatttta tttatttttt     840 aattttaata aatgattatt aaattttatt taatatataa atatttattg agtattattt     900
g                                                                      901
```

<210> SEQ ID NO 23
<211> LENGTH: 1301
<212> TYPE: DNA
<213> ORGANISM: Artificial Sequence
<220> FEATURE:
<223> OTHER INFORMATION: chemically treated genomic DNA (Homo sapiens)

<400> SEQUENCE: 23

```
gttagtttta aattttttgat tttaagtgat tcgtttgttt tggttttta aagtgttggg      60 attataggcg tgagttattg cgttaggttt ataattttat tattaaaata attttattgt    120
aaaagaatta gttaggtttt agacggaatg ggttttatga gtttttttt ttttttttgt    180 aaggttacgg tggttatttc gtgagttatt gttgttacgg ttaagttttt tttcggttat   240
tttttattat gaattatttt tgtagtgagt atagtattta ttttggcggg agggtttttt    300
agatatgagt aggatttgga ttaaggttag gttggaggag attttatgg gaaagaggga   360 ttttttgaat tttagatttt ttagttaaga tgatttattt atatgtcgtt tttgttattt   420 agtaaattt tttatgtagt ttgattatgt ttaggaaata ttttttgataa aaattagtgg   480 agattattgt tttagaggat tttcgggttt tttaggtaa atgttattta acgttttta    540 agtaaataga gttttgtttta taaaattcgg ggttcgggcg gttttttatt tttgattcgg   600
ggtcgttttt ggagtagaga ggaggtaatg gttattatgg agaataaggt gatttgcgtt    660
ttggttttgg tgtttatgtt ggttttcggt attttggtcg aggtttagat aggtaaggcg    720
tgtttttttt tgttttgtgg ggttatagtt agtttggta gttttcgtta ggagttattg    780 tttttatatat atattttga gtatttgttt tgtgttaggt gttgttttag gttttttaaaa   840
```

```
gtatatttaa tttataggat cggtaaaagt aggtggagag taatttaggg tggtagggtt        900
ttcggagatt ttcgagaagt gcgacgagga gggggttgtt tttagtcggg gttgtttttt        960
tgtgttagga agattatata attttttttaa gtgttatgtt ttaaagagga agtgttggcg      1020
tggggtttta gaatagtgtt tttgattgtt tatgttaata ttttttttag gggtagattt      1080
ttttaaggtt tatttagata ggtttaaatg tcggttttag tgatggttat ttgggagatt      1140 ttttttttata ggttcgaatg ttcgttttag tggtggttaa ttgggagatt ttttttttata    1200 ggttttggg  tttttttggg atttatgttt tgggagttaa agttattttt tttatgagtg      1260
cgtggttggt aatttatatt ttttggtgtt gttaagtgga t                          1301
```

<210> SEQ ID NO 24
<211> LENGTH: 1301
<212> TYPE: DNA
<213> ORGANISM: Artificial Sequence
<220> FEATURE:
<223> OTHER INFORMATION: chemically treated genomic DNA (Homo sapiens)

<400> SEQUENCE: 24

```
atttatttga taatattagg gaatatgggt tgttagttac gtatttatga gagaggtggt         60
tttgattttt agagtatgga ttttaggga gtttaggaat tgtaggaga gggttttta          120 gttggttatt attgggacgg gtattcgggt tgtgggaga gggtttttta ggtggttatt        180
attgggatcg gtatttgggt ttatttggat gggttttggg agggtttgtt tttggggag        240 atgttggtat gaatagttaa aagtattatt ttgagatttt acgttaatat ttttttttg        300 aaatatgata tttgggagga ttgtatagtt tttttaatat aggaaaatag tttcgattga       360
aggtagtttt tttttcgtcg tattttcga aggttttcgg gggttttgtt attttgagtt       420 atttttttatt tgttttttgtc gatttttgtaa attggatata tttttaaggg tttagaatag    480
tatttggtat aaaataggtg tttaaaaata tgtatgtaaa atagtggttt ttggcggagg       540
ttgttagagt tggttgtggt tttatagagt aggaagaagt acgttttatt tgtttgggtt      600
tcggttaggg tgtcgagggt tagtatggat attaggatta gggcgtagat tatttttgttt     660 tttatggtgg ttattgtttt tttttttgttt taaaggcgat ttcgagttag ggatgagagg     720
tcgttcgagt ttcggatttt ataggtagg ttttgtttgt ttaaagagcg ttagataata        780
tttgtttaag gaggttcggg gattttttga gataataatt tttattgatt tttattaaag      840 gtgttttttta gatatggtta agttatatgg aaggatttgt tgatagatag agacgatatg      900
tggtgaggtt attttggttg agggatttga gatttagaaa gtttttttttt tttatgggag      960 ttttttttaa tttgattttta atttaggttt tatttatatt tgagaggttt tttcgttagg    1020
gtaaatattg tatttattgt agaagtgatt tatagtgaga gatggtcgga aaaaggtttg      1080
gtcgtgataa tagtggttta cggggtggtt atcgtgattt tgtaggggga agggaaggag      1140
tttatgaagt ttatttcgtt taggtttaag ttaattttttt tatagtggaa ttgttttaat    1200
aatgaaattg taggtttggc gtagtggttt acgtttgtaa ttttaatatt tgggaggtt      1260 aaagtaggcg gattatttaa agttaggagt ttgagattag t                          1301
```

<210> SEQ ID NO 25
<211> LENGTH: 30001
<212> TYPE: DNA
<213> ORGANISM: Artificial Sequence
<220> FEATURE:
<223> OTHER INFORMATION: chemically treated genomic DNA (Homo sapiens)

```
<400> SEQUENCE: 25
tggaagtggt tttgttatga taaaaggtgt ggtatttgta taattttttag ataagaataa      60
agttatgatg ttaagatagt agtagtattg tttgttatat gtgatatttg aaaaatatga     120
taattatttt aatttgttta agtagtattt atggtgaggg tgaaatttta ttaatattgg     180
ttaatttatg gtgttttaaa aaattagtaa ggagataaat tgatggatta aaagataaat     240
tatttatagg tagataaata gaaggataga tagagttata attaaatatg tattttattt     300
aggtagaaag ataataatta gttttttaaga agtgatgtgt ttgttagaaa agttttgaat     360
atagaatttt ttgattttgt ttttaattta gttttttttag gtattatgtt gtataattag     420
gtgtaatttt ttaaaagttt ttatgataga attttttatt tgttaaatta ggttaataat     480
atttttattt tttttttaggg taaagatgtg aaatatttgg agaattttgg aaaatatgtt     540
ttttattaat tagagttttt tgatgtgata ttatttttttt tagtatttgg agtttagtta     600
atagatatat agtgtagttg tgaaattatg aagtatgaga atgtattatt aagggattgt     660
aggaggtttt ttattgaaaa gtgtagttgg ttatatttttt ggaagtaatt taaatatagg     720
ttgagggaga ggagtatttt ttagattttt tttagatttt attttttatg aattttaatt     780
tttttttttt atttagaaaa aataatgaga tttatagtgt agagatagaa aataaggttt     840
tgtgtgtttt taaattttat ttttaaaaat attatagtat tttggatgag atagttttga     900
atttttgtaa tagtataggt atgagagttt ttattgaaaa ataggagatt ggattgattt     960
tttttatttttt tttttatgtt tttaaaatt gaaaagttat atatataaat tatatttatt    1020
tatttttttt ggaaaaggtt aaaatgaatt taattttgga ttattttttaa taatgggata    1080
aatttgaatt gagaataatt tttagaatta gttttgtttt tttgtgataa aatggatttg    1140
tagaaagtta tttggtgttt ttttttagtt aatatttttat tataaataat gggtatgtaa    1200
tttagtattg ttttttatag gttatgtttt tggaattatt attttttgtat tttatttgtt    1260
tgttgatatt ttttttattta agatgttttt tttagtataa gaagttattt tttttaaaat    1320
tttaaatgat tttattataa taatagagtt gttaattaga tttaggtaag taatgataat    1380
aaaaatttga ttttttattta gagtgtagta tggtttaata taataattag agttttaata    1440
ggttttttta gattttatttt ttatttaatt tgtatgtttt tgtaatatag atgttttatt    1500
tatttggttt ttattttttat ttttttttgt ttttggaata aaattattta aatttaattt    1560
agagatttta ttttttttttg gaattattgg gaaatagttt tagtaaaatta tatttttgag    1620
atttttatatt aggttttagtt taaattgatt atttaagtat taattttttt gtggtttagg    1680
aatatttttg agtttatttt tttttttttta aattgtttag gataaatatt ggagtttggt    1740
ttttttgttt tttatttttaa ttattttttg tttttttttt tttagtatttt aaaatatttt    1800
tgatttttttt tatttttttaa gaaatatatt tgtttttttg ttttttgtatt attttttttgt    1860
ttatgaaata tttttataggt aagttttata ttttttttttt ttagaggttt ttggtttttt    1920
ggttttagtt gttattggtt tagtgtatta gttaatatttt tggatttttgg agttatataa    1980
atttagattt aaatttttat tatgttatttt attgtttatg tgatttgaag taatatttta    2040
tttattgtgg tttttagtag ttataagttt gtgtttttaat tagttgggtg atttttgggtt    2100
agtgatataa ttatggtaaa ttttattgtt tttatttgta aaatgatagt atttatttttg    2160
tagtgttggt ataaggaata agtgtgattg ttaatataaa agtgtttagt ataatagtta    2220
aattaattaa gtatttgta aatattagtt tttattatta ttattaattt aaatgattag    2280
atgtattttg tgtatattag gtttttttgag tttattttgt tttaataaaa tattattatt    2340
```

```
tttagtatgt ggtttatatt atattttatt agttagagga tatgtgaagt ttagagtgga   2400
aagttagggt agtaggaagt attgttatat tttatatagt taaagttatt taaatatgtt   2460
tgaatttgag ttttgttgag tttttatttg tttttatttt ttttgtgtgt tttagtttat   2520
taataaagta ggtttaatat aaatatatta aaagtttaaa tattgagatt atgataatga   2580
atatgagggt tatgattata aaatattatt gaattagaga tttgttatga aattatatgg   2640
tgaagattat aagggaggaa tttgtatata tattgagtgt tttgggattt taaagtggga   2700
agagttagtg ttttaattaa agagaaattt ggggtaggga attaattata atattagtta   2760
ttttattgaa tttaggtttg ttttagttga tgtagttgtt aattttttaat gttttttttt   2820 tttttaattg ttttttaattt attttttttag aaattgaaag tttattaaag aggatatttt   2880
tttagagagt tgttttagtt attataagtt tttgttagaa attttaagaa agtttataag   2940 gtattttat aaggtggtat tgagtaagtt agaagtattt taagtattaa ttattatgta   3000
aataagggtt ttattttag attttgttgt ttgtggtggt ggtgatgttg gtgttttttt   3060
tggaatttag tttaattttt aaaaaagtaa aaggagtata aatagtaata taaattatta   3120
ttatttatat taattaaaat agaagttttg aatgagtaag gagttagagg aggtaaaaaat  3180 tgggaattt gtatattaaa aggttttat aatttgaaaa ttaagattat gttggttaaa    3240
taggttgttt taaaattagt atagtaatta aatttgtttg taatgaatgt agatttaaat   3300
agtgatgtta gatttgataa ggatttgtaa attttaaaag agtgtaaaaa gattatagaa   3360
gaataatatt atattttgt atttatagaa atggttagtt taagagatgt atttagttta   3420
gggtggttgt aagttttatt ttttgaattt gttattagaa gttaaaagaa attttgtata   3480 attgttttg atggaaatat aaattggttg atgtaaatga aatatataaa gtagttggtg   3540
ttttatttat ttttataatt ataaatgaaa ttaaatgatt aaaaattata gattttgggg   3600
attttttttt tattgaggag tttatggaat ttgttttttt tagtattaat aattgtgttg   3660
atttattttt tttgtttaa ttttgtatat attaaaatta ggtggttatg aataaaattt    3720
agaaatataa tttatatttt aataaaatga ttttaaaatt attttatttt ttattgtggt   3780
tttatttgtt gtttataat gtaggttttt ttgggttttt gtttagaatg attttgttaa    3840
tgtagatgat agttagagtt gaatggggaa tttagaaatt ggggatttgg ttttttgatg   3900
taatttatat gttaatttat tttattagtt ttttttttat ttatagtttg gtaaagaata   3960
tgggtggagt tgttttgggt ttatttgtat atatgtttaa attgttttga aaaaggaagg   4020
gtaagaaaga gtggtatttta agttggaatt aggtaggtat tttagattaa gagatgaatt   4080
ggaaagggaa tatttgttag atatttgggg tttgaaggta gtttgtgtaa gttttatat    4140 ttttgagtgt gtgtatatag tggagagggt ggagtttgtt atttttaaat ttgaaaagat   4200
tgagagattt tagagggttt agatgtgtta aaggttagag ggattaatat ataggtttta   4260
ttatggaaag gtgggaaaa ggttgaata gaaaattgtt gtagaaggga agttattgag     4320
aggtaaggga gttttgaat aattaaaaag ttaagaataa gtaaaggaa ggaggttggg     4380 tgggggataa aaaaaagtag ttgatgtggt aattaagaat tggtgggag tttgggtagg    4440 ttatttttt ttttagatta gagttttatt agaaattttt ttaagtgttt ttttgtgttg    4500
ttaaagatga taatagtaaa ttaataagtg tttgaaatga aaggggatgt tgattagttt   4560
ttaggttata gattttttgt tgttagtttt ttttgaattt ttatagtgtg tttttgtatt   4620
gtttttttta agaagagtta tttttttattt ttattttttag gatgaaggta agtgtttagt  4680
```

```
tagtatattt attaaatgtt agttttggtt ttagtttttt gtttgtgtgg aaagtttatt    4740
gttatagtgt gtttagtttg ttggagGggGt agatagaaaa agtaagtttg gtttggtgat    4800
ttgtggggtt atgtattttt agggttggtt tggagttttt tagagtttaa tgttttTGGg    4860
ttagaattgt aaggttttgg tttgagtaaa gggtttgagt tattgtagtt gtgggagtgt    4920
tttttttatt tgaatgtatt tatttataaa taagtataaa attttTTTaa tagtagagga    4980
gaaagatttt tgttttaaaa ttaaagttgg gaattattgg aaattttgtt ttgagtgtga    5040
gatattggtt tgttattttt ttaattttta tatttttttt gtaatatgtt ttgatttaat    5100
aattttttta gtgtttagta ttgtttggat gttttaattg ggtaatttat tagtgagtta    5160 ataggtat ttatatattt ttttagtttta agtggttaag tattaattt gaaatgatta     5220 taaaatattg gaattggtaa tgtatagtaa ttttaatttta tatgtaaatt aattggttta   5280
ttttaaatgt ttttttttaaa aaaataatta ttgtattgta gtattggagg tatggattaa   5340
atttttagaa tagataattt ggaaataaga tttggattag gaagataatt tagaatagtt    5400
aataaattaa taatgtttga ggtagttaaa tattgttagt tattggtatt tatatatttg    5460
tttgttgtta gataaggagt tggggaaatt gtttgttagg gttgagatta taattttagag   5520 tgaagaaagt aaatggtagt atatagtttg ttatagtggg ttttgaaata atattgtatt    5580 tttttaaat tttgattttt gggtgatagg gagttggtgg aggttatttt atatttgttt     5640
atggttttgt tttaatttga ttatgaaatt gttgttttt ttgagttttt taatttgatt     5700
attattttaa tggttttgtt atttgtttta atatattggg gggaggagtg taattgagat    5760
ttttattaaa aattatttga atttatttag ttagtattgt tttatttaag tttagttttta   5820 tgggttgtat ttaattttttt gtgttttta tatattaaaa ttagattatt aaaatgttgg    5880
taggaaaggg tgaaggaaat ggtttaatgt tttagtttat tggaagatta ttattttttag   5940 atatagttta aaattttgag gaaataaaaa ggatatatgt tttgggggga aaatgttttta   6000 atatttaga atgggggtat tatttttttt attttagaga atttgtattg gagttgttta    6060
tgtaaaaatg taatatttttt gaaatttata gatatgtaag gttagtgttt tttttttttt   6120 aggttttttag tttaggtgat ttagttttaa aggagttagt attttgatg ttataattttt   6180 gtttatattt gtagggtaga gaattgtttg ttttgtttgg atgttttttt tatttttttt    6240
taatttgaag taattggaat ttaaatatag ttgttaaggt ttgttttttttt tttattgttt   6300 tgataaggga aaaatttgaa atttatgttt taaattagtt tggtggtttg tagtttttta    6360
gtattttgtt tttatgattg tatgtttaat gtatttttttg gtgattttgg gtattaatta   6420
gttgtttaat aggagtatga ttaaaaatgt aaaagaagga ttaggagtgt gaaatgtatg    6480 tttagtttttt tttatatatt tgaggaggga atgagaatta tttttgtattt tttattttt    6540 taggagttat ttgtattttt tattagttgt ttattttagt tgtattggtg ttgggtaagg    6600
tgaggattta aaagtttagt gtagtgtttg tggtggttgg gattggggtt aattagtttt    6660
tggtgggtga gattttagat agaagggggg tgagaggaat gtgagttttt tgagttttt     6720 tttttttagtt ttggtttgta aattttttgaa atttgaaagg ggaggagtt gtatgtgtgt    6780 attttgtgt tttttttagtg taatttttttt tttttttttt gtgtttttttt gtggattttt   6840 gaatttttttt gttttggtt tttttattttt tttttaattt ttttatgaga ttgttttattt    6900 ttgttattag ttgaaggtaa ggttgttttg ttatgagtgt ttttttaattttt ttataaaatg   6960 aaaagaaaaa aagggaggat tattagttta ttatttagag gaatgggggag gttgtaaaaa   7020 ttgttgatgg gtagaggtga agatgttttt tttggattgt atttttttggt gttttgtaat    7080
```

```
tagagtttag ttgtgggatt tgttgaagaa atttgatttt tttgttttgg tgagatttta   7140
aaaattagaa atagaaattt ttagagttag agaggaaata taattaaata gtatgtgggt   7200
attttttttt ttatttttttt tttttttaaat aatattgttt tgagtttttta ttgggtaaag   7260 agagaaagtt tgagttttta tggatgttat gtggaggtta gaaatggttt aaaatgtaga   7320
tttttaatta gttttttttg tggttgaaga ggttaatttt ttttataaaa tgagtttatt   7380
tgttgattgt tagttatttt aaagtgaagg gatttagtat ttaaaataaa ttgagtaagt   7440
ttgtttgttt gttttattg ttaatttaaa tgaatttaaa atatggagta atttaagaaa    7500
atatataata tgttttagat agttttttaaa agtaggaaaa gtttagtatt tatatagtga   7560
ttagggttag ttttaagtgt taagttttttt taaatgtatt tattttatgt atatttttttt   7620 gagttattat atatttttaa aattgtgagt attggtatat tgatttagga agagtaatat   7680 aattttaga gggaattttta tttttaatta gggattaaag agatgttttt ttaatagtgg   7740
gtttgagttt tgtttttaag taggaattaa tattggtggg aaaatttgaa tttaggagta   7800
atggttgtgt tttggtattt tttaaaaata tatattaata ggatgttttt gagattgaaa   7860
aaatattgtt ttatatgttt ggtagaagtt tttatatttg gtttttttagg tgaattatat   7920 ttatagttttt tttatttaga ggtaggatag agttaaaata ttttgtttat tattaaaata   7980 tatattttttg tttaagttaa gaaattagaa aattagggtt tagaagtaag gtatatttttt  8040 tgagtgagaa tatgttttgt aattttatat attttttgtt ttgtaggagt aaatgtggat   8100
ttgagggaaa tttttttttt tattttttatt ttttattttgt gtaatttaat attattttttg  8160 ttaggaattt taattttgtt attttaaaaa atgagatatt tgtgatttag ggtgaatttg   8220
ttgaatgtag gtatagtaga ggaaattttta gatttttatga gtgtttgagt tttgtttagt   8280
gtaaattttt tgtgaatatt gggttagtgt gtggttgtgt ttatttgtgt gttgatatttt  8340 ttagtatgtt tggtttattt gttttgattt tgggtgtggt gttttagtta agttgggttt   8400
agtgttttgg tttttttttag ttgataagtt tagtttgttt gttttttggtt gtggttttttt  8460 tattttttttt tattagttta ttttatttttt ttagatttttt ttttattttat tttttttttat  8520 ttttattgtg tttatttttta tttttgtttt ttattggttt tttattttttt tttttttgta   8580 gtttttttttt gttgtgattt ttttttttaa ttttgtaggt ttgaaagaag gttatatatg   8640
tatgtttata tttatatttt atatgttttg ttttaaataa ttttatgaat attgttttttt   8700 gttttgttttt ttgggttatt tttttttgttg tttttttttta gtttgttttg atttgttttt   8760
taaaagtatg ttttttgttttt tttgttgttt tggtgttttttt ttttttgattt attagggttg  8820 ttgggttggt gtagattgtt tttttttttt tttttatttta ttttttttttt tggttttttt   8880 ttttatagtg ggagtttgtg ttttttgttttt ttggttttggtt tttaagtgtt ttgttaggtt   8940 ttttttttttt ttgttttttttt ggttttggttt tttgattttt tggtttgttg gtatttgttt   9000 ttttttttttg ttttgtttttt tgttgttttt gtttgttttttt tttggtgttt gtttgggtgt   9060
tgtgtttgtt tttggattgt tagttgtgta gttgggtttg gttggttgtt tgtgtgttat   9120
tgtgtagtgg agtttggtgg aatttttgtt gatgttatgt tatttttttat atggagtagg   9180 agtagaggga agagagaggg atgagaggga gggagaggga agagagtgtg agattgagtg   9240
agaaagttgg agaggagtag aaagaaattg ttagtggtgg ttagattttg gaggttttag   9300
tgtatttgtg gatttttttg gaatttggta tttttaggag ttttgtagtt tttttaggtt   9360 tggttttttgg gtgtttgttg tgtagttgga ggtttggttt gttggaaatt gttttgggaa   9420
```

```
gtagtgggat gtggagatag tagtttttttt ttggtagttg gtaagtggag gttatttatt    9480
ttgtagggat gtgagataat gtgagtttgg aaatttgttt tattttggag aattttatt     9540 gtaggtgatt tgtggttttt ggggttaagt tttgtttaag gtaatgtagt tggtaaatag    9600
attttgtaaa gttttgtttt ttttgttttt tgttatagat attaataatt tatagggtgt   9660
tgaagttgag agggaagtta gattgtggtt ggtatttaaa atgaggtatt ttttttaaa     9720 ttttggtgtt aatattgtag gaataaattt ttgggttaag gattagtatt tttaagataa    9780
agggttgggt ataaagtttt agttattgga agattagtttt ttttttttatt gttatttatt  9840 gggaaaaaaa agaaaagaaa aagatttttat tttaattggt agttagtgat tttttaggtt   9900
taagtgaatt atttgggagt taggtttgga tgttaagtttt ttattatttt tttggattgt   9960 aatttttta aattgattat tagttaattt taatttggta ttttaggaga tatattttaa    10020
atggatgtag agaattattt tttagttgga gattaagaaa aaaattttg attttaaatt    10080 tttgaaatat gttttttttt tttagtttaa ttatttatt ttttttaagta atttagaaat   10140 taaattatta taaggtggtg tgattttttt ttatttttt gtgtgagtat tgttttatta    10200
aattaaatgg aaaaaatttt tattattata aatgtaaata ttagaattta tatattttaa   10260
aatattttta tgaaaaatta atttgattta aagaaattt tttgtatttg ttttagttta    10320
ttaattaaaa ttaaagatgt ttttattata taaaatatta ttttggtaga aatttattta   10380
aaatttaaat attaataata ttaagaaaat aaagtatata agtaaaataa attgaagatt   10440
tttgttgatg taatatgagt atataatatt ttaataatta aattttttt aaaaaattaa    10500 atagttattt tatttgtgga atgttttatt ttaatttagt aaaattatat ttaaattatt   10560
taggtgtttt gttttttaag ttaagtgtgt ttgtttttaa atgtttttaa agtatttata   10620
ttaattggtt gtaagaatg tatatatatg gtaaaatata gaattgaatt gagtagtatt    10680 ttaattttt taaataatta tttattataa attaatttat tggttaattt tataatttag    10740
tttatttaaa atatatgttt ttgtgttgtt tattttttaaa tttttttatta aagatttttgt 10800 tatggggtaa taaagtgtat gaaaaggggg gaaatgtgaa aggatttggg attatttgaa   10860 ttgtatttttt tttgtatttt tagttttgtg gtagttatta gaaattattt tttagtaaat  10920
tgttttattt tttagggttt gtttgtttgt tttgttatgg ttttttgttt tttgttagtt   10980
gtgtagtgtt ttttgtgtgt ttataatata aaatttaagt tggttaaaat aagagttttt   11040
ggtatatata ttttaattag aatatgaatt ttgggggtga gaattatttt ttattaggaa   11100
aagtttttta ttttaatttg tgagattagt tattgaagtt agttttgaag tttggtagtt   11160
aaatttttta tagaagattt gttttgatag ggtaagttta aggattagta ggtgggaatt   11220
ggaggttttt ttttaaaaaa ttattttttt tagttattta gatttagttt ttttagtagg   11280
tttggttatt aaatgaagta taaaaatgta agttttaagg tttattttga ttgtaaaata   11340 aattttaag ttataaggat atgtaggagt gagttaagga atatgttttg atttttttt     11400 tagttttag agtggagttt tatgagtttt tgaagatttg ttttgtattg ttttgtttgg    11460
tttttagtat tgaagtatgg ggaagtgggg ggaagaatgt gtaataattg attgatttta   11520
tattaagtaa tgtaattttt ttttttgta tatttattt tttaaaaaaa ataaataaat    11580
aaaaattatt tgtagttatt atttgtagtg ttttggttat tagttaataa tgtagttagt   11640
ttagatatat aaaaaaaaaa gattattgaa atgatgatga tatgtaaatt ttttttgaaa   11700
ttattataag taaatatttg aagtttggat taataaaatt ttatttgtgt tatttttatat  11760 tgagttagta gaaagttgtg ataatgaatt ttgtaatatt ttatgaatag atattttaat   11820
```

```
tagggattaa ttttgtgatt ttattgtaga attattaaat ttggagttgt taaattgtta   11880
tttttgggtt tatgggttta taaggattga attggtagag tttttgtttg tgttttgtt    11940
agtgggtggg ggaattgttt ggttgttttt attttggatt tttatgttat agtgttgggt   12000
agttttttt  gtaggtagtg attttggtta gaggtttttt agggtttagt ttttttagg    12060
agaggttgag atgtagggaa atggtattta ggttagaggt aggtttgtag tttttgttt    12120
tgtttttgtg tttttgttaa tttgataatg tttgttttta ttttgatttt tgtatttgtg   12180
tgaagtgggt tttttggttg ttggtgtatt ttggttagtg tggagagagg taggtgttga   12240
gattgaaggg gtttagggag ttttggattt ttttttttg tttttaaagt aattgtggtt    12300
tttttattta tttggtggag tttttttgaga tttatttttt ttggtttgtt tgtggtagag  12360
aagggggagt gtgttaaatg tttggttttgt tgtgttgtgg ttgaaaatgt gaaaagatt   12420
tggtttgttt gggagagaaa ggggagaat  tgggtagtag ttatattaga gttattttt    12480
tgttttggt  gggtagtaaa tttttaaga  atgtttgttt tgttttttt  agttttgttt   12540
agtttattta gtgttttttt tttgtgattt taaattatat tttagggtaa ttatttgtag   12600
taagtaaata aatggttggg ttagtatttt taggagaaag tgtggttaaa tatgaaaag    12660
tggttttttga tggatgagag gtttgaattt agtttgtttt tgaaatattt taggttaaga  12720
gtttgttttgt tttagaatta tagaaaattg agggaaattg ttgttaggga taggggtatg  12780
ttggtgttga tgttttataa atgtttattg agtttaatt  aatggataag tattgaaggg   12840
tggtttttgt atatagtttt ttaaagagaa aagttttttt tatttattta tttttgttgt   12900
tattgtgttt agatgagttt ttaattttgg tattgagatt tttgaaagta ggtttatagt   12960
tttttagta  tattgtggtt ttatagtttt ttaattttg  ggtatttttg tggtaatttt   13020
ggagggagat ttttttttga taaataaatg ttttgggttt gaggttaggt tggagatgtt   13080
gttgtatagt tagaggttgt taggttggaa aaatatgttt gaagtttagt atatagtagg   13140
tgtttaatag ttagtgtaat gtagttttat ttgagttttg tttatttgat ggttgttgtt   13200
ttttatagtt ttttttttttt tttgtttgt agataatggg gaatggagat taattgttgt   13260
aaattggtgt tggtgtgtgt gtaattaggt aagaattttt tttttttgtt tgggttattg   13320
gatgggaggt tgtgttatgt gagggtggta agagggtatt ggttttgtgg tgaggtttta   13380
gtgaggggtg ttttttttgag gggttagttt gggtaggaag gaaattagaa ttaaattgtt   13440
agtggttttt ttttgtggtg gggtggtgga ttaggaagta gtggtgtgtt gtgtattgaa   13500
gtttttagt  ttattttttt tggttggaat tgttggtaat tggggaggtg tagaaagagt   13560
atgttatttt gttttgggtt gttagagggt ttggggatg  gggatgttgt tagttttttt   13620
ttttaattgg gttttgtttt tttgttttt  ttttttttt  ggtttgtttt gttttttttt   13680
tttttttgt  ttttggttttt tttggttgt ggtttggat  gttttttttt gtatgtgggg   13740
tgggtgtgt  tgtggtttag gtgtgtagtt ggtggttgtt gaatgtttt  tttttaaga    13800
ttttgaaatt aaaaaggttg agtttatgga tttttttgag agttgaaaag aggtagttag   13860
tagtaagttt ttttttgtggt agtatttttgg tgttaatggt aaggttggga gggaagtgta   13920
ggtgtgtgt  tgggtatttg tttttgggat tttgggtttt gggtgaagtg taagaaggtg   13980
aggttgttag atttgatgtg tttgttgttt gaatttagat attttgtttt tgggtgggat   14040
gggaagtagt tgttttaggg atgttaattt ttttttttaa attatattgt attttgaga   14100
tttaatattt tttttttttt tttgtttgtt ttttgtggtt tgattttttg tgtatgtttt   14160
```

```
agtaaatttt ggtgtttagg ttggtgtgga aaagtggttt aatagtgatt tttgttgttt    14220
gttatatttt gttgtgtgta gtattattag ggtttattta gttatttagg tttttagtta    14280
tgttttattt agatttgtgg gtgtgtggtt tattgtggga ggtaagtaag ggaaatttga    14340
gttggtgaag gtttgttttg gttggttggg ggaggggtgg ggggttgata atattttga     14400 agagttggag ggtagttatt gtgtttagta gtttagggta gaatggaggt ttgttttgt     14460 tgatgtgaat ttgtttgaag tattggttgt taggttttgg gttttggtga tgttgttgtt    14520
tgattggttg gttttatttt ggaggaattg agggatattg ttagaggagg tttataggtt    14580
tatgtaaaaa gttaaaaagt ttttaattta tgttataggt ttttttttgaa ttgaaatttg   14640 ttttatgggg tggagggggg ggtgtaaggg atggaggagg gaagatgttt ttttttttaa    14700
atatatggaa aaaatttttt taaatttatt gttttttttat tttttttggtt ttgtagtaaa  14760 taagtgttta gttttaggag gttattgatt tttgataatg tgagtagata aagttttttt    14820 tttttttatag tttttggttt ttaatttttt ttttttggat taaagtgtaa gaatataaat   14880
gtaatatggg atggagggg gtgatttggg attttggtta aaaaaataaa ttgtattatt     14940
aagaagaaaa taaggttttt gtattggagt tttttgtga atttgagaga aaatgattat     15000
ttgttgaaat gaagtgttta aagtgattta gtgttttatg tttggatatt gtattatatt    15060
gttagttgtt ttgttgggtt agttaaatgt ttatttgttt gggattaatt ttatggggtt    15120 aaatggggt aatgtagaga taatgttgtg tgattttgt tatttagatt gtgttaaatt      15180
ttttttttgt ttgataattg gtagtaaaaa taaattatta gattgtagta tgtttgggat    15240
atggttaaaa attaagagta gtgatgattt tggggagaa tgttttgtgt gggtttagtt     15300
ttggttttgg ttagattaga ggagttttt aattttgttt tgtgtggggt gggtttgtag     15360
ttgttaagtt gaggttgata tttttttattg tgttgggagt tagagagatg taaaatgttt   15420
ttttttttta gttttatttt taggttttt agatatgggg aatgtatttt gaggataggt     15480
ggagaagttt atggtaggat gggttttg taggtgagta ggaaatggtt aagagtagag      15540
gagttttgtt tgtgttagtt ataagttgtg taggtgtttt tggttgtttg tttttgataa    15600
ttagtatata aagaattaga aataatgaat gattgttttt ttaattatta tttttaggtt    15660
tgtattgttt tagtgtatgt gaaaggtttt ttttttatat ttaatatgtt ttttttatt     15720 ttttgattga aaagaaaaat tgttgtttaa atatgtttaa tgttattaat taagaaaagg    15780
tatgtaatgg gaagaaatgt tgaaaatttt gatttaattg gtttttaagg aattagtaga    15840
tgataaaaaa aaattatatg agtgggtaaa gttatagtat tgttgaagga tagagtattt    15900
attttttttt gattttaagt taatttatgg aatatttaaa gttttggtta tagtttgttt    15960
gtaaaataaa aggattatt ttttgtgttt ttttaaagtt ttttttttgtt tttaaagaga    16020 aaaaagtttt ataatgatat atgatttttt taaaggttg tgatagttta ttatgttatt     16080
ttttttgttt ttgttttaa tgttgtttaa aaatattatg ttttgtttaa agattaaatg     16140
ttttgtatag gtagagttta tttttaagta gtttaggttt tgtttttttt ttttagtgag    16200 tttattttt ttggtatttt attgggtgga tgtttagttt ggatagaatt ttgaaatggg     16260
ggtagtatga gagtgattgg agattttaa aagttagagg tttgagagag ggtggatgta    16320
gttagtagaa gatggtgtag aagttagttg agaatgattt tttagagtaa agagattttt    16380
ttttggtttt ttttgttttg gggtttttga aaggaattta taaaatggtt ttattttta    16440 ggaggaggat ggattgattt ttttttgtta ttggtttaaa aagttttagg gtggtggttt    16500
tgggttttgt gttgaaattg gattgtattg tagtttttt ggatttgatg tttggttttg     16560
```

```
tgttttgata aggggtgggt attttttttg gttttttta ggaatgtatt aattgttaaa    16620
tagttttggt ttagtggatg ggttgaaagt gtttgattta agttgttggt gtgtatagat    16680
tttttttttt tgggaggtgg gttttatggt ttgttgtggt attttagtt gtgatatata    16740 tttttatatg tggtagtagt ttggttttaa ttttttttga aggatttggg ttaattttgg    16800
tggttttggt ggttgtagat ttttttttgt tgttttgttt ttgtgttttt tatttaatta    16860
gtgaatgttt gtggagtata tattatgtgg attttaatg tattttttga aagtaaataa    16920
tatagttttt tttgttgtta tgaagggatt ttaattttaa tatggatatt agtgagatta    16980
gtttagattg ttttagtaa aatgtaaat ggtggtgtgt ggggtggtga ttaaggtttt    17040
gagttttgtt agaaagaagg ggatgtgtag agaaggtgg agaattttag ttgtggttag    17100
tgtggaaggg ataggtgttt gttgaagggg gtatgaggtt tgaggaaaaa gtaatgaaat    17160
aggggtaagg agagtttttt attttttttt ttttgtttga ttttgttat tttattttt    17220 tttttttttt tttattttt gtgttaatta aatttgtagt ttatttgaaa ggtgttttgt    17280
tgtgttgtgg ttttttattt ttaggggaaa ttgtattagt tgtttgaaag tagttagttt    17340
ttgtggattt tgtttgtaa aagtggtttt tataggttgt gttttttgtt ttgatttgg    17400 tatataaagt ttttaaggt tggtttggtt gttattttt attgtttgtt gttaatatat    17460
gtagtagttg ttagagtggt ttggggggaaa aggaaatgta taatgaaagt ttatttgtga    17520
gtaggaatat attaatggaa taatttgatg ttttttttaat tttatgtaaa aagttttgtt    17580 gttttttttaa tattgattga atgggtaatt aatggttttt tatttaggtg aatatttgt    17640 aatttaagat aggtaaaaga taataagttt aaggtagaag ataaaaggtt taattgtagt    17700
ggtgtttgtt tgtttttat ttttaggggt ttttgattag gaaagttttt ttttagagga    17760
gaaaaaggta ggagtgggag aatatatatt tattatttg gggttagatt ttattgtagt    17820
atttgattat ttagtttagt tttttgttat tttgttttt tatttttagt tttttttttt    17880
gtattttttt ttttttttaa tttttttagg atgatttttt attattattg ttattatggt    17940
tttaataatt ttttttttta aatttatatt ttttatttt agtaattaat gaggttgttt    18000
tttgatttag gaggagattt ttttttttta gaatttaatg tgtagagttt tgagaatta    18060 aagtagttgg taggggagga agaaattaat agaaagggag agagtatata gaattgtgtg    18120
tgtatgttaa agagtgatta ggaatgatag agttaatttt tttgtgagga tttgatggga    18180
agagtgttta agatttttatt agtatgtttt taataggttg atattttaat ttaaattttt    18240
agaagtaata tattatttgg gttattataa tgaggtgggt tttttttttt ttgttagttg    18300 atagtttta aaatattatt ttgttaggga aataaaagtt ttattttaga ttataggtgg    18360 gtattttgg atttaggtga tttatggtta ttatgataat taatgttgaa tgttagttat    18420
tagtatgttt gggagagaga aaatagaaag aagggagagt aaaagaaata gaaagggag    18480 atggatataa gttggagagg gaagaaaaga gaaaagagg aagatagatg agtgtttaat    18540
ttaattgttg tttaaaaaag tggtgggggg gtgggatttt atttagtttt ttgttatttt    18600
tttttttttt gatttggata tttatgttta attttatatt ttatttttt ttttttttt    18660 ttaaatatat gtgttatatt attttttta ttttatttag tttggtaagt agttgttttt    18720
tggagattta gtgatatta ggaaaattgt ggtagtaata tgtaaatgtg aggaagtatt    18780
aatagtatgt ttgttgagtg attttagtaa atgttttttt tttaattttt tttttttttt    18840
tttttttagg ttattgtgag gtggtaattt ttattgttat ttgaatattg ttttttagg    18900
```

-continued

```
tagttatttt aaattttaaa tggttgagta gttagagttg tgggttggaa aaatgggtat    18960
tatttgtagg gatttagaga gggtggttgt tgtttaatat atttatagat ttttaattta    19020
gaaaataatt tttttttttt gataagttag agtttttaa atttattta ggaaatgggg     19080 aaaaggatag ttatagtgaa gttttaatt tttgggttat ttggttttat agttatgagg    19140
ggtggtgggt agtggattgt ttttagtttg gtttgtatgt agagaaaagt tagatattgg    19200
agggggtggg gtattttttg ggtaggatgt aaggttttta tttgattttt gtgttttatt    19260
aggagtttat atatttatgt ttattatgtg gttttaagtt gagtttaggt gggttttgtt    19320
tttgagttag tttgggtagg gtaggatttt tatttgttta aggtttaata gtttagggag    19380
atgtttaatt aagttatttt ttgggtgaat tttgaagata gattttttt aaaagttaga    19440 gattatttgg ttgagtttta ggttagattg atatggagag tttggtggta tagtttaatt    19500
gtttattgtt atggttagag ggattttgta taattaatat tgaagagtgt gaaattaaat    19560
aagattttaa gattggtaat tggtggtaaa tattagtata aaatatggtt gattttatgt    19620
tatatatttt tttttttttag ggtttttttt tgaaagaata agtaagaaat tttaattgag    19680 ataattttttg atgtttttta gatttaaaat tttatgttgg tattgggttt tttttttttg    19740
ttttatgtga gttatgtagt attttagtt tttttattag gatttttatta atgtttttg     19800 tattggaaat ttttgtgtta gaggttgaat ttatagtaat ttttaaaatt aattaagaag    19860
aatttagtta gaggttatag taatgttgga attataaaat gtaagatt tattttttt      19920 tggttttttt tttatttatg ttgtttatgt ttgtgtattt ataagtttta tgtatattaa    19980 attttttaaaa ttaattatta ttatgttata gagtttttat tggatagtgt ttttagttt    20040 ttattatata tttttttttt tttatgtaga tttattatgt tggtgttttg ttatataggg    20100
ggtttgagaa gaatgttatt taattgttgt tgttgtgagt gtgtaaagtg attaggagat    20160
taggagaatg ttgaaatttt tgttggaaaa atgtaaagaa aatttttatt ttgagttagt    20220
tgtttataga gttagtgtgt gtgtgtgtgt gtgtgtttgt aatataaaat ggatgtgaat    20280
atatatatat aaatagatat ggttttgttt ttattttaat ttgaattatt tagataattg    20340
tttttattta ttatttgatt ttaatgggtt tatataaatt aggatatttt attttttag    20400 gtatttaggt tgttgttgat ttttagtgtt tttaatattt tgtatatgtt ggtattatga    20460
ggagtagtta tgtgttttg ggttttttaa ttattttgga ggttgattga gttttttat     20520 atatgtatat ttgttgtgat gaaagtttta ttggtagagt ggagttatta gagtttttat    20580
taaaattttg tggggttatg agagatgggt ttagaaattt atatggtttt gtggggtttt    20640
ttggtttttt aaaataaggt attaatattt aagtttttaa aaatatttgt agtttggggg    20700
tttgaatttt gaaaaataag gagtgagggg ttgtgtatat taattatagt ggagattttt    20760
tttatttttt aatgtgatgg agttttttta tgaaatgaag ttttaagggg tatggtattg    20820
tggggattat agttatttg aggtttaaaa gaagaaattg gaatatgatt agtaaatata    20880
tttagtagaa aagagttgga ttttttattga tttagttata ggttattggt tggtagtgta    20940
atgggaggaa atatttattt tatatatata ttttatgatt ttgggggaat tagaggaaat    21000
ttaataagaa aatggttaga aatatttaaa attttttattt aaaagattta agtaaattag    21060
agttttatta gattaaaaat tattataaat gtaagagtat tgtttttagt gaaatgttgt    21120
ggggtttgag aaggagattt tttgttaaat ttttgggata aaatgtgtta tttaagtatt    21180
agataatgag tagaatgtaa attaatttaa ttttttttat taataggttg ttagtgtaat    21240
gtgtataatt tagtgataag attgtaggat ttaatatagt tggatgtatg agttttagtt    21300
```

```
aatgtagatt tgttatatga ggatgtgttt tattttgagt aggtgtttgt atgtgtggaa    21360
tggggtaaag tggaataaaa ggttaaaagt agaaatgttg atttaaagtt tattatgaag    21420
aaattttttt tttgtagtta aattattttt aaagtgggat gatattggtg aagaaagatt    21480 gaaaataat ttttatgtgt gttttggat tgtaagttta aaatggggag gagttgtaga     21540
tagggtttgg gggtggttag ggtaaaggag agatatataa gttgtaaata tatttgtagt    21600
ttgttttatt tattttgttt tatattgaat aagttttta attttgtgaa taaggataag     21660
gagggagtgt tttaaagata ttttatgttg gtattgtaaa ttattgattg taatgttaaa    21720
taaatatata tttagagatg ataatattaa ttttatagta aaataattgt ttatgtagaa    21780
atttagagga gattagtttg ttttttttag ttgatttatg ttgggggata aaaggatttt    21840
taaaaattat tttgaatatg tttggatttt tttttttaat tttttttggaa attaaatttg    21900 tttggaaata gtgttataaa gagttgatgt tttaaaggt gatttttttt gttttatata     21960
aataaggttt tgttttgtt agttgagtgt agttttaggt tttttgtttt tagtttatat     22020 atatttttt tgtttgtttg gattttaatg gtttaagata gttttgagtt tattgggaaa     22080
agaaaatgat tgtaaaaat tattttgaa attggttatt tggtaatatt tttaattgta      22140
tggaaattta ttaaggtata ttttatatat aattagttta aggttgttga ttttataggt    22200
tttatggatt taaatttgat tgataataaa gtaaataaga gagttgaatt taaagtgtgg   22260 ttttttggg ttaggatgag tttaatatag tgtataagga atttgaaaga tttaggatat     22320
gtgttttaat taatgttaag tagaatggat aagttttag tatttgaaa atgttgggtt      22380 agggttttt ttttattgtg tgttttttgt ttggggatta ataagtatta tagagaatgt    22440
gatttgaggt gatttttat ttttgtataa atttagagtg aattattaaa tagttgtttg     22500
tttaaagtta aggtaatttt tttttgatgg gtttatttgt ttttgattt ttaatttatt    22560 agtttgtttt tttaggggttt tgttttttttt gtaattaaag tttttttaga ttagtgtagt  22620
atttatttga taggttgttt ggaaaattta agattggaga ggtgatttgt tgttgttttt    22680 taaattttt agttttaagt aatgtgtttt ttttttatat ggggtggggg attggaaatg   22740
gatgtagtga gatataaaga gtgggtgttt tgttgatttt tgtatttttt tttttttgat    22800
tattttattt ttttttttta agttttgat ttttagtttt attttttat ttttgggttt      22860 gtattaaaag ttggattgtt ttgggttggg taggagttga attttttggga gtttgtttgt  22920 gtagatttag tgtgtatggt gaggtagtag tttggttttg tattgttgat aggtgtaggt   22980
aggatagttt ttttattgtg gtttggggtg ttttgattgg tgtggagtta tgttagttgt    23040
atttggagaa gggtttggga ggaggtggag gtggagaggg ttggggaggg ttgtggtgga    23100
gtgatgtttt ggtattagga agtttgtttt tggttttaag atgttaggtt aataggggaag  23160 tgtggagttg tagatttggt ttgttgtttg tttgggtgtt tggagttgag ttgtggtaag   23220
gtttggtttt tgtttgattg tttgaggggt gtgtgtgtgt gtgttgtgga gggtgtgttt   23280
agagggttgt gttgtggttg tagtggttgt tgttgttgta ggggatttaa tattatttat    23340 ttgttttttgt tattttgat atttttttgt tagggttgtt gtgtgggggg gggtgggta    23400 gagtgtggtt ggtgttagtt tttttattg gaggggtttt tgggggaggg agggagagaa    23460 gaaggggggtt tttgtttatt tttgttttgt tttggagttt ggaagtttgt tttttaaaga  23520
tgttttgagt ggtgtttttt tgtttatatt ttatgttttt gtttgtttgt tgattttttg    23580
tttttggatt ttttgttt g agtttttgg aggagatggg ggtagtttgg tttgagaatt   23640
```

```
tggtgggggt tgtgttttttt ggttttttttt gtagtgggga aattttgtgt ttagagtgtg   23700
atttggagtg ggtagtggtg gttatggggg tttggtgggg tagtagttaa ggattagtag   23760
agtgttgtgt tttttttgttt atgaattgta tgaaaggttt gttttatttg gagtattgag   23820
tagtggggat taagttgttg gttgtttttt tatttttttg ttattatttt tagttgttag   23880
ttatggtttt ggttttggtt tttggttagt tttggttgtt ggatttttttt aagtataggt   23940 tggaggtgta tattattttt gatatttta gtttggaggt tgtaggtaag gtgttgtgtt   24000
gttttgtaga tattttttgtt tagttgttttt gtgttatttg tttttttttg ttttaaggaa   24060
gttagttttt ttgggggggag gtgtggtggg agtggttgtt tgtttggttt tttgtagaat   24120
ttttgggagt tggaattttg attatttttgt atttttttag tttttttttg attggtttgg   24180
tttttggggt gttaagggtg tgagtaattt tgttgttttt tttatttgta ttttggtttt   24240
ttttttgttt tttgggttat aaaaatttta gtattttgat ttgaggatt ttagaggttg   24300 ttgatttttg ttttttgtttt ttttttggtt tttagttttt gaggagtttt atttgttagg   24360
aaattgtttg aaattatttta gaaatgtttt ttgtgaagag gtattttttt ttttttttg   24420 ggaaagggtt ggtgaatttt ggtgtttaat tgaattttta tattttttttt tagttttttt   24480 aaattgtatg gaaatttgag ttttttgtga ggggagggg ggtttgtaaa ttatgtgtgt   24540
gtgtgtgttt taggagattt ggtgtgtttg tgtagaggtg tataaatata tttgaaagta   24600
taggttataa aagtgaatgt gttgttgtag tgagataaat atgtaaataa aatgtgtggt   24660
gttgggggag gggaggaaat ggggtgtgga tatttatatt tgtgtttgta tattttatag   24720
gtgtagtgtt ttttgtggtt tggagttgtt gtgtgtattt ttttttggtg ttaggtagtt   24780
tagttttttt atggttttttg ttgttggttt agttggtgtt tgtgttgtag gtgggtatgt   24840
tgatgggaaa gtgtgtgtgt tttgttttta gagaaagata aaagtagta gggaagaat   24900 gaggatgtgg gtgttgagga tttgtttaag aagaagtggt aaaggtggta gtggatttat   24960
tttattagtt agtagtttta ggagttggag gttattttttt agaggaattg ttatttggat   25020
atgtttatat gtgaagaaat tgttgtgtgg attaattttta tggaagtttg agtttgggta   25080
ggagttagta tggagtttgg gagggatggg gggaggatgt tgtggaggta taggttaagt   25140
agattaggag agaatgtgga aggtagtgtt gtttgggagg gtgttggtgg ggtgtagttt   25200
tgtaaaggta gaaggttttg tggtggtttg gttgtgagat tatagttttt tttttgaggt   25260
tgataggatt gttgttttgg tttaggtttt tagagtggta ttggtttatt gttttgttat   25320
tttgtgattt tatgagttgg gttgtatggg taatttttttg tataggatat tgtgtttttg   25380
gtttgtagtt gttagagtag agttaataaa attttttatta ggttaagagt tgtgaatagg   25440
ttttaatttg tgagttttta ataaggaaaa tttgttagag atatggaaga gttggttttt   25500
tttgggaaat ttttgttttg gttttggttt agttttttttt tttttgggtt tgtgttttttt   25560 atatttttttt tatggttgtt ttggttattt aggttttttttt tatatttttt attttttagt   25620
tttgtgattt ttgggagtaa agttttaata tataattatt agttttttta gaaggagaaa   25680
gaaaaaaaga agaaagattt ttttgtttgg tttatttatt tttttttagg agttgaattt   25740
tggaaattga aatttatatt tttttttttta aattataatt atagttttgt aaaaagggtt   25800
tattttaatt ttgtagtaaa tttgtatttt atggattggt aaaaatgagt ttaaataaat   25860
aatttaatag taatgttttg gtttatgttg gttggtggaa gatttaaat ttgttaggat   25920 tttgaagta gaaaatagaa ttaagtaaat taagtggtat ttagaggttt tgttgttaaa   25980
aaaaaaaaat taagtgtttt gggtagaaaa aataaagttt ttggttagag tagagtaaat   26040
```

```
aaaaagaaga aaataatgat aaaaagaata aagattaaaa tgttttttta aattagaggg   26100
aatgaagata tttttggggt ggtatttgtg taaggtatga ggttatgttg gtggataaaa   26160
ggttgggaag aagttgaaaa tggttttagt ttaattgttt agagttagag ttgggttttg   26220
ggtggtgtgg ttttgagtaa ggttagtttt ttattagttt ttttgtatat taagggaatg   26280
ggttttttat gtattttttt tgtttgagta aagtttagat ggtttagggt agaaatggta   26340
agtaattaaa gatagagttt atgggttttt tgggattttt tgaaaatgtt ttttattttt   26400
gtttgttatt ttgtagtttt attttagtgt tttgtagttg tggtgttggg ttttttttgt   26460
agttgttttt tttttaggg tggttgtttg ttgagttaag tgggagtgag gtgtgttttt   26520
tatagtagtt gggtgtaaag aggaaggggg ataaaaagga aattaagaat gaaaggaaaa   26580
agagaaaaag tggattatat ggtgggttt ggtggagatg tgtaatgtga aatattattg   26640
gtgttagttt ggatatttta ggttaggttt ttttttaata tataaaagtt gttgtttggg   26700
gtgataggga ggtttgatgt ggattgggat tggggttgtg gttgggttat tggatatggg   26760
tggaagttgg ttggtttggg tggttgtttg taaagttaaa tgatttggtt gggtttggtg   26820
tgtggatagg tttgtggtgg gtttagggta aagaagaggt agagtgaaag aagggggaat   26880
ttttaaaatt attttttttg ggttttttgga gtttaatatg ttaagttttt ggagttaatg   26940
agttgatgaa gaggtggttt tttgttttt attttggttgt tttgttaggt gagaaagagt   27000
gttggtggtt tagttttgt taagggagta tgtattaggg ggtgggggat gatagtggag   27060
gttagggaag gaagggagga attgtgtggg agaaagagtg atttttagt gttttttag   27120 ttttttttt ttatttgtgg gtttgtggtt ttggaatgga agtaagtttg taaggtgttt   27180
tgggaagggt tggaaaagtt tgttgttttg tgtttgtttt atattaagtg ttttttggatt   27240 tggagaaatg tttggttgag tgattaaatt gtttgtaggt ttttatgtgt ttggttgagg   27300
tttgtggtgt agttttgagt tttagtttgt aggttagagt agattaggtt ttttgtgttt   27360
ggtggagatt tgggttagta attgaaagtt ggttttggta ttttggtgtg tagggtggtg   27420
tagtgaagtg aggttagggt gtgtgagtgt gttagtgtgt gtgttgggg aaggtggggg   27480 ttggttttg atggaagttt tagtaatttg tattgtggta tttgtttgtt ttttgtttt   27540 aattgttttt aggtttggtt taagaattgt tgggttaaat ggagaaagag ggagtgtaat   27600
tagtaggttg agttatgtaa gaatggtttt gggttgtagt ttaatgggtt tatgtagttt   27660
tatgatgata tgtatttagg ttattttttat aataattggg ttgttaaggg ttttatattt   27720 gttttttat ttattaagag ttttttttt tttaatttta tgaatgttaa ttttttgtta   27780
ttatagagta tgtttttttt attttaatttt attttgttta tgagtatgtt gtttagtatg   27840 gtgttttttag tagtgatagg tgttttgggt tttagtttta atagtttgaa taatttgaat   27900
aatttgagta gtttgttgtt gaattttgtg gtgttgatgt ttgtttgttt ttatgtgttg   27960 ttgattttt tgtatgttta tagggatatg tgtaatttga gttggttag tttgagattg   28020 aaagtaaagt agtatttag ttttggttat gttagtgtgt agaatttggt ttttaatttg   28080
agtgtttgtt agtatgtagt ggattggttt gtgtgagttg tatttatagt gttgggattt   28140
taggattttg ttgatggggg taattttgtt tttgaaagat tgggaattat gttagaaggt   28200
tgtgggtatt aaagaaaggg agagaaagag aagttatata gagaaaagga aattattgaa   28260
ttaaagagag agttttttg atttttaagg gatgttttta gtgtttgata tttttttatta   28320 taagtatttt taatagttgt aaggatatat atataaataa atgtttgatt ggatatgata   28380
```

```
ttttaatatt attataagtt tgttattttt taagtttagt attgttaata tttaaatgat    28440
tgaaaggatg tatatatatt gaaatgttaa attaatttta taaaagtagt tgttagtaat    28500
attataatag tgtttttaaa ggttaggttt taaaataaag tatgttatat agaagtgatt    28560
aggatttttt gtttgtgagt aagggagtgt atatattaaa tgttatattg tatgttttta    28620
atatattatt attattataa aaaatgtgtg aatattagtt ttagaatagt tttttttggtg   28680 gatgtaatga tgttttgaa attgttatgt ataatttatt ttgtgtataa tatttttgtat    28740 aatattattg ttttatttt tagtaaatat gaaataaatg tgttttattt tatgggagta    28800
aaatatattg tatataaatt ggtttggatt tttttttttt tttttttgtta ttaatttggt    28860 taggatattt tagttattgt ttttttaaata aattagttttt ttttgtttgt ttagttaaat    28920
atataaggta gtagttttta tttaaatttg gtagaaataa atgatagtta tttattagaa    28980 attaaaaga aaaaaaagg tattttttggg ggggaaaagg gttataaaat ttaattttgt    29040 tttttttaatt ttttttttggt ttaaatttag aggattttat tatggttagt aaataatatg    29100 aaaagaaaa aagaagaaag aaatttagta agttttattag tttaaaatga ttttttaagtt    29160 tattttttta tggggaaatt tatatttta gtaaattgtt ttggagaaat atttgtgtat     29220
gtatatatgt atagtttata tgtatttttt ttaggaggaa tatatttata ataaatttat    29280
agggaaatat ttttagtttta aaatatttag gttttatgt ttattttttag gtttaagtag   29340 agagattttt tatgttatat tgtattatta ttttaaatt ttttggagat attaaaagaa     29400
ataaagatga tttttaataa ttatagttttt ttagttttttt aaagaattta ggggttgaga  29460
ggttagagtg gagttttttg agtttgttg agtaatatgt agttgaggta aaggttatgt     29520
ttttggtgtt tgttttaaa taatattgat ttattaatttt taaatttgtt tgttttttgaa   29580 attatatagg attatagttt gtaaattgta ggataatgaa gtaaattaag atgaattata    29640
gttttggttt tttttgttat ttttttgatat ttaaataggg aatgagtttg gtgtgagtgt   29700
ttaaatgaat tttaagtatt tgatttttt ttatttgtga tttttagttt taaaaaaatg    29760
tgaaatttga ttttataata aatagaaata aatattattt agtttagag aatttatttt    29820 tatggtgtta ggaggttgt tgtggaggtg gggggaggga tgtgttgaga ttttttgtta    29880
tgtttgttaa tttttttgtat aattaaagtg ggtgagaata aatattatgt tggggaattt   29940
agagtaaaaa gtaattgttg atttttttgga gttgataata ttattgttttt tttgttttag  30000 t                                                                     30001

<210> SEQ ID NO 26
<211> LENGTH: 30001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 26
attaaggtga aaaataatg atattgttgg ttttagaaaa ttggtggtta ttttttgttt         60
taagtttttt agtgtggtgt tgttttttgt ttattttggt tgtgtggggg gttgataagt       120
ataataaaag attttagtat attttttttt ttatttttat aatgattttt ttagtgttat       180
gaggatgaat tttttgggat taagtggtat tgttttttat ttgttatgaa attaaatttt       240 atatttttt aaagttgaaa attgtggata aagaaggatt gggtgtttaa agtttatta        300 aatatttata ttgaatttat ttttttgttta gatgttagag gatggtaggg agggttaggg     360
ttgtaattta ttttgatttg ttttattgtt ttgtagtttg taaattataa ttttgtataa     420
```

```
ttttaggaat aagtaggttt agaattaatg ggttaatatt atttaaaata aaatattggg    480
agtatgattt ttgttttaat tatatattgt ttgataagat ttaggaaatt ttatttaat     540 tttttaattt ttgagttttt tgagaaattg aagggttgta gttattagaa attattttg     600 ttttttttaa tgttttaaa ggatttggaa atagtaatgt aatataatat gaaggatttt      660
tttatttaag tttgaagata aatgtggaag tttaaatatt ttgaattgga gatgttttt     720 tgtaaattta ttatagatgt atttttttg agagaaatgt atataaatta tatatgtata     780
tatgtataaa tattttttta gaataatttg ttagaggtgt aggttttttt gtaaaggagt    840
aaatttgaga gttattttaa gttgatggat ttgttaaatt tttttttttt ttttttttt     900 ttatattatt tgttagttat aatggaattt ttaggttta agttaaagaa aaattggaga    960
gataaaatta gattttgtag tttttttttt ttttgggaat gttttttttt tttttttag    1020 tttttgatga atggttatta tttattttta ttaaatttaa ataaggattg ttgttttgta    1080
tgtttaatta ggtaggtaga gggaattggt ttgtttagga agtagtgatt gagatgtttt   1140
ggttaagtta gtgatagagg aggggagaaa gaatttagat taatttgtat gtagtatatt   1200
ttatttttat gaaataaaat atatttgttt tatatttgtt gaaaagtaaa ataataaatt    1260
tgtatgaaat gttatatata gggtaggttg tatatagtag ttttagaaat attattgtat   1320
ttattagaga aattatttta aaattgatat ttatatattt tttataataa taataatatg    1380
ttagaaatat atagtgtggt atttagtata tatatttttt tgtttgtaag tgaaaaattt    1440 taattgttt tgtataatat gttttatttt aaagtttaat tttaaaaat attgttgtga     1500 tattattaat aattgttttt ataaaattaa tttgatattt tgatatatat atatttttt    1560 agttattaa atgttaataa tgttaaattt aaaaaataat aagtttatag taatgttaaa    1620
atgttatatt tagttaaata tttgtttgtg tatgtgttt tgtaattgtt agaaatattt     1680
gtagtgaaag atgttagata ttgaggatat ttttttgaaa ttaaaggagt tttttttttg   1740
atttagtggt tttttttttt ttatatagtt tttttttttt ttttttttt tagtgtttat    1800 gatttttag tataatttt agttttttaa gggtggagtt ttttatttg gtaaggtttt      1860 aggattttgg tgttgtgggt gtggtttata tgggttggtt tattgtatat tggtaagtat   1920
ttaggttgga ggttgggttt tgtatgttgg tgtagttgaa gttggagtgt tgttttgttt   1980 ttagtttag gttggttagg tttgagttat atgtgttttt ataaatatat ggaggagttg     2040
gtggtgtgta aggataggta ggtgttggta ttgtggaatt tagtgatggg ttatttaggt   2100
tgtttaagtt atttaggttg ttgagattgg agtttgggat gtttgttatt gttgagggta   2160
ttatgttgga tgatatgttt atggatgaga tagagttggg tggggaaaat atgttttgtg   2220 atgataggg gttgatgttt atagagttga agaaggggaa ttttggtg gataggagg       2280 tggatgtaag ttttttggtg gtttagttgt tgtaggaata gtttgggtat atgttgttgt   2340
agggttgtat gagtttattg aattgtggtt tgaagtatt tttgtatagt ttggtttgtt    2400
ggttgtgttt tttttttttt tatttggttt gatgattttt gaattaaatt tgggggtggt   2460
tggggtaagg gagtaaatag atgttatagt gtagattatt aaaatttta ttggaggtta     2520 attttgtttt ttttttgata tatatgttag tgtatttata tattttggtt ttgttttatt   2580
gtattgtttt gtatattaag atattagggt tagtttttag ttattggttt gggtttttat   2640
taagtgtagg agatttggtt tgttttggtt tgtgagttgg gatttggagt tatgttataa   2700
attttagttg aatgtatgga gatttgtgga tggtttgatt atttagttag gtgttttttt   2760
```

| | |
|---|---|
| aggtttaaaa atatttaatg taaaataaat gtggggtagt aggtttttt aatttttttt | 2820 |
| ggggtatttt gtaaatttgt ttttatttta aagttataga tttatggatg aggagaaggg | 2880 |
| gttggaaggg tattagagga ttgtttttt ttttatgtaa tttttttt tttttttga | 2940 |
| tttttattgt tgtttttat tttttggtat gtgtttttt aatagggatt aggttgttaa | 3000 |
| tattttttt tgtttagtaa aataattaaa taaagagtaa aagattattt ttttgttagt | 3060 |
| ttgttaattt taggagtttg gtatattaaa ttttgggaat ttggaaaggg tagttttgga | 3120 |
| gattttttt ttttttgttt tgttttttt ttatttaag tttattatag gtttgtttgt | 3180 |
| gtgttaggtt tagttgggtt gtttggtttt gtaggtggtt atttaggttg gttggttttt | 3240 |
| atttgtgttt ggtggtttag ttgtaatttt gattttaatt tatattgggt ttttttgttg | 3300 |
| ttttagatgg tggttttgt gtattggaga gaggtttggt ttgagatatt tgagttgata | 3360 |
| ttagtgatgt tttatattat atatttttgt tgggtttagt tgtgtaatt gtttttttt | 3420 |
| tttttttt tattttgat tttttttta tttttttt tttttgtatt tgattgttat | 3480 |
| aaaaagtatg ttttatttt atttggtttg ataagtagtt gttttggaag gagaggtagt | 3540 |
| tgtaaggaga gtttagtgtt gtggttataa agtattaggg tggagttgtg aatagtggg | 3600 |
| tggggtggga gggtgttt gaaggatttt agaaaattta tagattttgt ttttaattat | 3660 |
| ttgttatttt tattttaggt tatttaaatt ttgtttaggt gagaagagta tgtgagaggt | 3720 |
| ttgttttttt gatgtgtaag agagttaatg aaagattgat tttgtttaaa attatgttgt | 3780 |
| ttaggattta gttttggttt tggatagtta aattaaaatt attttaatt ttttttggt | 3840 |
| tttttattta ttagtatagt tttatgtttt gtataaatgt tatttagaga gtgtttttat | 3900 |
| tttttttgat ttgggagagt attttggttt ttattttt tattgttgtt tttttttt | 3960 |
| tgtttgtttt gtttaattg ggggtttat ttttttatt tagagtattt aatttttttt | 4020 |
| ttttaatagt aaagttttg gatgttgttt gatttgtttg attttgtttt ttgttttag | 4080 |
| aattttaata aatttggaat ttttattga ttagtataaa ttaggatgtt gttattgggt | 4140 |
| tatttatttg agtttatttt tgttaattta taaagtatag atttgttata agttaaggt | 4200 |
| aagtttttt tataaaatta tgattataat ttagaagagg gggtgtgagt tttaattttt | 4260 |
| agagtttaat ttttgagaga agataaataa attaagtaga aaagtttttt tttttttt | 4320 |
| tttttttt ttaagaggat tagtagttgt gtattaaaat tttgtttttg gagattataa | 4380 |
| aattaggaaa tagggtgtgt gggagagatt tgaatggttg aaataattgt aaagaaggtg | 4440 |
| taagaagtgt gagtttagga gggaaaaagt tgggttaggg ttgggataaa ggttttttag | 4500 |
| ggagggttaa ttttttgtg ttttggtgg gtttttttg ttaaaggttt ataggttgga | 4560 |
| gtttgtttgt ggttttggt ttggtaggga ttttattagt tttgttttgg taattgtaag | 4620 |
| ttaggaatat aatgttttgt gtagggatt gtttatgtag tttagtttgt gagattgtgg | 4680 |
| gatggtgggg tagtgagttg gtgttgtttt gggagtttga gttagggtgg tagttttgtt | 4740 |
| ggttttggag agggaattgt aatttgtaa ttaggttgtt gtgaggtttt ttgttttgt | 4800 |
| aaagttgtgt tttattggtg tttttttagg tggtgttgtt ttttatattt tttttggtt | 4860 |
| tatttggttt gtatttttat aatatttttt tttatttt tttagatttt gtgttggttt | 4920 |
| ttatttggat ttgggttttt gtaaggttgg tttatatagt gattttttg tgtgtggata | 4980 |
| tgtttgggta gtggttttt tggaaagtgg tttttagttt ttggagttgt tggttggtaa | 5040 |
| agtgagtttg ttgttgtttt tgttgttttt ttttagatgg gttttggtg tttatgtttt | 5100 |
| tatttttt ttgttggttt ttattttttt ttgaaaatga aatatatata tttttttgtt | 5160 |

```
agtatgttta tttgtaatgt ggatgttaat tggattggtg gtagaagttg tggaagagtt    5220
gggttgtttg gtgttggagg agggtgtgtg tggtggtttt gggttgtgag gagtgttgtg    5280
tttgtggggt gtgtaggtgt aagtgtgggt gtttgtgttt tatttttttt ttttttttag    5340
tgttgtatgt tttatttata tgtttatttt attgtagtgg tatatttatt tttatagttt    5400 gtgttttaa gtatatttat atattttgt gtagatatat taaattttt gggatgtgta      5460 tatgtgtgtg gtttatagat tttttttttt tttgtagaaa gtttagattt ttatgtggtt    5520
tgggaaggtt aggaaaagat gtggggattt ggttgggtat tgaagtttgt tggtttttt    5580 ttaaaaaaaa aaaaaaaatg tttttttgtg aagggtattt ttgagtggtt ttaggtaatt    5640
ttttaatgag tggagttttt tgggagttga agttgagag gaaatagggg atagaggttg    5700 gtggttttg aaggttttg aattaagatg ttgggatttt tgtgatttag gaaatagaag     5760
ggaggttagg gtatgaatag agagggtggt agaattgttt gtgttttag tgttttagga    5820 gttgggttg ttgagggaga attaaaggga tgtggggtag ttaaaattt ggttttgga      5880 agttttgtgg ggagttaggt gaatgattat ttttattatg ttttttttg gaggggttga    5940 ttttttggg gtgagaggga gtgggtggtg tagagtagtt gagtgggaat gtttgtaggg    6000
tggtgtggtg ttttatttgt ggttttggg ttggaggtgt tggagatggt gtgtattttt    6060
agtttgtgtt tggaggagtt tagtgattgg ggttgattgg gagttagaat tgaagttatg    6120
gttaatggtt ggggatggtg ataggaagat gaggagatgg ttgatagttt ggttttgtt    6180 gtttggtgtt ttaagtgaag tgggtttttt atgtagttta tggatgaggg agtgtgatgt    6240
tttattagtt tttggttatt gttttgttga gtttttgtag ttgttgttgt ttgttttggg    6300
ttgtgtttta ggtgtggagt tttttgttg tggggagagt taggggatgt aattttttgtt    6360 gagttttaa gttaagttgt ttttgttttt tttggaaggt ttaagtgaaa aagtttggag    6420
atggaaagtt agtgggtaaa tgaagatatg ggatgtgggt agaagggtat tatttagagt    6480
gtttttaggg agtaggtttt taagttttaa agtgaaataa gagtgggtaa agattttttt    6540
tttttttttt tttttttttt aagaattttt ttaataagga aagttaatgt tgattgtgtt    6600
ttgtttgttt ttttttttatg tggtagtttt gatagagaag tgttaagagt gataggata   6660 ggtaggtgat attagatttt ttgtggtggt agtagttgtt gtagttatga tgtggttttt    6720
tgagtgtatt ttttgtaatg tgtatatgta tattttttgg gtggttgaat aggagttggg    6780
ttttgttgta gtttagtttt aggtatttag gtgagtgatg gattagattt gtggttttgt    6840 gttttttgt tggtttaata tttttaaaatt agaggtgggt ttttggtgt tgagatgtta    6900 ttttgttgtg gttttttta gttttttttg ttttgttttt tttttagatt tttttttggg    6960
tgtgattgat gtggttttgt attaattagg atgtttgag ttgtggtgga gggattgttt    7020
tgtttgtatt tattagtagt gtggggttgg gttattgttt tgttgtgtgt attgggttta    7080
tataggtaag ttttttgggaa tttagttttt gtttagttta aggtgatttg gttttttagta   7140 tgaatttaaa ggtgaagaga tgaggttagg agttgaaggt ttgggagaag agagtggaat    7200
ggttaagaag agaaaggtat aaggattaat aagatattta ttttttgtgt tttattatat    7260 ttattttttaa tttttttattt tatataaaaa ggagatatgt tatttaaaat tagaaaattt    7320
gaaaaatagt aataaattat tttttttgatt ttaaattttt taaatagttt gttaagtgaa    7380
tgttgtgtta atttgaagaa gttttaattg taaagaagat agagttttga aaaggtaggt    7440 taataaaatta gaaattgaga agtaaatgga tttgttaaaa gaaaattatt ttgatttaa    7500
```

```
atgaataatt gtttggtggt ttattttgga tttatataag aataaaaagt tgttttagat    7560
tatgttttt gtgatgttta ttagttttta gatagaaaat atataataga agagaaattt     7620
taatttagtg ttttaaaat gttgaaagtt tatttatttt atttaatgtt gattaagata     7680
tatatttag atttttaaa tttttgtat attgtattaa gttgttta atttgagaga         7740
gttatgtttt aaatttgatt tttttgttta ttttattatt aattagattt aaatttataa    7800
agtttgtaga attaataatt ttgagttaat tatatatgaa atatgtttta atgaattttt    7860
atataattaa gaatgttgtt aaataattaa ttttaaggat aattttaat agttattttt     7920
tttttagt gagtttaagg ttgttttgag ttattaaagt ttaagtaggt agaaggggtg      7980
tgtgtgagtt aagggtgaaa agtttagaat tgtgtttaat tagtaaaagt aaaattttat    8040
ttatataaaa taaaaaaaat tattttgga gatattaatt ttttatagta ttgttttaa      8100
gtaaatttaa tttttaaaga aattaaagaa agaaatttaa atatatttaa aataattttt    8160
gaaagtttt ttgtttttta gtataggtta gttggagagg ataaattaat ttttttggg      8220
tttttgtatg ggtgattgtt ttattatgga gttagtgtta ttattttga atgtgtattt     8280
gtttgatatt atagttaatg atttgtaatg ttagtatgaa gtattttaa aatattttt     8340
ttttgttttt gtttataaga ttgggaaatt tatttgatgt ggaataaagt ggatgaagta    8400
gattataaat atatttgtaa tttatgtgtt tttttttgt tttgattatt tttaaatttt     8460
atttgtaatt ttttttatt ttaaatttgt agtttaaaga tgtatatgag aattgttttt     8520
tagtttttt ttattagtat tattttattt taagaataat ttagttgtaa gggaggaatt     8580
tttttatagt aagtttaaa ttagtatttt tgttttaat tttttatttt attttattt      8640
attttatata tatagatatt tgtttagagt aaaatatatt tttatgtgat aggtttgtat    8700
tagttgaggt ttatatattt agttatatta ggttttgtaa ttttattatt aaattatata   8760
tattatatta gtagtttgtt ggtaaagaag gttaaattaa tttatatttt gtttattatt   8820
tggtgtttaa atgatgtatt ttattttgga gatttggtgg agaattttt ttttagattt    8880
tatagtgttt tattgaagat aatgttttta tatttgtagt ggttttaat ttgataagat    8940
tttaatttgt ttaagttttt taaataaggg ttttaaatgt tttagttgt tttttttattg   9000
aatttttttt aattttttta agattataaa gtatatgtgt aaagtaaata ttttttttta   9060
ttgtattgtt agttgatgat ttataattaa gttaataaga atttagtttt tttttgttga   9120
atgtgtttat taattatatt ttagtttttt ttttaaatt ttagaatagt tgtggttttt    9180
ataatattat gttttttaaa gtttttatttt atgaagggat tttattatat taagaatga   9240
aaaaaatttt tattgtagtt agtatatata gttttttatt ttttgttttt taagatttaa   9300
attttagagt tgtaaatatt tttggaagtt tgggtgttaa tgttttattt tagaaagttg   9360
agaagtttta tagagttata tagatttta aatttatttt ttataaattt atagaattt    9420
gataaaagtt ttggtggttt tatttttattg atggaatttt tattatgata aatatatatg  9480
tatgaaggat tttaattagt ttttaaagtg gttgaaaaat ttaagggtat gtgattgttt   9540
tttatagtgt taatgtgtgt gagatgttgg aagtattggg gattagtagt agtttagatg   9600
tttaaaaaga taaggtgttt taatttgtgt ggatttattg aagttaagtg gtgaataaag   9660
ataattattt agataattta gattaaagta aaagtaaaat tatatttatt tgtatatata   9720
tatttatatt tattttatat tatagatata tatgtgtata tatatattgg ttttgtaaat   9780
aattgattta aagtgaggat ttttttgta ttttttagt aggagtttta atattttttt    9840
aatttttaa ttattttata tattatagt agtggtgatt gggtgatatt tttttaggt     9900
```

```
tttttgtgtg gtaggatatt aatatgataa gtttgtatgg ggaaaaggag gtatgtggtg    9960
ggaattaaga aatattgttt agtgaaaatt ttgtggtatg gtggtggttg attttggaga   10020
tttaatgtat ataagatttg tgggtgtata ggtataggta gtatggatga gaaaggggtt   10080
agaagaaaat aaattttatg tattttgtga ttttagtatt attgtgattt ttggttaagt   10140
ttttttttaat tggttttaga aattattatg agtttagttt ttaatataga aatttttaat   10200
atggagaata ttggtgggat tttgtaggg aaattagagg tgttgtatgg tttatgtggg   10260
gtaaagaagg aaagtttagt gttggtgtga ggttttgagt ttgggagata ttaggggttg   10320
ttttgattgg ggttttttgt ttatttttttt aaagaaagat tttagaggag ggaaatgtgt   10380
gatatggggt tagttgtgtt ttgtgttggt atttgttatt gattattagt tttaaagttt   10440
tatttaattt tatattttttt agtgttagtt gtgtaaagtt tttttggtta tggtagtgag   10500
tggttgggtt gtgttgttaa atttttgta ttaatttggt ttgggattta attaagtgat   10560
ttttgatttt tggaaagagt ttgttttttag agtttattta gaagatggtt taattagata   10620
ttttttttgag ttgttaggtt ttagatgggt gggagtttttg ttttgtttaa gttagtttaa   10680
ggatgaggtt tgtttggatt tagtttggag ttatgtgatg ggtgtgagtg tgtgagtttt   10740
tggtaaggtg tagaggttag atggagattt tgtattttgt ttgagaagtg ttttattttt   10800
tttaatattt ggttttttttt tgtatataaa ttaagttgaa aatagtttat tatttattat   10860
tttttatagt tatggaatta aataatttag aaattaaaag ttttattgta gttgttttttt   10920
tttttattttt ttaaatggaa tttaaaaagt tttggttttgt taaaagggga agattatttt   10980
ttgaattgga agtttgtaga tatattgagt aatagttatt ttttttgggt ttttgtaaat   11040
ggtatttatt tttttaatttt atagttttag ttgtttaatt atttgagatt tggggtaatt   11100
atttggggga atagtgttta gatggtagtg ggagttatta ttttatagtg gtttggggaa   11160
gagaagagaa agagattaga ggaggggta tttgttaaaa ttatttaatg aatatgttgt   11220
taatgttttt ttatatttgt atgttattgt tatagttttt ttaggtgtta ttgagttttt   11280
agaaagtaat tatttgttga attaagtaaa ataaggagaa tggtatagta tatgtgtttg   11340
gagaagggga aggaagggtg gaatatgaaa ttgagtatag atatttaggt taggaaagaa   11400
ggaagtggta aggggttaaa tgaagtttta ttttttttgtt atttttttaa ataatagttg   11460
gattaaatat ttatttgttt tttttttttt ttttttttttt ttttttttag tttatgttta   11520
tttttttttt ttattttttt tgtttttttt ttttttttgtt ttttttttt tagatatgtt   11580
ggtagttaat atttagtatt agttgttatg gtgattataa attatttaaa tttaaaaata   11640
tttatttata atttgagatg aagttttat ttttttagtg aaataatatt ttaaagttg   11700
ttagttgata aaaaaaagg aatttatttt attgtagtaa tttaagtaat atattatttt   11760
taaaggttta aattaaaatg ttagtttgtt aaaaatatgt tggtagagtt ttggatattt   11820
tttttgttag attttttataa agaagttgat tttgttattt ttggttgttt tttaatatat   11880
atatataatt ttgtatgttt ttttttttttt tattaatttt tttttttttt attaattatt   11940
ttagtttttta aagattttat gtattgggtt ttaaaagaaa agaattttttt tttggattag   12000
aaaatagttt tattggttgt tgaagtgaaa gatgtggggt ttaggggaa aggttattag   12060
gattataatg gtggtggtgg taggaggtta ttttagagga gttaagaaga aaaaaaaatg   12120
tagggagaag gattggaggt ggaaagatag agtaatagaa aattgagttg ggtgttagg   12180
tgttgtggtg aagtttagtt ttgaaatgat aggtatatat ttttttatttt ttgttttttt   12240
```

```
tttttttgag agaaaatttt tttagttaga gattttgggg ggtaggaggt gggtaaatgt    12300
tgttgtagtt gggttttttg tttttttattt tgggtttgtt gttttttgtt tattttggat    12360
tatagggtat ttgtttagat gaagagttat taattattta tttagttaat attaggaaga    12420
tgataaagtt tttatatag gattaagaag atattagatt gttttattag tatattttg      12480 tttatgaata agttttttgtt atatatttt tttttttttg agttgtttta ataattgttg    12540
tatatattag tagtgggtgg tgaggaataa tagttgaatt agtttttaaga aattttgtgt   12600 attgagttag tagtgaggaa tgtgatttgt gaagattatt tttgtgggta gggatttgta    12660
gggattgatt attttttggat aattggtata atttttttg ggggtgaaaa attataatgt    12720
ggtggggtat tttttaagtg agttgtagat ttgattggtg tggggggtgg gggaggggag    12780
gggagaatgg gatggtggag gttgggtgga ggaaagaaaa tggaaaattt ttttttatttt   12840 tattttgttg tttttttttt aagttttatg ttttttttgg taagtatttg ttttttttgt    12900
gttagttata gttagagttt tttatttttt tttatatatt ttttttttt tgataaggtt     12960 taggattttg gttattattt tatgtattat tattttgtgt tttgttagag atggtttggg    13020
ttgattttgt tggtgtttat gttaggatta aaatttttt atgatggtga ggaaaattgt     13080
attatttgtt tttaggggggt atattaggag tttatgtagt atatgtttg taaatatttg    13140 ttgattgaat gagaggtgtg ggggtgggggt ggtggagagg ggtttgtggt tgttaaggtt   13200
gttagggtta atttaggttt tttgaagaag gttgggattg agttgttgtt gtgtgtgaag    13260
gtgtgtgttg tggttggggg tgttataatg ggttatggag tttattttt agagggagga    13320 agtttgtgta tattagtgat ttgggttgaa tattttttagt ttatttattg ggttaaagtt   13380
atttaataat taatgtgttt ttgggggagg ttgggggaag tatttgtttt ttgtttgggat   13440 gtaaagttag gtgttaggtt taaaggggtt gtagtgtagt ttgattttag tatggaattt    13500
agagttgttg ttttgaaatt ttttaagtta gtgatagagg agggttagtt tgttttttttt   13560 ttgagggtga agattatttt atgagttttt tttaggattt ttaaagtaag aaaagttaaa    13620
gaaaggtttt tttgttttag ggggttgttt ttagttggtt tttatattat tttttgttag    13680
ttgtgtttat tttttttttaa atttttggtt tttaggggtt tttagttgtt tttgtgttat    13740
ttttgttttg gggttttatt taggttgggt atttgtttaa tggatattaa ggagaatggg    13800
atttattagg gaaggaaggt agagtttgga ttgtttagag gtggatttg tttatataga     13860 atgtttagtt tttaatgagg atatggtatt tttgggtggt gttggggta gaggtggaga     13920 gggtagtgta atagattatt atggttttt gaagaagtta tatgttattg tgaatttttt    13980
ttttttttaa aagtaaagaa aaatttttaaa aaaatataag aaataaattt ttttgttttta   14040 taagtaggtt gtggttagga ttttggatat tttataagtt aatttaaaat tagggaagga    14100
taggtgtttt atttttagt agtgttatag ttttgtttat ttgtgtgatt ttttttttgtt    14160 gtttattagt ttttttaaaag ttaattaaat taagattttt agtatttttt tttattatat   14220 gtttttttt aattaatggt attaaatgtg tttaggtagt aatttttttt tttggttaaa     14280
aagtagaaaa agatatattg agtgtagggg aagagttttt tatgtgtatt aaaataatgt   14340
gggtttgaaa gtaatggtta agaaagtaat tattattatt ttttagtttt ttatgtgtta   14400
gttattaaaa gtgaatgatt aggggtgttt gtgtggtttg tgattggtgt aagtagaatt    14460 ttttttgttttt tagttgtttt ttgtttattt atgaggattt tatttttattg taggttttttt  14520 tatttgttttt tagaatgtat ttttttatgtt taggaaattt ggggtaggga ttggggggaag  14580 gagatatttt gtgtttttttt ggttttttagt ataataagaa atgttagttt tggtttggtg   14640
```

```
attgtgagtt tgttttgtgt gaagtgagat tggggagttt ttttagtttg gttggagtta   14700 ggggttgagtt tgtgtaaagt attttttta gaagttattg ttgttttga tttttaatta   14760 tattttaaat atattatggt ttaataattt attttatta ttgattatta aatagaagaa   14820
gaatttaata taatttaaat gatagaaatt atgtgatgtt attttgtat tgttttatt   14880 taattttatg gggttaattt tggataagtg agtgtttaat tggtttagta gggtgattgg   14940
tggtgtagtg tagtgtttgg gtgtgaagta ttggattgtt ttagatgttt tattttaata   15000
aatgattatt ttttttaga tttatgggga aattttaatg taagattttt gtttttttt   15060 tagtaatatg gtttgttttt ttgattgggg ttttaaattg ttttttttta ttttatatta   15120
tatttgtatt tttatatttt aatttggaaa gaggggggtta ggggttgagg gttgtggggg   15180
ggggggggtt ttatttgttt atattattaa aggttaatag ttttttaagg ttaggtattt   15240
atttattatg gagttaggaa aatagaggaa tagtaaattt gaggggtttt tttttatgta   15300
tttgaaaaga aaggtatttt tttttttta ttttttatat ttttttttt gttttataga   15360 ataagttta atttaggaaa ggtttgtggt gtaggttgga gattttttaa tttttatat   15420 aagtttgtag attttttttg gtaatgtttt ttgattttt tagagtgaaa ttagttaatt   15480
aagtaatgat attgttaaaa tttaaggttt ggtaattagt attttaggta ggtttgtgtt   15540 gatagggta aattttatt ttattttggg ttgttaagta tagtggttgt tttttagttt   15600
tttagggatg ttgttggttt tttgttttt tttaattag ttaaagtaaa ttttttgttaa   15660 tttaagtttt ttttgttgt tttttgtgat gaattgtgta tttataagtt tgggtgggt   15720 gtggttgaga gtttgagtga ttgagtgggt tttggtggtg ttgtgtgtag tgggatataa   15780
tgagtgatag aggttgttgt tggattattt ttttatgtta gtttagatgt tgaggtttgt   15840
tggagtgtgt gtagggggatt agattatagg gagtgagtga gagggagaga gaggtgttgg   15900
gttttaggag tgtagtataa tttgggggaaa ggaattaatg ttttgggat ggttgttttt   15960 tgttttattt agaggtggag tgtttaagtt taagtagtag gtgtgttagg tttggtggtt   16020 ttgtttttt gtgttttgtt tgaggtttag agttttggag gtgggtgttt agtgtgtggt   16080
ttgtgttttt tttttggttt tattattggt gttaggatgt tgttgtggga agaatttgtt   16140
gttggttgtt tttttttggt ttttaggaga gtttgtgaat ttgattttt tgattttgga   16200 gtttttggag aagagatatt taatggttgt tggttgtatg tttgggttat gtgtgtgttt   16260
gttttatgtg tggagagagg tgttttggat tgtggttgaa aggagttggg gatgggagga   16320 ggggggagggg tgaggtaggt tggaggagaa agagggataa agagtaaaga tttagttaga   16380
ggaaagagtt gatggtattt ttgtttttg gattttttgg taatttgggg taggatggtg   16440 tattttttt gtgtttttt ggttgttggt ggttttagtt gggaggagta ggttgggggg   16500
ttttggtata tagtgtgttg ttgttttta gtttattgtt ttgttataggg gagaggttat   16560 tggtgatttg gttttgattt ttttttgtt taggttggtt ttttggggaa gtgttttttg   16620
ttggggtttt gttgtagggt tagtgttttt ttgttgtttt tatgtggtgt ggtttttgt   16680 ttgatgattt gggtaggaga aggggtttt tatttaattg tatatatgtt gatattagtt   16740
tgtggtagtt ggttttttt ttttgttatt tgtaaaatag aagagaagga aggttgtaag   16800
aagtggtggt tgttgagtga gtagggttta gatgagatta tgttatatta gttgttaggt   16860
gtttattgtg tgttaggttt taggtgtgtt ttttgatttt gatagttttt ggttgtgtag   16920
tagtattttt agtttagttt tgggtttagg atatttattt attaagaggg gattttttt   16980
```

```
tagagttgtt gtaaaagtgt ttagaggtta gaggattata aagttatagt gtgttgggga   17040
ggttgtggat ttatttttaa gaattttggt gttggggtta agaatttatt tgaatgtaat   17100
ggtagtggga gtgggtgggt ggagaggatt ttttttttg ggaagttgta tgtaaagatt    17160
atttttagt gtttgtttat tagttggagt ttggtaaata tttgtagaat attagtgtta    17220
atgtgttttt gttttagata gtagtttttt ttggtttttt gtaattttga aatgaatggg   17280
tttttggttt agggtgtttt aggagtgagt tgagtttggg tttttatttt attaggagtt   17340
atttttttat atttagttat attttttttt agagatatta atttggttat ttatttattt   17400
attataaata attattttaa agtatgattt aagattgtag aggagagata ttgggtggat   17460
tgagtgagat tgaggagagt agggtaaatg ttttggagg gtttattgtt tgttaaggat    17520
ggagaaatag ttttggtata attgttattt agttttttt tttttttttt tgggtgagtt    17580
aaatttttt tatgttttta attataatgt agtgagttaa gtatttaatg tgttttttt     17640
tttttgttat aggtaagttg ggagaggtgg gttttgaggg gttttattgg gtgggtagaa   17700
gagttgtggt tgttttaaag ataagaaaag aaggtttagg gttttttagg ttttttgat    17760
tttagtgttt gtttttttttt atgttaatta gggtatgttg atgattggag ggtttatttt   17820
gtgtgggtgt ggggattggg gtgggagtaa gtgttgttgg gttggtggag gtatagaggt   17880
ggggtaggga gttgtgggtt tgttttggt ttgagtattg ttttttttgtg ttttggtttt   17940
ttttgaagga agttgggttt tggggagttt ttggttaagg ttgttgttta taggaggggt   18000
tgtttggtgt tgtggtgtgg ggatttaggg tggggatggt taggtggttt ttttatttgt   18060
tagtgagaat gtgggtgggg attttgttga tttgattttt gtgggtttgt gggtttagaa   18120
gtagtagttt ggtggtttta gatttagtga ttttgtagta aaattatagg attagttttt   18180
gattgagatg tttgtttgtg agatattata aaatttatta ttagttttt ttattaattt     18240
gatatgaagt aatatagatg ggatttatt agtttagatt ttaaatgttt atttatgata   18300
attttggagg aaatttgtat gttattatta ttttgataat ttttttttttt tatatgtttg   18360
aattggttgt attattagtt ggtagttgga gtattgtaga tggtaattgt aaatagtttt   18420
tatttattta ttttttttaa agaatgaaat atataaaga aaagattgt gttgtttggt     18480
gtaaagttag ttaattatta tatatttttt tttttatttt tttgtgtttt agtgttgaag   18540
attaaataaa gtaatataaa ataaatttt aagaatttat agagtttat tttaaggatt     18600
gaaagaagg ttaaggtgtg ttttttagtt tatttttata tgttttgtg atttggagat     18660
ttattttgta gttaaaatga gttttgagat ttgtattttt atgttttatt taatgattag   18720
gtttattaga agaattgagt ttaaataatt ggggaagata attttttaaa aagagatttt   18780
taattttgt ttgttgattt ttaaatttgt tttattaaga taagtttttt gtgagaaatt    18840
tggttgttag attttggaat tggttttaat ggttaatttt ataaattgag atgggagatt   18900
tttttgatg ggaggtagtt tttatttta aagtttatgt tttagttgga atgtatatgt     18960
taaggatttt tgttttggtt aatttgggtt ttatattgtg agtatataaa agtattata    19020
tggttaatgg aggatgagga attatggtaa agtaggtagg taagttttaa gaataaaat    19080
aatttgttaa aaaataattt ttgatgatta ttgtaagatt gaaagtgtag gaaaaatata   19140
gtttgaataa tttagattt ttttatattt tttttttttt tatatatttt gttattttat    19200
aataaaattt ttaatggaaa gtttaaaaat aaatagtata ggaatatgtg ttttaaatga   19260
attaaattgt gaaattagtt agtaaattaa tttgtagtaa gtaattattt aaggaaatta   19320
aaatattgtt tagtttagtt ttgtatttta ttatgtgtat gtgttttta taattaatta    19380
```

```
atataagtgt tttaggaata tttgaagata aatatgttta atttaaggaa taaagtattt    19440
aaataattta agtgtaattt tgttgagtta aagtaaaata ttttataaat gaagtggtta    19500
tttaattttt tagggaaagt ttggttattg aaatgttgta tgtttatgtt atattaataa    19560 aaattttaa tttattttgt ttatgtgttt tgttttttg atattattgg tatttgaatt     19620
ttagatggat ttttgttaaa atgatatttt gtgtgataaa agtattttta gttttgattg    19680
atagattaaa ataaatgtaa ggaaattttt ttaaattaga ttaattttt ataaaaatat     19740 tttagaatgt atgaattttg atatttatat ttataatggt aaaagttttt tttgtttagt    19800
ttagtaagat aatatttata taaaagagta aaaaaaaatt atattatttt atgatagttt    19860 gattttaaa ttgtttaaga aagtaaagtg gttaaattgg aaaagaggaa tatattttgg     19920
aggtttagaa ttgaaaattt ttttttaat ttttagttgg aaaataattt tttgtattta     19980
tttaaagtgt attttttgaa gtgttagatt ggagttgatt ggtgattaat ttaaaggagt    20040
tataatttaa agaaatggtg agagtttggt atttaggttt ggttttagg taatttgttt     20100 gggtttgaga ggttattaat tgttagttaa gatggaattt ttttttttt tttttttt      20160 taatggataa taatgggaag ggggttaatt ttttagtagt tgaaattttg tatttagttt    20220 tttatttga gaatgttaat ttttggtttg aggatttgtt tttgtagtgt tggtattgag     20280
atttaaggga agatatttg ttttaaatgt tagttatggt ttggtttttt ttttgatttt     20340
agtattttgt agattgttag tgtttgtggt gggggatgaa aggaataggg ttttgtaagg    20400
tttgtttgtt gattgtgtta ttttgggtga aatttagttt taaaagttat aaattattta    20460
tggtgaagat tttttgaagt ggaataaatt tttagatttg tattattta tatttttgtg     20520 ggatagatgg tttttatta ttggttattg ggagagagtt gttgttttg tgttttattg      20580 tttttgggg tgattttag tgagttgagt ttttggttgt atggtaagtg tttgaaagtt      20640
gggtttgaga ggattgtagg gttttgagg gtgttaagtt ttgaaggagt ttatgggtgt     20700
attggggttt ttgaaatttta gttgttattg gtagttttt tttgtttttt tttagttttt    20760
ttgtttggtt ttgtattttt ttttttttt tttttttta tttttttt ttttttgt         20820 ttttattttg tgtggggagt gatgtgatgt tagtagagat tttattaaat tttattgtat    20880
agtggtgtgt gggtggttgg ttgagtttgg ttgtgtggtt ggtgatttag gagtgagtat    20940
agtgtttggg tgagtgttgg ggggagtgag taggggtgat gagaaatgag gtaggggagg    21000
gaagtagatg ttagtgggtt gaagagttgg gagttggagt tgggagagtg aaaggagagg    21060
ggatttggtg gggtatttag gagttaattg aggagtagga gtatggattt ttattgtgga    21120
aaggaggatt agaagggagg atgggatgga agagaagaaa aagtaatttg tgttaatttg    21180
gtagttttaa taaattaaag ggggagtgtt agggtagtgg ggagatagaa atgtattttt    21240
ggggagtaaa ttaggatggg ttgggaggaa gtgataggga aagtggttta agagatggaa    21300
taaaggataa tgtttatggg gttgtttggg atgaggtgtg tggagtgtgg gtgtgagtgt    21360
gtgtgtgtga ttttttttta ggtttgtaga gttgaggaaa gaggttatag taaagaggga    21420
ttgtggaggg aggaaagtga gagattggta gagggtggga gtggaggtgg gtgtggtggg    21480
gatgggagag gatgagtgaa gagaaattta gaagaatgga gtgagttagt gggagagggt    21540
gggagggtta tagttgggag tgaatgagtt aggtttgtta gttggggaag gttgggatgt    21600
tgggtttagt ttagttggga tattgtgttt gaggttaagg tgggtggatt aggtatgttg    21660
agagtgttgg tgtataggtg ggtatggtta tgtattgatt tagtgtttat gaagggtttg    21720
```

```
tattggataa ggtttagatg tttatagagt ttagaatttt ttttgttgta tttatattta    21780
ataagtttat tttgggttat ggatatttta tttttttaaaa tgatgaggtt aaggtttttg   21840
gtgaggatgg tattaaattg tatgggatag aagtgggggt gggggagaga gttttttttta  21900 agtttatatt tgttttttgta aagtaaagag tatgtgaaat tatagggtat attttttattt 21960 gaaaagtgtg ttttattttt gaattttgat tttttgattt tttgatttga gtaaagatgt   22020
gtattttggt agtgagtaga atattttggt tttgttttgt ttttgagtgg aaggattata   22080
aatataattt gtttggagga ttaggtgtga aggttttttgt taggtatatg ggataatgtt  22140
tttttaattt taagggtatt ttgttaatgt atgttttttgg aaagtgttgg aatatagtta  22200
ttgtttttgg atttggattt ttttattaat attaatttttt gtttgagagt aaaatttagg  22260
tttgttatta aaagatatt tttttggttt ttaattgaga ataaagtttt ttttaaaagt    22320
tgtattgttt tttttaaatt aatatattaa tatttgtaat tttagaaata tatagtgatt   22380
tgggagaatg tgtataaaat agatatgttt aaaaaagttt ggtgtttaaa attaattta    22440 gttattatat aggtgttggg ttttttttat tttttgggggt tgtttggaat atgttatgtg  22500 ttttttttgaa ttattttgtg ttttgaattt atttgagtta gtagtaaaaa taggtaaata  22560
aatttgttta atttgttttg agtgttaaat ttttttattt tgaaatagtt aatagttgat  22620
agatggattt attttatgga aagggttagt tttttttagtt atgaagaaaa ttgattagag  22680
atttatattt taagttattt ttaattttta tgtaatattt gtgaaaattt aaatttttttt 22740 tttttattta gtggaaattt aaagtagtgt tatttaaggg gagagaaatg aggggggaaaa  22800 tgtttatgtg ttgtttaatt gtattttttt tttgattttg agaatttta tttttggttt    22860 ttgaaatttt gttgaggtaa gaaaattaaa ttttttttaat aagttttata attgaatttt  22920
agttatagga tattggaaag tgtagtttga gaaagatatt tttattttttg tttattgatg  22980 attttttgtag ttttttttatt ttttttgagta atgggttaat aatttttttt tttttttttt 23040
ttattttgta gagattaaga ggtgtttgta gtagaatggt tttgtttttta gttggtggtg  23100 aggataggta attttatgga aaagttggaa gagaatgaga aaattaaaga tagaaagatt   23160
tagagatttg tggagagata tagggagagg gaagggagtt gtgttgaaaa gatgtaaaga   23220
tatgtgtgtg taatttttttt tttttttagg tttttagaggt ttgtaaatta gggttgagag   23280
gaaggggttt gggaagttta tgttttttttt gtttttttttt tgtttggagt tttgtttgtt  23340
agaggttggt taatttttagt tttggttgtt gtagatattg tgttgagttt ttgggtttttt  23400 gttttgttta gtgttagtgt agttgaagtg agtagttggg gggaaatgta aatggttttt   23460
ggagaaatag aagatataga atgattttta tttttttttt gagtgtgtgg aaggagttgg   23520
atatatgttt tatgtttttta atttttttttt tatattttta gttatatttt tattaaataa  23580
ttaattaatg tttagaatta ttagggaata tattaggtat gtaattgtag aagtagggtg   23640
ttggggggtt ataaattatt gagttgattt aagatgtgga tttaggtttt ttttttttgtt  23700 aaagtagtaa aggaagagtg ggtttgtgtg attgtattta gattttgatt attttaaatt   23760
agaagggggt ggagggagtg tttaagtaaa gtaagtaatt ttttgttttg tagatgtaaa   23820
taagattgta gtattaaagg tattagtttt ttagggttta gattgtttgg attgggagtt   23880
tggggaaggg gagatattaa ttttatgtat ttgtgaattt taaggatgtt atatttttat   23940
ataaataatt ttagtgtgga ttttttggaa tgggggagt aatatttta ttttagaata    24000 ttaaaatatt ttttttttaa agtgtatatt tttttattt ttttaaaatt tgaattatg    24060 tttaaagata atagttttttt agtaaattgg agtattggat tatttttttt attttttttt  24120
```

```
attgatattt tgatgatttg attttaatgt gtgggggta tagggaatta aatatagttt   24180
ataaaattaa gtttagatga aatagtgttg gttaagtggg tttagataat ttttaatgag   24240
aattttaatt atattttttt ttttaatatg ttgagataag tgatagaatt gttagaatgg   24300
taattaaatt ggaaagttta gggagaataa taattttgtg attaaattgg ggtaaaattg   24360
tggataaatg tggggtgatt tttgttaatt ttttgttatt taagagttag gatttgggaa   24420
aggtatagta ttattttaga gtttgttgtg atgggtgtg tgttattatt tatttttttt   24480
attttggatt atgattttaa ttttggtaag taatttttt agttttttat tgataataa   24540 gtgagtatgt aaatattaat ggttagtgat gtttaattgt tttaaatatt attgatttgt   24600
tggttgtttt aaattgtttt tttagtttag gttttgtttt tgaattgttt attttagagg   24660
tttgatttat gttttgatg ttataatata ataattgttt ttttaaaaaa ggtatttaag   24720
atgaattaat tgatttgtat ataaattaaa attattatgt gttgttgatt ttggtgtttt   24780
ataattattt tgaaattagt atttaattat ttgagttaaa agaatatata aatgtttgta   24840
ttgatttatt aatgaattat ttaattaaaa tgtttgggta atgttgggtg ttggaaagat   24900
tgttaaatta agatatatta taggagggat atgaagatta gaaaggtaat agattaatat   24960
tttgtattta aaatggagtt tttggtgatt tttagttta attttggagt aggggttttt   25020 ttttttttgtt gttaaaaaga ttttgtgttt gtttgtgagt gagtgtattt aagtggaagg   25080
aatgttttta tggttatggt ggtttaggtt ttttgtttgg attgggattt tatagtttta   25140
atttaggagt gttaaatttt ggaagatttt gggttagttt tggaggtgtg tggttttgta   25200
agttgttagg ttaagtttgt ttttttttgtt tgttttttgt gtaggttggg tgtgttatgg   25260
tagtgagttt tttgtgtaaa tggagagttg gaattaaagt tgatattaa tagatatgtt   25320 aattgagtat ttattttgt tttgagaata ggaataaaag gtagttttt ttaagagagg   25380 tggtgtaaag gtatgttata ggagtttaga aaaggttggt ggtgggaaat ttgtagtttg   25440
ggggttagtt aatatttttt tttatttaa gtatttattg atttgttgtt gttattttg   25500 gtgatgtaga aggatatttg aaagaattt tgatggggtt ttgatttgag aaaggaggtg   25560
atttgtttag gtttttatta aattttaat tattatatta attgtttttt tttattttttt   25620 atttgatttt tttttttttg tttattttta atttttttaat tatttagaaa tttttttatt   25680 tttagtggt tttttttttg tagtagtttt ttatttgaat tttttttttg tttttttgtg   25740
gtagggtttg tatattgatt ttttgatt ttggtatatt tgggttttt gaatttttt   25800 aattttttta gatttgagga tggtaggttt tatttttttt attgtgtgta tatatttaga   25860
gatatgaaaa tttatataga ttgttttta atttagggta tttaatagat gttttttttt   25920
tagtttgttt tttgatttga aatgtttgtt tgattttaat ttgatatta tttttttttg   25980 tttttttttt tttaaagtag tttggatatg tgtgtaagtg agtttagaat agttttattt   26040
atatttttta ttaaattgta aataaaagaa gaattaatga agtagattgg tatatagatt   26100
gtattaagag tttgaattt tagttttgg atttttttatt taattttggt tgttatttat   26160
attgatagag ttatttttaag tagaggttta gagaaatttg tattgtggga taataggtaa   26220
agttatagta aaaagtggaa taattttaaa gttatttat tagaatgtaa attgtatttt   26280
tgggttttgt ttgtaattat ttagttttaa tatatataga gttagatagg aaaaaatagg   26340
ttaatatagt tattggtatt agagaagata aattttatgg gttttttagt gaaagaaga   26400 tttttaaagt ttataatttt tgattattta atttttatttta taattgtggg aatgaataag   26460
```

```
atattaattg ttttatgtat tttatttata ttaattaatt tgtgttttta ttaaaagtag    26520
ttatatagaa ttttttttaa tttttggtag taagtttaga aaatgaagtt tatagttatt    26580
ttgaattgga tatattttt gagttgatta ttttgtaag tgtaggaata taatatgtt    26640 ttttatggt ttttttgtat tttttaggg tttgtaagtt tttattaggt ttgatattat    26700
tgtttgggtt tatatttatt ataagtaaat ttgattatta tgttgatttt aaaatagttt    26760
atttggttag tataatttta gttttaaat tataaaaatt ttaatata tgaagtttt    26820 agtttttatt ttttttagtt ttttgtttat ttaaaatttt tatttaatt ggtgtaagta    26880 ataataattt gtattattat ttgtattttt tttatttttt tggagattgg gttggatttt    26940
agagagaata ttagtattat tattattata aataataaaa tttaaaagta aagtttttat    27000
ttgtatgata attggtattt ggaatgtttt tgatttattt aatgttattt tataaaggta    27060
ttttgtaaat ttttttggaa ttttagtaa gagtttgtag taattggaat aattttttgg    27120
gaagatattt ttttgatgg gttttagtt tttggaggaa tagattgaga gtaattaggg    27180
agggagggga tattggaaat tggtagttat gttagttgaa ataagtttgg gtttagtaag    27240
gtgattgatg ttgtggttga tttttatt tgagttttt tttaattggg gtattgattt    27300
tttttatttt gggattttaa ggtatttggt gtgtatgtag attttttttt tgtggtttt    27360 attatgtggt tttgtagtag ttttttggtt taatgatatt ttatagttat agtttttata    27420
tttattatta tgattttaat gttaggtttt ttagtgtatt tatattaaat ttgttttatt    27480
agtaagttgg agtatatagg agagatgggg gtaagtaagg atttagtaga gtttaaattt    27540
agatatgttt aaatggttttt gattgtgtaa agtgtggtaa tgtttttgt tgttttagtt    27600 ttttatttta agttttatat gtttttggt taatgaagtg tgatataggt tatatgttag    27660
gaataatagt atttgttgag aataaagtga atttaggaaa tttggtatat ataaaatgta    27720
tttagttatt tgaattagta ataatggtaa aaattaatat ttatagagtg tttagttaat    27780
ttagttattg tattaaatat ttttgtattg ataattatat ttattttta tgttaatatt    27840 ataaggtagg tattgttatt ttataaatga agatagtgag gtttgttatg attgtgttat    27900
tggtttaagg ttatttagtt ggttagagta taagtttata attgttggag gttatagtgg    27960
ataggatatt gttttaggtt atgtaggtag taagtggtat agtgggaatt tgaatttagg    28020
tttgtgtaat tttaaagttt aaaatgttaa ttagtatatt gaattaatgg taattggaat    28080
tagaagatta ggggttttg ggggaaggaa atatagaatt tatttatgga atatttata    28140 aataaaagaa taatgtagag ataggaaagt aaatatattt tttgagggat ggagaaagtt    28200
agaaatgttt taaatgttaa agaggaggaa atgagaaatg attggatgag aaagtagaaa    28260
agttaaattt tggtatttgt tttgggtagt ttaggaagag aaaggtaagt ttagggatat    28320
ttttgagtta taggaaaatt aatgtttaga tggttagttt ggattaagtt taatataggaa    28380 ttttaggaat atggttatt agaattgttt tttagtaatt ttaagggaga ataaaatttt    28440
tgaattgggt ttaagtagtt ttatttaga agtaaagaga gatggaagta aggattgagt    28500
aataagaata tttatattgt aagaatatgt aagttgagta ggagtgaaat ttagaaaaat    28560
ttgttaggat tttggttgtt gtgttaaatt atgttatatt ttaagtagaa attagatttt    28620
tattattatt atttgtttag gttagttag taatttatt attgtagtaa agttatttga    28680
aattttaaga gaaatgattt tttgtgttga agaagatatt ttgggtggaa ggatgttagt    28740
agataaatgg agtgtaaaga tagtgatttt aaggatatag tttgtgggga gtaatattgg    28800
attatatatt tgttgtttgt ggtagaatgt tagttagggg agaatattag gtagttttt    28860
```

```
ataagtttat tttattataa aaagatagga ttgattttaa aggttatttt taatttaggt    28920
ttgttttatt attgaaaatg atttaaaatt ggatttattt tggttttttt taggagggat    28980
agataaatat aatttgtata tatggttttt tagtttlagg aagtatagga ggagaatgaa    29040
agaattaatt tagttttttg ttttttggta aaaattttta tatttgtgtt gttgtaagaa    29100
tttaagatta ttttgtttag aatgttgtgg tattttlgaa agtaaggttt gagggtatat    29160
agagttttat ttttlattlt tatgttgtgg attttattgt tttttttaaa tgggaaagag    29220
aaattagaat ttatagaaag taaggtttgg aaaggattta gagggtattt tttttttta    29280
gtttatgttt aaattatttt tagaaatata gttagttata tttttagta aagagttttt    29340
tatggttttt tggtaatgta tttttatgtt ttataatttt atagttatat tgtatattta    29400
ttgattaaat tttaagtatt gaagaaaatg atgttatatt aaaaagtttt aattagtagg    29460
gggtatgttt tttagagttt tttaaatatt ttatatttttt attttaaaaa aagatgaaaa    29520
tattattagt ttaatttaat agatggaaaa ttttgttata gagatttttla gagagttata    29580
tttggttatg tagtgtgatg tttgaaagaa ttaaattaaa aataaagtta ggaaattttta    29640
tgtttagggt tttttttagta gatatattat tttttlggggg ttggttatta tttttttgtt    29700
tgagtaaagt atatgtttga ttgtaatttt atttgttttt ttgtttgttt gtttgtgagt    29760
agtttatttt ttaatttatt aatttatttt tttgttagtt ttttaaaata ttataagtta    29820
attaatgttg ataaaatttt attttlatta tgagtgttat ttgagtagat tgagatggtt    29880
gttatatttt ttaaatatta tgtgtaataa atagtgttgt tattgttttla gtgttatgat    29940
tttgttttta tttggaaatt gtataaatat tatatttttt gttatgatag gattattttt    30000
a                                                                     30001

<210> SEQ ID NO 27
<211> LENGTH: 9001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 27
aggaagggtg gatgtagtta tttatatatg gtttgttttt ttggaggata attttatttg      60
ataaataatt gttttlattt gaatagaata aataaggttt tatgatgaag taaaatatta     120
aatatatatg tattaaaaaa tgtataatta ttttttltgga atgggttata tagagatgtg     180
ttttttaaaa tgttaagagt gtaaaaggat aaatagtgaa aaataaattt ttttttltatt     240
ttgttttttta gtttttltaat tttttttattt agaggtgaga atagaatttt tatattttt     300
agaatttttta tagttagaat tgtttatatg ttttttattgt tttltatttttt attttgttt     360
gtataaataa atgaattgtt tattatggaa atttttttaaa agatttgtta atatttttaat     420
aggaagtatt aatagtttat gtttltaggat tttgttttta taatttttgta atattatatt     480
atgatatttla atttaattttt tattaagttt tgttaaaaat ggattttaaa ttaagttgta     540
aattttttagt aatttggttt tgttttttttt ttlttgatag tattattaaa taaattttt     600
tattgttgaa agtaataagt ttggttttgt tttatttatt ggttgtgttg gtgatatttg     660
gggattgtta ttgaatagat gtatagaggg agtttttata ggtaggggtt tttttgtttg     720
tgtttttggg agagtatgtt ttgtatattt gttgtgttga tgaagatttt atagttttat     780
tagttgtggg taagggggtt tgaggtagtt ttaggtaagt tggggtttag tggggagaag     840
```

```
ttgtagaaga attgattaga ggattttagg aggttttaga gttgggtgag gtagagagtt    900
ttttgtgtgt ttttttttttt ttttgtaatt tgggga tttt ttgtattggg gtaggttttt   960
ggttaggtgt atgggaggaa gtatggagaa tttataagtt ttttgattt tt agtttaga   1020
tgttgttggg ttttttttgt tggagattgt gtttttttta aattttttgtg agtgttgtgg   1080
aagtatgtgg ggtttgggtt gttgagtgtt gtaagatagg ggagggagtt gggtgggaga   1140
gggaggggtg gtgttgggt ggggttttgat atagagtagg tgttgtgggt tgtagtatag   1200
tgtggagatt gtagttttgg agtttgggtt agggtttatt tgttttgta gtgttggttt   1260
gtgttttttt gttgtagtta ttggtgagtg tgtgtggtttt gagattttg ggttggatgt    1320
gtggtggttt tagttttga gtgtttgttt ttttgtttt gggttgtttg ggttttttgg    1380
gttttttggt ggttgtatgg agttaaggtg ttttgttttg ggtgttttt gtgggtgttg   1440
atttaggttg tttggagttt ggagtttaga gaggagagag atagttgggg agtttggtta   1500
ttgtgggtat ttttttttgtg ttgtagttgt ttgtttggtt tgttttttg ttttttttgtt    1560
ttttgttttg attttttttt tttttgtaga gttgttgttt agtgttttga ttttgttatt   1620
atgagagttt tgttggtgtg tttgttttt tgtgttttgg ttgtgagtga ttttaaagtg   1680
agtgtgttt tgttttgatt gatgttgttt aaggattttt gattagtatt aggggagagg    1740
aggggttgtt tagggagttg gggttttttg gattttattt atagtagggt tagatttttt    1800
ttaggaaatg ggataggggtg gtagtggagg tttgagaatt atggggttg gtattggttg   1860
gtaagggagg aagaggttgt tgggattgtt ttagtttgtg ggtatttggt agatgaagtt   1920
tgtttgggtt aatttatttt ttttggttgg aaatttatgg tttttt attt gagaattaga    1980
tatgaatagg gtgaggtgag agggagaggg aagagtgggt tttgggattg gggttagttt   2040
atttttattt tggagtttttt ggagtatggg attttttgatg aagtttttt ttgaattttt   2100
tttagggtag taatgaattt tattaagttt tatgtgagta tttattttta taatagttgg   2160
ttgtatagat aagtttgggaa ggtttaggg gatattttt ttttgttttt tgttgtaggg   2220
ttgtgttatt ttttattatt tttatttttt tttgttatt ttattttttgt ttttttttagt   2280
gaattgtgat tgtttaaatg gaggaatatg tgtgttaat aagtatttt ttaatattta   2340
ttggtgtaat tgtttaaaga aatttggagg gtagtattgt gaaataggta tggggatttt   2400
tattgtaatt gggagagaaa tttgggata gggaggatg ggtgggaggt aagagtaggt   2460
aggagttagg agttggaggt agggtgggtg atattttttat ttttatgtga taagtataaa   2520
tatatatata tgtttatgaa atagtggtta tataaatgtg aggtggggtt ggaaggagat   2580
tttgttagt tttttggtag gtttgaaatg atattttta aatgtttgtt ggtagttggg   2640
tatggtggtt tatgtttgta atttttagtat tttgagaggt taaggtgagt ggattatttg    2700
aggttaggag tttaagatta gtttggataa tatggtgtaa ttttgttttt attaaaaatg   2760
taaaaattag tttggtatgg tagtggatgt ttgtagtttt agttatttgg gaggttgagg    2820
taggagaatt gtttgaattt gggaggtaga gattttagtg agttgagatt atattattgt    2880
attttaattg ggtgatagag taagattta ttttaaaaaa aaaaaataaa agttagttgg   2940
aatgtttttt tttttttat attttttttat tttttttgtt tttgtagat aagttaaaaa    3000
tttgttatga ggggaatggt tattttt att gaggaaaggt tagtattgat attatgggtt   3060
ggttttgttt gttttggaat tttgttattg tttttttagta aatgtattat gtttatagat   3120
ttgatgtttt ttagttgggt ttggggaaat ataattattg taggtgaggt gggggtaata   3180
aggattaaaa gttttttta tagtttttta gaaatttttgt tattattttt tttttttaga    3240
```

-continued

```
gggttggtta tagtataaga gaagtgtggt ttttggttga gttttttttg agggaggag    3300
gtagggaagg ttttttgggt tggaatgata tttttttattt ttttgtgttg ttaggaattt  3360
agataattgg aggtgattttt ggtgttatgt gtaggtgggt ttaaagttgt ttgtttaaga  3420
gtgtatggtg tatgattgtg tagatggtga gtattattga tttgttgatg atagtggggt  3480
ggaaggggat aaatttatat gttttttat tttattatag gaggattgag gaggtggggg   3540
gtgtttgaga gggatgtttt ttttatttg tttttttaag atattttttt gtttgttttt   3600
taggaaaaaa gttttttttt tttttagaag aattaaaatt ttagtgtggt taaagatttt  3660
tgaggttttg ttttaagatt attgggggag aattattatt tattgagaat tagttttggt  3720
ttgtggttat ttataggagg tattgggggg gttttgttat ttatgtgtgt ggaggtagtt  3780
ttattagttt ttgttgggtg attagtgtta tatattgttt tatgtatggt tttgggtttt  3840
ttttttttga ttttttttgtt ttatttttaag tatatttttt tttttttttt agtaaagtgt 3900
tttgttttat tttttttta tttgttttg tttatgtagt ttatggtttt ggggataagt   3960
tgtgttttga ggttttagg gagggaagga agaagtggta gattttatgg gattaagttg   4020
tttgatgggt atttttttt atagtgatta tttaaagaag gaggattata ttgtttattt    4080
gggttgttta aggtttaatt ttaatatgta aggggagatg aagtttgagg tggaaaattt   4140
tattttatat aaggattata gtgttgatat gtttgtttat tataatgata ttggtgaggg  4200
ggaattttgt gattattgtg gttataatgg tttggggaga gtgggattta gggagagatt  4260
ggagttgagg ttgaagttgt ttggtggggt aggggtgggg tgagggattt tgaagttttg  4320
atatatatga taaagggagt ggtagggaag agttttatga agtttgaggg gtttggtgtt  4380
ttttgagaga gattttgaat ttttttaata agtagtttt tgtgagtgga aatagttttg    4440
tgggtatatg gtttgggttg ggaaggtttt gtttatatga attagaaaaa gatatatttt  4500
tttttgtggg atgtagtttt tgtttgtgtt aggatataga atttggagaa tggagttttg  4560
ggatggattt tagtttaatt attttagttg ggagtttttg tagaaatgat ttgtatagtt  4620
gtatgtagtg gttttggtta tttaagttttt ttttaatatt tggaataaag ttttttgggt  4680
atggggtagg ggaggttttt aggtgataag tgattagtag attttttttgg atgattgatt  4740
tagggatagg tatagttatt tttttggtat ttggagggga tagatgggga ttgtttaatt  4800
agtagtgatt tttttttttt gattttttgt ttttttttag ttttgttgaa gatttgtttt   4860
aaggagggta ggtgtgtgta gttatttttgg attatataga ttatttgttt gttttttgatg  4920
tataatgatt tttagtttgg tataagttgt gagattattg gttttggaaa agagaatttt  4980
agtaagtgat aattgtgatt gatttagaag gttttgagga gtgttttgat ttgaaaatga  5040
gtttagtgtg attaagggaa gattgtagag ttagaggtgg gagtattgag gtggtggtag  5100
atgggtttag ggatggatga agagtgttgt ttagggagtg atgggttgta aaggtaaata  5160
gatggtaggg gttataggtg gagtaaaggt ttagatttgt atggaagaga ataagggttt  5220
tttttggtag agatatttta tggtttttt ttttggtaga ttttagtgg atagataaat     5280
tttgatgtaa atgttttttt gttttttta tttagttgat tattttatt tggagtagtt    5340
gaaaatgatt gttgtgaagt tgattttta ttgggagtgt tagtagtttt attattatgg   5400
ttttgaagtt attattaaaa tgttgtgtgt tgttgattta tagtggaaaa tagattttttg  5460
ttaggtgagt gttttaagta tttttttta tttttttat attttttag agttttggg       5520
tttgttttag ttagtttaag ggtgtttttt tttagttaaa gttttaagta gttagaatta   5580
```

```
ggagtttagg tttttgaggg tttaaattag tttttatgtg tttgttagat attattaaaa   5640
aaattttagt tttgtgttag ttattttaga ttgggggtat gagattttag aaagaggaaa   5700
tagtaaaaga taatgtaatt tagtgtttag ggtgtgttgt gaattataaa tgattaggtg   5760
tttaggagag ggaggtgagt gttaatttga gggttaggga ggggaggttt taaaggaaat   5820
gtgatttgat aggtatttga agaggtagag ggaagaaagg aaggtgtttt agttgaaaga   5880
tataaaattg agaaggaggt tggtatattt tgggtgggga ggagaattag ggtttgggag   5940
tgtggatgga atagtggtag atgatagggt ttttaaagtt aagtagggga ttttaaattt   6000
gatgtggtag aaaatgggt tgtgttaggt atagtggttt atgtttgtaa ttttagtatt   6060
ttgggaggtt gaggtggatg gattatttga ggttaggagt ttgagattgg tttggttaat   6120
atggtgaaat tttgtgttta ttaaaaatgt aaaaaaaaat tagttaggtg tggtggtgtt   6180
tgtttgtaat tttagttaat taggaggttg agatatggga attgtttgag tataggaggt   6240
aagtttgtag tgagttgaga ttatgttatt gtatgttagt ttgggtgata gagtgagatt   6300
ttgtttttt tttgaaaaaa agaaagaaaa tgggaagttg ttaaggattt tgattgggaa   6360
atttttttt tttttttggta tggttgggtg atgggattag aaattttttt tttatttttt   6420
tagggtttat ttttttgtatt tttggtgtta tagggagatt taggggggatt ttttgtttgt   6480
ttttttttaag gttgtatgat tttgattgga attgtgagtt ggggttgtgg atgtgttttg   6540
aaggataagt taggtgttta tatgagagtt ttatatttt tattttggat ttgtagttat   6600
attaaggaag agaatggttt ggttttttga gggtttttag ggaggaaatg ggtattattt   6660
gttttttgt tggttgttat ttttgtagta gagttatttt tattagttgt aagaagagat   6720
tgggaagata ggttttgtat agatggattt gtttgtgtta tttattaggg tgaatgataa   6780
tagttttatt tttaggtata ggtttgggtg ttggttgttt agatttttt ggttaggatg   6840
gaggggtggt tttgatttaa tatgttattg attagtaatt tgttttttt tggattgaag   6900
tttgtaggag ttaaaaaggg tagggtattt tttgtgtatg ggtgaaggga gagttagttt   6960
ttttgatggt gggtatttgt gaggtttatg gttgagaaat gaataatttt ttaattagga   7020
agtgtaatag ttgaggtttt ttgagggagt ttagttaatg tgggagtagt ggtttgggga   7080
gtagagatat taatgatttt agggtagggt tttgatatt tatgaatgta ttaggaaata   7140
tatatgtgtg tgtatgtttg tatatttgtg tgtgggttgt gagtgtaagt gtgagtaaga   7200
gttggtgttt gattgttaag tttaaatatt tttttaaatt gtgtggattg tgatgttata   7260
tagagtggtt tttttggaga ggttataggt tattttgggg gttttttggg ttttttatgt   7320
gatagtgttt gggaatgtat tattttgtag tatgatttgt gattagtatt gttttagttt   7380
tattttata tagatgtttt tttttggtt agttatttt ttttttagt ttagtttatt   7440
taattttat tgggtggggt gaggattatt tttgtatatt gaatatttat attttattat   7500
ttttatttat attttttgtaa ttttaaataa aagtgattaa taaaatgtga ttttttgat   7560
gataaattt tttggtgttt gtatgggaag gagttggagt atataaaaag gagaaaataa   7620
taaaggtgga ttgtattta gagttttta tgggattgta ttttggatt taatggagtt   7680
ttgggaggta gaggttagga gagttgtagg gtagggttat tatagtattt aatgtatata   7740
aagtttttttt aaattataat tttatggttg tgtaagtagt gtataggttt agtgttagtt   7800
tttaattgtt tttttaattt gatgttttg tgtagtgtat attttgtata gttgtatatg   7860
gtggtttttt ttagggttaa ttttataata gtttttttat tttgttttta ataattttg   7920
agttgatttt aattaagaag aatatttgtg gttaggtgta gtggtttatg tttgtaattt   7980
```

| | |
|---|---|
| taatattttg agaggttgag gtgggagaat tgtttgagtt taggagtttg agattagttt | 8040 |
| gggaaattta gtgagatttt gttttgtaa aaaataaaaa aattagttag gtgtggtagt | 8100 |
| atatgtttgt agtttagtt atttgggagg ttgaggtagg aggattttaa gttaaggagt | 8160 |
| ttaagtttat agttagttga ttgtgttatt gtatttagt ttaggtgata gagtaagatt | 8220 |
| ttgttttaaa aaaaaaaaaa aaaaaaaaag aagaagaaga tttgtaagtg aaaattgttg | 8280 |
| gttaggttta gtggtttatg tttgtaattt agtattttgg gaagttgagg tgtgtggatt | 8340 |
| atttgaggtt aggagtttga gattagtttg attaatatag tgaaattta ttttattaa | 8400 |
| aaatataaaa aaattagttg ggtgtggggg tgggtgtttg taattttagt tatttgggag | 8460 |
| gttgaggtag gagaattatt tgaatttggg aggtagaggt tgtagtgagt tgagattgta | 8520 |
| ttattgtatt ttagtttggg tgatagaggg aagattttgt tttaaataaa taaaaaaata | 8580 |
| aataaagaaa gaaaattgtt tatttagaat gttagtttga ttttgtggta tttaggaaat | 8640 |
| aaaaaatata attttttatt atttgtgtgt gggattgatg ttggaatttt tttagtgtgt | 8700 |
| taatagagtt tgtgattagt tattgttatg tttatgatta gggggtttag aattttaaag | 8760 |
| ttggatgatg ttttaatggg ggtgattata tattttgaat aaaatattaa gttttgaaaa | 8820 |
| gttggggtgt agaaggtagg ttgggagata attgggtatt aaaaattaga attgttaagt | 8880 |
| tgtgttaatg ggttggggta gtgtttttta attgagttat ttgaggattt tttaaaatat | 8940 |
| gtatatttat atttatttg tagagattgt gatttaggtt agggttggtt ttaggttttg | 9000 |
| t | 9001 |

<210> SEQ ID NO 28
<211> LENGTH: 9001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 28

| | |
|---|---|
| atgagatttg gagttagttt tgatttgaat tataattttt ataggtggag tgtaggtgtg | 60 |
| tatattttaa aaggttttta gatgatttga ttaagaaata ttgttttaat ttattaatat | 120 |
| agtttggtaa ttttaatttt tgatatttaa ttattttta atttgttttt tatattttag | 180 |
| ttttttagaa tttgatgttt tgtttaaaat atatagttat tttattagg atattattta | 240 |
| gttttgagat tttgggtttt ttaattatag gtatagtaat ggttggttat agtttttgtt | 300 |
| aatatattga gaaattttta gtattagttt tatatataga tgatgggaaa ttatgttttt | 360 |
| tgttttttga atgttataga gttaagttgg tatttggat aagtaattt tttttttat | 420 |
| ttattttttt atttatttga ggtgaagttt tttttttgtt gtttaggttg gagtgtagtg | 480 |
| gtgtgatttt ggtttattgt aatttttgtt tttgggttt aaatgatttt tttgttttag | 540 |
| tttttttgagt agttgggatt ataggtattt atttttatat ttggttaatt tttttgtatt | 600 |
| tttagtagag atggggtttt attatgttgg ttaggttggt tttaaatttt tgattttagg | 660 |
| tgatttatat attttggttt tttaaagtgt tggattatag gtgtgagtta ttgagtttgg | 720 |
| ttagtaattt ttatttatag gttttttttt ttttttttt ttttttttt ttttgagata | 780 |
| gggttttgtt ttgttatttta ggttggagtg tagtggtata attagttgat tgtaaatttg | 840 |
| aatttttgg tttaggattt ttttgtttta gttttttaag tagttaggat tatagatatg | 900 |
| tgttattata tttggttaat tttttattt tttgtagaga taggtttta ttaagttttt | 960 |

```
taggttggtt ttaaatttttt gggtttaagt gattttttta ttttagttttt ttaaaatgtt    1020
aggattatag gtatgagtta ttatatttgg ttataggtgt ttttttttggt tgaggttagt    1080
ttaaggattg ttgggggtag agtgaagaga ttgttgtgga gttaattttta aagaagatta    1140
ttatgtatag ttgtataaga tgtgtattgt ataaaggtat taggttaagg aggtaattgg    1200
gagttgatat taagtttgta tattatttat atagttatgg gattgtggtt tggggaaatt    1260
ttgtatatat taagtgttgt ggtggttttg ttttatagtt tttttaattt ttattttttta    1320
aagttttatt aagtttagag atgtagtttt ataagaaatt ttagggtgta gtttattttt    1380
gttatttttt tttttttatg tattttaatt tttttttata taagtattag ggagatttgt    1440
tattagaaaa attatatttt attgattatt tttatttaaa attataaaaa tataaataaa    1500
aatagtgaaa tataaatatt tagtgtatag gagtggtttt tattttatttt agtgaggatt    1560
ggatgaatta ggttaaaagg aagggataat tggttaagaa agggatattt atgtgaaagt    1620
gaaattgaga tagtgttggt tataggttat gttgtagaat aatatatttt taggtattgt    1680
tatgtggggg atttaagagg ttttaggagt gatttataat tttttttagaa agattatttt    1740
gtgtggtatt atagtttata tagtttaagg aaatatttag atttaataat tagatattag    1800
tttttattta tatttatatt tatagtttat ataagtgt gtaaatatat atatatatat    1860
atatttttg atatatttat ggaatattag agttttgttt tgaagttgtt agtgttttg    1920
tttttaaat tgttgttttt atattggtta agtttttta agagattta gttgttat    1980
ttttaattg ggaaattatt tatttttaa ttatgggttt tataaatgtt tattgttggg    2040
ggagttggtt tttttttat ttatgtatag gagatgtttt gttttttta attttgtag    2100
gtttagttt agaaaagat aagttgttgg ttagtaatat gttgagttag gattattttt    2160
ttattttggt tagaggggtt tgggtagtta gtatttaggt ttatgtttga gggtaaagtt    2220
attgttgttt gttttggtgg gtggtatagg taaatttatt tgtgtagagt ttatttttt    2280
agtttttttt tatagttgat ggagatgatt ttattgtaaa aatgataatt agtaagaaag    2340
tgggtggtgt ttgttttttt tttggggatt tttagagggt taggttattt tttttttgg    2400
tgtgattgtg gatttagggt aagaagtgtg agattttgt gtagatgttt ggttttgttt    2460
ttagggtata tttatggttt tagtttataa ttttagttaa agttatgtgg ttttggaggg    2520
aatagatgag gggtttttttt gagttttttt gtgatgttaa agatataaaa gatgagtttt    2580
agagaagtga ggagggggatt tttgattttta ttattttaatt atattagaga gagggaagag    2640
tttttttagtt aaagttttta gtgattttttt attttttttt tttttttttgg ggggaggata    2700
gaattttgtt ttgttgttta ggttggtgtg taatgatgtg attttagttt attgtaaatt    2760
tgttttttgt gtttaagtga tttttatgtt ttagttttttt gattagttgg gattataggt    2820
aggtattatt atatttggtt aattttttt tgtatttta gtagatatag ggttttatta    2880
tgttggttag gttggttta aatttttggt tttaagtgat ttatttattt tggttttta    2940
aagtgttggg attataggta tgagttattg tgtttgatgt agtttatttt tttattatat    3000
taagtttaaa attttttgtt tggttttaaa agttttgtta tttgttatta ttttatttat    3060
atttttagat tttagttttt ttttttattt ggaatatgtt agttttttttt ttagttttgt    3120
attttttaat tgaaatattt tttttttttt ttttttgtttt tttaaatgtt tattaagtta    3180
tatttttttt aaagttttttt tttttttgatt tttaggttgg tatttatttt tttttttga    3240
atatttgatt atttatagtt tataatatat tttgggtatt gagttatatt gtttttttat    3300
gtttttttttt tttaggattt tgtgtttttta gtttgaagtg attagtgtag agttgggatt    3360
```

```
tttttggtaa tgtttggtaa atatataagg attggtttaa attttttaaag atttgagttt    3420
ttgattttgg ttatttaggg ttttggttag agagagatat ttttaagttg gttggaataa    3480
gtttaggagt tttggggaga tatggaagag gtggagagag atgtttggaa tatttatttg    3540
gtaggaattt gttttttatt gtgggttagt agtatatagt attttggtgg tgattttaga    3600
gttgtagtag tggggttgtt gatattttg gtgggaaatt agttttataa tagttatttt    3660
tagttgtttt ggatagagat agttggttag gtggagaaaa tagggaggtg tttgtattaa    3720
gatttatttg tttattggga gtttgttaga gagggggaatt ataaagtatt tttattaggg    3780
aaggttttta ttttttttta tgtaaatttg agttttttatt ttatttatag tttttattat    3840
ttatttattt ttgtagttta ttgtttttta aataatattt tttatttatt tttggatta    3900
tttgttattg ttttagtgtt tttattttta attttgtagt ttttttttga ttatgttggg    3960
tttattttta ggtaaaaata ttttttagga tttttaagt tagttgtaat tgttatttat    4020
tagaattttt ttttttaaag ttagtgattt tatagtttgt gttaaattgg ggattgttat    4080
atattgaggg taggtagatg gtttgtatag tttgggatgg ttgtgtatat ttgttttttt    4140
tggaatggat tttagtaag gttggggag atagagggt tagaggagaa agattattat    4200
tggttaggtg gttttattt gtttttttta agtgttgagg aagtagttat gtttattttt    4260
aggtagtta tttagggagg tttgttggtt gtttattatt tggaaatttt ttttgttta    4320
tgttttaagg gttttgtttt aggtgttgaa aaaggtttgg atggttagag ttattgtata    4380
tagttgtata ggttgttttt gtaaaaattt ttagttgagg tagttaggtt ggaatttatt    4440
ttaaggtttt attttttaag ttttatattt tagtatagat agaggttgta ttttataaag    4500
gaaggtgtgt ttttttttaa tttatataaa tagggttttt ttagtttaag ttatatattt    4560
atagggttgt tttatttgt aagaggttat ttgttgggga aatttagggt tttttttagag    4620
gagtattagg tttttagat tttatggaat tttttttgt tattttttt gttatgtata    4680
ttgaggtttt aaggttttt gttttatttt tgttttattg ggtagttta atttttagttt    4740
tagtttttt ttgggttta tttttttaa gttattatgg ttatagtagt tgtgggttt    4800
tttttatta atgttgttgt ggtgagtaag tgtgttagtg ttgtagtttt tgtgtaggat    4860
gaggttttt attttaaatt ttattttttt ttgtgtgttg gagttaagtt ttgagtgatt    4920
taggtagatg atgtagtttt ttttttttgg gtaattattg tgggagaaga tatttattaa    4980
atagtttagt tttatgaaat ttgttatttt tttttttt ttttagaggt tttaaagtat    5040
gatttgtttt taaggttatg ggtgtatgg ataggggtag atgagggaga aatgaggtgg    5100
aatattttgt tgggaaggag aaagggatgt gtttggggtg gggtagaaga gttgaagagg    5160
agaaatttag ggttgtatat gaagtagtgt gtggtgttga ttatttagta aggggttgatg    5220
aggttgtttt tatatatgta ggtgatagag tttttttggt gttttttgta gatggttgta    5280
aattagggtt ggttttgat ggtggtgaat tttttttaa taattttaaa gtggggtttt    5340
agagtttttt ggttatattg aaattttaat tttttggag gagaggaggg ttttttttttt    5400
ggaggataaa tagagggatg tttttaggag gtaggtagga gaaagtattt ttttggta    5460
ttttttattt ttttagtttt tttgtgatgg aataagggga tatgtaagtt tgtttttttt    5520
tatttattg ttattagtag gttagtgatg tttattattt gtgtagttat gtattatgta    5580
tttttggata agtagttta ggtttatttg tatatagtat tagggttgtt tttggttgtt    5640
tgggttttg gtaatataga aagatagggg atgttatttt aatttagagg gttttttttg    5700
```

```
tttttttttt ttagggaaga tttaattaga ggttgtattt tttttgtgtt atggttagtt      5760
ttttgggaga aggggatggt aataaggttt tgggaagtt gtagggaggg tttttggttt       5820
ttgttgtttt tattttattt gtagtaatta tgttttttta ggtttagttg aagagtatta     5880
gatttgtggg tatggtatgt ttgttgaagg atagtggtag agttttaggg taggtagggt      5940
tggtttatgg tgttagtgtt ggtttttttt tggtaaaagt gattattttt tttatagtag     6000 gttttttgatt tatttataag gggataggag gatgagagaa tatgagaaag agaagaatat    6060
tttaattaat ttttattttt tttttttgag atggagtttt gttttgttgt ttagttggag     6120
tgtagtggtg tgattttagt ttattgagat ttttgttttt taggtttaag taatttttt      6180 gttttagttt tttaagtagt tgggattata ggtatttatt attatgttag gttgatttt      6240 gtatttttag tagaggtagg gttatattat gttgttaggg ttggttttga atttttgatt    6300
ttaaatgatt tatttatttt gattttttaa aatgttggga ttataagtgt gagttattat     6360
gtttggttgt taatggatat tttaaagatg ttgttttaga tttgttagaa gattggatag    6420
ggtttttttt taatttttatt ttatatttgt gtggttattg ttttgtgagt gtgtgtgtgt    6480
gtttatgttt gttatatagg gatgaagatg ttatttattt tattttagt ttttaatttt      6540 tgtttgtttt tgtttttat ttatttttt ttgtttttaa attttttttt tagttgtagt       6600 ggagatttt atatttattt tatagtgttg tttttgaat tttttgggt agttgtatta        6660 gtgaatgttg gagaagtatt tgttggatat atatgttttt ttattagat agttatagtt     6720 tgttggagag aataaaggtg gggtaagtga gggggagtgg aagtggtaag gggtggtgta     6780
gttttgtagt agagggtagg gagggatgt ttttgaagt tttttaatt tgtttgtgta        6840 gttaattgtt gtaggggtgg atatttatat ggaatttgat gaagtttatt gttgttttgg     6900 aagagattg ggaggaggtt ttattaaagg tttatgttt tagggattt agggtgaggg       6960 taaattggtt ttaatttta aatttatttt ttttttttt ttttgttta ttttgtttgt      7020 atttagtttt taaatggaag attatgggtt tttagttagg agaaatggat tgatttaagt     7080 aagtttatt tattagatgt ttgtaggttg gggtagtttt ggtggttttt ttttttttg      7140 ttagttagtg ttaattttg tggttttaa gttttttgttg ttattttgtt ttatttttg      7200 gggagagttt ggttttgttg tggatggaat ttggaggatt ttagttttttt gagtagtttt    7260 tttttttttt tggtgttgat tagaggtttt tgggtagtat tagttaaagt aagagtgtat    7320
ttattttgga gttgtttatg attaggatgt agagaagtag gtgtgttagt agggtttta    7380 tggtggtgag gttggggtgt tagatggtgg ttttgtaaag gaaggagaag ttagggtaag     7440
aggtggagga atgggaaggt aggttaggtg ggtgattgta gtgtagggga gatgtttgtg     7500
gtgattaggt ttttttagtg tttttttt ttttgggttt tggatttttgg gtagtttgga     7560 ttggtatttg tgggggatgt ttgggatggg gtgttttgat tttgtgtagt tgttgggag    7620 tttagggagt ttgggtagtt tagggtgggg gaggtagatg tttgggagtt ggggttgttg    7680
tgtatttggt ttgggggattt taggattgtg gtatttattg gtggttgtgg taggagggtg    7740
tgagttggtg ttgtggggat aggtggattt tggtttgggt tttggggttg tggttttgt      7800 attgtgttgt gatttgtggt gtttgttta tattagggtt tgttttggtg ttgttttttt    7860
tttttttgtt tggtttttt ttttgttttg tagtgtttag tgatttggat tttgtgtgtt     7920
tttgtaatgt ttataaagat ttggggggaag tgtgatttt agtggagggg atttaatagt   7980
gtttggattg aggaattgag aggtttgtaa attttttgtg tttttttta tgtatttggt     8040 tgggggtttg ttttagtgta aggagttttt gaattgtaga gaggagagaa ggtgtatagg    8100
```

```
agatttttta ttttgtttag ttttgaagtt ttttggggtt ttttaattag ttttttttgta    8160 attttttttt gttgggtttt aatttgttta agattgtttt agattttttt gtttgtagtt    8220
gatggagttg tgaagttttt attaatgtga taaatgtatg agatatattt tttagaagt     8280 atagataga aaatttttgt ttgtaggggt tttttttgtg tgtttgttta gtggtagttt      8340
ttagatatta ttaatataat tagtggatgg aataaagttg ggtttattgt ttttggtagt    8400
aagggggttt gtttgatggt gttattagag ggggaaaggt aaggttagat tattgaaaat    8460
ttgtagtttg gtttaaagtt tgttttgat agggtttgat aaggattggg ttaggtgttg     8520
tgatatgatg ttataggatt gtgggaataa agttttaggg tataaattgt tggtgttttt    8580
tattgaagtg ttaatgggtt ttttgggaag tttttataat gagtaattta tttatttgtg    8640
taggtaagaa taaagtaaa gataatggaa atatgtagat agttttaatt gtggagtttt     8700
tggagggtgt ggaagttttg tttttatttt tgagtagagg aattgggaga ttggaggata    8760
aaataagagg aagattatt tttattgtt tgttttttta tattttaat attttaaaaa        8820 gtatattttt gtatagttta tttaaaaag ataattatgt ttttttaat gtatgtgtat       8880 ttagtgtttt attttattat agagttttgt ttatttatt tagatagaaa taattgttta     8940
ttaaataaaa ttgttttta gaaaatagaa ttatgtgtaa atgattgtat ttattttttt    9000
t                                                                     9001

<210> SEQ ID NO 29
<211> LENGTH: 6501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 29
tttgtgtttt tttttgttta agtatgaata tgtttttggg attaagagat taggtttgga      60
aatagaagaa tttgttgagt tgtaaaattt gtatggttta aattttattg aatattgttt     120 atttttttt taaatgattg tgtaatttat attttatttt taagagtttt tattttgatt     180
tgagaaatta gagtagtgaa aattattgtt attatgagta ttattttggg tttggtgttt    240
ttgttttgtt tttaataaat ttaagttgat tatagaggat attaggtttt ggtttttttt    300 tgggtttgt ggttaggttt tttttggaga ttttggttta ggagtggaga ttttggtgta     360
ggagtggtag ttttggagga ggggttgggt tttgggatgg agtgaagagg aatatggttg    420
tttttatttt ggtttaggtt tttttttag aggggttgta gaaatgtatt gattaggtta     480
tttaagaaaa gatagtattt ttgttaggtt agtatgtatt tttttaggg tttaatttt      540 tattgaagaa gaaagagttt ttttgttgt ttatttttt atgtagtttt ttaatagttg      600
ttttttgaat gttaattaaa gttattgttt tagggtttgg ggttatttta aggtattagg    660
agatgaggat ttttgttttt atgtgttttt ttgtttgttg tagggaggag tgtaatgaat    720
aaataattaa tataatgtgt tagttatttg tttttatttat taggaggtaa taagagttat   780
gaaagagaaa gttttgagta ggggagggga gtgaggtatg gtataggaga gtaggaggtt    840
gtttttttaa atataggagt ttagggggatt aattgggaag gtgtgggagg gggagggagg   900
gagttttata gatataggg agtgaattat gtttattttg ttagttttg atggtagttt      960 gtatatatta ttttttttt tttttttgttt ttagttttt ttagaaggag atttaatttg     1020
ttgtttaggt tggagtgtag tagggtgatt ttgatttatt gtaattttg ttttttaggt    1080
```

```
ttaagtgatt tttttgattt aattttaga gtagttagga ttataggtat ttgttattat    1140
gtttggttaa tttttgtatt ttttttttt gtagagatgg ggttttgtta tgttggttag    1200
gttagtttta aattttgat tttaagtgat ttgtttgttt tggttttta aagtgttggg     1260
attataggtg tgagttattg tgttaggttt ataattttat tattaaaata attttattgt   1320
aaaagaatta gtttaggttt agatggaatg ggttttatga gttttttttt ttttttttgt   1380
aaggttatgg tggttatttt gtgagttatt gttgttatgg ttaagtttt ttttggttat    1440
ttttattat gaattatttt tgtagtgagt atagtattta ttttggtggg agggttttt     1500
agatatgagt aggatttgga ttaaggttag gttggaggag atttttatgg gaaagaggga   1560
ttttttgaat tttagatttt ttagttaaga tgattttatt atatgttgtt tttgtttatt   1620
agtaaatttt tttatgtagt ttgattatgt ttaggaaata ttttttgataa aaattagtgg  1680
agattattgt tttagaggat ttttgggttt ttttaggtaa atgttattta atgttttta    1740
agtaaataga gtttgttta taaaattgg ggttggtg gtttttatt tttgattgg         1800
ggttgttt ggagtagaga ggaggtaatg gttattatg agaataaggt gatttgtgtt      1860
ttggttttgg tgtttatgtt ggttttggt attttggttg aggtttagat aggtaaggtg    1920
tgttttttt tgttttgtgg ggttatagtt agttttggta gttttttgtta ggagttattg   1980
ttttatatat atatttttga gtatttgttt tgtgttaggt gttgttttag gttttaaaa    2040
gtatatttaa tttataggat tggtaaaagt aggtggagag taatttaggg tggtagggtt   2100
tttggagatt tttgagaagt gtgatgagga ggggttgtt tttagttggg gttgttttt     2160
tgtgttagga agattatata attttttaa gtgttatgtt ttaaagagga agtgttggtg    2220
tgggttta gaatagtgtt tttgattgtt tatgttaata ttttttttag gggtagattt     2280
ttttaaggtt tatttagata ggtttaaatg ttggttttag tgatggtat ttgggagatt    2340
ttttttata ggtttgaatg tttgtttag tggtggtaa ttgggagatt tttttttata     2400
ggttttggg tttttttggg atttatgttt tgggagttaa agttattttt tttatgagtg    2460
tgtggttggt aatttatatt ttttggtgtt gttaagtgga ttggttgttt tgggttttt   2520
tagggagtgg aggaggaggt tattttgtt tttttgggaa gtgtttgtat tttaattttt    2580
ttatttgtag aatggattaa tggtttgttt tagggttgtt aggaaatgtt gtgtggtagt   2640
atttgtgatt tgtattttgt tagttgtggg gagttaata atttatttgt tgttattagg    2700
tatagtttta aggtggggt aggagaaagg ttttttatg ttttaaagt aagggttttt      2760
agagaggttt gaagagggag tgtttagtgg tgttgtttgt gttttttattg ttttttagtt  2820
atttttgat ttttgttgtg gggtattggg tttgagggg gggtttgggt agtgtagaag     2880
agtagttagt attgggttgt agtgggaaga ttttaagtt tatggtaggg agtggggag     2940
ttttggaatt tgagagagga agtggtttg gtgtatagaa tgaattgggt gggttttgt     3000
gttggttatt tttaggttta tttgtttgtg ttttgtttt tattttagtt tttagttttg    3060
ttttttgtgt tgtgggatta tagaggttgt ggtaaatttt ttttttatt ttatatattt    3120
tttggtttaa ggtttagagt ttttttgtgg gttatttagg tttatgatt tgttataatt    3180
gaaatttaga aaattgtgat tatagtttag tgtatttgtg tgtggaaatt attttattt    3240
attttatta tgtgataaag ataaagtggg tgggtaagat agagtttgtt ggaggtagag    3300
tattgggggt ggaaatttt ttttttgagg aggaaatttt tttgattttt aggatgatga    3360
ttttttttta ttatgggtt tttttttgatt tttatagtgt tttgggggtg ggtgatgatt   3420
attttatgt tgtgatggat ttagatttta ggagggtaag gttttatgg aagttgttgg    3480
```

```
gtagtgggag ttgaatatgg atttttttta gtaagttagg aatatttttt ttaaagatat    3540
tttgaggtag tttttgatag taaagtagat aagagaatag ttttttttgg ttttttttgg    3600
ggtgttttta tttgagttag tgtggttaga ttgagttttt ttttttttat gttttaaggt    3660
agggataggg attggagggt gttttgggtt ttttttttat ttttgttgt aggttgttaa     3720 ttattagatt ttaataggtt gttttttgag attttttgatt ttgtggagtt tagagtttga   3780
agttttggtg ttagaatttt ttgtataaga ttttgtggta gtttttagtt agttttattt    3840
gtttatgtgt tttttttttt tagatttttt ttttattgt tttgttttaa gttgttttat     3900
agtttgtatt ttttgttggt tttttttaga ttatttatt tggttttttt attttatttg     3960
taatgggttt ttattttttg aatatatttg ggttttggga atggtttttg tttatgtggt    4020
tttattttta tttggtgaat tttttttgt agggagtttt tttgttttgt ttaatttgtt     4080
tgttattggt tttttggggg agtgttttat ttttgtggtt attttgggta ttttgggatg    4140
atggttttgt gttgttttgt atatgttttt gtttttttttt tttattagat ttttagattt    4200
tttttttttt tttttttgaga tggagttttg ttttgttatt taggttggag tgtaatggtg    4260
tgattttggt ttattataat ttttgttttt tgggtttaag tgattttttt gttttagttt    4320
tttaagtagt tgggattata gatgtgtgtt ataatgtttg ttttatttt tgtattttta    4380 gtagagatgg ggttttatta ttttggttag gttggttttg aattttgat tttaagtgat     4440 ttattttttt tagtttttta aagtgttggg attataggta tgagtttggg tttagatatt    4500 tagatttta ttaatgattt tttttggttt aattttggg tttttttat ttggtatagt       4560 gtttggtttt tgttatgtta gtttttattt tttatgtata taaatggtgt ttagtaaata    4620
tttatgtatt gagtaaaatt taataattat tgttgaaat taaaaagtga ataaataagt     4680
tatttagaaa gatgtaaagt ttataaattt ggggtatttt gtattttttt tgagtgtaat    4740
gtttgtatat taggatgtga ggattatgtt ttttttttat gttttgaggg ttttatattt    4800
gttttattgg atagttgttg atgttattgg agaaggaagt tggatgggtg tgtgtatgat    4860
aatattaagg aatttagttt ataatttatt ttgttttta tttgtgtatt tttagagatg     4920
tgtatagtgg ttttttgtga aagatagaat tgtggttttt ttggtgttat gttttttttag  4980 tgtgtaaata agggttgttg ttttgatgat attgtttgtg gggttttttg gtgtttttat    5040
tttaatatta ttgatgtttt tttagaaggt atggtttttt tatatgatgg gttttgaaga    5100
tttagaatta gttagaaaag ttatttaaga ttatagaggt tttgattagt attattagtt    5160 atgttttttat atagagttat ggttgttagt ggtggtgtaa tggggtagtt tgagttaggt   5220
tgtatttagg tttaggaata gaaaggtagg gttaagggat ttgggaagaa atttgattt    5280 tttttggttt ttttttatat ttttaattaa aagtttggga agagttattg ttggtaatgt    5340 ttttttagttt gttaggata gagggggaag gtatgatgaa atttgaagat attttatgta    5400
tttttttttt tttttttttt ttgaaatgga gttttgtttt gttgttttttg agttggagtg   5460 taatggtgtg attttggttt attgtaattt ttgttttttg agtttaattt tagtttttta    5520
gtagttgaga ttataggtgt gtgttattat gtttagttaa attttttttg tattttttagt   5580 atagatgggg ttttattatg ttggttagat tggttttgaa ttttgatttt taggtgatttt   5640 gtttgtttta gttttttaga gagttgggat tataggtgtg agttattgtg tttggttgat    5700
agtttatgtt ttttaaagaa tgtgtttatg gatatttta agtaaaaatt ttgtaattgt    5760
ttaaatgtga aagaaaatgt ttatttttat taaagtattt tttttttttt tttttttatt    5820
```

```
tttgtagagg agtgtgaatt ttagatattt ttgtagggat ttgtttgtat tttgatgtgg    5880
tgttgttttt agtatggtga ttagttttag agtttggttg ttattttttat tggatatttt    5940 agatatgttt ttgtagttgt gttttggttt ataatataga ttgattgttt tgattttgat    6000
tatttaaaat tggtttaaaa attaaaagag attgatatta atttgtgttg tttattttt     6060 taaagaatat gaatgatttt tttttttttg aaagtgaagt gtagtgtttt attttgggtt    6120
tttgtagagg ttttgtattt tttgggtttt ttgagttggg atataagtgg gtagttgagt    6180
gtagaaagta gggatggtgg ggtgtatagt aggatagtgg ggtgtgtagt aggatagtgg    6240
ggtgtgtagt aggatggtgg ggtgtatagt aggatagtgg ggtgtgtagt aggatggtgg    6300
ggtgtgtagt gggatggtgg ggtgtgtagt aggatgtaag tttaagatgt attttttgttt   6360 aggtatgaaa atggatattg atttttttgg tattttttaa ttatttattg tggatgtttt    6420
agtgattaag tgatataagt tagttttttg tttatttgtt tttttaaata gaaattggtg    6480
taggagatga aatttgtagt a                                              6501

<210> SEQ ID NO 30
<211> LENGTH: 6501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 30
tgttataggt tttatttttt atgttaattt ttatttggga aagtaaataa atggaaagtt      60
aatttgtgtt atttggttgt tggggtattt gtagtgagta gttaagaaat gttaggggag     120
ttggtgttta tttttatgtt tggataagag tgtgttttgg atttgtgttt tgttgtatat    180
tttattgttt tgttgtatat tttattgttt tattgtatat tttattgttt tattgtatat    240
tttattgttt tattgtatat tttattgttt tattgtatat tttattgttt tattgtatat    300
tttattattt ttgttttttg tatttagttg tttatttgta tttagtttta ggaagtttag    360
aagatgtaga attttgtga gagtttaggg tgaaatgttg tgttttattt ttaaagaaag     420
gaaaattatt tatatttttt aaaagaatga atagtataga ttaatattga tttttttaa     480 tttttaggtt aattttgagt agttaaagtt agagtagtta atttgtgttg tgagttgagg    540
tatagttgta gaagtgtgtt tgaggtgttt ggtggaggtg gtagttgagt tttgggatta    600
attattgtgt tggggatggt attgtgttag gatgtaggta gatttttgta gaagtgttta    660
aaatttatat tttttatag gggtgagggg gagggagaaa gagatgtttt agtgaggata    720
aatatttttt tttatattta ataattata gagttttat tttaaagtat ttataggtat     780
attttttaga aaatatgaat tgttagttgg gtatggtggt ttatgtttgt aattttagtt    840
ttttgggagg ttgaggtggg tagattattt gaggttaaga gtttaagatt ggtttggtta    900
atatggtgaa attttgttta tattaaaaat ataaaaaaaa tttagttggg tgtagtggta    960
tatatttgta atttagtta ttaggaagtt gaggttgaat ttaggaggta gagattgtag   1020
tgagttaaga ttgtattatt gtattttagt ttaggggtaa tggagtgaga ttttatttta    1080 aaaaaaaaa aaaaaaaga atatatgaaa tgttttttaga ttttgttatg ttttttttttt   1140 ttatttttagg taagttagaa agtgttatta atagtggttt ttttaggtt tttggttaga    1200 gatgtgaaga gaagttgggg ggaaattagg tttttttttta agtttttag ttttgttttt    1260 ttattttttgg atttgaatgt agtttgattt aggttatttt attgtattat tattggtggt    1320
tgtgattttg tgtaaaggta tagttggtga tgttgattag agttttttgta gttttaaatg    1380
```

```
attttttttaa ttaattttaa atttttagaa tttattgtat aaaaaggtta tatttttttgg    1440 agggatgttg atggtattag gatagaagta ttagggatt ttatgaatgg tgttgttgaa       1500
atagtagttt ttatttgtat attgggaggg tgtgatatta ggaaaattat aattttgttt      1560
tttatggggg gttattgtat atgttttga aagtgtatag gtaagaagta aagtaagttg       1620
tgggttgaat ttttgatgt tattatgtat atatttattt agttttttt tttaatgata        1680 ttagtaattg tttagtgagg tggatataaa attttagga tatgagaggg agatgtggtt       1740
tttatatttt gatgtgtaaa tattatgttt agggaaaatg taaggtgttt taggtttgtg      1800
gattttgtat ttttttaggt aatttattta tttattttt aattttaata aatgattatt       1860
aaattttatt taatatataa atatttattg agtattattt gtgtgtatga aagtgggag       1920 ttagtatggt aaaagttagg tattgtgtta ggtgagagag atttagaaat taaaattaga      1980
gaagttatta ataagagttt aaatatttgg gtttaggttt atgtttgtaa ttttagtatt      2040
ttgggaggtt gaaggaggtg aattatttga ggttaggagt ttaagattag tttgattaaa     2100
atggtgaagt tttatttta ttaaaaatat aaaaaattag gtgggtattg tggtatatgt       2160 ttgtaattt agttatttgg gaggttgagg taggagaatt atttgaattt aggaggtaga       2220
ggttgtagtg agttaagatt gtattattgt attttagttt gagtgataga gtaagattt       2280 atttaaaaa aaaaaaaaa agagtttaag gatttgatgg aggagaaagg taagaatatg        2340
tgtgagataa tgtaaggtta ttgttttagg gtgtttaggg taattatggg ggtagggtat      2400
tttttggaga ggttaatgat aagtaggttg aataaagtag ggggttttt tgtaggagga      2460 ggtttattag gtgaagatgg agttgtatgg gtaaaggtta tttagagat ttaggtgtgt      2520 ttaggaggtg gaaatttatt gtaggtaagg tgagaggatt gggtggggtg gtttaggagg    2580
agttgataga gggtataagt tgtgaaatag tttgaagtag ggtagtgagg aaagggattt      2640
agaggaggaa gatatgtgga tagatggggt tggttggggg ttgttgtagg attttatgta     2700
agaggtttta atattagagt tttaggtttt gagttttgtg gaattaaagg ttttagaaag     2760
taatttatta ggatttggtg gttgatagtt tgtagtaggg ggtgaaagag agtttagag      2820 tattttttgg tttttgtttt tgtttgggg tataggaggg gaggaattta gtttggttat      2880
attggtttag gtgagggtgt tttaggggag gttgagaggg gttgtttttt tgtttgtttt     2940
gttattaggg attgttttga gatgttttg gagaaagtgt ttttggtttg ttgggaagga     3000
tttgtgttta gttttttgttg tttagtagtt tttatgggaa ttttgttttt ttggggtttg    3060
gatttattgt gatgtgaagg tgattattgt ttatttttgg gatattgtgg gggttaagag    3120
aggttttgtg gtgagggagg attattattt tggggttgg ggggttttt tttttaggga       3180 ggaagatttt tagttttggt gttttgtttt tggtagattt tgttttgttt atttgttttg     3240
tttttgttgt atgatggaaa taaatggaaa tggttttat atatgaatgt attaaattgt      3300
aattataatt tttagatttt tagttgtaat aggattatgg atttgagtga tttgtaaaga     3360
tgttttgagt tttgagttag agggtgtgtg gggtggggag gggagtttgt tatggttttt    3420
gtgattttat agtatagggg gtagagttgg gggttggggt ggggtaagg gtgtaggtag      3480 atgggtttgg gggtggttag tatgggatt tatttagttt gttttgtata ttgaggttat     3540
tttttttttt gggttttaaa gtttttttgt ttttgttat gggtttgggg gtttttttat     3600
tgtagtttaa tgttggttgt ttttttatgt tgtttaagtt tattttttag gtttggtatt     3660
ttatagtaga gattaagagg tggttggagg gtagtggggg tatggatagt attattgggt    3720
```

```
gtttttttttt taggttttttt tggaaattttt tgttttggaa atgtagaaag ttttttttttt     3780
tgtttttatt ttgaaattgt atttaataat ggtaaataag ttatttagtt ttttatagtt         3840
ggtaaagtgt aagttgtaga tgttgttata tagtattttt tgatagtttt agggtagatt         3900
gttgatttat tttgtaggta aaggagttga gatgtaaata ttttttaagg aagtaagaat         3960
ggttttttttt tttattttttt agaaggattt agggtaattg atttatttga taatattagg       4020
gaatatgggt tgttagttat gtatttatga gagaggtggt tttgattttt agagtatgga         4080
ttttagggga gtttaggaat tgtaggaga gggttttttta gttggttatt attgggatgg         4140
gtatttgggt ttgtgggaga gggttttttta ggtggttatt attgggattg gtatttgggt        4200
ttatttggat gggttttggg agggtttgtt tttgggggag atgttggtat gaatagttaa         4260
aagtattatt ttgagatttt atgttaatat ttttttttg aaatatgata tttgggagga          4320
ttgtatagtt ttttaatat aggaaaatag ttttgattga aggtagtttt tttttttgttg         4380
tatttttga aggttttttgg gggttttgtt attttgagtt atttttttatt tgttttttgtt       4440
gattttgtaa attggatata tttttaaggg tttagaatag tatttggtat aaaatatggtg        4500
tttaaaaata tgtatgtaaa atagtggttt ttggtggagg ttgttagagt tggttgtggt         4560
tttatagagt aggaagaagt atgttttatt tgtttggggtt ttggttaggg tgttgagggt       4620
tagtatggat attaggatta gggtgtagat tattttgttt tttatggtgg ttattgttttt       4680
ttttttgttt taaaggtgat tttgagttag ggatgagagg ttgtttgagt tttggattttt       4740
atagggtagg ttttgtttgt ttaaagagtg ttagataata tttgtttaag gaggttttggg       4800
gatttttga gataataatt tttattgatt tttattaaag gtgtttttta gatatggtta        4860
agttatatgg aaggatttgt tgatagatat agatgatatg tggtgaggtt attttggttg       4920
agggatttga gatttagaaa gttttttttt tttatgggag ttttttttttaa tttgatttta     4980
atttaggtttt tatttatatt tgagaggttt tttttgttagg gtaaatattg tatttattgt    5040
agaagtgatt tatagtgaga gatggttgga aaaaggtttg gttgtgataa tagtggttta        5100
tgggggtggtt attgtgatttt tgtaggggga agggaaggag tttatgaagt ttattttgtt    5160
taggtttaag ttaattttttt tatagtggaa ttgttttaat aatgaaattg taggtttggt       5220
gtagtggttt atgtttgtaa ttttaatatt ttgggaggtt aaagtaggtg gattatttaa        5280
agttaggagt ttgagattag tttggttaat atggtgaaat tttgttttta taaaaaaaaa         5340
aaatataaaa attagttagg tatggtggtg ggtgtttgta attttagtta ttttggaggt        5400
taagttagga gaattatttg aatttgggag gtggaggttg tagtgagttg agattatttt        5460
attgtatttt agtttgagtg atagattaag tttttttttg ggaggggttg ggggtaggag        5520
ggagaaaaaa atagtatata tgagttgtta ttaaaaattg ataaagtgaa tgtggtttat        5580
tttttttgtgt ttatggggtt ttttttttttt tttttttata tttttttttagt tggttttttg  5640
gattttttgta ttttagagga tagttttttttg tttttttgta ttatgttttta tttttttttt    5700
ttgtttggag tttttttttttt tatagttttt attattttttt ggtggataaa ataagtgatt     5760
gatatattat gttggttatt tatttattgt atttttttttt gtagtagatg ggagggtgta       5820
tgggagtaga agttttttatt ttttagtgtt ttgaggtggt tttagatttt agaatagtgg       5880
ttttgattgg tatttgagaa atagttgttg aagagttgta tgaagaaatg gataatagga        5940
gaaatttttt tttttttagt gagaaattag gttttgagga aatgtatgt tagtttaata         6000
aaggtattat tttttttttgg gtgatttagt tagtatattt ttgtagttttt tttgggaggg      6060
gagtttgggt tagaatgggg gtggttatgt ttttttttttgt tttattttag gatttagttt      6120
```

```
tttttttagg gttgttattt ttgtattggg gttttttattt ttgggttagg gtttttagga    6180
ggggtttgat tgtaggattt agggaggggt tgaggtttgg tgttttttgt ggttagttta    6240
agtttattga aaataggatg ggggtattag gtttagggtg gtgtttatag tgatggtggt    6300
ttttgttgtt ttaattttt ggattaaaat gggggtttt ggaaatggga tgtaaattgt      6360
ataattattt ggagaaaagg tgggtagtgt ttggtgaggt ttaagttata tagattttat    6420
agtttagtaa attttttttgt ttttaggttt ggtttttttaa ttttagaaat atgtttatat  6480
ttgggtagaa gaaaatatag g                                              6501
```

<210> SEQ ID NO 31
<211> LENGTH: 12001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 31

```
tatggattgt gtgattatta aatttggtat tttaggggt atttttttt tgagtaattt      60 ttataaatat gtttgtttgt aggatattta gattttttgg tttggtagta aagtaatata    120
agaataattt tgaatttgat gtttattttt gtttttttt taattttagg agttttttga    180
ggtttggatt aatttattga ttaggaaata gtatttggaa aggttaaata aaatattatt    240
tttagggaaa tagtatttgg aaaggttaaa taaaatatat tttttagtt tttttaaatt    300 ttttagaaga tatatttttt aaaaaataaa ttaagttagt aatatttaaa ttaaattttt    360
gttttgttta taatataaaa gatgataaaa aaattgttgg gaaggtgaga aattaattt     420 atttataatt agaagtaaag ttttttattta aaaatgtaat attatttaaa tttaatttgg   480
gaaataaaaa ggatttaaaa aatagtttgt taaagttaat ttgtaaataa gtgtgttttt    540 tttttttta agttgtattt taggtttaga gtatatgtgt aggttgtta tgtaggtaaa     600 tttgttatag ggatttgttg tatagattat tttgttattt aggtattaag ttttgtattt   660
aatagttatt tttttttgatt tttttttttt ttttatttgt tatttttaa taggttttag   720 tgtttgttgt tttttttttt gtatttatga gtttttttta tttagttttt atttataagt   780
gagaatatgt gttatttggt ttttggttt tgatttagtt tgttaaggat aatggttttt    840
agttttattt atattttgt aaaggtatg atttattttt tttttttaatt attttatttt    900 ttttattatt tttttttttt tttttaattt tgaattttat tatgttagtt taattatttt    960
tttttttttt ttttttttg tttatttgta tatagttaaa agatgttatg aatttttttt    1020
tttaatttag tatatgttta ttaaagattt aaaaatatta tttatattat ttagaattta   1080
gtttaagaaa ttattaaaaa ataaagttat tagaaagtaa ttgaattatt ttgttgagtt   1140
ataattttag attttgattt tgttttttt ttatttttag taggttattt tttttttttt    1200
tttaaattgt ttttttgta tttaataata tattttgtg gatttagaaa gggtggagta     1260
tgaggaaaag gaatatgata tatgtatttt agaggaaaat aataaataaa tatttttagga  1320 tggaaaatat tatttttatt tttattgagt tttttagagt ttatttgatt tgtgtaaatt    1380
agaaattagt agaatgatat taatgaatta atgaaaagta gaatgagtta ttagttgtaa    1440
taaaaagaat aaagaatttt aagaatatag ttttaattat gtatggttgt ggggagagaa    1500
aaataataaa atgttttttag tgaatatatt tttgagagaa gaaaggaaat atttaaggag    1560
aggataaaaa gagtaaatat taaaaatagg agtaagaatt ttattgtttt ttttagttga    1620
```

```
taaataaaaa ttgtatatat ttattgtgga taatatgata ttttgaggat tatgattatt      1680
tttgatttat aaattatatt taagaaaaag aaatttttaa aaagtttggg aatatatgaa      1740
gttgaaagaa tattaatatt tagataagga tagtatatga taaattattt ttgttttaat      1800 atttttttt aggaaattta aatatttttt agtgaagtat tagttttttg aaattaagta      1860
tgagaaaaaa aattaaattt atttgtggaa aaaagatat agttaaataa aaagtggtt       1920 gttataattt taagagtggt atgaataaaa tgattaatat tttttaagt gatagtataa      1980 atattaaaag ttttaataag tggaagtggt tttgttatga taaaaggtgt ggtatttgta     2040 taattttag ataagaataa agttatgatg ttaagatagt agtagtattg tttgttatat      2100
gtgatatttg aaaaatatga taattatttt aatttgttta agtagtattt atggtgaggg     2160
tgaaatttta ttaatattgg ttaatttatg gtgttttaaa aaattagtaa ggagataaat     2220
tgatggatta aaagataaat tatttatagg tagataaata gaaggataga tagagttata    2280
attaaatatg tattttattt aggtagaaag ataataatta gttttaaga agtgatgtgt      2340 ttgttagaaa agttttgaat atagaatttt ttgattttgt tttaaattta gtttttttag     2400
gtattatgtt gtataattag gtgtaatttt ttaaaagttt ttatgataga attttttatt     2460
tgttaaatta ggttaataat attttttattt ttttttaggg taaagatgtg aaatatttgg    2520
agaattttgg aaaatatgtt ttttattaat tagagttttt tgatgtgata ttattttttt    2580
tagtatttgg agtttagtta atagatatat agtgtagttg tgaaattatg aagtatgaga    2640
atgtattatt aagggattgt aggaggtttt ttattgaaaa gtgtagttgg ttatattttt    2700
ggaagtaatt taaatatagg ttgagggaga ggagtatttt ttagattttt tttagatttt    2760 atttttatg aatttaatt tttttttttt atttagaaaa aataatgaga tttatagtgt      2820
agagatagaa aataaggttt tgtgtgtttt taaattttat ttaaaaat attatagtat      2880 tttggatgag atagttttga attttttgtaa tagtataggt atgagagttt ttattagaaa    2940
ataggagatt ggattgattt ttttattttt tttttatgtt ttaaaatt gaaaagttat      3000 atatataat tatatttatt tattttttt ggaaaaggtt aaaatgaatt taattttgga     3060 ttattttaa taatgggata aatttgaatt gagaataatt tttagaatta gttttgtttt    3120
tttgtgataa aatggatttg tagaaagtta tttggtgttt ttttttagtt aatatttat    3180 tataaataat gggtatgtaa tttagtattg ttttttatag gttatgtttt tggaattatt    3240 attttttgtat tttatttgtt tgttgatatt ttttttattta agatgttttt tttagtataa    3300
gaagttattt ttttttaaaat tttaaatgat tttattataa taatagagtt gttaattaga    3360
tttaggtaag taatgataat aaaaatttga ttttttattta gagtgtagta tggtttaata    3420
taataattag agttttaata ggttttttta gattttattt ttatttaatt tgtatgtttt    3480
tgtaatatag atgttttat tatttggttt ttatttttat tttttttgt ttttggaata     3540 aaattattta aatttaattt agagattta ttttttttg gaattattgg gaaatagttt      3600
tagtaaatta tattttgag attttatatt aggtttagtt taaattgatt atttaagtat     3660 taatttttt gtggtttagg aatatttttg agtttatttt ttttttttta aattgtttag    3720
gataaatatt ggagtttggt ttttttgttt ttttatttaa ttattttttg ttttttttt    3780 tttagtattt aaaatatttt tgatttttttt tatttttaa gaaatatatt tgttttttg    3840 tttttgtatt atttttttgt ttatgaaata tttataggt aagttttata tttttttttt    3900
ttagaggttt ttggttttt ggtttagtt gttattggtt tagtgtatta gttaatattt     3960
tggattttgg agttatataa atttagattt aaattttat tatgttattt attgtttatg    4020
```

```
tgatttgaag taatatttta tttattgtgg tttttagtag ttataagttt gtgttttaat    4080
tagttgggtg attttgggtt agtgatataa ttatggtaaa ttttattgtt tttatttgta    4140
aaatgatagt atttattttg tagtgttggt ataaggaata agtgtgattg ttaatataaa    4200
agtgtttagt ataatagtta aattaattaa gtattttgta aatattagtt tttattatta    4260
ttattaattt aaatgattag atgtattttg tgtatattag gttttttgag tttattttgt    4320
ttttaataaa tattattatt tttagtatgt ggtttatatt atattttatt agttagagga    4380
tatgtgaagt ttagagtgga aagttagggt agtaggaagt attgttatat tttatatagt    4440
taaagttatt taaatatgtt tgaatttgag ttttgttgag tttttatttg tttttatttt    4500
ttttgtgtgt tttagtttat taataaagta ggtttaatat aaatatatta aaagtttaaa    4560
tattgagatt atgataatga atatgagggt tatgattata aaatattatt gaattagaga    4620
tttgttatga aattatatgg tgaagattat aagggaggaa tttgtatata tattgagtgt    4680
tttgggattt taaagtggga agagttagtg ttttaattaa agagaaattt ggggtaggga    4740
attaattata atattagtta ttttattgaa tttaggtttg ttttagttga tgtagttgtt    4800 aattttaat gtttttttt tttttaattg tttttaattt atttttttag aaattgaaag    4860
tttattaaag aggatatttt tttagagagt tgttttagtt attataagtt tttgttagaa    4920
attttaagaa agtttataag gtattttat aaggtggtat tgagtaagtt agaagtattt    4980
taagtattaa ttattatgta aataagggtt ttatttttag attttgttgt ttgtggtggt    5040
ggtgatgttg gtgtttttt tggaatttag tttaatttt aaaaagtaa aaggagtata    5100 aatagtaata taaattatta ttatttatat taattaaaat agaagttttg aatgagtaag    5160
gagttagagg aggtaaaaat tgggaatttt gtatattaaa aggtttttat aatttgaaaa    5220
ttaagattat gttggttaaa taggttgttt taaaattagt atagtaatta aatttgtttg    5280
taatgaatgt agatttaaat agtgatgtta gatttgataa ggatttgtaa attttaaaag    5340
agtgtaaaaa gattatagaa gaataatatt atatttttgt atttatagaa atggttagtt    5400
taagagatgt atttagttta gggtggttgt aagtttttatt ttttgaattt gttattagaa    5460
gttaaaagaa attttgtata attgttttg atggaaatat aaattggttg atgtaaatga    5520
aatatataaa gtagttggtg tttttatttat ttttataatt ataaatgaaa ttaaatgatt    5580
aaaaattata gattttgggg attttttttt tattgaggag tttatggaat ttgttttttt    5640
tagtattaat aattgtgttg atttattttt ttttgtttaa ttttgtatat attaaaatta    5700
ggtggttatg aataaaattt agaaatataa tttatatttt aataaaatga ttttaaaatt    5760
attttatttt ttattgtggt tttatttgtt gttttataat gtaggttttt ttgggttttt    5820
gtttagaatg attttgttaa tgtagatgat agttagagtt gaatgggaa tttagaaatt    5880 ggggatttgg gttttgatg taatttatat gttaatttat tttattagtt ttttttttat    5940
ttatagtttg gtaaagaata tgggtggagt tgttttgggt ttatttgtat atatgtttaa    6000
attgttttga aaaggaagg gtaagaaaga gtggtattta agttggaatt aggtaggtat    6060
tttagattaa gagatgaatt ggaaagggaa tatttgttag atattttggg tttgaaggta    6120
gtttgtgtaa gtttttatat ttttgagtgt gtgtatatag tggagagggt ggagtttgtt    6180
atttttaaat ttgaaaagat tgagagattt tagagggttt agatgtgtta aaggttagag    6240
ggattaatat ataggtttta ttatggaaag gtggggaaaa ggtttgaata gaaaattgtt    6300
gtagaaggga agttattgag aggtaaggga gttttttgaat aattaaaaag ttaagaataa    6360
```

```
gtaaaaggaa ggaggttggg tgggggataa aaaaaagtag ttgatgtggt aattaagaat    6420
ttggtgggag tttgggtagg ttattttttt ttttagatta gagttttatt agaaatttt     6480 ttaagtgttt ttttgtgttg ttaaagatga taatagtaaa ttaataagtg tttgaaatga    6540 aagggatgt tgattagttt ttaggttata gattttttgt tgttagtttt ttttgaattt     6600
ttatagtgtg tttttgtatt gtttttttta agaagagtta tttttttattt ttattttag    6660 gatgaaggta agtgtttagt tagtatattt attaaatgtt agttttggtt ttagttttt     6720 gtttgtgtgg aaagtttatt gttatagtgt gtttagtttg ttgaggggt agatagaaaa     6780 agtaagtttg gtttggtgat ttgtggggtt atgtatttt agggttggtt tggagttttt     6840
tagagtttaa tgttttggg ttagaattgt aaggttttgg tttgagtaaa gggtttgagt     6900
tattgtagtt gtgggagtgt ttttttatt tgaatgtatt tatttataaa taagtataaa     6960
atttttttaa tagtagagga gaaagatttt tgttttaaaa ttaaagttgg gaattattgg    7020
aaattttgtt ttgagtgtga gatattggtt tgttattttt ttaatttta tatttttttt     7080 gtaatatgtt ttgatttaat aatttttta gtgtttagta ttgtttggat gttttaattg     7140
ggtaatttat tagtgagtta atataggtat ttatatattt tttagttta agtggttaag    7200 tattaatttt gaaatgatta taaaatattg gaattggtaa tgtatagtaa ttttaattta    7260
tatgtaaatt aattggttta ttttaaatgt ttttttaaa aaaataatta ttgtattgta    7320
gtattggagg tatggattaa attttagaa tagataattt ggaaataaga tttggattag    7380
gaagataatt tagaatagtt aataaattaa taatgtttga ggtagttaaa tattgttagt    7440
tattggtatt tatatatttg tttgttgtta gataaggagt tggggaaatt gtttgttagg    7500
gttgagatta taattagag tgaagaaagt aaatggtagt atatagtttg ttatagtggg    7560
ttttgaaata atattgtatt ttttttaaat tttgattttt gggtgatagg gagttggtgg    7620
aggttatttt atatttgttt atggttttgt tttaatttga ttatgaaatt gttgttttt     7680 ttgagttttt taatttgatt attattttaa tggttttgtt atttgtttta atatattggg    7740
gggaggagtg taattgagat tttattaaa aattatttga atttatttag ttagtattgt     7800
tttatttaag tttagttttta tgggttgtat ttaattttt gtgtttttta tatattaaaa    7860
ttagattatt aaaatgttgg taggaaaggg tgaaggaaat ggtttaatgt tttagtttat    7920
tggaagatta ttatttttag atatagttta aaatttgag gaaataaaaa ggatatatgt    7980
tttgggggga aaatgtttta atattttaga atgggggtat tatttttttt attttagaga    8040
atttgtattg gagttgttta tgtaaaaatg taatattttt gaaatttata gatatgtaag    8100
gttagtgttt tttttttttt aggttttta tttaggtgat ttagttttaa aggagttagt     8160 attttgatg ttataatttt gtttatattt gtagggtaga gaattgtttg ttttgttggg     8220
atgttttttt tatttttttt taatttgaag taattggaat ttaaatatag ttgttaaggt    8280
ttgttttttt tttattgttt tgataaggga aaaatttgaa atttatgttt taaattagtt    8340
tggtggtttg tagtttttta gtattttgtt tttatgattg tatgtttaat gtattttttg    8400
gtgattttgg gtattaatta gttgtttaat aggagtatga ttaaaaatgt aaaagaagga    8460
ttaggagtgt gaaatgtatg tttagttttt tttatatatt tgaggaggga atgagaatta    8520
ttttgtattt tttatttttt taggagttat ttgtattttt tattagttgt ttattttagt    8580
tgtattggtg ttgggtaagg tgaggattta aaagtttagt gtagtgtttg tggtggttgg    8640 gattgggtt aattagtttt tggtgggtga gattttagat agaagggggg tgagaggaat     8700
gtgagttttt tgagtttttt tttttagtt ttggtttgta aattttgaa atttgaaagg      8760
```

```
ggagggagtt gtatgtgtgt attttttgtgt ttttttagtg taatttttttt tttttttttt    8820
gtgtttttt  gtggattttt  gaattttttt gttttggtt   ttttattttt  tttttaattt    8880
ttttatgaga ttgttattt   ttgttattag ttgaaggtaa  ggttgttttg  ttatgagtgt    8940
tttttaattt ttataaaatg  aaaagaaaaa aagggaggat  tattagttta  ttatttagag    9000
gaatggggag gttgtaaaaa  ttgttgatgg gtagaggtga  agatgttttt  tttggattgt    9060
attttttggt gttttgtaat  tagagtttag ttgtgggatt  tgttgaagaa  atttgatttt    9120
tttgttttgg tgagattttta aaaattagaa atagaaattt  ttagagttag  agaggaaata    9180
taattaaata gtatgtgggt  attttttttt ttattttttt  ttttttaaat  aatattgttt    9240
tgagttttta ttgggtaaag  agagaaagtt tgagttttta  tggatgttat  gtggaggtta    9300
gaaatggttt aaaatgtaga  ttttaatta  gttttttttg  tggttgaaga  ggttaattt     9360
ttttataaaa tgagtttatt  tgttgattgt tagttatttt  aaagtgaagg  gatttagtat    9420
ttaaaataaa ttgagtaagt  ttgtttgttt gtttttattg  ttaatttaaa  tgaatttaaa    9480
atatggagta atttaagaaa  atatataata tgttttagat  agttttttaaa agtagggaaa    9540
gtttagtatt tatatagtga  ttagggttag ttttaagtgt  taagttttttt taaatgtatt    9600
tattttatgt atattttttt  gagttattat atattttttaa aattgtgagt  attggtatat    9660
tgatttagga agagtaatat  aattttttaga gggaatttta tttttaatta  gggattaaag    9720
agatgttttt ttaatagtgg  gtttgagttt tgttttttaag taggaattaa  tattggtggg    9780
aaaatttgaa tttaggagta  atggttgtgt tttggtattt  tttaaaaata  tatattaata    9840
ggatgttttt gagattgaaa  aaatattgtt ttatatgttt  ggtagaagtt  tttatatttg    9900
gttttttagg tgaattatat  ttatagtttt tttatttaga  ggtaggatag  agttaaaata    9960
ttttgtttat tattaaaata  tatattttttg tttaagttaa gaaattagaa  aattagggtt   10020
tagaagtaag gtatatttttt tgagtgagaa tatgttttgt  aatttatat   attttttgtt   10080
ttgtaggagt aaatgtggat  ttgagggaaa tttttttttt tatttttatt  tttattttgt   10140
gtaatttaat attattttttg ttaggaattt taattttgtt  attttaaaaa  atgagatatt   10200
tgtgatttag ggtgaatttg  ttgaatgtag gtatagtaga  ggaaattttta gatttttatga  10260
gtgtttgagt tttgtttagt  gtaaatttttt tgtgaatatt gggttagtgt gtggttgtgt    10320
ttatttgtgt gttgatattt  ttagtatgtt tggtttatttt gttttgatttt tgggtgtggt   10380
gttttagtta agtttgggtttt agtgttttgg tttttttttag ttgataagtt tagtttgttt   10440
gttttttggtt gtggttttttt tattttttttt tattagttta ttttatttttt ttagatttttt  10500
ttttatttat tttttttttat ttttattgtg tttatttttta tttttgtttt ttattggttt    10560
tttatttttt ttttttttgta gttttttttttt gttgtgattt ttttttttttaa ttttgtaggt  10620
ttgaaagaag gttatatatg tatgtttata  tttatatttt  atatgtttttg ttttaaataa    10680
ttttatgaat attgtttttt  gttttgtttt  tgggttatt  ttttttgttg  ttttttttttta 10740
gtttgttttg atttgttttt  taaaagtatg  ttttttgtttt tttgttgttt tggtgttttt   10800
tttttgattt attagggttg  ttgggttggt  gtagattgtt  tttttttttt  ttttattttta 10860
ttttttttttt tggtttttttt tttttatagtg ggagtttgtg ttttttgtttt ttggttggtt   10920
tttaagtgtt ttgttaggtt  ttttttttttt ttgttttttttt ggtttttggtt tttgattttt  10980
tggttttgttg gtatttgttt  tttttttttg  ttttgttttt  tgttgttttt  gtttgttttt  11040
tttggtgttt gtttgggtgt  tgtgtttgtt  tttggattgt  tagttgtgta  gttgggtttg   11100
```

| | | | | |
|---|---|---|---|---|
| gttggttgtt | tgtgtgttat | tgtgtagtgg | agtttggtgg | aattttttgtt datgttatgt 11160 |
| tattttttat | atggagtagg | agtagaggga | agagagaggg | atgagaggga gggagaggag 11220 |
| agagagtgtg | agattgagtg | agaaagttgg | agaggagtag | aaagaaattg ttagtggtgg 11280 |
| ttagattttg | gaggttttag | tgtatttgtg | gattttttg | gaatttggta ttttaggag 11340 |
| ttttgtagtt | tttttaggtt | tggttttgg | gtgtttgttg | tgtagttgga ggtttggttt 11400 |
| gttggaaatt | gttttgggaa | gtagtgggat | gtggagatag | tagttttttt ttggtagttg 11460 |
| gtaagtggag | gttatttatt | ttgtagggat | gtgagataat | gtgagtttgg aaatttgttt 11520 |
| tattttggag | aattttatt | gtaggtgatt | tgtggttttt | ggggttaagt tttgtttaag 11580 |
| gtaatgtagt | tggtaaatag | attttgtaaa | gttttgtttt | ttttgtttt tgttatagat 11640 |
| attaataatt | tataggtgt | tgaagttgag | agggaagtta | gattgtggtt ggtatttaaa 11700 |
| atgaggtatt | ttttttaaa | ttttggtgtt | aatattgtag | gaataaattt ttgggttaag 11760 |
| gattagtatt | tttaagataa | agggttgggt | ataaagtttt | agttattgga agattagttt 11820 |
| tttttttatt | gttatttatt | gggaaaaaaa | agaaaagaaa | aagatttat ttaattggt 11880 |
| agttagtgat | tttttaggtt | taagtgaatt | atttgggagt | taggtttgga tgttaagttt 11940 |
| ttattatttt | tttggattgt | aattttttta | aattgattat | tagttaatt taatttgta 12000 |
| t | | | | 12001 |

<210> SEQ ID NO 32
<211> LENGTH: 12001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 32

| | | | | |
|---|---|---|---|---|
| gtgttagatt | ggagttgatt | ggtgattaat | ttaaaggagt | tataatttaa agaaatggtg 60 |
| agagtttggt | atttaggttt | ggttttagg | taatttgttt | gggttgaga ggttattaat 120 |
| tgttagttaa | gatggaattt | ttttttttt | ttttttttt | taatggataa taatgggaag 180 |
| ggggttaatt | ttttagtagt | tgaaattttg | tatttagttt | tttatttga gaatgttaat 240 |
| ttttggtttg | aggatttgtt | tttgtagtgt | tggtattgag | atttaaggga agatattttg 300 |
| ttttaaatgt | tagttatggt | ttggtttttt | ttttgatttt | agtatttgt agattgttag 360 |
| tgtttgtggt | gggggatgaa | aggaataggg | ttttgtaagg | tttgtttgtt gattgtgtta 420 |
| ttttgggtga | aatttagttt | taaaagttat | aaattattta | tggtgaagat ttttgaagt 480 |
| ggaataaatt | tttagatttg | tattatttta | tattttgtg | ggatagatgg ttttatta 540 |
| ttggttattg | ggagagagtt | gttgttttg | tgttttattg | tttttgggg tgatttttag 600 |
| tgagttgagt | ttttggttgt | atggtaagtg | tttgaaagtt | gggtttgaga ggattgtagg 660 |
| gttttgagg | gtgttaagtt | ttgaaggagt | ttatgggtgt | attggggttt ttgaaattta 720 |
| gttgttattg | gtagttttt | tttgtttttt | tttagtttt | ttgtttggtt ttgtattttt 780 |
| tttttttt | ttttttttta | tttttttt | ttttttgt | tttatttg tgtggggagt 840 |
| gatgtgatgt | tagtagagat | tttattaaat | tttattgtat | agtggtgtgt gggtggttgg 900 |
| ttgagtttgg | ttgtgtggtt | ggtgatttag | gagtgagtat | agtgtttggg tgagtgttgg 960 |
| ggggagtgag | taggggtgat | gagaaatgag | gtagggagg | gaagtagatg ttagtgggtt 1020 |
| gaagagttgg | gagttggagt | tgggagagtg | aaaggagagg | ggatttggtg gggtatttag 1080 |
| gagttaattg | aggagtagga | gtatggatt | ttattgtgga | aaggaggatt agaagggagg 1140 |

```
atgggatgga agagaagaaa aagtaatttg tgttaatttg gtagttttaa taaattaaag   1200
ggggagtgtt agggtagtgg ggagatagaa atgtattttt ggggagtaaa ttaggatggg   1260
ttgggaggaa gtgatagggg aagtggttta agagatggaa taaaggataa tgtttatggg   1320
gttgtttggg atgaggtgtg tggagtgtgg ggtgtgagtgt gtgtgtgtga ttttttttta   1380
ggtttgtaga gttgaggaaa gaggttatag taaagaggga ttgtggaggg aggaaagtga   1440
gagattggta gagggtggga gtggaggtgg ggtgtggtggg gatgggagag gatgagtgaa   1500
gagaaattta gaagaatgga gtgagttagt gggagagggt gggagggtta tagttgggag   1560
tgaatgagtt aggtttgtta gttggggaag gttgggatgt tgggtttagt ttagttggga   1620
tattgtgttt gaggttaagg tgggtggatt aggtatgttg agagtgttgg tgtataggtg   1680
ggtatggtta tgtattgatt tagtgtttat gaagggtttg tattggataa ggtttagatg   1740
tttatagagt ttagaatttt ttttgttgta tttatatttta ataagtttat tttgggttat   1800
ggatatttta ttttttaaaa tgatgaggtt aaggtttttg gtgaggatgg tattaaattg   1860
tatgggatag aagtgggggt gggggagaga gttttttta agtttatatt tgttttgta   1920 aagtaaagag tatgtgaaat tatagggtat attttatttt gaaagtgtg ttttattttt   1980 gaattttgat ttttgattt tttgatttga gtaaagatgt gtatttggt agtgagtaga   2040 atattttggt tttgttttgt ttttgagtgg aaggattata aatataattt gtttggagga   2100
ttaggtgtga aggttttgt taggtatatg ggataatgtt tttttaattt taagggtatt   2160
ttgttaatgt atgttttgg aaagtgttgg aatatagtta ttgttttgg attttggattt   2220 ttttattaat attaattttt gtttgagagt aaaatttagg tttgttatta aaaagatatt   2280
tttttggttt ttaattgaga ataaagtttt ttttaaaagt tgtattgttt tttttaaatt   2340
aatatattaa tatttgtaat tttagaaata tatagtgatt tgggagaatg tgtataaaat   2400
agatatgttt aaaaaagttt ggtgtttaaa attaattta gttattatat aggtgttggg   2460
ttttttttat ttttgggggt tgtttggaat atgttatgtg tttttttgaa ttattttgtg   2520
ttttgaattt atttgagtta gtagtaaaaa taggtaaata aatttgttta attttgtttg   2580
agtgttaaat ttttttattt tgaaatagtt aatagttgat agatggattt attttatgga   2640
aagggttagt ttttttagtt atgaagaaaa ttgattagag atttatattt taagttattt   2700
ttaattttta tgtaatattt gtgaaaattt aaattttttt tttttattta gtggaaattt   2760
aaagtagtgt tatttaaggg gagagaaatg aggggaaaa tgtttatgtg ttgtttaatt   2820 gtatttttt tttgattttg agaatttta ttttggtttt ttgaaatttt gttgaggtaa   2880
gaaaattaaa tttttttaat aagttttata attgaatttt agttatagga tattggaaag   2940
tgtagtttga gaaagatatt tttattttg tttattgatg attttgtag ttttttttatt   3000 tttttgagta atgggttaat aatttttttt tttttttttt ttatttttgta gagattaaga   3060 ggtgtttgta gtagaatggt tttgttttta gttggtggtg aggataggta attttatgga   3120
aaagttggaa gagaatgaga aaattaaaga tagaaagatt tagagatttg tggagagata   3180
tagggagagg gaagggagtt gtgttgaaaa gatgtaaaga tatgtgtgtg taattttttt   3240
tttttttagg ttttagaggt ttgtaaatta gggttgagag gaaggggttt ggaagtttaa   3300 tgttttttt gtttttttttt tgtttggagt tttgtttgtt agaggttggt taatttagt   3360 tttggttgtt gtagatattg tgttgagttt ttgggttttt gttttgttta gtgttagtgt   3420
agttgaagtg agtagttggt gggaaatgta aatggttttt ggagaaatag aagatataga   3480
```

```
atgattttta ttttttttttt gagtgtgtgg aaggagttgg atatatgttt tatgttttta    3540
atttttttt tatatttta gttatatttt tattaaataa ttaattaatg tttagaatta       3600
ttagggaata tattaggtat gtaattgtag aagtagggtg ttgggggggtt ataaattatt    3660
gagttgattt aagatgtgga ttttaggttt tttttttgtt aaagtagtaa aggaagagtg     3720
ggttttggtg attgtattta gattttgatt attttaaatt agaaggggggt ggagggagtg    3780
tttaagtaaa gtaagtaatt ttttgttttg tagatgtaaa taagattgta gtattaaagg     3840
tattagtttt tttagggtta gattgtttgg attgggagtt tggggaaggg gagatattaa     3900
ttttatgtat ttgtgaattt taaggatgtt atatttttat ataaataatt ttagtgtgga    3960
ttttttggaa tggggggagt aatattttta tttttagaata ttaaaatatt tttttttttaa   4020
agtgtatatt ttttttattt ttttaaaatt ttgaattatg tttaaagata atagtttttt    4080
agtaaattgg agtattggat tatttttttt attttttttt attgatattt tgatgatttg    4140
attttaatgt gtgggggggta tagggaatta aatatagttt ataaaattaa gtttagatga    4200
aatagtgttg gttaagtggg tttagataat ttttaatgag aattttaatt atattttttt    4260
ttttaatatg ttgagataag tgatagaatt gttagaatgg taattaaatt ggaaagttta     4320
gggagaataa taattttgtg attaaattgg ggtaaaattg tggataaatg tggggtgatt    4380
tttgttaatt ttttgttatt taagagttag gatttgggaa aggtatagta ttattttaga    4440
gtttgttgtg atgggttgtg tgttattatt tatttttttt attttggatt atgattttaa     4500
ttttggtaag taattttttt agtttttat ttgataataa gtgagtatgt aaatattaat     4560
ggttagtgat gtttaattgt tttaaatatt attgatttgt tggttgtttt aaattgtttt     4620
tttagtttag gttttgtttt tgaattgttt attttagagg tttgatttat gttttgatg     4680
ttataatata ataattgttt ttttaaaaaa ggtatttaag atgaattaat tgatttgtat    4740
ataaattaaa attattatgt gttgttgatt ttggtgtttt ataattattt tgaaattagt    4800
atttaattat ttgagttaaa agaatatata aatgtttgta ttgatttatt aatgaattat    4860
ttaattaaaa tgtttgggta atgttgggtg ttggaaagat tgttaaatta agatatatta    4920
taggagggat atgaagatta gaaaggtaat agattaatat tttgtattta aaatggagtt    4980
tttggtgatt tttagttta attttggagt aggggttttt ttttttttgtt gttaaaaaga    5040
ttttgtgttt gttgtgagt gagtgtattt aagtggaagg aatgttttta tggttatggt     5100
ggtttaggtt ttttgtttgg attgggattt tatagtttta atttaggagt gttaaatttt    5160
ggaagatttt gggttagttt tggaggtgtg tggttttgta agttgttagg ttaagtttgt    5220
tttttttgtt tgttttttg gtaggtgggg tgtgttatgg tagtgagttt tttgtgtaaa    5280
tggagagttg gaattaaagt tgatatttaa tagatatgtt aattgagtat ttattttgt     5340
tttgagaata ggaataaaag gtagtttttt ttaagagagg tggtgtaaag gtatgttata    5400
ggagtttaga aaaggttggt ggtgggaaat ttgtagtttg ggggttagtt aatatttttt    5460
tttattttaa gtatttattg atttgttgtt gttattttttg gtgatgtaga aggatatttg    5520
aaagaatttt tgatggggtt ttgatttgag aaaggaggtg atttgtttag gtttttatta    5580
aattttaat tattatatta attgtttttt tttattttt atttgatttt ttttttttg      5640
tttatttta atttttaat tatttagaaa ttttttttatt ttttagtggt tttttttttg    5700
tagtagtttt ttatttgaat tttttttttg ttttttttgtg gtagggttttg tatattgatt   5760
tttttgattt ttggtatatt tgggttttt gaaattttt aattttttta gatttgagga     5820
tggtaggttt tatttttttt attgtgtgta tatatttaga gatatgaaaa tttatataga    5880
```

```
ttgttttaa atttagggta tttaatagat gttttttttt tagtttgttt tttgatttga    5940
aatgtttgtt tgatttaat ttggatatta tttttttttg tttttttttt tttaaagtag    6000
tttggatatg tgtgtaagtg agtttagaat agttttattt atatttttta ttaaattgta    6060
aataaaagaa gaattaatga agtagattgg tatatagatt gtattaagag tttgaatttt    6120
tagttttgg atttttatt taattttggt tgttatttat attgatagag ttattttaag    6180
tagaggttta gagaaatttg tattgtggga taataggtaa agttatagta aaaagtggaa    6240
taattttaaa gttatttat tagaatgtaa attgtatttt tgggttttgt ttgtaattat    6300
ttagtttaa tatatataga gttagatagg aaaaaatagg ttaatatagt tattggtatt    6360
agagaagata aattttatgg gtttttagt gaaaagaaga ttttaaagt ttataatttt    6420
tgattattta attttattta taattgtggg aatgaataag atattaattg ttttatgtat    6480
tttattata ttaattaatt tgtgttttta ttaaaagtag ttatatagaa ttttttttaa    6540
tttttggtag taagtttaga aaatgaagtt tatagttatt ttgaattgga tatatttttt    6600
gagttgatta tttttgtaag tgtaggaata taatattgtt tttttatggt tttttttgtat    6660
tttttaggg tttgtaagtt tttattaggt ttgatattat tgtttgggtt tatatttatt    6720
ataagtaaat ttgattatta tgttgatttt aaaatagttt atttggttag tataatttta    6780
gttttaaat tataaaaatt ttttaatata tgaagttttt agtttttatt tttttagtt    6840
tttgtttat ttaaaatttt tattttaatt ggtgtaagta ataataattt gtattattat    6900
ttgtatttt tttatttttt tggagattgg gttggatttt agagagaata ttagtattat    6960
tattattata aataataaaa tttaaaagta aagttttat ttgtatgata attggtattt    7020
ggaatgtttt tgatttattt aatgttattt tataaaggta ttttgtaaat tttttttggaa    7080
tttttagtaa gagtttgtag taattggaat aattttttgg gaagatattt tttttgatgg    7140
gtttttagtt tttggaggaa tagattgaga gtaattaggg agggagggga tattggaaat    7200
tggtagttat gttagttgaa ataagtttgg gtttagtaag gtgattgatg ttgtggttga    7260
tttttattt tgagttttt tttaattggg gtattgattt tttttatttt gggattttaa    7320
ggtatttggt gtgtatgtag attttttttt tgtggttttt attatgtggt tttgtagtag    7380
gtttttggtt taatgatatt ttatagttat agttttata tttattatta tgattttaat    7440
gtttaggttt ttagtgtatt tatattaaat ttgtttttat agtaagttgg agtatatagg    7500
agagatgggg gtaagtaagg atttagtaga gtttaaattt agatatgttt aaatggtttt    7560
gattgtgtaa agtgtggtaa tgttttttgt tgttttagtt tttatttta agttttatat    7620
gtttttggt taatgaagtg tgatataggt tatatgttag gaataatagt atttgttgag    7680
aataaagtga atttaggaaa tttggtatat ataaaatgta tttagttatt tgaattagta    7740
ataatggtaa aaattaatat ttatagagtg tttagttaat ttagttattg tattaaatat    7800
ttttgtattg ataattatat ttatttttta tgttaatatt ataaggtagg tattgttatt    7860
ttataaatga agatagtgag gtttgttatg attgtgttat tggtttaagg ttatttagtt    7920
ggttagagta taagtttata attgttggag gttatagtgg ataggatatt gttttaggtt    7980
atgtaggtag taagtggtat agtgggaatt tgaatttagg tttgtgtaat tttaaagttt    8040
aaaatgttaa ttagtatatt gaattaatgg taattggaat tagaagatta ggggttttg    8100
ggggaaggaa atatagaatt tatttatgga atattttata aataaaagaa taatgtagag    8160
ataggaaagt aaatatattt tttgagggat ggagaaagtt agaaatgttt taaatgttaa    8220
```

```
agaggaggaa atgagaaatg attggatgag aaagtagaaa agttaaattt tggtatttgt    8280
tttgggtagt ttaggaagag aaaggtaagt ttagggatat ttttgagtta taggaaaatt    8340
aatgtttaga tggttagttt ggattaagtt taatatagga ttttaggaat atggtttatt    8400
agaattgttt tttagtaatt ttaagggaga ataaaatttt tgaattgggt ttaagtagtt    8460
ttattttaga agtaaagaga gatggaagta aggattgagt aataagaata tttatattgt    8520
aagaatatgt aagttgagta ggagtgaaat ttagaaaaat ttgttaggat tttggttgtt    8580
gtgttaaatt atgttatatt ttaagtagaa attagatttt tattattatt atttgtttag    8640
gtttagttag taatttatt attgtagtaa agttatttga aattttaaga gaaatgattt      8700
tttgtgttga agaagatatt ttgggtggaa ggatgttagt agataaatgg agtgtaaaga    8760
tagtgatttt aaggatatag tttgtgggga gtaatattgg attatatatt tgttgtttgt    8820
ggtagaatgt tagttagggg agaatattag gtagtttttt ataagtttat tttattataa    8880
aaagatagga ttgattttaa aggttatttt taatttaggt ttgttttatt attgaaaatg    8940
atttaaaatt ggatttattt tggttttttt taggagggat agataaatat aatttgtata    9000
tatggttttt tagttttagg aagtatagga ggagaatgaa agaattaatt tagtttttg      9060
ttttttggta aaaattttta tatttgtgtt gttgtaagaa tttaagatta ttttgtttag    9120
aatgttgtgg tattttgaa agtaaggttt gagggtatat agagtttat ttttttatttt      9180
tatgttgtgg attttattgt ttttttttaaa tgggaaagaa aaattagaat ttatagaaag    9240
taaggtttgg aaaggattta gagggtattt ttttttttta gtttatgttt aaattatttt    9300
tagaaatata gttagttata ttttttagta aagagttttt tatggttttt tggtaatgta    9360
tttttatgtt ttataatttt atagttatat tgtatattta ttgattaaat tttaagtatt    9420
gaagaaaatg atgttatatt aaaaagtttt aattagtagg gggtatgttt tttagagttt    9480
tttaaatatt ttatattttt attttaaaaa aagatgaaaa tattattagt ttaattaat     9540
agatggaaaa ttttgttata gagattttta gagagttata tttggttatg tagtgtgatg    9600
tttgaaagaa ttaaattaaa aataaagtta ggaaattta tgtttagggt tttttagta      9660
gatatattat ttttttggggg ttggttatta ttttttttgtt tgagtaaagt atatgtttga   9720
ttgtaatttt atttgttttt ttgtttgttt gtttgtgagt agtttatttt ttaatttatt    9780
aatttatttt tttgttagtt ttttaaaata ttataagtta attaatgttg ataaaatttt    9840
atttttatta tgagtgttat ttgagtagat tgagatggtt gttatatttt ttaaatatta    9900
tgtgtaataa atagtgttgt tattgtttta gtgttatgat tttgtttta tttggaaatt      9960
gtataaatat tatattttt gttatgatag gattatttt atttattagg atttttgata     10020
tttgtgttgt tatttgggag aatgttgatt attttgttta tgttattttt gaggttataa    10080
taattgtttt tttgtttagt tgtgttttttt ttttatagg tgaattagt tttttttttt      10140
atgtttgatt ttaagaaatt ggtgtttat tgaaagatgt ttaaatttttt tgagagaaaa    10200
tgttggagta agaataattt gttatgtatt gttttttattt gagtattaat gttttttttaa  10260
ttttatatgt ttttaaattt tttgagaatt ttttttttttt gaatgtaatt tatgaattaa   10320
aagtgattgt aattttaaaa atattatgtt gtttatagta aatatatata atttttattt   10380
gttaattaaaa aaagtaata gggttttat ttttattttt gatatttgtt ttttttattt     10440
tttttttaag tattttttttt tttttttag agatgtattt attgagagta ttttgttatt    10500
tttttttttt tgtagttatg tatgattaaa gttgtgtttt tgaaattttt tatttttttt    10560
gttataattg ataatttatt ttgttttttta ttaatttatt aatgttattt tattggtttt   10620
```

```
tgatttatat aaattaaata gattttagaa aatttaataa aaataaaaat aatgtttttt    10680
attttgaaat atttatttat tgttttttt  tagggtatat atattatatt tttttttttt    10740
atattttatt tttttgaat  ttataagaat gtgttattga atatagagaa aataatttaa    10800
gaaaggaaaa ggaatgattt gtttaaaatg aggaaaaagt agagttgagg tttaggattg    10860
tggtttaata agatgattta gttattttt  ggtagtttta ttttttggta atttttaag     10920 ttgagttttg gatgatgtaa ataatatttt tagattttta atgggtatat gttgaattaa    10980
aaagaaaaat ttatggtatt ttttaattat gtgtaaatga gtaaagaaaa aggaaagaaa    11040
aggagtggtt aaattgatat ggtagggttt aggattgggg gaagaagaaa gagtaataga    11100
gagagtggaa tagttaaaaa aagaatgaga ttatgttttt tgtagaaata tggatggagt    11160
tggaggttat tattttttagt aaattaaatt aggattagaa aattaaataa tgtatgtttt    11220
tatttataag tgggagttaa atgaggagaa tttatagata taaagagagg aataatagat    11280
attgggtttt attggaaggt ggtggatggg agaggggaga ggattagaaa aaataattat    11340
tgggtatgag gtttagtatt tgggtgataa aataatttgt ataataaatt tttgtgatag    11400
gtttatttat ataataaatt tgtatatgtg ttttgaattt gagatataat ttaaagaaaa    11460
agagagtgta tttgtttgta aattggtttt agtagattgt ttttgagtt  ttttttgttt    11520 tttaaattga atttaagtgg tattatattt ttaaatgaaa attttatttt taattatagg    11580
tgaagttaat tttttatttt tttaataatt tttttattat tttttgtatt gtaagtaagg    11640
taaagattta gtttaaatgt tgttagttta gtttattttt taaaaaatat attttttgag    11700
aggtttgaga aaattaagaa agtatatttt gtttagttt  tttaaatatt atttttttgg    11760
aaatagtatt ttgtttagtt tttttaaata ttatttttta attagtgagt tagtttagat    11820
tttagagggt ttttggaatt agaaagaagg taaggatgaa tattaggttt aagattattt    11880
ttatgttgtt ttattattaa attagaaaat ttggatgttt tgtaggtagg tatgtttatg    11940
agagttattt aaaaaagata tgttttttga agtgttaagt ttagtgatta tgtagtttat    12000
g                                                                   12001
```

<210> SEQ ID NO 33
<211> LENGTH: 4001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 33

```
tttttgtttt tagtttatat atatttttt  tgtttgtttg gattttaatg gtttaagata      60
gttttgagtt tattgggaaa agaaaatgat tgttaaaaat tatttttgaa attggttatt     120
tggtaatatt tttaattgta tggaaattta ttaaggtata ttttatatat aattagttta     180
aggttgttga tttataggt  tttatggatt taaatttgat tgataataaa gtaaataaga     240
gagttgaatt taaagtgtgg ttttttggg  ttaggatgag tttaatatag tgtataagga     300
atttgaaaga tttaggatat gtgttttaat taatgttaag tagaatggat aagttttag     360 tattttgaaa atgttgggtt aggttttttt ttttattgtg tgtttttgt  ttggggatta     420 ataagtatta tagagaatgt gatttgaggt gattttttat ttttgtataa atttagagtg     480
aattattaaa tagttgtttg tttaaagtta aggtaatttt tttttgatgg gtttatttgt     540
tttttgattt ttaattatt  agtttgtttt tttagggttt tgtttttttt gtaattaaag     600
```

-continued

```
ttttttttaga ttagtgtagt atttatttga taggttgttt ggaaaattta agattggaga    660
ggtgatttgt tgttgttttt taaattttt agttttaagt aatgtgtttt tttttatat       720
```

(Note: sequence data table follows)

| Sequence | Position |
|---|---|
| tttttttaga ttagtgtagt atttatttga taggttgttt ggaaaattta agattggaga | 660 |
| ggtgatttgt tgttgttttt taaattttt agttttaagt aatgtgtttt tttttatat | 720 |
| ggggtggggg attggaaatg gatgtagtga gatataaaga gtgggtgttt tgttgatttt | 780 |
| tgtatttttt tttttttgat tattttattt tttttttta agttttgat ttttagtttt | 840 |
| atttttttat ttttgggttt gtattaaaag ttggattgtt ttgggttggg taggagttga | 900 |
| attttttggga gtttgtttgt gtagatttag tgtgtatggt gaggtagtag tttggttttg | 960 |
| tattgttgat aggtgtaggt aggatagttt ttttattgtg gtttggggtg ttttgattgg | 1020 |
| tgtggagtta tgttagttgt atttggagaa gggtttggga ggaggtggag gtggagaggg | 1080 |
| ttggggaggg ttgtggtgga gtgatgtttt ggtattagga agtttgtttt tggttttaag | 1140 |
| atgttaggtt aataggggaag tgtggagttg tagatttggt ttgttgtttg tttgggtgtt | 1200 |
| tggagttgag ttgtggtaag gtttggttt tgtttgattg tttgagggt gtgtgtgtgt | 1260 |
| gtgttgtgga gggtgtgttt agagggttgt gttgtggttg tagtggttgt tgttgttgta | 1320 |
| ggggatttaa tattatttat ttgttttttgt tatttttgat attttttgt tagggttgtt | 1380 |
| gtgtggggggg ggggtgggta gagtgtggtt ggtgttagtt tttttattg gaggggtttt | 1440 |
| tggggagggg agggagagaa gaaggggggtt tttgtttatt tttgttttgt tttggagttt | 1500 |
| ggaagtttgt tttttaaaga tgttttgagt ggtgtttttt tgtttatatt ttatgttttt | 1560 |
| gtttgttgt tgatttttg ttttggatt ttttgtttg agttttttgg aggagatggg | 1620 |
| ggtagtttgg tttgagaatt tggtgggggt tgtgtttttt ggtttttttt gtagtgggga | 1680 |
| aattttgtgt ttagagtgtg atttggagtg ggtagtggtg gttatggggg tttggtgggg | 1740 |
| tagtagttaa ggattagtag agtgttgtgt tttttgttt atgaattgta tgaaaggttt | 1800 |
| gttttatttg gagtattgag tagtggggat taagttgttg gttgttttt tattttttg | 1860 |
| ttattatttt tagttgttag ttatggtttt ggttttggtt tttggttagt tttggttgtt | 1920 |
| ggattttttt aagtataggt tggaggtgta tattatttt gatattttta gtttggaggt | 1980 |
| tgtaggtaag gtgttgtgtt gttttgtaga tatttttgtt tagttgtttt gtgttatttg | 2040 |
| ttttttttt ttttaaggaa gttagttttt tggggggag gtgtggtggg agtggttgtt | 2100 |
| tgtttggttt tttgtagaat ttttgggagt tggaattttg attattttgt attttttag | 2160 |
| tttttttttg attggtttgg ttttgggggt gttaagggtg tgagtaattt tgttgttttt | 2220 |
| tttatttgta ttttggtttt tttttgttt tttgggttat aaaaatttta gtattttgat | 2280 |
| ttgaggattt ttagaggttg ttgattttg tttttgtttt ttttttggtt tttagttttt | 2340 |
| gaggagtttt atttgttagg aaattgtttg aaattattta gaaatgtttt ttgtgaagag | 2400 |
| gtatttttt tttttttg ggaaagggtt ggtgaattt ggtgtttaat tgaatttta | 2460 |
| tattttttt tagttttttt aaattgtatg gaaatttgag ttttttgtga ggggagggg | 2520 |
| ggtttgtaaa ttatgtgtgt gtgtgtgttt taggagattt ggtgtgtttg tgtagaggtg | 2580 |
| tataaatata tttgaaagta taggttataa aagtgaatgt gttgttgtag tgagataaat | 2640 |
| atgtaaataa aatgtgtggt gttggggggag gggaggaaat ggggtgtgga tatttatatt | 2700 |
| tgtgtttgta tattttatag gtgtagtgtt ttttgtggtt tggagttgtt gtgtgtattt | 2760 |
| tttttttggtg ttaggtagtt tagttttttt atggttttg ttgttggttt agttggtgtt | 2820 |
| tgtgttgtag gtgggtatgt tgatgggaaa gtgtgtgtgt tttgttttta gagaaagata | 2880 |
| aaagttagta ggggaagaat gaggatgtgg gtgttgagga tttgtttaag aagaagtggt | 2940 |
| aaaggtggta gtggatttat tttattagtt agtagtttta ggagttggag gttatttttt | 3000 |

```
agaggaattg ttatttggat atgtttatat gtgaagaaat tgttgtgtgg attaattta    3060 tggaagtttg agtttgggta ggagttagta tggagtttgg gagggatggg gggaggatgt    3120
tgtggaggta taggttaagt agattaggag agaatgtgga aggtagtgtt gtttgggagg    3180
gtgttggtgg ggtgtagttt tgtaaaggta gaaggttttg tggtggtttg gttgtgagat    3240
tatagttttt tttttgaggt tgataggatt gttgttttgg tttaggtttt tagagtggta    3300
ttggtttatt gttttgttat tttgtgattt tatgagttgg gttgtatggg taattttttg    3360
tataggatat tgtgttttg gtttgtagtt gttagagtag agttaataaa attttatta    3420 ggttaagagt tgtgaatagg ttttaatttg tgagtttta ataaggaaaa tttgttagag    3480
atatggaaga gttggttttt tttgggaaat ttttgttttg gttttggttt agttttttt    3540 tttttgggtt tgtgttttt atatttttt tatggttgtt ttggttattt aggttttttt    3600
tatatatttt attttttagt tttgtgattt ttgggagtaa agttttaata tataattatt    3660
agttttttta gaaggagaaa gaaaaaaaga agaaagatt ttttgtttgg tttatttatt    3720
tttttttagg agttgaattt tggaaattga aatttatatt tttttttta aattataatt    3780 atagttttgt aaaaagggtt tattttaatt ttgtagtaaa tttgtattt atggattggt    3840 aaaaatgagt ttaaataaat aatttaatag taatgttttg gtttatgttg gttggtggaa    3900 gatttaaat ttgttaggat tttggaagta gaaatagaa ttaagtaaat taagtggtat    3960
ttagaggttt tgttgttaaa aaaaaaaat taagtgtttt g                        4001

<210> SEQ ID NO 34
<211> LENGTH: 4001
<212> TYPE: DNA
<213> ORGANISM: Artificial Sequence
<220> FEATURE:
<223> OTHER INFORMATION: chemically treated genomic DNA (Homo sapiens)

<400> SEQUENCE: 34
tagagtattt aattttttt ttttaatagt aaagttttg gatgttgttt gatttgtttg      60
attttgtttt tgttttag aattttaata aatttggaat tttttattga ttagtataaa     120
ttaggatgtt gttattgggt tatttatttg agtttatttt tgttaattta taagtatag     180 atttgttata aagttaaggt aagtttttt tataaaatta tgattataat ttagaagagg     240
gggtgtgagt tttaattttt agagtttaat ttttgagaga agataaataa attaagtaga     300 aaagttttt tttttttttt ttttttttt ttaagaggat tagtagttgt gtattaaaat     360 tttgttttg gagattataa aattaggaaa tagggtgtgt gggagagatt tgaatggttg     420
aaataattgt aaagaaggtg taagaagtgt gagtttagga gggaaaaagt tgggttaggg     480
ttgggataaa ggttttttag ggagggttaa ttttttttgtg ttttggtgg gtttttttg     540 ttaaaggttt ataggttgga gtttgtttgt ggttttggt ttggtaggga tttattagt     600 tttgttttgg taattgtaag ttaggaatat aatgttttgt gtaggggatt gtttatgtag     660
tttagtttgt gagattgtgg gatggtgggg tagtgagttg gtgttgtttt gggagtttga     720
gttagggtgg tagttttgtt ggttttggag agggaattgt aatttttgtaa ttaggttgtt     780 gtgaggtttt tgttttttgt aaagttgtgt tttattggtg ttttttagg tggtgttgtt     840 ttttatattt tttttttggtt tattggttt gtattttat aatattttt tttttattttt     900 tttagatttt gtgttggttt ttatttggat ttgggttttt gtaaggttgg tttatatagt     960 gattttttg tgtgtggata tgtttgggta gtggtttttt tggaaagtgg tttttagttt    1020
```

```
ttggagttgt tggttggtaa agtgagtttg ttgttgtttt tgttgttttt ttttagatgg    1080
gttttggtg tttatgtttt tattttttt tgttggttt ttattttttt ttgaaaatga     1140
aatatatata ttttttgtt agtatgttta tttgtaatgt ggatgttaat tggattggtg    1200
gtagaagttg tggaagagtt gggttgtttg gtgttggagg agggtgtgtg tggtggtttt    1260
gggttgtgag gagtgttgtg tttgtggggt gtgtaggtgt aagtgtgggt gtttgtgttt    1320
tatttttttt ttttttttag tgttgtatgt tttatttata tgtttatttt attgtagtgg    1380
tatatttatt tttatagttt gtgtttttaa gtatatttat atattttgt gtagatatat    1440
taaattttt gggatgtgta tatgtgtgtg gtttatagat ttttttttt tttgtagaaa     1500
gtttagattt ttatgtggtt tgggaaggtt aggaaaagat gtggggattt ggttgggtat    1560
tgaagtttgt tggtttttt ttaaaaaaaa aaaaaaatg ttttttttgtg aagggtattt     1620
ttgagtggtt ttaggtaatt ttttaatgag tggagttttt tgggagttga aagttgagag    1680
gaaaatagg atagaggttg gtggtttttg aaggttttg aattaagatg ttgggatttt     1740
tgtgattag gaaatagaag ggaggttagg gtatgaatag agagggtggt agaattgttc    1800
gtgttttag tgttttagga gttgggttgg ttgagggaga attaaaggga tgtggggtag    1860
ttaaaatttt ggttttgga agtttgtgg ggagttaggg gaatgattat ttttattatg     1920
ttttttttg gagggttga tttttttggg gtgagaggga gtgggtggtg tagagtagtt    1980
gagtgggaat gtttgtaggg tggtgtgtg ttttatttgt ggttttggg ttggaggtgt     2040
tggagatggt gtgtatttt agtttgtgtt tggaggagtt tagtgattgg ggttgattgg    2100
gagttagaat tgaagttatg gttaatggtt ggggatggtg ataggaagat gaggagatgg    2160
ttgatagttt ggttttgtt gtttggtgtt ttaagtgaag tgggttttt atgtagttta    2220
tggatgaggt agtgtgatgt tttattagtt ttttggttatt gttttgttga gtttttgtag    2280
ttgttgttgt ttgttttggg ttgtgtttta ggtgtggagt ttttttgttg tggggagagt   2340
taggggatgt aatttttgtt gagttttaa gttaagttgt ttttgttttt tttgaaggt     2400
ttaagtgaaa aagtttggag atggaaagtt agtgggtaaa tgaagatatg ggatgtgggt    2460
agaagggtat tatttagagt gtttttaggg agtaggtttt taagttttaa agtgaaataa    2520
gagtgggtaa agattttttt tttttttttt tttttttttt aagaatttt ttaataagga    2580
aagttaatgt tgattgtgtt ttgtttgttt ttttttatg tggtagtttt gatagagaag    2640
tgttaagagt gataggata ggtaggtgat attagatttt ttgtggtggt agtagttgtt     2700
gtagttatga tgtggttttt tgagtgtatt ttttgtaatg tgtatatgta tatttttgg    2760
gtggttgaat aggagttggg ttttgttgta gtttagtttt aggtatttag gtgagtgatg    2820
gattagattt gtggttttgt gtttttttgt tggtttaata ttttaaaatt agaggtgggt    2880
ttttggtgt tgagatgtta ttttgttgtg gtttttttta gtttttttg tttttgtttt     2940
ttttagatt tttttttggg tgtgattgat gtggttttgt attaattagg atgttttgag    3000
ttgtggtgga gggattgttt tgtttgtatt tattagtagt gtggggttgg gttattgttt    3060
tgttgtgtgt attgggttta tataggtaag ttttgggaa tttagttttt gtttagttta    3120
aggtgatttg gttttagta tgaatttaaa ggtgaagaga tgaggttagg agttgaaggt    3180
ttgggagaag agagtggaat ggttaagaag agaaaggtat aaggattaat aagatattta    3240
ttttttgtgt tttattatat ttatttttaa ttttttattt tatataaaaa ggagatatgt    3300
tatttaaaat tagaaaattt gaaaaatagt aataaattat ttttttgatt ttaaattttt    3360
taaatagttt gttaagtgaa tgttgtgtta atttgaagaa gttttaattg taaagaagat    3420
```

```
agagttttga aaaggtaggt aataaaatta gaaattgaga agtaaatgga tttgttaaaa    3480
gaaaattatt ttgattttaa atgaataatt gtttggtggt ttattttgga tttatataag    3540
aataaaaagt tgttttagat tatgtttttt gtgatgttta ttagtttttta gatagaaaat    3600 atataataga agagaaattt taatttagtg tttttaaaat gttgaaagtt tatttatttt    3660
atttaatgtt gattaagata tatattttag attttttaaa tttttttgtat attgtattaa    3720 gtttgtttta atttgagaga gttatgtttt aaatttgatt ttttttgttta ttttattatt    3780 aattagattt aaatttataa agtttgtaga attaataatt ttgagttaat tatatatgaa    3840
atatgtttta atgaattttt ataataattaa gaatgttgtt aaataattaa ttttaaggat    3900
aatttttaat agttattttt tttttttagt gagtttaagg ttgttttgag ttattaaagt    3960
ttaagtaggt agaagggtg tgtgtgagtt aagggtgaaa a                         4001
```

<210> SEQ ID NO 35
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 35

```
aggaagggtg gatgtagtta tttatatatg gtttgttttt ttggaggata attttatttg      60
ataaataatt gttttatttt gaatagaata aataaggttt tatgatgaag taaaatatta     120
aatatatatg tattaaaaaa tgtataatta tttttttgga atgggttata tagagatgtg     180 tttttttaaaa tgttaagagt gtaaaaggat aaatagtgaa aaataaattt ttttttttatt    240 ttgtttttta gtttttttaat tttttttattt agaggtgaga atagaatttt tatattttttt   300 agaattttta tagttagaat tgtttatatg tttttattgt tttatttttt attttgtttt      360 gtataaaataa atgaattgtt tattatggaa atttttttaaa agatttgtta atattttaat    420
aggaagtatt aatagtttat gttttaggat tttgttttta taatttttgta atattatatt     480 atgatatttta atttaatttt tattaagttt tgttaaaaat ggatttttaaa ttaagttgta    540 aatttttagt aatttggttt tgttttttttt tttttgatag tattattaaa taaattttttt   600 tattgttgaa agtaataagt ttggttttgt tttatttatt ggttgtgttg gtgatatttg     660
gggattgtta ttgaatagat gtatagaggg agttttttata ggtaggggtt tttttgtttg    720 tgttttggg agagtatgtt ttgtatattt gttgtgttga tgaagatttt atagttttat      780
tagttgtggg taagggggtt tgaggtagtt ttaggtaagt tggggtttag tggggagaag     840
ttgtagaaga attgattaga ggattttagg aggtttaga gttgggtgag gtagagagtt      900
ttttgtgtgt ttttttttttt ttttgtaatt tggggatttt ttgtattggg gtaggtttt     960 ggttaggtgt atgggaggaa gtatggagaa tttataagtt ttttgattt ttagtttaga     1020 tgttgttggg tttttttttgt tggagattgt gttttttttta aatttttgtg agtgttgtgg   1080
aagtatgtgg ggtttgggtt gttgagtgtt gtaagatagg ggagggagtt gggtgggaga    1140
gggaggggtg gtgttgggt gggttttgat atagagtagg tgttgtgggt tgtagtatag     1200
tgtggagatt gtagttttgg agtttgggtt agggttatt tgttttttgta gtgttggttt    1260 gtgtttttttt gttgtagtta ttggtgagtg ttgtggtttt gagattttg ggttggatgt    1320 gtggtggttt tagttttga gtgtttgttt ttttttgtttt gggttgtttg ggtttttttgg    1380 gtttttttggt ggttgtatgg agttaaggtg ttttgttttg ggtgtttttt gtgggtgttg   1440
```

```
atttaggttg tttggagttt ggagtttaga gaggagagag atagttgggg agtttggtta      1500
ttgtgggtat tttttttgtg ttgtagttgt ttgtttggtt tgttttttg ttttttgtt        1560 ttttgttttg atttttttt tttttgtaga gttgttgttt agtgttttga ttttgttatt       1620
atgagagttt tgttggtgtg tttgtttttt tgtgttttgg ttgtgagtga ttttaaagtg      1680
agtgtgtttt tgttttgatt gatgttgttt aaggattttt gattagtatt aggggagagg     1740
aggggttgtt tagggagttg gggttttttg gattttattt atagtagggt tagattttt      1800 ttaggaaatg ggatagggtg gtagtggagg tttgagaatt atgggggttg gtattggttg      1860
gtaagggagg aagaggttgt tgggattgtt ttagttgtg ggtatttggt agatgaagtt      1920
tgtttgggtt aatttatttt ttttggttgg aaatttatgg ttttttattt gagaattaga     1980
tatgaatagg gtgaggtgag agggagaggg aagagtgggt tttgggattg gggttagttt     2040
atttttattt tggagttttt ggagtatggg attttgatg aagttttttt ttgaattttt      2100
tttagggtag taatgaattt tattaagttt tatgtgagta tttatttta taatagttgg     2160 ttgtatagat aagtttgggaa ggtttaggg gatatttttt ttttgttttt tgttgtaggg     2220
ttgtgttatt tttattatt tttatttttt tttgttatt ttattttgt tttttttagt       2280 gaattgtgat tgtttaaatg gaggaatatg tgtgtttaat aagtattttt ttaatattta     2340
ttggtgtaat tgtttaaaga aatttggagg gtagtattgt gaaataggta tggggatttt     2400
tattgtaatt gggagagaaa tttggggata gggagggatg ggtgggaggt aagagtaggt     2460
aggagttagg agttggaggt agggtgggtg atattttat t                          2501
```

<210> SEQ ID NO 36
<211> LENGTH: 2501
<212> TYPE: DNA
<213> ORGANISM: Artificial Sequence
<220> FEATURE:
<223> OTHER INFORMATION: chemically treated genomic DNA (Homo sapiens)

<400> SEQUENCE: 36

```
gatgaagatg ttatttattt tattttagt ttaattt tgtttgtttt tgttttttat        60
ttattttttt ttgttttaa atttttttt tagttgtagt ggagatttt atatttattt       120 tatagtgttg ttttttgaat tttttgggt agttgtatta gtgaatgttg gagaagtatt    180
tgttggatat atatgttttt ttattagat agttatagtt tgttggagag aataaaggtg    240
gggtaagtga gggggagtgg aagtggtaag gggtggtgta gttttgtagt agagggtagg    300
gaggggatgt tttttgaagt tttttaatt tgtttgtgta gttaattgtt gtaggggtgg    360
atatttatat ggaatttgat gaagtttatt gttgtttgg aagagatttg ggaggaggtt    420
ttattaaagg ttttatgttt tagggatttt agggtgaggg taaattggtt ttaattttaa     480
aatttatttt ttttttttt tttgttttta ttttgtttgt atttagtttt taaatggaag     540
attatgggtt tttagttagg agaaatggat tgatttaagt aagttttatt tattagatgt    600
ttgtaggttg gggtagtttt ggtggttttt ttttttttg ttagttagtg ttaatttttg     660
tggtttttaa gttttgttg ttatttgtt ttatttttg gggagagttt ggttttgttg      720
tggatggaat ttgaggatt ttagtttttt gagtagtttt ttttttttt tggtgttgat     780 tagaggtttt tgggtagtat tagttaaagt aagagtgtat ttattttgga gttgtttatg     840
attaggatgt agaaagtag gtgtgttagt agggttttta tggtggtgag gttgggtgt      900 tagatggtgg ttttgtaaag gaaggagaag ttagggtaag aggtggagga atgggaaggt    960
aggttaggtg ggtgattgta gtgtagggga gatgtttgtg gtgattaggt tttttagttg   1020
```

```
ttttttttttt ttttgggttt tggattttgg gtagtttgga ttggtatttg tggggatgt    1080 ttgggatggg gtgttttgat tttgtgtagt tgttggggag tttagggagt ttgggtagtt    1140
tagggtgggg gaggtagatg tttgggagtt ggggttgttg tgtatttggt ttggggattt    1200
taggattgtg gtatttattg gtggttgtgg taggagggtg tgagttggtg ttgtggggat    1260
aggtggattt tggtttgggt tttggggttg tggttttgt attgtgttgt gatttgtggt     1320
gtttgtttta tattagggtt tgttttggtg ttgttttttt ttttttgtt tggtttttt      1380 ttttgttttg tagtgtttag tgatttggat tttgtgtgtt tttgtaatgt ttataaagat    1440
ttgggggaag tgtgattttt agtggagggg atttaatagt gtttggattg aggaattgag    1500
aggtttgtaa attttttgtg tttttttta tgtatttggt tgggggtttg ttttagtgta     1560
aggagttttt gaattgtaga gaggagagaa ggtgtatagg agattttta ttttgtttag     1620 ttttgaagtt ttttggggtt tttaattag tttttttgta attttttttt gttgggtttt     1680
aatttgttta agattgtttt agattttttt gtttgtagtt gatggagttg tgaagttttt    1740
attaatgtga taaatgtatg agatatattt tttagaagt atagatagaa aaattttgt      1800 ttgtaggggt ttttttgtg tgtttgttta gtggtagttt ttagatatta ttaatataat    1860
tagtggatgg aataaagttg ggtttattgt ttttggtagt aaggggggttt gtttgatggt   1920 gttattagag ggggaaaggt aaggttagat tattgaaaat ttgtagtttg gtttaaagtt    1980 tgttttgat agggtttgat aaggattggg ttaggtgttg tgatatgatg ttataggatt     2040
gtgggaataa agttttaggg tataaattgt tggtgttttt tattgaagtg ttaatgggtt    2100
ttttgggaag tttttataat gagtaattta tttatttgtg taggtaagaa taaaagtaaa   2160
gataatggaa atatgtagat agttttaatt gtggaggttt tggagggtgt ggaagttttg    2220
tttttatttt tgagtagagg aattgggaga ttggaggata aaataagagg aagatttatt   2280
ttttattgtt tgttttttta tattttaat attttaaaaa gtatattttt gtatagttta    2340
ttttaaaaag ataattatgt atttttaat gtatgtgtat ttagtgtttt attttattat    2400
agagttttgt ttattttatt tagatagaaa taattgttta ttaaataaaa ttgtttttta   2460
gaaaaataga ttatgtgtaa atgattgtat ttattttttt t                        2501

<210> SEQ ID NO 37
<211> LENGTH: 901
<212> TYPE: DNA
<213> ORGANISM: Artificial Sequence
<220> FEATURE:
<223> OTHER INFORMATION: chemically treated genomic DNA (Homo sapiens)

<400> SEQUENCE: 37
taaatggtgt ttagtaaata tttatgtatt gagtaaaatt taataattat ttgttgaaat      60
taaaaagtga ataaataagt tatttagaaa gatgtaaagt ttataaattt ggggtatttt    120 gtatttttt tgagtgtaat gtttgtatat taggatgtga ggattatgtt ttttttttat     180
gttttgaggg ttttatattt gttttattgg atagttgttg atgttattgg agaaggaagt    240
tggatgggtg tgtgtatgat aatattaagg aatttagttt ataatttatt ttgttttta     300 tttgtgtatt tttagagatg tgtatagtgg ttttttgtga aagatagaat tgtggttttt    360
ttggtgttat gttttttag tgtgtaaata agggttgttg ttttgatgat attgtttgtg    420
gggttttttg gtgtttttat tttaatatta ttgatgtttt tttagaaggt atggtttttt    480
tatatgatgg gttttgaaga tttagaatta gttagaaaag ttatttaaga ttatagaggt    540
```

```
tttgattagt attattagtt atgtttttat atagagttat ggttgttagt ggtggtgtaa      600
tggggtagtt tgagttaggt tgtatttagg tttaggaata gaaaggtagg gttaagggat      660
ttgggaagaa atttgatttt ttttttggttt tttttttatat ttttaattaa aagtttggga   720
```
(note: line as printed) 
```
ttgggaagaa atttgatttt ttttggtttt tttttatat ttttaattaa aagtttggga       720
agagttattg ttggtaatgt tttttagttt gtttaggata gagggggaag gtatgatgaa      780
atttgaagat attttatgta tttttttttt tttttttttt ttgaaatgga gttttgtttt     840 gttgttttttg agttggagtg taatggtgtg attttggttt attgtaattt ttgttttttg    900
a                                                                      901
```

<210> SEQ ID NO 38
<211> LENGTH: 901
<212> TYPE: DNA
<213> ORGANISM: Artificial Sequence
<220> FEATURE:
<223> OTHER INFORMATION: chemically treated genomic DNA (Homo sapiens)

<400> SEQUENCE: 38

```
ttaggaggta gagattgtag tgagttaaga ttgtattatt gtattttagt ttagggtaa       60 tggagtgaga ttttatttta aaaaaaaaaa aaaaaaaga atatatgaaa tgttttaga       120 ttttgttatg tttttttttt ttattttagg taagttagaa agtgttatta atagtggttt     180 ttttaggtt tttggttaga gatgtgaaga gaagttgggg ggaaattagg ttttttttta      240
agttttttag ttttgttttt ttattttggg atttgaatgt agtttgattt aggttatttt    300
attgtattat tattggtggt tgtgattttg tgtaaaggta tagttggtga tgttgattag    360 agttttttgta gtttaaatg atttttttaa ttaattttaa attttagaa tttattgtat     420 aaaaaggtta tattttttgg agggatgttg atggtattag gatagaagta ttaggggatt    480
ttatgaatgg tgttgttgaa atagtagttt ttatttgtat attgggaggg tgtgatatta    540
ggaaaattat aattttgttt tttatggggg gttattgtat atgttttttga aagtgtatag    600 gtaagaagta aagtaagttg tgggttgaat ttttttgatgt tattatgtat atatttattt    660
agtttttttt ttaatgata ttagtaattg tttagtgagg tggatataaa attttagga     720 tatgagaggg agatgtggtt tttatatttt gatgtgtaaa tattatgttt agggaaaatg    780
taaggtgttt taggtttgtg gattttgtat tttttaggt aatttatta tttattttttt    840 aattttaata aatgattatt aaattttatt taatatataa atatttattg agtattattt    900
g                                                                     901
```

<210> SEQ ID NO 39
<211> LENGTH: 1301
<212> TYPE: DNA
<213> ORGANISM: Artificial Sequence
<220> FEATURE:
<223> OTHER INFORMATION: chemically treated genomic DNA (Homo sapiens)

<400> SEQUENCE: 39

```
gttagtttta aatttttgat tttaagtgat tgtttgtttt tggtttttta aagtgttggg      60
attataggtg tgagttattg tgttaggttt ataatttat tattaaaata atttttаttgt    120 aaaagaatta gttaggttt agatggaatg ggttttatga gttttttttt tttttttttgt    180 aaggttatgg tggttatttt gtgagttatt gttgttatgg ttaagttttt ttttggttat    240
tttttattat gaattatttt tgtagtgagt atagtattta ttttggtggg agggttttt    300 agatatgagt aggattgga ttaaggttag gttggaggag attttatgg gaaagaggga    360 ttttttgaat tttagatttt ttagttaaga tgatttatt atatgttgtt tttgtttatt     420
```

```
agtaaatttt tttatgtagt ttgattatgt ttaggaaata ttttttgataa aaattagtgg       480 agattattgt tttagaggat ttttgggttt ttttaggtaa atgttattta atgtttttta       540
agtaaataga gtttgtttta taaaatttgg ggtttgggtg gttttttatt tttgatttgg       600
ggttgttttt ggagtagaga ggaggtaatg gttattatgg agaataaggt gatttgtgtt       660
ttggttttgg tgtttatgtt ggttttggt attttggttg aggtttagat aggtaaggtg        720 tgttttttt tgttttgtgg ggttatagtt agttttggta gtttttgtta ggagttattg       780
ttttatatat atattttga gtatttgttt tgtgttaggt gttgttttag gtttttaaaa       840
gtatatttaa tttataggat tggtaaaagt aggtggagag taatttaggg tggtaggtt      900 tttggagatt tttgagaagt gtgatgagga ggggttgtt tttagttggg gttgttttt       960 tgtgttagga agattatata atttttttaa gtgttatgtt ttaaagagga agtgttggtg      1020 tggggttta gaatagtgtt tttgattgtt tatgttaata ttttttttag gggtagattt      1080
ttttaaggtt tatttagata ggtttaaatg ttggttttag tgatggttat ttgggagatt      1140
tttttttata ggtttgaatg tttgttttag tggtggttaa ttgggagatt tttttttata     1200 ggttttggg ttttttggg atttatgttt tgggagttaa agttattttt tttatgagtg       1260
tgtggttggt aatttatatt ttttggtgtt gttaagtgga t                          1301
```

<210> SEQ ID NO 40
<211> LENGTH: 1301
<212> TYPE: DNA
<213> ORGANISM: Artificial Sequence
<220> FEATURE:
<223> OTHER INFORMATION: chemically treated genomic DNA (Homo sapiens)

<400> SEQUENCE: 40

```
atttatttga taatattagg gaatatgggt tgttagttat gtatttatga gagaggtggt        60 tttgatttt agagtatgga ttttagggga gtttaggaat ttgtaggaga gggtttttta      120
gttggttatt attgggatgg gtatttgggt ttgtgggaga gggttttta ggtggttatt      180 attgggattg gtatttgggt ttatttggat gggttttggg agggtttgtt tttgggggag      240
atgttggtat gaatagttaa aagtattatt ttgagatttt atgttaatat ttttttttg      300 aaatatgata tttgggagga ttgtatagtt tttttaatat aggaaaatag ttttgattga      360
aggtagtttt tttttgttg tattttttga aggttttgg gggttttgtt attttgagtt       420
attttttatt tgttttgtt gattttgtaa attggatata ttttaagggg tttagaatag      480
tatttggtat aaaataggtg tttaaaaata tgtatgtaaa atagtggttt ttggtggagg      540
ttgttagagt tggttgtggt tttatagagt aggaagaagt atgttttatt tgtttgggtt      600
ttggttaggg tgttgagggt tagtatggat attaggatta gggtgtagat tattttgttt     660
tttatggtgg ttattgtttt tttttgttt taaaggtgat tttgagttag ggatgagagg       720
ttgtttgagt tttggatttt ataggtagg ttttgtttgt ttaaagagtg ttagataata      780
tttgtttaag gaggtttggg gatttttga gataataatt tttattgatt tttattaaag       840
gtgtttttta gatatggtta agttatatgg aaggatttgt tgatagatag agatgatatg      900
tggtgaggtt attttggttg agggatttga gatttagaaa gttttttttt tttatgggag      960
ttttttttaa tttgatttta atttaggttt tatttatatt tgagaggttt ttttgttagg     1020
gtaaatattg tatttattgt agaagtgatt tatagtgaga gatggttgga aaaaggtttg     1080
gttgtgataa tagtggttta tggggtggtt attgtgattt tgtagggga agggaaggag     1140
```

```
tttatgaagt ttattttgtt taggtttaag ttaatttttt tatagtggaa ttgttttaat      1200
aatgaaattg taggtttggt gtagtggttt atgtttgtaa ttttaatatt ttgggaggtt      1260
aaagtaggtg gattatttaa agttaggagt ttgagattag t                         1301
```

<210> SEQ ID NO 41
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 41

```
gtagggagg gaagtagatg t                                                 21
```

<210> SEQ ID NO 42
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 42

```
tcctcaactc tacaaaccta aaa                                              23
```

<210> SEQ ID NO 43
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 43

```
gagtgatagg gataggtagg tg                                               22
```

<210> SEQ ID NO 44
<211> LENGTH: 27
<212> TYPE: DNA
<213> ORGANISM: Artificial Sequence
<220> FEATURE:
<223> OTHER INFORMATION: chemically treated genomic DNA (Homo sapiens)

<400> SEQUENCE: 44

```
ccttaaacta aacaaaaact aaattcc                                          27
```

<210> SEQ ID NO 45
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 45

```
ggtaaggggg tttgaggt                                                    18
```

<210> SEQ ID NO 46
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 46

```
tccctcccct atcttacaa                                                   19
```

```
<210> SEQ ID NO 47
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 47
gagagagata gttggggagt tt                                              22

<210> SEQ ID NO 48
<211> LENGTH: 25
<212> TYPE: DNA
<213> ORGANISM: Artificial Sequence
<220> FEATURE:
<223> OTHER INFORMATION: chemically treated genomic DNA (Homo sapiens)

<400> SEQUENCE: 48
caaacaaact tcatctacca aatac                                           25

<210> SEQ ID NO 49
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 49
tgttagagtt ggttgtggtt tt                                              22

<210> SEQ ID NO 50
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 50
aactttctaa atctcaaatc cct                                             23

<210> SEQ ID NO 51
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 51
ttggtgatgt tgattagagt tt                                              22

<210> SEQ ID NO 52
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 52
taaaacacct tacattttcc ct                                              22

<210> SEQ ID NO 53
<211> LENGTH: 408
<212> TYPE: DNA
<213> ORGANISM: Artificial Sequence
<220> FEATURE:
<223> OTHER INFORMATION: chemically treated genomic DNA (Homo sapiens)
```

```
<400> SEQUENCE: 53 gcagggagg gaagcagatg ccagcgggcc gaagagtcgg gagccggagc cgggagagcg      60
aaaggagagg ggacctggcg gggcacttag gagccaaccg aggagcagga gcacggactc    120
ccactgtgga aaggaggacc agaagggagg atgggatgga agagaagaaa aagcaatctg    180
cgccaacccg gcagccctaa taaatcaaag ggggagcgcc agggcagcgg ggagacagaa    240
acgtactttt ggggagcaaa tcaggacggg ctggggaggaa gcgacaggga aagtggccca   300
agagacggaa caaaggacaa tgttcatggg gttgtttggg acgaggcgtg tggagtgtgg    360
gtgtgagcgt gcgtgtgtga ccttctttca ggcctgcaga gttgagga                 408

<210> SEQ ID NO 54
<211> LENGTH: 477
<212> TYPE: DNA
<213> ORGANISM: Artificial Sequence
<220> FEATURE:
<223> OTHER INFORMATION: chemically treated genomic DNA (Homo sapiens)

<400> SEQUENCE: 54
gagtgacagg gacaggtagg tgatattaga tcccctgcgg cggcagcagc cgctgcagcc     60
acgacgcggc cctctgagcg caccctccgc aacgcgcaca cgcacacccc tcgggcggtc    120
gaacaggagc cgggccttgc cgcagctcag ctccaggcac ccaggcgagc gacggaccag    180
atctgcggct ccgcgcttcc ctgttggcct aacatcttaa aaccagaggc gggcttcctg    240
gtgccgagac gtcactccgc cgcggccctc cccagccctc tccgcctccg cctcctccca    300
gacccttctc cgggtgcgac tgacgtggct ccgcaccaat caggacgccc cgagccgcgg    360
tggagggact gtcctgcctg cacctatcag cagtgcgggg ccgggctact gcctcgccgt    420
gcgcactggg tctacacagg caagctcccg ggaattcagc cctgcccag cccaagg        477

<210> SEQ ID NO 55
<211> LENGTH: 339
<212> TYPE: DNA
<213> ORGANISM: Artificial Sequence
<220> FEATURE:
<223> OTHER INFORMATION: chemically treated genomic DNA (Homo sapiens)

<400> SEQUENCE: 55
ggcaaggggg tctgaggcag tcttaggcaa gttggggccc agcggggaga agttgcagaa     60
gaactgatta gaggaccccca ggaggcttca gagctgggcg aggtagagag tctcctgtgc   120
gccttctctc ctctctgcaa ttcggggact ccttgcactg gggcaggccc ccggccaggt    180
gcatgggagg aagcacggag aatttacaag cctctcgatt cctcagtcca gacgctgttg    240
ggtcccctcc gctggagatc gcgcttcccc caaatctttg tgagcgttgc ggaagcacgc    300
ggggtccggg tcgctgagcg ctgcaagaca ggggaggga                          339

<210> SEQ ID NO 56
<211> LENGTH: 453
<212> TYPE: DNA
<213> ORGANISM: Artificial Sequence
<220> FEATURE:
<223> OTHER INFORMATION: chemically treated genomic DNA (Homo sapiens)

<400> SEQUENCE: 56
gagagagaca gctggggagc ctggtcaccg cgggcatctc ccctgcgctg cagtcgcccg     60
cctggcctgc cttcccgttc ctccgcctct tgccctgact tctccttcct ttgcagagcc   120
gccgtctagc gccccgacct cgccaccatg agagccctgc tggcgcgcct gcttctctgc   180
```

-continued

```
gtcctggtcg tgagcgactc caaagtgagt gcgctcttgc tttgactgat gctgcccaag    240
gacctctgat cagcaccagg ggagaggagg ggctgctcag ggagctgggg tcctccggat    300
tccatccaca gcagggccag actctcccca ggaaatggga cagggtggca gcggaggctt    360
gagaaccacg ggggttggca ctggctggca agggaggaag aggccgccgg gactgcccca    420
gcctgcgggc atctggtaga tgaagcttgc ttg                                 453
```

<210> SEQ ID NO 57
<211> LENGTH: 402
<212> TYPE: DNA
<213> ORGANISM: Artificial Sequence
<220> FEATURE:
<223> OTHER INFORMATION: chemically treated genomic DNA (Homo sapiens)

<400> SEQUENCE: 57

```
tgccagagct ggctgtggcc ccacagagca ggaagaagca cgccttacct gtctgggcct     60
cggccagggt gccgagggcc agcatggaca ccaggaccag ggcgcagatc accttgttct    120
ccatggtggc cattgcctcc tctctgctcc aaaggcgacc ccgagtcagg gatgagaggc    180
cgcccgagcc ccggatttta tagggcaggc tctgtttgct taaagagcgt tagataacat    240
ttgcctaagg aggcccgggg atcctctgag acaataatct ccactgattt ttatcaaagg    300
tgtttcctag acatggtcaa gctacatgga aggatttgct gatagacaga gacgacatgt    360
ggtgaggtca tcttggctga gggatctgag attcagaaag tc                       402
```

<210> SEQ ID NO 58
<211> LENGTH: 449
<212> TYPE: DNA
<213> ORGANISM: Artificial Sequence
<220> FEATURE:
<223> OTHER INFORMATION: chemically treated genomic DNA (Homo sapiens)

<400> SEQUENCE: 58

```
ctggtgatgc tgatcagagc ctctgtagtc ttaaatgact tttctaacta attctaaatc     60
ttcagaaccc atcgtataaa aaggccatac cttctggagg gacgtcgatg gtattaggat    120
agaagcacca ggggaccccca cgaacggtgt cgtcgaaaca gcagcccttta tttgcacact  180 gggagggcgt gacaccagga aaaccacaat tctgtctttc acggggggcc actgtacacg    240
tctctgaaag tgcacaggta agaagcaaag taagttgtgg gctgaattcc ttgatgttat    300
catgcacaca cccatccagc ttccttctcc aatgacatca gcaactgtcc agtgaggcgg    360
atataaaacc ctcaggacat gagagggaga cgtggtcctc acatcctgat gtgcaaacat    420
tacgctcagg gaaaatgcaa ggtgcccca                                      449
```

<210> SEQ ID NO 59
<211> LENGTH: 408
<212> TYPE: DNA
<213> ORGANISM: Artificial Sequence
<220> FEATURE:
<223> OTHER INFORMATION: chemically treated genomic DNA (Homo sapiens)

<400> SEQUENCE: 59

```
gtaggggagg gaagtagatg ttagcgggtc gaagagtcgg gagtcggagt cgggagagcg     60
aaaggagagg ggatttggcg gggtatttag gagttaatcg aggagtagga gtacggattt    120
ttattgtgga aaggaggatt agaagggagg atgggatgga agagaagaaa agtaatttg    180 cgttaattcg gtagttttaa taaattaaag ggggagcgtt agggtagcgg ggagatagaa    240
```

```
acgtattttt ggggagtaaa ttaggacggg ttgggaggaa gcgataggga aagtggttta    300
agagacggaa taaaggataa tgtttatggg gttgtttggg acgaggcgtg tggagtgtgg    360
gtgtgagcgt gcgtgtgtga tttttttttta ggtttgtaga gttgagga               408

<210> SEQ ID NO 60
<211> LENGTH: 408
<212> TYPE: DNA
<213> ORGANISM: Artificial Sequence
<220> FEATURE:
<223> OTHER INFORMATION: chemically treated genomic DNA (Homo sapiens)

<400> SEQUENCE: 60
tttttaattt tgtaggtttg aaagaaggtt atatacgtac gtttatattt atattttata    60
cgtttcgttt taaataattt tatgaatatt gttttttgtt tcgttttttg ggttattttt    120
tttgtcgttt tttttttagtt cgttttgatt tgtttttttaa aagtacgttt ttgttttttc    180
gttgttttgg cgttttttttt ttgatttatt agggttgtcg ggttggcgta gattgttttt    240
tttttttttt tatttatttt tttttttttgg tttttttttt tatagtggga gttcgtgttt    300 ttgttttttcg gttggttttt aagtgtttcg ttaggttttt tttttttttcg ttttttcggt    360 ttcggttttc gattttttcgg ttcgttggta tttgttttttt tttttttgt              408

<210> SEQ ID NO 61
<211> LENGTH: 477
<212> TYPE: DNA
<213> ORGANISM: Artificial Sequence
<220> FEATURE:
<223> OTHER INFORMATION: chemically treated genomic DNA (Homo sapiens)

<400> SEQUENCE: 61
gagtgatagg gataggtagg tgatattaga ttttttgcgg cggtagtagt cgttgtagtt    60
acgacgcggt tttttgagcg tattttttcgt aacgcgtata cgtatatttt cgggcggtc    120 gaataggagt cgggttttgt cgtagtttag tttttaggtat ttaggcgagc gacggattag    180
atttgcggtt tcgcgttttt ttgttggttt aatatttttaa aattagaggc gggtttttttg    240 gtgtcgagac gttatttcgt cgcggttttt tttagttttt ttcgttttcg ttttttttta    300 gattttttttt cgggtgcgat tgacgtggtt tcgtattaat taggacgttt cgagtcgcgg    360
tggagggatt gttttgtttg tatttattag tagtgcgggg tcgggttatt gtttcgtcgt    420
gcgtattggg tttatatagg taagttttcg ggaatttagt ttttgtttag tttaagg      477

<210> SEQ ID NO 62
<211> LENGTH: 477
<212> TYPE: DNA
<213> ORGANISM: Artificial Sequence
<220> FEATURE:
<223> OTHER INFORMATION: chemically treated genomic DNA (Homo sapiens)

<400> SEQUENCE: 62
ttttgggttg ggtaggagtt gaattttcgg gagtttgttt gtgtagattt agtgcgtacg    60
gcgaggtagt agttcggttt cgtattgttg ataggtgtag gtaggatagt ttttttatcg    120
cggttcgggg cgttttgatt ggtgcggagt tacgttagtc gtattcggag aagggtttgg    180
gaggaggcgg aggcggagag ggttgggggag ggtcgcggcg gagtgacgtt tcggtattag    240
gaagttcgtt tttggttttta agatgttagg ttaataggga agcgcggagt cgtagatttg    300
gttcgtcgtt cgtttgggtg tttggagttg agttgcggta aggttcggtt tttgttcgat    360
cgttcgaggg gtgtgcgtgt gcgcgttgcg gagggtgcgt ttagagggtc gcgtcgtggt    420
```

```
tgtagcggtt gttgtcgtcg tagggatttt aatattattt atttgttttt gttattt        477
```

<210> SEQ ID NO 63
<211> LENGTH: 339
<212> TYPE: DNA
<213> ORGANISM: Artificial Sequence
<220> FEATURE:
<223> OTHER INFORMATION: chemically treated genomic DNA (Homo sapiens)

<400> SEQUENCE: 63

```
ggtaaggggg tttgaggtag ttttaggtaa gttggggttt agcggggaga agttgtagaa         60
gaattgatta gaggatttta ggaggtttta gagttgggcg aggtagagag ttttttgtgc        120
gttttttttt tttttttgtaa ttcggggatt ttttgtattg gggtaggttt tcggttaggt        180
gtatgggagg aagtacggag aatttataag ttttttcgatt ttttagttta gacgttgttg        240 ggttttttc gttggagatc gcgtttttt taaattttg tgagcgttgc ggaagtacgc        300
ggggttcggg tcgttgagcg ttgtaagata ggggaggga                              339
```

<210> SEQ ID NO 64
<211> LENGTH: 339
<212> TYPE: DNA
<213> ORGANISM: Artificial Sequence
<220> FEATURE:
<223> OTHER INFORMATION: chemically treated genomic DNA (Homo sapiens)

<400> SEQUENCE: 64

```
ttttttttt gttttgtagc gtttagcgat tcggatttcg cgtgttttcg taacgtttat         60
aaagatttgg gggaagcgcg attttttagcg gaggggattt aatagcgttt ggattgagga        120
atcgagaggt ttgtaaattt ttcgtgtttt tttttatgta tttggtcggg ggtttgtttt        180
agtgtaagga gttttcgaat tgtagagagg agagaaggcg tataggagat ttttatttc        240 gtttagtttt gaagtttttt ggggttttt aattagtttt tttgtaattt tttttcgttg        300
ggttttaatt tgtttaagat tgttttagat tttttttgtt                             339
```

<210> SEQ ID NO 65
<211> LENGTH: 453
<212> TYPE: DNA
<213> ORGANISM: Artificial Sequence
<220> FEATURE:
<223> OTHER INFORMATION: chemically treated genomic DNA (Homo sapiens)

<400> SEQUENCE: 65

```
gagagagata gttggggagt ttggttatcg cgggtatttt ttttgcgttg tagtcgttcg         60
tttggtttgt ttttttcgttt tttcgttttt tgttttgatt tttttttttt ttgtagagtc        120
gtcgtttagc gtttcgattt cgttattatg agagttttgt tggcgcgttt gttttttttgc        180 gttttggtcg tgagcgattt taaagtgagt gcgttttttgt tttgattgat gttgtttaag        240 gattttgat tagtattagg ggagaggagg ggttgtttag ggagtggggg ttttcggat         300 tttatttata gtagggttag atttttttta ggaaatggga tagggtggta gcggaggttt        360
gagaattacg ggggttggta ttggttggta agggaggaag aggtcgtcgg gattgtttta        420
gtttgcgggt atttggtaga tgaagtttgt ttg                                    453
```

<210> SEQ ID NO 66
<211> LENGTH: 453
<212> TYPE: DNA
<213> ORGANISM: Artificial Sequence
<220> FEATURE:

<223> OTHER INFORMATION: chemically treated genomic DNA (Homo sapiens)

<400> SEQUENCE: 66

```
taagtaagtt ttatttatta gatgttcgta ggttggggta gtttcggcgg tttttttttt    60
ttttgttagt tagtgttaat tttcgttggt tttaagtttt cgttgttatt ttgttttatt   120
ttttggggag agtttggttt tgttgtggat ggaattcgga ggattttagt tttttgagta   180
gttttttttt ttttttggtg ttgattagag gttttgggt agtattagtt aaagtaagag    240
cgtatttatt ttggagtcgt ttacgattag gacgtagaga agtaggcgcg ttagtagggt   300
ttttatggtg gcgaggtcgg ggcgttagac ggcggttttg taaaggaagg agaagttagg   360
gtaagaggcg gaggaacggg aaggtaggtt aggcgggcga ttgtagcgta ggggagatgt   420
tcgcggtgat taggtttttt agttgttttt ttt                                453
```

<210> SEQ ID NO 67
<211> LENGTH: 402
<212> TYPE: DNA
<213> ORGANISM: Artificial Sequence
<220> FEATURE:
<223> OTHER INFORMATION: chemically treated genomic DNA (Homo sapiens)

<400> SEQUENCE: 67

```
tgttagagtt ggttgtggtt ttatagagta ggaagaagta cgttttattt gtttgggttt    60
cggttagggt gtcgagggtt agtatggata ttaggattag ggcgtagatt attttgtttt   120
ttatggtggt tattgttttt tttttgtttt aaaggcgatt tcgagttagg gatgagaggt   180
cgttcgagtt tcggattta tagggtaggt tttgtttgtt taaagagcgt tagataatat    240
ttgtttaagg aggttcgggg atttttgag ataataattt ttattgattt ttattaaagg    300
tgtttttag atatggttaa gttatatgga aggatttgtt gatagataga gacgatatgt   360
ggtgaggtta ttttggttga gggatttgag atttagaaag tt                     402
```

<210> SEQ ID NO 68
<211> LENGTH: 402
<212> TYPE: DNA
<213> ORGANISM: Artificial Sequence
<220> FEATURE:
<223> OTHER INFORMATION: chemically treated genomic DNA (Homo sapiens)

<400> SEQUENCE: 68

```
gattttttga attttagatt ttttagttaa gatgatttta ttatatgtcg ttttttgttta   60
ttagtaaatt ttttttatgta gtttgattat gtttaggaaa tattttttgat aaaaattagt  120
ggagattatt gttttagagg attttcgggt ttttttaggt aaatgttatt taacgttttt   180
taagtaaata gagtttgttt tataaaattc ggggttcggg cggttttta tttttgattc    240
ggggtcgttt ttggagtaga gaggaggtaa tggttattat ggagaataag gtgatttgcg   300
ttttggttttt ggtgtttatg ttggttttcg gtattttggt cgaggtttag ataggtaagg   360
cgtgtttttt tttgtttttgt ggggttatag ttagttttgg ta                    402
```

<210> SEQ ID NO 69
<211> LENGTH: 449
<212> TYPE: DNA
<213> ORGANISM: Artificial Sequence
<220> FEATURE:
<223> OTHER INFORMATION: chemically treated genomic DNA (Homo sapiens)

<400> SEQUENCE: 69

```
ttggtgatgt tgattagagt ttttgtagtt ttaaatgatt tttttaatta attttaaatt    60
```

```
tttagaattt atcgtataaa aaggttatat ttttggagg acgtcgatg gtattaggat      120 agaagtatta ggggatttta cgaacggtgt cgtcgaaata gtagtttta tttgtatatt      180 gggagggcgt gatattagga aaattataat tttgttttt acgggggtt attgtatacg      240 tttttgaaag tgtataggta agaagtaaag taagttgtgg gttgaatttt ttgatgttat      300
tatgtatata tttatttagt tttttttttt aatgatatta gtaattgttt agtgaggcgg      360
atataaaatt tttaggatat gagagggaga cgtggtttt atattttgat gtgtaaatat      420
tacgtttagg gaaaatgtaa ggtgtttta                                      449

<210> SEQ ID NO 70
<211> LENGTH: 449
<212> TYPE: DNA
<213> ORGANISM: Artificial Sequence
<220> FEATURE:
<223> OTHER INFORMATION: chemically treated genomic DNA (Homo sapiens)

<400> SEQUENCE: 70
tggggtattt tgtatttttt ttgagcgtaa tgtttgtata ttaggatgtg aggattacgt       60 tttttttta tgttttgagg gttttatatt cgttttattg gatagttgtt gatgttattg      120
gagaaggaag ttggatgggt gtgtgtatga taatattaag gaatttagtt tataatttat      180
tttgtttttt atttgtgtat ttttagagac gtgtatagtg gtttttcgtg aaagatagaa      240
ttgtggtttt tttggtgtta cgttttttta gtgtgtaaat aagggttgtt gtttcgacga      300
tatcgttcgt ggggttttt ggtgttttta ttttaatatt atcgacgttt ttttagaagg      360
tatggttttt ttatacgatg ggtttgaag atttagaatt agttagaaaa gttatttaag      420
attatagagg ttttgattag tattattag                                      449

<210> SEQ ID NO 71
<211> LENGTH: 408
<212> TYPE: DNA
<213> ORGANISM: Artificial Sequence
<220> FEATURE:
<223> OTHER INFORMATION: chemically treated genomic DNA (Homo sapiens)

<400> SEQUENCE: 71
gtaggggagg gaagtagatg ttagtgggtt gaagagttgg gagttggagt tgggagagtg       60
aaaggagagg ggatttggtg gggtatttag gagttaattg aggagtagga gtatggatt      120 ttattgtgga aaggaggatt agaagggagg atgggatgga agagaagaaa aagtaatttg      180
tgttaatttg gtagttttaa taaattaaag ggggagtgtt agggtagtgg ggagatagaa      240
atgtattttt ggggagtaaa ttaggatggg ttgggaggaa gtgataggga aagtggttta      300
agagatggaa taaaggataa tgtttatggg gttgtttggg atgaggtgtg tggagtgtgg      360
gtgtgagtgt gtgtgtgtga ttttttttta ggtttgtaga gttgagga                 408

<210> SEQ ID NO 72
<211> LENGTH: 408
<212> TYPE: DNA
<213> ORGANISM: Artificial Sequence
<220> FEATURE:
<223> OTHER INFORMATION: chemically treated genomic DNA (Homo sapiens)

<400> SEQUENCE: 72
tttttaattt tgtaggtttg aaagaaggtt atatatgtat gtttatattt atattttata       60
tgttttgttt taaataattt tatgaatatt gttttttgtt ttgttttttg ggttattttt      120
```

```
tttgttgttt ttttttagtt tgttttgatt tgtttttaa aagtatgttt tgttttttt    180 gttgttttgg tgttttttt ttgatttatt agggttgttg ggttggtgta gattgttttt    240 tttttttt tattttattt ttttttttgg tttttttt tatagtggga gtttgtgttt    300
ttgttttttg gttggttttt aagtgttttg ttaggtttt tttttttg tttttttggt    360 tttggttttt gattttttgg tttgttggta tttgtttttt tttttgt              408
```

<210> SEQ ID NO 73
<211> LENGTH: 477
<212> TYPE: DNA
<213> ORGANISM: Artificial Sequence
<220> FEATURE:
<223> OTHER INFORMATION: chemically treated genomic DNA (Homo sapiens)

<400> SEQUENCE: 73

```
gagtgatagg dataggtagg tgatattaga ttttttgtgg tggtagtagt tgttgtagtt    60
atgatgtggt tttttgagtg tattttttgt aatgtgtata tgtatatttt ttgggtggtt    120
gaataggagt tgggttttgt tgtagtttag ttttaggtat ttaggtgagt gatggattag    180
atttgtggtt ttgtgttttt ttgttggttt aatattttaa aattagaggt gggtttttg    240 gtgttgagat gttattttgt tgtggttttt tttagttttt tttgttttg ttttttttta    300 gattttttt tgggtgtgat tgatgtggtt ttgtattaat taggatgttt tgagttgtgg    360
tggagggatt gttttgtttg tatttattag tagtgtgggg ttgggttatt gttttgttgt    420
gtgtattggg tttatatagg taagtttttg ggaatttagt ttttgtttag tttaagg      477
```

<210> SEQ ID NO 74
<211> LENGTH: 477
<212> TYPE: DNA
<213> ORGANISM: Artificial Sequence
<220> FEATURE:
<223> OTHER INFORMATION: chemically treated genomic DNA (Homo sapiens)

<400> SEQUENCE: 74

```
ttttgggttg ggtaggagtt gaattttgg gagtttgttt gtgtagattt agtgtgtatg    60
gtgaggtagt agtttggttt tgtattgttg ataggtgtag gtaggatagt ttttttattg    120
tggtttgggg tgttttgatt ggtgtggagt tatgttagtt gtatttggag aagggtttgg    180
gaggaggtgg aggtggagag ggttggggag ggttgtggtg gagtgatgtt ttggtattag    240
gaagtttgtt tttggtttta agatgttagg ttaataggga agtgtggagt tgtagatttg    300
gtttgttgtt tgtttgggtg tttggagttg agttgtggta aggtttggtt tttgtttgat    360
tgtttgaggg gtgtgtgtgt gtgtgttgtg gagggtgtgt ttagagggtt gtgttgtggt    420
tgtagtggtt gttgttgttg tagggatttt aatattattt atttgttttt gttatttt    477
```

<210> SEQ ID NO 75
<211> LENGTH: 339
<212> TYPE: DNA
<213> ORGANISM: Artificial Sequence
<220> FEATURE:
<223> OTHER INFORMATION: chemically treated genomic DNA (Homo sapiens)

<400> SEQUENCE: 75

```
ggtaagggg tttgaggtag ttttaggtaa gttggggttt agtggggaga agttgtagaa    60
gaattgatta gaggattta ggaggtttta gagttgggtg aggtagagag ttttttgtgt    120 gtttttttt ttttttgtaa tttggggatt tttttgtattg gggtaggttt ttggttaggt    180
gtatgggagg aagtatggag aatttataag tttttgatt tttagttta gatgttgttg    240
```

-continued ggttttttt    gttggagatt    gtgtttttt    taaattttg    tgagtgttgt    ggaagtatgt    300 ggggttggg    ttgttgagtg    ttgtaagata    ggggaggga                                339

<210> SEQ ID NO 76
<211> LENGTH: 339
<212> TYPE: DNA
<213> ORGANISM: Artificial Sequence
<220> FEATURE:
<223> OTHER INFORMATION: chemically treated genomic DNA (Homo sapiens)

<400> SEQUENCE: 76
tttttttttt    gttttgtagt    gtttagtgat    ttggattttg    tgtgtttttg    taatgtttat    60
aaagatttgg    gggaagtgtg    atttttagtg    gaggggattt    aatagtgttt    ggattgagga    120
attgagaggt    ttgtaaattt    tttgtgtttt    ttttatgta    tttggttggg    ggtttgttt    180 agtgtaagga    gttttgaat     tgtagagagg    agagaaggtg    tataggagat    tttttatttt    240
gtttagtttt    gaagtttttt    ggggtttttt    aattagtttt    tttgtaattt    tttttgttg    300 ggttttaatt    tgtttaagat    tgtttagat    tttttgtt                                 339

<210> SEQ ID NO 77
<211> LENGTH: 453
<212> TYPE: DNA
<213> ORGANISM: Artificial Sequence
<220> FEATURE:
<223> OTHER INFORMATION: chemically treated genomic DNA (Homo sapiens)

<400> SEQUENCE: 77
gagagagata    gttggggagt    tggttattg     tgggtatttt    tttgtgttg     tagttgtttg    60 tttggtttgt    ttttttgttt    ttttgttttt    tgttttgatt    tttttttttt    ttgtagagtt    120
gttgtttagt    gttttgattt    tgttattatg    agagttttgt    tggtgtgttt    gttttttgt     180 gttttggttg    tgagtgattt    taaagtgagt    gtgttttgt     tttgattgat    gttgtttaag    240
gatttttgat    tagtattagg    ggagaggagg    ggttgtttag    ggagttgggg    tttttggat     300 tttatttata    gtagggttag    attttttta     ggaaatggga    tagggtggta    gtggaggttt    360
gagaattatg    ggggttggta    ttggttggta    agggaggaag    aggttgttgg    gattgttta     420 gtttgtgggt    atttggtaga    tgaagtttgt    ttg                                       453

<210> SEQ ID NO 78
<211> LENGTH: 453
<212> TYPE: DNA
<213> ORGANISM: Artificial Sequence
<220> FEATURE:
<223> OTHER INFORMATION: chemically treated genomic DNA (Homo sapiens)

<400> SEQUENCE: 78
taagtaagtt    ttatttatta    gatgtttgta    ggttggggta    gttttggtgg    tttttttttt    60
ttttgttagt    tagtgttaat    tttgtggtt     tttaagtttt    tgttgttatt    ttgtttatt     120 ttttggggag    agtttggttt    tgttgtggat    ggaatttgga    ggattttagt    tttttgagta    180
gttttttttt    tttttggtg     ttgattagag    gttttgggt     agtattagtt    aaagtaagag    240
tgtatttatt    ttggagttgt    ttatgattag    gatgtagaga    agtaggtgtg    ttagtaggg     300 ttttatggtg    gtgaggttgg    ggtgttagat    ggtggttttg    taaggaagg     agaagttagg    360 gtaagaggtg    gaggaatggg    aaggtaggtt    aggtgggtga    ttgtagtgta    gggagatgt     420 ttgtggtgat    taggttttt     agttgttttt    ttt                                       453

<210> SEQ ID NO 79
<211> LENGTH: 402
<212> TYPE: DNA
<213> ORGANISM: Artificial Sequence
<220> FEATURE:
<223> OTHER INFORMATION: chemically treated genomic DNA (Homo sapiens)

<400> SEQUENCE: 79

```
tgttagagtt ggttgtggtt ttatagagta ggaagaagta tgttttattt gtttgggttt      60
tggttagggt gttgagggtt agtatggata ttaggattag ggtgtagatt attttgtttt     120
ttatggtggt tattgttttt tttttgtttt aaaggtgatt ttgagttagg gatgagaggt     180
tgtttgagtt ttggatttta tagggtaggt tttgtttgtt taaagagtgt tagataatat     240
ttgtttaagg aggtttgggg atttttttgag ataataattt ttattgattt ttattaaagg    300
tgttttttag atatggttaa gttatatgga aggatttgtt gatagataga gatgatatgt     360
ggtgaggtta ttttggttga gggatttgag atttagaaag tt                        402
```

<210> SEQ ID NO 80
<211> LENGTH: 402
<212> TYPE: DNA
<213> ORGANISM: Artificial Sequence
<220> FEATURE:
<223> OTHER INFORMATION: chemically treated genomic DNA (Homo sapiens)

<400> SEQUENCE: 80

```
gattttttga attttagatt ttttagttaa gatgatttta ttatatgttg tttttgttta      60
ttagtaaatt tttttatgta gtttgattat gtttaggaaa tattttttgat aaaaattagt    120 ggagattatt gttttagagg attttttgggt ttttttaggt aaatgttatt taatgttttt    180
taagtaaata gagtttgttt tataaaattt ggggtttggg tggttttttta tttttgattt    240 ggggttgttt ttggagtaga gaggaggtaa tggttattat ggagaataag gtgatttgtg     300
ttttggtttt ggtgttatg ttggttttg gtatttggt tgaggtttag ataggtaagg        360
tgtgtttttt tttgttttgt ggggttatag ttagttttgg ta                        402
```

<210> SEQ ID NO 81
<211> LENGTH: 449
<212> TYPE: DNA
<213> ORGANISM: Artificial Sequence
<220> FEATURE:
<223> OTHER INFORMATION: chemically treated genomic DNA (Homo sapiens)

<400> SEQUENCE: 81

```
ttggtgatgt tgattagagt ttttgtagtt ttaaatgatt tttttaatta attttaaatt      60
tttagaattt attgtataaa aaggttatat tttttggagg gatgttgatg gtattaggat    120
agaagtatta ggggatttta tgaatggtgt tgttgaaata gtagttttta tttgtatatt    180
gggagggtgt gatattagga aaattataat tttgtttttt atggggggtt attgtatatg    240
tttttgaaag tgtataggta agaagtaaag taagttgtgg gttgaattt ttgatgttat     300 tatgtatata tttatttagt ttttttttttt aatgatatta gtaattgttt agtgaggtgg    360
atataaaatt tttaggatat gagagggaga tgtggttttt atattttgat gtgtaaatat    420
tatgtttagg gaaaatgtaa ggtgttta                                        449
```

<210> SEQ ID NO 82
<211> LENGTH: 420
<212> TYPE: DNA
<213> ORGANISM: Artificial Sequence

```
<220> FEATURE:
<223> OTHER INFORMATION: chemically treated genomic DNA (Homo sapiens)

<400> SEQUENCE: 82
tggggtattt tgtattttt ttgagtgtaa tgtttgtata ttaggatgtg aggattatgt    60
tttttttta tgttttgagg gttttatatt tgttttattg gatagttgtt gatgttattg   120
gagaaggaag ttggatgggt gtgtgtatga taatattaag gaatttagtt tataatttat   180
tttgtttttt atttgtgtat ttttagagat gtgtatagtg gttttttgtg aaagatagaa   240
ttgtggtttt tttggtgtta tgttttttta gtgtgtaaat aagggttgtt gttttgatga   300
tattgtttgt ggggttttt ggtgttttta ttttaatatt attgatgttt ttttagaagg   360
tatggttttt ttatatgatg ggttttgaag atttagaatt agttagaaaa gttatttaag   420

<210> SEQ ID NO 83
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 83
gatggtatta ggatagaagt atta                                          24

<210> SEQ ID NO 84
<211> LENGTH: 26
<212> TYPE: DNA
<213> ORGANISM: Artificial Sequence
<220> FEATURE:
<223> OTHER INFORMATION: chemically treated genomic DNA (Homo sapiens)

<400> SEQUENCE: 84
ccctcccaat atacaaataa aaacta                                        26

<210> SEQ ID NO 85
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 85
caccgttcgt aaaatcc                                                  17

<210> SEQ ID NO 86
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 86
acaccattca taaaatcccc taat                                          24

<210> SEQ ID NO 87
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 87
gataggtagg tgatattaga tttt                                          24
```

<210> SEQ ID NO 88
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 88
cctaaatacc taaaactaaa ctac                                          24

<210> SEQ ID NO 89
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 89
cgactcctat tcgaccgccc g                                             21

<210> SEQ ID NO 90
<211> LENGTH: 27
<212> TYPE: DNA
<213> ORGANISM: Artificial Sequence
<220> FEATURE:
<223> OTHER INFORMATION: chemically treated genomic DNA (Homo sapiens)

<400> SEQUENCE: 90
cccaactcct attcaaccac ccaaaaa                                       27

<210> SEQ ID NO 91
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 91
gtttttttta aatttttgtg ag                                            22

<210> SEQ ID NO 92
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 92
cctcccctat cttacaa                                                  17

<210> SEQ ID NO 93
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 93
acccgaaccc cgcgtacttc                                               20

<210> SEQ ID NO 94
<211> LENGTH: 24
<212> TYPE: DNA
<213> ORGANISM: Artificial Sequence
<220> FEATURE:
<223> OTHER INFORMATION: chemically treated genomic DNA (Homo sapiens)

```
<400> SEQUENCE: 94
acccaaaccc cacatacttc caca                                          24

<210> SEQ ID NO 95
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 95
ggtggttatt gttttttttt tgt                                           23

<210> SEQ ID NO 96
<211> LENGTH: 25
<212> TYPE: DNA
<213> ORGANISM: Artificial Sequence
<220> FEATURE:
<223> OTHER INFORMATION: chemically treated genomic DNA (Homo sapiens)

<400> SEQUENCE: 96
taaacaaaca aaacctaccc tataa                                         25

<210> SEQ ID NO 97
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 97
tccgaaactc gaacgacctc t                                             21

<210> SEQ ID NO 98
<211> LENGTH: 25
<212> TYPE: DNA
<213> ORGANISM: Artificial Sequence
<220> FEATURE:
<223> OTHER INFORMATION: chemically treated genomic DNA (Homo sapiens)

<400> SEQUENCE: 98
tccaaaactc aaacaacctc tcatc                                         25

<210> SEQ ID NO 99
<211> LENGTH: 26
<212> TYPE: DNA
<213> ORGANISM: Artificial Sequence
<220> FEATURE:
<223> OTHER INFORMATION: chemically treated genomic DNA (Homo sapiens)

<400> SEQUENCE: 99
ccctcccaat atacaaataa aaacta                                        26

<210> SEQ ID NO 100
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 100
agttggtgat gttgattaga gtt                                           23

<210> SEQ ID NO 101
```

```
<211> LENGTH: 15
<212> TYPE: DNA
<213> ORGANISM: Artificial Sequence
<220> FEATURE:
<223> OTHER INFORMATION: chemically treated genomic DNA (Homo sapiens)

<400> SEQUENCE: 101
acaccgttcg taaaa                                                          15

<210> SEQ ID NO 102
<211> LENGTH: 16
<212> TYPE: DNA
<213> ORGANISM: Artificial Sequence
<220> FEATURE:
<223> OTHER INFORMATION: chemically treated genomic DNA (Homo sapiens)

<400> SEQUENCE: 102
acaccattca taaaat                                                         16

<210> SEQ ID NO 103
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 103
ttctaatcct cctttccaca ataa                                                24

<210> SEQ ID NO 104
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 104 gtagggagg gaagtagatg tt                                                   22

<210> SEQ ID NO 105
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 105
agtcggagtc gggagagcga                                                     20

<210> SEQ ID NO 106
<211> LENGTH: 27
<212> TYPE: DNA
<213> ORGANISM: Artificial Sequence
<220> FEATURE:
<223> OTHER INFORMATION: chemically treated genomic DNA (Homo sapiens)

<400> SEQUENCE: 106
agttggagtt gggagagtga aaggaga                                             27

<210> SEQ ID NO 107
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 107
```

```
ggagtggagg aaattgagat                                              20

<210> SEQ ID NO 108
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 108
ccacacaaca aatactcaaa ac                                           22

<210> SEQ ID NO 109
<211> LENGTH: 33
<212> TYPE: DNA
<213> ORGANISM: Artificial Sequence
<220> FEATURE:
<223> OTHER INFORMATION: chemically treated genomic DNA (Homo sapiens)

<400> SEQUENCE: 109
tgggtgtttg taattttttgt tttgtgttag gtt                              33

<210> SEQ ID NO 110
<211> LENGTH: 16
<212> TYPE: DNA
<213> ORGANISM: Artificial Sequence
<220> FEATURE:
<223> OTHER INFORMATION: chemically treated genomic DNA (Homo sapiens)

<400> SEQUENCE: 110
agtagtgcgg ggtcgg                                                  16

<210> SEQ ID NO 111
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 111
agtagtgtgg ggttggg                                                 17

<210> SEQ ID NO 112
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 112
tgtagttacg acgcggt                                                 17

<210> SEQ ID NO 113
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 113
gttgtagtta tgatgtggtt tt                                           22

<210> SEQ ID NO 114
<211> LENGTH: 16
<212> TYPE: DNA
```

```
<210> SEQ ID NO 115
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 114
tttcgggcgg tcgaat                                                    16

<210> SEQ ID NO 115
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 115
ttttgggtgg ttgaatagga                                                20

<210> SEQ ID NO 116
<211> LENGTH: 16
<212> TYPE: DNA
<213> ORGANISM: Artificial Sequence
<220> FEATURE:
<223> OTHER INFORMATION: chemically treated genomic DNA (Homo sapiens)

<400> SEQUENCE: 116
taggcgagcg acggat                                                    16

<210> SEQ ID NO 117
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 117
taggtgagtg atggattaga t                                              21

<210> SEQ ID NO 118
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 118
tgtcgagacg ttatttcgt                                                 19

<210> SEQ ID NO 119
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 119
tggtgttgag atgttatttt gt                                             22

<210> SEQ ID NO 120
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 120
agttgggaga gtgaaagg                                                  18
```

```
<210> SEQ ID NO 121
<211> LENGTH: 16
<212> TYPE: DNA
<213> ORGANISM: Artificial Sequence
<220> FEATURE:
<223> OTHER INFORMATION: chemically treated genomic DNA (Homo sapiens)

<400> SEQUENCE: 121
gagtcgggag agcgaa                                                          16

<210> SEQ ID NO 122
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 122
tttgcgttaa ttcggtagt                                                       19

<210> SEQ ID NO 123
<211> LENGTH: 23
<212> TYPE: DNA
<213> ORGANISM: Artificial Sequence
<220> FEATURE:
<223> OTHER INFORMATION: chemically treated genomic DNA (Homo sapiens)

<400> SEQUENCE: 123
tttgtgttaa tttggtagtt tta                                                  23

<210> SEQ ID NO 124
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 124
agcgttaggg tagcgggg                                                        18

<210> SEQ ID NO 125
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 125
ggagtgttag ggtagtgg                                                        18

<210> SEQ ID NO 126
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 126
gggatgaggt gtgtgga                                                         17

<210> SEQ ID NO 127
<211> LENGTH: 16
<212> TYPE: DNA
<213> ORGANISM: Artificial Sequence
<220> FEATURE:
```

```
<223> OTHER INFORMATION: chemically treated genomic DNA (Homo sapiens)

<400> SEQUENCE: 127
ttgggacgag gcgtgt                                                     16

<210> SEQ ID NO 128
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 128
agcgggtcga agagtcgg                                                   18

<210> SEQ ID NO 129
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 129
agtgggttga agagttgg                                                   18

<210> SEQ ID NO 130
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 130
ttggttatcg cgggtatt                                                   18

<210> SEQ ID NO 131
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 131
gtttggttat tgtgggtatt t                                               21

<210> SEQ ID NO 132
<211> LENGTH: 24
<212> TYPE: DNA
<213> ORGANISM: Artificial Sequence
<220> FEATURE:
<223> OTHER INFORMATION: chemically treated genomic DNA (Homo sapiens)

<400> SEQUENCE: 132
tttgattttg ttattatgag agtt                                            24

<210> SEQ ID NO 133
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 133
tttcgatttc gttattatga ga                                              22
```

```
<210> SEQ ID NO 134
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 134
ttttggtcgt gagcgat                                                  17

<210> SEQ ID NO 135
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 135
gttttggttg tgagtgattt                                               20

<210> SEQ ID NO 136
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 136
aagaggtcgt cgggatt                                                  17

<210> SEQ ID NO 137
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 137
aggaagaggt tgttggga                                                 18

<210> SEQ ID NO 138
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 138
aggcgatttc gagttagg                                                 18

<210> SEQ ID NO 139
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 139
aggtgatttt gagttaggg                                                19

<210> SEQ ID NO 140
<211> LENGTH: 17
<212> TYPE: DNA
<213> ORGANISM: Artificial Sequence
<220> FEATURE:
<223> OTHER INFORMATION: chemically treated genomic DNA (Homo sapiens)
```

```
<400> SEQUENCE: 140
tgagaggtcg ttcgagt                                                    17

<210> SEQ ID NO 141
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 141
tgagaggttg tttgagttt                                                  19

<210> SEQ ID NO 142
<211> LENGTH: 22
<212> TYPE: DNA
<213> ORGANISM: Artificial Sequence
<220> FEATURE:
<223> OTHER INFORMATION: chemically treated genomic DNA (Homo sapiens)

<400> SEQUENCE: 142
tttgagtttt ggattttata gg                                              22

<210> SEQ ID NO 143
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 143
gttcgagttt cggattttat                                                 20

<210> SEQ ID NO 144
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 144
gtcgttcgag tttcgga                                                    17

<210> SEQ ID NO 145
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 145
aggttgtttg agttttgga                                                  19

<210> SEQ ID NO 146
<211> LENGTH: 16
<212> TYPE: DNA
<213> ORGANISM: Artificial Sequence
<220> FEATURE:
<223> OTHER INFORMATION: chemically treated genomic DNA (Homo sapiens)

<400> SEQUENCE: 146
gagcgttgcg gaagta                                                     16

<210> SEQ ID NO 147
<211> LENGTH: 18
```

```
<212> TYPE: DNA
<213> ORGANISM: Artificial Sequence
<220> FEATURE:
<223> OTHER INFORMATION: chemically treated genomic DNA (Homo sapiens)

<400> SEQUENCE: 147
tgtgagtgtt gtggaagt                                                  18

<210> SEQ ID NO 148
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 148
gttgttgagt gttgtaagat                                                20

<210> SEQ ID NO 149
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 149
ggtcgttgag cgttgta                                                   17

<210> SEQ ID NO 150
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 150
tgtggaagta tgtggggt                                                  18

<210> SEQ ID NO 151
<211> LENGTH: 16
<212> TYPE: DNA
<213> ORGANISM: Artificial Sequence
<220> FEATURE:
<223> OTHER INFORMATION: chemically treated genomic DNA (Homo sapiens)

<400> SEQUENCE: 151
ttgcggaagt acgcgg                                                    16

<210> SEQ ID NO 152
<211> LENGTH: 16
<212> TYPE: DNA
<213> ORGANISM: Artificial Sequence
<220> FEATURE:
<223> OTHER INFORMATION: chemically treated genomic DNA (Homo sapiens)

<400> SEQUENCE: 152
tacgcggggt tcgggt                                                    16

<210> SEQ ID NO 153
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 153
```

```
agtatgtggg gtttggg                                              17

<210> SEQ ID NO 154
<211> LENGTH: 17
<212> TYPE: DNA
<213> ORGANISM: Artificial Sequence
<220> FEATURE:
<223> OTHER INFORMATION: chemically treated genomic DNA (Homo sapiens)

<400> SEQUENCE: 154
ttcgggtcgt tgagcgt                                              17

<210> SEQ ID NO 155
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 155
gtttgggttg ttgagtgt                                             18

<210> SEQ ID NO 156
<211> LENGTH: 16
<212> TYPE: DNA
<213> ORGANISM: Artificial Sequence
<220> FEATURE:
<223> OTHER INFORMATION: chemically treated genomic DNA (Homo sapiens)

<400> SEQUENCE: 156
gagggacgtc gatggt                                               16

<210> SEQ ID NO 157
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 157
ggagggatgt tgatggta                                             18

<210> SEQ ID NO 158
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 158
gtgtcgtcga aatagtagt                                            19

<210> SEQ ID NO 159
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 159
ggtgttgttg aaatagtagt t                                         21

<210> SEQ ID NO 160
<211> LENGTH: 17
<212> TYPE: DNA
<213> ORGANISM: Artificial Sequence
```

```
<220> FEATURE:
<223> OTHER INFORMATION: chemically treated genomic DNA (Homo sapiens)

<400> SEQUENCE: 160
tttacgaacg gtgtcgt                                                          17

<210> SEQ ID NO 161
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 161
ggattttatg aatggtgttg t                                                     21

<210> SEQ ID NO 162
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 162
aatggtgttg ttgaaatagt a                                                     21

<210> SEQ ID NO 163
<211> LENGTH: 16
<212> TYPE: DNA
<213> ORGANISM: Artificial Sequence
<220> FEATURE:
<223> OTHER INFORMATION: chemically treated genomic DNA (Homo sapiens)

<400> SEQUENCE: 163
gaacggtgtc gtcgaa                                                           16

<210> SEQ ID NO 164
<211> LENGTH: 18
<212> TYPE: DNA
<213> ORGANISM: Artificial Sequence
<220> FEATURE:
<223> OTHER INFORMATION: chemically treated genomic DNA (Homo sapiens)

<400> SEQUENCE: 164
tacgaacggt gtcgtcga                                                         18

<210> SEQ ID NO 165
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 165
tatgaatggt gttgttgaaa t                                                     21
```